US011053550B2

(12) United States Patent
Moffitt et al.

(10) Patent No.: US 11,053,550 B2
(45) Date of Patent: Jul. 6, 2021

(54) GENE-EXPRESSION BASED SUBTYPING OF PANCREATIC DUCTAL ADENOCARCINOMA

(71) Applicant: The University of North Carolina at Chapel Hill, Chapel Hill, NC (US)

(72) Inventors: Richard Moffitt, Chapel Hill, NC (US); Jen Jen Yeh, Chapel Hill, NC (US); Naim Ur Rashid, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 999 days.

(21) Appl. No.: 15/518,900

(22) PCT Filed: Oct. 14, 2015

(86) PCT No.: PCT/US2015/055565

§ 371 (c)(1),
(2) Date: Apr. 13, 2017

(87) PCT Pub. No.: WO2016/061252

PCT Pub. Date: Apr. 21, 2016

(65) Prior Publication Data

US 2017/0233827 A1 Aug. 17, 2017

Related U.S. Application Data

(60) Provisional application No. 62/201,793, filed on Aug. 6, 2015, provisional application No. 62/063,719, filed on Oct. 14, 2014.

(51) Int. Cl.
*C12Q 1/6886* (2018.01)
*G16B 25/00* (2019.01)
*G01N 33/574* (2006.01)

(52) U.S. Cl.
CPC ..... *C12Q 1/6886* (2013.01); *G01N 33/57438* (2013.01); *G16B 25/00* (2019.02); *C12Q 2600/106* (2013.01); *C12Q 2600/112* (2013.01); *C12Q 2600/118* (2013.01); *C12Q 2600/156* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,974,164 | A | 10/1999 | Chee |
| 6,185,561 | B1 | 2/2001 | Balaban et al. |
| 6,229,911 | B1 | 5/2001 | Balaban et al. |
| 2007/0023179 | A1 | 2/2007 | Mita et al. |
| 2009/0203547 | A1 | 8/2009 | Banes et al. |

FOREIGN PATENT DOCUMENTS

| | | | |
|---|---|---|---|
| WO | WO 2004/046098 | A2 | 3/2004 |
| WO | WO 2007/001324 | A2 | 1/2007 |
| WO | WO 2007/056332 | A2 | 5/2007 |
| WO | WO 2007/070252 | A2 | 6/2007 |
| WO | WO 2014/056626 | A1 | 4/2014 |
| WO | WO 2020/191413 | A1 | 9/2020 |
| WO | WO 2020/205993 | A1 | 10/2020 |

OTHER PUBLICATIONS

Collisson, Eric A., et al. "Subtypes of pancreatic ductal adenocarcinoma and their differing responses to therapy." Nature medicine 17.4 (2011): 500-503, as also cited on the Jul. 13, 2017 IDS, herewith the inclusion of Supplementary Table 1a.*
Afsari et al. "Rank Discriminants for Predicting Phenotypes from RNA Expression." Ann Appl Stat, vol. 8, pp. 1469-1491 (2014).
Afsari et al. "Switch Box: an R package for k-Top Scoring Pairs classifier development." Bioinformatics, vol. 31, No. 2, pp. 273-274 (2015).
Alexandrov et al. "Signatures of mutational processes in human cancer." Nature, vol. 500, pp. 415-421 (2013).
Alexandrov et al. "Deciphering Signatures of Mutational Processes Operative in Human Cancer." Cell Reports, vol. 3, No. 1, pp. 246-259 (2013).
Biton et al. "Independent component analysis uncovers the landscape of the bladder tumor transcriptome and reveals insights into luminal and basal subtypes" Cell Rep, vol. 9, pp. 1235-1245(2014).
Bolker, BM. "Ecological models and data in R". Princeton University Press, pp. 215 (2008).
Breheny & Huang "Coordinate descent algorithms for nonconvex penalized regression, with applications to biological feature selection" Ann Appl Stat, vol. 5, pp. 232-253(2011).
Cancer Genome Atlas Research Network, "Integrated Genomic Analyses of Ovarian Carcinoma". Nature, 474, pp. 609-615 (2011).
Cancer Genome Atlas Research Network, "Comprehensive molecular characterization of human colon and rectal cancer." Nature, vol. 487, pp. 330-337(2012a).

(Continued)

*Primary Examiner* — G Steven Vanni
(74) *Attorney, Agent, or Firm* — Jenkins, Wilson, Taylor & Hunt, P.A.

(57) ABSTRACT

Methods for generating a prognostic and/or subtype signature for a subject with pancreatic ductal adenocarcinoma (PDAC) are provided. In some embodiments, the methods include determining expression levels for one or more genes listed in Tables 2-5, 9, 10, or 11, and/or the DE-S and/or DE-T subset of genes in PDAC cells obtained from the subject, wherein the determining provides a prognostic and/or subtype signature for the subject. Also provided are methods for classifying a subject diagnosed with pancreatic ductal adenocarcinoma (PDAC) as having an activated stroma subtype or a normal stroma subtype of PDAC and/or a basal subtype or a classical subtype of PDAC; and methods for identifying a differential treatment strategy for a subject diagnosed with pancreatic ductal adenocarcinoma (PDAC).

13 Claims, 22 Drawing Sheets

Specification includes a Sequence Listing.

(56) References Cited

OTHER PUBLICATIONS

Cancer Genome Atlas Research Network, “Comprehensive genomic characterization of squamous cell lung cancers” Nature, vol. 489, pp. 519-525 (2012b).
Cancer Genome Atlas Research Network, “Comprehensive molecular portraits of human breast tumours.” Nature, vol. 490, pp. 61-70(2012c).
Cancer Genome Atlas Research Network, “Integrated genomic characterization of endometrial carcinoma.” Nature, vol. 497, pp. 67-73(2013a).
Cancer Genome Atlas Research Network, “Comprehensive molecular characterization of clear cell renal cell carcinoma.” Nature, vol. 499, pp. 43-49(2013b).
Cancer Genome Atlas Research Network, “Genomic and epigenomic landscapes of adult de novo acute myeloid leukemia.” New Eng J Med, vol. 368, pp. 2059(2013c).
Cancer Genome Atlas Research Network, “Comprehensive molecular characterization of urothelial bladder carcinoma.” Nature, vol. 507, pp. 315-322 (2014a).
Cancer Genome Atlas Research Network, “Comprehensive molecular profiling of lung adenocarcinoma.” Nature, vol. 511, pp. 543-550(2014b).
Collisson et al. “Subtypes of Pancreatic Ductal Adenocarcinoma and Their Differing Responses to Therapy” Nat Med, vol. 17, pp. 500-503 (2011).
Crnogorac-Jurcevic et al. “Expression profiling of microdissected pancreatic adenocarcinomas.” Oncogene, vol. 21, pp. 4587-4594 (2002).
Dal Molin et al. “Very Long-term Survival Following Resection for Pancreatic Cancer Is Not Explained by Commonly Mutated Genes: Results of Whole-Exome Sequencing Analysis.” Clin Cancer Res, vol. 21, pp. 1944-1950 (2015).
Damrauer et al. “Intrinsic subtypes of high-grade bladder cancer reflect the hallmarks of breast cancer biology” Proc Nat Acad Sci U S A, vol. 111, No. 8 pp. 3110-3115 (2014).
Garrido-Laguna et al. “Tumor engraftment in nude mice and enrichment in stroma- related gene pathways predict poor survival and resistance to gemcitabine in patients with pancreatic cancer.” Clin Cancer Res, vol. 17, pp. 5793-5800 (2011).
Haeger et al. “Smad4 loss promotes lung cancer formation but increases sensitivity to DNA topoisomerase inhibitors.” Oncogene, vol. 35, No. 5, pp. 577-586 (2015).
Herrera et al. “Functional heterogeneity of cancer-associated fibroblasts from human colon tumors shows specific prognostic gene expression signature.” Clin Cancer Res, vol. 19, pp. 5914-5926 (2013).
Hoadley et al. “Multiplatform analysis of 12 cancer types reveals molecular classification within and across tissues of origin.” Cell, vol. 158, pp. 929-944(2014).
Hwang et al. “Cancer-associated stromal fibroblasts promote pancreatic tumor progression.” Cancer Res, vol. 68, pp. 918-926 (2008).
Iacobuzio-Donahue et al. “Exploration of global gene expression patterns in pancreatic adenocarcinoma using cDNA microarrays.” Am J Pathol, vol. 162, pp. 1151-1162 (2003).
Iacobuzio-Donahue et al. “DPC4 gene status of the primary carcinoma correlates with patterns of failure in patients with pancreatic cancer.” J Clin Oncol, vol. 27, pp. 1806-1813 (2009).
Ihle et al. “Effect of KRAS oncogene substitutions on protein behavior: implications for signaling and clinical outcome.” J Natl Cancer Inst, vol. 104, pp. 228-239 (2012).
Jones et al. “Core signaling pathways in human pancreatic cancers revealed by global genomic analyses.” Science, vol. 321, pp. 1801-1806 (2008).
Logsdon et al. “Molecular profiling of pancreatic adenocarcinoma and chronic pancreatitis identifies multiple genes differentially regulated in pancreatic cancer.” Cancer Res, vol. 63, pp. 2649-2657(2003).
McLendon et al. “Comprehensive genomic characterization defines human glioblastoma genes and core pathways.” Nature, vol. 455, pp. 1061-1068 (2008).
Parker et al. “Supervised risk predictor of breast cancer based on intrinsic subtypes.” J Clin Oncol, vol. 27, pp. 1160-1167(2009).
Prat et al. “Phenotypic and molecular characterization of the claudin-low intrinsic subtype of breast cancer.” Breast Cancer Res, vol. 12, pp. R68(2010).
Rubio-Viqueira et al. “An in vivo platform for translational drug development in pancreatic cancer.” Clin Cancer Res, vol. 12, pp. 4652-4661(2006).
Shi et al. “The MicroArray Quality Control (MAQC)-II study of common practices for the development and validation of microarray-based predictive models.” Nat Biotechnol, vol. 28, pp. 827-838(2010).
Shi et al. “Top scoring pairs for feature selection in machine learning and applications to cancer outcome prediction.” Bmc Bioinformatics, vol. 12, pp. 375(2011).
Stuart et al. “In silico dissection of cell-type-associated patterns of gene expression in prostate cancer.” Proc Nat Acad Sci U S A, vol. 101, pp. 615-620(2004).
Tibshirani et al. “Diagnosis of multiple cancer types by shrunken centroids of gene expression.” Proc Nat Acad Sci U S A, vol. 99, pp. 6567-6572(2002).
Wamunyokoli et al. “Expression profiling of mucinous tumors of the ovary identifies genes of clinicopathologic importance.” Clin Cancer Res, vol. 12, pp. 690-700(2006).
Wang et al. “In silico estimates of tissue components in surgical samples based on expression profiling data.” Cancer Res, vol. 70, pp. 6448-6455(2010).
Yabushita et al. “Metabolomic and Transcriptomic Profiling of Human K-Ras Oncogene Transgenic Rats With Pancreatic Ductal Adenocarcinomas.” Carcinogenesis, vol. 34, No. 6, pp. 1251-1259(2013).
Yoshihara et al. “Inferring tumour purity and stromal and immune cell admixture from expression data.” Nat Commun, vol. 4, pp. 2612(2013).
Zhang et al. “A Gata6-Wnt pathway required for epithelial stem cell development and airway regeneration.” Nat Genet, vol. 40, pp. 862-870(2008).
Biankin et al. “Pancreatic cancer genomes reveal aberrations in axon guidance pathway genes” Nature, vol. 491, pp. 399-405(2012).
Cohen et al. (2008) “Fibroblast activation protein and its relationship to clinical outcome in pancreatic adenocarcinoma.” Pancreas, 37:154-158.
Erkan et al. (2008) “The activated stroma index is a novel and independent prognostic marker in pancreatic ductal adenocarcinoma.” Clin Gastroenterol Hepatol 6:1155-1161.
Froeling et al. (2011) “Retinoic acid-induced pancreatic stellate cell quiescence reduces paracrine Wnt-β-catenin signaling to slow tumor progression.” Gastroenterol 141:1486-1497.
Ji et al. “LKB1 modulates lung cancer differentiation and metastasis.” Nature, vol. 448, pp. 807-810 (2007).
Cheng (2014) “A signature of epithelial-mesenchymal plasticity and stromal activation in primary tumor modulates late recurrence in breast cancer independent of disease subtype” Breast Cancer Research 16: Article 407.

* cited by examiner

SEQUENCE LISTING

```
<160> NUMBER OF SEQ ID NOS: 126

<210> SEQ ID NO 1
<211> LENGTH: 6012
<212> TYPE: DNA
<213> ORGANISM: Homo sapiens

<400> SEQUENCE: 1

ataacctcca ctctgaaagc agtcttcaca gaaacttttc acagaagtca aatagttaaa      60
```

-continued

```
gcaaattcta gatacatggt agagaccagg agaaaatatg aataactttc ttctaaacaa    120
ggagctcagt ggataaacca tacctctaga ttccttgctt ccattttccc agaagttttg    180
gtagcaggat gatgttggcc tcataatgtg agttagagag gagtccctct ttttcgactg    240
tttggaattg tttcagaagg aatgctacca gctcctcttg taccactggt agaattcagc    300
tgtgaatctg tctggtcctg ggcttttttt gattgacaag atgaggaaga gaaagatcag    360
tgtgtgtcaa caaacttggg ccttattatg caagaacttt cttaaaaaat ggagaatgaa    420
aagagagtcc ttaatggaat ggctgaattc attgctccta ctactttgtt tgtatatata    480
tcctcatagt catcaagtaa atgatttttc ttcactgctt accatggacc tgggacgggt    540
agatacattt aatgaatcca gattttctgt tgtatacaca cctgtcacca acacgaccca    600
acagataatg aataaagtag cctctactcc cttcctggca ggtaaagagg tcttgggact    660
gccagatgag gaaagtatta aagaattcac agcaaattat cctgaagaaa tagtaagagt    720
cacctttact aatacatact catatcattt gaagttcttg ctaggacatg gaatgccagc    780
aaagaaggag cacaaggacc atacagctca ttgttatgaa acaaatgaag atgtttactg    840
tgaagtttca gtattttgga aggaaggttt tgtggctctt caagctgcca ttaatgctgc    900
tattatagaa atcacaacaa atcactcagt gatggaggag ctgatgtcag ttactggaaa    960
aaatatgaag atgcattcct tcattggtca atcaggagtt ataactgatt tgtacctttt   1020
ttcctgcatt atttcatttt cctcattcat ttactatgca tctgttaatg tcacaagaga   1080
gaggaaaagg atgaaggcct tgatgacaat gatgggtctt cgggattcag cgttctggct   1140
ctcctggggt ttgctctatg ctggtttcat cttcattatg gcccttttct tggcacttgt   1200
tataagatct acccagttta tcattttgtc tggcttcatg gtagtcttca gcctctttct   1260
cctgtatgga ttatctttgg tagctttggc tttcttaatg agcatcttgg taaagaaatc   1320
tttcctcacc ggcctggtcg tgttcctcct cactgtcttt tgggggtgtc tggggttcac   1380
atcactgtac agacaccttc ctgcatcctt ggagtggatt ttaagcttgc ttagtccctt   1440
tgccttcatg cttggaatgg cccagctttt acacttggac tatgatttga attctaatgc   1500
atttcctcat ccatcggacg gctcaaatct cattgtagca acaaatttca tgttggcatt   1560
tgacacttgc ctctatctgg cattggcgat ttactttgaa aaaattttgc caaatgaata   1620
tggacatcga cgtccacctt tgtttttcct gaagtcctca ttttggtctc aaacacaaaa   1680
gactgatcac gtggcccttg aagatgaaat ggatgccgat ccttcatttc atgactcttt   1740
tgaacaagcg cctccagaat tccaagggaa agaagccatc agaatcagaa atgttacaaa   1800
agaatataaa ggaaagcctg ataaaataga agccttgaaa gatctggtat ttgacattta   1860
cgaaggccaa atcactgcaa tacttggtca cagtggagct ggaaagtcaa cactgctaaa   1920
cattcttagt gggttgtctg ttcccaccaa aggttcagtc accatctata acaataagct   1980
ttcagaaatg gctgacctag aaaatctcag caagctgacc ggagtttgtc cacaatccaa   2040
tgtgcaattt gacttcctca ctgtaagaga aaacctcaga ctctttgcta aaataaaagg   2100
gattctgcca caagaagtgg ataaagagat acaaagggtt ctgctggaat tggaaatgaa   2160
aaatattcag gatgttcttg ctcaaaactt aagtggtgga cagaaaagaa agctaacctt   2220
tgggattgcc attttaggag atcctcagat tttcctgttg gatgaaccaa ctgctggatt   2280
ggatcccttt tcaagacacc aagtatggaa ccttctgaaa gaacgcaaaa cagaccgcgt   2340
gatcctcttc agtacccagt tcatggatga ggccgacatc ctggcggaca ggaaagtatt   2400
tctctcccaa gggaagctaa agtgcgcggg ctcttctttg tttctaaaga agaaatgggg   2460
```

-continued

```
gattggatat cacttaagct tgcagttaaa tgaaatatgt gttgaggaaa acataacatc   2520
acttgttaaa cagcacatcc ctgatgccaa attatcagcc aaaagcgaag gaaaacttat   2580
ttatacatta cccttagaaa gaacaaataa atttccagaa ctttacaagg atcttgatag   2640
ctatcctgac ctaggaattg agaattatgg tgtttccatg acaactttga atgaagtatt   2700
cctgaagcta gaaggaaaat ctacaattaa tgaatcggac attgctattt tgggagaagt   2760
acaagcggaa aaagctgacg acactgaaag gcttgttgag atggaacaag tcctctcttc   2820
acttaacaag atgagaaaga caataggtgg tgtggctctc tggcgacagc aaatctgcgc   2880
aattgcaagg gttcgcttgt taaagttaaa gcatgaaaga aaagctcttt tagcactgct   2940
attaattcta atggctggat tttgccctct tcttgtggag tataccatgg tgaaaatata   3000
tcaaaacagt tacacctggg aactttctcc tcatttgtat ttccttgctc ctggacaaca   3060
accacatgac cctctcactc aactactgat catcaataaa acaggggcaa gcattgatga   3120
ctttatacag tctgtggagc accagaacat agctttagaa gtggatgcat ttggaactag   3180
aaatggcaca gatgacccat cttataatgg agccatcaca gtgtgttgta atgaaaagaa   3240
ttacagcttt tcgttagcat gcaatgccaa aagattgaat tgcttcccag ttcttatgga   3300
cattgttagt aatgggctac ttggaatggt taaaccatca gtacatatcc gaactgaaag   3360
aagtacattt ttggagaatg gacaggacaa tccaatcgga ttcctggcat atatcatgtt   3420
ctggctggtt ttaacatcga gttgcccacc ttacattgcc atgagcagca tcgatgatta   3480
taagaacaga gctcggtccc agctacggat ttccggactc tccccttctg cttactggtt   3540
tgggcaggcg ctggtggatg tttccctgta cttcttggtc ttcgttttta tatatttaat   3600
gagctacatt tcaaacttcg aagacatgct acttacaata attcatatta ttcaaatccc   3660
atgtgctgtt ggttattcct tttccctcat cttcatgaca tacgtgattt ccttcatctt   3720
tcgcaagggg agaaaaaata gtggcatttg gtcattttgt ttctatgttg tcactgtatt   3780
ctctgtggct ggatttgcgt tcagtatctt cgaaagtgat attccattta tcttcacttt   3840
tttaatacca cctgccacaa tgattggctg tttgttctta tcttctcatc ttctcttttc   3900
ttctctcttt tctgaagaac gaatggatgt acagccattt ctggtattcc taattccttt   3960
ccttcatttt atcatttttc tttttactct tcgatgtctg gaatggaagt ttggaaagaa   4020
atcaatgaga aaggatcctt tctttagaat ttctccaaga agtagtgatg tgtgtcaaaa   4080
tccagaagaa ccagaaggag aggatgaaga tgttcagatg gaaagagtga gaacagcaaa   4140
tgccttgaat tctactaatt ttgatgagaa gccagtcatc attgccagct gtctacgcaa   4200
ggagtatgca gggaagagga aaggctgttt ttccaagagg aagaataaga tagccacgag   4260
aaatgtctcc ttctgtgtta gaaaaggtga agttttagga ttattaggac acaatggagc   4320
tggtaaaagc acatccatta aggtgataac tggagacaca aaaccaactg ctggacaagt   4380
gctactgaaa gggagcggtg gaggggatgc cctggagttc ctggggtact gccctcagga   4440
gaacgcgctg tggcccaacc tgacagtgag gcagcacctg gaggtgtacg ccgccgtgaa   4500
agggctgagg aaaggggatg ctgaggttgc catcacacgg ttagtggatg cgctcaagct   4560
gcaggaccag ctgaagtctc ccgtgaagac cttgtcagag ggaataaaga gaaagctgtg   4620
ctttgtcctg agcatactgg ggaacccgtc agtggtgctt ctggatgagc cgtcgaccgg   4680
gatggacccc gaggggcagc agcaaatgtg gcaggccatc cgggccacct ttagaaacac   4740
ggaaaggggt gccctcctaa ccacccacta catggcagag gctgaggccg tgtgtgaccg   4800
```

```
agtggccatc atggtatctg ggaggttgag atgtatcggt tccatccaac acctgaaaag   4860
caaatttggc aaagattacc tgctggagat gaaggtgaag aacctggcac aagtggagcc   4920
cctccatgca gagatcctga ggcttttccc ccaggctgct cggcaggaaa ggtactcctc   4980
tctgatggtt tataagttgc cagtggaaga tgtgcaacct ttagcccaag ctttcttcaa   5040
attagagaag gttaaacaga gctttgacct agaggagtac agcctctcac agtctaccct   5100
ggagcaggtt ttcctggagc tctccaagga gcaggagctg ggtgattttg aggaggattt   5160
tgatccctca gtgaagtgga agctcctccc ccaggaagag ccttaaaacc ccaaattctg   5220
tgttcctgtt taaacccgtg gtttttttta aatacattta tttttatagc agcaatgttc   5280
tatttttaga aactatatta taagtacaga aatggttctc cgtgtggtgg gaggaggagg   5340
ttcgggtgct gggtaagtgc catgtcagtg tggacagagg catttgacta agccaacctc   5400
ctctcacagc ctctgtatct ctgcaggcca tactggttcc attgttctgt ataatactga   5460
ataaataaat ttacttttac atgatcgtat aagtttctag ataagataaa caaattttgt   5520
ttaaattttt ttaataaaaa tcttaaaaca cttttttttct aacctagact gagaaattca   5580
tgtttacttt tctaggtgta tgatactttg taaagttgat actttcctaa gaatttaaca   5640
tgtcatattt ttgaaataga tttaagtgtg cttcttattg ctaaaaatac taaatgtcat   5700
gggtcatagt atctgatatc aatatcgttg ataacatatc cacaggtaac accatgatgt   5760
aggcataaat ggaaaacaaa aaccctacta tttcaaatat attgtacttt tttatttctg   5820
taagccaact gtgtgccatt ttcactggac ttttaaatct agactttagt gatgtctaca   5880
ttgtaaatga tcttttgtgg atatttgtca cttggtttca gaaagttcac aaatgtagca   5940
acagctcaca tgactgagta ggtagaaaat gtgaaataaa tctcatatat atagttttga   6000
aataaaaaaa aa                                                       6012
```

<210> SEQ ID NO 2
<211> LENGTH: 1345
<212> TYPE: DNA
<213> ORGANISM: Homo sapiens

<400> SEQUENCE: 2

```
gcctctgggg ttttatattg ctctggtatt catgccaaag acacaccagc cctcagtcac     60
tgggagaaga acctctcata ccctcggtgc tccagtcccc agctcactca gccacacaca    120
ccatgtgtga agaggagacc accgcgctcg tgtgtgacaa tggctctggc ctgtgcaagg    180
caggcttcgc aggagatgat gccccccggg ctgtcttccc ctccattgtg ggccgccctc    240
gccaccaggg tgtgatggtg ggaatgggcc agaaagacag ctatgtgggg gatgaggctc    300
agagcaagcg agggatccta actctcaaat accccattga acacggcatc atcaccaact    360
gggatgacat ggagaagatc tggcaccact ccttctacaa tgagctgcgt gtagcacctg    420
aagagcaccc caccctgctc acagaggctc ccctaaatcc caaggccaac agggaaaaga    480
tgacccagat catgtttgaa accttcaatg tccctgccat gtacgtcgcc attcaagctg    540
tgctctccct ctatgcctct ggccgcacga caggcatcgt cctggattca ggtgatggcg    600
tcacccacaa tgtccccatc tatgaaggct atgccctgcc ccatgccatc atgcgcctgg    660
acttggctgg ccgtgacctc acggactacc tcatgaagat cctcacagag agaggctatt    720
cctttgtgac cacagctgag agagaaattg tgcgagacat caaggagaag ctgtgctatg    780
tggccctgga ttttgagaat gagatggcca cagcagcttc ctcttcctcc ctggagaaga    840
gctatgagct gccagatggg caggttatca ccattggcaa tgagcgcttc cgctgccctg    900
```

```
agaccctctt ccagccttcc tttattggca tggagtccgc tggaattcat gagacaacct    960
acaattccat catgaagtgt gacattgaca tccgtaagga cttatatgcc aacaatgtcc   1020
tctctggggg caccaccatg taccctggca ttgctgacag gatgcagaag gagatcacag   1080
ccctggcccc cagcaccatg aagatcaaga ttattgctcc cccagagcgg aagtactcag   1140
tctggatcgg gggctctatc ctggcctctc tctccacctt ccagcagatg tggatcagca   1200
agcctgagta tgatgaggca gggccctcca ttgtccacag gaagtgcttc taaagtcaga   1260
acaggttctc caaggatccc ctcgagacta ctctgttacc agtcatgaaa cattaaaacc   1320
tacaagcctt aaaaaaaaaa aaaaa                                         1345
```

<210> SEQ ID NO 3
<211> LENGTH: 4670
<212> TYPE: DNA
<213> ORGANISM: Homo sapiens

<400> SEQUENCE: 3

```
gcactcgctg gaaagcggct ccgagccagg ggctattgca aagccagggt gcgctaccgg     60
acggagaggg gagagccctg agcagagtga gcaacatcgc agccaaggcg gaggccgaag    120
aggggcgcca ggcaccaatc tccgcgttgc ctcagccccg gaggcgcccc agagcgcttc    180
ttgtcccagc agagccactc tgcctgcgcc tgcctctcag tgtctccaac tttgcgctgg    240
aagaaaaact tcccgcgcgc cggcagaact gcagcgcctc cttttagtga ctccgggagc    300
ttcggctgta gccggctctg cgcgcccttc caacgaataa tagaaattgt taattttaac    360
aatccagagc aggccaacga ggctttgctc tcccgacccg aactaaaggt ccctcgctcc    420
gtgcgctgct acgagcggtg tctcctgggg ctccaatgca gcgagctgtg cccgaggggt    480
tcggaaggcg caagctgggc agcgacatgg ggaacgcgga gcgggctccg gggtctcgga    540
gctttgggcc cgtacccacg ctgctgctgc tcgccgcggc gctactggcc gtgtcggacg    600
cactcgggcg cccctccgag gaggacgagg agctagtggt gccggagctg gagcgcgccc    660
cgggacacgg gaccacgcgc ctccgcctgc acgcctttga ccagcagctg gatctggagc    720
tgcggcccga cagcagcttt ttggcgcccg gcttcacgct ccagaacgtg gggcgcaaat    780
ccgggtccga gacgccgctt ccggaaaccg acctggcgca ctgcttctac tccggcaccg    840
tgaatggcga tcccagctcg gctgccgccc tcagcctctg cgagggcgtg cgcggcgcct    900
tctacctgct gggggaggcg tatttcatcc agccgctgcc cgccgccagc gagcgcctcg    960
ccaccgccgc cccaggggag aagccgccgg caccactaca gttccacctc ctgcggcgga   1020
atcggcaggg cgacgtcggc ggcacgtgcg gggtcgtgga cgacgagccc cggccgactg   1080
ggaaagcgga gaccgaagac gaggacgaag ggactgaggg cgaggacgaa ggggctcagt   1140
ggtcgccgca ggacccggca ctgcaaggcg taggacagcc cacaggaact ggaagcataa   1200
gaaagaagcg atttgtgtcc agtcaccgct atgtggaaac catgcttgtg gcagaccagt   1260
cgatggcaga attccacggc agtggtctaa agcattacct tctcacgttg ttttcggtgg   1320
cagccagatt gtacaaacac cccagcattc gtaattcagt tagcctggtg gtggtgaaga   1380
tcttggtcat ccacgatgaa cagaaggggc cggaagtgac ctccaatgct gccctcactc   1440
tgcggaactt ttgcaactgg cagaagcagc acaacccacc cagtgaccgg gatgcagagc   1500
actatgacac agcaattctt ttcaccagac aggacttgtg tgggtcccag acatgtgata   1560
ctcttgggat ggctgatgtt ggaactgtgt gtgatccgag cagaagctgc tccgtcatag   1620
```

aagatgatgg tttacaagct gccttcacca cagcccatga attaggccac gtgtttaaca 1680
tgccacatga tgatgcaaag cagtgtgcca gccttaatgg tgtgaaccag gattcccaca 1740
tgatggcgtc aatgctttcc aacctggacc acagccagcc ttggtctcct tgcagtgcct 1800
acatgattac atcatttctg gataatggtc atggggaatg tttgatggac aagcctcaga 1860
atcccataca gctcccaggc gatctccctg gcacctcgta cgatgccaac cggcagtgcc 1920
agtttacatt tggggaggac tccaaacact gccccgatgc agccagcaca tgtagcacct 1980
tgtggtgtac cggcacctct ggtggggtgc tggtgtgtca aaccaaacac ttcccgtggg 2040
cggatggcac cagctgtgga gaagggaaat ggtgtatcaa cggcaagtgt gtgaacaaaa 2100
ccgacagaaa gcattttgat acgccttttc atggaagctg gggaatgtgg gggccttggg 2160
gagactgttc gagaacgtgc ggtggaggag tccagtacac gatgagggaa tgtgacaacc 2220
cagtcccaaa gaatggaggg aagtactgtg aaggcaaacg agtgcgctac agatcctgta 2280
accttgagga ctgtccagac aataatggaa aaacctttag agaggaacaa tgtgaagcac 2340
acaacgagtt ttcaaaagct tcctttggga gtgggcctgc ggtggaatgg attcccaagt 2400
acgctggcgt ctcaccaaag gacaggtgca agctcatctg ccaagccaaa ggcattggct 2460
acttcttcgt tttgcagccc aaggttgtag atggtactcc atgtagccca gattccacct 2520
ctgtctgtgt gcaaggacag tgtgtaaaag ctggttgtga tcgcatcata gactccaaaa 2580
agaagtttga taaatgtggt gtttgcgggg gaaatggatc tacttgtaaa aaaatatcag 2640
gatcagttac tagtgcaaaa cctggatatc atgatatcat cacaattcca actggagcca 2700
ccaacatcga agtgaaacag cggaaccaga ggggatccag gaacaatggc agctttcttg 2760
ccatcaaagc tgctgatggc acatatattc ttaatggtga ctacactttg tccaccttag 2820
agcaagacat tatgtacaaa ggtgttgtct tgaggtacag cggctcctct gcggcattgg 2880
aaagaattcg cagctttagc cctctcaaag agcccttgac catccaggtt cttactgtgg 2940
gcaatgccct tcgacctaaa attaaataca cctacttcgt aaagaagaag aaggaatctt 3000
tcaatgctat ccccactttt tcagcatggg tcattgaaga gtggggcgaa tgttctaagt 3060
catgtgaatt gggttggcag agaagactgg tagaatgccg agacattaat ggacagcctg 3120
cttccgagtg tgcaaaggaa gtgaagccag ccagcaccag accttgtgca gaccatccct 3180
gcccccagtg gcagctgggg gagtggtcat catgttctaa gacctgtggg aagggttaca 3240
aaaaaagaag cttgaagtgt ctgtcccatg atggaggggt gttatctcat gagagctgtg 3300
atcctttaaa gaaacctaaa catttcatag acttttgcac aatggcagaa tgcagttaag 3360
tggtttaagt ggtgttagct ttgagggcaa ggcaaagtga ggaagggctg gtgcagggaa 3420
agcaagaagg ctggagggat ccagcgtatc ttgccagtaa ccagtgaggt gtatcagtaa 3480
ggtgggatta tgggggtaga tagaaaagga gttgaatcat cagagtaaac tgccagttgc 3540
aaatttgata ggatagttag tgaggattat taacctctga gcagtgatat agcataataa 3600
agccccgggc attattatta ttatttcttt tgttacatct attacaagtt tagaaaaaac 3660
aaagcaattg tcaaaaaaag ttagaactat tacaacccct gtttcctggt acttatcaaa 3720
tacttagtat catgggggtt gggaaatgaa aagtaggaga aaagtgagat tttactaaga 3780
cctgttttac tttacctcac taacaatggg gggagaaagg agtacaaata ggatctttga 3840
ccagcactgt ttatggctgc tatggtttca gagaatgttt atacattatt tctaccgaga 3900
attaaaactt cagattgttc aacatgagag aaaggctcag caacgtgaaa taacgcaaat 3960
ggcttcctct ttcctttttt ggaccatctc agtctttatt tgtgtaattc attttgagga 4020
aaaaacaact ccatgtattt attcaagtgc attaaagtct acaatggaaa aaaagcagtg 4080
aagcattaga tgctggtaaa agctagagga gacacaatga gcttagtacc tccaacttcc 4140
tttctttcct accatgtaac cctgctttgg gaatatggat gtaaagaagt aacttgtgtc 4200
tcatgaaaat cagtacaatc acacaaggag gatgaaacgc cggaacaaaa atgaggtgtg 4260
tagaacaggg tcccacaggt ttggggacat tgagatcact tgtcttgtgg tggggaggct 4320
gctgaggggt agcaggtcca tctccagcag ctggtccaac agtcgtatcc tggtgaatgt 4380
ctgttcagct cttctgtgag aatatgattt tttccatatg tatatagtaa aatatgttac 4440
tataaattac atgtacttta taagtattgg tttgggtgtt ccttccaaga aggactatag 4500
ttagtaataa atgcctataa taacatattt atttttatac atttatttct aatgaaaaaa 4560
acttttaaat tatatcgctt ttgtggaagt gcatataaaa tagagtattt atacaatata 4620
tgttactaga aataaaagaa cacttttgga aaaaaaaaaa aaaaaaaaaa 4670

<210> SEQ ID NO 4
<211> LENGTH: 996
<212> TYPE: DNA
<213> ORGANISM: Homo sapiens

<400> SEQUENCE: 4
aatcacttgg ggaaaggaag gttcgtttct gagttagcaa caagtaaatg cagcactagt 60
gggtgggatt gaggtatgcc ctggtgcata aatagagact cagctgtgct ggcacactca 120
gaagcttgga ccgcatccta gccgccgact cacacaaggc aggtgggtga ggaaatccag 180
agttgccatg gagaaaattc cagtgtcagc attcttgctc cttgtggccc tctcctacac 240
tctggccaga gataccacag tcaaacctgg agccaaaaag gacacaaagg actctcgacc 300
caaactgccc cagaccctct ccagaggttg gggtgaccaa ctcatctgga ctcagacata 360
tgaagaagct ctatataaat ccaagacaag caacaaaccc ttgatgatta ttcatcactt 420
ggatgagtgc ccacacagtc aagctttaaa gaaagtgttt gctgaaaata aagaaatcca 480
gaaattggca gagcagtttg tcctcctcaa tctggtttat gaaacaactg acaaacacct 540
ttctcctgat ggccagtatg tccccaggat tatgtttgtt gacccatctc tgacagttag 600
agccgatatc actggaagat attcaaatcg tctctatgct tacgaacctg cagatacagc 660
tctgttgctt gacaacatga agaaagctct caagttgctg aagactgaat tgtaaagaaa 720
aaaaatctcc aagcccttct gtctgtcagg ccttgagact tgaaaccaga agaagtgtga 780
gaagactggc tagtgtggaa gcatagtgaa cacactgatt aggttatggt ttaatgttac 840
aacaactatt ttttaagaaa aacaagtttt agaaatttgg tttcaagtgt acatgtgtga 900
aaacaatatt gtatactacc atagtgagcc atgattttct aaaaaaaaaa ataaatgttt 960
tgggggtgtt ctgttttctc caaaaaaaaa aaaaaa 996

<210> SEQ ID NO 5
<211> LENGTH: 763
<212> TYPE: DNA
<213> ORGANISM: Homo sapiens

<400> SEQUENCE: 5
agaaacatcc agaatacatt tccaacaaga gcactggcca agtcagcttc ttctgagaga 60
gtctctagaa gacatgatgc tacactcagc tttgggtctc tgcctcttac tcgtcacagt 120
ttcttccaac cttgccattg caataaaaaa ggaaaagagg cctcctcaga cactctcaag 180

-continued

```
aggatgggga gatgacatca cttgggtaca aacttatgaa gaaggtctct tttatgctca    240

aaaaagtaag aagccattaa tggttattca tcacctggag gattgtcaat actctcaagc    300

actaaagaaa gtatttgccc aaaatgaaga aatacaagaa atggctcaga ataagttcat    360

catgctaaac cttatgcatg aaaccactga taagaattta tcacctgatg ggcaatatgt    420

gcctagaatc atgtttgtag acccttcttt aacagttaga gctgacatag ctggaagata    480

ctctaacaga ttgtacacat atgagcctcg ggatttaccc ctattgatag aaaacatgaa    540

gaaagcatta agacttattc agtcagagct ataagagatg atagaaaaaa gccttcactt    600

caaagaagtc aaatttcatg aagaaaacct ctggcacatt gacaaatact aaatgtgcaa    660

gtatatagat tttgtaatat tactatttag ttttttaat gtgtttgcaa tagtcttatt    720

aaaataaatg ttttttaaat ctgagactga aaaaaaaaaa aaa                       763


<210> SEQ ID NO 6
<211> LENGTH: 2307
<212> TYPE: DNA
<213> ORGANISM: Homo sapiens

<400> SEQUENCE: 6

cagccatggt aggggtggag gtacaggcag caaacaatat ttaagatgct gacttgtgga     60

gcattcgggc ttggaaggaa agctataggc tacccattca gctcccctgt cagagactca    120

agctttgaga aaggctagca aagagcaagg aaagagagaa aacaacaaag tggcgaggcc    180

ctcagagtga aagcgtaagg ttcagtcagc ctgctgcagc tttgcagacc tcagctgggc    240

atctccagac tcccctgaag gaagagcctt cctcacccaa acccacaaaa gatgctgaaa    300

aagcctctct cagctgtgac ctggctctgc attttcatcg tggcctttgt cagccaccca    360

gcgtggctgc agaagctctc taagcacaag acaccagcac agccacagct caaagcggcc    420

aactgctgtg aggaggtgaa ggagctcaag gcccaagttg ccaaccttag cagcctgctg    480

agtgaactga acaagaagca ggagagggac tgggtcagcg tggtcatgca ggtgatggag    540

ctggagagca acagcaagcg catggagtcg cggctcacag atgctgagag caagtactcc    600

gagatgaaca accaaattga catcatgcag ctgcaggcag cacagacggt cactcagacc    660

tccgcagatg ccatctacga ctgctcttcc ctctaccaga agaactaccg catctctgga    720

gtgtataagc ttcctcctga tgacttcctg ggcagccctg aactggaggt gttctgtgac    780

atggagactt caggcggagg ctggaccatc atccagagac gaaaaagtgg ccttgtctcc    840

ttctaccggg actggaagca gtacaagcag ggctttggca gcatccgtgg ggacttctgg    900

ctggggaacg aacacatcca ccggctctcc agacagccaa cccggctgcg tgtagagatg    960

gaggactggg agggcaacct gcgctacgct gagtatagcc actttgtttt gggcaatgaa   1020

ctcaacagct atcgcctctt cctggggaac tacactggca atgtggggaa cgacgccctc   1080

cagtatcata acaacacagc cttcagcacc aaggacaagg acaatgacaa ctgcttggac   1140

aagtgtgcac agctccgcaa aggtggctac tggtacaact gctgcacaga ctccaacctc   1200

aatggagtgt actaccgcct gggtgagcac aataagcacc tggatggcat cacctggtat   1260

ggctggcatg gatctaccta ctccctcaaa cgggtggaga tgaaaatccg cccagaagac   1320

ttcaagcctt aaaaggaggc tgccgtggag cacggataca gaaactgaga cacgtggaga   1380

ctggatgagg gcagatgagg acaggaagag agtgttagaa agggtaggac tgagaaacag   1440

cctataatct ccaaagaaag aataagtctc caaggagcac aaaaaaatca tatgtaccaa   1500

ggatgttaca gtaaacagga tgaactattt aaacccactg ggtcctgcca catccttctc   1560
```

```
aaggtggtag actgagtggg gtctctctgc ccaagatccc tgacatagca gtagcttgtc   1620

ttttccacat gatttgtctg tgaaagaaaa taattttgag atcgttttat ctattttctc   1680

tacggcttag gctatgtgag ggcaaaacac aaatcccttt gctaaaaaga accatattat   1740

tttgattctc aaaggatagg cctttgagtg ttagagaaag gagtgaagga ggcaggtggg   1800

aaatggtatt tctattttta aatccagtga aattatcttg agtctacaca ttatttttaa   1860

aacacaaaaa ttgttcggct ggaactgacc caggctggac ttgcggggag gaaactccag   1920

ggcactgcat ctggcgatca gactctgagc actgcccctg ctcgccttgg tcatgtacag   1980

cactgaaagg aatgaagcac cagcaggagg tggacagagt ctctcatgga tgccggcaca   2040

aaactgcctt aaaatattca tagttaatac aggtatatct atttttattt actttgtaag   2100

aaacaagctc aaggagcttc cttttaaatt ttgtctgtag gaaatggttg aaaactgaag   2160

gtagatggtg ttatagttaa taataaatgc tgtaaataag catctcactt tgtaaaaata   2220

aaatattgtg gttttgtttt aaacattcaa cgtttctttt ccttctacaa taaacacttt   2280

caaaatgtga aaaaaaaaaa aaaaaaa                                       2307
```

```
<210> SEQ ID NO 7
<211> LENGTH: 2100
<212> TYPE: DNA
<213> ORGANISM: Homo sapiens

<400> SEQUENCE: 7
```

```
gagttgtgta attccccaga gcaggcctgg gcagtgtctg ggtggggcct gggagccaca     60

ggagacgccc aaagccaggc agagcccggg ggcgaggggg cggcaggcag gtgtagcgct    120

gccctgggag ggcttgcacc cccacaccca agtgagcggc ctgctcactc ctcagctgca    180

ggagccagac gtgtggagtc ccagcagagg ccaacctgtg tctcttcatc tccgtgagaa    240

aggtgccccc gaagtgaaag agatggcctg gtggaaagcc tggattgaac aggagggtgt    300

cacagtgaag agcagctccc acttcaaccc agaccctgat gcagagaccc tctacaaagc    360

catgaagggg atcgggacca acgagcaggc tatcatcgat gtgctcacca agagaagcaa    420

cacgcagcgg cagcagatcg ccaagtcctt caaggctcag ttcggcaagg acctcactga    480

gaccttgaag tctgagctca gtggcaagtt tgagaggctc attgtggccc ttatgtatcc    540

gccatacaga tacgaagcca aggagctgca tgacgccatg aagggcttag gaaccaagga    600

gggtgtcatc attgagatcc tggcctctcg gaccaagaac cagctgcggg agataatgaa    660

ggcgtatgag gaagactatg ggtccagcct ggaggaggac atccaagcag acacaagtgg    720

ctacctggag aggatcctgg tgtgcctcct gcagggcagc agggatgatg tgagcagctt    780

tgtggacccg gcactggccc tccaagacgc acaggatctg tatgcggcag gcgagaagat    840

tcgtgggact gatgagatga aattcatcac catcctgtgc acgcgcagtg ccactcacct    900

gctgagagtg tttgaagagt atgagaaaat tgccaacaag agcattgagg acagcatcaa    960

gagtgagacc catggctcac tggaggaggc catgctcact gtggtgaaat gcacccaaaa   1020

cctccacagc tactttgcag agagactcta ctatgccatg aagggagcag ggacgcgtga   1080

tgggaccctg ataagaaaca tcgtttcaag gagcgagatt gacttaaatc ttatcaaatg   1140

tcacttcaag aagatgtacg gcaagaccct cagcagcatg atcatggaag acaccagcgg   1200

cgactacaag aacgccctgc tgagcctggt gggcagcgac ccctgaggca cagaagaaca   1260

agagcaaaga ccatgaagcc agagtctcca ggactcctca ctcaacctcg gccatggacg   1320
```

```
caggttgggt gtgagggggg tcccagcctt tcggtcttct atttccctat ttccagtgct   1380

ttccagccgg gtttctgacc cagagggtgg aaccggcctg gactcctctt cccaacttcc   1440

tccaggtcat ttcccagtgt gagcacaatg ccaaccttag tgtttctcca gccagacaga   1500

tgcctcagca tgaagggctt ggggacttgt ggatcattcc ttcctccctg caggagcttc   1560

ccaagctggt cacagagtct cctgggcaca ggttatacag accccagccc cattcccatc   1620

tactgaaaca gggtctccac aagaggggcc agggaatatg ggtttttaac aagcgtctta   1680

caaaacactt ctctatcatg cagccggaga gctggctggg agccctttttg ttttagaaca   1740

cacatccttc agcagctgag aaatgaacac gaatccatcc caaccgagat gccattaaca   1800

ttcatctaaa aatgttaggc tctaaatgga cgaaaaattc tctcgccatc ttaataacaa   1860

aataaactac aaattcctga cccaaggaca ctgtgttata agaggcgtgg gctcccctgg   1920

tggctgacca ggtcagctgc cctggccttg cacccctctg catgcagcac agaagggtgt   1980

gaccatgccc tcagcaccac tcttgtcccc actgaacggc aactgagact gggtacctgg   2040

agattctgaa gtgcctttgc tgtggttttc aaaataataa agatttgtat tcaactcaaa   2100


<210> SEQ ID NO 8
<211> LENGTH: 1447
<212> TYPE: DNA
<213> ORGANISM: Homo sapiens

<400> SEQUENCE: 8

atccagattt gcttttacat tttcttgcct gagtctgagg tgaacagtga acatatttac     60

atttgattta acagtgaacc ttaattcttt ctggcttcac agtgaaacaa gtttatgcaa    120

tcgatcaaat attttcatcc ctgaggttaa caattaccat caaaatgttt tgtggagact    180

atgtgcaagg aaccatcttc ccagctccca atttcaatcc cataatggat gcccaaatgc    240

taggaggagc actccaagga tttgactgtg acaaagacat gctgatcaac attctgactc    300

agcgctgcaa tgcacaaagg atgatgattg cagaggcata ccagagcatg tatggccggg    360

acctgattgg ggatatgagg gagcagcttt cggatcactt caaagatgtg atggctggcc    420

tcatgtaccc accaccactg tatgatgctc atgagctctg gcatgccatg aagggagtag    480

gcactgatga gaattgcctc attgaaatac tagcttcaag aacaaatgga gaaattttcc    540

agatgcgaga agcctactgc ttgcaataca gcaataacct ccaagaggac atttattcag    600

agacctcagg acacttcaga gatactctca tgaacttggt ccaggggacc agagaggaag    660

gatatacaga ccctgcgatg gctgctcagg atgcaatggt cctatgggaa gcctgtcagc    720

agaagacggg ggagcacaaa accatgctgc aaatgatcct gtgcaacaag agctaccagc    780

agctgcggct ggttttccag gaatttcaaa atatttctgg gcaagatatg gtagatgcca    840

ttaatgaatg ttatgatgga tactttcagg agctgctggt tgcaattgtt ctctgtgttc    900

gagacaaacc agcctatttt gcttatagat tatatagtgc aattcatgac tttggtttcc    960

ataataaaac tgtaatcagg attctcattg ccagaagtga aatagacctg ctgaccataa   1020

ggaaacgata caaagagcga tatggaaaat ccctatttca tgatatcaga aattttgctt   1080

cagggcatta taagaaagca ctgcttgcca tctgtgctgg tgatgctgag gactactaaa   1140

atgaagagga cttggagtac tgtgcactcc tctttctaga cacttccaaa tagagatttt   1200

ctcacaaatt tgtactgttc atggcactat taacaaaact atacaatcat attttctctt   1260

ctatctttga aattattcta agccaaagaa aactatgaat gaaagtatat gatactgaat   1320

ttgcctacta tcctgaattt gcctactatc taatcagcaa ttaaataaat tgtgcatgat   1380
```

ggaataatag aaaaattgca ttggaataga ttttatttaa atgtgaacca tcaacaacct 1440
acaacaa 1447

<210> SEQ ID NO 9
<211> LENGTH: 1290
<212> TYPE: DNA
<213> ORGANISM: Homo sapiens

<400> SEQUENCE: 9
ggctgagcct ataaagcggc aggtgcgcgc cgccctacag acgttcgcac acctgggtgc 60
cagcgcccca gaggtcccgg gacagcccga ggcgccgcgc ccgccgcccc gagctcccca 120
agccttcgag agcggcgcac actcccggtc tccactcgct cttccaacac ccgctcgttt 180
tggcggcagc tcgtgtccca gagaccgagt tgccccagag accgagacgc cgccgctgcg 240
aaggaccaat gagagccccg ctgctaccgc cggcgccggt ggtgctgtcg ctcttgatac 300
tcggctcagg ccattatgct gctggattgg acctcaatga cacctactct gggaagcgtg 360
aaccattttc tggggaccac agtgctgatg gatttgaggt tacctcaaga agtgagatgt 420
cttcagggag tgagatttcc cctgtgagtg aaatgccttc tagtagtgaa ccgtcctcgg 480
gagccgacta tgactactca gaagagtatg ataacgaacc acaaatacct ggctatattg 540
tcgatgattc agtcagagtt gaacaggtag ttaagccccc ccaaaacaag acggaaagtg 600
aaaatacttc agataaaccc aaaagaaaga aaaagggagg caaaaatgga aaaaatagaa 660
gaaacagaaa gaagaaaaat ccatgtaatg cagaatttca aaatttctgc attcacggag 720
aatgcaaata tatagagcac ctggaagcag taacatgcaa atgtcagcaa gaatatttcg 780
gtgaacggtg tggggaaaag tccatgaaaa ctcacagcat gattgacagt agtttatcaa 840
aaattgcatt agcagccata gctgccttta tgtctgctgt gatcctcaca gctgttgctg 900
ttattacagt ccagcttaga agacaatacg tcaggaaata tgaaggagaa gctgaggaac 960
gaaagaaact tcgacaagag aatggaaatg tacatgctat agcataactg aagataaaat 1020
tacaggatat cacattggag tcactgccaa gtcatagcca taaatgatga gtcggtcctc 1080
tttccagtgg atcataagac aatggaccct tttgttatg atggttttaa actttcaatt 1140
gtcacttttt atgctatttc tgtatataaa ggtgcacgaa ggtaaaaagt atttttttcaa 1200 gttgtaaata atttatttaa tatttaatgg aagtgtattt attttacagc tcattaaact 1260
tttttaacca aacagaaaaa aaaaaaaaaa 1290

<210> SEQ ID NO 10
<211> LENGTH: 1530
<212> TYPE: DNA
<213> ORGANISM: Homo sapiens

<400> SEQUENCE: 10
actccaggag ctgcagcaga gcaggtaaca gctcttgcac ctgtttctct tgcacctgac 60
gtgcagctgc tcctacccac ctctcctggc tgagccttgc ctgatacagc agcccggagg 120
caccacttgc ttcccgagtc tcaccctccc aggcagctcc tacactcaac tgcttctcta 180
ggaaaggtct cacctccagc ctggagcagt cgggattaca gaaagcccca tccttggctt 240
agggagcgcc atgacgactg aaattggttg gtggaagctg actttcctcc ggaaaaagaa 300
atccactccc aaagtgctgt atgagatccc tgacacctat gcccaaacag agggagatgc 360
agaacccccg aggcctgacg ctggaggccc caacagcgac tttaacaccc gcctggagaa 420

-continued

```
gattgtggac aagagcacaa agggcaagca cgtcaaggtc tccaactcag gacgcttcaa    480
ggagaagaag aaagtgagag ccacgctggc agagaaccct aacctctttg atgatcacga    540
ggaaggacgg tcatcaaagt gaagggctga ggagggtgct agcacctctt ggctccctgc    600
catcagccag atctgagaca ggaccttgcc acgctggcct ctttggccat agctgaagct    660
gtggggccag ttgatacctg ctggcaggaa atggctgttt tttaggtttg tatttatgtg    720
ccgccacttt tgtaaggcct gggagatccc agggtcctcc accctccccc tgaccacata    780
caaaggcact ctagttcaag agtgaaaagt ctcacccagg aggaacagcc ctccttgaag    840
caatggcagg gccagcaggg aggtgggcat ggcagggaat ggagagagtg agccagacag    900
acttcacctc cttactggac acagggtcaa gggcgagttt caattgctgc tccctttact    960
ttctctacct gtgactactc cctggaccaa tcctgaggag ggcacatttt ccagaagcca   1020
cgtgataggg gctggtttct gtggagccag aggcagagac actgaacttg agctcacctc   1080
ctaacaccgg cagtaaactt cctggaactt tgccctcagg tgcggagggg acagaggacc   1140
ctggcactct gttagggtgc tgtagaagac tagattgatg gtagtttggc ctgttagttc   1200
ctgttttggc catgactttt gcagatggca agtcacacac cctcaaaggg aagctacacg   1260
ggccaaatcg gggggagtggg tggggaattt tctcctctcc ctttcctact ataatagtat   1320
ttaagacata tcagctccag agatgagtcc tggagccttg aattttgttt aacaaaataa   1380
ttgtaggttt ctctctgtaa taacaacgct ggaaaggcag agaacctctt ttatgctcat   1440
gtcttgcatt tattgagatg actgtttctc atgcctttat gttccttcat gtaagtaaag   1500
tggacctttg tgctcaaaaa aaaaaaaaaa                                    1530
```

<210> SEQ ID NO 11
<211> LENGTH: 7582
<212> TYPE: DNA
<213> ORGANISM: Homo sapiens

<400> SEQUENCE: 11

```
tctttcactc ttgggcctag cgaggcagct tatttttcct ttttctttca ttggtcacag     60
ttatttcttt tcagtgtgtc atcttctcta agtttctgag ggagtgttag cttgaggcct    120
tgccttgaca taatcagata taatcagaaa aatgaaaaat tccataggaa agagaactat    180
tttagccaag gtgtgcgaga gaaataccgc cactttcaag cactgttttc ttctactgga    240
gtctgctcaa tagggacgtc agctttgctg gggcttcctt tgacaagaga atcagaaccg    300
actggtgaca tttgtttcaa tgaaagcaac agtgtgaaga gtaagtagtt tttcctatta    360
ttcatctcac tcagtggaga taatgaactc ctctccactg ccaagatgag aaactaccat    420
ttcttacaca tggacacaaa gatgagaaca ataaacactg agacttcaaa aaggagggaa    480
ggagaaagag gaacaagact tgaaatctac ctatcagaac ttgcaattta ttctgatcaa    540
caatttgccc agctaaagta ctacatctgc cccctcttcc tgtggctgta ggggcacagc    600
aaaggtcact ggtctaacct ccttaaaggg actccgctaa cagaaaccac caaatggagt    660
ggagaaaaag aaaagggatc ccctatcccc aactccagcc atctagatta agaaaagcca    720
gctgactgga cagtagcaca gcccagtcac ctcatggaca aatttcctag gaaagaacct    780
ctcccatcta ttctacttat cactctcctt tgaggttccg gccacagatc ttcgcctgct    840
gctggaaatg gccctctcag tggactcatc gtggcatcgg tggcagtgga gagtcagaga    900
tggcttcccc cattgtccat cggaaaccac accgctgctc tctccagaga aagggagaca    960
gagctacaac ttgacacagc agcgggtcgt gttccccaac aacagcatat tccatcaaga   1020
```

-continued

```
ttgggaagag gtctccagga gataccctgg caacagaacc tgcacaacca aatacaccct   1080
cttcaccttc ctgccccgga atctctttga gcaatttcat agatgggcta acctctattt   1140
cctgttcctg gtgattttga actggatgcc ctccatggaa gtcttccaca gagaaatcac   1200
catgttacca ttggccattg tcctgttcgt catcatgatc aaggatggca tggaggactt   1260
caagagacac cgctttgata aagcaataaa ctgctccaac attcgaattt atgaaagaaa   1320
agagcagacc tatgtgcaga agtgctggaa ggatgtgcgc gtgggagact tcatccaaat   1380
gaaatgcaat gagattgtcc cagcagacat actcctcctt ttttcctctg accccaatgg   1440
gatatgccat ctggaaactg ccagcttgga tggagagaca aacctcaagc aaagatgtgt   1500
cgtgaagggc ttctcacagc aggaggtaca gttcgaacca gagcttttcc acaataccat   1560
cgtgtgtgag aaacccaaca accacctcaa caaatttaag ggttatatgg agcatcctga   1620
ccagaccagg actggctttg gctgtgagag tcttctgctt cgaggctgca ccatcagaaa   1680
caccgagatg gctgttggca ttgtcatcta tgcaggccat gagacgaaag ccatgctgaa   1740
caacagtggc ccccggtaca aacgcagcaa gattgagcgg cgcatgaata tagacatctt   1800
cttctgcatt gggatcctca tcctcatgtg ccttattgga gctgtaggtc acagcatctg   1860
gaatgggacc tttgaagaac accctccctt cgatgtgcca gatgccaatg gcagcttcct   1920
tcccagtgcc cttgggggct tctacatgtt cctcacaatg atcatcctgc tccaggtgct   1980
gatccccatc tctttgtatg tctccattga gctggtgaag ctcgggcaag tgttcttctt   2040
gagcaatgac cttgacctgt atgatgaaga gaccgattta tccattcaat gtcgagccct   2100
caacatcgca gaggacttgg gccagatcca gtacatcttc tccgataaga cggggaccct   2160
gacagagaac aagatggtgt tccgacgttg caccatcatg ggcagcgagt attctcacca   2220
agaaaatgct aagcgactgg agaccccaaa ggagctggac tcagatggtg aagagtggac   2280
ccaataccaa tgcctgtcct tctcggctag atgggcccag gatccagcaa ctatgagaag   2340
ccaaaaaggt gctcagcctc tgaggaggag ccagagtgcc cgggtgccca tccagggcca   2400
ctaccggcaa aggtctatgg ggcaccgtga aagctcacag cctcctgtgg ccttcagcag   2460
ctccatagaa aaagatgtaa ctccagataa aaacctactg accaaggttc gagatgctgc   2520
cctgtggttg gagaccttgt cagacagcag acctgccaag gcttccctct ccaccacctc   2580
ctccattgct gatttcttcc ttgccttaac catctgcaac tctgtcatgg tgtccacaac   2640
caccgagccc aggcagaggg tcaccatcaa accctcaagc aaggctctgg ggacgtccct   2700
ggagaagatt cagcagctct tccagaagtt gaagctattg agcctcagcc agtcattctc   2760
atccactgca ccctctgaca cagacctcgg ggagagctta ggggccaacg tggccaccac   2820
agactcggat gagagagatg atgcatctgt gtgcagtgga ggtgactcca ctgatgacgg   2880
tggctacagg agcagcatgt gggaccaggg cgacatcctg gagtctgggt caggcacttc   2940
cttggaggag gcattggagg ccccagccac agacctggcc aggcctgagt tctgttacga   3000
ggctgagagc cctgatgagg ccgccctggt gcacgctgcc catgcctaca gcttcacact   3060
agtgtcccgg acacctgagc aggtgactgt gcgcctgccc cagggcacct gcctcacctt   3120
cagcctcctc tgcaccctgg gctttgactc tgtcaggaag agaatgtctg tggttgtgag   3180
gcacccactg actggcgaga ttgttgtcta caccaagggt gctgactcgg tcatcatgga   3240
cctgctggaa gacccagcct gcgtacctga cattaatatg gaaaagaagc tgagaaaaat   3300
ccgagcccgg acccaaaagc atctagactt gtatgcaaga gatggcctgc gcacactatg   3360
```

-continued

```
cattgccaag aaggttgtaa gcgaagagga cttccggaga tgggccagtt tccggcgtga   3420
ggctgaggca tccctcgaca accgagatga gcttctcatg gaaactgcac agcatctgga   3480
gaatcaactc accttacttg gagccactgg gatcgaagac cggctgcagg aaggagttcc   3540
agatacgatt gccactctgc gggaggctgg gatccagctc tgggtcctga ctggagataa   3600
gcaggagaca gcggtcaaca ttgcccattc ctgcagactg ttaaatcaga ccgacactgt   3660
ttataccatc aatacagaga atcaggagac ctgtgaatcc atcctcaatt gtgcattgga   3720
agagctaaag caatttcgtg aactacagaa gccagaccgc aagctctttg gattccgctt   3780
accttccaag acaccatcca tcacctcaga agctgtggtt ccagaagctg gattggtcat   3840
cgatgggaag acattgaatg ccatcttcca gggaaagcta gagaagaagt ttctggaatt   3900
gacccagtat tgtcggtccg tcctgtgctg ccgctccacg ccactccaga agagtatgat   3960
agtcaagctg gtgcgagaca agttgcgcgt catgaccctt tccataggtg atggagcaaa   4020
tgatgtaagc atgattcaag ctgctgatat tggaattgga atatctggac aggaaggcat   4080
gcaggctgtc atgtccagcg actttgccat cacccgcttt aagcatctca agaagttgct   4140
gctcgtgcat ggccactggt gttactcgcg cctggccagg atggtggtgt actacctcta   4200
caagaacgtg tgctacgtca acctgctctt ctggtatcag ttcttctgtg gtttctccag   4260
ctccaccatg attgattact ggcagatgat attcttcaat ctcttcttta cctccttgcc   4320
tcctcttgtc tttggagtcc ttgacaaaga catctctgca gaaacactcc tggcattgcc   4380
tgagctatac aagagtggcc agaactctga gtgctataac ctgtcgactt tctggatttc   4440
tatggtggat gcattctacc agagcctcat ctgtttcttt atcccttacc tggcctataa   4500
gggctctgat atagatgtct ttacctttgg gacaccaatc aacaccatct ccctcaccac   4560
aatccttttg caccaggcaa tggaaatgaa gacatggacc attttccacg gagtcgtgct   4620
cctcggcagc ttcctgatgt actttctggt atccctcctg tacaatgcca cctgcgtcat   4680
ctgcaacagc ccaccaatc cctattgggt gatggaaggc cagctctcaa accccacttt    4740
ctacctcgtc tgctttctca caccagttgt tgctcttctc ccaagatact tttcctgtc    4800
tctgcaagga acttgtggga agtctctaat ctcaaaagct cagaaaattg acaaactccc   4860
cccagacaaa agaaacctgg aaatccagag ttggagaagc agacagaggc ctgcccctgt   4920
ccccgaagtg gctcgaccaa ctcaccaccc agtgtcatct atcacaggac aggacttcag   4980
tgccagcacc ccaaagagct ctaaccctcc caagaggaag catgtggaag agtcagtact   5040
ccacgaacag agatgtggca cggagtgcat gagggatgac tcatgctcag gggactcctc   5100
agctcaactc tcatccgggg agcacctgct gggacctaac aggataatgg cctactcaag   5160
aggacagact gatatgtgcc ggtgctcaaa gaggagcagc catcgccgat cccagagttc   5220
actgaccata tgaggagctg cagaaatctg tacaaactca acagaggcca cctagtcact   5280
ggtccacata acccttgacc ccttcttctt catagaggaa acaatgtgcc agtcttattc   5340
ttttcttcaa caaccttgac ttccatggag gaagtgctgg ccccaagggg tctgacacaa   5400
agacgggaaa cccagtcggc ctctagtttt ctgctgctct caggcagcac atcttgcaaa   5460
cagtttggag aaggaggctg tttttgttga atcgagttct caaatcggtt tagaccaaag   5520
ccattcttct gaccctctag ataagcgtag cctacaaccc agtgccgtaa gtttccaaga   5580
ttcaagaagt gtatcaaccc aggcaatatc tcaggatatg gaagtttctg ggtttattta   5640
cccctcagtg cccagagtta aagtttcaga agagacttgt gcacataagg gcttcatctc   5700
aagtgtattg cagtaatggc tgaatcgggg ttaacatccc ttccaggcac agcgagttgg   5760
```

```
ttctgctttt tgcctgtaag ccaaagaaaa gccacatcta aaaagctact actaaaagcc   5820

agaaagaaaa gtggatttga actcagtgtc acagactctt ctgagtgttt tagggtcaca   5880

gctagtgtaa gaggcatgaa gaatagacat gcaaaaggga acgggtgcac cagagacccc   5940

tgttttggct gacagaccat atgtcccacc agctggggaa tctgacaaga ggacataggt   6000

ggcactcttt ttttaaagct atttattgta tctattttta aataaaattg cccatcctca   6060

ttcagctctt agaacaaaag caaaaaaccc tgtaaatcag gagatataag cacatctgca   6120

cccagaatag gcccatatga tagggcaacc ctgagcttaa acaatgacat cttcaagggt   6180

agaactaatc tgaaacccca ttcagcctat tccagaatgg ggataggctg aaaccccctt   6240

ccagcctctg gaagacactg gcctgcatca gttagagtca gagcaagtgt cacttcacag   6300

ggaaaagaag gattatatag acttcctatc cctagagttt ataaatgtca actatataaa   6360

aaaagctcaa aacagtgtta aaggaatgaa cagtagaatt ttaataggct gtccaaagaa   6420

gccaggtctg ctgtgggcaa gtatagccta accctagtct tgtaaaataa gccagaaagg   6480

gttactgagc caccttaagc tagtacctat atagtaggca aaaagtacag aaatagatgc   6540

aataagtgtg gtgagtcttt gagcctacga gtcatgccac cagccataag ttgacctatc   6600

acttgagaac ctcctcagca aagatgccag aaaacattca atcaagttgg caaatgacac   6660

agggagctgg ccctctgacc atcttcctgg caaacctgga ctggaagggc catttgcagc   6720

actgtcctgg agctaataca ctgtttcact gcctctgcca tataatgatg ccagcactag   6780

ccagctggtg ggtatttgga ggaatcctgc atgaggattg cccaataagg ggcaggtaca   6840

catacctggc aaagtgatga tgatgtgaat tgtttccagt gaggggattg agtcaaaact   6900

tggatctcag gtacctcaat tttccccca atttctggct actactaaaa gccagaaaga   6960

acagaacagt ggcctcagga gatctgagtt tgaatccttg ctctctagga tgcaggtggc   7020

ttgaagcaga atgccacacc tgcaagttga ttagaactgc ctttcttccc aggcttgaca   7080

taggtattaa gtcaaaatta catgaaaccc agtggtaaaa aagcctctga aagctgtaac   7140

accctcagta ataacaaaag ggatttttat ttcacagcta aagggaaaat aggtggagaa   7200

gttaaaaaat aatgtctgat cctgttccta agttccaaac tatagccaac actctgatgc   7260

tgctcttttt cttgtaggac caaccgtccc agtttgcctg ggactttctc atttttacag   7320

agtcccaaat cctaggaaac tggagcaact ggtacaactg gtcacctact cttgcccctc   7380

tgtaaatcaa gccaactgtg accatccaat gtgccatctt acagggaaaa gttataacca   7440

ctattcccct ataacataat gctaatgatt gtacttagta catttttata cttttatgat   7500

attttactga ttggaaatgt catcctttat taaaaataaa catggttttc catagttgcc   7560

tgccaaaaaa aaaaaaaaaa aa                                            7582
```

<210> SEQ ID NO 12
<211> LENGTH: 4131
<212> TYPE: DNA
<213> ORGANISM: Homo sapiens

<400> SEQUENCE: 12

```
atcccgcccg catacagccc gcatcccgcc ggggaagcga gcccagtcca gcgctgcccg     60

tccagtcctc gcccaagatt taaagcccgc aagttttgtt cttgagacca gcgactttag    120

ctccgatgcg ggaaggaaag ccgacctccg atttggacat ttaaagagct gggcttgaac    180

ttcgtgagtt tcgctctaaa ctgcccttga aatgaagctg gacttggagg tggcatggaa    240
```

-continued

```
tattcacatg ggagagccgc atgaggccgc ccaccacgct tcctgaagga tgcccgtgtg    300
gaagaatttt gacgtgccag tgtcctcgtt ctacagggtg ttccattctt ccgcaatctc    360
agaaaaatgg gactaaaaga aactattttg taaaataaga agacttccat ttttaatgac    420
caacatgtat taagatggac acctactcta cgaaacacga agttctatgg tctcgaagaa    480
gcccgtgcct gtttaaaact gatcctaact aaaaacagac ttgagtggat atgagaatgt    540
tggttagtgg cagaagagtc aaaaaatggc agttaattat tcagttattt gctacttgtt    600
ttttagcgag cctcatgttt ttttgggaac caatcgataa tcacattgtg agccatatga    660
agtcatattc ttacagatac ctcataaata gctatgactt tgtgaatgat accctgtctc    720
ttaagcacac ctcagcgggg cctcgctacc aatacttgat taaccacaag gaaaagtgtc    780
aagctcaaga cgtcctcctt ttactgtttg taaaaactgc tcctgaaaac tatgatcgac    840
gttccggaat tagaaggacg tggggcaatg aaaattatgt tcggtctcag ctgaatgcca    900
acatcaaaac tctgtttgcc ttaggaactc ctaatccact ggagggagaa gaactacaaa    960
gaaaactggc ttgggaagat caaaggtaca atgatataat tcagcaagac tttgttgatt   1020
ctttctacaa tcttactctg aaattactta tgcagttcag ttgggcaaat acctattgtc   1080
cacatgccaa atttcttatg actgctgatg atgacatatt tattcacatg ccaaatctga   1140
ttgagtacct tcaaagttta gaacaaattg gtgttcaaga cttttggatt ggtcgtgttc   1200
atcgtggtgc ccctcccatt agagataaaa gcagcaaata ctacgtgtcc tatgaaatgt   1260
accagtggcc agcttaccct gactacacag ccggagctgc ctatgtaatc tccggtgatg   1320
tagctgccaa agtctatgag gcatcacaga cactaaattc aagtctttac atagacgatg   1380
tgttcatggg cctctgtgcc aataaaatag ggatagtacc gcaggaccat gtgttttttt   1440
ctggagaggg taaaactcct tatcatccct gcatctatga aaaaatgatg acatctcatg   1500
gacacttaga agatctccag gacctttgga agaatgctac agatcctaaa gtaaaaacca   1560
tttccaaagg ttttttttggt caaatatact gcagattaat gaagataatt ctcctttgta   1620
aaattagcta tgtggacaca taccccttgta gggctgcgtt tatctaatag tacttgaatg   1680
ttgtatgttt tcactgtcac tgagtcaaac ctggatgaaa aaaaccttta aatgttcgtc   1740
tataccctaa gtaaaatgag gacgaaagac aaatattttg aaagcctagt ccatcagaat   1800
gtttctttga ttctagaagc tgtttaatat cacttatcta cttcattgcc taagttcatt   1860
tcaaagaatt tgtatttaga aaaggtttat attattagtg aaaacaaaac taaagggaag   1920
ttcaagttct catgtaatgc cacatatata cttgaggtgt agagatgtta ttaagaagtt   1980
ttgatgttag aataattgct tttggaaaat accaaatgaa cgtacagtac aacatttcaa   2040
ggaaatgaat atattgttag accaggtaag caagtttatt tttgttaaag agcacttggt   2100
ggaggtagta ggggcaggga aaggtcagca taggagagaa agttcatgaa tctggtaaaa   2160
cagtctcttg ttcttaagag gagatgtaga aaaatgtgta caatgttatt ataaacagac   2220
aaatcacgtc ttaccacatc catgtagcta ctggtgttag agtcattaaa atacctttttt   2280
ttgcatcttt tttcaaagtt taatgtgaac ttttagaaaa gtgattaatg ttgccctaat   2340
actttatatg tttttaatgg attttttttt aagtattaga aaatgacaca taacacgggc   2400
agctggttgc tcatagggtc cttctctagg gagaaaccat tgttaattca aataagctga   2460
ttttaatgac gttttcaact ggtttttaaa tattcaatat tggtctgtgt ttaagtttgt   2520
tatttgaatg taatttacat agaggaatat aataatggag agacttcaaa tggaaagaca   2580
gaacattaca agcctaatgt ctccataatt ttataaaatg aaatcttagt gtctaaatcc   2640
```

```
ttgtactgat tactaaaatt aacccactcc tccccaacaa ggtcttataa accacagcac   2700
tttgttccaa gttcagagtt ttaaattgag agcattaaac atcaaagtta taatatctaa   2760
aacaatttat ttttcatcaa taactgtcag aggtgatctt tattttctaa atatttcaaa   2820
cttgaaaaca gagtaaaaaa gtgatagaaa agttgccagt ttggggttaa agcattttta   2880
aagctgcatg ttccttgtaa tcaaagagat gtgtctgaga tctaatagag taagttacat   2940
ttattttaca aagcaggata aaaatgtggc tataatacac actacctccc ttcactacag   3000
aaagaactag gtggtgtcta ctgctaggga gattatatga aggccaaaat aatgacttca   3060
gcaagagtga ctgaactcac tctaaggcct ttgactgcag aggcacctgt tagggaaaat   3120
cagatgtctc atataataag gtgatgtcgg aaacacgcaa aacaaaacga aaaaagattt   3180
ctcagtatac acaactgaat gatgatactt acaattttta gcaggtagct ttttaatgtt   3240
tacagaaatt ttaatttttt tctattttga aatttgaggc ttgtttacat tgcttagata   3300
atttagaatt tttaactaat gtcaaaacta cagtgtcaaa cattctaggt tgtagttact   3360
ttcagagtag atacagggtt ttagatcatt acagtttaag ttttctgacc aattaaaaaa   3420
acatagagaa caaaagcata tttgaccaag caacaagctt ataattaatt tttattagtt   3480
gattgattaa tgatgtattg ccttttgccc atatataccc tgtgtatcta tacttggaag   3540
tgtttaaggt tgccattggt tgaaaacata agtgtctctg gccatcaaag tgatcttgtt   3600
tacagcagtg cttttgtgaa acaattattt atttgctgaa agagctcttc tgaactgtgt   3660
ccttttaatt tttgcttaga atagaatgga acaagtttaa atttcaagga aatatgaagg   3720
cacttccttt ttttctaaga aggaagttgc tagatgattc cttcatcaca cttacttaaa   3780
gtactgagaa gagtatctgt aaataaaagg gttccaacct tttaaaaaag aaggaaaaaa   3840
ctttttggtg ctccagtgta gggctatctt tttaaaaaat gtcaacaaag ggaaaataaa   3900
ctatcagctt ggatggtcac ttgaatagaa gatggttata cacagtgtta ttgttaaaat   3960
tttttacct tttggttggt ttgcatcttt tttccatatt gttaatttta taccaaaatg   4020
ttaaatattt gtattacttg aattttgctc ttgtatggca aaataattag tgagtttaaa   4080
aaaaatctat agtttccaat aaacaactga aaaattatca tgaaaaaaaa a            4131
```

<210> SEQ ID NO 13
<211> LENGTH: 3475
<212> TYPE: DNA
<213> ORGANISM: Homo sapiens

<400> SEQUENCE: 13

```
actgggtaga atacttgggg tgccagggag gcattaatgc gagaggagtc aggtgctcag     60
tttttattgg agttgggagg gcagccccac atcaggaaga gaacctgttt ctgcaggatg    120
gtccggggag aagggaggac tccacccagg cttgtgtttg ccctgctctg tgtattcagc    180
cagcaggctc tgcacaagga agcaaagtgc agggagccag gctccaccga cagccaggca    240
ctgggcagca cgcactggag acccaggacc ctgtgcagga gcagctccgg gtgacacgag    300
gggactgaag atactcccac aggggctcag caggagcaat gggtaaccaa atgagtgttc    360
cccaaagagt tgaagaccaa gagaatgaac cagaagcaga gacttaccag gacaacgcgt    420
ctgctctgaa cggggttcca gtggtggtgt cgacccacac agttcagcac ttagaggaag    480
tcgacttggg aataagtgtc aagacggata atgtggccac ttcttccccc gagacaacgg    540
agataagtgc tgttgcggat gccaacggaa agaatcttgg gaaagaggcc aaacccgagg    600
```

```
caccagctgc taaatctcgt tttttcttga tgctctctcg gcctgtacca ggacgtaccg    660
gagaccaagc cgcagattca tcccttggat cagtgaagct tgatgtcagc tccaataaag    720
ctccagcgaa caaagaccca agtgagagct ggacacttcc ggtggcagct ggaccggggc    780
aggacacaga taaaacccca gggcacgccc cggcccaaga caaggtcctc tctgccgcca    840
gggatcccac gcttctccca cctgagacag ggggagcagg aggagaagct ccctccaagc    900
ccaaggactc cagctttttt gacaaattct tcaagctgga caagggacag gaaaaggtgc    960
caggtgacag ccaacaggaa gccaagaggg cagagcatca agacaaggtg gatgaggttc   1020
ctggcttatc agggcagtcc gatgatgtcc ctgcagggaa ggacatagtt gacggcaagg   1080
aaaaagaagg acaagaactt ggaactgcgg attgctctgt ccctggggac ccagaaggac   1140
tggagactgc aaaggacgat tcccaggcag cagctatagc agagaataat aattccatca   1200
tgagtttctt taaaactctg gtttcaccta acaaagctga aacaaaaaag gacccagaag   1260
acacgggtgc tgaaaagtca cccaccactt cagctgacct taagtcagac aaagccaact   1320
ttacatccca ggagacccaa ggggctggca agaattccaa aggatgcaac ccatcggggc   1380
acacacagtc cgtgacaacc cctgaacctg cgaaggaagg caccaaggag aaatcaggac   1440
ccacctctct gcctctgggc aaactgtttt ggaaaaagtc agttaaagag gactcagtcc   1500
ccacaggtgc ggaggagaat gtggtgtgtg agtcaccagt agagattata aagtccaagg   1560
aagtagaatc agccttacaa acagtggacc tcaacgaagg agatgctgca cctgaaccca   1620
cagaagcgaa actcaaaaga gaagaaagca aaccaagaac ctctctgatg gcgtttctca   1680
gacaaatgtc agtgaaaggg gatggaggga tcacccactc agaagaaata aatgggaaag   1740
actccagctg ccaaacatca gactccacag aaaagactat cacaccgcca gagcctgaac   1800
caacaggagc accacagaag ggtaaagagg gctcctcgaa ggacaagaag tcagcagccg   1860
agatgaacaa gcagaagagc aacaagcagg aagccaaaga accagcccag tgcacagagc   1920
aggccacggt ggacacgaac tcactgcaga atggggacaa gctccaaaag agacctgaga   1980
agcggcagca gtcccttggg ggcttcttta aaggcctggg accaaagcgg atgttggatg   2040
ctcaagtgca aacagaccca gtatccatcg gaccagttgg caaatccaag taaacaaatc   2100
agcacggttc ccaccaggtt ctcctgccac caagatgtgt tctccttact ccatctcctc   2160
cccaaacacg ctccatgtat atattcttct gatggccagc aaatgaaatt ctgcctagaa   2220
attaagcccg agctgttgta tattgaggtg tattatttac gtctctggtc cagtcttttc   2280
tggcaaataa cagtaaagat ggtttagcag gtcacctagt tgggtcagaa gagtcgatga   2340
tcaccaagca ggaaagggag ggaatagagg aatgtgttcg ggttaagtga tgaaaatggc   2400
agtggtggcc gggcgtggtg gctctcgcct gtaatctcag cactttggga ggccgaggca   2460
ggtggatcac ctgaggtcag gagttcaaga ctagcctggc caacatcatg aaaccccgtc   2520
tctactaaaa atacaaaaat tagccaggca tggtggcaca cacctgtagt cccagctact   2580
cgggagccca acgcacgaga accgcttgta cccaggaggt ggaggttgca gtgagccgaa   2640
gttgcaccat tgcactccac cctgggcgac agagcaagat tctatcaaaa aaaaaaaaag   2700
gcagtggcaa gtaagttata gaagagaaat gctgctagaa ggaattaagc gttgtagtaa   2760
atgcgtgctt atcctctaag cttgaagaag ggagacgaaa atccatttgt ttaaattcac   2820
atctcaagga gggagaaccc gggctgtgtt gggtggttgc caatttccta gaacggaatg   2880
tgtggggtat agaaaaagga atgaataagc gttgtttttc aaatagggtc cttgtaagtt   2940
attgatgaga gggaaaagat tgactgggga gggcttaaaa tgatttggga aaacaattgc   3000
```

-continued

```
ttttgaggct cagtgacaac ggcaaagatt acaacttaaa aaaaaaaaat aaataaaaaa   3060

taaaggaagt tgcacggtta ttttgcaaca caagggggcg gcaaggtccc catttttatc   3120

ctgtaatact gtatccctaa caaagatttg gtctctgcta tcttacatta ttaatgtttc   3180

tcagatggct gaggggctcg cttcatctgt tccgtctgac acttatctca agtgtgtctg   3240

tcattcctaa tgttctcagg atgtgctctg ataaaaccct ccccataacc tcagttaata   3300

aaaatttaca gaagacttct caaatacctg agttgttttt aatacctgta caaaggagta   3360

aataggaccc tgagtctatt aaaatgtaat tcaaagtagc atatgattga ctgacagtca   3420

tgtaaactgt atctttcttt ttctgattta ataaaaaata catttacttc taaag        3475
```

<210> SEQ ID NO 14
<211> LENGTH: 2239
<212> TYPE: DNA
<213> ORGANISM: Homo sapiens

<400> SEQUENCE: 14

```
tagacattta tgcagtggtt caaagtctag agtccctaca cttctggtac atgacagctg     60

tgtctcgatg gagtagactc tcagaacagc gcagtttgcc ctccgctcac gcagagcctc    120

tccgtggctt ccgcaccttg agcattaggc cagttctcct cttctctcta atccatccgt    180

cacctctcct gtcatccgtt tccatgccgt gaggtccatt cacagaacac atccatggct    240

ctcatgctca gtttggttct gagtctcctc aagctgggat cagggcagtg gcaggtgttt    300

gggccagaca agcctgtcca ggccttggtg ggggaggacg cagcattctc ctgtttcctg    360

tctcctaaga ccaatgcaga ggccatggaa gtgcggttct tcaggggcca gttctctagc    420

gtggtccacc tctacaggga cgggaaggac cagccattta tgcagatgcc acagtatcaa    480

ggcaggacaa aactggtgaa ggattctatt gcggaggggc gcatctctct gaggctggaa    540

aacattactg tgttggatgc tggcctctat gggtgcagga ttagttccca gtcttactac    600

cagaaggcca tctgggagct acaggtgtca gcactgggct cagttcctct catttccatc    660

acgggatatg ttgatagaga catccagcta ctctgtcagt cctcgggctg gttccccccgg   720

cccacagcga agtggaaagg tccacaagga caggatttgt ccacagactc caggacaaac    780

agagacatgc atggcctgtt tgatgtggag atctctctga ccgtccaaga gaacgccggg    840

agcatatcct gttccatgcg gcatgctcat ctgagccgag aggtggaatc cagggtacag    900

ataggagata cctttttcga gcctatatcg tggcacctgg ctaccaaagt actgggaata    960

ctctgctgtg gcctattttt tggcattgtt ggactgaaga ttttcttctc caaattccag   1020

tgtaagcgag agagagaagc atgggccggt gccttattca tggttccagc agggacagga   1080

tcagagatgc tcccacatcc agctgcttct cttcttctag tcctagcctc caggggccca   1140

ggcccaaaaa aggaaaatcc aggcggaact ggactggaga agaaagcacg gacaggcaga   1200

attgagagac gcccggaaac acgcagtgga ggtgactctg gatccagaga cggctcaccc   1260

gaagctctgc gtttctgatc tgaaaactgt aacccataga aaagctcccc aggaggtgcc   1320

tcactctgag aagagattta caaggaagag tgtggtggct tctcagagtt tccaagcagg   1380

gaaacattac tgggaggtgg acggaggaca caataaaagg tggcgcgtgg gagtgtgccg   1440

ggatgatgtg gacaggagga aggagtacgt gactttgtct cccgatcatg ggtactgggt   1500

cctcagactg aatggagaac atttgtattt cacattaaat ccccgtttta tcagcgtctt   1560

ccccaggacc ccacctacaa aaataggggt cttcctggac tatgagtgtg ggaccatctc   1620
```

-continued

```
cttcttcaac ataaatgacc agtcccttat ttataccctg acatgtcggt ttgaaggctt   1680

attgaggccc tacattgagt atccgtccta taatgagcaa aatggaactc ccatagtcat   1740

ctgcccagtc acccaggaat cagagaaaga ggcctcttgg caaagggcct ctgcaatccc   1800

agagacaagc aacagtgagt cctcctcaca ggcaaccacg cccttcctcc ccaggggtga   1860

aatgtaggat gaatcacatc ccacattctt ctttagggat attaaggtct ctctcccaga   1920

tccaaagtcc cgcagcagcc ggccaaggtg gcttccagat gaagggggac tggcctgtcc   1980

acatgggagt caggtgtcat ggctgccctg agctgggagg gaagaaggct gacattacat   2040

ttagtttgct ctcactccat ctggctaagt gatcttgaaa taccacctct caggtgaaga   2100

accgtcagga attcccatct cacaggctgt ggtgtagatt aagtagacaa ggaatgtgaa   2160

taatgcttag atcttattga tgacagagtg tatcctaatg gtttgttcat tatattacac   2220

tttcagtaaa aaaaaaaaa                                                2239
```

<210> SEQ ID NO 15
<211> LENGTH: 793
<212> TYPE: DNA
<213> ORGANISM: Homo sapiens

<400> SEQUENCE: 15

```
ggataacccg cggccgcgcc tgcccgctcg cacccctctc ccgcgcccgg ttctccctcg     60

cagcacctcg aagtgcgccc ctcgccctcc tgctcgcgcc ccgccgccat ggctgcctcc    120

cccgcgcggc ctgctgtcct ggccctgacc gggctggcgc tgctcctgct cctgtgctgg    180

ggcccaggtg gcataagtgg aaataaactc aagctgatgc ttcaaaaacg agaagcacct    240

gttccaacta agactaaagt ggccgttgat gagaataaag ccaaagaatt ccttggcagc    300

ctgaagcgcc agaagcggca gctgtgggac cggactcggc ccgaggtgca gcagtggtac    360

cagcagtttc tctacatggg ctttgacgaa gcgaaatttg aagatgacat cacctattgg    420

cttaacagag atcgaaatgg acatgaatac tatggcgatt actaccaacg tcactatgat    480

gaagactctg caattggtcc ccggagcccc tacggcttta ggcatggagc cagcgtcaac    540

tacgatgact actaaccatg acttgccaca cgctgtacaa gaagcaaata gcgattctct    600

tcatgtatct cctaatgcct tacactactt ggtttctgat ttgctctatt tcagcagatc    660

ttttctacct actttgtgtg atcaaaaaag aagagttaaa acaacacatg taaatgcctt    720

ttgatatttc atgggaatgc ctctcattta aaaatagaaa taaagcattt tgttaaaaag    780

aaaaaaaaaa aaa                                                       793
```

<210> SEQ ID NO 16
<211> LENGTH: 672
<212> TYPE: DNA
<213> ORGANISM: Homo sapiens

<400> SEQUENCE: 16

```
caggccagcc ctggggcgcc ttaaaaaccg gagctggcgc ttggcatcgc cactctgggc     60

aggatccaac gtcgctccag ctgctcttga cgactccaca gataccccga agccatggca    120

agcaagggct tgcaggacct gaagcaacag gtggagggga ccgcccagga agccgtgtca    180

gcggccggag cggcagctca gcaagtggtg gaccaggcca cagaggcggg gcagaaagcc    240

atggaccagc tggccaagac cacccaggaa accatcgaca agactgctaa ccaggcctct    300

gacaccttct ctgggattgg gaaaaaattc ggcctcctga aatgacagca gggagacttg    360

ggtcggcctc ctgaaatgac agcagggaga cttgggtgac ccccttcca ggcgccatct    420
```

agcacagcct ggccctgatc tccgggcagc caccacctcc tcggtctgcc ccctcattaa 480
aattcacgtt cccaccctgt gtccacttca tgattcctcg caagctgggc ccagtcctct 540
catcccaaga gcagagccac cgtagccgga gtcctagcct cccaaattcg gaaatccaat 600
ccaacggtct caggaatgtt ttccatcccg ccacgcgcct cccgaagctc ccagaccgga 660
ggctcagccc cc 672

<210> SEQ ID NO 17
<211> LENGTH: 899
<212> TYPE: DNA
<213> ORGANISM: Homo sapiens

<400> SEQUENCE: 17
cccgagcgcc ggccgggcca tgacccccgc tgctctgtct tgcaggctcg tcgccgcggc 60
cccccgagcc cgaccgccgc cgccaccacc accagcgccc gggcgggcct cgcgcgcctc 120
gggcgcggct ccgcagtgag cccaccaaga aggaagcggc ctgcagaggt gccgacatgg 180
ggcttaagat gtcctgcctg aaaggctttc aaatgtgtgt cagcagcagc agcagcagcc 240
acgacgaggc ccccgtcctg aacgacaagc acctggacgt gcccgacatc atcatcacgc 300
cccccacccc cacgggcatg atgctgccga gggacttggg gagcacagtc tggctggatg 360
agacagggtc gtgcccagat gatggagaaa tcgacccaga agcctgagga ggtgtcctgg 420
gtttggctgg ctggctcctg ctccagcggc ccggcttcag gtgtccgggg gcgtggctgc 480
ctggagcagg tgtgctgaat accctggatg ggaactgagc gaacccgggc ctccgctcag 540
agagacgtgg caggaccagc gaggaatcca gcctgtccac ttccagaaca gtgtttccca 600
ggccccgctg agtggaccgg acctctgaca cctccaggtt cttgctgact ccggcctggt 660
gaaagggagc gccatggtcc tggctgttgg ggtcccaggg agaggctctc ttctggacaa 720
acacaccctc ccagccccca gggctgtgca aacacatgcc cctgccataa gcaccaacaa 780
gaacttcttg caggtggagt ggctgttttt tataagttgt tttacagata cggaaacagt 840
ccaaaatggg atttataatt tctttttgc attataaata aagatcctct gtaacaaaa 899

<210> SEQ ID NO 18
<211> LENGTH: 2362
<212> TYPE: DNA
<213> ORGANISM: Homo sapiens

<400> SEQUENCE: 18
actcagccca gtggccctct gagctgttcc ttcttgaccg gcacacacag ctcgcttctt 60
cactttcttt tccatccact gccggaccca agccagcctt ccagggagca gccatgcctt 120
acctctaccg ggccccaggg cctcaggcac acccggttcc caaggacgcc cggatcaccc 180
actcctcagg ccagagcttt gagcaaatga ggcaggagtg cctgcagaga ggcaccctgt 240
ttgaggatgc agacttccca gccagcaatt cctccctgtt ctacagtgag aggccgcaga 300 tccccttgt gtggaaacga ccaggggaaa tcgtgaaaaa cccagaattc attcttggag 360
gggccaccag gactgatatc tgccagggag agctgggaga ctgctggcta ttagccgcca 420
tcgcctccct tacgcttaat caaaaagcac tggccagagt catcccccag gaccaaagct 480
ttggccctgg ttatgccggg atattccatt tccagttctg gcagcacagt gagtggctgg 540
acgtggtgat cgatgaccgc ctgcccacct tcagggaccg cttggttttc ctccactctg 600
ccgaccacaa cgagttctgg agcgccttgc tggaaaaagc ctacgccaag ctaaatggga 660

```
gctatgaagc tctgaaggga ggcagcgcca tcgaggccat ggaagacttc actgggggtg    720

tggcagagac cttccaaact aaagaggccc ccgagaactt ctatgagatt ctagagaagg    780

ctttgaagag aggctccctg ctgggctgct tcattgatac cagaagtgct gcagaatctg    840

aggcccggac gccgtttggt cttattaagg gtcatgccta cagtgtaacg ggaattgacc    900

aggtaagctt ccgaggccag agaatcgagc tcatccgaat ccggaaccct tggggccagg    960

ttgagtggaa cgggtcgtgg agcgacagtt ctccggagtg gcgttctgtt ggtccagctg   1020

agcagaagcg tctgtgtcac actgctctgg atgatgggga attctggatg gcatttaagg   1080

acttcaaggc ccactttgat aaagtggaga tctgcaacct cactcccgat gccctggagg   1140

aagacgcgat ccacaaatgg gaggtgacgg tccatcaggg aagctgggtt cgcggctcca   1200

cggctggggg ctgccgcaat ttcctggata ccttttggac caatccacaa ataaaattgt   1260

ctctgactga gaaagatgag ggcaggaggg agtgtagttt ccttgtagcc ctgatgcaga   1320

aagatagaag gaaactcaag agatttggtg ccaatgtgct gacaatcggc tatgccattt   1380

atgagtgccc tgacaaagac gaacacctga acaaagactt cttcagatac cacgcttctc   1440

gggccagaag caagacgttc atcaacctga gagaagtctc cgaccggttc aagctgcccc   1500

ctggggagta catcctgatt cccagcactt ttgagcccca ccaggaagct gatttctgtc   1560

tgagaatctt ttcagagaaa aaagccatta cccgggatat ggatggaaat gtagacattg   1620

accttcctga gcctccaaag ccaactccac ctgaccagga gacagaggag gagcagcggt   1680

ttcgggctct gtttgaacaa gtcgctggtg aggacatgga ggtgacagca gaggaacttg   1740

agtatgtttt aaatgctgtg ctgcaaaaga aaaaggacat caaattcaag aagctaagcc   1800

tgatctcctg taaaaacatc atttccctga tggacaccag cggcaatggg aagctggagt   1860

ttgatgaatt caaagtgttc tgggacaagc tgaagcagtg gattaacctt ttccttcggt   1920

ttgatgctga caagtccggc accatgtcta cctatgaact acggactgca ctgaaagctg   1980

caggctttca gctgagcagc cacctcctgc agctgattgt gctcaggtat gcggatgagg   2040

agctccagct ggacttcgat gacttcctca actgcctggt ccggctggag aatgcgagcc   2100

gggtgttcca ggctctcagt acaaagaaca aggagttcat tcatctcaat ataaatgagt   2160

tcatccattt gacaatgaac atctgaggct gccttgtaga gatgcagcct gcccagctga   2220

atcttggctt ctggaccttg accttcagaa cttctcttgg tgtggaacca ttacgcccag   2280

ggttcactcc cctctcatcg tccggccttc tcccttcatc ttgatctggg aagaatgaaa   2340

tgaactcagc tacactctct ga                                            2362
```

<210> SEQ ID NO 19
<211> LENGTH: 9170
<212> TYPE: DNA
<213> ORGANISM: Homo sapiens

<400> SEQUENCE: 19

```
gcgcgcccat ttcagattac taaactcgaa ttaagaggga aaaaaaatca gggaggaggt     60

ggcaagccac accccacggt gcccgcgaac ttccccggca gcggactgta gcccaggcag    120

acgccgtcga gatgcagggc ccaccgctcc tgaccgccgc ccacctcctc tgcgtgtgca    180

ccgccgcgct ggccgtggct cccgggcctc ggtttctggt gacagcccca gggatcatca    240

ggcccggagg aaatgtgact attggggtgg agcttctgga acactgccct tcacaggtga    300

ctgtgaaggc ggagctgctc aagacagcat caaacctcac tgtctctgtc ctggaagcag    360

aaggagtctt tgaaaaaggc tcttttaaga cacttactct tccatcacta cctctgaaca    420
```

gtgcagatga gatttatgag ctacgtgtaa ccggacgtac ccaggatgag attttattct 480
ctaatagtac ccgcttatca tttgagacca agagaatatc tgtcttcatt caaacagaca 540
aggccttata caagccaaag caagaagtga agtttcgcat tgttacactc ttctcagatt 600
ttaagcctta caaaacctct ttaaacattc tcattaagga ccccaaatca aatttgatcc 660
aacagtggtt gtcacaacaa agtgatcttg gagtcatttc caaaactttt cagctatctt 720
cccatccaat acttggtgac tggtctattc aagttcaagt gaatgaccag acatactatc 780
aatcatttca ggtttcagaa tatgtattac caaaatttga agtgactttg cagacaccat 840
tatattgttc tatgaattct aagcatttaa atggtaccat cacggcaaag tatacatatg 900
ggaagccagt gaaaggagac gtaacgctta catttttacc tttatccttt tggggaaaga 960
agaaaaatat tacaaaaaca tttaagataa atggatctgc aaacttctct tttaatgatg 1020
aagagatgaa aaatgtaatg gattcttcaa atggactttc tgaatacctg gatctatctt 1080
cccctggacc agtagaaatt ttaaccacag tgacagaatc agttacaggt atttcaagaa 1140
atgtaagcac taatgtgttc ttcaagcaac atgattacat cattgagttt tttgattata 1200
ctactgtctt gaagccatct ctcaacttca cagccactgt gaaggtaact cgtgctgatg 1260
gcaaccaact gactcttgaa gaaagaagaa ataatgtagt cataacagtg acacagagaa 1320
actatactga gtactggagc ggatctaaca gtggaaatca gaaaatggaa gctgttcaga 1380
aaataaatta tactgtcccc caaagtggaa cttttaagat tgaattccca atcctggagg 1440
attccagtga gctacagttg aaggcctatt tccttggtag taaaagtagc atggcagttc 1500
atagtctgtt taagtctcct agtaagacat acatccaact aaaaacaaga gatgaaaata 1560
taaaggtggg atcgcctttt gagttggtgg ttagtggcaa caaacgattg aaggagttaa 1620
gctatatggt agtatccagg ggacagttgg tggctgtagg aaaacaaaat tcaacaatgt 1680
tctctttaac accagaaaat tcttggactc caaaagcctg tgtaattgtg tattatattg 1740
aagatgatgg ggaaattata agtgatgttc taaaaattcc tgttcagctt gtttttaaaa 1800
ataagataaa gctatattgg agtaaagtga aagctgaacc atctgagaaa gtctctctta 1860
ggatctctgt gacacagcct gactccatag ttgggattgt agctgttgac aaaagtgtga 1920
atctgatgaa tgcctctaat gatattacaa tggaaaatgt ggtccatgag ttggaacttt 1980
ataacacagg atattattta ggcatgttca tgaattcttt tgcagtcttt caggaatgtg 2040
gactctgggt attgacagat gcaaacctca cgaaggatta tattgatggt gtttatgaca 2100
atgcagaata tgctgagagg tttatggagg aaaatgaagg acatattgta gatattcatg 2160
acttttcttt gggtagcagt ccacatgtcc gaaagcattt tccagagact tggatttggc 2220
tagacaccaa catgggttac aggatttacc aagaatttga agtaactgta cctgattcta 2280
tcacttcttg ggtggctact ggttttgtga tctctgagga cctgggtctt ggactaacaa 2340
ctactccagt ggagctccaa gccttccaac catttttcat ttttttgaat cttccctact 2400
ctgttatcag aggtgaagaa tttgctttgg aaataactat attcaattat ttgaaagatg 2460
ccactgaggt taaggtaatc attgagaaaa gtgacaaatt tgatattcta atgacttcaa 2520
atgaaataaa tgccacaggc caccagcaga cccttctggt tcccagtgag gatggggcaa 2580
ctgttctttt tcccatcagg ccaacacatc tgggagaaat tcctatcaca gtcacagctc 2640
tttcacccac tgcttctgat gctgtcaccc agatgatttt agtaaaggct gaaggaatag 2700
aaaaatcata ttcacaatcc atcttattag acttgactga caataggcta cagagtaccc 2760

-continued

```
tgaaaacttt gagtttctca tttcctccta atacagtgac tggcagtgaa agagttcaga   2820
tcactgcaat tggagatgtt cttggtcctt ccatcaatgg cttagcctca ttgattcgga   2880
tgccttatgg ctgtggtgaa cagaacatga taaattttgc tccaaatatt tacattttgg   2940
attatctgac taaaaagaaa caactgacag ataatttgaa agaaaaagct ctttcattta   3000
tgaggcaagg ttaccagaga gaacttctct atcagaggga agatggctct ttcagtgctt   3060
ttgggaatta tgacccttct gggagcactt ggttgtcagc ttttgtttta agatgtttcc   3120
ttgaagccga tccttacata gatattgatc agaatgtgtt acacagaaca tacacttggc   3180
ttaaaggaca tcagaaatcc aacggtgaat tttgggatcc aggaagagtg attcatagtg   3240
agcttcaagg tggcaataaa agtccagtaa cacttacagc ctatattgta acttctctcc   3300
tgggatatag aaagtatcag cctaacattg atgtgcaaga gtctatccat tttttggagt   3360
ctgaattcag tagaggaatt tcagacaatt atactctagc ccttataact tatgcattgt   3420
catcagtggg gagtcctaaa gcgaaggaag ctttgaatat gctgacttgg agagcagaac   3480
aagaaggtgg catgcaattc tgggtgtcat cagagtccaa actttctgac tcctggcagc   3540
cacgctccct ggatattgaa gttgcagcct atgcactgct ctcacacttc ttacaatttc   3600
agacttctga gggaatccca attatgaggt ggctaagcag gcaaagaaat agcttgggtg   3660
gttttgcatc tactcaggat accactgtgg ctttaaaggc tctgtctgaa tttgcagccc   3720
taatgaatac agaaaggaca aatatccaag tgaccgtgac ggggcctagc tcaccaagtc   3780
ctgtaaagtt tctgattgac acacacaacc gcttactcct tcagacagca gagcttgctg   3840
tggtacagcc aacggcagtt aatatttccg caaatggttt tggatttgct atttgtcagc   3900
tcaatgttgt atataatgtg aaggcttctg ggtcttctag aagacgaaga tctatccaaa   3960
atcaagaagc ctttgattta gatgttgctg taaaagaaaa taaagatgat ctcaatcatg   4020
tggatttgaa tgtgtgtaca agcttttcgg gcccgggtag gagtggcatg gctcttatgg   4080
aagttaacct attaagtggc tttatggtgc cttcagaagc aatttctctg agcgagacag   4140
tgaagaaagt ggaatatgat catggaaaac tcaacctcta tttagattct gtaaatgaaa   4200
cccagttttg tgttaatatt cctgctgtga gaaactttaa agtttcaaat acccaagatg   4260
cttcagtgtc catagtggat tactatgagc caaggagaca ggcggtgaga agttacaact   4320
ctgaagtgaa gctgtcctcc tgtgaccttt gcagtgatgt ccagggctgc cgtccttgtg   4380
aggatggagc ttcaggctcc catcatcact cttcagtcat tttattttc tgtttcaagc    4440
ttctgtactt tatggaactt tggctgtgat ttatttttaa aggactctgt gtaacactaa   4500
catttccagt agtcacatgt gattgttttg ttttcgtaga agaatactgc ttctattttg   4560
aaaaaagagt ttttttcttt tctatggggt tgcagggatg gtgtacaaca ggtcctagca   4620
tgtatagctg catagatttc ttcacctgat ctttgtgtgg aagatcagaa tgaatgcagt   4680
tgtgtgtcta tattttcccc tctcaaaatc ttttagaatt tttttggagg tgtttgtttt   4740
ctccagaata aaggtattac tttagaatag gtattctcct cattttgtga aagaaatgaa   4800
cctagattct taagcattat tacacatcca tgtttgctta aagatggatt tccctgggaa   4860
tgggagaaaa cagccagcag gaggagcttc atctgttccc ttcccacctc caacctagcc   4920
ctactgccca ccccacccca acccacccca tgcccagtgg tctcagtaga tacttcttaa   4980
ctggaaattc tttcttttca gaatctaggt ggtgaatttt ttttaagtgg cacggtcttt   5040
ttctgcttga aatctgatca caccccccag ccattgccct ccctctcttt ttcctctgta   5100
gagaaatgtg aggggcagta catttactgt gcttttcaca ccatctcaga ggttgaggag   5160
```

```
catactgaaa attgccctgg ggggtgctgg gtgtgctgtc tccttcccac atcctcagcc   5220
ccacaccagc tctatttcag ggtgagagt cagagagcac tgcaatatgt gcttcatggg   5280
atttcgattc gaagatccta gaccagggag acactgtgag ccagggatac aacaaaatac   5340
taggtaagtc actgcagacc gacctccctg cagtttggga aagaagctgg gtttgtggag   5400
aatcagagca tcttgacatg actgctgacc taaagatccc tggcattggc cagggatcct   5460
gtggaacctc ttctagttca ggggtgtgag cattagactg ccagttgtct agtgacatct   5520
gatgcttgct gtgaactttt aagatccccg aatcctgagc acctcaatct ttaattgccc   5580
tgtattccga agggtaatat aatttatctg gatggaaatt ttaaagatga atcccccttt   5640
tttcttttct tctctctttt ctttccttct ccctttcttc tttgccttct aaatatactg   5700
aaatgattta gatatgtgtc aacaattaat gatcttttat tcaatctaag aaatggttta   5760
gtttttctct ttagctctat ggcatttcac tcaagtggac aggggaaaaa gtaattgcca   5820
tgggctccaa agaatttgct ttatgttttt agctatttaa aaataaatcc atcaaaaata   5880
aagtatgcaa atgtatcttt taaagttaat ttttaaaaat gctcttattt tagtgaattt   5940
tcagaaatta tagtggaatg gatgctcata tattgcttat ggatattttg gataccaaag   6000
taggaataac tgacattcag tattttaaag ctggcaaacc tgtacataga aaatagatcc   6060
ccagacagtg gtctatgaag agggcagtta agtatcaaat acttaatttt cttgcctttt   6120
tttcttaagt ggggaaaagt ttctagatct cttacacctc tgacacaatc tgttctaaaa   6180
caggcacttg taatgttggg gcctccttgt aaacgtgttt ttgcccttta ctctctggga   6240
gttctttaaa ggtgaaatca tcttacaaag aaattggggg agggtcttgg caaaggactt   6300
tcccctcctc tttcctggcc tgggaacctt atactgacaa tcaatacttt atattttaaa   6360
gtatataatt tatagttaac ttctagtgta atatattagg aaacactaga atggaaaggc   6420
cattggaaga caggttgtat cttttttaga ccatatttcc ttgtttaaaa actatcattt   6480
gaatactttt ttggtgaaga actccatgtt ttcaagttaa aggtcacctc gtaggccagg   6540
cgcagtggct catgcctgta atcccagcac tctgggaggc tgaggcgggt gaatcacaag   6600
gttaggagtt tgagaccagc ctggccaata tggtgaaacc ccgtccctac taaaaataca   6660
aaatttagcc aggcgtggtg gcatgcacct gtagtcccac ctactcggga ggctgaggca   6720
ggagaatcac ttgaacctga gagacagagg ttgcagtgag ccgagatcac gccactgcac   6780
tccagcctgg gggacagagt gagattctgt ctcaaaaaac aaaaaacaaa aaagtcacct   6840
tgtaactcat ctctttttat tgtaagttta ttaaaaatga agaggacaac aatgagaagg   6900
aacataaagg gttagctagc actgtctcct ggtgcatggg gctgtgcaga tgtcccggcc   6960
acttcttcct tcatacttcc cttagagaac ttgctctgct acaagcagtg ggcttggact   7020
aaaagtgatt aaaataccac aggcataagg agaaaaggag tatatgtagt agtaataatt   7080
actagtataa attattttct tcacatgcta tgagtaataa tattaaaaaa ctcattttac   7140
cattaagatt ccttatgctg aagctcttcc atttagaata ctgtcaatgt catttactgg   7200
tatgaactaa agtcccctt cttttccact cactgggaac cttagtaaaa caccagcata   7260
tcttacctct ctttctgact ggccgatgct tccagagact gaatgttggg aaaacctagt   7320
agccaaacaa ttctaggaca gaataacatt tttatatttg gttccaccat cttattacat   7380
ttagttatag ttttaaaaaa gaaattcaag cccattaaaa tatgtctggt caatgaaatg   7440
cttcctttta ttgtgttgtg ctattgtact ttgtttttca aaacattgta aaaatagtat   7500
```

-continued

```
ctttggttta gtattttgga ttatatatta taatctgagg agtgttttgc ttatgtagaa   7560

tccagatata tttctgttac ctaggagatg ttacttacat atgtaatact gtatcctgca   7620

cgtggaaata ttcagaattg tagatagcat aactctccct gctcctattc ttttgagcct   7680

aggtataatt tttttttttt ttttagaaaa agacatattt agctttaatt tctatttatg   7740

ctaaacatat ttataagtag tctgtcaata taataccaac tatttttatt tttacataat   7800

tcaattattt catttgacat gtctggcaga ctcaagacat taagtaaaaa attggaacta   7860

tgatttttct ttgtcatttt ttaaaaaaga attattttat taacctgctg gcatataatc   7920

tggagttctt ttcacaacct tactttttct gatttgcttt attgaatgat tgaatactca   7980

tttctttcta aaaatatgtt gtaaattctc ccttggcaag atttctccct atgagggtag   8040

ttattatttg agtctgccaa gtggttacca tggggcaagg tgccatgatg tattcttggg   8100

tgcattggtt ttttgcgcat tgtaaattta agacacttat agtaagtgga ctcattcata   8160

gatgagtttc agaacctttt acgttctcgg tagaggcttc tgtcggacag gcagaagagt   8220

gtattcctca cttttttttt tgtcttcaaa ttccagtaag gcatagcact tttaagaaat   8280

tagaattttt ctatcatcta tgcaaatgat atttatgtta atattaaata tcttatgtta   8340

cactgggagt aatttgaggt gcaattattt ttattactac tttgaataga ggaccattat   8400

ccttctttct tcagaaaact aagaagtaag tgtaactttt aaagtaagta tatatcagtg   8460

agagtaggct tgttttacaa ctatttctag ccagtgagtt gtgttttcat gtctcatcaa   8520

aagacaatac cacattgcat cattttacaa aatatgttgt cattttcatt tcagttgtaa   8580

cataggaaaa tagatatttc ctagatgatt tctgagtttc ttactgcaaa gaacagttat   8640

aaattggtat acatgtgtct ctgtaatagg gataatattg atatatctgt tgctacatat   8700

ttaagaatca ttctatctta tgttgtcttg aggccaagat ttaccacgtt tgcccagtgt   8760

attgaattgg tggtagaagg tagttccatg ttccatttgt agatctttaa gattttatct   8820

ttgataactt taatagaatg tggctcagtt ctggtccttc aagcctgtat ggtttggatt   8880

ttcagtaggg gacagttgat gtggagtcaa tctctttggt acacaggaag ctttataaaa   8940

tttcattcac gaatctctta ttttgggaag ctgttttgca tatgagaaga acactgttga   9000

aataaggaac taaagcttta tatattgatc aaggtgattc tgaaagtttt aatttttaat   9060

gttgtaatgt tatgttattg ttaattgtac tttattatgt attcaataga aaatcatgat   9120

ttattaataa aagcttaaat tctcatctat ttaaaaaaaa aaaaaaaaaa              9170


<210> SEQ ID NO 20
<211> LENGTH: 3654
<212> TYPE: DNA
<213> ORGANISM: Homo sapiens

<400> SEQUENCE: 20

agatgccgcg ggggccgctc gcagccgccg ctgacttgtg aatgggaccg ggactggggc     60

cgggactgac accgcagcgc ttgccctgcg ccagggactg gcggctcgga ggttgcgtcc    120

accctcaagg gccccagaaa tcactgtgtt ttcagctcag cggccctgtg acattccttc    180

gtgttgtcat ttgttgagtg accaatcaga tgggtggagt gtgttacaga aattggcagc    240

aagtatccaa tgggtgaaga agaagctaac tggggacgtg ggcagccctg acgtgatgag    300

ctcaaccagc agagacattc catcccaaga gaggtctgcg tgacgcgtcc gggaggccac    360

cctcagcaag accaccgtac agttggtgga aggggtgaca gctgcattct cctgtgccta    420

ccacgtaacc aaaaatgaag gagaactact gtttacaagc cgccctggtg tgcctgggca    480
```

tgctgtgcca cagccatgcc tttgccccag agcggcgggg gcacctgcgg ccctccttcc 540
atgggcacca tgagaagggc aaggaggggc aggtgctaca gcgctccaag cgtggctggg 600
tctggaacca gttcttcgtg atagaggagt acaccgggcc tgaccccgtg cttgtgggca 660
ggcttcattc agatattgac tctggtgatg ggaacattaa atacattctc tcaggggaag 720
gagctggaac cattttttgtg attgatgaca aatcagggaa cattcatgcc accaagacgt 780
tggatcgaga agagagagcc cagtacacgt tgatggctca ggcggtggac agggacacca 840
atcggccact ggagccaccg tcggaattca ttgtcaaggt ccaggacatt aatgacaacc 900
ctccggagtt cctgcacgag acctatcatg ccaacgtgcc tgagaggtcc aatgtgggaa 960
cgtcagtaat ccaggtgaca gcttcagatg cagatgaccc cacttatgga aatagcgcca 1020
agttagtgta cagtatcctc gaaggacaac cctatttttc ggtggaagca cagacaggta 1080
tcatcagaac agccctaccc aacatggaca gggaggccaa ggaggagtac cacgtggtga 1140
tccaggccaa ggacatgggt ggacatatgg gcggactctc agggacaacc aaagtgacga 1200
tcacactgac cgatgtcaat gacaacccac caaagtttcc gcagagcgta taccagatgt 1260
ctgtgtcaga agcagccgtc cctggggagg aagtaggaag agtgaaagct aaagatccag 1320
acattggaga aaatggctta gtcacataca atattgttga tggagatggt atggaatcgt 1380
ttgaaatcac aacggactat gaaacacagg agggggtgat aaagctgaaa aagcctgtag 1440
attttgaaac caaaagagcc tatagcttga aggtagaggc agccaacgtg cacatcgacc 1500
cgaagtttat cagcaatggc cctttcaagg acactgtgac cgtcaagatc tcagtagaag 1560
atgctgatga gccccctatg ttcttggccc caagttacat ccacgaagtc caagaaaatg 1620
cagctgctgg caccgtggtt gggagagtgc atgccaaaga ccctgatgct gccaacagcc 1680
cgataaggta ttccatcgat cgtcacactg acctcgacag atttttcact attaatccag 1740
aggatggttt tattaaaact acaaaacctc tggatagaga ggaaacagcc tggctcaaca 1800
tcactgtctt tgcagcagaa atccacaatc ggcatcagga agccaaagtc ccagtggcca 1860
ttagggtcct tgatgtcaac gataatgctc ccaagtttgc tgccccttat gaaggtttca 1920
tctgtgagag tgatcagacc aagccacttt ccaaccagcc aattgttaca attagtgcag 1980
atgacaagga tgacacggcc aatggaccaa gatttatctt cagcctaccc cctgaaatca 2040
ttcacaatcc aaatttcaca gtcagagaca accgagataa cacagcaggc gtgtacgccc 2100
ggcgtggagg gttcagtcgg cagaagcagg acttgtacct tctgcccata gtgatcagcg 2160
atggcggcat cccgcccatg agtagcacca acaccctcac catcaaagtc tgcgggtgcg 2220
acgtgaacgg ggcactgctc tcctgcaacg cagaggccta cattctgaac gccggcctga 2280
gcacaggcgc cctgatcgcc atcctcgcct gcatcgtcat tctcctggtc attgtagtat 2340
tgtttgtgac cctgagaagg caaaagaaag aaccactcat tgtctttgag gaagaagatg 2400
tccgtgagaa catcattact tatgatgatg aagggggtgg ggaagaagac acagaagcct 2460
ttgatattgc caccctccag aatcctgatg gtatcaatgg atttatcccc cgcaaagaca 2520
tcaaacctga gtatcagtac atgcctagac ctgggctccg gccagcgccc aacagcgtgg 2580
atgtcgatga cttcatcaac acgagaatac aggaggcaga caatgacccc acggctcctc 2640
cttatgactc cattcaaatc tacggttatg aaggcagggg ctcagtggcc gggtccctga 2700
gctccctaga gtcggccacc acagattcag acttggacta tgattatcta cagaactggg 2760
gacctcgttt taagaaacta gcagatttgt atggttccaa agacactttt gatgacgatt 2820
cttaacaata acgatacaaa tttggcctta agaactgtgt ctggcgttct caagaatcta 2880
gaagatgtgt aaacaggtat ttttttaaat caaggaaagg ctcatttaaa acaggcaaag 2940
ttttacagag aggatacatt taataaaact gcgaggacat caaagtggta aatactgtga 3000 aataccttttt ctcacaaaaa ggcaaatatt gaagttgttt atcaacttcg ctagaaaaaa 3060
aaaacacttg gcatacaaaa tatttaagtg aaggagaagt ctaacgctga actgacaatg 3120
aagggaaatt gtttatgtgt tatgaacatc caagtctttc ttcttttttta agttgtcaaa 3180 gaagcttcca caaaattaga aaggacaaca gttctgagct gtaatttcgc cttaaactct 3240
ggacactcta tatgtagtgc atttttaaac ttgaaatata taatattcag ccagcttaaa 3300
cccatacaat gtatgtacaa tacaatgtac aattatgtct cttgagcatc aatcttgtta 3360
ctgctgattc ttgtaaatct ttttgcttct actttcatct taaactaata cgtgccagat 3420
ataactgtct tgtttcagtg agagacgccc tatttctatg tcatttttaa tgtatctatt 3480
tgtacaattt taaagttctt attttagtat acgtataaat atcagtattc tgacatgtaa 3540
gaaaatgtta cggcatcaca cttatatttt atgaacattg tactgttgct ttaatatgag 3600
cttcaatata agaagcaatc tttgaaataa aaaaagattt ttttttaaaa aaaa 3654

<210> SEQ ID NO 21
<211> LENGTH: 3698
<212> TYPE: DNA
<213> ORGANISM: Homo sapiens

<400> SEQUENCE: 21
ggaagaggga gtgttcccgg gggagatact ccagtcgtag caagagtctc gaccactgaa 60
tggaagaaaa ggacttttaa ccaccatttt gtgacttaca gaaaggaatt tgaataaaga 120
aaactatgat acttcaggcc catcttcact ccctgtgtct tcttatgctt tatttggcaa 180
ctggatatgg ccaagagggg aagtttagtg gacccctgaa acccatgaca ttttctattt 240
atgaaggcca agaaccgagt caaattatat tccagtttaa ggccaatcct cctgctgtga 300
cttttgaact aactggggag acagacaaca tatttgtgat agaacgggag ggacttctgt 360
attacaacag agccttggac agggaaacaa gatctactca caatctccag gttgcagccc 420
tggacgctaa tggaattata gtggagggtc cagtccctat caccataaaa gtgaaggaca 480
tcaacgacaa tcgacccacg tttctccagt caaagtacga aggctcagta aggcagaact 540
ctcgcccagg aaagcccttc ttgtatgtca atgccacaga cctggatgat ccggccactc 600
ccaatggcca gctttattac cagattgtca tccagcttcc catgatcaac aatgtcatgt 660
actttcagat caacaacaaa acgggagcca tctctcttac ccgagaggga tctcaggaat 720
tgaatcctgc taagaatcct tcctataatc tggtgatctc agtgaaggac atgggaggcc 780
agagtgagaa ttccttcagt gataccacat ctgtggatat catagtgaca gagaatattt 840
ggaaagcacc aaaacctgtg gagatggtgg aaaactcaac tgatcctcac cccatcaaaa 900
tcactcaggt gcggtggaat gatcccggtg cacaatattc cttagttgac aaagagaagc 960
tgccaagatt cccattttca attgaccagg aaggagatat ttacgtgact cagcccttgg 1020
accgagaaga aaaggatgca tatgtttttt atgcagttgc aaaggatgag tacggaaaac 1080
cactttcata tccgctggaa attcatgtaa aagttaaaga tattaatgat aatccaccta 1140
catgtccgtc accagtaacc gtatttgagg tccaggagaa tgaacgactg ggtaacagta 1200
tcgggaccct tactgcacat gacagggatg aagaaaatac tgccaacagt tttctaaact 1260
acaggattgt ggagcaaact cccaaacttc ccatggatgg actcttccta atccaaacct 1320

```
atgctggaat gttacagtta gctaaacagt ccttgaagaa gcaagatact cctcagtaca   1380
acttaacgat agaggtgtct gacaaagatt tcaagaccct ttgttttgtg caaatcaacg   1440
ttattgatat caatgatcag atccccatct ttgaaaaatc agattatgga aacctgactc   1500
ttgctgaaga cacaaacatt gggtccacca tcttaaccat ccaggccact gatgctgatg   1560
agccatttac tgggagttct aaaattctgt atcatatcat aaagggagac agtgagggac   1620
gcctgggggt tgacacagat ccccatacca acaccggata tgtcataatt aaaaagcctc   1680
ttgattttga aacagcagct gtttccaaca ttgtgttcaa agcagaaaat cctgagcctc   1740
tagtgtttgg tgtgaagtac aatgcaagtt cttttgccaa gttcacgctt attgtgacag   1800
atgtgaatga agcacctcaa ttttcccaac acgtattcca agcgaaagtc agtgaggatg   1860
tagctatagg cactaaagtg ggcaatgtga ctgccaagga tccagaaggt ctggacataa   1920
gctattcact gaggggagac acaagaggtt ggcttaaaat tgaccacgtg actggtgaga   1980
tctttagtgt ggctccattg gacagagaag ccggaagtcc atatcgggta caagtggtgg   2040
ccacagaagt aggggggtct tccttgagct ctgtgtcaga gttccacctg atccttatgg   2100
atgtgaatga caaccctccc aggctagcca aggactacac gggcttgttc ttctgccatc   2160
ccctcagtgc acctggaagt ctcattttcg aggctactga tgatgatcag cacttatttc   2220
ggggtcccca ttttacattt tccctcggca gtggaagctt acaaaacgac tgggaagttt   2280
ccaaaatcaa tggtactcat gcccgactgt ctaccaggca cacagagttt gaggagaggg   2340
agtatgtcgt cttgatccgc atcaatgatg gggtcggcc accccttggaa ggcattgttt   2400
ctttaccagt tacattctgc agttgtgtgg aaggaagttg tttccggcca gcaggtcacc   2460
agactgggat acccactgtg ggcatggcag ttggtatact gctgaccacc cttctggtga   2520
ttggtataat tttagcagtt gtgtttatcc gcataaagaa ggataaaggc aaagataatg   2580
ttgaaagtgc tcaagcatct gaagtcaaac ctctgagaag ctgaatttga aaaggaatgt   2640
ttgaatttat atagcaagtg ctatttcagc aacaaccatc tcatcctatt acttttcatc   2700
taacgtgcat tataattttt taaacagata ttccctcttg tcctttaata tttgctaaat   2760
atttcttttt tgaggtggag tcttgctctg tcgcccaggc tggagtacag tggtgtgatc   2820
ccagctcact gcaacctccg cctcctgggt tcacatgatt ctcctgcctc agcttcctaa   2880
gtagctgggt ttacaggcac ccaccaccat gcccagctaa tttttgtatt tttaatagag   2940
acggggtttc gccatttggc caggctggtc ttgaactcct gacgtcaagt gatctgcctg   3000
ccttggtctc ccaatacagg catgaaccac tgcacccacc tacttagata tttcatgtgc   3060
tatagacatt agagagattt ttcatttttc catgacattt ttcctctctg caaatggctt   3120
agctacttgt gtttttccct tttggggcaa gacagactca ttaaatattc tgtacatttt   3180
ttctttatca aggagatata tcagtgttgt ctcatagaac tgcctggatt ccatttatgt   3240
tttttctgat tccatcctgt gtccccttca tccttgactc ctttggtatt tcactgaatt   3300
tcaaacattt gtcagagaag aaaaacgtga ggactcagga aaaataaata aataaaagaa   3360
cagccttttc ccttagtatt aacagaaatg tttctgtgtc attaaccatc tttaatcaat   3420
gtgacatgtt gctctttggc tgaaattctt caacttggaa atgacacaga cccacagaag   3480
gtgttcaaac acaacctact ctgcaaacct tggtaaagga accagtcagc tggccagatt   3540
tcctcactac ctgccatgca tacatgctgc gcatgttttc ttcattcgta tgttagtaaa   3600
gttttggtta ttatatattt aacatgtgga agaaaacaag acatgaaaag agtggtgaca   3660
```

aatcaagaat aaacactggt tgtagtcagt tttgtttg 3698

<210> SEQ ID NO 22
<211> LENGTH: 6241
<212> TYPE: DNA
<213> ORGANISM: Homo sapiens

<400> SEQUENCE: 22
atactgacag tgttgtggta ctaaaagcac aagcgtctgt aactctgggc aatggggcac 60
atcgagagtt tgctgagaag actgtgaagc aaaaagaaga aagtttttcc tactcttcct 120
tatgtgtcca acacgaagtt tgctgttcag ttttcacaga acttctagaa gttgaagtta 180
caaaggtata tagaaggtac acagaatcag aaaagattat aaaagaaagc aagatttttg 240
ttagtgacgt cctgtttcct ctgaagagta atagttggaa tcaaaagagt caacgcaatg 300
aactgttatt tactgctgcg ttttatgttg ggaattcctc tcctatggcc ttgtcttgga 360
gcaacagaaa actctcaaac aaagaaagtc aagcagccag tgcgatctca tttgagagtg 420
aagcgtggct gggtgtggaa ccaatttttt gtaccagagg aaatgaatac gactagtcat 480
cacatcggcc agctaagatc tgatttagac aatggaaaca attctttcca gtacaagctt 540
ttgggagctg gagctggaag tacttttatc attgatgaaa gaacaggtga catatatgcc 600
atacagaagc ttgatagaga ggagcgatcc ctctacatct taagagccca ggtaatagac 660
atcgctactg gaagggctgt ggaacctgag tctgagtttg tcatcaaagt ttcggatatc 720
aatgacaatg aaccaaaatt cctagatgaa ccttatgagg ccattgtacc agagatgtct 780
ccagaaggaa cattagttat ccaggtgaca gcaagtgatg ctgacgatcc ctcaagtggt 840
aataatgctc gtctcctcta cagcttactt caaggccagc catatttttc tgttgaacca 900
acaacaggag tcataagaat atcttctaaa atggatagag aactgcaaga tgagtattgg 960
gtaatcattc aagccaagga catgattggt cagccaggag cgttgtctgg aacaacaagt 1020
gtattaatta aactttcaga tgttaatgac aataagccta tatttaaaga aagtttatac 1080
cgcttgactg tctctgaatc tgcacccact gggacttcta taggaacaat catggcatat 1140
gataatgaca taggagagaa tgcagaaatg gattacagca ttgaagagga tgattcgcaa 1200
acatttgaca ttattactaa tcatgaaact caagaaggaa tagttatatt aaaaaagaaa 1260
gtggattttg agcaccagaa ccactacggt attagagcaa aagttaaaaa ccatcatgtt 1320
cctgagcagc tcatgaagta ccacactgag gcttccacca ctttcattaa gatccaggtg 1380
gaagatgttg atgagcctcc tcttttcctc cttccatatt atgtatttga agtttttgaa 1440
gaaaccccac agggatcatt tgtaggcgtg gtgtctgcca cagacccaga caataggaaa 1500
tctcctatca ggtattctat tactaggagc aaagtgttca atatcaatga taatggtaca 1560
atcactacaa gtaactcact ggatcgtgaa atcagtgctt ggtacaacct aagtattaca 1620
gccacagaaa aatacaatat agaacagatc tcttcgatcc cactgtatgt gcaagttctt 1680
aacatcaatg atcatgctcc tgagttctct caatactatg agacttatgt ttgtgaaaat 1740
gcaggctctg gtcaggtaat tcagactatc agtgcagtgg atagagatga atccatagaa 1800
gagcaccatt tttactttaa tctatctgta gaagacacta acaattcaag ttttacaatc 1860
atagataatc aagataacac agctgtcatt ttgactaata gaactggttt taaccttcaa 1920
gaagaacctg tcttctacat ctccatctta attgccgaca atggaatccc gtcacttaca 1980
agtacaaaca cccttaccat ccatgtctgt gactgtggtg acagtgggag cacacagacc 2040
tgccagtacc aggagcttgt gctttccatg ggattcaaga cagaagtcat cattgctatt 2100
ctcatttgca ttatgatcat atttgggttt attttttga ctttgggttt aaaacaacgg 2160
agaaaacaga ttctatttcc tgagaaaagt gaagatttca gagagaatat attccaatat 2220
gatgatgaag ggggtggaga agaagataca gaggcctttg atatagcaga gctgaggagt 2280
agtaccataa tgcgggaacg caagactcgg aaaaccacaa gcgctgagat caggagccta 2340
tacaggcagt ctttgcaagt tggccccgac agtgccatat tcaggaaatt cattctggaa 2400
aagctcgaag aagctaatac tgatccgtgt gcccctcctt ttgattccct ccagacctac 2460
gcttttgagg gaacagggtc attagctgga tccctgagct ccttagaatc agcagtctct 2520
gatcaggatg aaagctatga ttaccttaat gagttgggac ctcgctttaa aagattagca 2580
tgcatgtttg gttctgcagt gcagtcaaat aattagggct ttttaccatc aaaattttta 2640
aaagtgctaa tgtgtattcg aacccaatgg tagtcttaaa gagttttgtg ccctggctct 2700
atggcgggga aagccctagt ctatggagtt ttctgatttc cctggagtaa atactccatg 2760
gttattttaa gctacctaca tgctgtcatt gaacagagat gtggggagaa atgtaaacaa 2820
tcagctcaca ggcatcaata caaccagatt tgaagtaaaa taatttagga agatattaaa 2880
agtagatgag aggacacaag atgtagtcga tccttatgcg attatatcat tatttactta 2940
ggaaagagta aaaataccaa acgagaaaat ttaaaggagc aaaaatttgc aagtcaaata 3000
gaaatgtaca aatcgagata acatttacat ttctatcata ttgacatgaa aattgaaaat 3060
gtatagtcag agaaattttc atgaattatt ccatgaagta ttgtttcctt tatttaaaaa 3120
aaaaaaaaaa aaaaaagaat gctaggtaat cttcgtagaa aactagaaag tatgataaac 3180
aacagttgga ggaatccatg gaaaatagac gagaaaatgt aaataaggct ttctggggat 3240
cacagaactt ttgtatgaat aaaagcctta taaaaccagc tctggcatat gactaaaata 3300
ttcctctact atttttcaat gtcatctaat gcaaacgctc aacctttta aatggttaat 3360 gtgagaaagg cactgaatta agatatctta gtgttatttt atttactcaa ttttcatctt 3420
tcacactgta agaataaaat gtttttgtgg ttaagttcct gatactatat agagataaac 3480
tttaaaactt taacacctag gataatgtgg gtgattacat aaatgtttaa aaacatttac 3540
cttatatgga aagcagattt ctgactaaga tgccatgatt cattctagtt tgatatttta 3600
aaactttgcc aagagcactc tttaaaactg atttcaaatt tgaacagata cttggtgtat 3660
acaaattaat cagagttata tagtataaat ttgtattatt tttgatatta caactttgta 3720
ttaaaaagga aaatatattt aggtgtttgt catagatttt ttttcatatg caactcaaaa 3780
cacattctta tgtcaaaata caatagcaaa atacaagtca atatttactc ataattaaat 3840
gcaaacttta tgaaactggt ggaaagtgtg gaaaaattta agtaaatttt tacctctact 3900
aaaaattatt tagacaactt aaaggaatac tggattcaaa cttcagttac tattcactgt 3960
aaatattatg atcaactgaa ctgacttacc attcatggga taaaacatga tacaattctc 4020
agtatttgct tttctgttaa gagcttggaa tatgactgat gcttcagtgt cattttttta 4080
ttattgaata taaaattagg tgcaatagat acatttattg tagccttaag aaggaaatca 4140
atgctaagct gttgggcata aaactttaca gtaacattag ataacaagat aataaaacac 4200
tttaatttta atcgaccttt taagaatgat ctttattatt ctatccaaat caaggtagac 4260
ttcaaaattt atggtttgaa caggaagaaa gtagtgaata caaaattctt aaaattggtt 4320
catatgatca ttttttatt aatagcatgt gagactaagc tgaaccaaac tggccatata 4380
tgttaaatca aataatttga gtaattttga aatattgatg aagtagttaa atggttataa 4440

-continued

```
tatattttat tggtactttg aaatttaaac atctatatca cataataaag aaagtttttc   4500
atcaatctga aacaggcacc attaaattgg tgacacaaat attatcattt cacaaaagct   4560
tgagaaaacc agatttgaag tgaaataatt taggaagata ttaaaagtgg atgagaggac   4620
ataagatgta gtcaatcctt aacgcaatga taccattatt aggaaagagg aaaaatacca   4680
aacaagagaa aatttaaagg agcaaaaatt tgcaagtcaa atagaaatgc acaaatcgag   4740
agaacattta catttctatc acattgacat gaaaattgaa aatgtatagt cagagaaatt   4800
ttcatgaatt attccatgaa gtgttgtttc ctttatttaa aaagaatgct aggtaatctt   4860
agtagaaaac taaaaagtat gataaacaac agatggaaga attcatggaa aatagacgag   4920
aaaaagtaaa taaggctttc tggagatgac ggaaattttg tatgaataaa agccttataa   4980
acaatgaata catttggata aacaactcat taaaatgcac attaatggaa tacctgtaca   5040
aatagtttta atacttgtgt ccagtggcac taaagagata tattaaaata gattctggtt   5100
gagttgatta taagattgtc aatcatagga tacacaggga aagcacagac acgattgctc   5160
atctctttgg tagtctaaaa tatgttcctt ttaaccacat caaaagatac tatctgattc   5220
taatacagaa ggtgcaactt cctaggaatt atactttgta ttatattcaa taattatttt   5280
atgttttgca tcacatgggt gttgcaagaa cacagctctt aaactaaaaa ggcattacat   5340
taagaattta tttttgtaaa ttttaataaa ctctaaatta atgcaaaata tttatgaaaa   5400
tagcacagct tcacattaat acccacagta cttaaatatc tcccttagtt gactcacagc   5460
tttgtatgta agcttcaaat ttttaatggt aaaaataaga aaattaggac tagcgaactg   5520
ctagttgttc cctcagtgca tgtgcttgag cctaacagat ctttgtttga attagttact   5580
ttcaattaag cgaacatata atatttgtta aactgcttaa tctttccaga tctcactttg   5640
taaaatgacg tccaatcaac ctatttcaca tggttgttat gaagaattaa taataagata   5700
tgtaaaacca gcagcaccaa tagtgcctga caaaatataa ctgctcaata aataacagtg   5760
aattattata acaacagcta atggtattct attggaacac atggtctgtt tcttttccaa   5820
ttctgagtga tctcaacagc ctcacggcac attgaaaata aaagtcaact tcctcacctt   5880
ccccataggc catggacttt cccatctcta cccacttgtg cagtttctcc tctttcctct   5940
ctcctcctca gttactaaag caatcttcct tcaaacactt ctattttcca ttacatcact   6000
tcattcaggt tggtgatcag ctgcaacttc ctcagaaaga ccactgctgc ttccagtgac   6060
cctggctttg tcttgctttg tattagatta ctcagctccc tggtattatt gttgtcttta   6120
tcgcttatta gaatgtaacc cttaatgggc aagaaattgt cagtcttgtt catttatcat   6180
cgtataaaaa atgtttctag cacacagaaa gtgaccaata aatatttctg gaattaatgt   6240
a                                                                   6241
```

<210> SEQ ID NO 23
<211> LENGTH: 2601
<212> TYPE: DNA
<213> ORGANISM: Homo sapiens

<400> SEQUENCE: 23

```
gaggctcagc acagaaggag gaaggacagc agggccaaca gtcacagcag ccctgaccag     60
agcattcctg gagctcaagc tcctctacaa agaggtggac agagaagaca gcagagacca    120
tgggaccccc ctcagcccct ccctgcagat tgcatgtccc ctggaaggag gtcctgctca    180
cagcctcact tctaaccttc tggaacccac ccaccactgc caagctcact attgaatcca    240
cgccgttcaa tgtcgcagag gggaaggagg ttcttctact cgcccacaac ctgccccaga    300
```

```
atcgtattgg ttacagctgg tacaaaggcg aaagagtgga tggcaacagt ctaattgtag    360
gatatgtaat aggaactcaa caagctaccc cagggcccgc atacagtggt cgagagacaa    420
tataccccaa tgcatccctg ctgatccaga acgtcaccca gaatgacaca ggattctata    480
ccctacaagt cataaagtca gatcttgtga atgaagaagc aaccggacag ttccatgtat    540
acccggagct gcccaagccc tccatctcca gcaacaactc caaccccgtg gaggacaagg    600
atgctgtggc cttcacctgt gaacctgagg ttcagaacac aacctacctg tggtgggtaa    660
atggtcagag cctcccggtc agtcccaggc tgcagctgtc caatggcaac atgaccctca    720
ctctactcag cgtcaaaagg aacgatgcag gatcctatga atgtgaaata cagaacccag    780
cgagtgccaa ccgcagtgac ccagtcaccc tgaatgtcct ctatggccca gatgtcccca    840
ccatttcccc ctcaaaggcc aattaccgtc caggggaaaa tctgaacctc tcctgccacg    900
cagcctctaa cccacctgca cagtactctt ggtttatcaa tgggacgttc cagcaatcca    960
cacaagagct ctttatcccc aacatcactg tgaataatag cggatcctat atgtgccaag   1020
cccataactc agccactggc ctcaatagga ccacagtcac gatgatcaca gtctctggaa   1080
gtgctcctgt cctctcagct gtggccaccg tcggcatcac gattggagtg ctggccaggg   1140
tggctctgat atagcagccc tggtgtattt tcgatatttc aggaagactg gcagattgga   1200
ccagaccctg aattcttcta gctcctccaa tcccatttta tcccatggaa ccactaaaaa   1260
caaggtctgc tctgctcctg aagccctata tgctggagat ggacaactca atgaaaattt   1320
aaagggaaaa ccctcaggcc tgaggtgtgt gccactcaga gacttcacct aactagagac   1380
agtcaaactg caaaccatgg tgagaaattg acgacttcac actatggaca gcttttccca   1440
agatgtcaaa acaagactcc tcatcatgat aaggctctta ccccctttta atttgtcctt   1500
gcttatgcct gcctctttcg cttggcagga tgatgctgtc attagtattt cacaagaagt   1560
agcttcagag ggtaacttaa cagagtgtca gatctatctt gtcaatccca acgttttaca   1620
taaaataaga gatcctttag tgcacccagt gactgacatt agcagcatct ttaacacagc   1680
cgtgtgttca aatgtacagt ggtccttttc agagttggac ttctagactc acctgttctc   1740
actccctgtt ttaattcaac ccagccatgc aatgccaaat aatagaattg ctccctacca   1800
gctgaacagg gaggagtctg tgcagtttct gacacttgtt gttgaacatg gctaaataca   1860
atgggtatcg ctgagactaa gttgtagaaa ttaacaaatg tgctgcttgg ttaaaatggc   1920
tacactcatc tgactcattc tttattctat tttagttggt ttgtatcttg cctaaggtgc   1980
gtagtccaac tcttggtatt accctcctaa tagtcatact agtagtcata ctccctggtg   2040
tagtgtattc tctaaaagct ttaaatgtct gcatgcagcc agccatcaaa tagtgaatgg   2100
tctctctttg gctggaatta caaaactcag agaaatgtgt catcaggaga acatcataac   2160
ccatgaagga taaaagcccc aaatggtggt aactgataat agcactaatg ctttaagatt   2220
tggtcacact ctcacctagg tgagcgcatt gagccagtgg tgctaaatgc tacatactcc   2280
aactgaaatg ttaaggaaga agatagatcc aattaaaaaa aattaaaacc aatttaaaaa   2340
aaaaaagaac acaggagatt ccagtctact tgagttagca taatacagaa gtcccctcta   2400
ctttaacttt tacaaaaaag taacctgaac taatctgatg ttaaccaatg tatttatttc   2460
tgtggttctg tttccttgtt ccaatttgac aaaacccact gttcttgtat tgtattgccc   2520
agggggagct atcactgtac ttgtagagtg gtgctgcttt aattcataaa tcacaaataa   2580
aagccaatta gctctataac t                                             2601
```

<210> SEQ ID NO 24
<211> LENGTH: 6885
<212> TYPE: DNA
<213> ORGANISM: Homo sapiens

<400> SEQUENCE: 24
gacgacgttt gggagccttt gctgagtcca gggagagagg cgtcccccac cgtgccgctg 60
cagctcgggc agagccgcca agctttgggg tgctgaggaa cctctaatca tctcccatgg 120
atttgtgatc agcgttgcag ctctcccagc agccctggac agtggccccc agcagtcagc 180
atgtggctgc cgcgcgtctc cagcacagca gtgaccgcgc tcctcctggc gcagaccttc 240
ctcctcctct ttctggtttc ccggccaggg ccctcgtccc cagcaggcgg cgaggcgcgc 300
gtgcatgtgc tggtgctgtc ctcgtggcgc tcgggctcgt ccttcgtggg ccaactcttc 360
aaccagcacc ccgacgtctt ctacctaatg gagcccgcgt ggcacgtgtg gaccaccctg 420
tcgcagggca gcgccgcaac gctgcacatg gctgtgcgcg acctggtgcg ctccgtcttc 480
ctgtgcgaca tggacgtgtt tgatgcctat ctgccttggc gccgcaacct gtccgacctc 540
ttccagtggg ccgtgagccg tgcactgtgc tcgccacccg cctgcagtgc ctttccccga 600
ggcgccatca gcagcgaggc cgtgtgcaag ccactgtgcg cgcggcagtc cttcaccctg 660
gcccgggagg cctgccgctc ctacagccac gtggtgctca aggaggtgcg cttcttcaac 720
ctgcaggtgc tctacccgct gctcagcgac cccgcgctca acctacgcat cgtgcacctg 780
gtgcgcgacc cgcgggccgt gctgcgctcc cgggagcaga cagccaaggc tctggcgcgt 840
gacaacggca tcgtgctggg caccaacggc acgtgggtgg aggccgaccc cggcctgcgc 900
gtggtgcgcg aggtgtgccg tagccacgta cgcatcgccg aggccgccac actcaagccg 960 ccacccttc tgcgcggccg ctaccgcctg gtgcgcttcg aggacctggc gcgggagccg 1020
ctggcagaaa tccgtgcgct ctacgccttc actgggctca gtctcacgcc acagctcgag 1080
gcctggatcc ataacatcac ccacggatct ggacctggtg cgcgccgcga agccttcaag 1140
acttcgtcca ggaatgcgct caacgtctcc caggcctggc gccatgcgct gccctttgcc 1200
aagatccgcc gcgtgcagga actgtgcgct ggtgcgctgc agctgctggg ctaccggcct 1260
gtgtactctg aggacgagca gcgcaacctc gcccttgatc tggtgctgcc acgaggcctg 1320
aacggcttca cttgggcatc atccaccgcc tcgcaccccc gaaattagtg gaggccacag 1380
ttgtagcagg cgctaggccc gggaggagag tgcatggtgc agagggggct ggggcgcacg 1440
gagaagcagg tccctatatt gaccaaggag tttgtggtac gacccctccc cctccccaag 1500
taggcaagga ctgcacgttt ctttctctct tgattcttgg ttttcctttg agtcctctgg 1560
agctgccttc tcatcaggtg cactcttcat ggaaagcaac tcttgcccct cctcctctgg 1620
gcacagggtg tgcgttcaga tgacttggct cctactcaag ggctttcttc ccctttaact 1680
ctctccttct ggtgacacat cctgcagcag ctgagggggt gccctggcac tggctgggag 1740
tggagaggca ctgtggtgaa atggctccag aggtctgtac atcacataca tatgcacaca 1800
ggcacacatg gcaaaactcg gaagtgaaag gacttgtctg aaatcacatg gtgagaagga 1860
ggatgaaggg aggagagagc ttttgctctg ggtctccagt ggataggaga ggacctgcct 1920
cctgggtgag aagggtcaga ttttcctatt ttaattgctt tagggaagag caagcagagt 1980
catgaccagg gacacagctg agagatagag gaggctgtga atgctgagac cagagtttat 2040
catgctggac aagcctggaa ggaggcaata agtgggaaag gtaggaggag agaaggctgg 2100
ggagggctgg gcagcaagcc aggcacagtg agtggcagag caagaggggg aaagcaggat 2160
cagtgcctgg aaggcaggtg tgcccgtcag cggggagtgg aactcatcag gcttgccaag 2220
aggttggaag ggaaatggct ctgggctgga actgtcttcc cttggtcctt ctggtccagg 2280
ccttggagga aagcagagga tgatccctgc ctgtgagcca cacctcctag ctctgggggc 2340
aaaggggctt agtaaaggaa tgctggatgt gtagagggtt tagtcccgag ctcaggaaat 2400
gagagcctat aagtgcccag tacatgttta aaagaagagc tcatggaacc tctggaaagg 2460
acagggaagt tgagttagcc acataaatga acccaagtca cattggaaca cagagctggt 2520
ctgggaactg tgttggctgc caacagaact tctgaccctg ttacctgtga aatgaggcag 2580
tttccctcac gttgccatca gctaccagga gcgatgctgg tggtcactag cttctgatcc 2640
tcatcctggg tgtggccaca gattggggga acctggattg tggagtcaca tcctccctgc 2700
aaagcaagca gggcaaggga gatctggcat tttctgcttt acgtggaggg agaacaggca 2760
cattagcctt gaagctgaag ctcattttag gttccttcca ggtttagaag cttcaaccaa 2820
atgaaacttg aatctgtccc tcgtgacaat tataggagga aggtatttaa aaccccagat 2880
ttatgaatgt gtactacatg gcttagagaa tgtctttgtt cttgttcagg tggttataac 2940
aaaatacctt aagagtgggt aacttggctg gatgcagtgg ctcatgcctg taatcccagc 3000
actgtgggag gccgaggggg atgaatcacc tgaggtcagg cattcaagaa cagcctggcc 3060
aacatggcga agcccctcct ctactaaaaa tacaaaatta gcgaggcatg gtcgcacata 3120
cctgtaatcc cagctcctcg ggaagctgag gcaggagaat cgcttgaacc caggaggcgg 3180
aggttgcagt gagccaagat cacgccattg cactccagcc tgggtgacag agcaagactc 3240
catctcaaaa aaaaaaaaaa gactgggtaa cttataaaca aatgttcttc tcacaagtct 3300
ggagactggg aagtccaaga tcaagccacc agtgctgtct gatgagggcc cactttttca 3360
aagacagtgc cttctagctg tgtcctctta tcgtagaaga tgggagacag ctctccaggg 3420
ccattttttt tttttttttt tttttttga gatggagtct ggctctgtcg cccaggctgg 3480
agtgcagtgg cacaatctcg gctcactgca acctctgcct ctctctgcct cctgagttca 3540
agcaattctc ctgcctcagc ctcctgagga gctgggacta cagggatgca ccaccatgcc 3600
cagctaattt ttgtattttt gtagacactg ggtttcacca tattggccag gttggtctca 3660
aactcctgac ctcaagtgat ctgcccacct cagcctccca aagtgctgag attacaggca 3720
tgagccactg tacccagtct ccagggcctt ttaaagaatg tcactaatcc cattcttgag 3780
gtctccacct tcattatcta atcacctccc aaaggctcca catcccaaca ccatcatatt 3840
gtgggttaag atttcaacca caagccaggc gtggtggctc atgcctgtaa tcccagcatt 3900
ttggaaggct gaggcaggtg gatcacttga ggtcaggagt ttgagaccag cctggccaac 3960
atggtgaaac cccatctcta ctaaaaataa aaaaaattag ccgggtgtgg tggtgcacac 4020
ctgtaattcc agctactcag gaggctgagg caggagaatc ccttgaatcc aggaggcgga 4080
cagtgcagtg agccgagata atgccactgc actccagcct ggatgacaga gcaagactcc 4140
atctcatgcc cagccagcat gcccaacaag cttcatttgc ccctgtttag gtcacaaatt 4200
ttattgatgg ctgcaattaa tggcctcttg gtatccaagt cctttgttgt atgacccatc 4260
cattctcccc tgactcccaa ggtgtcagga catgcttgac tggctcctga atttgctctc 4320
tgcgcatggg cagtacagtc aagcctcaca gtgaacccag gtcagctttc aggacaaaga 4380
aagtggcctg gctgactagg cacagtaaag ccagggctgg gtaggtacat acttgtgctg 4440
atcacgtatg tcttatatct ctgtgagagt gcagtcccaa caggaaggtt taatcactgg 4500

-continued

```
ggactgccca atgctgtgac agggcacaga gctctgggtt gctgtggggg tgactgcatt   4560
gaccactgtt agtggtttgc tgtgttgaca ctctgtgctg tgtgaccatg gctcctgcca   4620
tcaagaagta gagtctgttt ctccacctct gaatccaggc tggtcctgtg acttgctttg   4680
tcctgtagac aagtgtagtg caacttcctg tgagccagtt tgaagcatag gccttggaag   4740
caaaacttta cctccacctg tcttaggttt tcagctgggg ctctgctgtg atttgattgt   4800
gtctcccaaa gttggaacct tgatccccag tgttgtgagg tgaggcttga tggaaagtaa   4860
attacgccgt gcgggttatg cccttgtgaa tgggtagaga acattatttc tgggcgcagg   4920
catggtagct catgtctgta atcccagcat tttgggaggt tgaggtgtgc ggattacttg   4980
aggtcaggag tttgagacca gcctggccaa caaggtaaaa caccatttct agttaaaata   5040
caaaaattag ccaggtgtgg tggcacatgc ctgtaaggcc agctacttgg gaggctgaga   5100
caggagaatc gcttgaaccc aggaggcaga gattgcagtg agctgagatc gcaccactgt   5160
actccagcct gggcaacaaa gcgagagtct gtcttaaaaa aaaccaccat tatttcagga   5220
gtgagttggt tatcctgaga gtggtgcctt ttaaatgaag gagttcattc tttgtctttc   5280
tctcgccctc actttgccct tctgccatat gatgccttcc atcatgctag gacacagcaa   5340
gaaggctctc gctagatgct ggctccttga tcttgggctt cccagcctcc agaactgtaa   5400
gccaatacac ttctatttat tatatatgac ccttgctggg ttcagtggct cacgcctgta   5460
atcccaatac tttgcaaggc tgaggcagga ggatcacttg agaccaggca ctcaagacca   5520
gcctgggcaa catagtgaga ccccatctct acaaagttaa aaaaaaatta gcagggcatg   5580
gtgtcgtgca cctgtagtcc tagctacttg ggaggctgag ttgggaggac tgcttgaccc   5640
tgggaggttg aggctacatt gaaccatgat catgccagtg cactccagcc tgagtgacag   5700
agcaagacac ctatctctaa ataaatgacc ccatctgtgg tattgttata gcaaaacaaa   5760
acagattaag agagactttt taatgaaaag acagattcac aaagaaaaac aatgtttttg   5820
tttctgtttt tttgaggcag agtcttgctc ttgtccccca ggctggagtg cagtggcgcc   5880
atcttggctc actgcaacct ccgcctccca gtttcaagcg attctcctgc ctcagcctcc   5940
cgagtagctg ggattacaga tgtacaccac cacgcccggc taattttttt tgtattttta   6000
gtagagatgg ggtttcacca tgtcgatcag gctgggctgg aactcctgac ctcaggtgat   6060
ccacctgcct tggcctccca atgtgctagg attacaggca tgagccactg tacctggcga   6120
aaaacagttt gttaacacag gcagccaaca tcactcagga taagcctcaa tgaaaagtaa   6180
caaagtgatg gcttggaaca ctgtcttaca cagcattttt aaaaaataca ataaatttgt   6240
agagatagga tgaccaagga caacagtttt aggcttccaa aggtggtaaa ctatgggatg   6300
gtaaatatcc gagaggaagc tgatgcaaca ggatttgtct gcagcagcct ctggtaccac   6360
ctctgagtca agggttgtgt ccagtgatgg agagtttata tcgtgccttt aggcagaaaa   6420
ggggagggaa acctgaactt ttcctgcact ttctgcttct taattgcctt cagctgaaaa   6480
tcattttta tgtgaaaaag gcatagtctg agctgacgcc tctgctttcc tccacctgaa   6540
gagaacctgc gtgctgctcc tttgcttcgg acctccgcct ctgcccggga gaaagcccag   6600
gccagcctgc tggacaagca gagaccatga gaaggagagt tcaggggtcc caaaccaggc   6660
catcctagac cagccagctc cagctgatcc gcacgcagcc acttcggcta ccttctactg   6720
gccaaaggga gtcccagggc tcacccagat tcagaggtgg ggaaactgag tccaccactt   6780
gagaagagta gctataaaga catatgagcg aggccagctg agcccagcac tgcggccaag   6840
tcgaagactt taggagcaat aaaagtgctt attgtgtttc agtca                    6885
```

<210> SEQ ID NO 25
<211> LENGTH: 1174
<212> TYPE: DNA
<213> ORGANISM: Homo sapiens

<400> SEQUENCE: 25
aatgtccatt agcataaccc ttcctcagga agagtgagat tttatatttg acaataaagt 60
gttagactcc atttctaaat accagacttc aaaagataag gttcaaaagt gttataagaa 120
gatattcctt tttttgtcct agagaactta ttttcctgtg aaaatgccta ccacaaagaa 180
gacattgatg ttcttatcaa gctttttcac cagccttggg tccttcattg taatttgctc 240
tattcttggg acacaagcat ggatcaccag tacaattgct gttagagact ctgcttcaaa 300
tgggagcatt ttcatcactt acggactttt tcgtggggag agtagtgaag aattgagtca 360
cggacttgca gaaccaaaga aaaagtttgc agttttagag atactgaata attcttccca 420
aaaaactctg cattcggtga ctatcctgtt cctggtcctg agtttgatca cgtcgctgct 480
gagctctggg tttaccttct acaacagcat cagcaaccct taccagacat tcctggggcc 540
gacgggggtg tacacctgga acgggctcgg tgcatccttc gtttttgtga ccatgatact 600
gtttgtggcg aacacgcagt ccaaccaact ctccgaagag ttgttccaaa tgctttaccc 660
ggcaaccacc agtaaaggaa cgacccacag ttacggatac tcgttctggc tcatactgct 720
cgtcattctt ctaaatatag tcactgtaac catcatcatt ttctaccaga aggccagata 780
ccagcggaag caggagcaga gaaagccaat ggaatatgct ccaagggacg gaattttatt 840
ctgaattctc tttcatctca ttttggcgtt gcatctattg tacatcagcc ctgagtagta 900
actggttagc ttctctggac aattcagcat ggtaacgtga ctgtcatctg tgacagcatt 960
tgtgtttcat gacactgtgt tcttcattga tgctgtactc ctgaaaattt ttcccacaag 1020
gttggggaaa tgaatgggaa atgtcgctgg tctgtgtggt attcaaagca gtagtatcat 1080
gatgagcgta acgacccttc tgacctggtc tcacgatctg aaataataaa aggctgtgtc 1140
atgcaaaaaa aaaaaaaaaa aaaaaaaaaa aaaa 1174

<210> SEQ ID NO 26
<211> LENGTH: 5927
<212> TYPE: DNA
<213> ORGANISM: Homo sapiens

<400> SEQUENCE: 26
tcgtcggagc agacgggagt ttctcctcgg ggtcggagca ggaggcacgc ggagtgtgag 60
gccacgcatg agcggacgct aaccccctcc ccagccacaa agagtctaca tgtctagggt 120
ctagacatgt tcagctttgt ggacctccgg ctcctgctcc tcttagcggc caccgccctc 180
ctgacgcacg gccaagagga aggccaagtc gagggccaag acgaagacat cccaccaatc 240
acctgcgtac agaacggcct caggtaccat gaccgagacg tgtggaaacc cgagccctgc 300
cggatctgcg tctgcgacaa cggcaaggtg ttgtgcgatg acgtgatctg tgacgagacc 360
aagaactgcc ccggcgccga agtccccgag ggcgagtgct gtcccgtctg ccccgacggc 420
tcagagtcac ccaccgacca agaaaccacc ggcgtcgagg gacccaaggg agacactggc 480
ccccgaggcc caaggggacc cgcaggcccc cctggccgag atggcatccc tggacagcct 540
ggacttcccg gacccccgg accccccgga cctcccggac cccctggcct cggaggaaac 600
tttgctcccc agctgtctta tggctatgat gagaaatcaa ccggaggaat ttccgtgcct 660

-continued

```
ggccccatgg gtccctctgg tcctcgtggt ctccctggcc cccctggtgc acctggtccc    720
caaggcttcc aaggtccccc tggtgagcct ggcgagcctg gagcttcagg tcccatgggt    780
ccccgaggtc cccaggtcc ccctggaaag aatggagatg atggggaagc tggaaaacct    840
ggtcgtcctg gtgagcgtgg gcctcctggg cctcagggtg ctcgaggatt gcccggaaca    900
gctggcctcc ctggaatgaa gggacacaga ggtttcagtg gtttggatgg tgccaaggga    960
gatgctggtc ctgctggtcc taagggtgag cctggcagcc ctggtgaaaa tggagctcct   1020
ggtcagatgg gcccccgtgg cctgcctggt gagagaggtc gccctggagc ccctggccct   1080
gctggtgctc gtggaaatga tggtgctact ggtgctgccg ggccccctgg tcccaccggc   1140
cccgctggtc ctcctggctt ccctggtgct gttggtgcta agggtgaagc tggtccccaa   1200
gggccccgag gctctgaagg tccccagggt gtgcgtggtg agcctggccc ccctggccct   1260
gctggtgctg ctggccctgc tggaaaccct ggtgctgatg gacagcctgg tgctaaaggt   1320
gccaatggtg ctcctggtat tgctggtgct cctggcttcc ctggtgcccg aggcccctct   1380
ggaccccagg gccccggcgg ccctcctggt cccaagggta acagcggtga acctggtgct   1440
cctggcagca aaggagacac tggtgctaag ggagagcctg gccctgttgg tgttcaagga   1500
ccccctggcc ctgctggaga ggaaggaaag cgaggagctc gaggtgaacc cggacccact   1560
ggcctgcccg gacccctgg cgagcgtggt ggacctggta gccgtggttt ccctggcgca   1620
gatggtgttg ctggtcccaa gggtcccgct ggtgaacgtg gttctcctgg ccctgctggc   1680
cccaaaggat ctcctggtga agctggtcgt cccggtgaag ctggtctgcc tggtgccaag   1740
ggtctgactg gaagccctgg cagccctggt cctgatggca aaactggccc ccctggtccc   1800
gccggtcaag atggtcgccc cggaccccca ggcccacctg gtgcccgtgg tcaggctggt   1860
gtgatgggat tccctggacc taaaggtgct gctggagagc ccggcaaggc tggagagcga   1920
ggtgttcccg gacccctgg cgctgtcggt cctgctggca aagatggaga ggctggagct   1980
cagggacccc ctggccctgc tggtcccgct ggcgagagag gtgaacaagg ccctgctggc   2040
tcccccggat tccagggtct ccctggtcct gctggtcctc caggtgaagc aggcaaacct   2100
ggtgaacagg gtgttcctgg agaccttggc gcccctggcc cctctggagc aagaggcgag   2160
agaggtttcc ctggcgagcg tggtgtgcaa ggtcccctg gtcctgctgg tccccgaggg   2220
gccaacggtg ctcccggcaa cgatggtgct aagggtgatg ctggtgcccc tggagctccc   2280
ggtagccagg gcgcccctgg ccttcaggga atgcctggtg aacgtggtgc agctggtctt   2340
ccagggccta agggtgacag aggtgatgct ggtcccaaag gtgctgatgg ctctcctggc   2400
aaagatggcg tccgtggtct gactggcccc attggtcctc ctggccctgc tggtgcccct   2460
ggtgacaagg gtgaaagtgg tcccagcggc cctgctggtc ccactggagc tcgtggtgcc   2520
cccggagacc gtggtgagcc tggtccccc ggccctgctg gctttgctgg ccccctggt   2580
gctgacggcc aacctggtgc taaaggcgaa cctggtgatg ctggtgctaa aggcgatgct   2640
ggtcccctg gccctgccgg acccgctgga cccctggcc ccattggtaa tgttggtgct   2700
cctggagcca aaggtgctcg cggcagcgct ggtccccctg gtgctactgg tttccctggt   2760
gctgctggcc gagtcggtcc tcctggcccc tctggaaatg ctggaccccc tggccctcct   2820
ggtcctgctg gcaaagaagg cggcaaaggt ccccgtggtg agactggccc tgctggacgt   2880
cctggtgaag ttggtcccc tggtcccct ggccctgctg gcgagaaagg atcccctggt   2940
gctgatggtc ctgctggtgc tcctggtact cccgggcctc aaggtattgc tggacagcgt   3000
ggtgtggtcg gcctgcctgg tcagagagga gagagaggct tccctggtct tcctggcccc   3060
```

```
tctggtgaac ctggcaaaca aggtccctct ggagcaagtg gtgaacgtgg tccccctggt   3120
cccatgggcc cccctggatt ggctggaccc cctggtgaat ctggacgtga gggggctcct   3180
ggtgccgaag gttcccctgg acgagacggt tctcctggcg ccaagggtga ccgtggtgag   3240
accggccccg ctggaccccc tggtgctcct ggtgctcctg gtgcccctgg ccccgttggc   3300
cctgctggca agagtggtga tcgtggtgag actggtcctg ctggtcccgc cggtcctgtc   3360
ggccctgttg gcgcccgtgg ccccgccgga ccccaaggcc cccgtggtga caagggtgag   3420
acaggcgaac agggcgacag aggcataaag ggtcaccgtg gcttctctgg cctccagggt   3480
ccccctggcc ctcctggctc tcctggtgaa caaggtccct ctggagcctc tggtcctgct   3540
ggtccccgag gtcccccctgg ctctgctggt gctcctggca aagatggact caacggtctc   3600
cctggcccca ttgggccccc tggtcctcgc ggtcgcactg gtgatgctgg tcctgttggt   3660
ccccccggcc ctcctggacc tcctggtccc cctggtcctc ccagcgctgg tttcgacttc   3720
agcttcctgc cccagccacc tcaagagaag gctcacgatg gtggccgcta ctaccgggct   3780
gatgatgcca atgtggttcg tgaccgtgac ctcgaggtgg acaccaccct caagagcctg   3840
agccagcaga tcgagaacat ccggagccca gagggcagcc gcaagaaccc cgcccgcacc   3900
tgccgtgacc tcaagatgtg ccactctgac tggaagagtg gagagtactg gattgacccc   3960
aaccaaggct gcaacctgga tgccatcaaa gtcttctgca acatggagac tggtgagacc   4020
tgcgtgtacc ccactcagcc cagtgtggcc cagaagaact ggtacatcag caagaacccc   4080
aaggacaaga ggcatgtctg gttcggcgag agcatgaccg atggattcca gttcgagtat   4140
ggcggccagg gctccgaccc tgccgatgtg gccatccagc tgaccttcct gcgcctgatg   4200
tccaccgagg cctcccagaa catcacctac cactgcaaga acagcgtggc ctacatggac   4260
cagcagactg gcaacctcaa gaaggccctg ctcctccagg gctccaacga gatcgagatc   4320
cgcgccgagg gcaacagccg cttcacctac agcgtcactg tcgatggctg cacgagtcac   4380
accggagcct ggggcaagac agtgattgaa tacaaaacca ccaagacctc ccgcctgccc   4440
atcatcgatg tggccccctt ggacgttggt gccccagacc aggaattcgg cttcgacgtt   4500
ggccctgtct gcttcctgta aactccctcc atcccaacct ggctccctcc cacccaacca   4560
actttccccc caacccggaa acagacaagc aacccaaact gaaccccctc aaaagccaaa   4620
aaatgggaga caatttcaca tggactttgg aaaatatttt tttcctttgc attcatctct   4680
caaacttagt ttttatcttt gaccaaccga acatgaccaa aaaccaaaag tgcattcaac   4740
cttaccaaaa aaaaaaaaaa aaaaagaata aataaataac tttttaaaaa aggaagcttg   4800
gtccacttgc ttgaagaccc atgcgggggt aagtcccttt ctgcccgttg ggcttatgaa   4860
accccaatgc tgccctttct gctcctttct ccacaccccc cttggggcct cccctccact   4920
ccttcccaaa tctgtctccc cagaagacac aggaaacaat gtattgtctg cccagcaatc   4980
aaaggcaatg ctcaaacacc caagtggccc ccaccctcag cccgctcctg cccgcccagc   5040
acccccaggc cctgggggac ctggggttct cagactgcca aagaagcctt gccatctggc   5100
gctcccatgg ctcttgcaac atctcccctt cgtttttgag gggtcatgc cgggggagcc   5160
accagcccct cactgggttc ggaggagagt caggaagggc cacgacaaag cagaaacatc   5220
ggatttgggg aacgcgtgtc aatcccttgt gccgcagggc tgggcgggag agactgttct   5280
gttccttgtg taactgtgtt gctgaaagac tacctcgttc ttgtcttgat gtgtcaccgg   5340
ggcaactgcc tgggggcggg gatgggggca gggtggaagc ggctccccat tttataccaa   5400
```

```
aggtgctaca tctatgtgat gggtggggtg gggagggaat cactggtgct atagaaattg   5460

agatgccccc ccaggccagc aaatgttcct ttttgttcaa agtctatttt tattccttga   5520

tatttttctt tttttttttt tttttttgtg gatggggact tgtgaatttt tctaaaggtg   5580

ctatttaaca tgggaggaga gcgtgtgcgg ctccagccca gcccgctgct cactttccac   5640

cctctctcca cctgcctctg gcttctcagg cctctgctct ccgacctctc tcctctgaaa   5700

ccctcctcca cagctgcagc ccatcctccc ggctccctcc tagtctgtcc tgcgtcctct   5760

gtccccgggt ttcagagaca acttcccaaa gcacaaagca gtttttcccc ctaggggtgg   5820

gaggaagcaa aagactctgt acctattttg tatgtgtata ataatttgag atgtttttaa   5880

ttattttgat tgctggaata aagcatgtgg aaatgaccca aacataa                5927
```

<210> SEQ ID NO 27
<211> LENGTH: 5411
<212> TYPE: DNA
<213> ORGANISM: Homo sapiens

<400> SEQUENCE: 27

```
gtgtcccata gtgtttccaa acttggaaag ggcgggggag ggcgggagga tgcggagggc     60

ggaggtatgc agacaacgag tcagagtttc cccttgaaag cctcaaaagt gtccacgtcc    120

tcaaaaagaa tggaaccaat ttaagaagcc agccccgtgg ccacgtccct tcccccattc    180

gctccctcct ctgcgccccc gcaggctcct cccagctgtg gctgcccggg cccccagccc    240

cagccctccc attggtggag gcccttttgg aggcacccta gggccaggga aacttttgcc    300

gtataaatag ggcagatccg ggctttatta ttttagcacc acggcagcag gaggtttcgg    360

ctaagttgga ggtactggcc acgactgcat gcccgcgccc gccaggtgat acctccgccg    420

gtgacccagg ggctctgcga cacaaggagt ctgcatgtct aagtgctaga catgctcagc    480

tttgtggata cgcggacttt gttgctgctt gcagtaacct tatgcctagc aacatgccaa    540

tctttacaag aggaaactgt aagaaagggc ccagccggag atagaggacc acgtggagaa    600

aggggtccac caggcccccc aggcagagat ggtgaagatg gtcccacagg ccctcctggt    660

ccacctggtc ctcctggccc ccctggtctc ggtgggaact ttgctgctca gtatgatgga    720

aaaggagttg gacttggccc tggaccaatg ggcttaatgg gacctagagg cccacctggt    780

gcagctggag ccccaggccc tcaaggtttc caaggacctg ctggtgagcc tggtgaacct    840

ggtcaaactg gtcctgcagg tgctcgtggt ccagctggcc ctcctggcaa ggctggtgaa    900

gatggtcacc ctggaaaacc cggacgacct ggtgagagag gagttgttgg accacagggt    960

gctcgtggtt tccctggaac tcctggactt cctggcttca aaggcattag gggacacaat   1020

ggtctggatg gattgaaggg acagcccggt gctcctggtg tgaagggtga acctggtgcc   1080

cctggtgaaa atggaactcc aggtcaaaca ggagcccgtg ggcttcctgg tgagagagga   1140

cgtgttggtg cccctggccc agctggtgcc cgtggcagtg atggaagtgt gggtcccgtg   1200

ggtcctgctg gtcccattgg gtctgctggc cctccaggct tcccaggtgc ccctggcccc   1260

aagggtgaaa ttggagctgt tggtaacgct ggtcctgctg gtcccgccgg tccccgtggt   1320

gaagtgggtc ttccaggcct ctccggcccc gttggacctc ctggtaatcc tggagcaaac   1380

ggccttactg gtgccaaggg tgctgctggc cttcccggcg ttgctggggc tcccggcctc   1440

cctggacccc gcggtattcc tggccctgtt ggtgctgccg gtgctactgg tgccagagga   1500

cttgttggtg agcctggtcc agctggctcc aaaggagaga gcggtaacaa gggtgagccc   1560

ggctctgctg ggccccaagg tcctcctggt cccagtggtg aagaaggaaa gagaggccct   1620
```

aatggggaag ctggatctgc cggccctcca ggacctcctg ggctgagagg tagtcctggt 1680
tctcgtggtc ttcctggagc tgatggcaga gctggcgtca tgggccctcc tggtagtcgt 1740
ggtgcaagtg gccctgctgg agtccgagga cctaatggag atgctggtcg ccctggggag 1800
cctggtctca tgggacccag aggtcttcct ggttcccctg gaaatatcgg ccccgctgga 1860
aaagaaggtc ctgtcggcct ccctggcatc gacggcaggc ctggcccaat tggcccagct 1920
ggagcaagag gagagcctgg caacattgga ttccctggac ccaaaggccc cactggtgat 1980
cctggcaaaa acggtgataa aggtcatgct ggtcttgctg gtgctcgggg tgctccaggt 2040
cctgatggaa acaatggtgc tcagggacct cctggaccac agggtgttca aggtggaaaa 2100
ggtgaacagg gtccccctgg tcctccaggc ttccagggtc tgcctggccc ctcaggtccc 2160
gctggtgaag ttggcaaacc aggagaaagg ggtctccatg gtgagtttgg tctccctggt 2220
cctgctggtc caagagggga acgcggtccc ccaggtgaga gtggtgctgc cggtcctact 2280
ggtcctattg gaagccgagg tccttctgga cccccagggc ctgatggaaa caagggtgaa 2340
cctggtgtgg ttggtgctgt gggcactgct ggtccatctg gtcctagtgg actcccagga 2400
gagaggggtg ctgctggcat acctggaggc aagggagaaa agggtgaacc tggtctcaga 2460
ggtgaaattg gtaaccctgg cagagatggt gctcgtggtg ctcctggtgc tgtaggtgcc 2520
cctggtcctg ctggagccac aggtgaccgg ggcgaagctg gggctgctgg tcctgctggt 2580
cctgctggtc ctcggggaag ccctggtgaa cgtggtgagg tcggtcctgc tggccccaat 2640
ggatttgctg gtcctgctgg tgctgctggt caacctggtg ctaaaggaga aagaggagcc 2700
aaagggccta agggtgaaaa cggtgttgtt ggtcccacag gccccgttgg agctgctggc 2760
ccagctggtc caaatggtcc ccccggtcct gctggaagtc gtggtgatgg aggcccccct 2820
ggtatgactg gtttccctgg tgctgctgga cggactggtc ccccaggacc ctctggtatt 2880
tctggccctc ctggtccccc tggtcctgct gggaaagaag ggcttcgtgg tcctcgtggt 2940
gaccaaggtc cagttggccg aactggagaa gtaggtgcag ttggtccccc tggcttcgct 3000
ggtgagaagg gtccctctgg agaggctggt actgctggac ctcctggcac tccaggtcct 3060
cagggtcttc ttggtgctcc tggtattctg ggtctccctg gctcgagagg tgaacgtggt 3120
ctaccaggtg ttgctggtgc tgtgggtgaa cctggtcctc ttggcattgc cggccctcct 3180
ggggcccgtg gtcctcctgg tgctgtgggt agtcctggag tcaacggtgc tcctggtgaa 3240
gctggtcgtg atggcaaccc tgggaacgat ggtcccccag gtcgcgatgg tcaacccgga 3300
cacaagggag agcgcggtta ccctggcaat attggtcccg ttggtgctgc aggtgcacct 3360
ggtcctcatg gccccgtggg tcctgctggc aaacatggaa accgtggtga aactggtcct 3420
tctggtcctg ttggtcctgc tggtgctgtt ggcccaagag gtcctagtgg cccacaaggc 3480
attcgtggcg ataagggaga gcccggtgaa aaggggccca gaggtcttcc tggcttaaag 3540
ggacacaatg gattgcaagg tctgcctggt atcgctggtc accatggtga tcaaggtgct 3600
cctggctccg tgggtcctgc tggtcctagg ggccctgctg gtccttctgg ccctgctgga 3660
aaagatggtc gcactggaca tcctggtaca gttggacctg ctggcattcg aggccctcag 3720
ggtcaccaag gccctgctgg cccccctggt ccccctggcc ctcctggacc tccaggtgta 3780
agcggtggtg gttatgactt tggttacgat ggagacttct acagggctga ccagcctcgc 3840
tcagcacctt ctctcagacc caaggactat gaagttgatg ctactctgaa gtctctcaac 3900
aaccagattg agacccttct tactcctgaa ggctctagaa agaacccagc tcgcacatgc 3960
cgtgacttga gactcagcca cccagagtgg agcagtggtt actactggat tgaccctaac 4020
caaggatgca ctatggatgc tatcaaagta tactgtgatt tctctactgg cgaaacctgt 4080
atccgggccc aacctgaaaa catcccagcc aagaactggt ataggagctc caaggacaag 4140
aaacacgtct ggctaggaga aactatcaat gctggcagcc agtttgaata taatgtagaa 4200
ggagtgactt ccaaggaaat ggctacccaa cttgccttca tgcgcctgct ggccaactat 4260
gcctctcaga acatcaccta ccactgcaag aacagcattg catacatgga tgaggagact 4320
ggcaacctga aaaaggctgt cattctacag ggctctaatg atgttgaact tgttgctgag 4380
ggcaacagca ggttcactta cactgttctt gtagatggct gctctaaaaa gacaaatgaa 4440
tggggaaaga caatcattga atacaaaaca aataagccat cacgcctgcc cttccttgat 4500
attgcacctt tggacatcgg tggtgctgac caggaattct ttgtggacat tggcccagtc 4560
tgtttcaaat aaatgaactc aatctaaatt aaaaaagaaa gaaatttgaa aaaactttct 4620
ctttgccatt tcttcttctt cttttttaac tgaaagctga atccttccat ttcttctgca 4680
catctacttg cttaaattgt gggcaaaaga gaaaaagaag gattgatcag agcattgtgc 4740
aatacagttt cattaactcc ttcccccgct cccccaaaaa tttgaatttt tttttcaaca 4800
ctcttacacc tgttatggaa aatgtcaacc tttgtaagaa aaccaaaata aaaattgaaa 4860
aataaaaacc ataaacattt gcaccacttg tggcttttga atatcttcca cagagggaag 4920
tttaaaaccc aaacttccaa aggtttaaac tacctcaaaa cactttccca tgagtgtgat 4980
ccacattgtt aggtgctgac ctagacagag atgaactgag gtccttgttt tgttttgttc 5040
ataatacaaa ggtgctaatt aatagtattt cagatacttg aagaatgttg atggtgctag 5100
aagaatttga gaagaaatac tcctgtattg agttgtatcg tgtggtgtat tttttaaaaa 5160
atttgattta gcattcatat tttccatctt attcccaatt aaaagtatgc agattatttg 5220
cccaaatctt cttcagattc agcatttgtt ctttgccagt ctcattttca tcttcttcca 5280
tggttccaca gaagctttgt ttcttgggca agcagaaaaa ttaaattgta cctattttgt 5340
atatgtgaga tgtttaaata aattgtgaaa aaaatgaaat aaagcatgtt tggttttcca 5400
aaagaacata t 5411

<210> SEQ ID NO 28
<211> LENGTH: 5490
<212> TYPE: DNA
<213> ORGANISM: Homo sapiens

<400> SEQUENCE: 28
ggctgagttt tatgacgggc ccggtgctga agggcaggga acaacttgat ggtgctactt 60
tgaactgctt ttcttttctc ctttttgcac aaagagtctc atgtctgata tttagacatg 120
atgagctttg tgcaaaaggg gagctggcta cttctcgctc tgcttcatcc cactattatt 180
ttggcacaac aggaagctgt tgaaggagga tgttcccatc ttggtcagtc ctatgcggat 240
agagatgtct ggaagccaga accatgccaa atatgtgtct gtgactcagg atccgttctc 300
tgcgatgaca taatatgtga cgatcaagaa ttagactgcc ccaacccaga aattccattt 360
ggagaatgtt gtgcagtttg cccacagcct ccaactgctc ctactcgccc tcctaatggt 420
caaggacctc aaggccccaa gggagatcca ggccctcctg gtattcctgg gagaaatggt 480
gaccctggta ttccaggaca accagggtcc cctggttctc ctggcccccc tggaatctgt 540
gaatcatgcc ctactggtcc tcagaactat tctccccagt atgattcata tgatgtcaag 600
tctggagtag cagtaggagg actcgcaggc tatcctggac cagctggccc cccaggccct 660

```
cccggtcccc ctggtacatc tggtcatcct ggttcccctg gatctccagg ataccaagga    720
cccccctggtg aacctgggca agctggtcct tcaggccctc caggacctcc tggtgctata    780
ggtccatctg gtcctgctgg aaaagatgga gaatcaggta gacccggacg acctggagag    840
cgaggattgc ctggacctcc aggtatcaaa ggtccagctg ggatacctgg attccctggt    900
atgaaaggac acagaggctt cgatggacga aatggagaaa agggtgaaac aggtgctcct    960
ggattaaagg gtgaaaatgg tcttccaggc gaaaatggag ctcctggacc catgggtcca   1020
agaggggctc ctggtgagcg aggacggcca ggacttcctg gggctgcagg tgctcggggt   1080
aatgacggtg ctcgaggcag tgatggtcaa ccaggccctc ctggtcctcc tggaactgcc   1140
ggattccctg gatcccctgg tgctaagggt gaagttggac ctgcagggtc tcctggttca   1200
aatggtgccc ctggacaaag aggagaacct ggacctcagg gacacgctgg tgctcaaggt   1260
cctcctggcc ctcctgggat taatggtagt cctggtggta aaggcgaaat gggtcccgct   1320
ggcattcctg gagctcctgg actgatggga gcccggggtc ctccaggacc agccggtgct   1380
aatggtgctc ctggactgcg aggtggtgca ggtgagcctg gtaagaatgg tgccaaagga   1440
gagcccggac cacgtggtga acgcggtgag gctggtattc caggtgttcc aggagctaaa   1500
ggcgaagatg gcaaggatgg atcacctgga gaacctggtg caaatgggct tccaggagct   1560
gcaggagaaa ggggtgcccc tgggttccga ggacctgctg gaccaaatgg catcccagga   1620
gaaaagggtc ctgctggaga gcgtggtgct ccaggccctg cagggcccag aggagctgct   1680
ggagaacctg gcagagatgg cgtccctgga ggtccaggaa tgaggggcat gcccggaagt   1740
ccaggaggac caggaagtga tgggaaacca gggcctcccg gaagtcaagg agaaagtggt   1800
cgaccaggtc ctcctgggcc atctggtccc cgaggtcagc ctggtgtcat gggcttcccc   1860
ggtcctaaag gaaatgatgg tgctcctggt aagaatggag aacgaggtgg ccctggagga   1920
cctggccctc agggtcctcc tggaaagaat ggtgaaactg gacctcaggg acccccaggg   1980
cctactgggc ctggtggtga caaaggagac acaggacccc ctggtccaca aggattacaa   2040
ggcttgcctg gtacaggtgg tcctccagga gaaaatggaa aacctgggga accaggtcca   2100
aagggtgatg ccggtgcacc tggagctcca ggaggcaagg gtgatgctgg tgcccctggt   2160
gaacgtggac ctcctggatt ggcaggggcc ccaggactta gaggtggagc tggtcccccct   2220
ggtcccgaag gaggaaaggg tgctgctggt cctcctgggc cacctggtgc tgctggtact   2280
cctggtctgc aaggaatgcc tggagaaaga ggaggtcttg gaagtcctgg tccaaagggt   2340
gacaagggtg aaccaggcgg tccaggtgct gatggtgtcc cagggaaaga tggcccaagg   2400
ggtcctactg gtcctattgg tcctcctggc ccagctggcc agcctggaga taagggtgaa   2460
ggtggtgccc ccggacttcc aggtatagct ggacctcgtg gtagccctgg tgagagaggt   2520
gaaactggcc ctccaggacc tgctggtttc cctggtgctc ctggacagaa tggtgaacct   2580
ggtggtaaag gagaaagagg ggctccgggt gagaaaggtg aaggaggccc tcctggagtt   2640
gcaggacccc ctggaggttc tggacctgct ggtcctcctg gtccccaagg tgtcaaaggt   2700
gaacgtggca gtcctggtgg acctggtgct gctggcttcc ctggtgctcg tggtcttcct   2760
ggtcctcctg gtagtaatgg taacccagga cccccaggtc ccagcggttc tccaggcaag   2820
gatgggcccc caggtcctgc gggtaacact ggtgctcctg gcagccctgg agtgtctgga   2880
ccaaaaggtg atgctggcca accaggagag aagggatcgc ctggtgccca gggcccacca   2940
ggagctccag gcccacttgg gattgctggg atcactggag cacggggtct tgcaggacca   3000
```

```
ccaggcatgc caggtcctag gggaagccct ggccctcagg gtgtcaaggg tgaaagtggg   3060
aaaccaggag ctaacggtct cagtggagaa cgtggtcccc ctggacccca gggtcttcct   3120
ggtctggctg gtacagctgg tgaacctgga agagatggaa accctggatc agatggtctt   3180
ccaggccgag atggatctcc tggtggcaag ggtgatcgtg gtgaaaatgg ctctcctggt   3240
gcccctggcg ctcctggtca tccaggccca cctggtcctg tcggtccagc tggaaagagt   3300
ggtgacagag gagaaagtgg ccctgctggc cctgctggtg ctcccggtcc tgctggttcc   3360
cgaggtgctc ctggtcctca aggcccacgt ggtgacaaag gtgaaacagg tgaacgtgga   3420
gctgctggca tcaaaggaca tcgaggattc cctggtaatc caggtgcccc aggttctcca   3480
ggccctgctg gtcagcaggg tgcaatcggc agtccaggac ctgcaggccc cagaggacct   3540
gttggaccca gtggacctcc tggcaaagat ggaaccagtg gacatccagg tcccattgga   3600
ccaccagggc ctcgaggtaa cagaggtgaa agaggatctg agggctcccc aggccaccca   3660
gggcaaccag gccctcctgg acctcctggt gcccctggtc cttgctgtgg tggtgttgga   3720
gccgctgcca ttgctgggat tggaggtgaa aaagctggcg gttttgcccc gtattatgga   3780
gatgaaccaa tggatttcaa aatcaacacc gatgagatta tgacttcact caagtctgtt   3840
aatggacaaa tagaaagcct cattagtcct gatggttctc gtaaaaaccc cgctagaaac   3900
tgcagagacc tgaaattctg ccatcctgaa ctcaagagtg gagaatactg ggttgaccct   3960
aaccaaggat gcaaattgga tgctatcaag gtattctgta atatggaaac tggggaaaca   4020
tgcataagtg ccaatccttt gaatgttcca cggaaacact ggtggacaga ttctagtgct   4080
gagaagaaac acgtttggtt tggagagtcc atggatggtg gttttcagtt tagctacggc   4140
aatcctgaac ttcctgaaga tgtccttgat gtgcagctgg cattccttcg acttctctcc   4200
agccgagctt cccagaacat cacatatcac tgcaaaaata gcattgcata catggatcag   4260
gccagtggaa atgtaaagaa ggccctgaag ctgatggggt caaatgaagg tgaattcaag   4320
gctgaaggaa atagcaaatt cacctacaca gttctggagg atggttgcac gaaacacact   4380
ggggaatgga gcaaaacagt ctttgaatat cgaacacgca aggctgtgag actacctatt   4440
gtagatattg caccctatga cattggtggt cctgatcaag aatttggtgt ggacgttggc   4500
cctgtttgct ttttataaac caaactctat ctgaaatccc aacaaaaaaa atttaactcc   4560
atatgtgttc ctcttgttct aatcttgtca accagtgcaa gtgaccgaca aaattccagt   4620
tatttatttc caaaatgttt ggaaacagta taatttgaca aagaaaaatg atacttctct   4680
ttttttgctg ttccaccaaa tacaattcaa atgctttttg ttttattttt ttaccaattc   4740
caatttcaaa atgtctcaat ggtgctataa taaataaact tcaacactct ttatgataac   4800
aacactgtgt tatattcttt gaatcctagc ccatctgcag agcaatgact gtgctcacca   4860
gtaaaagata acctttcttt ctgaaatagt caaatacgaa attagaaaag ccctccctat   4920
tttaactacc tcaactggtc agaaacacag attgtattct atgagtccca gaagatgaaa   4980
aaaattttat acgttgataa aacttataaa tttcattgat taatctcctg gaagattggt   5040
ttaaaaagaa aagtgtaatg caagaattta aagaaatatt tttaaagcca caattatttt   5100
aatattggat atcaactgct tgtaaaggtg ctcctctttt ttcttgtcat tgctggtcaa   5160
gattactaat atttgggaag gctttaaaga cgcatgttat ggtgctaatg tactttcact   5220
tttaaactct agatcagaat tgttgacttg cattcagaac ataaatgcac aaaatctgta   5280
catgtctccc atcagaaaga ttcattggca tgccacaggg gattctcctc cttcatcctg   5340
taaaggtcaa caataaaaac caaattatgg ggctgctttt gtcacactag catagagaat   5400
```

gtgttgaaat ttaactttgt aagcttgtat gtggttgttg atcttttttt tccttacaga 5460
cacccataat aaaatatcat attaaaattc 5490

<210> SEQ ID NO 29
<211> LENGTH: 8455
<212> TYPE: DNA
<213> ORGANISM: Homo sapiens

<400> SEQUENCE: 29
ccgcactctc cgtccccgcg gctggcgcag gacctcactc gagcggagcg cccacgggga 60
gcgggtcgcg gggcggcggc ggcgaggagg aggcgagaag gagttggagg aggaggagga 120
ggaggcgagg gcgagctagc ccagcggggt cccggccgcc ccgcgggcca aagtcgagcc 180
ctcccgcccg tgggcgagcg cgccagccgc cccttccaga acagccgccg ccacaaagaa 240
gaacgggggg tgccgaggtc cccatgacct cctaaagtgg tgcggtccct gctgagtgcg 300
ctgcccgggc cgtgacccgc gcccctgtgc gtccccgcgc gcctccgagc gcccctgtgc 360
gccccggccc gcgccccgcc ggcatggacg tccatacccg ctggaaagcg cgcagcgcgc 420
tccgcccggg cgccccgctg ctgccccccgc tgctgctgct gctgctgtgg gcgccgcctc 480
cgagccgcgc agctcagcca gcagatctcc tgaaggttct agattttcac aacttgcctg 540
atggaataac aaagacaaca ggcttttgcg ccacgcggcg atcttccaaa ggcccggatg 600
tcgcttacag agtcaccaaa gacgcgcagc tcagcgcacc caccaagcag ctgtaccctg 660
cgtctgcatt tcccgaggac ttctccatcc taacaactgt gaaagccaag aaaggcagcc 720
aggccttcct ggtctccatc tacaacgagc agggtatcca gcagattggg ctggagctgg 780
gccgctctcc cgtcttcctc tacgaggacc acacggggaa gcctggcccg gaagactacc 840
ccctcttccg gggcatcaac ctgtcagatg gcaagtggca cagaattgct ctcagcgtcc 900
acaagaaaaa tgtcaccttg atcctcgact gtaaaaagaa gaccaccaaa ttcctcgacc 960
gcagcgacca ccccatgatc gacatcaatg gcatcatcgt gtttggcacc cggatcctgg 1020
atgaggaggt gtttgagggt gacatccagc agctgctctt tgtctcggac caccgggcag 1080
cttatgatta ctgtgagcac tacagccctg actgtgacac cgcagtacct gacaccccac 1140
agtcgcagga ccccaatcca gatgaatatt acacggaagg agacggcgag ggtgagacct 1200
attactacga ataccccctac tacgaagacc ccgaagacct agggaaggag cccacccccca 1260 gcaagaagcc cgtggaagct gccaaagaaa ccacagaggt ccccgaggag ctgaccccga 1320
cccccacgga agctgctccc atgcctgaaa ccagtgaagg ggctgggaag gaagaggacg 1380
tcggcatcgg ggactatgac tacgtgccca gtgaggacta ctacacgccc tcaccgtatg 1440
atgacctcac ctatggcgag ggggaggaga accccgacca gcccacagac ccaggcgctg 1500
gggccgaaat tcccaccagc accgccgaca cctccaactc ctccaatcca gctccgcctc 1560
caggggaagg tgcggatgac ttggaggggg agttcactga ggaaacgatc cggaaccttg 1620
acgagaacta ctacgacccc tactacgacc ccaccagctc cccgtcggag atcgggccgg 1680
gaatgccggc gaaccaggat accatctatg aagggattgg aggacctcgg ggcgagaaag 1740
gccaaaaggg agaaccagcg attatcgagc cgggcatgct catcgagggc ccgcctggcc 1800
cagaaggccc cgcgggtctt cccggacctc caggaaccat gggtcccact ggccaagtcg 1860
gggaccctgg agaaaggggc ccccctggac gcccaggcct tcctggggcc gatggcctgc 1920
ccggtcctcc aggaaccatg ctcatgctgc ccttccggtt tggaggtggc ggcgatgcgg 1980

-continued

```
gctccaaagg ccccatggtc tcagcccagg agtcccaggc gcaagccatt ctccagcagg   2040
ccaggttggc actgagggga ccagctggcc cgatgggtct cacagggaga cctggccctg   2100
tgggtccccc tgggagcgga ggtttgaagg gcgagccggg agacgtgggg cctcagggtc   2160
ctcgaggtgt gcaaggcccg cctggtccgg ccgggaagcc cggaagacgg ggtcgggctg   2220
ggagtgatgg agccagagga atgcctggac aaactggccc caagggtgac cggggtttcg   2280
acggcctggc tgggttgcca ggcgagaagg gccacagggg tgaccctggt ccttccggcc   2340
caccaggacc tccgggagac gatggagaaa ggggtgacga cggagaagtt gggcccaggg   2400
ggctgcctgg ggagcccggg ccacgtggtc tgcttgggcc gaaggggccc ccaggtcctc   2460
ccggacctcc cggtgtcacg ggtatggacg gccagccggg gccaaaagga aatgtgggtc   2520
cccagggaga gcctggcccc ccaggacagc agggtaatcc aggcgcccag ggtcttccag   2580
gcccccaggg tgcaattggt cctccaggag aaaagggtcc cttggggaaa ccaggccttc   2640
caggaatgcc cggtgctgac ggacccccgg gacaccctgg caaagaaggc cctccaggag   2700
agaaaggagg tcagggtcca cctggccccc agggtccgat tggctaccca ggtcctcgag   2760
gagtcaaggg ggccgatggc atccgtggtc tgaagggcac aaagggcgag aagggtgaag   2820
acggctttcc tgggtttaaa ggagacatgg gcatcaaggg tgatcggggg gagatcggcc   2880
cacccggtcc caggggagaa gatggccctg aaggcccaaa gggtcgcgga ggtcccaatg   2940
gtgaccccgg tcctctggga ccccctgggg agaagggaaa actcggagtc ccagggttac   3000
cagggtatcc aggaagacaa ggaccaaagg gctctattgg attccctgga tttcctggcg   3060
ccaatggaga gaagggcggc agggggaccc ctggaaagcc aggaccgcgg gggcagcgag   3120
gcccaacggg tccgaggggt gaaagaggcc cccggggcat cactgggaag cctggcccca   3180
agggcaactc cggaggtgac ggcccagctg gccctcctgg tgaacgggga cccaatggac   3240
cccaaggacc cacaggattt cctggaccaa agggcccccc tggccctcca ggcaaggatg   3300
gactcccagg acaccctgga cagagaggcg agactggttt ccaaggcaag accggccctc   3360
caggcccccc cggcgtggtc ggccctcagg gtcccacggg agaaacgggc ccaatgggtg   3420
agcgtggcca ccctgggccc cctggacccc ccggtgaaca ggggcttccg ggccttgctg   3480
gaaaagaagg gacgaagggt gacccaggcc ctgcaggcct ccctgggaaa gatggccctc   3540
caggattacg tggtttccct ggggaccgag ggcttcctgg tccagtggga gctcttggac   3600
tgaaaggcaa tgaagggccc cctggcccac caggccctgc gggatctcca ggggagagag   3660
gtccagctgg agccgctggg cccatcggaa ttccagggag acctgggccc cagggacccc   3720
cagggccggc aggagagaaa ggggctcctg gcgagaaagg cccacaaggc ccagctggcc   3780
gagacggtct ccaggggcct gtggggctcc cgggtccagc tggccctgtg ggtcccccctg  3840
gagaagacgg agataaggga gagatcgggg agccggggca gaaaggaagc aagggggaca   3900
aaggagaaca gggtcctcct gggcctacag gtcctcaagg ccccatcgga cagccaggcc   3960
cctctggagc tgacggcgag ccggggcctc ggggccagca gggccttttc gggcagaaag   4020
gtgatgaagg tcccagaggc tttcctggac cccctgggcc agtggggctg cagggtttgc   4080
caggacctcc aggcgagaag ggtgagacag gagacgtggg ccagatgggc cccccgggtc   4140
cccctggccc ccgaggaccc tccggagctc caggtgctga tggcccacaa ggtcccccag   4200
gtggaatagg aaaccctggt gcagtgggag agaagggcga gcctggcgaa gcaggtgagc   4260
ctggccttcc gggagaaggc ggcccccccgg gacccaaagg agaaagggga gagaagggcg  4320
agtcaggccc ttcaggtgct gccggacccc ctggacccaa aggccctccc ggagatgatg   4380
```

gtcccaaagg cagccctggc ccagtgggtt ttcctggaga tcctggcccc cccggagagc 4440
ctggccccgc gggtcaagat ggtcccccctg gtgacaaagg agatgatggt gaacccgggc 4500
agacgggatc ccccggccct actggtgaac caggtccatc ggggcctcca ggaaaaaggg 4560
gtcccccagg ccccgcaggc cccgaaggca gacagggaga gaaaggggcc aagggagaag 4620
ccggcttgga aggccctcct gggaagactg gccccatcgg cccccagggg gcccctggga 4680
agcccggacc ggatggcctt cgagggatcc ctggccctgt gggagaacaa ggtctcccag 4740
gatccccagg cccggacggt ccccccggcc ccatgggtcc cccaggactt cccggcctca 4800
aaggagattc tggtcccaaa ggtgaaaagg gtcatccagg cctgatcggg ctcatcggtc 4860
ctccgggtga acagggtgag aagggcgacc gtggtctccc tggcccccag ggctcctccg 4920
gtcctaaggg agaacagggt atcactggtc cttctggccc gattgggcct cctgggcccc 4980
ctggcctgcc gggtccgcct ggtccaaaag gtgctaaggg ctcctcgggt ccaactggcc 5040
cgaagggtga ggcaggccac ccaggacccc caggcccccc gggcccccg ggagaggtca 5100 tccagcccct gccaatccag gcatccagga cgcggcggaa catcgacgcc agccagctgc 5160
tggacgacgg gaatggcgag aactacgtgg actacgcgga cggcatggaa gagatcttcg 5220
gctctctcaa ctctctgaag ctggagattg agcagatgaa acggcccctg ggcacgcagc 5280
agaaccccgc ccgcacctgc aaggacctgc agctctgcca ccccgacttc ccagatggtg 5340
aatactgggt cgatcctaac caaggatgct ccagggattc cttcaaggtt tactgcaact 5400
tcacagccgg ggggtcgaca tgcgtcttcc ctgacaagaa gtccgaaggg gccagaatca 5460
cttcttggcc caaagaaaac ccgggctcct ggttcagtga attcaagcgt gggaaactgc 5520
tctcctatgt ggacgccgag ggcaaccctg tgggtgtggt acagatgacc ttcctgcggc 5580
tgctgagcgc ctctgcccac cagaacgtca cctaccactg ctaccagtca gtggcctggc 5640
aggacgcagc cacgggcagc tacgacaagg ccctccgctt cctgggctcc aacgacgagg 5700
agatgtccta tgacaacaac ccctacatcc gcgccctggt ggacggctgt gctaccaaga 5760
aaggctacca gaagacggtt ctggagatcg acaccccccaa agtggagcag gtgcccatcg 5820
tggacatcat gttcaatgac ttcggtgaag cgtcacagaa atttggattt gaagtggggc 5880
cggcttgctt catgggctag gagccgccga gcccgggctc ccgagagcaa cctcgtgacc 5940
tcagcatgcc attcgttcgt gagtgtcccg tgcacgtcct gaccctggac agtgaaggct 6000
tctccctccc ctcccacctg acttcatcta cgcctcggca ccacggggtg tgggacccca 6060
gcccggagag aacagaggga aggagccgcg cccccacctg gagctgaatc acatgaccta 6120
gctgcacccc agcgcctggg cccgccccac gctctgtcca cacccacgcg ccccgggagc 6180
ggggccatgc ctccagcccc ccagctcgcc cgacccatcc tgttcgtgaa taggtctcag 6240
gggttggggg agggactgcc agatttggac actatatttt tttctaaatt caacttgaag 6300
atgtgtattt cccctgacct tcaaaaaatg ttccaaggta agcctcgtaa aggtcatccc 6360
accatcacca aagcctccgt ttttaacaac ctccaacacg atccatttag aggccaaatg 6420
tcattctgca ggtgccttcc cgatggatta aaggtgctta tgtttttgtg agttttaagt 6480
aaatatttgt attgtattgt tataaatgtt aagtgtgcct ggctttcaat catgcacgga 6540
aacccagtct cagtcccacg gacagaatgg gcgaggcatg gattctgggt tgcagtaccg 6600
ttctgattag aaataggaag tctccccacc cccgccctgg ccaagaacgt gcaataaatt 6660
ggaagtttgc cccggggcag caagaattta tgctgccatt gaaaagcagg taccagtgcc 6720

-continued cctttcaga cagtttttga ttcgctctag acttttttt tttttaatag ggaaaaaatt 6780
tgataatttt ctttttttcta catgcactta agactaaaac acaggtttgg attaatttta 6840
tttgcttcct ttttccgctt ttcttcccgc agagcctgat gggagaatgt ccagggcagg 6900
gaaaccacat tttttgtagg tgataactca atgaaaattg gtgcttattt tttacacttc 6960
tctcttgtgg ctctcttgtg gtgctatcta tctgttttaa ggtctccttg aaggcgcact 7020
ggggaccctg gccatgcctc gttctccctg ctttctttat cctgttattg cctccacagt 7080
ctgttgccaa ggactctaag atcaatgcac gtcactttcc tttccactgg gcaggatagc 7140
caagcacact ccctcctgcg ctctcccgcc ccggtgcgtc cactcccgag ggctgttatg 7200
aggactgggt tgtgcctact tgatttgaaa acacacacaa gcaataaaaa gcctcttcct 7260
gcattgtctg tggtgtgacc atagcagatt atatttggtt cctgaatgtt tgtggtgcta 7320
atttctgtgt ttgttccaag ccgttcagtc atgccatgcg ctgcctcggt agatggagta 7380
atgtacaatg aactccatga gtctctccag ggctgcctgc agcacgtctt ttccaagtag 7440
cctatttgga ttcccatctc aaatgtcctg gatgcgagcg tcagcggctc cagagctcgg 7500
ggcgggtgag gtcccctttg gggaaccctt tcctggccat cgaggtcggg gggctgccgt 7560
ctgtgggcag gaggacccga ggggcagcca ggaaaggcga tctcttcact gtgaaaagtt 7620
gcccgggtgc agcgcctttt ccttctacca tgggaaatgc aggctgggcc cttggggtga 7680
gcctgcgggg ctctggtgct gtccccgacc cccaccacca ccagaatgca gttccagctt 7740
aggaagccac aaacaagcca cccaggagga acaaaacacc gccagcgtgg attttccaaa 7800
tttccctgga aagtaagtct cgctcttgcc aaagaaaagt ctggcttgga gagtctctgg 7860
agcccaggat gccagcatgt gccaatgact gtcaccttca tctcttcaaa agaaaagcca 7920
tagccgagga ctgtcccgcg acccccgtgg actgcgtcta ggtcatgtga ttctgttttc 7980
atttctcatc ccatccaatt tgtccttttc tcctgtcatt ttcttcctct gtggtccctt 8040
caaagttgtt ataatttgta ctgaacttca aaatgtgtcc cgttctcccc agaccactct 8100
agccacagta tattgcaata aaattacttc ttatatttgc agaaattctt ttggtgtaat 8160 tttattttt cctctcaata tatataattg gacaaacgct ggcaaaaaga aaaaaatggt 8220
aagcaaaaaa cccaagataa agtttcgagg acatcaggcc ttttgaaata caatgtcaaa 8280
tgacacattg tacggtttca aaaaatccgc tagacatgtc ataagtttta actgtaatgc 8340
ccaggaaagg atatcttaaa atattctaaa cttgtgtaac aaaggaataa ttaactgtaa 8400
tagtttttca ataaatcgag ttgggtgttt ccaccgtaaa aaaaaaaaaa aaaaa 8455

<210> SEQ ID NO 30
<211> LENGTH: 6930
<212> TYPE: DNA
<213> ORGANISM: Homo sapiens

<400> SEQUENCE: 30
gaccgttgct tggcagacac tggatggtta tgagcctgaa caagctgaaa aggggcagga 60
aaagaagtgg aggcagcatt cttcctattt aaagctgcat cgcttgaaaa aagttttcgc 120
agactgtgct ggagctggtg ctgaaaaagg gggtttgcag aggctgccct ggggctggtg 180
ctgaaagaag agcccacagc tgacttcatg gtgctacaat aacctcagaa tctacttttc 240
actctcagga gaacccacat gtctaatatt tagacatgat ggcaaactgg gcggaagcaa 300
gacctctcct cattcttatt gttttattag ggcaatttgt ctcaataaaa gcccaggaag 360
aagacgagga tgaaggatat ggtgaagaaa tagcctgcac tcagaatggc cagatgtact 420
taaacaggga catttggaaa cctgcccctt gtcagatctg tgtctgtgac aatggagcca 480
ttctctgtga caagatagaa tgccaggatg tgctggactg tgccgaccct gtaacgcccc 540
ctggggaatg ctgtcctgtc tgttcacaaa cacctggagg tggcaataca aattttggta 600
gaggaagaaa gggacaaaag ggagaaccag gattagtgcc tgttgtaaca ggcatacgtg 660
gtcgtccagg accggcagga cctccaggat cacagggacc aagaggagag cgagggccaa 720
aaggaagacc tggccctcgt ggacctcagg gaattgatgg agaaccaggt gttcctggtc 780
aacctggtgc tccaggacct cctggacatc cgtcccaccc aggacccgat ggcttgagca 840
ggccgttttc agctcaaatg gctgggttgg atgaaaaatc tggacttggg agtcaagtag 900
gactaatgcc tggctctgtg ggtcctgttg gcccaagggg accacagggt ttacaaggac 960
agcaaggtgg tgcaggacct acaggacctc ctggtgaacc tggtgatcct ggaccaatgg 1020
gtccgattgg ttcacgtgga ccagagggcc ctcctggtaa acctggggaa gatggtgaac 1080
ctggcagaaa tggaaatcct ggtgaagtgg gatttgcagg atctccggga gctcgtggat 1140
ttcctggggc tcctggtctt ccaggtctga agggtcaccg aggacacaaa ggtcttgaag 1200
gccctaaagg tgaagttgga gcacctggtt ccaagggtga agctggcccc actggtccaa 1260
tgggtgccat gggtcctctg ggtccgaggg gaatgccagg agagagaggg agacttgggc 1320
cacagggtgc tcctggacaa cgaggtgcac atggtatgcc tggaaaacct ggaccaatgg 1380
gtcctcttgg gataccaggc tcttctggtt ttccaggaaa tcctggaatg aagggagaag 1440
caggtcctac aggggcgcga ggccctgaag gtcctcaggg gcagagaggt gaaactgggc 1500 cccaggtcc agttggctct ccaggtcttc ctggtgcaat aggaactgat ggtactcctg 1560
gtgccaaagg cccaacgggc tctccgggta cctctggtcc tcctggctca gcagggcctc 1620
ctggatctcc aggacctcag ggtagcactg gtcctcaggg aattcgaggc caaccgggtg 1680
atccaggagt tccaggtttc aaaggagaag ctggcccaaa aggggaacca gggccacatg 1740
gtattcaggg tccgataggc ccacccggtg aagaaggcaa aagaggtccc agaggtgacc 1800
caggaacagt tggtcctcca gggccagtgg gagaaagggg tgctcctggc aatcgtggtt 1860
ttccaggctc tgatggttta cctgggccaa agggtgctca aggagaacgg ggtcctgtag 1920
gttcttcagg acccaaagga agccaggggg atccaggacg tccaggggaa cctgggcttc 1980
caggtgctcg ggtttgaca ggaaatcctg gtgttcaagg tcctgaagga aaacttggac 2040
ctttgggtgc gccaggggaa gatggccgtc caggtcctcc aggctccata ggaatcagag 2100
ggcagcccgg gagcatgggc cttccaggcc ccaaaggtag cagtggtgac cctgggaaac 2160
ctggagaagc aggaaatgct ggagttcctg ggcagagggg agctcctgga aaagatggtg 2220
aagttggtcc ttctggtcct gtgggcccgc cgggtctagc tggtgaaaga ggagaacaag 2280
gacctccagg ccccacaggt tttcaggggc ttcctggtcc tccagggcct cctggagaag 2340
gtggaaaacc aggtgatcaa ggtgttcctg gagatcccgg agcagttggc ccgttaggac 2400
ctagaggaga acgaggaaat cctggggaaa gaggagaacc tgggataact ggactccctg 2460
gtgagaaggg aatggctgga ggacatggtc ctgatggccc aaaaggcagt ccaggtccat 2520
ctgggacccc tggagataca ggcccaccag gtcttcaagg tatgccggga gaaagaggaa 2580
ttgcaggaac tcctggcccc aagggtgaca gaggtggcat aggagaaaaa ggtgctgaag 2640
gcacagctgg aaatgatggt gcaagaggtc ttccaggtcc tttgggccct ccaggtccgg 2700
caggtcctac tggagaaaag ggtgaacctg gtcctcgagg tttagttggc cctcctggct 2760

```
cccggggcaa tcctggttct cgaggtgaaa atgggccaac tggagctgtt ggttttgccg   2820
gaccccaggg tcctgacgga cagcctggag taaaaggtga acctggagag ccaggacaga   2880
agggagatgc tggttctcct ggaccacaag gtttagcagg atcccctggc cctcatggtc   2940
ctaatggtgt tcctggacta aaaggtggtc gaggaaccca aggtccgcct ggtgctacag   3000
gatttcctgg ttctgcgggc agagttggac ctccaggccc tgctggagct ccaggacctg   3060
cgggacccct aggggaaccc gggaaggagg gacctccagg tcttcgtggg gaccctggct   3120
ctcatgggcg tgtgggagat cgaggaccag ctggcccccc tggtggccca ggagacaaag   3180
gggacccagg agaagatggg caacctggtc cagatggccc ccctggtcca gctggaacga   3240
ccgggcagag aggaattgtt ggcatgcctg ggcaacgtgg agagagaggc atgcccggcc   3300
taccaggccc agcgggaaca ccaggaaaag taggaccaac tggtgcaaca ggagataaag   3360
gtccacctgg acctgtgggg cccccaggct ccaatggtcc tgtaggggaa cctggaccag   3420
aaggtccagc tggcaatgat ggtaccccag gacgggatgg tgctgttgga gaacgtggtg   3480
atcgtggaga ccctgggcct gcaggtctgc caggctctca gggtgcccct ggaactcctg   3540
gccctgtggg tgctccagga gatgcaggac aaagaggaga tccgggttct cggggtccta   3600
taggaccacc tggtcgagct gggaaacgtg gattacctgg accccaagga cctcgtggtg   3660
acaaaggtga tcatggagac cgaggcgaca gaggtcagaa gggccacaga ggctttactg   3720
gtcttcaggg tcttcctggc cctcctggtc caaatggtga acaaggaagt gctggaatcc   3780
ctggaccatt tggcccaaga ggtcctccag gcccagttgg tccttcaggt aaagaaggaa   3840
accctgggcc acttgggcca attggacctc caggtgtacg aggcagtgta ggagaagcag   3900
gacctgaggg ccctcctggt gagcctggcc cacctggccc tccgggtccc cctggccacc   3960
ttacagctgc tcttggggat atcatggggc actatgatga aagcatgcca gatccacttc   4020
ctgagtttac tgaagatcag gcggctcctg atgacaaaaa caaaacggac ccaggggttc   4080
atgctaccct gaagtcactc agtagtcaga ttgaaaccat gcgcagcccc gatggctcga   4140
aaaagcaccc agcccgcacg tgtgatgacc taaagctttg ccattccgca aagcagagtg   4200
gtgaatactg gattgatcct aaccaaggat ctgttgaaga tgcaatcaaa gtttactgca   4260
acatggaaac aggagaaaca tgtatttcag caaacccatc cagtgtacca cgtaaaacct   4320
ggtgggccag taaatctcct gacaataaac ctgtttggta tggtcttgat atgaacagag   4380
ggtctcagtt cgcttatgga gaccaccaat cacctaatac agccattact cagatgactt   4440
ttttgcgcct tttatcaaaa gaagcctccc agaacatcac ttacatctgt aaaaacagtg   4500
taggatacat ggacgatcaa gctaagaacc tcaaaaaagc tgtggttctc aaaggggcaa   4560
atgacttaga tatcaaagca gagggaaata ttagattccg gtatatcgtt cttcaagaca   4620
cttgctctaa gcggaatgga aatgtgggca agactgtctt tgaatataga acacagaatg   4680
tggcacgctt gcccatcata gatcttgctc ctgtggatgt tggcggcaca gaccaggaat   4740
tcggcgttga aattgggcca gtttgttttg tgtaaagtaa gccaagacac atcgacaatg   4800
agcaccacca tcaatgacca ccgccattca caagaacttt gactgtttga agttgatcct   4860
gagactcttg aagtaatggc tgatcctgca tcagcattgt atatatggtc ttaagtgcct   4920
ggcctcctta tccttcagaa tatttatttt acttacaatc ctcaagtttt aattgatttt   4980
aaatattttt caatacaaca gtttaggttt aagatgacca atgacaatga ccacctttgc   5040
agaaagtaaa ctgattgaat aaataaatct ccgttttctt caatttattt cagtgtaatg   5100
aaaaagttgc ttagtattta tgaggaaatt cttcttcctg gcaggtagct taaagagtgg   5160
```

ggtatataga gccacaacac atgtttattt tgcttggctg cagttgaaaa atagaaatta 5220
gtgccctttt gtgacctctc attccaagat tgtcaattaa aaatgagttt aaaatgttta 5280
acttgtgatc gagacctaca tgcatgtctt gatattgtgt aactataata gagactcttt 5340
aaggagaatc ttaaaaaaaa aaaaacgttt ctcactgtct taaatagaat ttttaaatag 5400
tatatattca gtggcatttt ggagaacaaa gtgaatttac ttcgacttct taaatttttg 5460
taaaagacta taagtttaga catctttctc attcaaattt aaagatatct ttctcctctt 5520
gatcaatcta tcaatattga tagaagtcac actagtatat accatttaat acatttacac 5580
tttcttattt aagaagatat tgaatgcaaa ataattgaca tatagaactt tacaaacata 5640
tgtccaagga ctctaaattg agactcttcc acatgtacaa tctcatcatc ctgaagccta 5700
taatgaagaa aaagatctag aaactgagtt gtggagctga ctctaatcaa atgtgatgat 5760
tggaattaga ccatttggcc tttgaacttt cataggaaaa atgacccaac atttcttagc 5820
atgagctacc tcatctctag aagctgggat ggacttacta ttcttgttta tattttagat 5880
actgaaaggt gctatgcttc tgttattatt ccaagactgg agataggcag ggctaaaaag 5940
gtattattat ttttccttta atgatggtgc taaaattctt cctataaaat tccttaaaaa 6000
taaagatggt ttaatcacta ccattgtgaa aacataactg ttagacttcc cgtttctgaa 6060
agaaagagca tcgttccaat gcttgttcac tgttcctctg tcatactgta tctggaatgc 6120
tttgtaatac ttgcatgctt cttagaccag aacatgtagg tccccttgtg tctcaatact 6180 tttttttttct taattgcatt tgttggctct attttaattt ttttctttta aaataaacag 6240
ctgggaccat cccaaaagac aagccatgca tacaactttg gtcatgtatc tctgcaaagc 6300
atcaaattaa atgcacgctt ttgtcatgtc agtggttttt gttttgtgaa attcctttga 6360
ccatattaga tctatttcat ttccaatagt gaaaaggaga tgtggtggta tactttgttt 6420
gccatttgtt taaaagatac aacggatacc ttctatcatg tatgtactgg cttataaatg 6480
aaaatctatc tacaacatta cccacaaagg caacatgaca ccaattatca ctgcctctgc 6540
ccttaaaaat gtcagagtag tattattgat aaaaagggca agcaatagat ttttcatgac 6600
tgaataaact gtaataataa aacatatgtc tcaaagtgta tcacatatga atttagccta 6660
attgttttca gtttcattct caatatttag tttacaacat cattttcccc taaactggtt 6720
atattttgac ctgtatatct taaatttgag tatttatatg cctaaataca tgtgtgagtt 6780
ttgtttgact tccaagtcca aactataaga ttatataagt tcatatagat gaatcagaaa 6840
tatgtggtaa tactattaag tcacaaacac taacaatttc caactataga aataacagtt 6900
cttatttgga ttttgggaat gctaccaata 6930

<210> SEQ ID NO 31
<211> LENGTH: 3307
<212> TYPE: DNA
<213> ORGANISM: Homo sapiens

<400> SEQUENCE: 31
caccttctgc actgctcatc tgggcagagg aagcttcaga aagctgccaa ggcaccatct 60
ccaggaactc ccagcacgca gaatccatct gagaatatgc tgccacaaat accctttttg 120
ctgctagtat ccttgaactt ggttcatgga gtgttttacg ctgaacgata ccaaatgccc 180
acaggcataa aaggcccact acccaacacc aagacacagt tcttcattcc ctacaccata 240
aagagtaaag gtatagcagt aagaggagag caaggtactc ctggtccacc aggccctgct 300

```
ggacctcgag ggcacccagg tccttctgga ccaccaggaa aaccaggcta cggaagtcct    360
ggactccaag gagagccagg gttgccagga ccaccgggac catcagctgt agggaaacca    420
ggtgtgccag gactcccagg aaaaccagga gagagaggac catatggacc aaaaggagat    480
gttggaccag ctggcctacc aggaccccgg ggcccaccag gaccacctgg aatccctgga    540
ccggctggaa tttctgtgcc aggaaaacct ggacaacagg gacccacagg agccccagga    600
cccaggggct ttcctggaga aaagggtgca ccaggagtcc ctggtatgaa tggacagaaa    660
ggggaaatgg gatatggtgc tcctggtcgt ccaggtgaga ggggtcttcc aggccctcag    720
ggtcccacag gaccatctgg ccctcctgga gtgggaaaaa gaggtgaaaa tggggttcca    780
ggacagccag gcatcaaagg tgatagaggt tttccgggag aaatgggacc aattggccca    840
ccaggtcccc aaggccctcc tggggaacga gggccagaag gcattggaaa gccaggagct    900
gctggagccc caggccagcc agggattcca ggaacaaaag gtctccctgg ggctccagga    960
atagctgggc cccagggcc tcctggcttt gggaaaccag gcttgccagg cctgaaggga   1020
gaaagaggac ctgctggcct tcctgggggt ccaggtgcca aggggaaca agggccagca   1080
ggtcttcctg ggaagccagg tctgactgga ccccctggga atatgggacc ccaaggacca   1140
aaaggcatcc cgggtagcca tggtctccca ggccctaaag gtgagacagg gccagctggg   1200
cctgcaggat accctggggc taagggtgaa aggggttccc ctgggtcaga tggaaaacca   1260
gggtacccag gaaaaccagg tctcgatggt cctaagggta acccagggtt accaggtcca   1320
aaaggtgatc ctggagttgg aggacctcct ggtctcccag gccctgtggg cccagcagga   1380
gcaaagggaa tgcccggaca caatggagag gctggcccaa gaggtgcccc tggaatacca   1440
ggtactagag gccctattgg gccaccaggc attccaggat tccctgggtc taaaggggat   1500
ccaggaagtc ccggtcctcc tggcccagct ggcatagcaa ctaagggcct caatggaccc   1560
accgggccac cagggcctcc aggtccaaga ggccactctg gagagcctgg tcttccaggg   1620
ccccctgggc ctccaggccc accaggtcaa gcagtcatgc ctgagggttt tataaaggca   1680
ggccaaaggc ccagtctttc tgggacccct cttgttagtg ccaaccaggg ggtaacagga   1740
atgcctgtgt ctgcttttac tgttattctc tccaaagctt acccagcaat aggaactccc   1800
ataccatttg ataaaatttt gtataacagg caacagcatt atgacccaag gactggaatc   1860
tttacttgtc agataccagg aatatactat ttttcatacc acgtgcatgt gaaagggact   1920
catgtttggg taggcctgta taagaatggc acccctgtaa tgtacaccta tgatgaatac   1980
accaaaggct acctggatca ggcttcaggg agtgccatca tcgatctcac agaaaatgac   2040
caggtgtggc tccagcttcc caatgccgag tcaaatggcc tatactcctc tgagtatgtc   2100
cactcctctt tctcaggatt cctagtggct ccaatgtgag tacacacaga gctaatctaa   2160
atcttgtgct agaaaaagca ttctctaact ctaccccacc ctacaaaatg catatggagg   2220
taggctgaaa agaatgtaat tttattttc tgaaatacag atttgagcta tcagaccaac   2280
aaaccttccc cctgaaaagt gagcagcaac gtaaaaacgt atgtgaagcc tctcttgaat   2340
ttctagttag caatcttaag gctctttaag gttttctcca atattaaaaa atatcaccaa   2400
agaagtcctg ctatgttaaa aacaaacaac aaaaaacaaa caacaaaaaa aaaattaaaa   2460
aaaaaaacag aaatagagct ctaagttatg tgaaatttga tttgagaaac tcggcatttc   2520
ctttttaaaa aagcctgttt ctaactatga atatgagaac ttctaggaaa catccaggag   2580
gtatcatata actttgtaga acttaaatac ttgaatattc aaatttaaaa gacactgtat   2640
cccctaaaat atttctgatg gtgcactact ctgaggcctg tatggcccct ttcatcaata   2700
```

tctattcaaa tatacaggtg catatatact tgttaaagct cttatataaa aaagccccaa 2760
aatattgaag ttcatctgaa atgcaaggtg ctttcatcaa tgaacctttt caaacttttc 2820
tatgattgca gagaagcttt ttatataccc agcataactt ggaaacaggt atctgaccta 2880
ttcttattta gttaacacaa gtgtgattaa tttgatttct ttaattcctt attgaatctt 2940
atgtgatatg attttctgga tttacagaac attagcacat gtaccttgtg cctcccattc 3000
aagtgaagtt ataatttaca ctgagggttt caaaattcga ctagaagtgg agatatatta 3060
tttatttatg cactgtactg tatttttata ttgctgttta aaacttttaa gctgtgcctc 3120
acttattaaa gcacaaaatg ttttacctac tccttattta cgacgcaata aaataacatc 3180
aatagatttt taggctgaat taatttgaaa gcagcaattt gctgttctca accattcttt 3240
caaggctttt cattgttcaa agttaataaa aaagtaggac aataaagtga aaaaaaaaaa 3300
aaaaaaa 3307

<210> SEQ ID NO 32
<211> LENGTH: 7291
<212> TYPE: DNA
<213> ORGANISM: Homo sapiens

<400> SEQUENCE: 32
acacagtact ctcagcttgt tggtggaagc ccctcatctg ccttcattct gaaggcaggg 60
cccggcagag gaaggatcag agggtcgcgg ccggagggtc ccggccggtg gggccaactc 120
agagggagag gaaagggcta gagacacgaa gaacgcaaac catcaaattt agaagaaaaa 180
gccctttgac tttttccccc tctccctccc caatggctgt gtagcaaaca tccctggcga 240
taccttggaa aggacgaagt tggtctgcag tcgcaatttc gtgggttgag ttcacagttg 300
tgagtgcggg gctcggagat ggagccgtgg tcctctaggt ggaaaacgaa acggtggctc 360
tgggatttca ccgtaacaac cctcgcattg accttcctct tccaagctag agaggtcaga 420
ggagctgctc cagttgatgt actaaaagca ctagattttc acaattctcc agagggaata 480
tcaaaaacaa cgggattttg cacaaacaga aagaattcta aaggctcaga tactgcttac 540
agagtttcaa agcaagcaca actcagtgcc ccaacaaaac agttatttcc aggtggaact 600
ttcccagaag acttttcaat actatttaca gtaaaaccaa aaaaaggaat tcagtctttc 660
cttttatcta tatataatga gcatggtatt cagcaaattg gtgttgaggt tgggagatca 720
cctgtttttc tgtttgaaga ccacactgga aaacctgccc cagaagacta tcccctcttc 780
agaactgtta acatcgctga cgggaagtgg catcgggtag caatcagcgt ggagaagaaa 840
actgtgacaa tgattgttga ttgtaagaag aaaaccacga aaccacttga tagaagtgag 900
agagcaattg ttgataccaa tggaatcacg gtttttggaa caaggatttt ggatgaagaa 960
gtttttgagg gggacattca gcagtttttg atcacaggtg atcccaaggc agcatatgac 1020
tactgtgagc attatagtcc agactgtgac tcttcagcac ccaaggctgc tcaagctcag 1080
gaacctcaga tagatgagta tgcaccagag gatataatcg aatatgacta tgagtatggg 1140
gaagcagagt ataaagaggc tgaaagtgta acagagggac ccactgtaac tgaggagaca 1200
atagcacaga cggaggcaaa catcgttgat gattttcaag aatacaacta tggaacaatg 1260
gaaagttacc agacagaagc tcctaggcat gtttctggga caaatgagcc aaatccagtt 1320
gaagaaatat ttactgaaga atatctaacg ggagaggatt atgattccca gaggaaaaat 1380
tctgaggata cactatatga aaacaaagaa atagacggca gggattctga tcttctggta 1440

-continued

```
gatggagatt taggcgaata tgatttttat gaatataaag aatatgaaga taaaccaaca   1500
agccccccta atgaagaatt tggtccaggt gtaccagcag aaactgatat tacagaaaca   1560
agcataaatg gccatggtgc atatggagag aaaggacaga aaggagaacc agcagtggtt   1620
gagcctggta tgcttgtcga aggaccacca ggaccagcag gacctgcagg tattatgggt   1680
cctccaggtc tacaaggccc cactggaccc cctggtgacc ctggcgatag gggcccccca   1740
ggacgtcctg gcttaccagg ggctgatggt ctacctggtc ctcctggtac tatgttgatg   1800
ttaccgttcc gttatggtgg tgatggttcc aaaggaccaa ccatctctgc tcaggaagct   1860
caggctcaag ctattcttca gcaggctcgg attgctctga gaggcccacc tggcccaatg   1920
ggtctaactg gaagaccagg tcctgtgggg gggcctggtt catctggggc caaaggtgag   1980
agtggtgatc caggtcctca gggccctcga ggcgtccagg gtccccctgg tccaacggga   2040
aaacctggaa aaaggggtcg tccaggtgca gatggaggaa gaggaatgcc aggagaacct   2100
ggggcaaagg gagatcgagg gtttgatgga cttccgggtc tgccaggtga caaaggtcac   2160
aggggtgaac gaggtcctca aggtcctcca ggtcctcctg gtgatgatgg aatgagggga   2220
gaagatggag aaattggacc aagaggtctt ccaggtgaag ctggcccacg aggtttgctg   2280
ggtccaaggg gaactccagg agctccaggg cagcctggta tggcaggtgt agatggcccc   2340
ccaggaccaa aagggaacat gggtccccaa ggggagcctg ggcctccagg tcaacaaggg   2400
aatccaggac ctcagggtct tcctggtcca caaggtccaa ttggtcctcc tggtgaaaaa   2460
ggaccacaag gaaaaccagg acttgctgga cttcctggtg ctgatgggcc tcctggtcat   2520
cctgggaaag aaggccagtc tggagaaaag ggggctctgg gtccccctgg tccacaaggt   2580
cctattggat acccgggccc ccggggagta aagggagcag atggtgtcag aggtctcaag   2640
ggatctaaag gtgaaaaggg tgaagatggt tttccaggat tcaaaggtga catgggtcta   2700
aaaggtgaca gaggagaagt tggtcaaatt ggcccaagag ggaagatgg ccctgaagga    2760
cccaaaggtc gagcaggccc aactggagac ccaggtcctt caggtcaagc aggagaaaag   2820
ggaaaacttg gagttccagg attaccagga tatccaggaa gacaaggtcc aaagggttcc   2880
actggattcc ctgggtttcc aggtgccaat ggagagaaag gtgcacgggg agtagctggc   2940
aaaccaggcc ctcggggtca gcgtggtcca acgggtcctc gaggttcaag aggtgcaaga   3000
ggtcccactg ggaaacctgg gccaaagggc acttcaggtg gcgatggccc tcctggccct   3060
ccaggtgaaa gaggtcctca aggacctcag ggtccagttg gattccctgg accaaaaggc   3120
cctcctggac cacctgggaa ggatgggctg ccaggacacc ctgggcaacg tggggagact   3180
ggatttcaag gcaagaccgg ccctcctggg ccagggggag tggttggacc acagggacca   3240
accggtgaga ctggtccaat aggggaacgt gggcatcctg gccctcctgg ccctcctggt   3300
gagcaaggtc ttcctggtgc tgcaggaaaa gaaggtgcaa agggtgatcc aggtcctcaa   3360
ggtatctcag ggaaagatgg accagcagga ttacgtggtt tcccagggga aagaggtctt   3420
cctggagctc agggtgcacc tggactgaaa ggaggggaag gtccccaggg cccaccaggt   3480
ccagttggct caccaggaga acgtgggtca gcaggtacag ctggcccaat tggtttacca   3540
gggcgcccgg gacctcaggg tcctcctggt ccagctggag agaaaggtgc tcctggagaa   3600
aaaggtcccc aagggcctgc agggagagat ggagttcaag gtcctgttgg tctcccaggg   3660
ccagctggtc ctgccggctc ccctggggaa gacggagaca agggtgaaat tggtgagccg   3720
ggacaaaaag gcagcaaggg tgacaaggga gaaaatggcc ctcccggtcc cccaggtctt   3780
caaggaccag ttggtgcccc tggaattgct ggaggtgatg gtgaaccagg tcctagagga   3840
```

-continued

```
cagcagggga tgtttgggca aaaaggtgat gagggtgcca gaggcttccc tggacctcct   3900
ggtccaatag gtcttcaggg tctgccaggc ccacctggtg aaaaaggtga aaatggggat   3960
gttggtccca tggggccacc tggtcctcca ggcccaagag gccctcaagg tcccaatgga   4020
gctgatggac cacaaggacc cccagggtct gttggttcag ttggtggtgt tggagaaaag   4080
ggtgaacctg gagaagcagg gaacccaggg cctcctgggg aagcaggtgt aggcggtccc   4140
aaaggagaaa gaggagagaa aggggaagct ggtccacctg gagctgctgg acctccaggt   4200
gccaaggggc caccaggtga tgatggccct aagggtaacc cgggtcctgt tggttttcct   4260
ggagatcctg gtcctcctgg ggaacctggc cctgcaggtc aagatggtgt tggtggtgac   4320
aagggtgaag atggagatcc tggtcaaccg ggtcctcctg gcccatctgg tgaggctggc   4380
ccaccaggtc ctcctggaaa acgaggtcct cctggagctg caggtgcaga gggaagacaa   4440
ggtgaaaaag gtgctaaggg ggaagcaggt gcagaaggtc ctcctggaaa aaccggccca   4500
gtcggtcctc agggacctgc aggaaagcct ggtccagaag gtcttcgggg catccctggt   4560
cctgtgggag aacaaggtct ccctggagct gcaggccaag atggaccacc tggtcctatg   4620
ggacctcctg gcttacctgg tctcaaaggt gaccctggct ccaagggtga aaagggacat   4680
cctggtttaa ttggcctgat tggtcctcca ggagaacaag gggaaaaagg tgaccgaggg   4740
ctccctggaa ctcaaggatc tccaggagca aaaggggatg gggaattcc  tggtcctgct   4800
ggtcccttag gtccacctgg tcctccaggt ttaccaggtc ctcaaggccc aaagggtaac   4860
aaaggctcta ctggacccgc tggccagaaa ggtgacagtg gtcttccagg gcctcctggg   4920
tctccaggtc cacctggtga agtcattcag cctttaccaa tcttgtcctc caaaaaaacg   4980
agaagacata ctgaaggcat gcaagcagat gcagatgata atattcttga ttactcggat   5040
ggaatggaag aaatatttgg ttccctcaat tccctgaaac aagacattga gcatatgaaa   5100
tttccaatgg gtactcagac caatccagcc cgaacttgta aagacctgca actcagccat   5160
cctgacttcc cagatggtga atattggatt gatcctaacc aaggttgctc aggagattcc   5220
ttcaaagttt actgtaattt cacatctggt ggtgagactt gcatttatcc agacaaaaaa   5280
tctgagggag taagaatttc atcatggcca aaggagaaac caggaagttg gtttagtgaa   5340
tttaagaggg gaaaactgct ttcatactta gatgttgaag gaaattccat caatatggtg   5400
caaatgacat tcctgaaact tctgactgcc tctgctcggc aaaatttcac ctaccactgt   5460
catcagtcag cagcctggta tgatgtgtca tcaggaagtt atgacaaagc acttcgcttc   5520
ctgggatcaa atgatgagga gatgtcctat gacaataatc cttttatcaa aacactgtat   5580
gatggttgtg cgtccagaaa aggctatgaa aagactgtca ttgaaatcaa tacaccaaaa   5640
attgatcaag tacctattgt tgatgtcatg atcaatgact ttggtgatca gaatcagaag   5700
ttcggatttg aagttggtcc tgtttgtttt cttggctaag attaagacaa agaacatatc   5760
aaatcaacag aaaatatacc ttggtgccac caacccattt tgtgccacat gcaagttttg   5820
aataaggatg gtatagaaaa caacgctgca tatacaggta ccatttagga aataccgatg   5880
cctttgtggg ggcagaatca catggcaaaa gctttgaaaa tcataaagat ataagttggt   5940
gtggctaaga tggaaacagg gctgattctt gattcccaat tctcaactct ccttttccta   6000
tttgaatttc tttggtgctg tagaaaacaa aaaaagaaaa atatatattc ataaaaaata   6060
tggtgctcat tctcatccat ccaggatgta ctaaaacagt gtgtttaata aattgtaatt   6120
attttgtgta cagttctata ctgttatctg tgtccatttc caaaacttgc acgtgtccct   6180
```

gaattccatc tgactctaat tttatgagaa ttgcagaact ctgatggcaa taaatatatg 6240
tattatgaaa aaataaagtt gtaatttctg atgactctaa gtccctttct ttggttaata 6300
ataaaatgcc tttgtatata ttgatgttga agagttcaat tatttgatgt cgccaacaaa 6360
attctcagag ggcaaaaatc tggaagactt ttggaagcac actctgatca actcttctct 6420
gccgacagtc attttgctga atttcagcca aaaatattat gcattttgat gctttattca 6480
aggctatacc tcaaactttt tcttctcaga atccaggatt tcacaggata cttgtatata 6540
tggaaaacaa gcaagtttat atttttggac agggaaatgt gtgtaagaaa gtatattaac 6600
aaatcaatgc ctccgtcaag caaacaatca tatgtatact tttttctac gttatctcat 6660 ctccttgttt tcagtgtgct tcaataatgc aggttaatat taaagatgga aattaagcaa 6720
ttatttatga atttgtgcaa tgttagattt tcttatcaat caagttcttg aatttgattc 6780
taagttgcat attataacag tctcgaaaat tattttactt gcccaacaaa tattactttt 6840
ttcctttcaa gataatttta taaatcattt gacctaccta attgctaaat gaataacata 6900
tggtggactg ttattaagag tatttgtttt aagtcattca ggaaaatcta aacttttttt 6960
tccactaagg tatttacttt aaggtagctt gaaatagcaa tacaatttaa aaattaaaaa 7020
ctgaattttg tatctatttt aagtaatata tgtaagactt gaaaataaat gttttatttc 7080
ttatataaag tgttaaatta attgatacca gatttcactg gaacagtttc aactgataat 7140
ttatgacaaa agaacatacc tgtaatattg aaattaaaaa gtgaaatttg tcataaagaa 7200
tttcttttat ttttgaaatc gagtttgtaa atgtcctttt aagaagggag atatgaatcc 7260
aataaataaa ctcaagtctt ggctacctgg a 7291

<210> SEQ ID NO 33
<211> LENGTH: 2471
<212> TYPE: DNA
<213> ORGANISM: Homo sapiens

<400> SEQUENCE: 33
agaaagcgag cagccaccca gctccccgcc accgccatgg tccccgacac cgcctgcgtt 60
cttctgctca ccctggctgc cctcggcgcg tccggacagg gccagagccc gttgggctca 120
gacctgggcc cgcagatgct tcgggaactg caggaaacca acgcggcgct gcaggacgtg 180
cgggagctgc tgcggcagca ggtcagggag atcacgttcc tgaaaaacac ggtgatggag 240
tgtgacgcgt gcgggatgca gcagtcagta cgcaccggcc tacccagcgt gcggcccctg 300
ctccactgcg cgcccggctt ctgcttcccc ggcgtggcct gcatccagac ggagagcggc 360
gcgcgctgcg gcccctgccc cgcgggcttc acgggcaacg gctcgcactg caccgacgtc 420
aacgagtgca acgcccaccc ctgcttcccc cgagtccgct gtatcaacac cagcccgggg 480
ttccgctgcg aggcttgccc gccggggtac agcggcccca cccaccaggg cgtggggctg 540
gctttcgcca aggccaacaa gcaggtttgc acggacatca acgagtgtga gaccgggcaa 600
cataactgcg tccccaactc cgtgtgcatc aacacccggg gctccttcca gtgcggcccg 660
tgccagcccg gcttcgtggg cgaccaggcg tccggctgcc agcggcgcgc acagcgcttc 720
tgccccgacg gctcgcccag cgagtgccac gagcatgcag actgcgtcct agagcgcgat 780
ggctcgcggt cgtgcgtgtg tgccgttggc tgggccggca acgggatcct ctgtggtcgc 840
gacactgacc tagacggctt cccggacgag aagctgcgct gcccggagcg ccagtgccgt 900
aaggacaact gcgtgactgt gcccaactca gggcaggagg atgtggaccg cgatggcatc 960
ggagacgcct gcgatccgga tgccgacggg gacggggtcc ccaatgaaaa ggacaactgc 1020
ccgctggtgc ggaacccaga ccagcgcaac acggacgagg acaagtgggg cgatgcgtgc 1080
gacaactgcc ggtcccagaa gaacgacgac caaaaggaca cagaccagga cggccggggc 1140
gatgcgtgcg acgacgacat cgacggcgac cggatccgca accaggccga caactgccct 1200
agggtaccca actcagacca gaaggacagt gatggcgatg gtatagggga tgcctgtgac 1260
aactgtcccc agaagagcaa cccggatcag gcggatgtgg accacgactt tgtgggagat 1320
gcttgtgaca gcgatcaaga ccaggatgga gacggacatc aggactctcg ggacaactgt 1380
cccacggtgc ctaacagtgc ccaggaggac tcagaccacg atggccaggg tgatgcctgc 1440
gacgacgacg acgacaatga cggagtccct gacagtcggg acaactgccg cctggtgcct 1500
aaccccggcc aggaggacgc ggacagggac ggcgtgggcg acgtgtgcca ggacgacttt 1560
gatgcagaca aggtggtaga caagatcgac gtgtgtccgg agaacgctga agtcacgctc 1620
accgacttca gggccttcca gacagtcgtg ctggacccgg agggtgacgc gcagattgac 1680
cccaactggg tggtgctcaa ccagggaagg gagatcgtgc agacaatgaa cagcgaccca 1740
ggcctggctg tgggttacac tgccttcaat ggcgtggact tcgagggcac gttccatgtg 1800
aacacggtca cggatgacga ctatgcgggc ttcatctttg gctaccagga cagctccagc 1860
ttctacgtgg tcatgtggaa gcagatggag caaacgtatt ggcaggcgaa ccccttccgt 1920
gctgtggccg agcctggcat ccaactcaag gctgtgaagt cttccacagg ccccggggaa 1980
cagctgcgga acgctctgtg gcatacagga gacacagagt cccaggtgcg gctgctgtgg 2040
aaggacccgc gaaacgtggg ttggaaggac aagaagtcct atcgttggtt cctgcagcac 2100
cggccccaag tgggctacat cagggtgcga ttctatgagg gccctgagct ggtggccgac 2160
agcaacgtgg tcttggacac aaccatgcgg ggtggccgcc tgggggtctt ctgcttctcc 2220
caggagaaca tcatctgggc caacctgcgt taccgctgca atgacaccat cccagaggac 2280
tatgagaccc atcagctgcg gcaagcctag ggaccagggt gaggacccgc cggatgacag 2340
ccaccctcac cgcggctgga tggggggctct gcacccagcc ccaaggggtg gccgtcctga 2400
gggggaagtg agaagggctc agagaggaca aaataaagtg tgtgtgcagg gaaaaaaaaa 2460
aaaaaaaaaa a 2471

<210> SEQ ID NO 34
<211> LENGTH: 618
<212> TYPE: DNA
<213> ORGANISM: Homo sapiens

<400> SEQUENCE: 34
gcggccgcaa gctcggcact cacggctctg agggctccga cggcactgac ggccatggcg 60
cgttcgaacc tcccgctggc gctgggcctg gccctggtcg cattctgcct cctggcgctg 120
ccacgcgacg cccgggcccg gccgcaggag cgcatggtcg gagaactccg ggacctgtcg 180
cccgacgacc cgcaggtgca gaaggcggcg caggcggccg tggccagcta caacatgggc 240
agcaacagca tctactactt ccgagacacg cacatcatca aggcgcagag ccagctggtg 300
gccggcatca agtacttcct gacgatggag atggggagca cagactgccg caagaccagg 360
gtcactggag accacgtcga cctcaccact tgcccccctgg cagcaggggc gcagcaggag 420
aagctgcgct gtgactttga ggtccttgtg gttccctggc agaactcctc tcagctccta 480
aagcacaact gtgtgcagat gtgataagtc cccgagggcg aaggccattg ggtttggggc 540
catggtggag ggcacttcag gtccgtgggc cgtatctgtc acaataaatg gccagtgctg 600
cttcttgcaa aaaaaaaa 618

<210> SEQ ID NO 35
<211> LENGTH: 1279
<212> TYPE: DNA
<213> ORGANISM: Homo sapiens

<400> SEQUENCE: 35
gggagggaga gaggcgcgcg ggtgaaaggc gcattgatgc agcctgcggc ggcctcggag 60
cgcggcggag ccagacgctg accacgttcc tctcctcggt ctcctccgcc tccagctccg 120
cgctgcccgg cagccgggag ccatgcgacc ccagggcccc gccgcctccc cgcagcggct 180
ccgcggcctc ctgctgctcc tgctgctgca gctgcccgcg ccgtcgagcg cctctgagat 240
ccccaagggg aagcaaaagg cgcagctccg gcagagggag gtggtggacc tgtataatgg 300
aatgtgctta caagggccag caggagtgcc tggtcgagac gggagccctg gggccaatgg 360
cattccgggt acacctggga tcccaggtcg ggatggattc aaaggagaaa agggggaatg 420
tctgagggaa agctttgagg agtcctggac acccaactac aagcagtgtt catggagttc 480
attgaattat ggcatagatc ttgggaaaat tgcggagtgt acatttacaa agatgcgttc 540
aaatagtgct ctaagagttt tgttcagtgg ctcacttcgg ctaaaatgca gaaatgcatg 600
ctgtcagcgt tggtatttca cattcaatgg agctgaatgt tcaggacctc ttcccattga 660
agctataatt tatttggacc aaggaagccc tgaaatgaat tcaacaatta atattcatcg 720
cacttcttct gtggaaggac tttgtgaagg aattggtgct ggattagtgg atgttgctat 780
ctgggttggt acttgttcag attacccaaa aggagatgct tctactggat ggaattcagt 840
ttctcgcatc attattgaag aactaccaaa ataaatgctt taattttcat ttgctacctc 900
tttttttatt atgccttgga atggttcact taaatgacat tttaaataag tttatgtata 960
catctgaatg aaaagcaaag ctaaatatgt ttacagacca aagtgtgatt tcacactgtt 1020
tttaaatcta gcattattca ttttgcttca atcaaaagtg gtttcaatat ttttttagt 1080 tggttagaat actttcttca tagtcacatt ctctcaacct ataatttgga atattgttgt 1140
ggtcttttgt tttttctctt agtatagcat ttttaaaaaa atataaaagc taccaatctt 1200
tgtacaattt gtaaatgtta agaatttttt ttatatctgt taaataaaaa ttatttccaa 1260
caaccttaat atctttaaa 1279

<210> SEQ ID NO 36
<211> LENGTH: 2322
<212> TYPE: DNA
<213> ORGANISM: Homo sapiens

<400> SEQUENCE: 36
atcattcggc cctcagactg ggctgggcag gtctgagagt tagggaaagt ccgttcccac 60
tgccctcggg gagagaagaa aggagggggc aagggagaag ctgctggtcg gactcacaat 120
gaaaacgctc cttcttttgc tgctggtgct cctggagctg ggagaggccc aaggatccct 180
tcacagggtg cccctcagga ggcatccgtc cctcaagaag aagctgcggg cacggagcca 240
gctctctgag ttctggaaat cccataattt ggacatgatc cagttcaccg agtcctgctc 300
aatggaccag agtgccaagg aacccctcat caactacttg gatatggaat acttcggcac 360
tatctccatt ggctccccac cacagaactt cactgtcatc ttcgacactg gctcctccaa 420
cctctgggtc ccctctgtgt actgcactag cccagcctgc aagacgcaca gcaggttcca 480
gccttcccag tccagcacat acagccagcc aggtcaatct ttctccattc agtatggaac 540

```
cgggagcttg tccgggatca ttggagccga ccaagtctct gtggaaggac taaccgtggt    600
tggccagcag tttggagaaa gtgtcacaga gccaggccag acctttgtgg atgcagagtt    660
tgatggaatt ctgggcctgg gatacccctc cttggctgtg ggaggagtga ctccagtatt    720
tgacaacatg atggctcaga acctggtgga cttgccgatg ttttctgtct acatgagcag    780
taacccagaa ggtggtgcgg ggagcgagct gatttttgga ggctacgacc actcccattt    840
ctctgggagc ctgaattggg tcccagtcac caagcaagct tactggcaga ttgcactgga    900
taacatccag gtgggaggca ctgttatgtt ctgctccgag ggctgccagg ccattgtgga    960
cacagggact tccctcatca ctggcccttc cgacaagatt aagcagctgc aaaacgccat   1020
tggggcagcc cccgtggatg gagaatatgc tgtggagtgt gccaacctta acgtcatgcc   1080
ggatgtcacc ttcaccatta acggagtccc ctataccctc agcccaactg cctacaccct   1140
actggacttc gtggatggaa tgcagttctg cagcagtggc tttcaaggac ttgacatcca   1200
ccctccagct gggcccctct ggatcctggg ggatgtcttc attcgacagt tttactcagt   1260
ctttgaccgt gggaataacc gtgtgggact ggccccagca gtcccctaag gaggggcctt   1320
gtgtctgtgc ctgcctgtct gacagacctt gaatatgtta ggctggggca ttctttacac   1380
ctacaaaaag ttattttcca gagaatgtag ctgtttccag ggttgcaact tgaattaaga   1440
ccaaacagaa catgagaata cacacacaca cacacatata cacacacaca cacttcacac   1500
atacacacca ctcccaccac cgtcatgatg gaggaattac gttatacatt catattttgt   1560
attgattttt gattatgaaa atcaaaaatt ttcacatttg attatgaaaa tctccaaaca   1620
tatgcacaag cagagatcat ggtataataa atccctttgc aactccactc agccctgaca   1680
acccatccac acacggccag gcctgtttat ctacactgct gcccactcct ctctccagct   1740
ccacatgctg tacctggatc attctgaagc aaattccgag cattacatca ttttgtccat   1800
aaatatttct aacatcctta aatatacaat cggaattcaa gcatctccca ttgtcccaca   1860
aatgtttggc tgtttttgta gttggattgt ttgtattagg attcaagcaa ggcccatata   1920
ttgcatttat ttgaaatgtc tgtaagtctc tttccatcta cagagtttag cacatttgaa   1980
cgttgctggt tgaaatcccg aggtgtcatt tgacatggtt ctctgaactt atctttccta   2040
taaaatggta gttagatctg gaggtctgat tttgtggcaa aaatacttcc taggtggtgc   2100
tgggtacttc ttgttgcatc ctgtcaggag gcagataatg ctggtgcctc tctattggta   2160
atgttaagac tgctgggtgg gtttggagtt cttggcttta atcattcatt acaaagttca   2220
gcattttaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aa                       2322
```

<210> SEQ ID NO 37
<211> LENGTH: 4542
<212> TYPE: DNA
<213> ORGANISM: Homo sapiens

<400> SEQUENCE: 37

```
ggtaggcgcg cccagacctg agacgggttg ggactgggct gcgtcacgcg cgggctctaa     60
gcgcccgggg ccccgcccag tggccggcac agccaatcgc agcgcgggaa ggcggtgggg    120
gcggggaagg ccgcctggaa acttaaatcc cgaggcgggc gaacctgcac cagaccgcgg    180
acgtctgtaa tctcagaggc ttgtttgctg agggtgcctg cgcagctgcg acggctgctg    240
gttttgaaac atgaatcttt cgctcgtcct ggctgccttt tgcttgggaa tagcctccgc    300
```

-continued

```
tgttccaaaa tttgaccaaa atttggatac aaagtggtac cagtggaagg caacacacag    360
aagattatat ggcgcgaatg aagaaggatg gaggagagca gtgtgggaaa agaatatgaa    420
aatgattgaa ctgcacaatg gggaatacag ccaagggaaa catggcttca caatggccat    480
gaatgctttt ggtgacatga ccaatgaaga attcaggcag atgatgggtt gctttcgaaa    540
ccagaaattc aggaagggga aagtgttccg tgagcctctg tttcttgatc ttcccaaatc    600
tgtggattgg agaaagaaag gctacgtgac gccagtgaag aatcagaaac agtgtggttc    660
ttgttgggct tttagtgcga ctggtgctct tgaaggacag atgttccgga aaactgggaa    720
acttgtctca ctgagcgagc agaatctggt ggactgttcg cgtcctcaag gcaatcaggg    780
ctgcaatggt ggcttcatgg ctagggcctt ccagtatgtc aaggagaacg gaggcctgga    840
ctctgaggaa tcctatccat atgtagcagt ggatgaaatc tgtaagtaca gacctgagaa    900
ttctgttgct aatgacactg gcttcacagt ggtcgcacct ggaaaggaga aggccctgat    960
gaaagcagtc gcaactgtgg ggcccatctc cgttgctatg gatgcaggcc attcgtcctt   1020
ccagttctac aaatcaggca tttattttga accagactgc agcagcaaaa acctggatca   1080
tggtgttctg gtggttggct acggctttga aggagcaaat tcgaataaca gcaagtattg   1140
gctcgtcaaa aacagctggg gtccagaatg gggctcgaat ggctatgtaa aaatagccaa   1200
agacaagaac aaccactgtg gaatcgccac agcagccagc taccccaatg tgtgagctga   1260
tggatggtga ggaggaagga cttaaggaca gcatgtctgg ggaaatttta tcttgaaact   1320
gaccaaacgc ttattgtgta agataaacca gttgaatcat tgaggatcca agttgagatt   1380
ttaattctgt gacattttta caagggtaaa atgttaccac tactttaatt attgttatac   1440
acagctttat gatatcaaag actcattgct taattctaag acttttgaat tttcattttt   1500
taaaaagatg tacaaaacag tttgaaataa attttaattc gtatataaag gtgggccttt   1560
ttttaatgca ttggcttttt gtgtagtcag gaaatataat taagctctga aataataact   1620
tcatgtgcca atggtatgtt aggagaaaga tgctagcaga aagctggctt cctggctctt   1680
gagtagttat aaaaatacag actttatatc agctgcccag ttactgtgtg ttacccaact   1740
cctgaatcta ccaaaatttg ataaacaatt tggaaggaca aacctacatt tttttttttt   1800
atgagacgga gtctctctca ctctgtcacc aaggctggag tgcagtagtg tgatctcagc   1860
tcactgcaac ctctgcctcc cgggtttaag caattctctg cctcagcctc ccgagtagct   1920
gggattacag gcgcgtgcca ccacgcctag tgtattttta gtagagagag ggtttcacca   1980
tcttggccag gctggtcttg aactctcgac ctcgtgatcc acctgcctca gcctcccaaa   2040
gtgttgggat tacagatgtg agccactgcg cccagcccct aaattgtttt agtaaagaag   2100
aaagcagttg actttttaga aaaggaaatg tcttcttcct ttgacacata acctcaagat   2160
ggttaggtta cgtgataaaa agtgaagctg cttgttactg gagcctctct gaattgctgg   2220
tgaccacttt gcagtctgag gaagacgcag gtgcaagtaa gttaccaagg gtattttgtt   2280
ttcattccaa gtctctgatg acatattcca cctagctctt ctagaaaagc ttatttgtta   2340
actagtgtta gcaaaaataa atggtgtggt taacaaatct caggcatttg acagtagctg   2400
gagaaatttg ttcaaggtcc acaagagatg aggctgggct acaaaaagag gcctctggcc   2460
gaagatggat aagagatcac aagtgaaagg tcagaagtca ctaggccaga ctctggctac   2520
ctaatccctg aattaaaaat aaactcaaaa tggggggaaa aaggctaagc atatagttac   2580
acaggtagta aatacaaata aaacgatatt tttgcatatt taaaatactg gaagaaagta   2640
caccaaactt gtgggtgaat tatgggtggt tatttaactc gtttagtgaa aagcatgtat   2700
```

ttttatgagc aggagaaaat agtaaagata tacccacatt ctgcaggcta aaggagagcc 2760
ctgtgtgtgt tttaaaagcc catgtttcca gtcaaataaa aaattaccgg ggatgagctg 2820
gtgaaattta atcgaaaggt gatccattgt gaatgcaatg ggagggaagg ggcatgtggg 2880
actgtgtatc ccaaaaaccc tttgatagcc tatgtccaca gccatctctg gaaaatccag 2940
tctaccatat tcagtcttga gtttctctg agaaaggatt ccttcgtctt tgcagcagca 3000
ggctaagttg gtactctcca cagattcttg gaacaacaac ccaggctcta aggaaacatc 3060
taggcactaa attgaatgaa agagtgatgg ctttttattc aaataaaaaa atttcaaatc 3120
tgtcaaaaca gcacccctcg gaaaactaaa atagagatat ttcaagattt tataattttc 3180
aaagaccttt gaaatatttt aaacttgtga aaagttacaa acctgatgtg ttgtctaaaa 3240
gcgtttttca aacaagccag tagacttgaa aaatctagtc tgaagcacag acttaaccaa 3300
tatttgctgg ggatatgccc ccaaatctgg ccataaacaa aatctctgca gtactgtgac 3360
aggttcatga tggccatgac gccatgctga aggtttaccg gaatgagagc aaggaacacc 3420
tggaccaccc agggcgggaa aacggcttaa aggcgttcct aaactacaaa caatagcatg 3480
agcgatctgt gccttaagga catgttcctg ctgcagataa ctagccagac cccatgcctt 3540
tgtttcgttt gggaaggaat acttttagtt aatctataat ctatagaaac aatgtttatc 3600
actggcttgc tgtcaataaa catgggtaaa tctctgttcg gggctctcag ctctgaaagc 3660
tgtgagtccc ctgatttccc actctgcatg ctatatttct gggtgtgtgt ctttaatttc 3720
tctagcgcct ctgggttagg gtctccatga ccaagctggt ctcggcaaat atttcctata 3780
ctcgaacatc taaattgttt gttttcttac ttgaattgca aaggaagtaa ggaagggtga 3840
gatagaaatc actgagcata ttaagaggga ggagtttgct gatgtgggag tgtagttatg 3900
acacttgggc atcatactag aggctatgga cttagcaata aggaaacatc cactcagccc 3960
tatgtgtggt tcatgtgtat gttttgccta tgaaagttga aactgttttc taaatgttat 4020
ttccttttgt aactgataaa atttctaaaa agcaaagaag aaacttttct gtattaaaaa 4080
taacaaacat tagtaaatgt atatatacag tcatgtgttg cttaatgatg gggatacatt 4140
ctgagaaatg tgtcttgggt gatttcatcg tgacgtgaac atcatagagt acactgacac 4200
aaacctagat ggtatagcct attacacacc taggctatat ggtacagcct gttgctccta 4260
agctacgcac ctgtgcaaca catcactgtg ctgagtactg tacacagttg taacacagtg 4320
gtaagtattc gtgtatctga acagaaaagt acagtaaaaa tataggatca taattttatg 4380
ggaccactat catatatgca gtcactgacc aaaacatcac acagcacatg acttgtgtgt 4440
atggatatct caattgtaaa caatttcaca aatgttcatt atctcttttt aagtaagtta 4500
ataagtaaaa ctattactaa gctgcaaaaa aaaaaaaaaa aa 4542

<210> SEQ ID NO 38
<211> LENGTH: 2099
<212> TYPE: DNA
<213> ORGANISM: Homo sapiens

<400> SEQUENCE: 38
aatcactgct gtgcagggca ggaaagctcc acacacacag cccagcaaac agcagcacgc 60
tgctgaaaaa aagactcaga ggagagagat aaggaaggaa agtagtgatg gatctcatcc 120
caaacttggc cgtggaaacc tggcttctcc tggctgtcag cctgatactc ctctatctat 180
atggaacccg tacacatgga ctttttaaga agcttggaat tccagggccc acacctctgc 240

-continued

```
cttttttggg aaatgctttg tccttccgta agggctattg gacgtttgac atggaatgtt    300
ataaaaagta tagaaaagtc tggggtattt atgactgtca acagcctatg ctggctatca    360
cagatcccga catgatcaaa acagtgctag tgaaagaatg ttattctgtc ttcacaaacc    420
ggaggccttt cgggccagtg ggatttatga aaaatgccat ctctatagct gaggatgaag    480
aatggaagag aatacgatca ttgctgtctc caacattcac cagcggaaaa ctcaaggaga    540
tggtccctat cattgcccag tatggagatg tgttggtgag aaatctgagg cgggaagcag    600
agacaggcaa gcctgtcacc ttgaaacacg tctttggggc ctacagcatg gatgtgatca    660
ctagcacatc atttggagtg agcatcgact ctctcaacaa tccacaagac ccctttgtgg    720
aaaacaccaa gaagctttta agatttaatc cattagatcc attcgttctc tcaataaaag    780
tctttccatt ccttacccca attcttgaag cattaaatat cactgtgttt ccaagaaaag    840
ttataagttt tctaacaaaa tctgtaaaac agataaaaga aggtcgcctc aaagagacac    900
aaaagcaccg agtggatttc cttcagctga tgattgactc tcagaattca aaagactctg    960
agacccacaa agctctgtct gatctggagc tcatggccca atcaattatc tttatttttg   1020
ctggctatga aaccacgagc agtgttctct ccttcattat atatgaactg gccactcacc   1080
ctgatgtcca gcagaaagtg cagaaggaaa ttgatacagt tttacccaat aaggcaccac   1140
ccacctatga tactgtgcta cagttggagt atcttgacat ggtggtgaat gaaacactca   1200
gattattccc agttgctatg agacttgaga gggtctgcaa aaaagatgtt gaaatcaatg   1260
ggatgtttat tcccaaaggg gtggtggtga tgattccaag ctatgttctt catcatgacc   1320
caaagtactg gacagagcct gagaagttcc tccctgaaag gttcagtaaa aagaacaagg   1380
acaacataga tccttacata tacacaccct ttggaagtgg acccagaaac tgcattggca   1440
tgaggtttgc tctcgtgaac atgaaacttg ctctagtcag agtccttcag aacttctcct   1500
tcaaaccttg taaagaaaca cagatccccc tgaaattacg ctttggagga cttcttctaa   1560
cagaaaaacc cattgttcta aaggctgagt caagggatga gaccgtaagt ggagcctgat   1620
ttccctaagg acttctggtt tgctctttaa gaaagctgtg ccccagaaca ccagagacct   1680
caaattactt tacaaataga accctgaaat gaagacgggc ttcatccaat gtgctgcata   1740
aataatcagg gattctgtac gtgcattgtg ctctctcatg gtctgtatag agtgttatac   1800
ttggtaatat agaggagatg accaaatcag tgctggggaa gtagatttgg cttctctgct   1860
tctcatagga ctatctccac cacccccagt tagcaccatt aactcctcct gagctctgat   1920
aacataatta acatttctca ataatttcaa ccacaatcat taataaaaat aggaattatt   1980
ttgatggctc taacagtgac atttatatca tgtgttatat ctgtagtatt ctatagtaag   2040
ctttatatta agcaaatcaa taaaaacctc tttacaaaag taaaaaaaaa aaaaaaaaa    2099
```

<210> SEQ ID NO 39
<211> LENGTH: 6093
<212> TYPE: DNA
<213> ORGANISM: Homo sapiens

<400> SEQUENCE: 39

```
gcctgccagc tagccggagc cgcgggtgag cgcggcgagc ggcgaccctg gtgaggagcg     60
cggcgcggga ggcacgttcc ttagctccgc cgcggccgtc ctccgcggct cgaggactcc    120
gcttccttcc ctcccctccc ctgcgctccg gcctggggtc tcggcgcggg gagcggaggg    180
aagggacgaa ggaggagtag gtgaaagcgg ggtgaggggc ggaagggtcc cggcgcgggg    240
tgaggcgagg gctgcctctt gttctcccgc cgctgccgcc gtctcctggt cgggtgccgc    300
```

-continued

```
ggccagaggc gcgcggggct gccgaggcac ccgcactatg caggcagact gccggccgcc    360
gcgatggcga gccgggcggt ggtgagagcc aggcgctgcc cgcagtgtcc ccaagtccgg    420
gccgcggccg ccgcccccgc ctgggccgcg ctccccctct cccgctccct ccctccctgc    480
tccaactcct cctccttctc catgcctctg ttcctcctgc tcttacttgt cctgctcctg    540
ctgctcgagg acgctggagc ccagcaaggt gatggatgtg gacacactgt actaggccct    600
gagagtggaa cccttacatc cataaactac ccacagacct atcccaacag cactgtttgt    660
gaatgggaga tccgtgtaaa gatgggagag agagttcgca tcaaatttgg tgactttgac    720
attgaagatt ctgattcttg tcactttaat tacttgagaa tttataatgg aattggagtc    780
agcagaactg aaataggcaa atactgtggt ctggggttgc aaatgaacca ttcaattgaa    840
tcaaaaggca atgaaatcac attgctgttc atgagtggaa tccatgtttc tggacgcgga    900
tttttggcct catactctgt tatagataaa caagatctaa ttacttgttt ggacactgca    960
tccaattttt tggaacctga gttcagtaag tactgcccag ctggttgtct gcttcctttt   1020
gctgagatat ctggaacaat tcctcatgga tatagagatt cctcgccatt gtgcatggct   1080
ggtgtgcatg caggagtagt gtcaaacacg ttgggcggcc aaatcagtgt tgtaattagt   1140
aaaggtatcc cctattatga aagttctttg gctaacaacg tcacatctgt ggtgggacac   1200
ttatctacaa gtctttttac atttaagaca agtggatgtt atggaacact ggggatggag   1260
tctggtgtga tcgcggatcc tcaaataaca gcatcatctg tgctggagtg gactgaccac   1320
acagggcaag agaacagttg gaaacccaaa aaagccaggc tgaaaaaacc tggaccgcct   1380
tgggctgctt ttgccactga tgaataccag tggttacaaa tagatttgaa taaggaaaag   1440
aaaataacag gcattataac cactggatcc accatggtgg agcacaatta ctatgtgtct   1500
gcctacagaa tcctgtacag tgatgatggg cagaaatgga ctgtgtacag agagcctggt   1560
gtggagcaag ataagatatt tcaaggaaac aaagattatc accaggatgt gcgtaataac   1620
tttttgccac caattattgc acgttttatt agagtgaatc ctacccaatg gcagcagaaa   1680
attgccatga aaatggagct gctcggatgt cagtttattc ctaaaggtcg tcctccaaaa   1740
cttactcaac ctccacctcc tcggaacagc aatgacctca aaaacactac agcccctcca   1800
aaaatagcca aaggtcgtgc cccaaaattt acgcaaccac tacaacctcg cagtagcaat   1860
gaatttcctg cacagacaga acaaacaact gccagtcctg atatcagaaa tactaccgta   1920
actccaaatg taaccaaaga tgtagcgctg gctgcagttc ttgtccctgt gctggtcatg   1980
gtcctcacta ctctcattct catattagtg tgtgcttggc actggagaaa cagaaagaaa   2040
aaaactgaag gcacctatga cttaccttac tgggaccggg caggttggtg gaaaggaatg   2100
aagcagtttc ttcctgcaaa agcagtggac catgaggaaa ccccagttcg ctatagcagc   2160
agcgaagtta atcacctgag tccaagagaa gtcaccacag tgctgcaggc tgactctgca   2220
gagtatgctc agccactggt aggaggaatt gttggtacac ttcatcaaag atctaccttt   2280
aaaccagaag aaggaaaaga agcaggctat gcagacctag atccttacaa ctcaccaggg   2340
caggaagttt atcatgccta tgctgaacca ctcccaatta cggggcctga gtatgcaacc   2400
ccaatcatca tggacatgtc agggcacccc acaacttcag ttggtcagcc ctccacatcc   2460
actttcaagg ctacggggaa ccaacctccc ccactagtgg gaacttacaa tacacttctc   2520
tccaggactg acagctgctc ctcagcccag gcccagtatg ataccccgaa agctgggaag   2580
ccaggtctac ctgccccaga cgaattggtg taccaggtgc cacagagcac acaagaagta   2640
```

tcaggagcag gaagggatgg ggaatgtgat gtttttaaag aaatcctttg aagatgatgc 2700
tgctttttac aaagcatcgt tttaaagcac atggcctttt ttttttaatt attagtggta 2760
gtaatatata gaatgtatta cataactgtc actgaagtgg ttggggaaaa tgtggtgact 2820
gaggtacagg aaactactaa tcttgccatc ttgctttaag gtgttatggt ggcacagtta 2880
ctgctcgcct gttaaatttc aaatgtcctg tttgatacta ctgtagaaca ctatttttaa 2940
tacagaaaaa gctccctata atgcacttca gagaaattaa aaatcacaga gtatttatta 3000
ccaatgctgc aggtacatta atgaactcga gatggctctg taagcctgac tggcaataac 3060
gcacggtact gttcttgaaa tacctaatgg cttgaaattc tagtctgttt gtgaaagatg 3120
ggtactatca tgatttcctc ttctattcct atattctttt ctggattttt tttaataatt 3180
agtgatataa gcattgtttt tattgcagcc atatccactt atccatctta agatctgtag 3240
ctgggatttt ctgacttgta atgagcaggg ggattgcttt ttcactttgt gacactcttt 3300
agagctttaa tgcttcacag tatatggcct ggtctcatcc ttgcgtgttc cacttgaggc 3360
cctttggtgt cttgccccat tcttgtgttt ataaaatgtt tgagtatttc tgatgagtga 3420
tgcttgcctt agtctcatga attcagatcc cttcatgtcc tttaagtatg ctcctcaatg 3480
tgtaaacagg aacaacttta tgatttgaaa gctttaaagg agattcttct cccaccccca 3540
actttatttg caatgggatt tttcctagga gagttatgaa aagttgaagg cttctaaggg 3600
aatactgtaa acatgaccca cttatattta tcacagtgaa aggcaaaatt attcactcag 3660
aagtaatata aattacctct ttaaaaagta accagaattt gtcctttttg gttttataca 3720
ttcacaaaca tatacatttt tcttgagtct caaggtattt tatattttta gtcagaaaaa 3780
ataattttc atttcagttt tccataaact gttacacaaa atataaacct aacgtgtatt 3840
tttcaggact gcgtgatcgt gcactttgtg tggtaagagg tttgagtagt cctatatgtc 3900
acctagggaa cagacattat agcttactag caaatgaata ttcatgcctt gtttttgata 3960
cctcctggca gcttccatgt caccacttgt tcatacctgc ccagagctag ttttagacat 4020
ggcaaaatag aaatcatctg taatttatta gctaacaatg taaaaccatc ttttaaagcc 4080
ttcagactgt caagacgaca tgagcagctc accatatgat aaaaatacat aaatttgaca 4140
ttccctcttc cataaacctt tgtttgtaga tttaatgttg aacagtactt ttccataaag 4200
ttctagtcac ttctgttggc ctgagccacc agattatgat gttgccagaa ttcactcaat 4260
ttgaataaag atgaacagta tttgttttct tgtttccatg aattatatca gtattctaaa 4320
acatcgcttc agaaagagaa ctgtttattt ctgcaggctt cctgtccttt tgtggtatgg 4380
tttttggcc ttattttcac tggcttttcc ttctccaaac tttgaggcgt gatttcattc 4440
attgaagaat caatacatat tttgtttcaa aatgtttgaa acaaaagaca tagatggtag 4500
acttttatta aaacatatat ggatgtggaa agcacatata ttaatgcagt catccctttt 4560
caggtgggaa gagagcaaac cagttgattt tttaattcat ccttagtaca cagagaatat 4620
acttttcctc aagtaatata cctgtttgaa gctttaagag agatgttttt ggtaactatt 4680
tcattttccc aaagaagttt gctattcttg tgttaattgt gtatacctga ttgtttttc 4740
ctggaggttt ttgttgttgt tgtttagttt tgggtttttt ttttttaag aggggcaagt 4800
gttttctgaa atgatgcata ttttaagact cgattcatat tgccactgtg ctatccttga 4860
actaccaata atttttataa aatatctagt ttttactact tttatataaa ctttactttc 4920
cagatgaaga gctgagcctg attcaaatgg tttttctgct ttatacttct ttttagttca 4980
ttggttttta tagtagaggt tttctatttt tttttttt tttttacta catttatatg 5040 tctgatacat atacggcttt ggagacaatc aagtaacaac tgaaaatgtg aaagtaacca 5100
tatctgacaa aattcccttg aatttttatc ctttgcttgc aacatttaag actcaaagtc 5160
actggtatat tggattaagt tttttcctgt taatgcaatt atagaaatac atcggagaca 5220
caacaaatgt ggccattaca ggtttcataa aattacactg acttggctgt tacttgatct 5280
taggaaacag cacagtttaa gatattgtga attctgactt atactttatt aaatgctgta 5340
aatctaaata gatcctgttg gatgtgatgg gtctagtcca gtttatttaa gttcatgttt 5400
cactgtttgc actttgcatt gaacaatggg tttattcgct gatgtaaacg gttcgagtga 5460
agaattaatg cagtaagtat gacaacacat acacacttgc ctctccccat ctccagaaga 5520
ggggagcaga gtccgagctt atctaaatat gaatgtggcc acaaagctgt ggaaggtgac 5580
aaagcttaaa cacctttgcc ctggctctgc attgtcacct agagagcaag aggtctatag 5640
aaacatcatg tcacatgaaa cgattctctg ctttttggtt ctgaacttga agtccctaaa 5700
ctgcaaaatc taagagttgg gtggttatta aaatgctttt aaagtcaact gtggcaccaa 5760
ttctaatgta atccaacttg tgactgtttt tttttgtttt gttttgtttt tgtgtgtgtg 5820
tgtgtggcac tgggaaaagt ggaaacaaac atgtattgaa atacatattg gaaataaaaa 5880
tggtttgagc gtcagtgata ttctcccaga atgtacttat cttacctcgg catgtactgt 5940
agtcactcag tatttgtata tgttgctaga atttagattg taaaatagtg aaattttaat 6000
gtgttcattt gtttttaatg tatatatgtc ttgctcagat tatttggttt aaataaaaca 6060
accttgaggt ttgtagcttt tccttatact ata 6093

<210> SEQ ID NO 40
<211> LENGTH: 2090
<212> TYPE: DNA
<213> ORGANISM: Homo sapiens

<400> SEQUENCE: 40
ggcacatgtg gctggaaatg caagaagagg gaaacgtgtg gcttggagtt tcaagaagag 60
tgactgtctc agtgccgagt gcctcagcag cttctccaca tgctcttcag tccccaaagt 120
tggagaatcc catcaaggag agtagccctg taaggaattc gaatttccag catttttcac 180
ctctgacaga gcccagacac catgaacgca agtgaattcc gaaggagagg gaaggagatg 240
gtggattacg tggccaacta catggaaggc attgagggac gccaggtcta ccctgacgtg 300
gagcccgggt acctgcggcc gctgatccct gccgctgccc ctcaggagcc agacacgttt 360
gaggacatca tcaacgacgt tgagaagata atcatgcctg ggtgacgca ctggcacagc 420 ccctacttct tcgcctactt ccccactgcc agctcgtacc cggccatgct tgcggacatg 480
ctgtgcgggg ccattggctg catcggcttc tcctgggcgg caagcccagc atgcacagag 540
ctggagactg tgatgatgga ctggctcggg aagatgctgg aactaccaaa ggcatttttg 600
aatgagaaag ctggagaagg gggaggagtg atccagggaa gtgccagtga agccaccctg 660
gtggccctgc tggccgctcg gaccaaagtg atccatcggc tgcaggcagc gtccccagag 720
ctcacacagg ccgctatcat ggagaagctg gtggcttact catccgatca ggcacactcc 780
tcagtggaaa gagctgggtt aattggtgga gtgaaattaa aagccatccc ctcagatggc 840
aacttcgcca tgcgtgcgtc tgccctgcag gaagccctgg agagagacaa agcggctggc 900
ctgattcctt tctttatggt tgccaccctg gggaccacaa catgctgctc ctttgacaat 960
ctcttagaag tcggtcctat ctgcaacaag gaagacatat ggctgcacgt tgatgcagcc 1020

-continued

```
tacgcaggca gtgcattcat ctgccctgag ttccggcacc ttctgaatgg agtggagttt   1080

gcagattcat tcaactttaa tccccacaaa tggctattgg tgaattttga ctgttctgcc   1140

atgtgggtga aaaagagaac agacttaacg ggagccttta gactggaccc cacttacctg   1200

aagcacagcc atcaggattc agggcttatc actgactacc ggcattggca gataccactg   1260

ggcagaagat ttcgctcttt gaaaatgtgg tttgtattta ggatgtatgg agtcaaagga   1320

ctgcaggctt atatccgcaa gcatgtccag ctgtcccatg agtttgagtc actggtgcgc   1380

caggatcccc gctttgaaat ctgtgtggaa gtcattctgg ggcttgtctg ctttcggcta   1440

aagggttcca acaaagtgaa tgaagctctt ctgcaaagaa taaacagtgc caaaaaaatc   1500

cacttggttc catgtcacct cagggacaag tttgtcctgc gctttgccat ctgttctcgc   1560

acggtggaat ctgcccatgt gcagcgggcc tgggaacaca tcaaagagct ggcggccgac   1620

gtgctgcgag cagagaggga gtaggagtga agccagctgc aggaatcaaa aattgaagag   1680

agatatatct gaaaactgga ataagaagca aataaatatc atcctgcctt catggaactc   1740

agctgtctgt ggcttcccat gtctttctcc aaagttatcc agagggttgt gattttgtct   1800

gcttagtatc tcatcaacaa agaaatatta tttgctaatt aaaaagttaa tcttcatggc   1860

catagctttt attcattagc tgtgattttt gttgattaaa acattataga ttttcatgtt   1920

cttgcagtca tcagaagtgg taggaaagcc tcactgatat attttccagg gcaatcaatg   1980

ttcacgcaac ttgaaattat atctgtggtc ttcaaattgt cttttgtcat gtggctaaat   2040

gcctaataaa caattcaagt gaaatactaa aaaaaaaaaa aaaaaaaaaa              2090
```

<210> SEQ ID NO 41
<211> LENGTH: 2268
<212> TYPE: DNA
<213> ORGANISM: Homo sapiens

<400> SEQUENCE: 41

```
gtctcccctc gccgcatcca ctctccggcc ggccgcctgc ccgccgcctc ctccgtgcgc     60

ccgccagcct cgcccgcgcc gtcaccatga gccaggccta ctcgtccagc cagcgcgtgt    120

cctcctaccg ccgcaccttc ggcggggccc cgggcttccc actcggctcc ccgctgagtt    180

cgcccgtgtt cccgcgggcg ggtttcggct ctaagggctc ctccagctcg gtgacgtccc    240

gcgtgtacca ggtgtcgcgc acgtcgggcg gggccggggg cctggggtcg ctgcgggcca    300

gccggctggg gaccacccgc acgccctcct cctacggcgc aggcgagctg ctggacttct    360

cactggccga cgcggtgaac caggagtttc tgaccacgcg caccaacgag aaggtggagc    420

tgcaggagct caatgaccgc ttcgccaact acatcgagaa ggtgcgcttc ctggagcagc    480

agaacgcggc gctcgccgcc gaagtgaacc ggctcaaggg ccgcgagccg acgcgagtgg    540

ccgagctcta cgaggaggag ctgcgggagc tgcggcgcca ggtggaggtg ctcactaacc    600

agcgcgcgcg cgtcgacgtc gagcgcgaca acctgctcga cgacctgcag cggctcaagg    660

ccaagctgca ggaggagatt cagttgaagg aagaagcaga gaacaatttg gctgccttcc    720

gagcggacgt ggatgcagct actctagctc gcattgacct ggagcgcaga attgaatctc    780

tcaacgagga gatcgcgttc cttaagaaag tgcatgaaga ggagatccgt gagttgcagg    840

ctcagcttca ggaacagcag gtccaggtgg agatggacat gtctaagcca gacctcactg    900

ccgccctcag ggacatccgg gctcagtatg agaccatcgc ggctaagaac atttctgaag    960

ctgaggagtg gtacaagtcg aaggtgtcag acctgaccca ggcagccaac aagaacaacg   1020

acgccctgcg ccaggccaag caggagatga tggaataccg acaccagatc cagtcctaca   1080
```

-continued

```
cctgcgagat tgacgccctg aagggcacta acgattccct gatgaggcag atgcgggaat   1140
tggaggaccg atttgccagt gaggccagtg gctaccagga caacattgcg cgcctggagg   1200
aggaaatccg gcacctcaag gatgagatgg cccgccatct gcgcgagtac caggacctgc   1260
tcaacgtgaa gatggccctg gatgtggaga ttgccaccta ccggaagctg ctggagggag   1320
aggagagccg gatcaatctc cccatccaga cctactctgc cctcaacttc cgagaaacca   1380
gccctgagca aaggggttct gaggtccata ccaagaagac ggtgatgatc aagaccatcg   1440
agacacggga tggggaggtc gtcagtgagg ccacacagca gcagcatgaa gtgctctaaa   1500
gacagagacc ctctgccacc agagaccgtc ctcacccctg tcctcactgc tccctgaagc   1560
cagccttctt ccatcccagg acaccacacc cagcctcagt cctcccctca cagcctctga   1620
cccctcctca ctggccatcc ctcgtggtcc ccaacagcga catagcccat ccctgcctgg   1680
tcacagggca tgccccggcc acctctgcgg accccagctg tgagccttgg ctgttggcag   1740
tgagtgagcc tggctcttgt gctggatgga gcccaggcgg gagcggtggc cctgtccctc   1800
ccacctctgt gacctcaggc actagccttt ggctctggag acagccccag agcagggtgt   1860
tgggatactg cagggccagg actgagcccc gcagacctcc ccagccccta gcccaggaga   1920
gagaaagcca ggcaggtagc caggggggact agcccctgtg gagactgggg ggcttgaaat   1980
tgtccccgtg gtctcttact ttcctttccc cagcccaggg tggacttaga aagcaggggc   2040
tacaagaggg aatccccgaa ggtgctggag gtgggagcag gagattgaga aggagagaaa   2100
gtgggtgaga tgctggagaa gagaggagag gagagaggca gagagcggtc tcaggctggt   2160
gggaggggcg cccacctccc cacgccctcc cctcccctgc tgcaggggct ctggagagaa   2220
acaataaaga gattcacaca caagccaaaa aaaaaaaaaa aaaaaaaa                2268
```

<210> SEQ ID NO 42
<211> LENGTH: 1993
<212> TYPE: DNA
<213> ORGANISM: Homo sapiens

<400> SEQUENCE: 42

```
aggaagaaaa tataaagtac acttttaaaa catgaagtct tcatagcagc ttatagtcgt     60
tcagagaaac atgttccact gagaatgact tgagagagag gattacatca ttatgccaga    120
aggaagaagc cactgtgcat gctctatcac cagcctcacc ctcctggtca gccttacaag    180
agtgacactg gatatactcc agaagttgga cccaccacag cctgcacact ggacttcttg    240
gcttttatga gctattcaag agatatttag tcatcacgtt gtgtcacaat gggagtgact    300
cacagagcaa ggagagaacc tgaggattcc tcacacatgt agtactcaga gctctacgga    360
aacccaggca cctcgacctc aagaggatca gcctggccag ggtggcacaa ctcttccttc    420
cccgtgcaca gcaggaaagc tgccatcagc tgagcaagtc caccaacagt ttctgtgtcc    480
cacttcatct ttaataagga caccatcttc ttgtattata caagaaagga gtgtacctat    540
cacacacagg gggaaaaatg ctcttttggg tgctaggcct cctaatcctc tgtggttttc    600
tgtggactcg taaaggaaaa ctaaagattg aagacatcac tgataagtac atttttatca    660
ctggatgtga ctcgggcttt ggaaacttgg cagccagaac ttttgataaa aagggatttc    720
atgtaatcgc tgcctgtctg actgaatcag gatcaacagc tttaaaggca gaaacctcag    780
agagacttcg tactgtgctt ctggatgtga ccgacccaga gaatgtcaag aggactgccc    840
agtgggtgaa gaaccaagtt ggggagaaag gtctctgggg tctgatcaat aatgctggtg    900
```

-continued

```
ttcccggcgt gctggctccc actgactggc tgacactaga ggactacaga gaacctattg     960

aagtgaacct gtttggactc atcagtgtga cactaaatat gcttcctttg gtcaagaaag    1020

ctcaagggag agttattaat gtctccagtg ttggaggtcg ccttgcaatc gttggagggg    1080

gctatactcc atccaaatat gcagtggaag gtttcaatga cagcttaaga cgggacatga    1140

aagcttttgg tgtgcacgtc tcatgcattg aaccaggatt gttcaaaaca aacttggcag    1200

atccagtaaa ggtaattgaa aaaaaactcg ccatttggga gcagctgtct ccagacatca    1260

aacaacaata tggagaaggt tacattgaaa aaagtctaga caaactgaaa ggcaataaat    1320

cctatgtgaa catggacctc tctccggtgg tagagtgcat ggaccacgct ctaacaagtc    1380

tcttccctaa gactcattat gccgctggaa aagatgccaa aattttctgg atacctctgt    1440

ctcacatgcc agcagctttg caagactttt tattgttgaa acagaaagca gagctggcta    1500

atcccaaggc agtgtgactc agctaaccac aaatgtctcc tccaggctat gaaattggcc    1560

gatttcaaga acacatctcc ttttcaaccc cattccttat ctgctccaac ctggactcat    1620

ttagatcgtg cttatttgga ttgcaaaagg gagtcccacc atcgctggtg gtatcccagg    1680

gtccctgctc aagttttctt tgaaaaggag ggctggaatg gtacatcaca taggcaagtc    1740

ctgccctgta tttaggcttt gcctgcttgg tgtgatgtaa gggaaattga aagacttgcc    1800

cattcaaaat gatctttacc gtggcctgcc ccatgcttat ggtccccagc atttacagta    1860

acttgtgaat gttaagtatc atctcttatc taaatattaa aagataagtc aaacattaaa    1920

aaaaaaaaaa aaaaaaaaaa aaaaaaaaaa aaaaaaaaaa aaaaaaaaaa aaaaaaaaaa    1980

aaaaaaaaaa aaa                                                       1993
```

<210> SEQ ID NO 43
<211> LENGTH: 838
<212> TYPE: DNA
<213> ORGANISM: Homo sapiens

<400> SEQUENCE: 43

```
gggtcacagc accctcctga aaactgcagc ttccttctca ccttgaagaa taatcctaga      60

aaactcacaa aatgtgtgat gcttttgtag gtacctggaa acttgtctcc agtgaaaact     120

ttgatgatta tatgaaagaa gtaggagtgg gctttgccac caggaaagtg gctggcatgg     180

ccaaacctaa catgatcatc agtgtgaatg gggatgtgat caccattaaa tctgaaagta     240

cctttaaaaa tactgagatt tccttcatac tgggccagga atttgacgaa gtcactgcag     300

atgacaggaa agtcaagagc accataacct tagatggggg tgtcctggta catgtgcaga     360

aatgggatgg aaaatcaacc accataaaga gaaaacgaga ggatgataaa ctggtggtgg     420

aatgcgtcat gaaaggcgtc acttccacga gagtttatga gagagcataa gccaagggac     480

gttgacctgg actgaagttc gcattgaact ctacaacatt ctgtgggata tattgttcaa     540

aaagatattg ttgttttcca tgatttagca agcaactaat tttctcccaa gctgatttta     600

ttcaatatgg ttacgttggt taaataaact ttttttagat ttagaaggtg atgtaatgat     660

gtattcattg tgcttatgat gtattcttag tcataactga gtgaaggaaa tgggaaattt     720

gcattatttc tttgttctga tatgaataat aacatatttc ataataattc aaggtaaaaa     780

gggatatcta tggatttccc taggtaggag ataacaagta tgtaccatta ctgaatat       838
```

<210> SEQ ID NO 44
<211> LENGTH: 1322
<212> TYPE: DNA
<213> ORGANISM: Homo sapiens

<400> SEQUENCE: 44
tcctcaaagg aggggcagag cctgcgcagg gcaggagcag ctggcccact ggcggcccgc 60
aacactccgt ctcaccctct gggcccactg catctagagg agggccgtct gtgaggccac 120
taccctcca gcaactggga ggtgggactg tcagaagctg gcccagggtg gtggtcagct 180
gggtcaggga cctacggcac ctgctggacc acctcgcctt ctccatcgaa gcagggaagt 240
gggagcctcg agccctcggg tggaagctga ccccaagcca cccttcacct ggacaggatg 300
agagtgtcag gtgtgcttcg cctcctggcc ctcatctttg ccatagtcac gacatggatg 360
tttattcgaa gctacatgag cttcagcatg aaaaccatcc gtctgccacg ctggctggca 420
gcctcgccca ccaaggagat ccaggttaaa aagtacaagt gtggcctcat caagccctgc 480
ccagccaact actttgcgtt taaaatctgc agtggggccg ccaacgtcgt gggccctact 540
atgtgctttg aagaccgcat gatcatgagt cctgtgaaaa acaatgtggg cagaggccta 600
aacatcgccc tggtgaatgg aaccacggga gctgtgctgg gacagaaggc atttgacatg 660
tactctggag atgttatgca cctagtgaaa ttccttaaag aaattccggg gggtgcactg 720
gtgctggtgg cctcctacga cgatccaggg accaaaatga acgatgaaag caggaaactc 780
ttctctgact tggggagttc ctacgcaaaa caactgggct tccgggacag ctgggtcttc 840
ataggagcca aagacctcag ggtaaaagc cccttgagc agttcttaaa gaacagccca 900
gacacaaaca aatacgaggg atggccagag ctgctggaga tggagggctg catgcccccg 960
aagccatttt agggtggctg tggctcttcc tcagccaggg gcctgaagaa gctcctgcct 1020
gacttaggag tcagagcccg gcaggggctg aggaggagga gcagggggtg ctgcgtggaa 1080
ggtgctgcag gtccttgcac gctgtgtcgc gcctctcctc ctcggaaaca gaaccctccc 1140
acagcacatc ctacccggaa gaccagcctc agagggtcct tctggaacca gctgtctgtg 1200
gagagaatgg ggtgctttcg tcagggactg ctgacggctg gtcctgagga aggacaaact 1260
gcccagactt gagcccaatt aaattttatt tttgctggtt ttgaatgaaa aaaaaaaaaa 1320
aa 1322

<210> SEQ ID NO 45
<211> LENGTH: 4596
<212> TYPE: DNA
<213> ORGANISM: Homo sapiens

<400> SEQUENCE: 45
gatgacttgg agaacagtca cttcctcttt ctgggctaca gttttctcat cagtaactga 60
agagcttgca gtaccttcaa cattccttca ggtgaggact tctctttgat cactgctatg 120
gtttgaatgt gtctcctaaa gttcatgtgt tggaagcttg atccccagtg caaaagtgtt 180
gggaggtggg gcctaatgag aagtaattag gccatgagta ttctgccctc atgtattcat 240
gagattaatg tcattatcat gggagcgggt ttgttaaaat gagttcggcc ccttccttct 300
ctctctttct tctgccatac agtatgggat gcacagtgca gaaggtctta ccagatactg 360
gcaccatgct tttggacttc tcagccccca gaaccatgag ccaaataaat ttctgttcat 420
tataaatcac ccagtctgtg gcatcctgtt agagcagcat aaatggacta agataatccc 480
tataaagagt ggcaacagaa cagttcccag ctcactggca gaatcctatg atcaactagt 540
aatgtctgcc agggaaggag gatgagtggc actaacatgt acggtgtgtt tgctcactgt 600
tctacaggat tcaactagaa tctctgggtc tgtgtgaaga ccaagagctg ggaacagaag 660

-continued

```
cagggctcta gagggaaaag tttctttcgg attccttttt tttgttttgt tttaaagagc    720
tgctctgtga gaagacaagg agaaaatggt ccctacagga tactcacctc tgtctcaggg    780
agacactcaa gcatttattc aaccaagaaa gagaattagt tccaggtgaa aggagaaccc    840
cagaataccc acctactttt aaaattctcc cctatgcata ttcaggaacc aatcagagga    900
tctgtaatgc gctgtgagta gaaagggaag gggaatggga aagaaaaaag tgaagcttgg    960
aatggtggaa agtacatggg ctctgccatt taccagctaa gtgatcttgg gcaagtaact   1020
tgacctttct gagcctcggt ttcctctttg gtgaaatgag gactaataat ccatttctcc   1080
ctcagtacag acagccagca tgcagtgagc actcagcgat ggccaagtat gggagaagcc   1140
atgctggaat gaacatgtgg gaccattttg tgcagtttct cagcgccaac actgactggt   1200
cccctgggct cgtgggccgc cggcagcctc ggctcgttct ccagacagtg ttccaagaag   1260
ccacttccag cgaggaagcg ttggcctgag aactggaacc tctgcggtct ctgcaaacac   1320
gacaatgaca aacacttgag agggcatggg agaaaggagc tccttcatag ggcagggagg   1380
ggtgggcact tgggtgtgac caaggagagg aggcgcgcct ggtcaacagc tctccctggc   1440
ccgtgtccag ctccctcctc acacagagag gggggcgcat ctcagggatg gcatctttcc   1500
cccccacagg gaaattctta tctttgaaac agcatgggaa tcgaggcacc caggagggga   1560
gcagaggcag gcaggcctcc ttcaggccca tcctccagct gggctggtgg tgccagggag   1620
gctccctgct tggtaacaaa ggcctgaggg agagttgcga aacccagcag gaaagccggc   1680
tcaccttcgc ctccccctgc ggctgggagg agaggaaata tcccatggct gactgtgcca   1740
aggaggtgtc tgagccagcc ctcccggccc gagggcaggg caggtggccc tgagagataa   1800
gccaatcccg cagctgcaga tgaggagttc tgagaagcat tgctcaggac agcggtaaat   1860
cacttcttgg aggtgccctg cacgccggtc ctgggagcag gcggcctccc gggggtgcgg   1920
gagccccact cctccgtggt gtgttccatt tgcttcccac atctggagga gctgacgtgc   1980
cagcctcccc cagcaccacc cagggacggg aggcatgagc cggtcaaggc acctgggcaa   2040
aatccggaag cgtctggaag atgtcaagag ccagtgggtc cggccagcca gggctgactt   2100
tagtgacaac gagagtgccc ggctggccac ggacgccctc ttggatgggg gttctgaagc   2160
ctactggcgg gtgctcagcc aggaaggcga ggtggacttc ttgtcctcgg tggaggccca   2220
gtacatccag gcccaggcca gggagccccc gtgtccccca gacaccctgg gaggggcgga   2280
agcaggccct aagggactgg actccagctc cctacagtcc ggcacctact tccctgtggc   2340
ctcagagggc agcgagccgg ccctactgca cagctgggcc tcagctgaga agccctacct   2400
gaaggaaaaa tccagcgcca ctgtgtactt ccagaccgtc aagcacaaca acatcagaga   2460
cctcgtccgc cgctgcatca cccggactag ccaggtcctg gtcatcctga tggatgtgtt   2520
cacggatgtg gagatcttct gtgacattct agaggcagcc aacaagcgtg gggtgttcgt   2580
ttgtgtgctc ctggaccagg gaggtgtgaa gctcttccag gagatgtgtg acaaagtcca   2640
gatctctgac agtcacctca agaacatttc catccggagt gtggaaggag agatatactg   2700
tgccaagtca ggcaggaaat tcgctggcca aatccgggag aagttcatca tctcggactg   2760
gagatttgtc ctgtctggat cttacagctt cacctggctc tgcggacacg tgcaccggaa   2820
catcctctcc aagttcacag gccaggcggt ggagctgttt gacgaggagt tccgccacct   2880
ctacgcctcc tccaagcctg tgatgggcct gaagtccccg cggctggtcg cccccgtccc   2940
gcccggagca gccccggcca atggccgcct tagcagcagc agtggctccg ccagtgaccg   3000
cacgtcctcc aacccccttca gcggccgctc ggcaggcagc caccccggta cccgaagtgt   3060
```

```
gtccgcgtct tcagggccct gtagccccgc ggccccacac ccgcctccac cgccccggtt   3120
ccagccccac caaggccctt ggggagcccc gagtccccag gcccacctct ccccgcggcc   3180
ccacgacggc ccgcccgccg ctgtctacag caacctgggg gcctacaggc ccacgcggct   3240
gcagctggag cagctgggcc tggtgccgag gctgactcca acctggaggc ccttcctgca   3300
ggcctcccct cacttctgaa ggtcccatcc cctgctgccc tccgcaggcc cagggctggg   3360
cactccctga gacccaaaga cccacctcaa cgacgagtgg cgttgagcca cttccctttg   3420
aaaagacact caaaatcact gccatggttc aatgttccca ggccccaggc catccacttg   3480
ccggccccca ccagttcttg ggttccccgc tctagtttga cctgtgcagc acattccaga   3540
aggttccagg gaggttgtgg ggcagctaga ggacaaaatc atgaaaacag agtccctgtc   3600
ttccagagat catccggggc tttaatatta atggccccca aaactccgta agaagcagga   3660
aatgcagccc aagttttaca aatgggtaaa cagaggcact gagagataga tggtagtttg   3720
gtacttctgg ttcccagtgc ccaggaatgg tccactccca agaaattcag gaaagaaaga   3780
ctgaggagaa ggtgtgggaa cattctggat gtttcgggag agttggggaa actcctcctc   3840
ttaggaaagg ctaatactag ggtatccttg ggcccaatga attaggggtg aggccccaga   3900
acccgttatc tatgagttgt atgggggagc catctgaagc tgtagccacc agggatgcag   3960
ctagctgagg agtttggggt gttgggttgg acaaggcagg ttagtagact cagattcttg   4020
cttcaaagag ccttgggctg gcctggaggt ccctggagtc tagactggac ctaggagctt   4080
gagttgtcag gggccaggac tggccccact gcagtgccca ggccagtctt gagcagcagg   4140
gagggctcag ctgtccccag atccaggtgc ctctgaccag cctggtcacc tcctgaggaa   4200
taaatgctga acctcacaag ccccatcatt catttcttct caattcacag tgcccctctt   4260
tgtttctggg gtggaactag gtcctgaggg cacagcctag ctgagtgcaa agaaatatag   4320
gatgcttaga aagcatacag gaggggccag gcgtggtggc tcatgcctgt aatcccagaa   4380
ctttgggatg ccaaggtggt tggattacct gagatcaggt ggattacctg gtctcgagac   4440
cagcctgacc aatatggtga aaccccgtct ctactaaaaa tacaaaaatt aggctgagac   4500
aggagaattg cttgaaccca ggaagcagag gttgcaatga gctgagattg catcactgca   4560
ctccagcatg ggcaacaaag caagactccg tcacag                             4596
```

<210> SEQ ID NO 46
<211> LENGTH: 2815
<212> TYPE: DNA
<213> ORGANISM: Homo sapiens

<400> SEQUENCE: 46

```
aagaacgccc ccaaaatctg tttctaattt tacagaaatc ttttgaaact tggcacggta     60
ttcaaaagtc cgtggaaaga aaaaaacctt gtcctggctt cagcttccaa ctacaaagac    120
agacttggtc cttttcaacg gttttcacag atccagtgac ccacgctctg aagacagaat    180
tagctaactt tcaaaaacat ctggaaaaat gaagacttgg gtaaaaatcg tatttggagt    240
tgccacctct gctgtgcttg ccttattggt gatgtgcatt gtcttacgcc cttcaagagt    300
tcataactct gaagaaaata caatgagagc actcacactg aaggatattt taaatggaac    360
attttcttat aaaacatttt ttccaaactg gatttcagga caagaatatc ttcatcaatc    420
tgcagataac aatatagtac tttataatat tgaaacagga caatcatata ccattttgag    480
taatagaacc atgaaaagtg tgaatgcttc aaattacggc ttatcacctg atcggcaatt    540
```

-continued

```
tgtatatcta gaaagtgatt attcaaagct ttggagatac tcttacacag caacatatta    600
catctatgac cttagcaatg gagaatttgt aagaggaaat gagcttcctc gtccaattca    660
gtatttatgc tggtcgcctg ttgggagtaa attagcatat gtctatcaaa acaatatcta    720
tttgaaacaa agaccaggag atccaccttt tcaaataaca tttaatggaa gagaaaataa    780
aatatttaat ggaatcccag actgggttta tgaagaggaa atgcttgcta caaaatatgc    840
tctctggtgg tctcctaatg gaaaattttt ggcatatgcg gaatttaatg atacggatat    900
accagttatt gcctattcct attatggcga tgaacaatat cctagaacaa taaatattcc    960
atacccaaag gctggagcta agaatcccgt tgttcggata tttattatcg ataccactta   1020
ccctgcgtat gtaggtcccc aggaagtgcc tgttccagca atgatagcct caagtgatta   1080
ttatttcagt tggctcacgt gggttactga tgaacgagta tgtttgcagt ggctaaaaag   1140
agtccagaat gtttcggtcc tgtctatatg tgacttcagg gaagactggc agacatggga   1200
ttgtccaaag acccaggagc atatagaaga aagcagaact ggatgggctg gtggattctt   1260
tgtttcaaca ccagttttca gctatgatgc catttcgtac tacaaaatat ttagtgacaa   1320
ggatggctac aaacatattc actatatcaa agacactgtg gaaaatgcta ttcaaattac   1380
aagtggcaag tgggaggcca taaatatatt cagagtaaca caggattcac tgttttattc   1440
tagcaatgaa tttgaagaat accctggaag aagaaacatc tacagaatta gcattggaag   1500
ctatcctcca agcaagaagt gtgttacttg ccatctaagg aaagaaaggt gccaatatta   1560
cacagcaagt ttcagcgact acgccaagta ctatgcactt gtctgctacg gcccaggcat   1620
ccccatttcc acccttcatg atggacgcac tgatcaagaa attaaaatcc tggaagaaaa   1680
caaggaattg gaaaatgctt tgaaaaatat ccagctgcct aaagaggaaa ttaagaaact   1740
tgaagtagat gaaattactt tatggtacaa gatgattctt cctcctcaat ttgacagatc   1800
aaagaagtat cccttgctaa ttcaagtgta tggtggtccc tgcagtcaga gtgtaaggtc   1860
tgtatttgct gttaattgga tatcttatct tgcaagtaag gaagggatgg tcattgcctt   1920
ggtggatggt cgaggaacag ctttccaagg tgacaaactc ctctatgcag tgtatcgaaa   1980
gctgggtgtt tatgaagttg aagaccagat tacagctgtc agaaaattca tagaaatggg   2040
tttcattgat gaaaaaagaa tagccatatg gggctggtcc tatggaggat acgtttcatc   2100
actggccctt gcatctggaa ctggtctttt caaatgtggt atagcagtgg ctccagtctc   2160
cagctgggaa tattacgcgt ctgtctacac agagagattc atgggtctcc caacaaagga   2220
tgataatctt gagcactata agaattcaac tgtgatggca agagcagaat atttcagaaa   2280
tgtagactat cttctcatcc acggaacagc agatgataat gtgcactttc aaaactcagc   2340
acagattgct aaagctctgg ttaatgcaca agtggatttc caggcaatgt ggtactctga   2400
ccagaaccac ggcttatccg gcctgtccac gaaccactta tacacccaca tgacccactt   2460
cctaaagcag tgtttctctt tgtcagacta aaaacgatgc agatgcaagc ctgtatcaga   2520
atctgaaaac cttatataaa cccctcagac agtttgctta ttttattttt tatgttgtaa   2580
aatgctagta taaacaaaca aattaatgtt gttctaaagg ctgttaaaaa aaagatgagg   2640
actcagaagt tcaagctaaa tattgtttac attttctggt actctgtgaa agaagagaaa   2700
agggagtcat gcattttgct ttggacacag tgttttatca cctgttcatt tgaagaaaaa   2760
taataaagtc agaagttcaa gtgctaaaaa aaaaaaaaaa aaaaaaaaaa aaaaa        2815
```

<210> SEQ ID NO 47
<211> LENGTH: 1369

<212> TYPE: DNA
<213> ORGANISM: Homo sapiens

<400> SEQUENCE: 47
gaatcattgc actccctact agagcggatg tgatgaggga aaaggagaac tcagcacttt 60
ccctgcagga accggctccc tcggaggggc gtggctggga ggagctgtga gtaacgtgcc 120
acagtgttgt aaaaacccag tgagtgttat aaaaacccag tcagcctggc tcctgttgaa 180
tagtctaccc cccttgcact ctacctgaca cagctgcagc ctgcaattca ctcgcactgc 240
ctgggattgc actggatccg tgtgctcaga acaaggtgaa cgcccagctg cagccatgaa 300
gatctgtagc ctcaccctgc tctccttcct cctactggct gctcaggtgc tcctggtgga 360
ggggaaaaaa aaagtgaaga atggacttca cagcaaagtg gtctcagaac aaaaggacac 420
tctgggcaac acccagatta agcagaaaag caggcccggg aacaaaggca agtttgtcac 480
caaagaccaa gccaactgca gatgggctgc tactgagcag gaggagggca tctctctcaa 540
ggttgagtgc actcaattgg accatgaatt ttcctgtgtc tttgctggca atccaacctc 600
atgcctaaag ctcaaggatg agagagtcta ttggaaacaa gttgcccgga atctgcgctc 660
acagaaagac atctgtagat attccaagac agctgtgaaa accagagtgt gcagaaagga 720
ttttccagaa tccagtctta agctagtcag ctccactcta tttgggaaca caaagcccag 780
gaaggagaaa acagagatgt cccccaggga gcacatcaaa ggcaaagaga ccaccccctc 840
tagcctagca gtgacccaga ccatggccac caaagctccc gagtgtgtgg aggacccaga 900
tatggcaaac cagaggaaga ctgccctgga gttctgtgga gagacttgga gctctctctg 960
cacattcttc ctcagcatag tgcaggacac gtcatgctaa tgaggtcaaa agagaacggg 1020
ttcccttaag agatgtcatg tcgtaagtcc ctctgtatac tttaaagctc tctacagtcc 1080
ccccaaaata tgaacttttg tgcttagtga gtgcaacgaa atatttaaac aagttttgta 1140 tttttttgctt ttgtgtttttg gaatttgcct tatttttctt ggatgcgatg ttcagaggct 1200
gtttcctgca gcatgtattt ccatggccca cacagctatg tgtttgagca gcgaagagtc 1260
tttgagctga atgagccaga gtgataattt cagtgcaacg aactttctgc tgaattaatg 1320
gtaataaaac tctgggtgtt tttcagaaat acattcaaaa aaaaaaaaa 1369

<210> SEQ ID NO 48
<211> LENGTH: 8815
<212> TYPE: DNA
<213> ORGANISM: Homo sapiens

<400> SEQUENCE: 48
gcccgcgccg gctgtgctgc acagggggag gagagggaac cccaggcgcg agcgggaaga 60
ggggacctgc agccacaact tctctggtcc tctgcatccc ttctgtccct ccacccgtcc 120
ccttccccac cctctggccc ccaccttctt ggaggcgaca acccccggga ggcattagaa 180
gggatttttc ccgcaggttg cgaagggaag caaacttggt ggcaacttgc ctcccggtgc 240
gggcgtctct cccccaccgt ctcaacatgc ttaggggtcc ggggcccggg ctgctgctgc 300
tggccgtcca gtgcctgggg acagcggtgc cctccacggg agcctcgaag agcaagaggc 360
aggctcagca aatggttcag ccccagtccc cggtggctgt cagtcaaagc aagcccggtt 420
gttatgacaa tggaaaacac tatcagataa atcaacagtg ggagcggacc tacctaggca 480
atgcgttggt ttgtacttgt tatggaggaa gccgaggttt taactgcgag agtaaacctg 540
aagctgaaga gacttgcttt gacaagtaca ctgggaacac ttaccgagtg ggtgacactt 600

-continued

```
atgagcgtcc taaagactcc atgatctggg actgtacctg catcggggct gggcgaggga    660
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct cacccccagc ctcctcccta tggccactgt gtcacagaca   1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatggagag ccatgtgtct taccattcac ctacaatggc aggacgttct   1380
actcctgcac cacagaaggg cgacaggacg gacatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattggag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca agtggtcctg   2100
tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatggggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
```

acctgcagtt tgtggaagtg acagacgtga aggtcaccat catgtggaca ccgcctgaga 3060
gtgcagtgac cggctaccgt gtggatgtga tccccgtcaa cctgcctggc gagcacgggc 3120
agaggctgcc catcagcagg aacacctttg cagaagtcac cgggctgtcc cctggggtca 3180
cctattactt caaagtcttt gcagtgagcc atgggaggga gagcaagcct ctgactgctc 3240
aacagacaac caaactggat gctcccacta acctccagtt tgtcaatgaa actgattcta 3300
ctgtcctggt gagatggact ccacctcggg cccagataac aggataccga ctgaccgtgg 3360
gccttacccg aagaggacag cccaggcagt acaatgtggg tccctctgtc tccaagtacc 3420
cactgaggaa tctgcagcct gcatctgagt acaccgtatc cctcgtggcc ataaagggca 3480
accaagagag ccccaaagcc actggagtct ttaccacact gcagcctggg agctctattc 3540
caccttacaa caccgaggtg actgagacca ccattgtgat cacatggacg cctgctccaa 3600
gaattggttt taagctgggt gtacgaccaa gccagggagg agaggcacca cgagaagtga 3660
cttcagactc aggaagcatc gttgtgtccg gcttgactcc aggagtagaa tacgtctaca 3720
ccatccaagt cctgagagat ggacaggaaa gagatgcgcc aattgtaaac aaagtggtga 3780
caccattgtc tccaccaaca aacttgcatc tggaggcaaa ccctgacact ggagtgctca 3840
cagtctcctg ggagaggagc accaccccag acattactgg ttatagaatt accacaaccc 3900
ctacaaacgg ccagcaggga aattctttgg aagaagtggt ccatgctgat cagagctcct 3960
gcacttttga taacctgagt cccggcctgg agtacaatgt cagtgtttac actgtcaagg 4020
atgacaagga aagtgtccct atctctgata ccatcatccc agaggtgccc caactcactg 4080
acctaagctt tgttgatata accgattcaa gcatcggcct gaggtggacc ccgctaaact 4140
cttccaccat tattgggtac cgcatcacag tagttgcggc aggagaaggt atccctattt 4200
ttgaagattt tgtggactcc tcagtaggat actacacagt cacagggctg gagccgggca 4260
ttgactatga tatcagcgtt atcactctca ttaatggcgg cgagagtgcc cctactacac 4320
tgacacaaca aacggctgtt cctcctccca ctgacctgcg attcaccaac attggtccag 4380
acaccatgcg tgtcacctgg gctccacccc catccattga tttaaccaac ttcctggtgc 4440
gttactcacc tgtgaaaaat gaggaagatg ttgcagagtt gtcaatttct ccttcagaca 4500
atgcagtggt cttaacaaat ctcctgcctg gtacagaata tgtagtgagt gtctccagtg 4560
tctacgaaca acatgagagc acacctctta gaggaagaca gaaaacaggt cttgattccc 4620
caactggcat tgacttttct gatattactg ccaactcttt tactgtgcac tggattgctc 4680
ctcgagccac catcactggc tacaggatcc gccatcatcc cgagcacttc agtgggagac 4740
ctcgagaaga tcgggtgccc cactctcgga attccatcac cctcaccaac ctcactccag 4800
gcacagagta tgtggtcagc atcgttgctc ttaatggcag agaggaaagt cccttattga 4860
ttggccaaca atcaacagtt tctgatgttc cgagggacct ggaagttgtt gctgcgaccc 4920
ccaccagcct actgatcagc tggatgctc ctgctgtcac agtgagatat tacaggatca 4980
cttacggaga gacaggagga aatagccctg tccaggagtt cactgtgcct gggagcaagt 5040
ctacagctac catcagcggc cttaaacctg gagttgatta taccatcact gtgtatgctg 5100
tcactggccg tggagacagc cccgcaagca gcaagccaat ttccattaat taccgaacag 5160
aaattgacaa accatcccag atgcaagtga ccgatgttca ggacaacagc attagtgtca 5220
agtggctgcc ttcaagttcc cctgttactg gttacagagt aaccaccact cccaaaaatg 5280
gaccaggacc aacaaaaact aaaactgcag gtccagatca aacagaaatg actattgaag 5340

-continued

```
gcttgcagcc cacagtggag tatgtggtta gtgtctatgc tcagaatcca agcggagaga   5400
gtcagcctct ggttcagact gcagtaacca acattgatcg ccctaaagga ctggcattca   5460
ctgatgtgga tgtcgattcc atcaaaattg cttgggaaag cccacagggg caagtttcca   5520
ggtacagggt gacctactcg agccctgagg atggaatcca tgagctattc cctgcacctg   5580
atggtgaaga agacactgca gagctgcaag gcctcagacc gggttctgag tacacagtca   5640
gtgtggttgc cttgcacgat gatatggaga gccagcccct gattggaacc cagtccacag   5700
ctattcctgc accaactgac ctgaagttca ctcaggtcac acccacaagc ctgagcgccc   5760
agtggacacc acccaatgtt cagctcactg gatatcgagt gcgggtgacc cccaaggaga   5820
agaccggacc aatgaaagaa atcaaccttg ctcctgacag ctcatccgtg gttgtatcag   5880
gacttatggt ggccaccaaa tatgaagtga gtgtctatgc tcttaaggac actttgacaa   5940
gcagaccagc tcagggagtt gtcaccactc tggagaatgt cagcccacca agaagggctc   6000
gtgtgacaga tgctactgag accaccatca ccattagctg gagaaccaag actgagacga   6060
tcactggctt ccaagttgat gccgttccag ccaatggcca gactccaatc cagagaacca   6120
tcaagccaga tgtcagaagc tacaccatca caggtttaca accaggcact gactacaaga   6180
tctacctgta caccttgaat gacaatgctc ggagctcccc tgtggtcatc gacgcctcca   6240
ctgccattga tgcaccatcc aacctgcgtt tcctggccac cacacccaat tccttgctgg   6300
tatcatggca gccgccacgt gccaggatta ccggctacat catcaagtat gagaagcctg   6360
ggtctcctcc cagagaagtg gtccctcggc cccgccctgg tgtcacagag gctactatta   6420
ctggcctgga accgggaacc gaatatacaa tttatgtcat tgccctgaag aataatcaga   6480
agagcgagcc cctgattgga aggaaaaaga cagacgagct tccccaactg gtaacccttc   6540
cacaccccaa tcttcatgga ccagagatct tggatgttcc ttccacagtt caaaagaccc   6600
ctttcgtcac ccaccctggg tatgacactg gaaatggtat tcagcttcct ggcacttctg   6660
gtcagcaacc cagtgttggg caacaaatga tctttgagga acatggtttt aggcggacca   6720
caccgcccac aacggccacc cccataaggc ataggccaag accataccyg ccgaatgtag   6780
gtgaggaaat ccaaattggt cacatcccca gggaagatgt agactatcac ctgtacccac   6840
acggtccggg actcaatcca aatgcctcta caggacaaga agctctctct cagacaacca   6900
tctcatgggc cccattccag gacacttctg agtacatcat ttcatgtcat cctgttggca   6960
ctgatgaaga acccttacag ttcagggttc ctggaacttc taccagtgcc actctgacag   7020
gcctcaccag aggtgccacc tacaacatca tagtggaggc actgaaagac cagcagaggc   7080
ataaggttcg ggaagaggtt gttaccgtgg gcaactctgt caacgaaggc ttgaaccaac   7140
ctacggatga ctcgtgcttt gacccctaca cagtttccca ttatgccgtt ggagatgagt   7200
gggaacgaat gtctgaatca ggctttaaac tgttgtgcca gtgcttaggc tttggaagtg   7260
gtcatttcag atgtgattca tctagatggt gccatgacaa tggtgtgaac tacaagattg   7320
gagagaagtg ggaccgtcag ggagaaaatg gccagatgat gagctgcaca tgtcttggga   7380
acggaaaagg agaattcaag tgtgaccctc atgaggcaac gtgttatgat gatgggaaga   7440
cataccacgt aggagaacag tggcagaagg aatatctcgg tgccatttgc tcctgcacat   7500
gctttggagg ccagcggggc tggcgctgtg acaactgccg cagacctggg ggtgaaccca   7560
gtcccgaagg cactactggc cagtcctaca accagtattc tcagagatac catcagagaa   7620
caaacactaa tgttaattgc ccaattgagt gcttcatgcc tttagatgta caggctgaca   7680
gagaagattc ccgagagtaa atcatctttc caatccagag gaacaagcat gtctctctgc   7740
```

caagatccat ctaaactgga gtgatgttag cagacccagc ttagagttct tctttctttc 7800
ttaagccctt tgctctggag gaagttctcc agcttcagct caactcacag cttctccaag 7860
catcaccctg ggagtttcct gagggttttc tcataaatga gggctgcaca ttgcctgttc 7920
tgcttcgaag tattcaatac cgctcagtat tttaaatgaa gtgattctaa gatttggttt 7980
gggatcaata ggaaagcata tgcagccaac caagatgcaa atgttttgaa atgatatgac 8040
caaaatttta agtaggaaag tcacccaaac acttctgctt tcacttaagt gtctggcccg 8100
caatactgta ggaacaagca tgatcttgtt actgtgatat tttaaatatc cacagtactc 8160
actttttcca aatgatccta gtaattgcct agaaatatct ttctcttacc tgttatttat 8220
caatttttcc cagtattttt atacggaaaa aattgtattg aaaacactta gtatgcagtt 8280
gataagagga atttggtata attatggtgg gtgattattt tttatactgt atgtgccaaa 8340
gctttactac tgtggaaaga caactgtttt aataaaagat ttacattcca caacttgaag 8400
ttcatctatt tgatataaga caccttcggg ggaaataatt cctgtgaata ttcttttca 8460 attcagcaaa catttgaaaa tctatgatgt gcaagtctaa ttgttgattt cagtacaaga 8520
ttttctaaat cagttgctac aaaaactgat tggtttttgt cacttcatct cttcactaat 8580
ggagatagct ttacactttc tgctttaata gatttaagtg gaccccaata tttattaaaa 8640
ttgctagttt accgttcaga agtataatag aaataatctt tagttgctct tttctaacca 8700
ttgtaattct tcccttcttc cctccacctt tccttcattg aataaacctc tgttcaaaga 8760
gattgcctgc aagggaaata aaaatgacta agatattaaa aaaaaaaaaa aaaaa 8815

<210> SEQ ID NO 49
<211> LENGTH: 6578
<212> TYPE: DNA
<213> ORGANISM: Homo sapiens

<400> SEQUENCE: 49
ctcagtggcg gagcgcggct gccggtgtgc ggccgggagc gatcgccgcg gggcaggggc 60
gcggcgggca ccgcgcagag cgcgcagaac agacggacgg cggcggggac ccgacggcgg 120
cgcctcggca ctccccagac tccggccagc gccccccctgc cagccgcaag cacccagccc 180
cggcccaccc cgggctctcg atggcccccg aggccggggc gaccctgcgc gcgccgcgcc 240
ggctgtcctg ggcggcgctg ctgctcttgg ccgcgctgct ccccgtcgcc tcctcggcgg 300
cggcctcagt tgaccaccca ctgaagccaa ggcatgtgaa actgctgtcc actaaaatgg 360
gcctgaaagt cacgtgggac ccacccaaag atgctaccag tagacctgtg gagcattaca 420
acattgccta tgggaagtca ctgaaaagtc ttaaatacat caaggtgaat gcggagacat 480
actccttcct tattgaggat gtggagccgg gggtagtgta ctttgtgctg cttactgcag 540
aaaaccacag tggagtgagc cgtcctgttt acagagctga aagcccacct ggaggtgaat 600
ggatcgagat tgatggtttt cccattaagg gtccaggacc atttaatgaa accgtcacag 660
aaaaggaagt gcccaacaag cccttgcgtg tgcgtgtccg gtcctcagat gacaggctgt 720
ccgttgcgtg gaaggcacca cgcctgtctg gagccaagag tccacgcaga tcacggggtt 780
ttctcctggg ctacggggag agtggccgga agatgaatta tgttccactg acaagagatg 840
aacggacaca cgaaattaaa aagctagcct cggaatccgt gtatgtggtc tccctgcagt 900
ccatgaactc tcagggccgg agccaaccag tctacagggc tgccctaaca aagcgaaaga 960
tttcagaaga ggacgaattg gatgtacctg acgacatcag cgtccgggtt atgtcatctc 1020

-continued

```
agtctgtgct tgtgtcctgg gtggatcctg ttctggaaaa acagaagaaa gttgttgcat   1080
caagacagta caccgtgcgc tatcgagaga agggggaatt ggccaggtgg gattataagc   1140
agatcgctaa caggcgtgtg ctgattgaga acctgattcc agacactgtg tatgaatttg   1200
cagtccgtat ttcacagggt gaaagagatg gcaaatggag tacgtcagtc ttccaaagaa   1260
caccagaatc tgcccctacc acagctcctg aaaacttgaa cgtctggcca gtcaatggca   1320
aacctacagt tgtcgctgca tcttgggatg cgctaccaga gactgagggg aaagtgaaag   1380
aatacattct ttcatacgcc ccggctctca aaccatttgg agcaaagtcc ctcacctatc   1440
ctggagacac tacttctgcc ctggtggatg gtctgcagcc tggggaacgc tatcttttca   1500
aaatccgggc cacaaacagg agaggcctgg gacctcactc caaagccttc attgtcgcta   1560
tgccaacaac cagtaaggcg gatgttgagc agaacacgga ggacaatggg aaacccgaaa   1620
aacctgagcc ttcctcacct tctcccagag ctccagcttc ctcccaacac ccctctgtgc   1680
ctgcttctcc ccaagggaga aatgccaagg accttcttct tgacttgaag aacaaaatat   1740
tggctaatgg tggggcgccc cgaaaacccc agcttcgcgc caagaaggca gaggagctgg   1800
atcttcagtc gacagaaatc actggggagg aggagctggg ttcccgggag gactcgccca   1860
tgtcaccctc agacacccaa gaccagaaac ggaccctgag gccgccaagt agacacggcc   1920
actcggtggt tgctcccggc aggactgcag tgagggcccg gatgccagcg ctgccccgaa   1980
gggaaggcgt agataagcct ggcttttccc tggccacgca gccccgccca ggggcgcccc   2040
cctcggcttc ggcctctcct gcccaccacg cgtccaccca gggcacctct catcgtcctt   2100
ccctgcctgc cagcttgaat gacaacgact tggtggactc agacgaagat gagcgcgctg   2160
tgggctccct ccaccccaag ggcgccttcg cccagccccg gccagccctg tcccccagcc   2220
gccagtcccc gtccagcgtt ctccgcgaca gaagctctgt gcaccccggc gcaaagccag   2280
cctcgccggc ccggaggacc ccccattcag ggggccgcaga ggaagattcc agtgcctcag   2340
ccccaccctc aagactttct ccaccccatg gggatcatc tcggctgctg cccacccagc   2400
cacacctgag ctctccactt tccaagggcg ggaaggatgg tgaggacgcc ccagccacca   2460
actccaatgc gccatcacgg tccaccatgt cctcctccgt ctcttctcat ctctcgtcca   2520
ggacgcaggt ctctgaggga gcggaggctt ctgatggtga aagccacggt gacggcgata   2580
gggaagacgg cggaaggcag gcggaggcca cggcccagac gctgcgggcc cggcctgcct   2640
ctggacactt ccatttgctc agacacaaac cctttgctgc caacgggagg tctccaagca   2700
ggttcagcat tgggcgggga cctcggctgc agccctccag ctccccacag tcgactgtgc   2760
cctcccgagc ccaccccagg gttccctctc actctgattc ccaccctaag cttagctcag   2820
gtatccatgg agacgaggag gatgagaagc cgcttcctgc caccgttgtc aatgaccacg   2880
tgccttcctc ctccaggcag cccatctccc ggggctggga ggacttaagg agaagcccgc   2940
agagaggggc cagcctgcat cggaaggaac ccatcccaga gaaccccaaa tccacagggg   3000
cagatacaca tcctcagggc aagtactcct ccctggcctc caaggctcag gatgttcaac   3060
agagcacaga cgcggacacg gagggtcatt ctcccaaagc acagccaggg tccacagacc   3120
gccacgcgtc ccctgctcgt ccgcccgcag cacggtcaca gcagcatccc agtgttccca   3180
gaaggatgac acccggccgg gccccacaac agcagccccc tcctcccgtc gccacgtccc   3240
agcaccaccc gggaccccag agcagagacg cgggtcggtc accttcccag cccaggctct   3300
cactgaccca ggccgggcgg ccccgcccca cgtcgcaggg ccgctcccac tcctcctcgg   3360
acccttacac ggcgagctcc agagggatgc tccccacggc cctccagaac caggacgagg   3420
```

-continued

```
atgcccaggg cagctacgac gacgacagca cagaagtcga ggcccaggat gtgcgggccc   3480
ccgcgcacgc cgcgcgcgcc aaggaggcag ctgcgtccct tcccaagcac cagcaggtgg   3540
agtctcccac aggcgcaggg gcaggtggcg accacaggtc ccagcgcgga catgcggcct   3600
cccccgccag gcccagccga cccggcggcc cccagtcccg cgcccgggta cccagcaggg   3660
cagcgccggg gaagtcggag cctccttcca agcggcccct gtcctccaag tcccagcagt   3720
cggtctcagc cgaggacgac gaggaggagg acgcgggatt ttttaaaggc gggaaagaag   3780
accttctgtc ttcctctgtg ccaaagtggc cctcttcctc cactcccagg ggcggcaaag   3840
acgccgatgg gagcctcgcc aaggaagaga gggagcctgc catcgcgctt gcccctcgcg   3900
gagggagcct ggctcctgtg aagcgacctc tccccccacc tccaggcagc tcccccaggg   3960
cctcccacgt cccttcccga ctgccgcctc gcagcgctgc caccgtgagc cccgtcgcgg   4020
gcacccaccc ctggccgcag tacaccacgc gcgccccacc tggccacttc tccaccaccc   4080
cgatgctgtc cttgcgccag aggatgatgc atgccagatt ccgtaaccct ctctcccgac   4140
agcctgccag accctcttac agacaaggtt ataatggcag accaaatgta gaagggaaag   4200
tccttcctgg tagtaatgga aaaccgaatg gacagagaat tatcaatggc cctcaaggaa   4260
caaagtgggt tgtggacctt gatcgtgggt tagtattgaa tgcagaagga aggtacctcc   4320
aagattcaca tggaaatcct cttcggatta aactaggagg agatggtcga accattgtag   4380
atctggaagg gacccccgtg gtgagtcctg acggcctccc actctttggg caggggcgac   4440
atggcacacc tctggccaat gcccaagata agccaatttt gagtcttgga ggaaagccgc   4500
tggtgggctt ggaggtcatc aaaaaaacca cccatccccc taccactacc atgcagccca   4560
ccactactac gacgcccctg cctaccacta caaccccgag gcccaccact gccaccaccc   4620
gccgcacgac caccacccgc cgcacgacca ccaggcgtcc aacaaccaca gtccgaacca   4680
ctacgcggac aaccaccacc accaccccca cacccaccac tcccatcccc acctgtcccc   4740
ctgggacctt ggaacggcac gacgatgatg gcaacctgat aatgagctcc aatgggatcc   4800
cagagtgcta cgctgaagaa gatgagttct caggcttgga gactgacact gcagtaccta   4860
cggaagaggc ctacgttata tatgatgaag attatgaatt tgagacgtca aggccaccaa   4920
ccaccactga gccttcgacc actgctacca caccgagggt gatcccagag gaaggcgcca   4980
tcagttcctt tcctgaagaa gaatttgatc tggctggaag gaaacgattt gttgctcctt   5040
acgtgacgta cctaaataaa gacccatcag ccccgtgctc tctgactgat gcactggatc   5100
acttccaagt ggacagcctg gatgaaatca tccccaatga cctgaagaag agtgacctgc   5160
ctccccagca tgctccccgc aacatcaccg tggtggccgt ggaaggttgc cactcatttg   5220
tcattgtgga ctgggacaaa gccaccccag gagatgtggt cacaggttac ttggtttaca   5280
gtgcatccta tgaagacttc atcaggaaca agtggtccac tcaagcttca tcagtaactc   5340
acttgcccat tgagaaccta aagcccaaca cgaggtatta ttttaaagtg caagcacaaa   5400
atcctcatgg ctacggacct atcagccctt cggtctcatt tgtcaccgaa tcagataatc   5460
ctctgcttgt tgtgaggccc ccaggcggtg agcctatctg gatcccattc gctttcaaac   5520
atgatcccag ctacacggac tgccatggac ggcaatatgt gaagcgcacg tggtatcgaa   5580
agttcgtggg agttgttctt tgtaattcac tgaggtataa aatctacctc agtgacaacc   5640
tgaaagatac attctacagc attggagaca gctggggaag aggtgaagac cattgccaat   5700
ttgtggattc acaccttgat ggaagaacag ggcctcagtc ctatgtagaa gccctcccta   5760
```

-continued

```
ctattcaagg ctactatcgc cagtatcgtc aggagcctgt caggtttggg aacatcggct   5820

tcggaacccc ctactactat gtgggctggt acgagtgtgg ggtctccatc cctggaaagt   5880

ggtaatcaca ggaccgtcat gctgcaagct tgccctgccc agccccacca actaagtcgc   5940

actaggggct gtgagcaaag acagccagcg tgctcagccc cgctgcccta ggtgccagga   6000

aggtcataga tggacactgg ccattctggt catctcagtc tggaactcag tcccacttct   6060

tggcctggac aatgaacagg attcagtttt gctgttaact ttgcttctct acttttttt   6120

gtttgtttgt aatagcacat cccagagaca tcagaaacca gcaactgatt cagtgtgatt   6180

tccagacttt ttaggcatga aattcggaca cttcagtatt tccaggaata gcatatgcac   6240

gctgttcttg cttcatggaa tgctacatgc tttctgtttt tctcattttg gatttctcca   6300

aaactaactg aatttaagct tcaggtccct ttgtatgcag tagaaaggaa ttattaaaaa   6360

caccaccaaa gaaaataaat atatcctact tgaaatttac tctatggact tacccactgc   6420

tagaataaat gtatcaaatc ttatttgtaa attctcaatt ttgatatata tatgtatata   6480

tgcatataca tatccacact tgtctgcaag aatattgatt aaaattgcta aatttgtact   6540

tgttcaccag aaaaaaaaaa aaaaaaaaaa aaaaaaaa                           6578
```

<210> SEQ ID NO 50
<211> LENGTH: 3219
<212> TYPE: DNA
<213> ORGANISM: Homo sapiens

<400> SEQUENCE: 50

```
actgtaggca ccaccgggcg ccgaatggct gttttctaac tgggatcctc ggtgacgtat     60

ggctgcctgc cccttggcag ctgtctttat ggaccagtag gcagagcgaa attgacgctg    120

acaagacttt tgcatcttgg aagggactgt aatctactgt agtgaagaac agagcctctc    180

aatcagacgg gtgtaaataa gagacggagg ggagtccaaa agaaaaggaa gaggaggaaa    240

aacaagtgtg tgttgggggg aacaggggga aaagcatttt tggtggatgg tatgaagcca    300

gccatggaaa ctgcagccga ggaaaatact gaacaaagcc aagagagaaa agtgaacagc    360

agagctgaaa tggaaattgg caggtaccac tggatgtacc caggctcaaa gaaccaccag    420

taccatcccg tgccaaccct gggggacagg gctagcccct tgagcagtcc aggctgcttt    480

gaatgctgca tcaagtgtct gggaggagtc ccctacgcct ccctggtggc caccatcctc    540

tgcttctccg gggtggcctt attctgcggc tgtgggcatg tggctctcgc aggcaccgtg    600

gcgattcttg agcaacactt ctccaccaac gccagtgacc atgccttgct gagcgaggtg    660

atacaactga tgcagtatgt catctatgga attgcgtcct ttttcttctt gtatgggatc    720

attctgttgg cagaaggctt ttacaccaca agtgcagtga aagaactgca cggtgagttt    780

aaaacaaccg cttgtggccg atgcatcagt ggaatgttcg ttttcctcac ctatgtgctt    840

ggagtggcct ggctgggtgt gtttggtttc tcagcggtgc ccgtgtttat gttctacaac    900

atatggtcaa cttgtgaagt catcaagtca ccgcagacca acgggaccac gggtgtggag    960

cagatctgtg tggatatccg acaatacggt atcattcctt ggaatgcttt ccccggaaaa   1020

atatgtggct ctgccctgga gaacatctgc aacacaaacg agttctacat gtcctatcac   1080

ctgttcattg tggcctgtgc aggagctggt gccaccgtca ttgccctgat ccacttcctc   1140

atgatactgt cttctaactg ggcttactta aaggatgcga gcaaaatgca ggcttaccag   1200

gatatcaaag caaaggaaga acaggaactg caagatatcc agtctcggtc aaaagaacaa   1260

ctcaattctt acacataaat gtttgccaga gtgtttcggc cgacgtattt acagctctga   1320
```

```
caaatcatca gacagctgct ctgcagtaca gatgtgtatc ccaccaaact aatgtagatg   1380
tacaaacact tcactgtctg tctcaagctg ctgggatgta tctctaggaa aaccttccag   1440
tgggtaaatc tttttcttta gaacaaatat tggaggtttc atgttagcca ttttaaaagg   1500
caacactttg acaaaatgat cgttcatact ttgggaattt gtggcatgtt cacatttatt   1560
gctagggcaa ttctaccaag acactcaatg gaatatgtca cactccttaa tagggacctg   1620
tgactcctta ataaggacct gtgacatgcc cagcatcaag ggataagacc gtaaattcac   1680
atatatgcca tctgtcctca agtgttatct acataggaaa taaaatggaa ttgatgtaaa   1740
gttccatttc tgacagctga catttattaa actttggatc aaagataatg tgattcttat   1800
gattgatttc tcaaactagc ttttccctcc caagtccagg acccattaat ttcctgagcc   1860
aatcagaaat atatttttca ataatgctaa aattagctac aattctgctg accctactat   1920
taaagaatct ggatgctgga ctcactgaca agctttccag aagcaatttt ataacagatt   1980
tcattttaac aaaatactga tccaattttc attattcttg agaaatgtca gctttgcctt   2040
aatgagtatt tgctttaaat ttctaagaat ttatatcata actagagacc caaatatctt   2100
tcacagaatt ttgttccata aatgtttttc ttaattatta agaagtgtta ccttattaaa   2160
atgaccacca ttctaaacca tttttcagtg gtctggatac gaagtttaca gtttcatacc   2220
aactatctaa aacctaattg caaattgacc acagacctct aacctcctac ttttatagac   2280
ttgaatactt aagtaattta aattagggtt ggtatttcat ttttttctta tctaaatctt   2340
agtttcctgg aataataaag tttgatgttc agcaagagaa ctgcttgagt ttaagccatt   2400
ttcaaaagaa acttgccttt tacattattg tgttccagaa cattaagtga ctgtaggtac   2460
tgggtattag tgatggtaaa ctttgtgttg ctctttatga aatgatccat ataactgttg   2520
ggtgcatcag tgcttttcaa aggggctgct tactataggg ttaactatgt atattcattg   2580
ttaagagtta acttgtggtt tggctgtttc ctggatttta taacatacat gtgcagaaat   2640
gtattcaaat gaaaggaagc atacctttat caagatgcta ttaaaattga acatcaagta   2700
taatatttca tttggattct cttttttggt taatgcctaa aaatgcctat ttgggatttt   2760
ttttttttt taaattaaga gaagctctct tctgtgtaga acagttgttc caaaatagct   2820
tagtgttttg ttttcctgtt gcatgacaga tttaactatt ctttccagca gtggaggtgc   2880
tgtcagagtc cagtgttcta gaagaggcag tgtctaaagc ctaattttac ttttctaatt   2940
ctggtagcta ttaccaggaa tttttgaaag ttttgtttaa gtagtctaat atttttttatg   3000
taaagagcat taaattttgc tatgtataaa tttttgtaac ctaacagtga atcaatattt   3060
tctatcagtg ccaagggctt cctgtagttc tattcaagtg ttacaataaa tatttgtaga   3120
taatagtcaa tacttgtgta tgcttatttt aaagatctat ttaggtggaa atagttgtgg   3180
atgtactaag agtaatgaaa taaaattata gcttcaaaa                          3219
```

<210> SEQ ID NO 51
<211> LENGTH: 1521
<212> TYPE: DNA
<213> ORGANISM: Homo sapiens

<400> SEQUENCE: 51

```
ttacattagc aagagagcaa gttgttccag tagtcgcctg gcaggagaat ttgaaagggt     60
gccccaaagg acaatctcta aaggggtaag ggagatacct accttgtctg gtaggggaga    120
tgtttcgttt tcatgcttta ccagaaaatc cacttccctg ccgaccttag tttcaaagct    180
```

tattcttaat tagagacaag aaacctgttt caacttgaag acaccgtatg aggtgaatgg 240
acagccagcc accacaatga aagaaatcaa accaggaata acctatgctg aacccacgcc 300
tcaatcgtcc ccaagtgttt cctgacacgc atctttgctt acagtgcatc acaactgaag 360
aatggggttc aacttgacgc ttgcaaaatt accaaataac gagctgcacg gccaagagag 420
tcacaattca ggcaacagga gcgacgggcc aggaaagaac accacccttc acaatgaatt 480
tgacacaatt gtcttgccgg tgctttatct cattatattt gtggcaagca tcttgctgaa 540
tggtttagca gtgtggatct tcttccacat taggaataaa accagcttca tattctatct 600
caaaaacata gtggttgcag acctcataat gacgctgaca tttccatttc gaatagtcca 660
tgatgcagga tttggacctt ggtacttcaa gtttattctc tgcagataca cttcagtttt 720
gttttatgca aacatgtata cttccatcgt gttccttggg ctgataagca ttgatcgcta 780
tctgaaggtg gtcaagccat ttggggactc tcggatgtac agcataacct tcacgaaggt 840
tttatctgtt tgtgtttggg tgatcatggc tgttttgtct ttgccaaaca tcatcctaac 900
aaatggtcag ccaacagagg acaatatcca tgactgctca aaacttaaaa gtcctttggg 960
ggtcaaatgg catacggcag tcacctatgt gaacagctgc ttgtttgtgg ccgtgctggt 1020
gattctgatc ggatgttaca tagccatatc caggtacatc cacaaatcca gcaggcaatt 1080
cataagtcag tcaagccgaa agcgaaaaca taaccagagc atcagggttg ttgtggctgt 1140
gtttttacc tgctttctac catatcactt gtgcagaatt ccttttactt ttagtcactt 1200
agacaggctt ttagatgaat ctgcacaaaa aatcctatat tactgcaaag aaattacact 1260
tttcttgtct gcgtgtaatg tttgcctgga tccaataatt tactttttca tgtgtaggtc 1320
attttcaaga aggctgttca aaaaatcaaa tatcagaacc aggagtgaaa gcatcagatc 1380
actgcaaagt gtgagaagat cggaagttcg catatattat gattacactg atgtgtaggc 1440
cttttattgt ttgttggaat cgatatgtac aaagtgtaaa taaatgtttc ttttcattat 1500
ccttgcttga gcccatcaaa a 1521

<210> SEQ ID NO 52
<211> LENGTH: 2021
<212> TYPE: DNA
<213> ORGANISM: Homo sapiens

<400> SEQUENCE: 52
ggcccggacg ggacgtgcgc gctcaaaggt tgcccgtctc tgacgcccgc atttcctggt 60
ctggagccgg ctgagccaca gcagggtcgc cgcggggtcc cggggccgtg ctcccctgcc 120
cctcccggga gcgcgcgggg cggggcgggg cggggcggga ccaggcgggc gagctgggcc 180
ctcgcccctc cctcgggcgg tcacctgggc acgggcgctg caggtgtcgg ggcctcaacc 240
ttgcggagcc gacagccatc gatcctcggg tggcctcgag gtggtggcag ggccgccccc 300
tgcagtccgg agacgaacgc acggaccggg cctccggagg caggttcggc tggaaggaac 360
cgctctcgct tcgtcctaca cttgcgcaaa tgtctccgag cttactcaca tagcatattg 420
gtatatcaaa atgaaatgca aggaaccaaa aataacataa ttgaaggcag taaaagtgaa 480
attaaatagg aagatcatca gtcaaggaag acccactgga gaggacagaa aatgaagcag 540
tgttttatca tgtgtatttc agcaggtctt cttgaaattt aactaaaaat atgactgctc 600
tctcttcaga gaactgctct tttcagtacc agttacgtca aacaaaccag cccctagatg 660
ttaactatct gctattcttg atcatacttg ggaaaatatt attaaatatc cttacactag 720
gaatgagaag aaaaaacacc tgtcaaaatt ttatggaata tttttgcatt tcactagcat 780

```
tcgttgatct tttacttttg gtaaacattt ccattatatt gtatttcagg gattttgtac     840
ttttaagcat taggttcact aaataccaca tctgcctatt tactcaaatt atttccttta     900
cttatggctt tttgcattat ccagttttcc tgacagcttg tatagattat tgcctgaatt     960
tctctaaaac aaccaagctt tcatttaagt gtcaaaaatt attttatttc tttacagtaa    1020
ttttaatttg gatttcagtc cttgcttatg ttttgggaga cccagccatc taccaaagcc    1080
tgaaggcaca gaatgcttat tctcgtcact gtcctttcta tgtcagcatt cagagttact    1140
ggctgtcatt tttcatggtg atgattttat ttgtagcttt cataacctgt tgggaagaag    1200
ttactacttt ggtacaggct atcaggataa cttcctatat gaatgaaact atcttatatt    1260
ttccttttc atcccactcc agttatactg tgagatctaa aaaaatattc ttatccaagc    1320
tcattgtctg ttttctcagt acctggttac catttgtact acttcaggta atcattgttt    1380
tacttaaagt tcagattcca gcatatattg agatgaatat tccctggtta tactttgtca    1440
atagttttct cattgctaca gtgtattggt ttaattgtca caagcttaat ttaaaagaca    1500
ttggattacc tttggatcca tttgtcaact ggaagtgctg cttcattcca cttacaattc    1560
ctaatcttga gcaaattgaa aagcctatat caataatgat ttgttaatat tattaattaa    1620
aagttacagc tgtcataaga tcataatttt atgaacagaa agaactcagg acatattaaa    1680
aaataaactg aactaaaaca acttttgccc cctgactgat agcatttcag aatgtgtctt    1740
ttgaagggct atgataccag ttattaaata gtgttttatt ttaaaaacaa aataattcca    1800
agaagttttt atagttattc agggacacta tattacaaat attactttgt tattaacaca    1860
aaaagtgata agagttaaca tttggctata ctgatgtttg tgttactcaa aaaaactact    1920
ggatgcaaac tgttatgtaa atctgagatt tcactgacaa ctttaagata tcaacctaaa    1980
catttttatt aaatgttcaa atgaaagcaa gaaaaaaaaa a                        2021
```

<210> SEQ ID NO 53
<211> LENGTH: 4150
<212> TYPE: DNA
<213> ORGANISM: Homo sapiens

<400> SEQUENCE: 53

```
actcggtgcg ccttccgcgg accgggcgac ccagtgcacg gccgccgcgt cactctcggt      60
cccgctgacc ccgcgccgag ccccggcggc tctggccgcg gccgcactca gcgccacgcg     120
tcgaaagcgc aggccccgag gacccgccgc actgacagta tgagccgcac agcctacacg     180
gtgggagccc tgcttctcct cttggggacc ctgctgccgg ctgctgaagg gaaaaagaaa     240
gggtcccaag gtgccatccc cccgccagac aaggcccagc acaatgactc agagcagact     300
cagtcgcccc agcagcctgg ctccaggaac cgggggcggg gccaagggcg gggcactgcc     360
atgcccgggg aggaggtgct ggagtccagc caagaggccc tgcatgtgac ggagcgcaaa     420
tacctgaagc gagactggtg caaaacccag ccgcttaagc agaccatcca cgaggaaggc     480
tgcaacagtc gcaccatcat caaccgcttc tgttacggcc agtgcaactc tttctacatc     540
cccaggcaca tccggaagga ggaaggttcc tttcagtcct gctccttctg caagcccaag     600
aaattcacta ccatgatggt cacactcaac tgccctgaac tacagccacc taccaagaag     660
aagagagtca cacgtgtgaa gcagtgtcgt tgcatatcca tcgatttgga ttaagccaaa     720
tccaggtgca cccagcatgt cctaggaatg cagccccagg aagtcccaga cctaaaacaa     780
ccagattctt acttggctta aacctagagg ccagaagaac cccagctgc ctcctggcag      840
```

```
gagcctgctt gtgcgtagtt cgtgtgcatg agtgtggatg ggtgcctgtg ggtgtttta     900
gacaccagag aaaacacagt ctctgctaga gagcactccc tattttgtaa acatatctgc     960
tttaatgggg atgtaccaga aacccacctc accccggctc acatctaaag ggcggggcc     1020
gtggtctggt tctgactttg tgtttttgtg ccctcctggg gaccagaatc tcctttcgga   1080
atgaatgttc atggaagagg ctcctctgag ggcaagagac ctgttttagt gctgcattcg   1140
acatggaaaa gtccttttaa cctgtgcttg catcctcctt tcctcctcct cctcacaatc   1200
catctcttct taagttgata gtgactatgt cagtctaatc tcttgtttgc caaggttcct   1260
aaattaattc acttaaccat gatgcaaatg tttttcattt tgtgaagacc ctccagactc   1320
tgggagaggc tggtgtgggc aaggacaagc aggatagtgg agtgagaaag ggagggtgga   1380
gggtgaggcc aaatcaggtc cagcaaaagt cagtagggac attgcagaag cttgaaaggc   1440
caataccaga acacaggctg atgcttctga gaaagtcttt tcctagtatt taacagaacc   1500
caagtgaaca gaggagaaat gagattgcca gaaagtgatt aactttggcc gttgcaatct   1560
gctcaaacct aacaccaaac tgaaaacata aatactgacc actcctatgt tcggacccaa   1620
gcaagttagc taaaccaaac caactcctct gctttgtccc tcaggtggaa aagagaggta   1680
gtttagaact ctctgcatag gggtgggaat taatcaaaaa cctcagaggc tgaaattcct   1740
aataccttc ctttatcgtg gttatagtca gctcatttcc attccactat ttcccataat   1800
gcttctgaga gccactaact tgattgataa agatcctgcc tctgctgagt gtacctgaca   1860
gtagtctaag atgagagagt ttagggacta ctctgtttta gcaagagata ttttgggggt   1920
ctttttgttt taactattgt caggagattg ggctaaagag aagacgacga gagtaaggaa   1980
ataaagggaa ttgcctctgg ctagagagta gttaggtgtt aatacctggt agagatgtaa   2040
gggatatgac ctccctttct ttatgtgctc actgaggatc tgaggggacc ctgttaggag   2100
agcatagcat catgatgtat tagctgttca tctgctactg gttggatgga cataactatt   2160
gtaactattc agtatttact ggtaggcact gtcctctgat taaacttggc ctactggcaa   2220
tggctactta ggattgatct aagggccaaa gtgcagggtg ggtgaacttt attgtacttt   2280
ggatttggtt aacctgtttt cttcaagcct gaggttttat atacaaactc cctgaatact   2340
ctttttgcct tgtatcttct cagcctccta gccaagtcct atgtaatatg gaaaacaaac   2400
actgcagact tgagattcag ttgccgatca aggctctggc attcagagaa cccttgcaac   2460
tcgagaagct gtttttattt cgtttttgtt ttgatccagt gctctcccat ctaacaacta   2520
aacaggagcc atttcaaggc gggagatatt ttaaacaccc aaaatgttgg gtctgatttt   2580
caaactttta aactcactac tgatgattct cacgctaggc gaatttgtcc aaacacatag   2640
tgtgtgtgtt ttgtatacac tgtatgaccc caccccaaat ctttgtattg tccacattct   2700
ccaacaataa agcacagagt ggatttaatt aagcacacaa atgctaaggc agaattttga   2760
gggtgggaga gaagaaaagg gaaagaagct gaaaatgtaa aaccacacca gggaggaaaa   2820
atgacattca gaaccagcaa acactgaatt tctcttgttg ttttaactct gccacaagaa   2880
tgcaatttcg ttaacggaga tgacttaagt tggcagcagt aatcttcttt taggagcttg   2940
taccacagtc ttgcacataa gtgcagattt ggctcaagta aagagaattt cctcaacact   3000
aacttcactg ggataatcag cagcgtaact accctaaaag catatcacta gccaaagagg   3060
gaaatatctg ttcttcttac tgtgcctata ttaagactag tacaaatgtg gtgtgtcttc   3120
caactttcat tgaaaatgcc atatctatac catattttat tcgagtcact gatgatgtaa   3180
tgatatattt tttcattatt atagtagaat atttttatgg caagatattt gtggtcttga   3240
```

```
tcatacctat taaaataatg ccaaacacca aatatgaatt ttatgatgta cactttgtgc   3300
ttggcattaa aagaaaaaaa cacacatcct ggaagtctgt aagttgtttt ttgttactgt   3360
aggtcttcaa agttaagagt gtaagtgaaa aatctggagg agaggataat ttccactgtg   3420
tggaatgtga atagttaaat gaaaagttat ggttatttaa tgtaattatt acttcaaatc   3480
ctttggtcac tgtgatttca agcatgtttt ctttttctcc tttatatgac tttctctgag   3540
ttgggcaaag aagaagctga cacaccgtat gttgttagag tcttttatct ggtcagggga   3600
aacaaaatct tgacccagct gaacatgtct tcctgagtca gtgcctgaat ctttattttt   3660
taaattgaat gttccttaaa ggttaacatt tctaaagcaa tattaagaaa gactttaaat   3720
gttattttgg aagacttacg atgcatgtat acaaacgaat agcagataat gatgactagt   3780
tcacacataa agtccttttta aggagaaaat ctaaaatgaa aagtggataa acagaacatt   3840
tataagtgat cagttaatgc ctaagagtga aagtagttct attgacattc ctcaagatat   3900
ttaatatcaa ctgcattatg tattatgtct gcttaaatca tttaaaaacg gcaaagaatt   3960
atatagacta tgaggtacct tgctgtgtag gaggatgaaa ggggagttga tagtctcata   4020
aaactaattt ggcttcaagt ttcatgaatc tgtaactaga atttaatttt caccccaata   4080
atgttctata tagcctttgc taaagagcaa ctaataaatt aaacctattc tttctgtgaa   4140
aaaaaaaaaa                                                          4150
```

<210> SEQ ID NO 54
<211> LENGTH: 3044
<212> TYPE: DNA
<213> ORGANISM: Homo sapiens

<400> SEQUENCE: 54

```
gctttattgt ttgcttgttt tgttccggag tcggggccgg gagggagtgc aggaggaggg     60
atccaagctt ccaagcctct gctccgctct ccttctatcc agttggtctt tagggcactg    120
aaggaaactc ttcttcagaa ataacctttt aacttttctt ctgtcagctg cctgccaatc    180
acggagccag aggctgaggg gaggctttga gccggtctgc gagtccggaa ggcaaagatc    240
gcgaagcttg gcgctccaga acgctcaggg ggcaggtgac acagtcgtgg gttccccggc    300
gggcgctggc ttgacagttt cctccccgcc cactggcagg ggagcgcccc gccgggctgc    360
acgcgcgcgc gcgcaggggg gcataaaagc cgcggccgcg cggagacgcg gagctcgccc    420
accgcccgcc ccagcagtgg ctgcaccatg cacgtgaacg gcaaagtggc gctggtgacc    480
ggcgcggctc agggcatagg cagagccttt gcagaggcgc tgctgcttaa gggcgccaag    540
gtagcgctgg tggattggaa tcttgaagca ggtgtacagt gtaaagctgc cctggatgag    600
cagtttgaac ctcagaagac tctgttcatc cagtgcgatg tggctgacca gcaacaactg    660
agagacactt ttagaaaagt tgtagaccac tttggaagac tggacatttt ggtcaataat    720
gctggagtga ataatgagaa aaactgggaa aaaactctgc aaattaattt ggtttctgtt    780
atcagtggaa cctatcttgg tttggattac atgagtaagc aaaatggagg tgaaggcggc    840
atcattatca atatgtcatc tttagcagga ctcatgcccg ttgcacagca gccggtttat    900
tgtgcttcaa agcatggcat agttggattc acacgctcag cagcgttggc tgctaatctt    960
atgaacagtg gtgtgagact gaatgccatt tgtccaggct ttgttaacac agccatcctt   1020
gaatcaattg aaaaagaaga aaacatggga caatatatag aatataagga tcatatcaag   1080
gatatgatta aatactatgg aattttggac ccaccattga ttgccaatgg attgataaca   1140
```

```
ctcattgaag atgatgcttt aaatggtgct attatgaaga tcacaacttc taagggaatt   1200

cattttcaag actatgatac aactccattt caagcaaaaa cccaatgaac agcttatgtg   1260

ttagccatag ctgaaaataa gcacaaatag cttatattca gatcctatct tcatttgaat   1320

atagctttta aatgaaatgt tacagtttga agttttcctt catgcacttg gtgataaacg   1380

ttttctaaat ttttagttaa gtatatggat aaaaagttat gaactattaa aaatgtgatg   1440

tggaccaaag gctaggttgt aatcttgata gtctaaaaaa tgatcaaaac aaatgatttt   1500

caaggaatat tcaatattct gcctttcaga aagtgtattt atatctgtgc ttcataaata   1560

ttaatgttct tcagaacatc attttaaagg agatacttga attgttattt aaatcaaacc   1620

agatgtaaaa cactcacata caagttcata ctttaaaaga ggaaagctac ttaacaatga   1680

caaatatttc acaataataa tttttactta tataccatct ttcaactgaa catttcagtt   1740

cttccaagag cttcttagag tagtatattt tgggggcagt caaggaataa actacagtgt   1800

aaacatatcc cagatgaaaa ctgctgtatg gaaaaatgac agaaagtaac tgattgacac   1860

tgttgattca cagttcagcc tcctatctgg gaaagacatt tctttcctct gctcacttta   1920

agaactttta ccgactccaa aaatctcagg aattaaactt ttaacagtta cagcaataaa   1980

gaatagttag tactccaaaa atattatatt taagatgctc aacaagaaaa aaatgcaaat   2040

gtaatatttt tttcaaatta cttctttatt gacttgtcca aatttcaaaa gtgcctaccc   2100

ttcaataaaa ctttttttatt ctgatctcca taaattactt agtcttctat gtatagctat   2160

caaggaaata aaaccaattt tgccacagcc acaactgtaa atgtttttgt acccatgctg   2220

aaactcataa caacacagac ataaaaatag ctgtgaggtt ttgctttttt tgttgtcagc   2280

tatcttaaga atcattaaat acacctgctt tgggtaaaac tctttgcaag cagtaattaa   2340

cactagtaac agtgaaagca caagatttcc aaatcagtcg ttttctcaaa aaaatatcgt   2400

ataagtgact catcctgtct gctaactcca gacctcccag cttgaagcca aatctttcca   2460

tgtgagattg atatggattt cctagaagta ctggaatgtt gtcatatctt gccctatttt   2520

aattctgcta tagaaaacaa ttgccttcac ttttaaggag taatttgaat attaataact   2580

ctggtctaga ttttcatata atgtattaaa gacaaagtag tgaacatcaa tgaacatctg   2640

atagagataa actgtaatca ggcataagct tgtttgtatg ttctggcagt gactaatcag   2700

taaatgatgt cggtttgccc agtatcactt atcttctgta tttttcctct gtcgtgtaaa   2760

tagtataacc ttttcattta tggacaattt tttggactag tagccttcaa tatacattct   2820

gctttgaatt aattttttca aatcaataaa ttatgtagac atttaaaatc aaatatcaag   2880

tagaattgaa aaatgtgagt tacataagtt aaaaacttac tttaaatctt accttctata   2940

ggtagctcta aataaattca tatggttata tggcatctct ggtgtatact gattgagaaa   3000

ataattaaac tgaagttagg ggaggggaaa aaaaaaaaaa aaaa                    3044
```

<210> SEQ ID NO 55
<211> LENGTH: 3891
<212> TYPE: DNA
<213> ORGANISM: Homo sapiens

<400> SEQUENCE: 55

```
gagagcgtag tggaggaggc gcggttgtga gtagtaccgg gagtggggtg atcccgggct     60

aggggagcgc ggcggccgcg atcgggctta gtcggagctc cgaagggagt gactaggaca    120

cccgggtggg ctacttttct tccggtgctt ttgctttttt tttcctttgg gctcgggctg    180

agtgtcgccc actgagcaaa gattccctcg taaaacccag agcgaccctc ccgtcaattg    240
```

ttgggctcgg gagtgtcgcg gtgccccgag cgcgccgggc gcggaggcaa agggagcgga 300
gccggccgcg gacggggccc ggagcttgcc tgcctccctc gctcgcccca gcgggttcgc 360
tcgcgtagag cgcagggcgc gcgcgatgaa ggcggtgagc ccggtgcgcc cctcgggccg 420
caaggcgccg tcgggctgcg gcggcgggga gctggcgctg cgctgcctgg ccgagcacgg 480
ccacagcctg ggtggctccg cagccgcggc ggcggcggcg gcggcagcgc gctgtaaggc 540
ggccgaggcg gcggccgacg agccggcgct gtgcctgcag tgcgatatga acgactgcta 600
tagccgcctg cggaggctgg tgcccaccat cccgcccaac aagaaagtca gcaaagtgga 660
gatcctgcag cacgttatcg actacatcct ggacctgcag ctggcgctgg agacgcaccc 720
ggccctgctg aggcagccac caccgcccgc gccgccacac cacccggccg ggacctgtcc 780
agccgcgccg ccgcggaccc cgctcactgc gctcaacacc gacccggccg gcgcggtgaa 840
caagcagggc gacagcattc tgtgccgctg agccgcgctg tccaggtgtg cggccgcctg 900
agcccgagcc aggagcacta gagagggagg gggaagagca gaagttagag aaaaaaagcc 960
accggaggaa aggaaaaaac atcggccaac ctagaaacgt tttcattcgt cattccaaga 1020
gagagagagg aaagaaaaat acaactttca ttctttcttt gcacgttcat aaacattcta 1080
catacgtatt ctcttttgtc tcttcattta taactgctgt gaattgtaca tttctgtgtt 1140
ttttggaggt gcagttaaac ttttaagctt aagtgtgaca ggactgataa atagaagatc 1200
aagagtagat ccgactttag aagcctactt tgtgaccaag gagctcaatt tttgttttga 1260
agctttacta atctaccaga gcattgtaga tattttttt ttacatctat tgtttaaaat 1320
agatgattat aacggggcag agaactttct tttctctgca agaatgttac atattgtata 1380
gataaatgag tgacatttca taccatgtat atatagagat gttctataag tgtgagaaag 1440
tatatgcttt aatagatact gtaattataa gatattttta attaaatatt tttttgtaaa 1500
tattatgtgt gtgttttttt ttaatctatg ggaatatttc ttttggaaaa tcatttttca 1560
gctcaattac agagctcttg atatcttgaa tgtcttttct gtttggcctg gctcttaatt 1620
tgcttttgtt ttgcccagta tagactcgga agtaacagtt atagctagtg gtcttgcatg 1680
attgcatgag atgtttaatc acaaattaaa cttgttctga gtccattcaa atgtgttttt 1740
ttaaatgtag attgaaatct ttgtatttga agcatacatg ttgaaaatac accttatcag 1800
tttttaagta cagggtttta tagtgtaata tatacagagt aagtgtttgt ttttgttttt 1860
caactgaggt caaaatggat tctgaatgat tttgcatatg ggatgaggaa atgcttggat 1920
ccttaaggag tttacgaaat ctgctgtttt atcaaagtga aaaaaaattg cttattactc 1980
ttcattttac actaaagctt aatgtcacta agtttcatgt ctgtacagat tatttaaatc 2040
atggaaatga aaaaaatgtt ctctgcttgc taccaaagga caaactcttg gaaatgaaca 2100
ctttctgctt tccttcctcc aaagaattaa taggcaacag tgggagaaaa aaaaggcata 2160
atggcaaatc cttcaagcag ggataaaagt cgatcttcaa acattaactt aagcagacca 2220
aaaattctga tgaccgcatc tagattattt ttttataaaa atgattttca ctatagctat 2280
gttacgctaa gctactgtcc aatctcttgt gatgtgtaac ttttacatgt gaatattaaa 2340
gtagatttct ctgtcttgta ctgtgatttc tggtctcatt tctttaaaac cttactctta 2400
tttttctttt aaggctcttt tttctcctta aggaaggtaa tattttctag gttagatagg 2460
actatcaggg tttgtgaaca ttatgcattt aatgttatgg gtactttaca cacaagttag 2520
atggaatttt tagagtgaaa gaattaagta ggatttaatt gggtgctttg taaatagtca 2580

```
actgtgtgta taacgtggtc tgtttgattt ttaaaaggaa aggatttgtt tcagattata   2640
caagaataaa agtattatag acccaaggga cttcttatga ggtcaaattc agatatttat   2700
atgaatatga aataccatgg tccctagtag tcagttgaag tggcaatgtc taaacagaaa   2760
tgaacaaaac taatgctagc aggttaaaat caatcaaaat gtttaaaaat tgattctgtc   2820
ctcagcatgt tatttcctca gctctgataa tttactggtc ttgagtattt tgagaatttg   2880
atgttgaacg ttataaagtc aaagaactgc ttgtttagat gaggtttatt tttatttttg   2940
atattattca ttcttgtcac acatcaagaa gaaaacacta gagtgctgct ggaattccaa   3000
atctgaagaa ttctaacgac tgcattcttt gttattaaaa agggcacaat ccttcctttt   3060
tatttggcag tttaatttca gtaggaagca tgtcacatgt gcactgttgg ttagaattat   3120
gcatctgtca tgcctgactg ctgaacccta cctaagcctt ttggcgcagt ttaaaactta   3180
tactggtgga ctgtgaacct caaaacaaat gggtattttt gggttttgag gatagatgtt   3240
actccttaaa gtttgtattt ggggcatgaa aaactactga aagaagaaaa gtgctacaga   3300
tactacattt caaagagttg gcattttccc tttggccact caagcagcat ttgatgtatc   3360
taaagaaaca aagtcattgt ttattttta aaaaattata tgcagttgta caagatacta   3420
cattccattg aaatgttggc tatgtcctaa ccaggcaacc agataacaaa aacattttga   3480
gtcttttatc taggtagttc taattattca gctacttagt ttaacaaagg aaaatatcct   3540
gacttctctc atttcatttg tagactttc attgtatagg cacaaccaaa gagtcagact   3600
ggtttaaaac tccagaagga aaaaaagtat cccacacagt ggatgttgtt tctaagaatg   3660
ctacaaaatc ctgacatctc agacatctca atgttaaagg aagaaaaaaa ataccttttc   3720
atttcaaaga actaatatac tttgatattg tgtaaacctt actcaagttt attgtcaagc   3780
tttaactgcc tttttagaac tttttaaaat ttcgagccca caaatctatt gtattagttg   3840
ccttctataa caataaatct tcactgagca aaaggcaaaa aaaaaaaaaa a            3891
```

<210> SEQ ID NO 56
<211> LENGTH: 7370
<212> TYPE: DNA
<213> ORGANISM: Homo sapiens

<400> SEQUENCE: 56

```
ttttgtagat aaatgtgagg attttctcta aatccctctt ctgtttgcta aatctcactg     60
tcactgctaa attcagagca gatagagcct gcgcaatgga ataaagtcct caaaattgaa    120
atgtgacatt gctctcaaca tctcccatct ctctggattt ctttttgctt cattattcct    180
gctaaccaat tcattttcag actttgtact tcagaagcaa tgggaaaaat cagcagtctt    240
ccaacccaat tatttaagtg ctgcttttgt gatttcttga aggtgaagat gcacaccatg    300
tcctcctcgc atctcttcta cctggcgctg tgcctgctca ccttcaccag ctctgccacg    360
gctggaccgg agacgctctg cggggctgag ctggtggatg ctcttcagtt cgtgtgtgga    420
gacaggggct tttatttcaa caagcccaca gggtatggct ccagcagtcg gagggcgcct    480
cagacaggca tcgtggatga gtgctgcttc cggagctgtg atctaaggag gctggagatg    540
tattgcgcac ccctcaagcc tgccaagtca gctcgctctg tccgtgccca gcgccacacc    600
gacatgccca agacccagaa gtatcagccc ccatctacca acaagaacac gaagtctcag    660
agaaggaaag gaagtacatt tgaagaacgc aagtagaggg agtgcaggaa acaagaacta    720
caggatgtag gaagaccctc ctgaggagtg aagagtgaca tgccaccgca ggatcctttg    780
ctctgcacga gttacctgtt aaactttgga acacctacca aaaaataagt ttgataacat    840
```

```
ttaaaagatg ggcgtttccc ccaatgaaat acacaagtaa acattccaac attgtcttta    900
ggagtgattt gcaccttgca aaaatggtcc tggagttggt agattgctgt tgatctttta    960
tcaataatgt tctatagaaa agaaaaaaaa aatatatata tatatatatc ttagtccctg   1020
cctctcaaga gccacaaatg catgggtgtt gtatagatcc agttgcacta aattcctctc   1080
tgaatcttgg ctgctggagc cattcattca gcaaccttgt ctaagtggtt tatgaattgt   1140
ttccttattt gcacttcttt ctacacaact cgggctgttt gttttacagt gtctgataat   1200
cttgttagtc tatacccacc acctcccttc ataaccttta tatttgccga atttggcctc   1260
ctcaaaagca gcagcaagtc gtcaagaagc acaccaattc taacccacaa gattccatct   1320
gtggcatttg taccaaatat aagttggatg cattttattt tagacacaaa gctttatttt   1380
tccacatcat gcttacaaaa aagaataatg caaatagttg caactttgag gccaatcatt   1440
tttaggcata tgttttaaac atagaaagtt tcttcaactc aaaagagttc cttcaaatga   1500
tgagttaatg tgcaacctaa ttagtaactt tcctcttttt attttttcca tatagagcac   1560
tatgtaaatt tagcatatca attatacagg atatatcaaa cagtatgtaa aactctgttt   1620
tttagtataa tggtgctatt ttgtagtttg ttatatgaaa gagtctggcc aaaacggtaa   1680
tacgtgaaag caaaacaata ggggaagcct ggagccaaag atgacacaag gggaagggta   1740
ctgaaaacac catccatttg ggaaagaagg caaagtcccc ccagttatgc cttccaagag   1800
gaacttcaga cacaaaagtc cactgatgca aattggactg gcgagtccag agaggaaact   1860
gtggaatgga aaaagcagaa ggctaggaat tttagcagtc ctggtttctt tttctcatgg   1920
aagaaatgaa catctgccag ctgtgtcatg gactcaccac tgtgtgacct tgggcaagtc   1980
acttcacctc tctgtgcctc agtttcctca tctgcaaaat gggggcaata tgtcatctac   2040
ctacctcaaa ggggtggtat aaggtttaaa aagataaaga ttcagatttt ttttaccctg   2100
ggttgctgta agggtgcaac atcagggcgc ttgagttgct gagatgcaag gaattctata   2160
aataacccat tcatagcata gctagagatt ggtgaattga atgctcctga catctcagtt   2220
cttgtcagtg aagctatcca aataactggc caactagttg ttaaaagcta acagctcaat   2280
ctcttaaaac acttttcaaa atatgtggga agcatttgat tttcaatttg attttgaatt   2340
ctgcatttgg ttttatgaat acaaagataa gtgaaaagag agaaaggaaa agaaaaagga   2400
gaaaaacaaa gagatttcta ccagtgaaag gggaattaat tactctttgt tagcactcac   2460
tgactcttct atgcagttac tacatatcta gtaaaacctc gtttaatact ataaataata   2520
ttctattcat tttgaaaaac acaatgattc cttcttttct aggcaatata aggaaagtga   2580
tccaaaattt gaaatattaa aataatatct aataaaaagt cacaaagtta tcttctttaa   2640
caaactttac tcttattctt agctgtatat acattttttt aaaagtttgt taaaatatgc   2700
ttgactagag tttccagttg aaaggcaaaa acttccatca caacaagaaa tttcccatgc   2760
ctgctcagaa gggtagcccc tagctctctg tgaatgtgtt ttatccattc aactgaaaat   2820
tggtatcaag aaagtccact ggttagtgta ctagtccatc atagcctaga aaatgatccc   2880
tatctgcaga tcaagatttt ctcattagaa caatgaatta tccagcattc agatctttct   2940
agtcacctta gaacttttttg gttaaaagta cccaggcttg attatttcat gcaaattcta   3000
tattttacat tcttggaaag tctatatgaa aaacaaaaat aacatcttca gtttttctcc   3060
cactgggtca cctcaaggat cagaggccag gaaaaaaaaa aaaaagactc cctggatctc   3120
tgaatatatg caaaaagaag gccccattta gtggagccag caatcctgtt cagtcaacaa   3180
```

```
gtattttaac tctcagtcca acattatttg aattgagcac ctcaagcatg cttagcaatg   3240
ttctaatcac tatggacaga tgtaaaagaa actatacatc atttttgccc tctgcctgtt   3300
ttccagacat acaggttctg tggaataaga tactggactc ctcttcccaa gatggcactt   3360
ctttttattt cttgtcccca gtgtgtacct tttaaaatta ttccctctca acaaaacttt   3420
ataggcagtc ttctgcagac ttaacgtgtt ttctgtcata gttagatgtg ataattctaa   3480
gagtgtctat gacttatttc cttcacttaa ttctatccac agtcaaaaat cccccaagga   3540
ggaaagctga aagatgcact gccatattat ctttcttaac tttttccaac acataatcct   3600
ctccaactgg attataaata aattgaaaat aactcattat accaattcac tattttattt   3660
tttaatgaat taaaactaga aaacaaattg atgcaaaccc tggaagtcag ttgattacta   3720
tatactacag cagaatgact cagatttcat agaaaggagc aaccaaaatg tcacaaccca   3780
aaactttaca agctttgctt cagaattaga ttgctttata attcttgaat gaggcaattt   3840
caagatattt gtaaaagaac agtaaacatt ggtaagaatg agctttcaac tcataggctt   3900
atttccaatt taattgacca tactggatac ttaggtcaaa tttctgttct ctcttcccca   3960
aataatatta aagtattatt tgaacttttt aagatgaggc agttcccctg aaaaagttaa   4020
tgcagctctc catcagaatc cactcttcta gggatatgaa aatctcttaa cacccaccct   4080
acatacacag acacacacac acacacacac acacacacac acacacacat tcaccctaag   4140
gatccaatgg aatactgaaa agaaatcact tccttgaaaa ttttattaaa aaacaaacaa   4200
acaaacaaaa agcctgtcca cccttgagaa tccttcctct ccttggaacg tcaatgtttg   4260
tgtagatgaa accatctcat gctctgtggc tccagggttt ctgttactat tttatgcact   4320
tgggagaagg cttagaataa aagatgtagc acattttgct ttcccattta ttgtttggcc   4380
agctatgcca atgtggtgct attgtttctt taagaaagta cttgactaaa aaaaaaagaa   4440
aaaaagaaaa aaaagaaagc atagacatat ttttttaaag tataaaaaca acaattctat   4500
agatagatgg cttaataaaa tagcattagg tctatctagc caccaccacc tttcaacttt   4560
ttatcactca caagtagtgt actgttcacc aaattgtgaa tttgggggtg caggggcagg   4620
agttggaaat tttttaaagt tagaaggctc cattgttttg ttggctctca aacttagcaa   4680
aattagcaat atattatcca atcttctgaa cttgatcaag agcatggaga ataaacgcgg   4740
gaaaaaagat cttataggca aatagaagaa tttaaaagat aagtaagttc cttattgatt   4800
tttgtgcact ctgctctaaa acagatattc agcaagtgga gaaaataaga acaaagagaa   4860
aaaatacata gatttacctg caaaaaatag cttctgccaa atccccccttg ggtattcttt   4920
ggcatttact ggtttataga agacattctc ccttcaccca gacatctcaa agagcagtag   4980
ctctcatgaa aagcaatcac tgatctcatt tgggaaatgt tggaaagtat ttccttatga   5040
gatgggggtt atctactgat aaagaaagaa tttatgagaa attgttgaaa gagatggcta   5100
acaatctgtg aagatttttt gtttcttgtt tttgtttttt tttttttttt actttataca   5160
gtctttatga atttcttaat gttcaaaatg acttggttct tttcttcttt ttttatatca   5220
gaatgaggaa taataagtta aacccacata gactctttaa aactataggc tagatagaaa   5280
tgtatgtttg acttgttgaa gctataatca gactatttaa aatgttttgc tatttttaat   5340
cttaaaagat tgtgctaatt tattagagca gaacctgttt ggctctcctc agaagaaaga   5400
atctttccat tcaaatcaca tggctttcca ccaatatttt caaaagataa atctgattta   5460
tgcaatggca tcatttattt taaaacagaa gaattgtgaa agtttatgcc cctcccttgc   5520
aaagaccata aagtccagat ctggtagggg ggcaacaaca aaaggaaaat gttgttgatt   5580
```

-continued

```
cttggttttg gattttgttt tgttttcaat gctagtgttt aatcctgtag tacatatttg   5640
cttattgcta ttttaatatt ttataagacc ttcctgttag gtattagaaa gtgatacata   5700
gatatctttt ttgtgtaatt tctatttaaa aaagagagaa gactgtcaga agctttaagt   5760
gcatatggta caggataaag atatcaattt aaataaccaa ttcctatctg gaacaatgct   5820
tttgtttttt aaagaaacct ctcacagata agacagaggc ccaggggatt tttgaagctg   5880
tctttattct gcccccatcc caacccagcc cttattattt tagtatctgc ctcagaattt   5940
tatagagggc tgaccaagct gaaactctag aattaaagga acctcactga aaacatatat   6000
ttcacgtgtt ccctcttttt ttttttcctt tttgtgagat ggggtctcgc actgtccccc   6060
aggctggagt gcagtggcat gatctcggct cactgcaacc tccacctcct gggtttaagc   6120
gattctcctg cctcagcctc ctgagtagct gggattacag gcacccacca ctatgcccgg   6180
ctaatttttt ggatttttaa tagagacggg gttttaccat gttggccagg ttggtctcaa   6240
actcctgacc ttgtgatttg cccgcctcag cctcccaaat tgctgggatt acaggcatga   6300
gccaccacac cctgcccatg tgttccctct taatgtatga ttacatggat cttaaacatg   6360
atccttctct cctcattctt caactatctt tgatggggtc tttcaagggg aaaaaaatcc   6420
aagctttttt aaagtaaaaa aaaaaaaaga gaggacacaa aaccaaatgt tactgctcaa   6480
ctgaaatatg agttaagatg gagacagagt ttctcctaat aaccggagct gaattacctt   6540
tcactttcaa aaacatgacc ttccacaatc cttagaatct gccttttttt atattactga   6600
ggcctaaaag taaacattac tcattttatt ttgcccaaaa tgcactgatg taaagtagga   6660
aaaataaaaa cagagctcta aaatcccttt caagccaccc attgacccca ctcaccaact   6720
catagcaaag tcacttctgt taatccctta atctgatttt gtttggatat ttatcttgta   6780
cccgctgcta aacacactgc aggagggact ctgaaacctc aagctgtcta cttacatctt   6840
ttatctgtgt ctgtgtatca tgaaaatgtc tattcaaaat atcaaaacct ttcaaatatc   6900
acgcagctta tattcagttt acataaaggc cccaaatacc atgtcagatc tttttggtaa   6960
aagagttaat gaactatgag aattgggatt acatcatgta ttttgcctca tgtattttta   7020
tcacacttat aggccaagtg tgataaataa acttacagac actgaattaa tttcccctgc   7080
tactttgaaa ccagaaaata atgactggcc attcgttaca tctgtcttag ttgaaaagca   7140
tatttttat taaattaatt ctgattgtat ttgaaattat tattcaattc acttatggca   7200
gaggaatatc aatcctaatg acttctaaaa atgtaactaa ttgaatcatt atcttacatt   7260
tactgtttaa taagcatatt ttgaaaatgt atggctagag tgtcataata aaatggtata   7320
tctttcttta gtaattacat taaaattagt catgtttgat taattagttc             7370
```

<210> SEQ ID NO 57
<211> LENGTH: 2171
<212> TYPE: DNA
<213> ORGANISM: Homo sapiens

<400> SEQUENCE: 57

```
aaagttacat tttctctgga actctcctag gccactccct gctgatgcaa catctgggtt     60
tgggcagaaa ggagggtgct tcggagcccg ccctttctga gcttcctggg ccggctctag    120
aacaattcag gcttcgctgc gactcagacc tcagctccaa catatgcatt ctgaagaaag    180
atggctgaga tggacagaat gctttatttt ggaaagaaac aatgttctag gtcaaactga    240
gtctaccaaa tgcagacttt cacaatggtt ctagaagaaa tctggacaag tcttttcatg    300
```

-continued

```
tggtttttct acgcattgat tccatgtttg ctcacagatg aagtggccat tctgcctgcc    360

cctcagaacc tctctgtact ctcaaccaac atgaagcatc tcttgatgtg gagcccagtg    420

atcgcgcctg gagaaacagt gtactattct gtcgaatacc agggggagta cgagagcctg    480

tacacgagcc acatctggat ccccagcagc tggtgctcac tcactgaagg tcctgagtgt    540

gatgtcactg atgacatcac ggccactgtg ccatacaacc ttcgtgtcag ggccacattg    600

ggctcacaga cctcagcctg gagcatcctg aagcatccct ttaatagaaa ctcaaccatc    660

cttacccgac ctgggatgga gatcaccaaa gatggcttcc acctggttat tgagctggag    720

gacctggggc cccagtttga gttccttgtg gcctactgga ggagggagcc tggtgccgag    780

gaacatgtca aaatggtgag gagtgggggt attccagtgc acctagaaac catggagcca    840

ggggctgcat actgtgtgaa ggcccagaca ttcgtgaagg ccattgggag gtacagcgcc    900

ttcagccaga cagaatgtgt ggaggtgcaa ggagaggcca ttcccctggt actggccctg    960

tttgcctttg ttggcttcat gctgatcctt gtggtcgtgc cactgttcgt ctggaaaatg   1020

ggccggctgc tccagtactc ctgttgcccc gtggtggtcc tcccagacac cttgaaaata   1080

accaattcac cccagaagtt aatcagctgc agaagggagg aggtggatgc ctgtgccacg   1140

gctgtgatgt ctcctgagga actcctcagg gcctggatct cataggtttg cggaagggcc   1200

caggtgaagc cgagaacctg gtctgcatga catggaaacc atgaggggac aagttgtgtt   1260

tctgttttcc gccacggaca agggatgaga gaagtaggaa gagcctgttg tctacaagtc   1320

tagaagcaac catcagaggc agggtggttt gtctaacaga acactgactg aggcttaggg   1380

gatgtgacct ctagactggg ggctgccact tgctggctga gcaaccctgg gaaaagtgac   1440

ttcatccctt cggtcctaag ttttctcatc tgtaatgggg gaattaccta cacacctgct   1500

aaacacacac acacagagtc tctctctata tatacacacg tacacataaa tacacccagc   1560

acttgcaagg ctagagggaa actggtgaca ctctacagtc tgactgattc agtgtttctg   1620

gagagcagga cataaatgta tgatgagaat gatcaaggac tctacacact gggtggcttg   1680

gagagcccac tttcccagaa taatccttga gagaaaagga atcatgggag caatggtgtt   1740

gagttcactt caagcccaat gccggtgcag aggggaatgg cttagcgagc tctacagtag   1800

gtgacctgga ggaaggtcac agccacactg aaaatgggat gtgcatgaac acggaggatc   1860

catgaactac tgtaaagtgt tgacagtgtg tgcacactgc agacagcagg tgaaatgtat   1920

gtgtgcaatg cgacgagaat gcagaagtca gtaacatgtg catgtttgtt gtgctccttt   1980

tttctgttgg taaagtacag aattcagcaa ataaaaaggg ccaccctggc caaaagcggt   2040

ctttaaaaaa aaaaaaaaaa aaaaaaaaaa aaaaaaaaaa aaaaaaaaaa aaaaaaaaaa   2100

aaaaaaaaaa aaaaaaaaaa aaaaaaaaaa aaaaaaaaaa aaaaaaaaaa aaaaaaaaaa   2160

aaaaaaaaaa a                                                        2171
```

```
<210> SEQ ID NO 58
<211> LENGTH: 2175
<212> TYPE: DNA
<213> ORGANISM: Homo sapiens

<400> SEQUENCE: 58

agtacagtat aaaacttcac agtgccaata ccatgaagag gagctcagac agctcttacc     60

acatgataca agagccggct ggtggaagag tggggaccag aaagagaatt tgctgaagag    120

gagaaggaaa aaaaaaacac caaaaaaaaa aataaaaaaa tccacacaca caaaaaaacc    180

tgcgcgtgag gggggaggaa aagcagggcc ttttaaaaag gcaatcacaa caacttttgc    240
```

```
tgccaggatg cccttgcttt ggctgagagg atttctgttg gcaagttgct ggattatagt    300

gaggagttcc cccaccccag gatccgaggg gcacagcgcg gcccccgact gtccgtcctg    360

tgcgctggcc gccctcccaa aggatgtacc caactctcag ccagagatgg tggaggccgt    420

caagaagcac attttaaaca tgctgcactt gaagaagaga cccgatgtca cccagccggt    480

acccaaggcg gcgcttctga acgcgatcag aaagcttcat gtgggcaaag tcggggagaa    540

cgggtatgtg gagatagagg atgacattgg aaggagggca gaaatgaatg aacttatgga    600

gcagacctcg gagatcatca cgtttgccga gtcaggaaca gccaggaaga cgctgcactt    660

cgagatttcc aaggaaggca gtgacctgtc agtggtggag cgtgcagaag tctggctctt    720

cctaaaagtc cccaaggcca acaggaccag gaccaaagtc accatccgcc tcttccagca    780

gcagaagcac ccgcagggca gcttggacac aggggaagag gccgaggaag tgggcttaaa    840

gggggagagg agtgaactgt tgctctctga aaaagtagta gacgctcgga agagcacctg    900

gcatgtcttc cctgtctcca gcagcatcca gcggttgctg gaccagggca agagctccct    960

ggacgttcgg attgcctgtg agcagtgcca ggagagtggc gccagcttgg ttctcctggg   1020

caagaagaag aagaaagaag aggaggggga agggaaaaag aagggcggag gtgaaggtgg   1080

ggcaggagca gatgaggaaa aggagcagtc gcacagacct ttcctcatgc tgcaggcccg   1140

gcagtctgaa gaccaccctc atcgccggcg tcggcggggc ttggagtgtg atggcaaggt   1200

caacatctgc tgtaagaaac agttctttgt cagtttcaag gacatcggct ggaatgactg   1260

gatcattgct ccctctggct atcatgccaa ctactgcgag ggtgagtgcc cgagccatat   1320

agcaggcacg tccgggtcct cactgtcctt ccactcaaca gtcatcaacc actaccgcat   1380

gcggggccat agcccctttg ccaacctcaa atcgtgctgt gtgcccacca agctgagacc   1440

catgtccatg ttgtactatg atgatggtca aaacatcatc aaaaaggaca ttcagaacat   1500

gatcgtggag gagtgtgggt gctcatagag ttgcccagcc cagggggaaa gggagcaaga   1560

gttgtccaga gaagacagtg gcaaaatgaa gaaattttta aggtttctga gttaaccaga   1620

aaaatagaaa ttaaaaacaa aacaaaaaaa aaaacaaaaa aaaacaaaag taaattaaaa   1680

acaaaacctg atgaaacaga tgaaggaaga tgtggaaaaa atccttagcc agggctcaga   1740

gatgaagcag tgaaagagac aggaattggg agggaaaggg agaatggtgt accctttatt   1800

tcttctgaaa tcacactgat gacatcagtt gtttaaacgg ggtattgtcc tttccccct    1860

tgaggttccc ttgtgagcct tgaatcaacc aatctagtct gcagtagtgt ggactagaac   1920

aacccaaata gcatctagaa agccatgagt ttgaaagggc ccatcacagg cactttccta   1980

cccaattacc caggtcataa ggtatgtctg tgtgacactt atctctgtgt atatcagcat   2040

acacacacac acacacacac acacacacac acacaggcat ttccacacat tacatatata   2100

cacatactgg taaaagaaca atcgtgtgca ggtggtcaca cttccttttt ctgtaccact   2160

tttgcaacaa aacaa                                                    2175
```

```
<210> SEQ ID NO 59
<211> LENGTH: 5035
<212> TYPE: DNA
<213> ORGANISM: Homo sapiens

<400> SEQUENCE: 59
```

```
gcaggcgccg cgccgaggag gctgccgctc tggcttgccg ccccccgccg ccgctgcaca     60

ccggacccag ccgccgtgcc gcgggccatg gacctgccca ggggcctggt ggtggcctgg    120
```

-continued

```
gcgctcagcc tgtggccagg gttcacggac accttcaaca tggacaccag gaagccccgg    180
gtcatccctg gctccaggac cgccttcttt ggctacacag tgcagcagca cgacatcagt    240
ggcaataagt ggctggtcgt gggcgcccca ctggaaacca atggctacca gaagacggga    300
gacgtgtaca agtgtccagt gatccacggg aactgcacca aactcaacct gggaagggtc    360
accctgtcca acgtgtccga gcggaaagac aacatgcgcc tcggccttag tctcgccacc    420
aaccccaagg acaacagctt cctggcctgc agccccctct ggtctcatga gtgtgggagc    480
tcctactaca ccacagggat gtgttcaaga gtcaactcca acttcaggtt ctccaagacc    540
gtggccccag ctctccaaag gtgccagacc tacatggaca tcgtcattgt cctggatggc    600
tccaacagca tctaccccctg ggtggaggtt cagcacttcc tcatcaacat cctgaaaaag    660
ttttacattg gcccagggca gatccaggtt ggagttgtgc agtatggcga agatgtggtg    720
catgagtttc acctcaacga ctacaggtct gtaaaagatg tggtggaagc tgccagccac    780
attgagcaga gaggaggaac agagacccgg acggcatttg gcattgaatt tgcacgctca    840
gaggctttcc agaagggtgg aaggaaagga gccaagaagg tgatgattgt catcacagat    900
ggggagtccc acgacagccc agacctggag aaggtgatcc agcaaagcga aagagacaac    960
gtaacaagat atgcggtggc cgtcctgggc tactacaacc gcagggggat caatccagaa   1020
acttttctaa atgaaatcaa atacatcgcc agtgaccctg atgacaagca cttcttcaat   1080
gtcactgatg aggctgcctt gaaggacatt gtcgatgccc tgggggacag aatcttcagc   1140
ctggaaggca ccaacaagaa cgagacctcc tttgggctgg agatgtcaca gacgggcttt   1200
tcctcgcacg tggtggagga tggggttctg ctgggagccg tcggtgccta tgactggaat   1260
ggagctgtgc taaaggagac gagtgccggg aaggtcattc ctctccgcga gtcctacctg   1320
aaagagttcc ccgaggagct caagaaccat ggtgcatacc tggggtacac agtcacatcg   1380
gtcgtgtcct ccaggcaggg gcgggtgtac gtggccggag ccccccggtt caaccacacg   1440
ggcaaggtca tcctgttcac catgcacaac aaccggagcc tcaccatcca ccaggctatg   1500
cggggccagc agataggctc ttactttggg agtgaaatca cctcggtgga catcgacggc   1560
gacggcgtga ctgatgtcct gctggtgggc gcacccatgt acttcaacga gggccgtgag   1620
cgaggcaagg tgtacgtcta tgagctgaga cagaacctgt ttgtttataa cggaacgcta   1680
aaggattcac acagttacca gaatgcccga tttgggtcct ccattgcctc agttcgagac   1740
ctcaaccagg attcctacaa tgacgtggtg gtgggagccc ccctggagga caaccacgca   1800
ggagccatct acatcttcca cggcttccga ggcagcatcc tgaagacacc taagcagaga   1860
atcacagcct cagagctggc taccggcctc cagtattttg gctgcagcat ccacgggcaa   1920
ttggacctca atgaggatgg gctcatcgac ctggcagtgg gagcccttgg caacgctgtg   1980
attctgtggt cccgcccagt ggttcagatc aatgccagcc tccactttga gccatccaag   2040
atcaacatct tccacagaga ctgcaagcgc agtggcaggg atgccacctg cctggccgcc   2100
ttcctctgct tcacgcccat cttcctggca ccccatttcc aaacaacaac tgttggcatc   2160
agatacaacg ccaccatgga tgagaggcgg tatacaccga gggcccacct ggacgagggc   2220
ggggaccgat tcaccaacag agccgtactg ctctcctccg gccaggagct ctgtgagcgg   2280
atcaacttcc atgtcctgga cactgctgac tacgtgaagc cagtgacctt ctcagtcgag   2340
tattccctgg aggaccctga ccatggcccc atgctggacg acggctggcc caccactctc   2400
agagtctcgg tgcccttctg gaacggctgc aatgaggatg agcactgtgt ccctgacctt   2460
gtgttggatg cccggagtga cctgcccacg gccatggagt actgccagag ggtgctgagg   2520
```

-continued

```
aagcctgcgc aggactgctc cgcatacacg ctgtccttcg acaccacagt cttcatcata   2580
gagagcacac gccagcgagt ggcggtggag gccacactgg agaacagggg cgagaacgcc   2640
tacagcacgg tcctaaatat ctcgcagtca gcaaacctgc agtttgccag cttgatccag   2700
aaggaggact cagacggtag cattgagtgt gtgaacgagg agaggaggct ccagaagcaa   2760
gtctgcaacg tcagctatcc cttcttccgg gccaaggcca aggtggcttt ccgtcttgat   2820
tttgagttca gcaaatccat cttcctacac cacctggaga tcgagctcgc tgcaggcagt   2880
gacagtaatg agcgggacag caccaaggaa gacaacgtgg ccccccttacg cttccacctc   2940
aaatacgagg ctgacgtcct cttcaccagg agcagcagcc tgagccacta cgaggtcaag   3000
cccaacagct cgctggagag atacgatggt atcgggcctc ccttcagctg catcttcagg   3060
atccagaact tgggcttgtt ccccatccac gggatgatga tgaagatcac cattcccatc   3120
gccaccagga gcggcaaccg cctactgaag ctgagggact tcctcacgga cgaggcgaac   3180
acgtcctgta acatctgggg caatagcact gagtaccggc ccaccccagt ggaggaagac   3240
ttgcgtcgtg ctccacagct gaatcacagc aactctgatg tcgtctccat caactgcaat   3300
atacggctgg tccccaacca ggaaatcaat ttccatctac tggggaacct gtggttgagg   3360
tccctaaaag cactcaagta caaatccatg aaaatcatgg tcaacgcagc cttgcagagg   3420
cagttccaca gccccttcat cttccgtgag gaggatccca gccgccagat cgtgtttgag   3480
atctccaagc aagaggactg gcaggtcccc atctggatca ttgtaggcag caccctgggg   3540
ggcctcctac tgctggccct gctggtcctg gcactgtgga agctcggctt ctttagaagt   3600
gccaggcgca ggagggagcc tggtctggac cccaccccca aagtgctgga gtgaggctcc   3660
agaggagact ttgagttgat gggggccagg acaccagtcc aggtagtgtt gagacccagg   3720
cctgtggccc caccgagctg gagcggagag gaagccagct ggctttgcac ttgacctcat   3780
ctcccgagca atggcgcctg ctccctccag aatggaactc aagctggttt taagtggaac   3840
tgccctactg ggagactggg acacctttaa cacagacccc tagggattta aagggacacc   3900
cctacacaca cccaggccca tgccaaggcc tccctcaggc tctgtggagg gcatttgctg   3960
ccccagctac taaggtgcta ggaattcgta atcatcccca tcctccagag aaacccaggg   4020
aggaagactg taaatacgaa cccaatctgc acactccagg cctctagttc cagaaggatc   4080
caagacaaaa cagatctgaa ttctgccctt ttctctcacc catcccaccc ctccattggc   4140
tcccaagtca cacccactcc cttccccata gataggcccc tggggctccc gaagaatgaa   4200
cccaagagca agggcttgat ggtgacagct gcaagccagg gatgaagaaa gactctgaga   4260
tgtggagact gatggccagg caagtgggac caggatactg gacgctgtcc tgagatgaga   4320
ggtagccggg ctctgcaccc acgtgcattc acattgaccg caactcacac attcccccac   4380
cagctgcagc cccttgctct cagctgccaa ccctcccggg tcacttttgt tcccaggtac   4440
ctcatgggaa gcatgtggat gacacaatcc ctggggctgt gcattcccac gtcttcttgc   4500
tgcagcctgc ccctagacat ggacgcaccg gcctggctgc agctgggcag caggggtagg   4560
ggtagggagc ctcccctccc tgtatcaccc cctccctaca cacacacaca cacacacaca   4620
cacacacaca cacacacaca cacacacaca cacacactgc ctcccatcct tccctcatgc   4680
ccgccagtgc acagggaagg gcttggccag cgctgttgag ggtcccctc tggaatgcac   4740
tgaataaagc acgtgcaagg actcccggag cctgtgcagc cttggtggca aatatctcat   4800
ctgccggccc ccaggacaag tggtatgacc agtgataatg ccccaaggac aaggggcgtg   4860
```

cctggcgccc agtggagtaa tttatgcctt agtcttgttt tgaggtagaa atgcaagggg 4920
gacacatgaa aggcatcagt ccccctgtgc atagtacgac ctttactgtc gtatttttga 4980
aaaattaaaa atacagtgtt taaaaacaaa aaaaaaaaaa aaaaaaaaaa aaaaa 5035

<210> SEQ ID NO 60
<211> LENGTH: 3070
<212> TYPE: DNA
<213> ORGANISM: Homo sapiens

<400> SEQUENCE: 60
gagcccagag ccagagagcg cgctgggcgg tgctgggcac ccgcggagtg gaacggggct 60
ggtggaatgc acagggtcgc agcgcttggg ccaccctcgg tcagagggcg ccgtgtccag 120
cgagcaaacg ggcgccccgg agccttgctg agaggcagct ctgggctttc ccagctccga 180
agtcaatact gagatcccag atgtgtccag agacatcctg aagaggctcg ggggtggagg 240
agccttagtg tgtccacaaa gggactcctg aaactgactg agagccagtg gatttgccag 300
cagtctgagc ttctaccgag tcttccccca cctcaatccc tgttgctatg gagactacca 360
atggaacgga gacctggtat gagagcctgc atgccgtgct gaaggctcta aatgccactc 420
ttcacagcaa tttgctctgc cggccagggc cagggctggg gccagacaac cagactgaag 480
agaggcgggc cagcctacct ggccgtgatg acaactccta catgtacatt ctctttgtca 540
tgtttctatt tgctgtaact gtgggcagcc tcatcctggg atacacccgc tcccgcaaag 600
tggacaagcg tagtgacccc tatcatgtgt atatcaagaa ccgtgtgtct atgatctaac 660
acgagagggc tgggacggtg gaagaccaag acacctgggg attgcgtctg gggcctccag 720
aactctgctg tggactgcat caggtctcag tgtccctatc tgtaagatca acaagaaaca 780
cggttaaggg aggtcgtcac tggggtggga gaagaggggc tggtagaccg aagccttgtg 840
cataaggatt ttttcccagg aaaagataga ctttataaac agtgggagcc catgaacaaa 900
catataaaag tagcaacaga taatgaccaa taactggttc agtggctgga gtattagggg 960
cctggggatt ggagaacgga gaagaagttg tagcagaggg aaatgagaca ggaagatgct 1020
ctggggacac atttttttatg tgttatcttc agccatgaga agcagtgatg actatcccat 1080
atcacagata tgatttacca ccaccaccct gcccccgctc ccgtgaagaa agcagggcaa 1140
gtgctgtgct gcccatttgg gcctgcatag tgccatgatt ggaacccagg aactctggtc 1200
tccttgccta gtgcttttca aaactctgtg ctacacagga gtggatccag gcctgaaggt 1260
catacaattc tggggactct ctttaagaaa aagaattcta aaatatctta cttttgcaaa 1320
cattatgaaa atatactgcc acattaatat gttgctaggg cccctgctag gaccttaaga 1380
aggagctcat gtgagtcagg accctgaatg ttaggcctcg ttagctctat ggttcatatg 1440
cttcttgaac caagtcacag ggcacttccc agccacattg ccaggcaaca ggactaaact 1500
acctccaaag caagcagtct tttcagtttt gactgagtga tgtgagaaac ttcttttctt 1560
ttcttttctt tttttttttt tgagacagtc tccctatgtc acccaggctg tggtgcagca 1620
acccaatctt ggctcactgc aacccccacc tcccgggttc aagcaattat cctgcctcag 1680
ccacctgagt agctgggatt acaggttcct gtcaccacac ccagttaatt tatatatata 1740
tatatatata tatatttaag tagagacagg gtttcacatg ttgcccaggc tggtctcgaa 1800
ctcctgtcct caagttatct gcccattttg gtctcccaaa gtgctgggat tacaagtgta 1860
agccaccacg actatctgag agaagttttc tgatgtcatg ttgaatctgc ttctaaaaga 1920
ctgatactgc caaggtgggc ggatcacctg aggtcaggag ttcgagacca gcctggccaa 1980
catggtgaaa ccccatctac taaaaaaata caaaaattag ccagacctgg tggcgggtgc 2040
ccgtattccc agctacttgg gaggctgagg caggagaatt gtttgaaccc gggaggtgga 2100
ggttgcagta agccaagatc acgccactgc actccagcct gggtgacaga gcaaggctct 2160
gtctcaaaaa aaaacaaaaa caaaaacaaa aaagactgat atcgcaccta aattattatt 2220
atattaaaag aagcagagta tgagagacag gtacatggtc cagtaggaag agaagcagcc 2280
ctgattctac cacttaaggt gatgtatgat cttaggctgg acacttctct ccctcatccg 2340
ttttcctctt caacataatg aaatagactt gaaagtctct aaggctctat cagttctgac 2400
attctaggct tcatatacat taagttgagc catatgtaat cactgtgttt gtaggttaga 2460
aacagctgag tatcgtagtt tcatatatgg ttccagctaa tacatgcaat gtggctggtg 2520
aacacttctg aattcagaaa ctatcccaga tctcagctag aaccatccac tgttctgttt 2580
gtccagtttc aacttaaggg atctccatgc ggtccctgga agtacccatt gaaacatgcg 2640
tatttgtgta tagcagaact ctgaaataat attctgacag cagttatctc tgaggaattg 2700
ggttataggt gattttccct ttccgcatga taaatttatg taatatttga ctgacttgac 2760
cgtaagtatg ttacttgtat aataaaagga aaaaaggtac ttctattttg aaaaaataaa 2820
aataaaagcc tttgggttct tgaatggagg atcatggaac acatttgctg ccatatgcag 2880
ttatgttgat gctctgcaaa cctgtgctga gccctgttgc tcaagccctt cctcatctct 2940
tcttgaggga gaaggtggag acttccttaa ggagatgtga catatgggaa gacaacagat 3000
tcagaaattt acgtggatag gactttagac accacccagc ccaaacttcc aaataaaata 3060
tggaacgcaa 3070

<210> SEQ ID NO 61
<211> LENGTH: 2450
<212> TYPE: DNA
<213> ORGANISM: Homo sapiens

<400> SEQUENCE: 61
atatttcata cctttctaga aactgggtgt gatctcactg ttggtaaagc ccagcccttc 60
ccaacctgca agctcacctt ccaggactgg gcccagccca tgctctccat atataagctg 120
ctgccccgag cctgattcct agtcctgctt ctcttccctc tctcctccag cctctcacac 180
tctcctcagc tctctcatct cctggaacca tggccagcac atccaccacc atcaggagcc 240
acagcagcag ccgccggggt ttcagtgcca actcagccag gctccctggg gtcagccgct 300
ctggcttcag cagcgtctcc gtgtcccgct ccaggggcag tggtggcctg ggtggtgcat 360
gtggaggagc tggctttggc agccgcagtc tgtatggcct gggggggctcc aagaggatct 420 ccattggagg gggcagctgt gccatcagtg gcggctatgg cagcagagcc ggaggcagct 480
atggctttgg tggcgccggg agtggatttg gtttcggtgg tggagccggc attggctttg 540
gtctgggtgg tggagccggc cttgctggtg gctttggggg ccctggcttc cctgtgtgcc 600
cccctggagg catccaagag gtcaccgtca accagagtct cctgactccc ctcaacctgc 660
aaatcgatcc caccatccag cgggtgcggg ctgaggagcg tgaacagatc aagaccctca 720
acaacaagtt tgcctccttc atcgacaagg tgcggttcct ggagcagcag aacaaggttc 780
tggaaacaaa gtggaccctg ctgcaggagc agggcaccaa gactgtgagg cagaacctgg 840
agccgttgtt cgagcagtac atcaacaacc tcaggaggca gctggacagc attgtcgggg 900
aacggggccg cctggactca gagctcagag gcatgcagga cctggtggag gacttcaaga 960
acaaatatga ggatgaaatc aacaagcgca cagcagcaga gaatgaattt gtgactctga 1020
agaaggatgt ggatgctgcc tacatgaaca aggttgaact gcaagccaag gcagacactc 1080
tcacagacga gatcaacttc ctgagagcct tgtatgatgc agagctgtcc cagatgcaga 1140
cccacatctc agacacatct gtggtgctgt ccatggacaa caaccgcaac ctggacctgg 1200
acagcatcat cgctgaggtc aaggcccaat atgaggagat tgctcagaga agccgggctg 1260
aggctgagtc ctggtaccag accaagtacg aggagctgca ggtcacagca ggcagacatg 1320
gggacgacct gcgcaacacc aagcaggaga ttgctgagat caaccgcatg atccagaggc 1380
tgagatctga gatcgaccac gtcaagaagc agtgcgccaa cctgcaggcc gccattgctg 1440
atgctgagca gcgtggggag atggccctca aggatgccaa gaacaagctg gaagggctgg 1500
aggatgccct gcagaaggcc aagcaggacc tggcccggct gctgaaggag taccaggagc 1560
tgatgaatgt caagctggcc ctggacgtgg agatcgccac ctaccgcaag ctgctggagg 1620
gtgaggagtg caggctgaat ggcgaaggcg ttggacaagt caacatctct gtggtgcagt 1680
ccaccgtctc cagtggctat ggcggtgcca gtggtgtcgg cagtggctta ggcctgggtg 1740
gaggaagcag ctactcctat ggcagtggtc ttggcgttgg aggtggcttc agttccagca 1800
gtggcagagc cattgggggt ggcctcagct ctgttggagg cggcagttcc accatcaagt 1860
acaccaccac ctcctcctcc agcaggaaga gctataagca ctaaagtgcg tctgctagct 1920
ctcggtccca cagtcctcag gcccctctct ggctgcagag ccctctcctc aggttgcctt 1980
tcctctcctg gcctccagtc tcccctgctg tcccaggtag agctgggtat ggatgcttag 2040
tgccctcact tcttctctct ctctctatac catctgagca cccattgctc accatcagat 2100
caacctctga ttttacatca tgatgtaatc accactggag cttcactgtt actaaattat 2160
taatttcttg cctccagtgt tctatctctg aggctgagca ttataagaaa atgacctctg 2220
ctccttttca ttgcagaaaa ttgccagggg cttatttcag aacaacttcc acttactttc 2280
cactggctct caaactctct aacttataag tgttgtgaac cccccacccag gcagtatcca 2340 tgaaagcaca agtgactagt cctatgatgt acaaagcctg tatctctgtg atgatttctg 2400
tgctcttcgc tgtttgcaat tgctaaataa agcagattta taatacaata 2450

<210> SEQ ID NO 62
<211> LENGTH: 2345
<212> TYPE: DNA
<213> ORGANISM: Homo sapiens

<400> SEQUENCE: 62
cgcctccagc ctccaacgct cgccacagcc ctctcatctc ctggaaccat ggccagcaca 60
tccaccacca tcaggagcca cagcagcagc cgccggggtt tcagtgccaa ctcagccagg 120
ctccctgggg tcagccgctc tggcttcagc agcatctccg tgtcccgctc caggggcagt 180
ggtggcctgg gtggtgcatg tggaggagct ggctttggca gccgcagtct gtatggcctg 240
gggggctcca agaggatctc cattggaggg ggcagctgtg ccatcagtgg cggctatggc 300
agcagagccg gaggcagcta tggctttggt ggcgccggga gtggatttgg tttcggtggt 360
ggagccggca ttggctttgg tctgggtggt ggagccggcc ttgctggtgg ctttgggggc 420
cctggcttcc ctgtgtgccc ccctggaggc atccaagagg tcaccgtcaa ccagagtctc 480
ctgactcccc tcaacctgca aattgacccc gccatccagc gggtgcgggc cgaggagcgt 540
gagcagatca agaccctcaa caacaagttt gcctccttca tcgacaaggt gcggttccta 600
gagcagcaga acaaggttct ggacaccaag tggaccctgc tgcaggagca gggcaccaag 660
actgtgaggc agaacctgga gccgttgttc gagcagtaca tcaacaacct caggaggcag 720
ctggacagca tcgtcgggga acggggccgc ctggactcgg agctgagaaa catgcaggac 780
ctggtggagg acctcaagaa caaatatgag gatgaaatca acaagcgcac agcagcagag 840
aatgaatttg tgactctgaa gaaggatgtg gatgctgcct acatgaacaa ggttgaactg 900
caagccaagg cagacactct cacagatgag atcaacttcc tgagagcctt gtatgatgca 960
gagctgtccc agatgcagac ccacatctca gacacatccg tggtgctatc catggacaac 1020
aaccgcaacc tggacctgga cagcatcatc gctgaggtca aggcccaata cgaggagatt 1080
gctcagagga gccgggctga ggctgagtcc tggtaccaga ccaagtacga ggagctgcag 1140
gtcacagcag gcagacatgg ggacgacctg cgcaacacca agcaggagat tgctgagatc 1200
aaccgcatga tccagaggct gagatctgag atcgaccatg tcaagaagca gtgtgccagc 1260
ctgcaggctg ccattgctga tgctgagcag cgtggggaga tggcactcaa ggatgctaag 1320
aacaagctgg aagggctgga ggatgccctg cagaaggcca agcaggacct ggcccggctg 1380
ctgaaggagt accaggagct gatgaatgtc aagctggccc tggatgtgga gatcgccacc 1440
taccgcaagc tgctggaggg cgaggagtgc aggctgaatg gcgaaggcgt tggacaagtc 1500
aacgtctctg tagtacagtc caccatctcc agtggctatg gcggtgccag cggtgtcggc 1560
agtggcttag gcctgggtgg aggaagcagc tactcctatg gcagtggtct tggcattgga 1620
ggtggcttca gttccagcag tggcagagcc attgggggtg gcctcagctc tgttggaggc 1680
ggcagttcca ccatcaagta caccaccacc tcctcctcca gcaggaagag ctacaagcac 1740
taaagtgctg cctccagctc tcggtcccac agtcctcagg cccttctctg gctgcagagc 1800
cgtctcctca ggttgcctat cctctcctgg cctctagtct tccctgctct ccgaggtaga 1860
gctgggtatg gatgcttagt gccctcactt ctctctgtct atacctgccc catctgagca 1920
cccattgctc accatcagat caacctttga ttttacatca taatgtattc accaatggag 1980
cttcactttg ttactaaatt attaatttct tgcctccaaa attgttctct ctgaggctga 2040
gcattataag aaaatgatct ctgttccttt tcattactga aaatcgcctg gggcttattt 2100
cagaacaact tccacttatt ttccattggc ccccaaactc cctaagttaa aagtattgtg 2160
aacccccgcc ccgcagtatg catggaagca caagtgacta gtcgtatgat gtacacagtc 2220
tttctccctg tgatgatttc tctgctcttt gctctttgta atttctaaat aaagcaggtt 2280
ttagaataaa aaaaaaaaaa aaaaaaaaaa aaaaaaaaaa aaaaaaaaaa aaaaaaaaaa 2340
aaaaa 2345

<210> SEQ ID NO 63
<211> LENGTH: 1753
<212> TYPE: DNA
<213> ORGANISM: Homo sapiens

<400> SEQUENCE: 63
cagccccgcc cctacctgtg gaagcccagc cgcccgctcc cgcggataaa aggcgcggag 60
tgtccccgag gtcagcgagt gcgcgctcct cctcgcccgc cgctaggtcc atcccggccc 120
agccaccatg tccatccact tcagctcccc ggtattcacc tcgcgctcag ccgccttctc 180
gggccgcggc gcccaggtgc gcctgagctc cgctcgcccc ggcggccttg gcagcagcag 240
cctctacggc ctcggcgcct cacggccgcg cgtggccgtg cgctctgcct atgggggccc 300
ggtgggcgcc ggcatccgcg aggtcaccat taaccagagc ctgctggccc cgctgcggct 360

```
ggacgccgac ccctccctcc agcgggtgcg ccaggaggag agcgagcaga tcaagaccct    420

caacaacaag tttgcctcct tcatcgacaa ggtgcggttt ctggagcagc agaacaagct    480

gctggagacc aagtggacgc tgctgcagga gcagaagtcg gccaagagca gccgcctccc    540

agacatcttt gaggcccaga ttgctggcct tcggggtcag cttgaggcac tgcaggtgga    600

tgggggccgc ctggaggcgg agctgcggag catgcaggat gtggtggagg acttcaagaa    660

taagtacgaa gatgaaatta accaccgcac agctgctgag aatgagtttg tggtgctgaa    720

gaaggatgtg gatgctgcct acatgagcaa ggtggagctg gaggccaagg tggatgccct    780

gaatgatgag atcaacttcc tcaggaccct caatgagacg gagttgacag agctgcagtc    840

ccagatctcc gacacatctg tggtgctgtc catggacaac agtcgctccc tggacctgga    900

cggcatcatc gctgaggtca aggcgcagta tgaggagatg gccaaatgca gccgggctga    960

ggctgaagcc tggtaccaga ccaagtttga gaccctccag gcccaggctg ggaagcatgg   1020

ggacgacctc cggaataccc ggaatgagat ttcagagatg aaccgggcca tccagaggct   1080

gcaggctgag atcgacaaca tcaagaacca gcgtgccaag ttggaggccg ccattgccga   1140

ggctgaggag cgtggggagc tggcgctcaa ggatgctcgt gccaagcagg aggagctgga   1200

agccgccctg cagcggggca agcaggatat ggcacggcag ctgcgtgagt accaggaact   1260

catgagcgtg aagctggccc tggacatcga gatcgccacc taccgcaagc tgctggaggg   1320

cgaggagagc cggttggctg gagatggagt gggagccgtg aatatctctg tgatgaattc   1380

cactggtggc agtagcagtg gcggtggcat tgggctgacc ctcgggggaa ccatgggcag   1440

caatgccctg agcttctcca gcagtgcggg tcctgggctc ctgaaggctt attccatccg   1500

gaccgcatcc gccagtcgca ggagtgcccg cgactgagcc gcctcccacc actccactcc   1560

tccagccacc acccacaatc acaagaagat tcccacccct gcctcccatg cctggtccca   1620

agacagtgag acagtctgga aagtgatgtc agaatagctt ccaataaagc agcctcattc   1680

tgaggcctga gtgatccacg tgaaaaaaaa aaaaaaaaaa aaaaaaaaaa aaaaaaaaaa   1740

aaaaaaaaaa aaa                                                      1753
```

<210> SEQ ID NO 64
<211> LENGTH: 1861
<212> TYPE: DNA
<213> ORGANISM: Homo sapiens

<400> SEQUENCE: 64

```
cactcaaggt gtgcaggcag ctgtgtttgt caggaaggca gaaggagttg gctttgcttt     60

aggggaggag acgaggtccc acaacaccct ctgaagggta tataaggagc cccagcgtgc    120

agcctggcct ggtacctcct gccagcatct cttgggtttg ctgagaactc acgggctcca    180

gctacctggc catgaccacc acatttctgc aaacttcttc ctccaccttt gggggtggct    240

caacccgagg gggttccctc ctggctgggg gaggtggctt tggtgggggg agtctctctg    300

ggggaggtgg aagccgaagt atctcagctt cttctgctag gtttgtctct tcagggtcag    360

gaggaggata tgggggtggc atgagggtct gtggctttgg tggaggggct ggtagtgttt    420

tcggtggagg ctttggaggg ggcgttggtg ggggttttgg tggtggcttt ggtggtggcg    480

atggtggtct cctctctggc aatgagaaaa ttaccatgca gaacctcaat gaccgcctgg    540

cctcctacct ggacaaggta cgtgccctgg aggaggccaa tgctgacctg gaggtgaaga    600

tccatgactg gtaccagaag cagaccccaa ccagcccaga atgcgactac agccaatact    660

tcaagaccat tgaagagctc cgggacaaga tcatggccac caccatcgac aactcccggg    720
```

tcatcctgga gatcgacaat gccaggctgg ctgcggacga cttcaggctc aagtatgaga 780
atgagctggc cctgcgccag ggcgttgagg ctgacatcaa cggcttgcgc cgagtcctgg 840
atgagctgac cctggccagg actgacctgg agatgcagat cgagggcctg aatgaggagc 900
tagcctacct gaagaagaac cacgaagagg agatgaagga gttcagcagc cagctggccg 960
gccaggtcaa tgtggagatg gacgcagcac cgggtgtgga cctgacccgt gtgctggcag 1020
agatgaggga gcagtacgag gccatggcgg agaagaaccg ccgggatgtc gaggcctggt 1080
tcttcagcaa gactgaggag ctgaacaaag aggtggcctc caacacagaa atgatccaga 1140
ccagcaagac ggagatcaca gacctgagac gcacgatgca ggagctggag atcgagctgc 1200
agtcccagct cagcatgaaa gctgggctgg agaactcact ggccgagaca gagtgccgct 1260
atgccacgca gctgcagcag atccaggggc tcattggtgg cctggaggcc cagctgagtg 1320
agctccgatg cgagatggag gctcagaacc aggagtacaa gatgctgctt gacataaaga 1380
cacggctgga gcaggagatc gctacttacc gcagcctgct cgagggccag gatgccaaga 1440
tggctggcat tggcatcagg gaagcctctt caggaggtgg tggtagcagc agcaatttcc 1500
acatcaatgt agaagagtca gtggatggac aggtggtttc ttcccacaag agagaaatct 1560
aagtgtctat tgcaggagaa acgtcccttg ccactcccca ctctcatcag gccaagtgga 1620
ggactggcca gagggcctgc acatgcaaac tccagtccct gccttcagag agctgaaaag 1680
ggtccctcgg tcttttattt cagggctttg catgcgctct attcccccctc tgcctctccc 1740 caccttcttt ggagcaagga gatgcagctg tattgtgtaa caagctcatt tgtacagtgt 1800
ctgttcatgt aataaagaat tacttttcct tttgcaaata aaaaaaaaaa aaaaaaaaaa 1860
a 1861

<210> SEQ ID NO 65
<211> LENGTH: 1720
<212> TYPE: DNA
<213> ORGANISM: Homo sapiens

<400> SEQUENCE: 65
agttaggagg gccccgcctt ccccagctgc atataaaggt ctctggggtt ggaggcagcc 60
acagcacgct ctcagccttc ctgagcacct ttccttcttt cagccaactg ctcactcgct 120
cacctccctc cttggcacca tgaccacctg cagccgccag ttcacctcct ccagctccat 180
gaagggctcc tgcggcatcg gaggcggcat cgggggcggc tccagccgca tctcctccgt 240
cctggccgga gggtcctgcc gtgcccccag cacctacggg ggcggcctgt ctgtctcctc 300
tcgcttctcc tctgggggag cctgcgggct gggggggcggc tatggcggtg gcttcagcag 360
cagcagcagc tttggtagtg gcttcggggg aggatatggt ggtggccttg gtgctggctt 420
cggtggtggc ttgggtgctg gctttggtgg tggttttgct ggtggtgatg ggcttctggt 480
gggcagtgag aaggtgacca tgcagaacct caatgaccgc ctggcctcct acctggacaa 540
ggtgcgtgct ctggaggagg ccaacgccga cctggaagtg aagatccgtg actggtacca 600
gaggcagcgg cccagtgaga tcaaagacta cagtccctac ttcaagacca tcgaggacct 660
gaggaacaag atcattgcgg ccaccattga gaatgcgcag cccattttgc agattgacaa 720
tgccaggctg gcagccgatg acttcaggac caagtatgag catgaactgg ccctgcggca 780
gactgtggag gccgacgtca atggcctgcg ccgggtgttg gatgagctga ccctggccag 840
gactgacctg gagatgcaga tcgaaggcct gaaggaggag ctggcctacc tgaggaagaa 900

-continued

```
ccacgaggag gagatgcttg ctctgagagg tcagaccggc ggagatgtga acgtggagat    960

ggatgctgca cctggcgtgg acctgagccg catcctgaat gagatgcgtg accagtacga   1020

gcagatggca gagaaaaacc gcagagacgc tgagacctgg ttcctgagca agaccgagga   1080

gctgaacaaa gaagtggcct ccaacagcga actggtacag agcagccgca gtgaggtgac   1140

ggagctccgg agggtgctcc agggcctgga gattgagctg cagtcccagc tcagcatgaa   1200

agcatccctg gagaacagcc tggaggagac caaaggccgc tactgcatgc agctgtccca   1260

gatccaggga ctgattggca gtgtggagga gcagctggcc cagctacgct gtgagatgga   1320

gcagcagagc caggagtacc agatcttgct ggatgtgaag acgcggctgg agcaggagat   1380

tgccacctac cgccgcctgc tggagggcga ggatgcccac ctttcctccc agcaagcatc   1440

tggccaatcc tattcttccc gcgaggtctt cacctcctcc tcgtcctctt cgagccgtca   1500

gacccggccc atcctcaagg agcagagctc atccagcttc agccagggcc agagctccta   1560

gaactgagct gcctctacca cagcctcctg cccaccagct ggcctcacct cctgaaggcc   1620

cgggtcagga ccctgctctc ctggcgcagt tcccagctat ctcccctgct cctctgctgg   1680

tggtgggcta ataaagctga ctttctggtt gatgcaaaaa                         1720
```

```
<210> SEQ ID NO 66
<211> LENGTH: 1574
<212> TYPE: DNA
<213> ORGANISM: Homo sapiens

<400> SEQUENCE: 66

atcgctacgc ccacttggtg gcctataaag gaagcgggcg aaccccggca gccctacaca     60

acttggggcc cctctcctct ccagcccttc tcctgtgtgc ctgcctcctg ccgccgccac    120

catgaccacc tccatccgcc agttcacctc ctccagctcc atcaagggct cctccggcct    180

ggggggcggc tcgtcccgca cctcctgccg gctgtctggc ggcctgggtg ccggctcctg    240

caggctggga tctgctggcg gcctgggcag caccctcggg ggtagcagct actccagctg    300

ctacagcttt ggctctggtg gtggctatgg cagcagcttt gggggtgttg atgggctgct    360

ggctggaggt gagaaggcca ccatgcagaa cctcaatgac cgcctggcct cctacctgga    420

caaggtgcgt gccctggagg aggccaacac tgagctggag gtgaagatcc gtgactggta    480

ccagaggcag gccccggggc ccgcccgtga ctacagccag tactacagga caattgagga    540

gctgcagaac aagatcctca cagccaccgt ggacaatgcc aacatcctgc tacagattga    600

caatgcccgt ctggctgctg atgacttccg caccaagttt gagacagagc aggccctgcg    660

cctgagtgtg gaggccgaca tcaatggcct gcgcagggtg ctggatgagc tgaccctggc    720

cagagccgac ctggagatgc agattgagaa cctcaaggag gagctggcct acctgaagaa    780

gaaccacgag gaggagatga acgccctgcg aggccaggtg ggtggtgaga tcaatgtgga    840

gatggacgct gccccaggcg tggacctgag ccgcatcctc aacgagatgc gtgaccagta    900

tgagaagatg gcagagaaga accgcaagga tgccgaggat tggttcttca gcaagacaga    960

ggaactgaac cgcgaggtgg ccaccaacag tgagctggtg cagagtggca agagtgagat   1020

ctcggagctc cggcgcacca tgcaggcctt ggagatagag ctgcagtccc agctcagcat   1080

gaaagcatcc ctggagggca acctggcgga gacagagaac cgctactgcg tgcagctgtc   1140

ccagatccag gggctgattg gcagcgtgga ggagcagctg gcccagcttc gctgcgagat   1200

ggagcagcag aaccaggaat acaaaatcct gctggatgtg aagacgcggc tggagcagga   1260

gattgccacc taccgccgcc tgctggaggg agaggatgcc cacctgactc agtacaagaa   1320
```

agaaccggtg accacccgtc aggtgcgtac cattgtggaa gaggtccagg atggcaaggt 1380
catctcctcc cgcgagcagg tccaccagac cacccgctga ggactcagct accccggccg 1440
gccacccagg aggcagggag gcagccgccc catctgcccc acagtctccg gcctctccag 1500
cctcagcccc ctgcttcagt cccttcccca tgcttccttg cctgatgaca ataaagcttg 1560
ttgactcagc tatg 1574

<210> SEQ ID NO 67
<211> LENGTH: 1805
<212> TYPE: DNA
<213> ORGANISM: Homo sapiens

<400> SEQUENCE: 67
gagacacact ctgccccaac catcctgaag ctacaggtgc tccctcctgg aatctccaat 60
ggatttcagt cgcagaagct tccacagaag cctgagctcc tccttgcagg cccctgtagt 120
cagtacagtg ggcatgcagc gcctcgggac gacacccagc gtttatgggg gtgctggagg 180
ccggggcatc cgcatctcca actccagaca cacggtgaac tatgggagcg atctcacagg 240
cggcggggac ctgtttgttg gcaatgagaa aatggccatg cagaacctaa atgaccgtct 300
agcgagctac ctagaaaagg tgcggaccct ggagcagtcc aactccaaac ttgaagtgca 360
aatcaagcag tggtacgaaa ccaacgcccc gagggctggt cgcgactaca gtgcatatta 420
cagacaaatt gaagagctgc gaagtcagat taaggatgct caactgcaaa atgctcggtg 480
tgtcctgcaa attgataatg ctaaactggc tgctgaggac ttcagactga agtatgagac 540
tgagagagga atacgtctaa cagtggaagc tgatctccaa ggcctgaata aggtctttga 600
tgacctaacc ctacataaaa cagatttgga gattcaaatt gaagaactga ataaagacct 660
agctctcctc aaaaaggagc atcaggagga agtcgatggc ctacacaagc atctgggcaa 720
cactgtcaat gtggaggttg atgctgctcc aggcctgaac cttggcgtca tcatgaatga 780
aatgaggcag aagtatgaag tcatggccca gaagaacctt caagaggcca aagaacagtt 840
tgagagacag actgcagttc tgcagcaaca ggtcacagtg aatactgaag aattaaaagg 900
aactgaggtt caactaacgg agctgagacg cacctcccag agccttgaga tagaactcca 960
gtcccatctc agcatgaaag agtctttgga gcacactcta gaggagacca aggcccgtta 1020
cagcagccag ttagccaacc tccagtcgct gttgagctct ctggaggccc aactgatgca 1080
gattcggagt aacatggaac gccagaacaa cgaataccat atccttcttg acataaagac 1140
tcgacttgaa caggaaattg ctacttaccg ccgccttctg gaaggagaag acgtaaaaac 1200
tacagaatat cagttaagca ccctggaaga gagagatata aagaaaacca ggaagattaa 1260
gacagtcgtg caagaagtag tggatggcaa ggtcgtgtca tctgaagtca aagaggtgga 1320
agaaaatatc taaatagcta ccagaaggag atgctgctga ggttttgaaa gaaatttggc 1380
tataatctta tctttgctcc ctgcaagaaa tcagccataa gaaagcacta ttaatactct 1440
gcagtgatta gaaggggtgg ggtggcggga atcctattta tcagactctg taattgaata 1500
taaatgtttt actcagagga gctgcaaatt gcctgcaaaa atgaaatcca gtgagcacta 1560
gaatatttaa aacatcatta ctgccatctt tatcatgaag cacatcaatt acaagctgta 1620
gaccacctaa tatcaatttg taggtaatgt tcctgaaaat tgcaatacat ttcaattata 1680
ctaaacctca caaagtagag gaatccatgt aaattgcaaa taaaccactt tctaattttt 1740
tcctgtttct gaattgtaaa accccctttg ggagtccctg gtttcttatt gagccaattt 1800
ctggg 1805

<210> SEQ ID NO 68
<211> LENGTH: 967
<212> TYPE: DNA
<213> ORGANISM: Homo sapiens

<400> SEQUENCE: 68
aaaaagggac tggttgctag tggaaacctc agagtgaaac tcacccagct ttagtaacca 60
actcgattgc atagacttta gataaccatg tgaaggggat tctaccatca gaaaagaggc 120
caaacttcta tcatcatggt ggatgtgaag tgtctgagtg actgtaaatt gcagaaccaa 180
cttgagaagc ttggattttc acctggccca atactacctt ccaccagaaa gttgtatgaa 240
aaaaagttag tacagttgtt ggtctcacct ccctgtgcac cacctgtgat gaatggaccc 300
agagagctgg atggagcgca ggacagtgat gacagcgaag agcttaatat cattttgcaa 360
ggaaatatca tactctcaac agaaaaaagc aagaaactca aaaaatggcc tgaggcttcc 420
accactaaac gcaaagctgt agatacctat tgcttggatt ataagccttc caagggaaga 480
aggtgggctg caagagcacc aagcaccaga atcacatatg ggactatcac caaagagaga 540
gactactgcg cggaagacca gactatcgag agctggagag aagaaggttt cccagtgggc 600
ttgaagcttg ctgtgcttgg tattttcatc attgtggtgt ttgtctacct gactgtggaa 660
aataagtcgc tgtttggtta agtaatttag gagcaaagca atgctccaag cgaggcctcc 720
tgcttcagga aagaaccaaa acactaccct gaagggccag cctagcctgc agccctccct 780
tgcagggagc cttcccttgc actgtgctgc tctcacagat cggtgtctgg gctcagccag 840
gtggaaggaa cctgcctaac caggcacctg tgttaagagc atgatggtta ggaaatcccc 900
caagtcatgt caactctcat taaaggtgct tccatatttg agcaggcgtc aaacaaggaa 960
aaaaaaa 967

<210> SEQ ID NO 69
<211> LENGTH: 1291
<212> TYPE: DNA
<213> ORGANISM: Homo sapiens

<400> SEQUENCE: 69
tggtcaccag ggaagctggc aagggaaggg agactagggt gcgctctagg agaagccgac 60
agcctgagag tcccagaaga ggagccctgt ggaccctccc ctgccagcca ctcccttacc 120
ctgggtataa gagccaccac cgcctgccat ccgccaccat ctcccactcc tgcagctctt 180
ctcacaggac cagccactag cgcagcctcg agcgatggcc tatgtccccg caccgggcta 240
ccagcccacc tacaacccga cgctgcctta ctaccagccc atcccgggcg ggctcaacgt 300
gggaatgtct gtttacatcc aaggagtggc cagcgagcac atgaagcggt tcttcgtgaa 360
ctttgtggtt gggcaggatc cgggctcaga cgtcgccttc cacttcaatc cgcggtttga 420
cggctgggac aaggtggtct tcaacacgtt gcagggcggg aagtggggca gcgaggagag 480
gaagaggagc atgcccttca aaaagggtgc cgcctttgag ctggtcttca tagtcctggc 540
tgagcactac aaggtggtgg taaatggaaa tcccttctat gagtacgggc accggcttcc 600
cctacagatg gtcacccacc tgcaagtgga tggggatctg caacttcaat caatcaactt 660
catcggaggc cagcccctcc ggccccaggg acccccgatg atgccacctt accctggtcc 720
cggacattgc catcaacagc tgaacagcct gcccaccatg gaaggacccc caaccttcaa 780
cccgcctgtg ccatatttcg ggaggctgca aggagggctc acagctcgaa gaaccatcat 840

```
catcaagggc tatgtgcctc ccacaggcaa gagctttgct atcaacttca aggtgggctc    900

ctcaggggac atagctctgc acattaatcc ccgcatgggc aacggtaccg tggtccggaa    960

cagccttctg aatggctcgt ggggatccga ggagaagaag atcacccaca acccatttgg   1020

tcccggacag ttctttgatc tgtccattcg ctgtggcttg gatcgcttca aggtttacgc   1080

caatggccag cacctctttg actttgccca tcgcctctcg gccttccaga gggtggacac   1140

attggaaatc cagggtgatg tcaccttgtc ctatgtccag atctaatcta ttcctggggc   1200

cataactcat gggaaaacag aattatcccc taggactcct ttctaagccc ctaataaaat   1260

gtctgagggt gtctcatgaa aaaaaaaaaa a                                  1291
```

<210> SEQ ID NO 70
<211> LENGTH: 3967
<212> TYPE: DNA
<213> ORGANISM: Homo sapiens

<400> SEQUENCE: 70

```
agttgtcggg tcttattggc cgctgattag accagccggg gtccactagc cctgggctgc     60

agggaggctg ctgcgtccag tgaacacttc agcacctgta gcacagaagg gccaaggagc    120

tgcagtcctc gaccagcagg aggtttgctc ctcagcccac tcgctgcatc cagatcagct    180

cacccctctc ccttccctgc ccaccaggac tctgatagcc cctggcagcc acagcccatt    240

ttgccaagat gtctagagta gccaaatatc gccggcaggt gagtgaagac cccgacatcg    300

acagcctgct ggagaccctg tctcccgagg agatggagga gctggagaag gagctggacg    360

tggtggaccc agacgggagt gttcccgtgg ggctgcggca gagaaaccag acggagaaac    420

agtccacggg tgtgtacaac cgggaggcca tgctcaactt ctgtgaaaag gagaccaaga    480

aacttatgca gagggagatg tccatggatg aaagcaagca agtggagacc aagacagatg    540

ccaagaatgg agaggaaagg ggcagagatg ccagcaaaaa agccctgggc cccagacggg    600

actcagatct ggggaaggag ccaaagaggg gtggtttaaa gaaaagcttc tctagagaca    660

gagatgaagc tggtggcaag agtggcgaga agcccaagga ggagaagatc atccggggca    720

ttgacaaggg ccgggtcagg gctgcagtgg ataagaagga ggcagggaag gatgggagag    780

gagaggagag ggcagtggcc accaagaagg aagaggagaa gaaagggagt gacaggaaca    840

caggcttgag cagggacaag gataaaaaga gagaggagat gaaggaggtg gccaagaaag    900

aggatgatga gaaggtaaaa ggggagcgta ggaacacaga caccagaaaa gagggtgaga    960

agatgaaaag agcaggtggg aacacagaca tgaaaaagga ggatgagaag gtaaaaagag   1020

gaactgggaa cacagacacc aaaaaggacg atgaaaaagt caagaagaat gaacccttac   1080

atgaaaagga agccaaggat gacagcaaga ccaaaacacc cgagaaacag acgcccagtg   1140

gccccaccaa gccctctgaa ggaccggcca aggtggagga ggaggcagct cccagcatat   1200

ttgatgagcc tctggagaga gtgaagaaca atgaccccga gatgactgag gtgaacgtca   1260

acaactcaga ctgcatcaca aatgagatct tggtccggtt tactgaggct ctggagttca   1320

acactgtggt taagctgttc gccttggcca acacgcgagc cgatgaccac gtggcctttg   1380

ccattgccat catgctcaag gccaacaaga ccatcaccag cctcaacctg gactccaacc   1440

acatcacagg caaaggcatc ctggccatct tccgggccct cctccagaac aacacgctga   1500

ccgagctccg cttccacaac cagcgacaca tctgtggagg caagacggag atggagatcg   1560

ccaagctgct gaaggagaat actaccctgc tcaagctggg ctaccatttt gagctggccg   1620
```

```
ggccccgaat gactgtcacc aatctgctca gccgcaacat ggacaagcag agacaaaagc   1680
ggctgcagga gcaaaggcag gcacaggaag ccaagggaga gaagaaggat ctgctggagg   1740
tacccaaggc cggggccgtg gctaagggct ccccaaaacc ttcacctcaa ccatctccaa   1800
agccctctcc aaagaactca cccaaaaaag gggtgctcc agctgcccca ccaccccctc   1860
cccctccctt ggctccaccc cttatcatgg agaacctgaa gaattcactc tcaccagcta   1920
cccagaggaa gatgggagac aaagtcctcc ctgcccagga gaagaactcc cgtgaccagc   1980
tattggctgc catccgctcc agcaacctca agcagctcaa gaaggtggaa gtgcccaaac   2040
tgcttcagta ggaccaggct gccaggcacc atctgccaat gccatgactg ctcaggcctc   2100
acctcccagg gctacacaga ccctgcccac cccatccctg gctgacctgc tgtggatgtc   2160
cctattctgc catgggagag tccaggcctg ggtcacgctc aaggaaggat gccttatctc   2220
ttctcacttt ccttttcttg tctctgaggc tctccaaatt ttgctttagt acatggagct   2280
caggtttctg gacaagaaga gtccttttag cacatcactg agaagatggc actgtccagg   2340
gcccatgtag ctggcaagct gcaaaaggcc tgtgatccag gaaagatgtc ccacagggac   2400
cacatccacc ccagccccac tgccctccag ggccaggatt caggcctctg aggagcccac   2460
ggggcaaagc tgctgggcca gtggcactct gtgtgggaaa atggcagaaa gatggagagg   2520
catgggggcc caaaggggag cgtggggagg ggctgaggat accccaaagt ccaggctaat   2580
tagaggatgt ggcaggggca gtggcctgga tgcacagtgc ctgatgggag taggctccag   2640
acaggaggag tgggacagac agcagctgga cttgaaggtt tgatgccaaa gcagacattt   2700
tcctcacacc cacctgctgc tgtatgaata gctgtgtatc tgtttttcca taagattttg   2760
ataatatata caaacettta gctgtgaatg gctgtgcccc acctgttgtc ctgaactgtg   2820
agtcctgatc ctaaccctgg gctccctgga ggactctaga agctcaggtt ccctgccaca   2880
ctatttgagt tggccaagaa ataaattcac atcctcagaa agtgcagcat ggaggaaaat   2940
ctgaactcta agcagaagac tctccactga cctggttgtc caggtctaga aggccaggcc   3000
tctactaggt ctgctcctga accagtcctg ctgcctggag tcagtagcca gagttgttct   3060
caggggtgct ggggcagagt ggagcccagg gtgctgggat ggctatatta ggcatgttca   3120
gggatgctca ttccatgact ctgcctaacc atgggctcag ggccaggtcc tcacagcagt   3180
cacaggccca ggaaggcggc aggcagagaa gtggagtgac tatttggaga atagcaccca   3240
tatctgtgtg ccctagggct cagaggggcc tcatcttccc cagccctccc cacctgctca   3300
ccaattccac ttcctgcccc aactgcagga atgctgacaa tgctgccatg cccaccatcg   3360
ggtgtaggtg aaaggcatct ttctgaattt cattctcttg aaggtgctgc caccccttgg   3420
cactgtggaa ctgccacctt gggtctgtgt cacttgtagg tttctctgcc tccaggttgc   3480
ctcaacagca ggaggcacag cagtttcacc atctttgagg tgagggtggg gtgccccagc   3540
taggaagcaa gatcgctgtg ctaggtctga ccaaaaccag agggcagtct agtcctgggg   3600
gtaaagccct cagatcccag ggtacactct tctccattcc ctccacccac ttgcctgtca   3660
ccccagtcac ctaagcaatc actgggccca gaggagagga gacagacaca cactggctcc   3720
tggacctaaa gggtatgagc tggagctaag gccagctaga gcttccactg tcagccctca   3780
ctgtcagtcc cactgcaccc ccctgtgcct gctgggcact gggcactagc tagatgcttt   3840
aggttgcttc agctgatcct tcaactctgt gaggtggata ccaatattct attttgcaga   3900
tagaatttgg cccagagagg ttaactaata tatccatgat cacacagcta ataaaagtca   3960
gagctca                                                             3967
```

<210> SEQ ID NO 71
<211> LENGTH: 1121
<212> TYPE: DNA
<213> ORGANISM: Homo sapiens

<400> SEQUENCE: 71
tgtgaacctg gggctcttgg gcagcaacac gttgcagctt ccacctagca agccacgccg 60
ggaccaggtc ccatctgatg gaggagaatc aattcaagga gatgcccttc ctttacagaa 120 cacccttttaa cagcatccag gaggaacgag aggctgcaat actgaggctt tcaaagtact 180
cacgaggatg tccgagaatg gctgtgatgc caggcttctg gcaggttcca gactccatca 240
caagcccagc atccctgcac cagatctgac atcgctgctg ttgtgccagc tgtttatgaa 300
gggcctgagt agctagcagg tttttatcag gagccctgct gggggcttag acaccaaaag 360
agaagtctca tcctctgtag ttcttcttgt gaatgtcctt ttagaaaaac aattagaacc 420
aaccacaagc accaaagtcc taatgggatc tcctgcgagc acatatcaag caggattgtt 480
gctatttctc ctcactggct ctttggacag actgtgtgag ctcctggagg gttccactgt 540
atctaccctt tgacactgac cagttggcac atggtgactt attccaatgt gttgattgaa 600
aatgtgaacg tacagccagt gctgtgtgcg ggaggactct ctcctcctca gtggggccac 660
accgtgcact attaatggag ccccactcct ttgcacagcc tggccatgca gtggctcata 720
ttgaggtttt agccaactga aatctcccgt gcatttttct gacaagccag ctaggcctct 780
gctatgctgt ccttgtgtct ttcatttgat gaccttaagg gtgggactgt tttatcttaa 840
gttacaggtg gtcaagtcca gcccaaggac agcaactctg agggtcaagc ctcataggct 900
aactggatag atgttctctg ctttgccacc cactggagcc cgacctgccc cactaattta 960
tatttcccct ggtctcattt tgtacttttt atttataatt caccccttaaa gtgtatgtgt 1020 ctcttataag ctgcctccga tctttcatgg tatgaggtgg ttacctaaat aaagaaggag 1080
atttggcctt tgtttttatg taaaaaaaaa aaaaaaaaaa a 1121

<210> SEQ ID NO 72
<211> LENGTH: 6141
<212> TYPE: DNA
<213> ORGANISM: Homo sapiens

<400> SEQUENCE: 72
gtttcagatt tgggatattg gtgtttctgt tttggagaaa ttattctttt tctttttaat 60
ttgaagaaaa atcatcagtc ttggaataca gaagagaaac tagaaatata cgtattttgt 120
ttcacatttg aacagtcatt cttgaggaat actccatacc tgagtagaca gccatgtggc 180
catcgcagct actaattttc atgatgctct tagctccaat aattcatgct ttcagccgtg 240
ccccaattcc aatggctgtg gtccgcagag agctatcctg tgagagctat cctatagagc 300
ttcgctgtcc aggaacagac gtcatcatga tagaaagtgc caactatggc aggactgatg 360
acaaaatttg tgactctgac cctgctcaga tggagaatat ccgatgttat ctgccagatg 420
cctataagat tatgtctcaa agatgcaata acagaaccca gtgtgcagtg gtggcaggtc 480
ctgatgtttt tccagacccg tgtccaggaa cctataaata ccttgaagtg cagtatgaat 540
gtgtccctta caaagtggaa caaaaagttt ttctttgtcc tggactacta aaaggagtat 600
accagagtga acatttgttt gagtccgacc accaatctgg ggcgtggtgc aaagaccctc 660
tgcaggcatc tgacaagatt tattatatgc cctggactcc ctacagaact gataccctga 720

-continued

```
ctgagtattc atccaaggat gacttcattg ctggaagacc aactacaacc tacaagctcc    780
ctcacagggt ggatggcaca ggatttgtag tgtatgatgg agctttgttc ttcaacaaag    840
agcgcaccag gaacatagta aagtttgatt tgcggactag gataaagagt ggagaggcta    900
tcatagcaaa tgccaattac catgatacct ccccttaccg atggggaggc aaatctgaca    960
tagacctggc agtagatgag aatgggctat gggtaatcta tgcaacagaa caaaacaatg   1020
gtaaaattgt cattagtcaa ttgaaccctt acaccctacg gatcgaagga acatgggata   1080
ctgcatatga taaaaggtca gcttccaatg cctttatgat ttgtggaatt ctgtatgtgg   1140
tcaaatctgt atatgaggat gatgacaatg aggctactgg aaataagatt gactacattt   1200
acaacactga ccaaagcaag gatagtttgg tggatgtacc ctttcctaat tcataccagt   1260
acattgcagc tgtggattac aaccccaggg acaacctact ttatgtatgg aataactatc   1320
acgtcgtgaa atattctttg gattttggac ctctggatag tagatcaggg caggcacatc   1380
atggacaagt ttcatacatt tctccgccaa ttcaccttga ctctgagcta gaaagaccct   1440
ctgttaaaga tatctctacc acaggacctc ttggcatggg aagcactacc accagtacca   1500
cccttcggac cacaactttg agcccaggaa ggagtaccac cccgtcagtg tcaggaagaa   1560
gaaaccggag tactagtacc ccatctccag ctgtcgaggt acttgatgac atgaccacac   1620
accttccatc agcatcgtcc caaatcccag ctctcgaaga gagctgtgag gctgtggaag   1680
cccgagaaat catgtggttt aagactcgtc aaggacagat agcaaagcag ccatgccctg   1740
caggaactat aggtgtatca acttatctat gccttgctcc tgatggaatt tgggatcccc   1800
aaggtccaga tctcagcaac tgttcttctc cttgggtcaa tcatataaca cagaagttga   1860
aatctggtga aacagctgcc aacattgcta gagagctggc tgaacagaca agaaatcact   1920
tgaatgctgg ggacatcacc tactctgtcc gggccatgga ccagctggta ggcctcctag   1980
atgtacagct tcggaacttg accccaggtg gaaaagatag tgctgcccgg agtttgaaca   2040
agcttcagaa aagagagcgc tcttgcagag cctatgtcca ggcaatggtc gagacagtta   2100
acaacctcct tcagccacaa gctttgaatg catggagaga cctgactacg agtgatcagc   2160
tgcgtgcggc caccatgttg cttcatactg tggaggaaag tgcttttgtg ctggctgata   2220
accttttgaa gactgacatt gtcagggaga atacagacaa tattaaattg gaagttgcaa   2280
gactgagcac agaaggaaac ttagaagacc taaaatttcc agaaaacatg ggccatggaa   2340
gcactatcca gctgtctgca aataccttaa agcaaaatgg ccgaaatgga gagatcagag   2400
tggcctttgt cctgtataac aacttgggtc cttatttatc cacggagaat gccagtatga   2460
agttgggaac ggaagctttg tccacaaatc attctgttat tgtcaattcc cctgttatta   2520
cggcagcaat aaacaaagag ttcagtaaca aggtttattt ggctgatcct gtggtattta   2580
ctgttaaaca tatcaagcag tcagaggaaa atttcaaccc taactgttca ttttggagct   2640
actccaagcg tacaatgaca ggttattggt caacacaagg ctgtcggctc ctgacaacaa   2700
ataagacaca tactacatgc tcttgtaacc acctaacaaa ttttgcagta ctgatggcac   2760
atgtggaagt taagcacagt gatgcggtcc atgacctcct tctggatgtg atcacgtggg   2820
ttggaatttt gctgtccctt gtttgtctcc tgatttgcat cttcacattt tgcttttttcc   2880
gggggctcca gagtgaccgt aacaccatcc acaagaacct ctgcatcagt ctctttgtag   2940
cagagctgct cttcctgatt gggatcaacc gaactgacca accaattgcc tgtgctgttt   3000
tcgctgccct gttacatttc ttcttcttgg ctgccttcac ctggatgttc ctggaggggg   3060
tgcagcttta tatcatgctg gtggaggttt ttgagagtga acattcacgt aggaaatact   3120
```

```
tttatctggt cggctatggg atgcctgcac tcattgtggc tgtgtcagct gcagtagact   3180
acaggagtta tggaacagat aaagtatgtt ggctccgact tgacacctac ttcatttgga   3240
gttttatagg accagcaact ttgataatta tgcttaatgt aatcttcctt gggattgctt   3300
tatataaaat gtttcatcat actgctatac tgaaacctga atcaggctgt cttgataaca   3360
tcaactatga ggataacaga cccttcatca agtcatgggt tataggtgca atagctcttc   3420
tctgcctatt aggattgacc tgggcctttg gactcatgta tattaatgaa agcacagtca   3480
tcatggccta tctcttcacc attttcaatt ctctacaggg aatgtttata tttattttcc   3540
attgtgtcct acagaagaag gtacgaaaag agtatgggaa atgcctgcga acacattgct   3600
gtagtggcaa aagtacagag agttccattg gttcagggaa aacatctggt tctcgaactc   3660
ctggacgcta ctccacaggc tcacagagcc gaatccgtag aatgtggaat gacacggttc   3720
gaaagcagtc agagtcttcc tttattactg gagacataaa cagttcagcg tcactcaaca   3780
gagaggggct tctgaacaat gccagggata caagtgtcat ggatactcta ccactgaatg   3840
gtaaccatgg caatagttac agcattgcca gcggcgaata cctgagcaac tgtgtgcaaa   3900
tcatagaccg tggctataac cataacgaga ccgccctaga gaaaaagatt ctgaaggaac   3960
tcacttccaa ctatatccct tcttacctga acaaccatga gcgctccagt gaacagaaca   4020
ggaatctgat gaacaagctg gtgaataacc ttggcagtgg aagggaagat gatgccattg   4080
tcctggatga tgccacctcg tttaaccacg aggagagttt gggcctggaa ctcattcatg   4140
aggaatctga tgctcctttg ctgcccccaa gagtatactc caccgagaac caccagccac   4200
accattatac cagaaggcgg atcccccaag accacagtga gagctttttc cctttgctaa   4260
ccaacgagca cacagaagat ctccagtcac cccatagaga ctctctctat accagcatgc   4320
cgacactggc tggtgtggcc gccacagaga gtgttaccac cagcacccag accgaacccc   4380
caccggccaa atgtggtgat gccgaagatg tttactacaa aagcatgcca aacctaggct   4440
ccagaaacca cgtccatcag ctgcatactt actaccagct aggtcgcggc agcagtgatg   4500
gatttatagt tcctccaaac aaagatggga cccctcccga gggaagttca aaaggaccgg   4560
ctcatttggt cactagtcta tagaagatga cacagaaatt ggaaccaaca aaactgctaa   4620
caccttgttg actgttctga gttgatataa gcagtggtaa taatgtgtgt actcctaaat   4680
ctttatgctg tcctctaaag acaaacacaa actctcagac tttttttttt ttaatgggat   4740
ttttaggtca gcccagggga gaaagataac tgctaaaatt cccctgtacc ccatcctttc   4800
ttgtcctttc cccttcagat ggagacttca ttatgttaat gaacaagata tgaagaaaat   4860
ggcactcatt gtggccttgt tgaattatgt tgtgtatgtt ttaacatctc tgatgctgtg   4920
ttactaaaat tacaaggacc tgctttttaa aaggccagaa caattgtctg aaattagtaa   4980
caatgctgca tctagattgg agtgctgcac aaacaaacat aagagcaaag caaaactgta   5040
tcacataggg tttttggtca ctcacaacct gaattcacca cagctggaat agctgtggaa   5100
aacaaaataa aacaacaaaa ttaataatga aatggagggg aattctagaa ttatatgcta   5160
aatgcatatt ttatgatttg ctgtattaac tgatgataaa actaatggca gaaaaagaag   5220
ttgagcaatt tctatgtaat gtacagatac tagcattgca catatagtct gctttctgtt   5280
cctccagaat ttgagtcctg ttaatgtagt agaaaaaaaa aaaagaaatt ttcttttttct   5340
tttgtgctgg tcttgcaagt ttgtctacca gtaagagagc aaagtttcct tcctttcttc   5400
tctttcttca ttttcttttt ttctttttttg ccttttattc ctttaaaatt tcgcctggca   5460
```

```
aaaaataaat aaatggaact atcactttat aagaatcatt ttctagtaat gcaaacaaat   5520

tattttttac aaaaaaacaa aataaataaa attagacttc cttccctcac tatatatctt   5580

tatgcagtca gaatatttcc aacagtgttt tttgcaaatt agagcaggac aaacttttat   5640

gtttacaggg cacgtctgtt gtaatgcaaa gcatatttgg caagcagttc atcaccagga   5700

cactagctat gattctagaa gtcaaaaggt gtctatagaa ctagtggggc ttctgcatgt   5760

gaaaaacggt tttccatagg cattaaagtg ctgaatgctc agtctgatca acaagtgggc   5820

acctgcacta ccacttttta gaggaaattc actccctcgt aagcattgga aggtcaaatt   5880

attttgaagt gatttttta aaaaaaagtc ttctgtttat taacaggaaa atttatttat   5940

ttgacaggat tttgagtaat gtaggaatac aaaaggtaaa ttagcagcac atataatttt   6000

tttttaattt atgatccatt ttgtatggtc tcaaagttgg atgacctcat tactaatatt   6060

tgttgtaaaa gtgaaacttg tttgccaacc aataaacaac tgattgagat ttagaagata   6120

ttgtaaaaaa aaaaaaaaaa a                                             6141


<210> SEQ ID NO 73
<211> LENGTH: 2116
<212> TYPE: DNA
<213> ORGANISM: Homo sapiens

<400> SEQUENCE: 73

acagtgagct tccttatttg aagcaggact caattcttgg ttaaaagcta tggtatttga     60

gctagttaaa cacatatctc tctcccattc catagggaat gagctgggct gtcctttctc    120

cccacgttca cctgcacttc gttagagagc agtgttcaca tgccacacca caagatcccc    180

acaatgacat aactccattc agagactggc gtgactgggc tggtctcccc cacccccctt    240

cagctcttgt atcactcaga atctggcagc cagttccgtc ctgacagagt tcacagcata    300

tattggtgga ttcttgtcca tagtgcatct gctttaagaa ttaacgaaag cagtgtcaag    360

acagtaagga ttcaaaccat ttgccaaaaa tgagtctaag tgcatttact ctcttcctgg    420

cattgattgg tggtaccagt ggccagtact atgattatga ttttccccta tcaatttatg    480

ggcaatcatc accaaactgt gcaccagaat gtaactgccc tgaaagctac ccaagtgcca    540

tgtactgtga tgagctgaaa ttgaaaagtg taccaatggt gcctcctgga atcaagtatc    600

tttaccttag gaataaccag attgaccata ttgatgaaaa ggcctttgag aatgtaactg    660

atctgcagtg gctcattcta gatcacaacc ttctagaaaa ctccaagata aaagggagag    720

ttttctctaa attgaaacaa ctgaagaagc tgcatataaa ccacaacaac ctgacagagt    780

ctgtgggccc acttcccaaa tctctggagg atctgcagct tactcataac aagatcacaa    840

agctgggctc ttttgaagga ttggtaaacc tgaccttcat ccatctccag cacaatcggc    900

tgaaagagga tgctgtttca gctgctttta aaggtcttaa atcactcgaa taccttgact    960

tgagcttcaa tcagatagcc agactgcctt ctggtctccc tgtctctctt ctaactctct   1020

acttagacaa caataagatc agcaacatcc ctgatgagta tttcaagcgt tttaatgcat   1080

tgcagtatct gcgtttatct cacaacgaac tggctgatag tggaatacct ggaaattctt   1140

tcaatgtgtc atccctggtt gagctggatc tgtcctataa caagcttaaa aacataccaa   1200

ctgtcaatga aaaccttgaa aactattacc tggaggtcaa tcaacttgag aagtttgaca   1260

taaagagctt ctgcaagatc ctggggccat tatcctactc caagatcaag catttgcgtt   1320

tggatggcaa tcgcatctca gaaaccagtc ttccaccgga tatgtatgaa tgtctacgtg   1380

ttgctaacga agtcactctt aattaatatc tgtatcctgg aacaatattt tatggttatg   1440
```

```
tttttctgtg tgtcagtttt catagtatcc atattttatt actgtttatt acttccatga   1500

attttaaaat ctgagggaaa tgttttgtaa acatttattt tttttaaaga aaagatgaaa   1560

ggcaggccta tttcatcaca agaacacaca catatacacg aatagacatc aaactcaatg   1620

ctttatttgt aaatttagtg tttttttatt tctactgtca aatgatgtgc aaaacctttt   1680

actggttgca tggaaatcag ccaagtttta taatccttaa atcttaatgt tcctcaaagc   1740

ttggattaaa tacatatgga tgttactctc ttgcaccaaa ttatcttgat acattcaaat   1800

ttgtctggtt aaaaaatagg tggtagatat tgaggccaag aatattgcaa aatacatgaa   1860

gcttcatgca cttaaagaag tatttttaga ataagaattt gcatacttac ctagtgaaac   1920

ttttctagaa ttatttttca ctctaagtca tgtatgtttc tctttgatta tttgcatgtt   1980

atgtttaata agctactagc aaaataaaac atagcaaatg gcatcactgt gtttgacttc   2040

ttgtgaaatt tctgtacttt gtatataaaa tacataaaac aatagattag aaatcaaaag   2100

atatctctgg cctgca                                                   2116
```

<210> SEQ ID NO 74
<211> LENGTH: 806
<212> TYPE: DNA
<213> ORGANISM: Homo sapiens

<400> SEQUENCE: 74

```
gcccaccccc gcccagcccg tgcctataag gccttggcaa tgcaggggcc cgcactgctc     60

ccagacgaca tcagagatga ggacagcatt gctgctcctt gcagccctgg ctgtggctac    120

agggccagcc cttaccctgc gctgccacgt gtgcaccagc tccagcaact gcaagcattc    180

tgtggtctgc ccggccagct ctcgcttctg caagaccacg aacacagtgg agcctctgag    240

gggaatctg gtgaagaagg actgtgcgga gtcgtgcaca cccagctaca ccctgcaagg     300

ccaggtcagc agcggcacca gctccaccca gtgctgccag gaggacctgt gcaatgagaa    360

gctgcacaac gctgcaccca cccgcaccgc cctcgcccac agtgccctca gcctggggct    420

ggccctgagc ctcctggccg tcatcttagc cccagcctg tgaccttccc cccagggaag     480

gcccctcatg cctttccttc cctttctctg ggattccac acctctcttc cccagccgca     540

acgggggtgc caggagcccc aggctgaggg cttccccgaa agtctgggac caggtccagg    600

tgggcatgga atgctgatga cttggagcag gccccacaga ccccacagag gatgaagcca    660

ccccacagag gatgcagccc ccagctgcat ggaaggtgga ggacagaagc cctgtggatc    720

cccggatttc acactccttc tgttttgttg ccgtttattt ttgtactcaa atctctacat    780

ggagataaat gatttaaacc agaaaa                                         806
```

<210> SEQ ID NO 75
<211> LENGTH: 1516
<212> TYPE: DNA
<213> ORGANISM: Homo sapiens

<400> SEQUENCE: 75

```
aaatactggg gccagctcac cctggtcagc ctagcactct gacctagcag tcaacatgaa     60

ggctctcatt gttctggggc ttgtcctcct ttctgttacg gtccagggca aggtctttga    120

aaggtgtgag ttggccagaa ctctgaaaag attgggaatg gatggctaca ggggaatcag    180

cctagcaaac tggatgtgtt tggccaaatg ggagagtggt tacaacacac gagctacaaa    240

ctacaatgct ggagacagaa gcactgatta tgggatattt cagatcaata gccgctactg    300
```

gtgtaatgat ggcaaaaccc caggagcagt taatgcctgt catttatcct gcagtgcttt 360
gctgcaagat aacatcgctg atgctgtagc ttgtgcaaag agggttgtcc gtgatccaca 420
aggcattaga gcatgggtgg catggagaaa tcgttgtcaa aacagagatg tccgtcagta 480
tgttcaaggt tgtggagtgt aactccagaa ttttccttct tcagctcatt ttgtctctct 540
cacattaagg gagtaggaat taagtgaaag gtcacactac cattatttcc ccttcaaaca 600
aataatattt ttacagaagc aggagcaaaa tatggccttt cttctaagag atataatgtt 660
cactaatgtg gttattttac attaagccta caacattttt cagtttgcaa atagaactaa 720
tactggtgaa aatttaccta aaaccttggt tatcaaatac atctccagta cattccgttc 780 ttttttttt tgagacagtc tcgctctgtc gcccaggctg gagtgcagtg gcgcaatctc 840
ggctcactgc aacctccacc tcccgggttc acgccattct cctgcctcag cctcccgagt 900
agctgggatt acgggcgccc gccaccacgc ccggctaatt ttttgtattt ttagtagaga 960
cagggtttca ccgtgttagc caggatggtc tcgatctcct gaccttgtga tccacccacc 1020
tcggcctccc aaagtgctgg gattacaggc gtgagccact gcgcccggcc acattcagtt 1080
cttatcaaag aaataaccca gacttaatct tgaatgatac gattatgccc aatattaagt 1140
aaaaaatata agaaaaggtt atcttaaata gatcttaggc aaaataccag ctgatgaagg 1200
catctgatgc cttcatctgt tcagtcatct ccaaaaacag taaaaataac cactttttgt 1260
tgggcaatat gaaattttta aaggagtaga ataccaaatg atagaaacag actgcctgaa 1320
ttgagaattt tgatttctta aagtgtgttt ctttctaaat tgctgttcct taatttgatt 1380
aatttaattc atgtattatg attaaatctg aggcagatga gcttacaagt attgaaataa 1440
ttactaatta atcacaaatg tgaagttatg catgatgtaa aaaatacaaa cattctaatt 1500
aaaggctttg caacac 1516

<210> SEQ ID NO 76
<211> LENGTH: 2383
<212> TYPE: DNA
<213> ORGANISM: Homo sapiens

<400> SEQUENCE: 76
gaaagcagtt ctctgggacc accttctttt ggcttcaacc tctcccactc ttgacatctg 60
agtagctcag ggaagctctt ccaggtccga ctgttcatat gtaaaggaga ctggccgctg 120
gggctcagga ccgggattat ccgagctctg cagaagtgca ccgctattgc tttgggaggt 180
taaaaaaaaa atcacacggt ttccagtgaa aaagtgacag agggtggtgg cctttggaac 240
cgccgtgaag tcttctgcct ggaacccgaa acttgcatgc tatggaacac ccgctctttg 300
gctgcctgcg cagccctcac gccacggcgc aaggcttgca cccgttctcc caatcctctc 360
tcgccctcca tggaagatct gaccatatgt cttaccccga gctctctact tcttcctcat 420
cttgcataat cgcgggatac cccaacgaag agggcatgtt tgccagccag catcacaggg 480
ggcaccacca ccaccaccac caccaccacc atcaccacca tcagcagcag cagcaccagg 540
ctctgcaaac caactggcac ctcccgcaga tgtcttcccc accgagtgcg gctcggcaca 600
gcctctgcct ccagcccgac tctggagggc ccccagagtt ggggagcagc ccgcccgtcc 660
tgtgctccaa ctcttccagc ttgggctcca gcaccccgac tggggccgcg tgcgcgccgg 720
gggactacgg ccgccaggca ctgtcacctg cggaggcgga gaagcgaagc ggcggcaaga 780
ggaaaagcga cagctcagac tcccaggaag gaaattacaa gtcagaagtc aacagcaaac 840
ccaggaaaga aaggacagca tttaccaaag agcaaatcag agaacttgaa gcagaatttg 900
cccatcataa ttatctcacc agactgaggc gatacgagat agcagtgaat ctggatctca 960
ctgaaagaca ggtgaaagtc tggttccaaa acaggcggat gaagtggaag agggtaaagg 1020
gtggacagca aggagctgcg gctcgggaaa aggaactggt gaatgtgaaa aagggaacac 1080
ttctcccatc agagctgtcg ggaattggtg cagccaccct ccagcaaaca ggggactcta 1140
tagcaaatga agacagtcac gacagtgacc acagctcaga gcatgcgcac ttatgatata 1200
aacagaggac cagctccatt ctcaggaaag aaatgttgtg atggcaagcc ttacccaaat 1260
atcgtttaca cagagagatg actatggcag tgatgtttaa tattattaaa tccaggcatt 1320
tcgaatctgt ttttcatgat ttatagaggg tttacacaaa gtgccactta ttaaagagct 1380
tccacagtga agatggagaa ggtgaacttg ctttgaatat tccagatgtg tttggtcgtg 1440
cgtatggcag tgagcaggta tgtgtttgct tttgcttgca ctgaaaatta aattgctatc 1500
aagagcaaac tatgaacggt tttttattca agatgtctcc agagtgaaga tgccgaggat 1560
gaacttgcat tgaacattcc agatgtgtga gatcatgtgt attacagtgg gcaggtattt 1620
gcttttgctt gcactgaaaa ttaaattgct atcaagaata aaccatgaaa cattttatcc 1680
tgaacagcca cagtgcctga attcactcaa gtggataaaa agtgtatttt aactctgtat 1740
atattaccct taagtcattt tcctgtcttc actaatttag caatgcattc atattagctg 1800
atgaaaatag gcactcacaa tgacaaccag agccagtttc ttgtcttttt tatacatttt 1860
gtcatcccag agacaatcag tatgtgctta cctgtgttca agtagagaaa aatacagtag 1920
agtctgatag gacatattct tgtaccacag acaaaacaaa tcttatgttg catttactat 1980
caactgctgc taatacgtta ttataaaact tacctagctc ctgaattctt cctatcttat 2040
agcttaaaac aattaggatc ataggcaaat cagttacctt gcagaaagag ctttgtatga 2100
cagacattgt cttattttat ttctgtaaaa tattagctgt atgaatatga tttaattaac 2160
aagaaaacat ttcttcctga ttgacaacag tgttagacaa ggtgcaaagc gaaactggtt 2220
gctcaagttg atagaaaaca aaattctgaa tatcttcaaa ttaaattcgg taaaaacaca 2280
ttattttttc atatgtgatg tattcatgca gaacaactat ctttgtattt tgtttttaaa 2340
atgtgtttaa taaatgatcc tttgtaaata aaaaaaaaaa aaa 2383

<210> SEQ ID NO 77
<211> LENGTH: 6695
<212> TYPE: DNA
<213> ORGANISM: Homo sapiens

<400> SEQUENCE: 77
gccctcgccg cccgcggcgc cccgagcgct ttgtgagcag atgcggagcc gagtggaggg 60
cgcgagccag atgcggggcg acagctgact tgctgagagg aggcggggag gcgcggagcg 120
cgcgtgtggt ccttgcgccg ctgacttctc cactggttcc tgggcaccga aagataaacc 180
tctcataatg aaggcccccg ctgtgcttgc acctggcatc ctcgtgctcc tgtttacctt 240
ggtgcagagg agcaatgggg agtgtaaaga ggcactagca aagtccgaga tgaatgtgaa 300
tatgaagtat cagcttccca acttcaccgc ggaaacaccc atccagaatg tcattctaca 360
tgagcatcac attttccttg gtgccactaa ctacatttat gttttaaatg aggaagacct 420
tcagaaggtt gctgagtaca agactgggcc tgtgctggaa cacccagatt gtttcccatg 480
tcaggactgc agcagcaaag ccaatttatc aggaggtgtt tggaaagata acatcaacat 540
ggctctagtt gtcgacacct actatgatga tcaactcatt agctgtggca gcgtcaacag 600

```
agggacctgc cagcgacatg tctttcccca caatcatact gctgacatac agtcggaggt    660
tcactgcata ttctccccac agatagaaga gcccagccag tgtcctgact gtgtggtgag    720
cgccctggga gccaaagtcc tttcatctgt aaaggaccgg ttcatcaact tctttgtagg    780
caataccata aattcttctt atttcccaga tcatccattg cattcgatat cagtgagaag    840
gctaaaggaa acgaaagatg gttttatgtt tttgacggac cagtcctaca ttgatgtttt    900
acctgagttc agagattctt accccattaa gtatgtccat gcctttgaaa gcaacaattt    960
tatttacttc ttgacggtcc aaagggaaac tctagatgct cagacttttc acacaagaat   1020
aatcaggttc tgttccataa actctggatt gcattcctac atggaaatgc ctctggagtg   1080
tattctcaca gaaaagagaa aaaagagatc cacaaagaag gaagtgttta atatacttca   1140
ggctgcgtat gtcagcaagc ctggggccca gcttgctaga caaataggag ccagcctgaa   1200
tgatgacatt cttttcgggg tgttcgcaca aagcaagcca gattctgccg aaccaatgga   1260
tcgatctgcc atgtgtgcat tccctatcaa atatgtcaac gacttcttca acaagatcgt   1320
caacaaaaac aatgtgagat gtctccagca tttttacgga cccaatcatg agcactgctt   1380
taataggaca cttctgagaa attcatcagg ctgtgaagcg cgccgtgatg aatatcgaac   1440
agagtttacc acagctttgc agcgcgttga cttattcatg ggtcaattca gcgaagtcct   1500
cttaacatct atatccacct tcattaaagg agacctcacc atagctaatc ttgggacatc   1560
agagggtcgc ttcatgcagg ttgtggtttc tcgatcagga ccatcaaccc ctcatgtgaa   1620
ttttctcctg gactcccatc cagtgtctcc agaagtgatt gtggagcata cattaaacca   1680
aaatggctac acactggtta tcactgggaa gaagatcacg aagatcccat tgaatggctt   1740
gggctgcaga catttccagt cctgcagtca atgcctctct gccccaccct ttgttcagtg   1800
tggctggtgc cacgacaaat gtgtgcgatc ggaggaatgc ctgagcggga catggactca   1860
acagatctgt ctgcctgcaa tctacaaggt tttcccaaat agtgcacccc ttgaaggagg   1920
gacaaggctg accatatgtg gctgggactt tggatttcgg aggaataata aatttgattt   1980
aaagaaaact agagttctcc ttggaaatga gagctgcacc ttgactttaa gtgagagcac   2040
gatgaataca ttgaaatgca cagttggtcc tgccatgaat aagcatttca atatgtccat   2100
aattatttca aatggccacg ggacaacaca atacagtaca ttctcctatg tggatcctgt   2160
aataacaagt atttcgccga aatacggtcc tatggctggt ggcactttac ttactttaac   2220
tggaaattac ctaaacagtg ggaattctag acacatttca attggtggaa aaacatgtac   2280
tttaaaaagt gtgtcaaaca gtattcttga atgttatacc ccagcccaaa ccatttcaac   2340
tgagtttgct gttaaattga aaattgactt agccaaccga gagacaagca tcttcagtta   2400
ccgtgaagat cccattgtct atgaaattca tccaaccaaa tcttttatta gtacttggtg   2460
gaaagaacct ctcaacattg tcagttttct attttgcttt gccagtggtg ggagcacaat   2520
aacaggtgtt gggaaaaacc tgaattcagt tagtgtcccg agaatggtca taaatgtgca   2580
tgaagcagga aggaacttta cagtggcatg tcaacatcgc tctaattcag agataatctg   2640
ttgtaccact ccttccctgc aacagctgaa tctgcaactc cccctgaaaa ccaaagcctt   2700
tttcatgtta gatgggatcc tttccaaata ctttgatctc atttatgtac ataatcctgt   2760
gtttaagcct tttgaaaagc cagtgatgat ctcaatgggc aatgaaaatg tactggaaat   2820
taagggaaat gatattgacc ctgaagcagt taaaggtgaa gtgttaaaag ttggaaataa   2880
gagctgtgag aatatacact tacattctga agccgtttta tgcacggtcc ccaatgacct   2940
gctgaaattg aacagcgagc taaatataga gtggaagcaa gcaatttctt caaccgtcct   3000
```

tggaaaagta atagttcaac cagatcagaa tttcacagga ttgattgctg gtgttgtctc 3060
aatatcaaca gcactgttat tactacttgg gtttttcctg tggctgaaaa agagaaagca 3120
aattaaagat ctgggcagtg aattagttcg ctacgatgca agagtacaca ctcctcattt 3180
ggataggctt gtaagtgccc gaagtgtaag cccaactaca gaaatggttt caaatgaatc 3240
tgtagactac cgagctactt ttccagaaga tcagtttcct aattcatctc agaacggttc 3300
atgccgacaa gtgcagtatc ctctgacaga catgtccccc atcctaacta gtggggactc 3360
tgatatatcc agtccattac tgcaaaatac tgtccacatt gacctcagtg ctctaaatcc 3420
agagctggtc caggcagtgc agcatgtagt gattgggccc agtagcctga ttgtgcattt 3480
caatgaagtc ataggaagag ggcattttgg ttgtgtatat catgggactt tgttggacaa 3540
tgatggcaag aaaattcact gtgctgtgaa atccttgaac agaatcactg acataggaga 3600
agtttcccaa tttctgaccg agggaatcat catgaaagat tttagtcatc ccaatgtcct 3660
ctcgctcctg ggaatctgcc tgcgaagtga agggtctccg ctggtggtcc taccatacat 3720
gaaacatgga gatcttcgaa atttcattcg aaatgagact cataatccaa ctgtaaaaga 3780
tcttattggc tttggtcttc aagtagccaa aggcatgaaa tatcttgcaa gcaaaaagtt 3840
tgtccacaga gacttggctg caagaaactg tatgctggat gaaaaattca cagtcaaggt 3900
tgctgatttt ggtcttgcca gagacatgta tgataaagaa tactatagtg tacacaacaa 3960
aacaggtgca aagctgccag tgaagtggat ggctttggaa agtctgcaaa ctcaaaagtt 4020
taccaccaag tcagatgtgt ggtcctttgg cgtgctcctc tgggagctga tgacaagagg 4080
agccccacct tatcctgacg taaacacctt tgatataact gtttacttgt tgcaagggag 4140
aagactccta caacccgaat actgcccaga cccccttatat gaagtaatgc taaaatgctg 4200
gcaccctaaa gccgaaatgc gcccatcctt ttctgaactg gtgtcccgga tatcagcgat 4260
cttctctact ttcattgggg agcactatgt ccatgtgaac gctacttatg tgaacgtaaa 4320
atgtgtcgct ccgtatcctt ctctgttgtc atcagaagat aacgctgatg atgaggtgga 4380
cacacgacca gcctccttct gggagacatc atagtgctag tactatgtca aagcaacagt 4440
ccacactttg tccaatggtt ttttcactgc ctgaccttta aaaggccatc gatattcttt 4500
gctcttgcca aaattgcact attataggac ttgtattgtt atttaaatta ctggattcta 4560
aggaatttct tatctgacag agcatcagaa ccagaggctt ggtcccacag gccacggacc 4620
aatggcctgc agccgtgaca acactcctgt catattggag tccaaaactt gaattctggg 4680
ttgaattttt taaaaatcag gtaccacttg atttcatatg ggaaattgaa gcaggaaata 4740
ttgagggctt cttgatcaca gaaaactcag aagagatagt aatgctcagg acaggagcgg 4800
cagccccaga acaggccact catttagaat tctagtgttt caaaacactt ttgtgtgttg 4860
tatggtcaat aacatttttc attactgatg gtgtcattca cccattaggt aaacattccc 4920
ttttaaatgt ttgtttgttt tttgagacag gatctcactc tgttgccagg gctgtagtgc 4980
agtggtgtga tcatagctca ctgcaacctc cacctcccag gctcaagcct cccgaatagc 5040
tgggactaca ggcgcacacc accatccccg gctaattttt gtatttttttg tagagacggg 5100
gttttgccat gttgccaagg ctggtttcaa actcctggac tcaagaaatc cacccacctc 5160
agcctcccaa agtgctagga ttacaggcat gagccactgc gcccagccct tataaatttt 5220
tgtatagaca ttcctttggt tggaagaata tttataggca atacagtcaa agtttcaaaa 5280
tagcatcaca caaaacatgt ttataaatga acaggatgta atgtacatag atgacattaa 5340

-continued gaaaatttgt atgaaataat ttagtcatca tgaaatattt agttgtcata taaaaaccca 5400
ctgtttgaga atgatgctac tctgatctaa tgaatgtgaa catgtagatg ttttgtgtgt 5460 attttttaa atgaaaactc aaaataagac aagtaatttg ttgataaata tttttaaaga 5520
taactcagca tgtttgtaaa gcaggataca ttttactaaa aggttcattg gttccaatca 5580
cagctcatag gtagagcaaa gaaagggtgg atggattgaa aagattagcc tctgtctcgg 5640
tggcaggttc ccacctcgca agcaattgga aacaaaactt ttggggagtt ttattttgca 5700
ttagggtgtg ttttatgtta agcaaaacat actttagaaa caaatgaaaa aggcaattga 5760
aaatcccagc tatttcacct agatggaata gccaccctga gcagaacttt gtgatgcttc 5820
attctgtgga attttgtgct tgctactgta tagtgcatgt ggtgtaggtt actctaactg 5880
gttttgtcga cgtaaacatt taaagtgtta tattttttat aaaaatgttt atttttaatg 5940
atatgagaaa aattttgtta ggccacaaaa acactgcact gtgaacattt tagaaaaggt 6000
atgtcagact gggattaatg acagcatgat tttcaatgac tgtaaattgc gataaggaaa 6060
tgtactgatt gccaatacac cccaccctca ttacatcatc aggacttgaa gccaagggtt 6120
aacccagcaa gctacaaaga gggtgtgtca cactgaaact caatagttga gtttggctgt 6180
tgttgcagga aaatgattat aactaaaagc tctctgatag tgcagagact taccagaaga 6240
cacaaggaat tgtactgaag agctattaca atccaaatat tgccgtttca taaatgtaat 6300
aagtaatact aattcacaga gtattgtaaa tggtggatga caaaagaaaa tctgctctgt 6360
ggaaagaaag aactgtctct accagggtca agagcatgaa cgcatcaata gaaagaactc 6420
ggggaaacat cccatcaaca ggactacaca cttgtatata cattcttgag aacactgcaa 6480
tgtgaaaatc acgtttgcta tttataaact tgtccttaga ttaatgtgtc tggacagatt 6540
gtgggagtaa gtgattcttc taagaattag atacttgtca ctgcctatac ctgcagctga 6600
actgaatggt acttcgtatg ttaatagttg ttctgataaa tcatgcaatt aaagtaaagt 6660
gatgcaacat cttgtaaaaa aaaaaaaaaa aaaaa 6695

<210> SEQ ID NO 78
<211> LENGTH: 2276
<212> TYPE: DNA
<213> ORGANISM: Homo sapiens

<400> SEQUENCE: 78
aagcccagca gccccggggc ggatggctcc ggccgcctgg ctccgcagcg cggccgcgcg 60
cgccctcctg cccccgatgc tgctgctgct gctccagccg ccgccgctgc tggcccgggc 120
tctgccgccg gacgcccacc acctccatgc cgagaggagg gggccacagc cctggcatgc 180
agccctgccc agtagcccgg cacctgcccc tgccacgcag gaagcccccc ggcctgccag 240
cagcctcagg cctccccgct gtggcgtgcc cgacccatct gatgggctga gtgcccgcaa 300
ccgacagaag aggttcgtgc tttctggcgg gcgctgggag aagacggacc tcacctacag 360
gatccttcgg ttcccatggc agttggtgca ggagcaggtg cggcagacga tggcagaggc 420
cctaaaggta tggagcgatg tgacgccact cacctttact gaggtgcacg agggccgtgc 480
tgacatcatg atcgacttcg ccaggtactg gcatggggac gacctgccgt ttgatgggcc 540
tgggggcatc ctggcccatg ccttcttccc caagactcac cgagaagggg atgtccactt 600
cgactatgat gagacctgga ctatcgggga tgaccagggc acagacctgc tgcaggtggc 660
agcccatgaa tttggccacg tgctggggct gcagcacaca acagcagcca aggccctgat 720
gtccgccttc tacacctttc gctacccact gagtctcagc ccagatgact gcaggggcgt 780

-continued tcaacaccta tatggccagc cctggcccac tgtcacctcc aggaccccag ccctgggccc 840
ccaggctggg atagacacca atgagattgc accgctggag ccagacgccc cgccagatgc 900
ctgtgaggcc tcctttgacg cggtctccac catccgaggc gagctctttt tcttcaaagc 960
gggctttgtg tggcgcctcc gtgggggcca gctgcagccc ggctacccag cattggcctc 1020
tcgccactgg cagggactgc ccagccctgt ggacgctgcc ttcgaggatg cccagggcca 1080
catttggttc ttccaaggtg ctcagtactg ggtgtacgac ggtgaaaagc cagtcctggg 1140
ccccgcaccc ctcaccgagc tgggcctggt gaggttcccg gtccatgctg ccttggtctg 1200
gggtcccgag aagaacaaga tctacttctt ccgaggcagg gactactggc gtttccaccc 1260
cagcacccgg cgtgtagaca gtcccgtgcc ccgcagggcc actgactgga gaggggtgcc 1320
ctctgagatc gacgctgcct tccaggatgc tgatggctat gcctacttcc tgcgcggccg 1380
cctctactgg aagtttgacc ctgtgaaggt gaaggctctg gaaggcttcc cccgtctcgt 1440
gggtcctgac ttctttggct gtgccgagcc tgccaacact ttcctctgac catggcttgg 1500
atgccctcag ggtgctgacc cctgccaggc ccacgaatat caggctagag acccatggcc 1560
atctttgtgg ctgtgggcac caggcatggg actgagccca tgtctcctca gggggatggg 1620
gtggggtaca accaccatga caactgccgg gagggccacg caggtcgtgg tcacctgcca 1680
gcgactgtct cagactgggc agggaggctt tggcatgact taagaggaag ggcagtcttg 1740
ggcccgctat gcaggtcctg gcaaacctgg ctgccctgtc tccatccctg tccctcaggg 1800
tagcaccatg gcaggactgg gggaactgga gtgtccttgc tgtatccctg ttgtgaggtt 1860
ccttccaggg gctggcactg aagcaagggt gctggggccc catggccttc agccctggct 1920
gagcaactgg gctgtagggc agggccactt cctgaggtca ggtcttggta ggtgcctgca 1980
tctgtctgcc ttctggctga caatcctgga aatctgttct ccagaatcca ggccaaaaag 2040
ttcacagtca aatggggagg ggtattcttc atgcaggaga ccccaggccc tggaggctgc 2100
aacatacctc aatcctgtcc caggccggat cctcctgaag cccttttcgc agcactgcta 2160
tcctccaaag ccattgtaaa tgtgtgtaca gtgtgtataa accttcttct tctttttttt 2220
tttttaaact gaggattgtc attaaacaca gttgttttct aaaaaaaaaa aaaaaa 2276

<210> SEQ ID NO 79
<211> LENGTH: 1369
<212> TYPE: DNA
<213> ORGANISM: Homo sapiens

<400> SEQUENCE: 79
aaacaggaaa taaatacgaa tgaaactgag ctctaagcag catgtaacct ggcctgcatc 60
caggaaatag aggacttcgg atccttctaa ccctaccacc caactggccc cagtacattc 120
attctctcag gaaaaaaaac aaggtcccca cagcaaagaa aaggaatagg atcaagagat 180
acgtggctgc tggcagagca agcatgaatt cgatgacttc agcagttccg gtggccaatt 240
ctgtgttggt ggtggcaccc cacaatggtt atcctgtgac cccaggaatt atgtctcacg 300
tgcccctgta tccaaacagc cagccgcaag tccacctagt tcctgggaac ccacctagtt 360
tggtgtcgaa tgtgaatggg cagcctgtgc agaaagctct gaaagaaggc aaaaccttgg 420
gggccatcca gatcatcatt ggcctggctc acatcggcct cggctccatc atggcgacgg 480
ttctcgtagg ggaatacctg tctatttcat tctacggagg ctttcccttc tggggaggct 540
tgtggtttat catttcagga tctctctccg tggcagcaga aaatcagcca tattcttatt 600
gcctgctgtc tggcagtttg ggcttgaaca tcgtcagtgc aatctgctct gcagttggag 660
tcatactctt catcacagat ctaagtattc cccacccata tgcctacccc gactattatc 720
cttacgcctg gggtgtgaac cctggaatgg cgatttctgg cgtgctgctg gtcttctgcc 780
tcctggagtt tggcatcgca tgcgcatctt cccactttgg ctgccagttg gtctgctgtc 840
aatcaagcaa tgtgagtgtc atctatccaa acatctatgc agcaaaccca gtgatcaccc 900
cagaaccggt gacctcacca ccaagttatt ccagtgagat ccaagcaaat aagtaaggct 960
acagattctg gaagcatctt tcactgggac caaaagaagt cctcctccct ttctgggctt 1020
ccataaccca ggtcgttcct gttctgacag ctgaggaaac gtctctccca ctgtttgtac 1080
tctcaccttc attcttcaat tcagtctagg aaaccatgct gtttctctat caagaagaag 1140
acagagattt taaacagatg ttaaccaaga gggactccct agggcacatg catcagcaca 1200
tatgtgggca tccagcctct ggggccttgg cacacacaca ttcgtgtgct ctgctgcatg 1260
tgagcttgtg ggttagagga acaaatatct agacattcaa tcttcactct ttcaattgtg 1320
cattcattta ataaatagat actgagcatt caaaaaaaaa aaaaaaaaa 1369

<210> SEQ ID NO 80
<211> LENGTH: 2187
<212> TYPE: DNA
<213> ORGANISM: Homo sapiens

<400> SEQUENCE: 80
tgccaggctc tccaccccca cttcccaatt gaggaaaccg aggcagagga ggctcagcgc 60
cacgcactcc tctttctgcc tggccggcca ctcccgtctg ctgtgacgcg cggacagaga 120
gctaccggtg gacccacggt gcctccctcc ctgggatcta cacagaccat ggccttgcca 180
acggctcgac ccctgttggg gtcctgtggg acccccgccc tcggcagcct cctgttcctg 240
ctcttcagcc tcggatgggt gcagccctcg aggaccctgg ctggagagac agggcaggag 300
gctgcgcccc tggacggagt cctggccaac ccacctaaca tttccagcct ctcccctcgc 360
caactccttg gcttcccgtg tgcggaggtg tccggcctga gcacggagcg tgtccgggag 420
ctggctgtgg ccttggcaca gaagaatgtc aagctctcaa cagagcagct gcgctgtctg 480
gctcaccggc tctctgagcc ccccgaggac ctggacgccc tcccattgga cctgctgcta 540
ttcctcaacc cagatgcgtt ctcggggccc caggcctgca cccgtttctt ctcccgcatc 600
acgaaggcca atgtggacct gctcccgagg ggggctcccg agcgacagcg gctgctgcct 660
gcggctctgg cctgctgggg tgtgcggggg tctctgctga gcgaggctga tgtgcgggct 720
ctgggaggcc tggcttgcga cctgcctggg cgctttgtgg ccgagtcggc cgaagtgctg 780
ctaccccggc tggtgagctg cccgggaccc ctggaccagg accagcagga ggcagccagg 840
gcggctctgc agggcggggg accccctac ggcccccgt cgacatggtc tgtctccacg 900
atggacgctc tgcggggcct gctgcccgtg ctgggccagc ccatcatccg cagcatcccg 960
cagggcatcg tggccgcgtg gcggcaacgc tcctctcggg acccatcctg gcggcagcct 1020
gaacggacca tcctccggcc gcggttccgg cgggaagtgg agaagacagc ctgtccttca 1080
ggcaagaagg cccgcgagat agacgagagc ctcatcttct acaagaagtg ggagctggaa 1140
gcctgcgtgg atgcggccct gctggccacc cagatggacc gcgtgaacgc catcccttc 1200 acctacgagc agctggacgt cctaaagcat aaactggatg agctctaccc acaaggttac 1260
cccgagtctg tgatccagca cctgggctac ctcttcctca agatgagccc tgaggacatt 1320
cgcaagtgga atgtgacgtc cctggagacc ctgaaggctt tgcttgaagt caacaaaggg 1380
cacgaaatga gtcctcaggt ggccaccctg atcgaccgct ttgtgaaggg aaggggccag 1440
ctagacaaag acaccctaga caccctgacc gccttctacc ctgggtacct gtgctccctc 1500
agccccgagg agctgagctc cgtgcccccc agcagcatct gggcggtcag gccccaggac 1560
ctggacacgt gtgacccaag gcagctggac gtcctctatc ccaaggcccg ccttgctttc 1620
cagaacatga acgggtccga atacttcgtg aagatccagt ccttcctggg tggggccccc 1680
acggaggatt tgaaggcgct cagtcagcag aatgtgagca tggacttggc cacgttcatg 1740
aagctgcgga cggatgcggt gctgccgttg actgtggctg aggtgcagaa acttctggga 1800
ccccacgtgg agggcctgaa ggcggaggag cggcaccgcc cggtgcggga ctggatccta 1860
cggcagcggc aggacgacct ggacacgctg gggctggggc tacagggcgg catccccaac 1920
ggctacctgg tcctagacct cagcatgcaa gaggccctct cggggacgcc ctgcctccta 1980
ggacctggac ctgttctcac cgtcctggca ctgctcctag cctccaccct ggcctgaggg 2040
ccccactccc ttgctggccc cagccctgct ggggatcccc gcctggccag gagcaggcac 2100
gggtggtccc cgttccaccc caagagaact cgcgctcagt aaacgggaac atgccccctg 2160
cagacacgta aaaaaaaaaa aaaaaaa 2187

<210> SEQ ID NO 81
<211> LENGTH: 6882
<212> TYPE: DNA
<213> ORGANISM: Homo sapiens

<400> SEQUENCE: 81
gggagatttg gacgctccgg cctgggaggt gcgtcagatc cgagctcgcc atccagtttc 60
ctctccacta gtccccccag ttggagatct gggaccaaca aggcaccatg gcgcagaagg 120
gccaactcag tgacgatgag aagttcctct ttgtggacaa aaacttcatc aacagcccag 180
tggcccaggc tgactgggcc gccaagagac tcgtctgggt cccctcggag aagcagggct 240
tcgaggcagc cagcattaag gaggagaagg gggatgaggt ggttgtggag ctggtggaga 300
atggcaagaa ggtcacggtt gggaaagatg acatccagaa gatgaaccca cccaagttct 360
ccaaggtgga ggacatggcg gagctgacgt gcctcaacga agcctccgtg ctacacaacc 420
tgagggagcg gtacttctca gggctaatat atacgtactc tggcctcttc tgcgtggtgg 480
tcaaccccta taaacacctg cccatctact cggagaagat cgtcgacatg tacaagggca 540
agaagaggca cgagatgccg cctcacatct acgccatcgc agacacggcc taccggagca 600
tgcttcaaga tcgggaggac cagtccattc tatgcacagg cgagtctgga gccgggaaaa 660
ccgaaaacac caagaaggtc attcagtacc tggccgtggt ggcctcctcc cacaagggca 720
agaaagacac aagtatcacg ggagagctgg aaaagcagct tctacaagca aacccgattc 780
tggaggcttt cggcaacgcc aaaacagtga agaacgacaa ctcctcacga ttcggcaaat 840
tcatccgcat caacttcgac gtcacgggtt acatcgtggg agccaacatt gagacctatc 900
tgctagaaaa atcacgggca attcgccaag ccagagacga gaggacattc cacatctttt 960
actacatgat tgctggagcc aaggagaaga tgagaagtga cttgcttttg gagggcttca 1020
acaactacac cttcctctcc aatggctttg tgcccatccc agcagcccag gatgatgaga 1080
tgttccagga aaccgtggag gccatggcaa tcatgggttt cagcgaggag gagcagctat 1140
ccatattgaa ggtggtatca tcggtcctgc agcttggaaa tatcgtcttc aagaaggaaa 1200
gaaacacaga ccaggcgtcc atgccagata acacagctgc tcagaaagtt tgccacctca 1260

-continued

```
tgggaattaa tgtgacagat ttcaccagat ccatcctcac tcctcgtatc aaggttgggc   1320
gagatgtggt acagaaagct cagacaaaag aacaggctga ctttgctgta gaggctttgg   1380
ccaaggcaac atatgagcgc cttttccgct ggatactcac ccgcgtgaac aaagccctgg   1440
acaagaccca tcggcaaggg gcttccttcc tggggatcct ggatatagct ggatttgaga   1500
tctttgaggt gaactccttc gagcagctgt gcatcaacta caccaacgag aagctgcagc   1560
agctcttcaa ccacaccatg ttcatcctgg agcaggagga gtaccagcgc gagggcatcg   1620
agtggaactt catcgacttt gggctggacc tacagccctg catcgagctc atcgagcgac   1680
cgaacaaccc tccaggtgtg ctggccctgc tggacgagga atgctggttc cccaaagcca   1740
cggacaagtc tttcgtggag aagctgtgca cggagcaggg cagccacccc aagttccaga   1800
agcccaagca gctcaaggac aagactgagt tctccatcat ccattatgct gggaaggtgg   1860
actataatgc gagtgcctgg ctgaccaaga atatggaccc gctgaatgac aacgtgactt   1920
ccctgctcaa tgcctcctcc gacaagtttg tggccgacct gtggaaggac gtggaccgca   1980
tcgtgggcct ggaccagatg gccaagatga cggagagctc gctgcccagc gcctccaaga   2040
ccaagaaggg catgttccgc acagtggggc agctgtacaa ggagcagctg ggcaagctga   2100
tgaccacgct acgcaacacc acgcccaact tcgtgcgctg catcatcccc aaccacgaga   2160
agaggtccgg caagctggat gcgttcctgg tgctggagca gctgcggtgc aatggggtgc   2220
tggaaggcat tcgcatctgc cggcagggct tccccaaccg gatcgtcttc caggagttcc   2280
gccaacgcta cgagatcctg gcggcgaatg ccatccccaa aggcttcatg gacgggaagc   2340
aggcctgcat tctcatgatc aaagccctgg aacttgaccc caacttatac aggatagggc   2400
agagcaaaat cttcttccga actggcgtcc tggcccacct agaggaggag cgagatttga   2460
agatcaccga tgtcatcatg gccttccagg cgatgtgtcg tggctacttg gccagaaagg   2520
cttttgccaa gaggcagcag cagctgaccg ccatgaaggt gattcagagg aactgcgccg   2580
cctacctcaa gctgcggaac tggcagtggt ggaggctttt caccaaagtg aagccactgc   2640
tgcaggtgac acggcaggag gaggagatgc aggccaagga ggatgaactg cagaagacca   2700
aggagcggca gcagaaggca gagaatgagc ttaaggagct ggaacagaag cactcgcagc   2760
tgaccgagga gaagaacctg ctacaggaac agctgcaggc agagacagag ctgtatgcag   2820
aggctgagga gatgcgggtg cggctggcgg ccaagaagca ggagctggag gagatactgc   2880
atgagatgga ggcccgcctg gaggaggagg aagacagggg ccagcagcta caggctgaaa   2940
ggaagaagat ggcccagcag atgctggacc ttgaagaaca gctggaggag gaggaagctg   3000
ccaggcagaa gctgcaactt gagaaggtca cggctgaggc caagatcaag aaactggagg   3060
atgagatcct ggtcatggat gatcagaaca ataaactatc aaaagaacga aaactccttg   3120
aggagaggat tagtgactta acgacaaatc ttgcagaaga ggaagaaaag gccaagaatc   3180
ttaccaagct gaaaaacaag catgaatcta tgatttcaga actggaagtg cggctaaaga   3240
aggaagagaa gagccgacag gagctggaga agctgaaacg gaagctggag ggtgatgcca   3300
gcgacttcca cgagcagatc gctgacctcc aggcgcagat cgcagagctc aagatgcagc   3360
tggccaagaa ggaggaggag ctgcaggcgg ccctggccag gcttgacgat gaaatcgctc   3420
agaagaacaa tgccctgaag aagatccggg agctggaggg ccacatctca gacctccagg   3480
aggacctgga ctcagagcgg gccgccagga acaaggctga aaagcagaag cgagacctcg   3540
gcgaggagct ggaggcccta aagacagagc tggaagacac actggacagc acagccactc   3600
agcaggagct cagggccaag agggagcagg aggtgacggt gctgaagaag gccctggatg   3660
```

aagagacgcg gtcccatgag gctcaggtcc aggagatgag gcagaaacac gcacaggcgg 3720
tggaggagct cacagagcag cttgagcagt tcaagagggc caaggcgaac ctagacaaga 3780
ataagcagac gctggagaaa gagaacgcag acctggccgg ggagctgcgg gtcctgggcc 3840
aggccaagca ggaggtggaa cataagaaga agaagctgga ggcgcaggtg caggagctgc 3900
agtccaagtg cagcgatggg gagcgggccc gggcggagct caatgacaaa gtccacaagc 3960
tgcagaatga agttgagagc gtcacaggga tgcttaacga ggccgagggg aaggccatta 4020
agctggccaa ggacgtggcg tccctcagtt cccagctcca ggacacccag gagctgcttc 4080
aagaagaaac ccggcagaag ctcaacgtgt ctacgaagct gcgccagctg gaggaggagc 4140
ggaacagcct gcaagaccag ctggacgagg agatggaggc caagcagaac ctggagcgcc 4200
acatctccac tctcaacatc cagctctccg actcgaagaa gaagctgcag gactttgcca 4260
gcaccgtgga agctctggaa gaggggaaga agaggttcca gaaggagatc gagaacctca 4320
cccagcagta cgaggagaag gcggccgctt atgataaact ggaaaagacc aagaacaggc 4380
ttcagcagga gctggacgac ctggttgttg atttggacaa ccagcggcaa ctcgtgtcca 4440
acctggaaaa gaagcagagg aaatttgatc agttgttagc cgaggagaaa aacatctctt 4500
ccaaatacgc ggatgagagg gacagagctg aggcagaagc cagggagaag gaaaccaagg 4560
ccctgtccct ggctcgggcc cttgaagagg ccttggaagc caaagaggaa ctcgagcgga 4620
ccaacaaaat gctcaaagcc gaaatggaag acctggtcag ctccaaggat gacgtgggca 4680
agaacgtcca tgagctggag aagtccaagc gggccctgga gacccagatg gaggagatga 4740
agacgcagct ggaagagctg gaggacgagc tgcaagccac ggaggacgcc aaactgcggc 4800
tggaagtcaa catgcaggcg ctcaagggcc agttcgaaag ggatctccaa gcccgggacg 4860
agcagaatga ggagaagagg aggcaactgc agagacagct tcacgagtat gagacggaac 4920
tggaagacga gcgaaagcaa cgtgccctgg cagctgcagc aaagaagaag ctggaagggg 4980
acctgaaaga cctggagctt caggccgact ctgccatcaa ggggagggag gaagccatca 5040
agcagctacg caaactgcag gctcagatga aggactttca aagagagctg gaagatgccc 5100
gtgcctccag agatgagatc tttgccacag ccaaagagaa tgagaagaaa gccaagagct 5160
tggaagcaga cctcatgcag ctacaagagg acctcgccgc cgctgagagg gctcgcaaac 5220
aagcggacct cgagaaggag gaactggcag aggagctggc cagtagcctg tcgggaagga 5280
acgcactcca ggacgagaag cgccgcctgg aggcccggat cgcccagctg gaggaggagc 5340
tggaggagga gcagggcaac atggaggcca tgagcgaccg ggtccgcaaa gccacacagc 5400
aggccgagca gctcagcaac gagctggcca cagagcgcag cacggcccag aagaatgaga 5460
gtgcccggca gcagctcgag cggcagaaca aggagctccg gagcaagctc cacgagatgg 5520
agggggccgt caagtccaag ttcaagtcca ccatcgcggc gctggaggcc aagattgcac 5580
agctggagga gcaggtcgag caggaggcca gagagaaaca ggcggccacc aagtcgctga 5640
agcagaaaga caagaagctg aaggaaatct tgctgcaggt ggaggacgag cgcaagatgg 5700
ccgagcagta caaggagcag gcagagaaag gcaatgccag ggtcaagcag ctcaagaggc 5760
agctggagga ggcagaggag gagtcccagc gcatcaacgc caaccgcagg aagctgcagc 5820
gggagctgga tgaggccacg gagagcaacg aggccatggg ccgcgaggtg aacgcactca 5880
agagcaagct caggcgagga aacgagacct ctttcgttcc ttctagaagg tctggaggac 5940
gtagagttat tgaaaatgca gatggttctg aggaggaaac ggacactcga gacgcagact 6000

-continued

```
tcaatggaac caaggccagt gaataagcaa ctttctacag ttttgcacca cggcaagaaa   6060

accaaaaacc aaaacaaaca aacaaaaaaa acccaacaac aacccagaac aaagcaaaac   6120

ccagcagact gtacttagca ttgtctaaat ccattctcaa attccaaata tcacagacac   6180

ccctcacaca aggaatataa aaaccaccac cctccagcct gggcaacgta gtaaaacctc   6240

atctatacaa gaatttaaaa ataagctggg cgtggtggta cacacctgtg gtcccagcta   6300

ctagggaggc tgagccagga agaacgctcc agcccaggac ttcgaggctg caatgagcta   6360

taattgcatc attgcactcc agcctgggca acagagaccc tgtctcaacc accaccacca   6420

ccaccacccc tactacccct gtattcaagg taaaaattga agtttgtatg atgtaagaga   6480

tgagaaaaac ccaacaggaa acacagacac atcctccagt tctatcaatg gattgtgcag   6540

acactgagtt tttagaaaaa catatccacg gtaaccggtc cctggcaatt ctgtttacat   6600

gaaatgggga gaaagtcacc gaaatgggtg ccgccggccc ccactcccaa ttcattccct   6660

aacctgcaaa cctttccaac ttctcacgtc aggcctttga gaattctttc cccctctcct   6720

ggtttccaca cctcagacac gcacagttca ccaagtgcct tctgtagtca catgaattga   6780

aaaggagacg ctgctcccac ggaggggagc aggaatgctg cactgtttac accctgactg   6840

tgcttaaaaa cactttcact aataaatggt tataaatcac aa                      6882
```

<210> SEQ ID NO 82
<211> LENGTH: 3658
<212> TYPE: DNA
<213> ORGANISM: Homo sapiens

<400> SEQUENCE: 82

```
aatgcaaggg ggagttcaat gaaactggga catctataca catgtgaggg agcctgggct     60

ggaagaggca gcaaaaggga aaatcagaag agtggacact ggcaagagga gggcagcctt    120

tttcccagct tccttgcacc atggacagct cccattaagc cacctctcca tcctggggcc    180

aggactctta tgccccattc ctgtcaaatt gagatttcat ccaccattct ccaaggacag    240

tgaagttata ccctagttcc agtgttggga tcagtggccc ctctggacat gcctctcctg    300

gaaggttctg tgggggtgga ggatcttgtc ctcctggaac ccttggtgga ggagtcactg    360

ctcaagaatc ttcagcttcg ctatgaaaac aaggagattt atacctacat tgggaatgtg    420

gtgatctcag tgaatcccta tcaacagctt cccatctatg ggccagagtt cattgccaaa    480

tatcaagact atactttcta tgagctgaag ccccatatct acgcattggc aaatgtggcg    540

taccagtcac tgagggacag ggaccgagac cagtgtatcc tcatcacagg cgagagtgga    600

tcagggaaga ctgaggccag caagctggtg atgtcttatg tggctgccgt ctgtgggaaa    660

ggagagcagg tgaactctgt gaaggagcag ctgctacagt ctaacccagt gctggaggct    720

tttggcaatg ccaagaccat tcgcaacaac aattcctccc gatttggaaa atacatggat    780

attgaatttg acttcaaggg atcccccctc ggtggtgtca tcacaaacta tctgcttgag    840

aaatcccgat tagtgaagca gctcaaagga gaaaggaact tccacatctt ctatcagctg    900

ctggctggag cagatgaaca gctgctgaag gccctgaagc ttgagcggga tacaactggc    960

tatgcctatc tgaatcatga agtatccaga gtggatggca tggacgacgc ctccagcttc   1020

agggctgtac agagtgcaat ggcagtgatt gggttctcgg aggaggagat tcgacaagtg   1080

ctagaggtga catccatggt gctaaagctg gggaacgtgt tggtggctga tgagttccag   1140

gccagtggga taccagcaag tggcatccgt gatgggagag gtgttcggga gattggggag   1200

atggtgggct tgaattcaga agaagtagag agagctttgt gctcgaggac catggaaaca   1260
```

-continued gccaaggaaa aggtggtcac tgcactgaat gttatgcagg ctcagtatgc tcgggacgcc 1320
ctggctaaga acatctacag ccgcctcttt gactggatag tgaatcgaat caatgagagc 1380
atcaaggtgg gcatcgggga aaagaagaag gtaatgggag tccttgatat ctacggtttt 1440
gagatattag aggataatag ctttgagcaa tttgtgatca actactgcaa tgagaagctg 1500
cagcaggtgt tcatagagat gaccctgaaa gaagagcaag aggaatataa gagagaaggc 1560
ataccgtgga caaaggtgga ctactttgat aatggcatca tttgtaagct cattgagcat 1620
aatcagcgag gtatcctggc catgttggat gaggagtgcc tgcggcctgg ggtggtcagt 1680
gactccactt tcctagcaaa gctgaaccag ctcttctcca agcatggcca ctacgagagc 1740
aaagtcaccc agaatgccca gcgtcagtat gaccacacca tgggcctcag ctgcttccgc 1800
atctgccact atgcgggcaa ggtgacatac aacgtgacca gctttattga caagaataat 1860
gacctactct tccgagacct gttgcaggcc atgtggaagg cccagcaccc cctccttcgg 1920
tccttgtttc ctgagggcaa tcctaagcag gcatctctca aacgccccc gactgctggg 1980
gcccagttca agagttctgt ggccatcctc atgaagaatc tgtattccaa gagccccaac 2040
tacatcaggt gcataaagcc caatgagcat cagcagcgag gtcagttctc ttcagacctg 2100
gtggcaaccc aggctcggta cctgggactg ctggagaacg tacgggtgcg acgggcaggc 2160
tatgcccacc gccagggtta tgggcccttc ctggaaaggt accgattgct gagccggagc 2220
acctggcctc actggaatgg gggagaccgg gaaggtgttg agaaggtcct gggggagctg 2280
agcatgtcct cgggggagct ggcctttggc aagacaaaga tcttcattag aagccccaag 2340
actcttttct acctcgaaga acagaggcgc ctgagactcc agcagctggc cacactcata 2400
cagaagattt accgaggctg gcgctgccgc acccactacc aactgatgcg aaagagtcag 2460
atcctcatct cctcttggtt tcggggaaac atgcaaaaga aatgctatgg gaagataaag 2520
gcatccgtgt tattgatcca ggcttttgtg agagggtgga aggcccgaaa gaattatcgc 2580
aaatatttcc ggtcagaggc tgccctcacc ttggcagatt tcatctacaa gagcatggta 2640
cagaaattcc tactggggct gaagaacaat ttgccatcca caaacgtctt agacaagaca 2700
tggccagccg ccccctacaa gtgcctcagc acagcaaatc aggagctgca gcagctcttc 2760
taccagtgga agtgcaagag gttccgggat cagctgtccc cgaagcaggt agagatcctg 2820
agggaaaagc tctgtgccag tgaactgttc aagggcaaga aggcttcata tccccagagt 2880
gtccccattc cattctgtgg tgactacatt gggctgcaag ggaaccccaa gctgcagaag 2940
ctgaaaggcg gggaggaggg gcctgttctg atggcagagg ccgtgaagaa ggtcaatcgt 3000
ggcaatggca agacttcttc tcggattctc ctcctgacca agggccatgt gattctcaca 3060
gacaccaaga agtcccaggc caaaattgtc attgggctag acaatgtggc tggggtgtca 3120
gtcaccagcc tcaaggatgg gctctttagc ttgcatctga gtgagatgtc atcggtgggc 3180
tccaaggggg acttcctgct ggtcagcgag catgtgattg aactgctgac caaaatgtac 3240
cgggctgtgc tggatgccac gcagaggcag cttacagtca ccgtgactga gaagttctca 3300
gtgaggttca aggagaacag tgtggctgtc aaggtcgtcc agggccctgc aggtggtgac 3360
aacagcaagc tacgctacaa aaaaaagggg agtcattgct tggaggtgac tgtgcagtga 3420
ggagggggca ccatgcagag atggcagttg cttcctcctg aaccagcact aatccccctc 3480
tgccctcctg tgtgggagga tctctaaccc ctctgatcgt ggcgcatggc ttggggatta 3540
aactaccctt gaagaggacc cttgtcccaa acccttcttg ttctctcctc caaaagtagc 3600

```
ttcctccaac ccgcagcctc tctgcacact aataaaacat gtggcttgga aaggttca     3658


<210> SEQ ID NO 83
<211> LENGTH: 4499
<212> TYPE: DNA
<213> ORGANISM: Homo sapiens

<400> SEQUENCE: 83

gccgccgccg cggccaagcg agcgccgtcg gggcgggtgg gcgggaagaa gcggcgggcc     60

cgaggtgggg gggagcagag agagcgcgcc caccaccttc ccttcccccc tcgatgggag    120

cgggggcgtc ccggctcctg cagccgccag aggagggaga gccgggggcc gtcgcttcgg    180

agttggggct gagcagtcct cggggagagc gcgccaagac cgctgcagcc gctggctgac    240

ggaaggagag ttttacatgg aagtggctta cagaaacttg gcgctgaggt gcagggaagc    300

cagaaactct ttgtgtctct aaggccgatg aggaatttgg aaacacatgt gggacataca    360

agcgttggat atagaggact gagcaggggg aggaacattt aagctgatgg aagtggaagt    420

ggaagttgct gtacattggc agcaaggcct ccgagttagc ttttgaatgc agttaactgg    480

tttctcttaa ctgtggaatt cattgaaaag tcagactccg agtggtcgtt ccaggatatc    540

ttgaaaagcc caggttaaac ccatccagag taatggctgc ggccttaccc aggaccctgg    600

gggagttgca gctgtataga atattacaaa aagccaatct actttcttat tttgatgcct    660

ttatccaaca aggtggtgat gatgtccagc aactctgtga agcaggagaa gaggagtttt    720

tggaaatcat ggcactcgtg ggcatggcta gcaagcccct tcatgttaga aggctgcaga    780

aggctttgag agactgggtc acaaaccctg ggcttttcaa tcagccactg acttcccttc    840

ctgtcagtag catacccatc tataaattac cagagggatc accaacatgg ctgggaatat    900

cctgcagtag ttatgaaagg agtagcaatg cccgggaacc tcatttaaaa atccccaaat    960

gtgctgccac cacctgtgtg cagagcttgg gacaggggaa gtcagatgtg gttgggagcc   1020

tagcactgca gagtgttggt gagtccagac tctggcaagg ccaccatgcc actgagagcg   1080

agcacagcct ctccccagca gacctgggct cccccgcgtc cccaaaggag agcagtgagg   1140

cgctggatgc tgctgctgcg ctctctgtgg ctgagtgtgt ggagcggatg gcccccacac   1200

tgccaaaaag tgacttgaat gaagtgaaag agctgctaaa aaccaacaag aagttggcca   1260

aaatgattgg tcacatcttt gagatgaacg atgatgatcc acacaaagag gaggaaattc   1320

ggaaatacag tgcaatatat ggcagatttg actcaaagag gaaggatggg aaacatctca   1380

cacttcatga gctcactgtt aatgaagcgg ctgctcaact ctgtgtgaag gataatgccc   1440

tgctgacaag aagagatgag ctttttgcct tggctcgaca gatttctcga gaagtcacct   1500

ataaatatac ttacagaacc accaagtcaa aatgtggaga aagagatgaa ttatccccaa   1560

agagaattaa agtggaggat gggtttccag atttccagga ttctgtgcaa acactcttcc   1620

agcaggctag agctaagagt gaagaacttg cagctcttag ttcacagcag cctgaaaagg   1680

tgatggcaaa gcagatggag ttcctttgca accaagctgg ctatgagaga ctgcagcatg   1740

ccgagaggag gttgtctgca gggctttaca ggcagagctc agaagagcac agtcctaacg   1800

gcttgacttc cgataactca gatggacaag gagaaagacc tttgaatctc cgaatgccta   1860

atttacagaa cagacaaccc catcattttg tggtggatgg ggagctgagc agactttacc   1920

ccagtgaggc aaagtcccac tcatcagaga gccttgggat tttaaaagac taccctcatt   1980

cagcttttac cttagaaaag aaagtcatca aaacagagcc tgaagattca agatagctgt   2040

gatttctctc accgttctct ggaaatggca tcagatttaa ggataatact ccatcataga   2100
```

```
aataagcctt aataaccagt gttgcctcat tcagctcaaa cagatttcat agccaaagca   2160
aaaggactgg tacggtagtc tgtggaaacc aggaagataa aacaacagcc acaaaagaga   2220
aaatcaagag tgttgcaatc tataacagta atattgattc attcacattc ctgtgttaag   2280
tcattttata tggaaaggct tacaaatcaa tattgtaagc attcattatt taagaatgta   2340
caatgtattt gtgtaattta tagaagtaaa atctagatgt tgagacctgt ttggtctaat   2400
agatgtggat acagtttatt ttacttgaaa ttttgttgtc tactttgtgt gtttaacgta   2460
aatatatgtc agagtttaga atctgcctgc agttgtgaaa aagaaagctt aagtgatgca   2520
gttattggca agattgcaat gattatggaa aaatagaaag cgaatactca gtttaagcca   2580
aggaaaatat tgtggattta atatttgata aaactgattt tgtttaacag gaaattttta   2640
gcattcagtc atataacatc tggttatcaa tgcacgttta cacaataaat acttgagtgg   2700
aggaaagtta aaaagatgag caatagagta gaaaatatat cttaaactag ttgacctaga   2760
ttgtattaat agctacttaa gatgtttcaa agataggaag ctattgcttg gacagagaac   2820
ttgaaataag tggacccatg tataaaagct ttgacttaaa cattgatatt tcagaatgtg   2880
ttaaatagat taagacacag taagttaacc ctacatgtta taaagatggc gactgttaac   2940
aaaggctgta acagattaag tactatttta tatccagaaa gtcttctcta tgtagagaag   3000
tcagagagac tagatgcttt cactagggaa tgtcttccca cccagccatc acaaatgtgg   3060
acaatcactg catccacatc tgtaggcata tttctatgga agtttaattg acagctatat   3120
tcattattta ttttacaatt tcatttttct acacctttga gatttatgaa tgcagttttt   3180
tcttaaaatt tattttaact tgacagtatg tttttagttc ccccaattta attaatggac   3240
catgtgcata tatatgggag tgtgcttaca tgttaataat ttacttgcat acttatgaga   3300
atttcacatt ggaattcata atggtaaaac aacatacatc tgccaatata cgttttttct   3360
gttggtttaa gagaagataa ctgacagctt tacctacttc ctacagatgc atctaaaccc   3420
agatattact gagaagagtg tattgactct gagtgtaaga gagtatgtgt tttttttgttt   3480
ttagttctgc tctagatcat aattgtaaaa aatattaagt cataatctgt tacactaaaa   3540
tttgtcagcc aaatgttaga tgaaatgtct gcactgtagt ctcagatcac tgtcacgtat   3600
ataaattgct tcttcatttt aatttgtaga agtactttac agtaggaaac gccagtaaac   3660
aacttttata ctgttaaaag gctttttcc ccttcctaaa tgttttaatt gtaccatagt   3720
gttttgctca ctgaagaagc ttcttatgga ccttgcaact ttgttgctag cttgaggttg   3780
attattgtgg ttgtattgtt cactgtgtgt agaaatagta tgagtacgat ttcaatagac   3840
tgttcagttt ttaatattag ccatagcact ggttagtata tctcagtagt ttcatgaaac   3900
gtttcctgta ttctaatcta ttttgaaaca ttttgttttt ttttaattgt gtcttacagt   3960
caagtttgta gattttcata agccacaatt ttaaaagatg cagtaatctt ccaacttcca   4020
atatttatcc attcgttgtg gacccacaga ttgcatcttt aaattcataa taagtttcct   4080
taactatctt atgtttctag tctttcaagc ttagtgataa ggtggaagca caagaaaaat   4140
ttcagtagaa tacagttttt attttgtaaa cactaatgta ttaaacttgc tatacattaa   4200
agcaaataat atatattttt atttgaattg tatatgtgaa ttggaagtta taattagttg   4260
atttttcat tttgttagag gtattttcac tgaacaaggt caattggtta cctcagtatt   4320
acagccaata tagtccaagg gaccatttct ccccgagtct cttacacttt attgtgcgat   4380
gtccacgttt ttgtgactct tcaagctgtt ggtgaggtgg gacgaatgca cttgcttcct   4440
```

gtggcaataa agattttctg tgcctcacaa aaaaaaaaaa aaaaaaaaaa aaaaaaaaa 4499

<210> SEQ ID NO 84
<211> LENGTH: 3068
<212> TYPE: DNA
<213> ORGANISM: Homo sapiens

<400> SEQUENCE: 84
cacatggaaa ctgttcttaa agctgctggg ccctgaaatt ttactcagca gtttgaaatc 60
aagacatagc ttttctcatt caccctccca cttggggcta atgcacagac atgaacatct 120
attgaggaaa accacaaaaa acttcaaaac agctacaacg gtatcctaag aatatttcaa 180
ttaaatatta gtatgtctgc tgaaggcact taattattaa gaaacttaaa attatcaatc 240
tttcttgaat ttctgataga gaagtaaaac tattttccaa aactattttt cagaatgttc 300
actgatacat aaaaactgct agcatctaat taaagatcac taagggttaa atactgttct 360
ctggccctta ctgcgcacac cctgccaaaa catcctctaa gcttttaaat attgcttcga 420
tggtctgaat ttttatttcc agggaaaaag agagttttgt cccacagtca gcaggccact 480
agtttattaa cttccagtca ccttgatttt tgctaaaatg aagactctgc agtctacact 540
tctcctgtta ctgcttgtgc ctctgataaa gccagcacca ccaacccagc aggactcacg 600
cattatctat gattatggaa cagataattt tgaagaatcc atatttagcc aagattatga 660
ggataaatac ctggatggaa aaaatattaa ggaaaaagaa actgtgataa tacccaatga 720
gaaaagtctt caattacaaa aagatgaggc aataacacca ttacctccca agaaagaaaa 780
tgatgaaatg cccacgtgtc tgctgtgtgt ttgtttaagt ggctctgtat actgtgaaga 840
agttgacatt gatgctgtac caccccttacc aaaggaatca gcctatcttt acgcacgatt 900
caacaaaatt aaaaagctga ctgccaaaga ttttgcagac atacctaact taagaagact 960
cgattttaca ggaaatttga tagaagatat agaagatggt actttttcaa aactttctct 1020
gttagaagaa ctttcacttg ctgaaaatca actactaaaa cttccagttc ttcctcccaa 1080
gctcacttta tttaatgcaa aatacaacaa aatcaagagt aggggaatca aagcaaatgc 1140
attcaaaaaa ctgaataacc tcaccttcct ctacttggac cataatgccc tggaatccgt 1200
gcctcttaat ttaccagaaa gtctacgtgt aattcatctt cagttcaaca acatagcttc 1260
aattacagat gacacattct gcaaggctaa tgacaccagt tacatccggg accgcattga 1320
agagatacgc ctggagggca atccaatcgt cctgggaaag catccaaaca gttttatttg 1380
cttaaaaaga ttaccgatag ggtcatactt ttaacctcta ttggtacaac atataaatga 1440
aagtacacct acactaatag tctgtctcaa caatgagtaa aggaacttaa gtattggttt 1500
aatattaacc ttgtatctca ttttgaagga atttaatatt ttaagcaagg atgttcaaaa 1560
tcttacatat aataagtaaa aagtaagact gaatgtctac gttcgaaaca aagtaatatg 1620
aaaatattta aacagcatta caaaatccta gtttatacta gactaccatt taaaaatcat 1680
gtttttatat aaatgcccaa atttgagatg cattattcct attactaatg atgtaagtac 1740
gaggataaat ccaagaaact ttcaactctt tgcctttcct ggcctttact ggatcccaaa 1800
agcatttaag gtacatgttc caaaaacttt gaaaagctaa atgtttccca tgatcgctca 1860
ttcttctttt atgattcata cgttattcct tataaagtaa gaactttgtt ttcctcctat 1920
caaggcagct attttattaa atttttcact tagtctgaga aatagcagat agtctcatat 1980
ttaggaaaac tttccaaata aaataaatgt tattctctga taaagagcta atacagaaat 2040
gttcaagtta ttttactttc tggtaatgtc ttcagtaaaa tattttcttt atctaaatat 2100
taacattcta agtctaccaa aaaaagtttt aaactcaagc aggccaaaac caatatgctt 2160
ataagaaata atgaaaagtt catccatttc tgataaagtt ctctatggca aagtctttca 2220
aatacgagat aactgcaaaa tattttcctt ttatactaca gaaatgagaa tctcatcaat 2280
aaattagttc aagcataaga tgaaaacaga atattctgtg gtgccagtgc acactacctt 2340
cccacccata cacatccatg ttcactgtaa caaactgaat attcacaata aagcttctga 2400
gtaacacttt ctgattactc atgataaact gacatggcta actgcaagaa ttaaatcttc 2460
tatctgagag taataattta tgatgactca gtggtgccag agtaaagttt ctaaaataac 2520
attcctctca cttgtacccc actaaaagta ttagactaca cattacattg aagttaaaca 2580
caaaattatc agtgttttag aaacatgagt ccggactgtg taagtaaaag tacaaacatt 2640
atttccacca taaagtatgt attgaaatca agttgtctct gtgtacagaa tacatactta 2700
ttcccatttt taagcatttg cttctgtttt ccctacctag aatgtcagat gtttttcagt 2760
tatctcccca tttgtcaaag ttgacctcaa gataacattt ttcattaaag catctgagat 2820
ctaagaacac aattattatt ctaacaatga ttattagctc attcacttat tttgataact 2880
aatgatcaca gctattatac tactttctcg ttattttgtg tgcatgcctc atttccctga 2940
cttaaacctc actgagagcg caaaatgcag ctttatactt tttactttca attgcctagc 3000
acaatagtga gtacatttga attgaatata taataaatat tgcaaaataa aatccatcta 3060
aatagaaa 3068

<210> SEQ ID NO 85
<211> LENGTH: 1020
<212> TYPE: DNA
<213> ORGANISM: Homo sapiens

<400> SEQUENCE: 85
ggccttccaa agtgctggga ttacaggcgt gagtcaccgc gcccggccaa ataaaataaa 60
atgttaaagc aaattcagga ctacccctcc tccaagtctt ctgttccctt tgggcgccca 120
ggtgagcggg ggaggggctg ggggagtaat aacatcaaaa gagcgccttt tcctccctta 180
ttccgaggag acttccctgg gcctgactcc cggtcctgtc cccagcgccc cgcggcctct 240
ggagcccctt cagtgaccaa gatacagaga tcaggacgcc tttgcgccgc cccaggtgcc 300
cgcccctagc tggctctgct tgggccgcga gggaaggtga ggtcgggggc ggagccgggg 360
cgtgacagcc ggggtgtgtg tccgccgggc ttggtgcctc cggtggccct gcagcaccgt 420
cccacctctg ccaccctccg atggggccgc tacctgtgtg cctgccaatc atgctgctcc 480
tgctactgcc gtcgctgctg ctgctgctgc ttctacctgg ccccgggtcc ggcgaggcct 540
ccaggatatt acgtgtgcac cggcgtggga tcctggaact ggcaggaact gtgggttgtg 600
ttggtccccg aacccccatc gcctatatga aatatggttg cttttgtggc ttgggaggcc 660
atggccagcc ccgcgatgcc attgactggt gctgccatgg ccacgactgt tgttacactc 720
gagctgagga ggccggctgc agccccaaga cagagcgcta ctcctggcag tgcgtcaatc 780
agagcgtcct gtgcggaccg gcagagaaca aatgccaaga actgttgtgc aagtgtgacc 840
aggagattgc taactgctta gcccaaactg agtacaactt aaagtacctc ttctaccccc 900
agttcctatg tgagccggac tcgcccaagt gtgactgact accttgactt gaaatgctct 960
tttgcacaag gaaataaagc gtcctctcag taatgaaaaa aaaaaaaaaa aaaaaaaaaa 1020

<210> SEQ ID NO 86

<211> LENGTH: 7434
<212> TYPE: DNA
<213> ORGANISM: Homo sapiens

<400> SEQUENCE: 86
gcctgggaaa gatgctggat cctgcagtaa ccacaacagc atcctctccc tgcgccaggg 60
acctgccagc cggagagatg actgattaga tcagattaga tccggagccc cgctctgcag 120
aagggggccc caggggcggg ggaggaggac cccagctggc ctgagctggg gggaggggtg 180
ccttggggct cgcagagtta gagctttcca gcgcggggat cacacctcag aagccgccac 240
aatgaaagac ggaacacatt tctacaccca gtgactggcc aggtcccaga ggaaaacaaa 300
aaatttgact tgaaaatatc gaccttggac atgtccaata aaacaggtgg gaaacgcccg 360
gctaccacca acagtgacat acccaaccac aacatggtgt ccgaggtccc tccagagcgg 420
cccagcgtcc gggcaactcg cacagcccgc aaagccgtcg cctttggcaa gcgctcacac 480
tccatgaagc ggaaccccaa tgcacctgtc accaaggcgg gctggctctt caaacaggcc 540
agctccgggg ttaagcagtg gaacaagcgc tggttcgtcc tggtggatcg ctgcctcttc 600
tactataaag atgagaagga agagagtatc ctgggcagca tcccccctcct gagcttccgg 660 gtagccgcag tgcagccctc agacaacatc agccggaaac acacgtttaa ggctgagcat 720
gccggggtcc gcacctactt cttcagtgcc gagagccccg aggagcaaga ggcctggatc 780
caggccatgg gggaggctgc tcgagtacag atccctccag cccagaagtc agtgccccaa 840
gctgtgcggc acagccatga gaagccagac tcggagaacg tcccacccag caagcaccac 900
cagcagccac cccacaacag cctccctaag cctgagccag aggccaagac tcgaggggag 960
ggtgatggcc gaggctgtga gaaggcagag agaaggcctg agaggccaga agtcaagaaa 1020
gagcctccgg tgaaagccaa tggcctccca gctggaccgg agccagcctc agagccgggc 1080
agcccttacc ccgagggccc aagagtgcca gggggtgggg aacagcctgc ccagcccaat 1140
ggctggcagt accactcccc aagccggcca gggagcacag ctttcccgtc tcaggatgga 1200
gagactgggg gacaccggcg gagtttccca ccacgcacca accctgacaa aattgcccag 1260
cgcaagagct ccatgaacca gcttcagcag tgggtgaatc tgcgccgggg ggtacccccg 1320
cctgaagacc ttcggagtcc ctctaggttc tatcctgtgt ctcgcagggt ccctgagtac 1380
tatggcccct actcctccca gtaccccgat gattatcagt actacccgcc aggagtgcgg 1440
ccggagagca tctgttccat gccggcctat gatcggatca gcccgccctg ggccctggag 1500
gacaagcgcc atgccttccg caatgggggt ggccctgcct accagctgcg agagtggaag 1560
gagcccgcca gctacgggcg gcaggatgcc accgtctgga tcccaagccc ctcccggcag 1620
ccagtctatt atgatgagct ggatgccgcc tctagctccc tgcgccgcct gtccctgcag 1680
ccccgctccc actctgtgcc ccgctcaccc agccagggct cctacagccg tgcccgcatt 1740
tactcccctg tccgctcacc cagtgcccgt tttgagcggc tgccacctcg cagtgaggac 1800
atctatgctg accctgctgc ctatgtgatg aggcgatcca tcagctcccc caaggtccct 1860
ccatacccag aagtgttccg ggacagcctc cacacctaca agttaaacga gcaagacaca 1920
gataagctgc tgggaaaatt gtgtgagcag aacaaggtgg tgagggagca ggaccggctg 1980
gtgcagcagc tccgagctga gaaggagagc ctggaaagtg ccttgatggg gacccaccag 2040
gagctggaga tgtttggaag ccagcccgcc tacccagaaa agctgcgaca caaaaaggat 2100
tcactgcaga accagctcat caacatccgc gtggagctgt ctcaggcgac cacggccctg 2160
acaaacagca ccatagagta tgagcacctc gagtctgagg tctctgccct gcacgatgac 2220

```
ctctgggagc agctcaattt ggacacccag aatgaggtgc tgaaccggca aatccaaaag   2280
gagatctgga ggatccagga cgtgatggag gggctgagga agaacaaccc ctcccggggc   2340
acggacaccg ccaagcacag aggaggactt ggcccctcag ccacctacag ctccaacagc   2400
ccggccagcc ccctcagctc tgccagcctc accagccccc tgagcccctt ttcactggtg   2460
tcgggctctc aggggtcccc caccaagcct ggctccaacg agcccaaggc aaactatgaa   2520
caaagcaaga aagaccccca ccagacattg cccctggaca cccccagaga catcagcctt   2580
gtgcccacca ggcaagaggt agaggcagag aagcaggcag ctctcaacaa agttggcgtt   2640
gtgccccctc ggacaaaatc gcccactgat gatgaggtga ccccatcagc agtggtaaga   2700
aggaatgcca gtgggctcac caatggactc tcctcccagg aacgccccaa gagtgctgtg   2760
tttcctggcg aggggaaggt caagatgagc gtggaggagc agattgaccg aatgcggcgg   2820
caccagagtg gctccatgag ggagaagcgg aggagcctgc agctcccggc cagcccggcc   2880
cccgacccca gtccccggcc agcctacaaa gtggtgcgcc gccaccgcag catccatgag   2940
gtagacatct ccaacctgga ggcagccctg cgggcagagg agcctggcgg gcatgcctac   3000
gagacacccc gggaggaaat tgcccggctt cgcaaaatgg agctagagcc ccagcattat   3060
gacgtggaca tcaataagga gctctccact ccagacaaag tcctcatccc tgaacggtac   3120
attgacctgg agcctgacac tcccctgagc cctgaggagt tgaaggagaa gcagaagaag   3180
gtggagagga tcaagacact cattgccaaa tccagtatgc agaacgtggt gcccatcggc   3240
gagggggact ctgtggacgt gccccaggac tcagagagcc agctgcagga gcaggagaag   3300
cggattgaaa tctcctgcgc cctggcgacc gaggcctccc gcaggggccg catgctgtct   3360
gtgcaatgtg ccaccccaag ccctcccacc tcccctgctt ccccggctcc tccagcaaac   3420
cccctgtcgt ctgaatcccc acggggcgcc gacagcagct ataccatgcg ggtctgagct   3480
ctgactgcaa gccctggctg aggccaatgc tgtgaagctc cacagagcca cattctgaag   3540
ccgtcctctg cccacctgag gtcctggctc cccaccctgg cccccctgccc ctgcactccc   3600
atgggaatgc cgcagggagc caggctgggg ccatgggctg ctgccagagg accgtggata   3660
cctcagtgtc cacacaccca ccatgcccag ccctggagcc atcactactc acaccgtggt   3720
cctgggccag ggcctgagat gacagtgggg agcaccatcc tcattaatgt ccaagtcaca   3780
gggagcctca gccttgccct ggctggggtt gtggtgactc cagtggaaca ttccctgatg   3840
ggggacatgc cgtggtggag aacacacctg tggctatctt atgtgaggac tagaggtgaa   3900
gaggagatgg acactgcctc tggagccagc ctgacaccaa ggacagcact tgtcatcatc   3960
cctatcctcg tcagccccac cctactgcct cagctggacc cagggctttg acacaaaccc   4020
agtgctttgc ttatgggtgc tcgctggggt ccggtggaga ctgaccaccc tgcttgagcc   4080
aaagacaagg tgatgagaga tggggagagg ccattggctc ccagagggaa cagtgctggc   4140
tgtggctaga gaacagcagg tctgtgcagt gtctgagggc aggttgggaa gggtagcaga   4200
gagagagaga cagaaagaga gagagagaga gagagagaga gagatcctca gagtggaagg   4260
agggggaagc agcaggacac attggcaagt caagcaggaa ggagggagat ggaaagggga   4320
tatcagattg gtttcccccg gtggagcctt aggttagtgc ccagtgcagt gccagactgt   4380
ctcctctgct cctcccacct catccctagg aggacccacc agtggagcac atgcagcctc   4440
agtggagatg cttggtgtgg ggatctgggt gaagggggtt gagtagcgac tgcctgggag   4500
atggctgtta gtaggtctgt gcctggtgtc tgcctcgcca tcctggggta aggggcagag   4560
```

-continued

```
agaaggactt gtcttatgta gggtgtggtc agccttgggg ccttacctac ccagttccat   4620
gatatttctt gccctgttcc ccctggaatg tgcagtgggc cagctgagag tacgccttga   4680
ggaggggga tgaggcctta atctgggagg cctatccccc tatcccaggc atcccagacg   4740
aggactggct gaggctaggc gctctcatga tccacctgcc ccgggagggc agcggggaag   4800
acagagaaaa gcaaacgcat tcctcctcag ctccacccac ctggagacga atgtagccag   4860
agaggaggaa ggagggaaac tgaagacacc gtggcccctc ggccttctct ctgctagagt   4920
tgccgctcag aggcttcagc ctgacttcca gcggtcccaa gaacacctac taattcctct   4980
gcactccttc atggctggga cagttactgg ttcatatgca agtaaagatg acaatttact   5040
caacaaatat ttatcgagca ccttttatgt accaggcact gttgtaggtg cttaggatat   5100
tctcatgttt ctgagggatt acagcctggg aggattccac cgatcttcac ttctagcagg   5160
tttttaaac gtgacccttg gctgtatttc ccatcttcac agttcaagca ccccaaacct   5220
gccctttctc ccctgcagac tggcaggtgg gattggctcc caggtcattt cctctctctc   5280
tctttctccc aagcctttct ccctccacag gaaacagatt tttcagggcc ttccatgcct   5340
gccactttgt ccgtctcttt tttttttttt aaagtaatat tttttagaaa tacatgtaaa   5400
ataccaagaa ataatgtctg cgcctctgcc acctctctct catctcttat ttcataaagc   5460
tggctcttta tgttgcttta catgccttaa tatatgtttt atggagatta tacatattat   5520
agatctatat atgtaatata tttgtttgga tgtctgatct tttcctacag ttcctgccca   5580
ggcctgtttt tctctccctt attttccaca tcattcctag catatcaaga ccatacccct   5640
tgccttttttg atccaaagaa ggggagagga aagacttatt ttaagacatc tattttatgc   5700
ttttgtttaa aaaaagcaaa tctattttca aattgtgcaa tgtctgaatg gaattggcaa   5760
atgaggtgag gagatggggt aactgccttt aggtcccaac cctgtgcctg tccctctgcc   5820
acagtggctt ccttccatcc tattccccag tcacgaaagg gctggtcccc agagctcacc   5880
cagaaagcat cttgccgggg gcagggcatt ccctcggaag tcctggccta aggattttat   5940
tacactgtct gctcctgatg accctctgcg gttgtcaggc gtgaatcctc tggaaggaac   6000
tgtttgcagt tgtatgcaca aaggagaccc atgcaggcat gcaccccaga tgggctgcta   6060
gactacccct cttcatcagc ctgctggaaa gagcagacag cgtaacagca gcctatgcca   6120
aacagcacta aggatgtcag tgtacgagac ggtgcgaagc ccagaggagg cggcttggga   6180
tcctctgggc catccctggc cctgtagcac agacacatac aagttccttg gacttgtcac   6240
actcctttc acttgatccc tctctggcct gggtcacatt tatgacatcc cccctctgca   6300
acctttctct ctgggggctg taccaaaggc atggtacctc agtctggtat ccagactgtg   6360
aaatcagcct ctgggccaag gagggtccta cagacaaggt ggcatctcaa cctcacccaa   6420
gaaacccccg ggactttacc ccagcaggct gccactgggg caccgaacta agccagctca   6480
gccttccaag ctgcttagcc tttgtcaacc atcaaagtgg ggaaagggtc tctggccttg   6540
caaggatttg ggcaggatgg aagtctttgt ctaggtctga aatcaagggc ttgggaatct   6600
agagcagagc tcctggccag cgtttgaagc ctggcctccc acctggggca tttactgaca   6660
ccctgtcgcc agcctagaac atcctgctct gaatgaacag agcccagatg gggtccaga    6720
gctaagtgac ccacctgggg aagctctgat tattcatcca gggccttctc aatgagcaca   6780
ttacctccat gatcaataac caagaggctg cagtcaaata ctgctactgt cactttgaag   6840
attttctaag ggcacaagtg gcacacttgc tctccggcct ttgggagagg catgttcttg   6900
ggcagggctg gctacggcaa gagggaacca attcctttcc cctttaggca ccctctacct   6960
```

ggcagctctt aaaactaaga aaaaatatga tatacacaca cattatatat atatatatat 7020
atacacacac acacacacac acacgtatat ctatttatgc acatattggg gccaatttga 7080
tttgctagta ttagacaata aactgtacaa ggaaatttat tatctcagtg tctttattta 7140
gcataaaagt ggccttagaa gaagggtgaa ggttagatag atggaatctc tgtcagggga 7200
caaacagctg tagcatcccc ttagcatctt tctagccaat gagccccctc cccaggagga 7260
gggatggcct gactgaaaca ggtgagagtt tgcttccccc tttcagcagc attcttttta 7320
gatttaggta ctgaagaatc ccagtgagtt ctgcatttgt atcttgcaag tttgtataaa 7380
cccaatacag gaaataaaat gaatggtttg tataaaaaaa aaaaaaaaaa aaaa 7434

<210> SEQ ID NO 87
<211> LENGTH: 3038
<212> TYPE: DNA
<213> ORGANISM: Homo sapiens

<400> SEQUENCE: 87
tcaatcagaa agccctttc attgcaggag aagaggacaa agatactcag agagaaaaag 60
taaaagaccg aagaaggagg ctggagagac caggatcctt ccagctgaac aaagtcagcc 120
acaaagcaga ctagccagcc ggctacaatt ggagtcagag tcccaaagac atgggcttgt 180
tagagtgctg tgcaagatgt ctggtagggg ccccctttgc ttccctggtg gccactggat 240
tgtgtttctt tggggtggca ctgttctgtg gctgtggaca tgaagccctc actggcacag 300
aaaagctaat tgagacctat ttctccaaaa actaccaaga ctatgagtat ctcatcaatg 360
tgatccatgc cttccagtat gtcatctatg gaactgcctc tttcttcttc ctttatgggg 420
ccctcctgct ggctgagggc ttctacacca ccggcgcagt caggcagatc tttggcgact 480
acaagaccac catctgcggc aagggcctga gcgcaacggt aacagggggc cagaagggga 540
ggggttccag aggccaacat caagctcatt ctttggagcg ggtgtgtcat tgtttgggaa 600
aatggctagg acatcccgac aagtttgtgg gcatcaccta tgccctgacc gttgtgtggc 660
tcctggtgtt tgcctgctct gctgtgcctg tgtacattta cttcaacacc tggaccacct 720
gccagtctat tgccttcccc agcaagacct ctgccagtat aggcagtctc tgtgctgatg 780
ccagaatgta tggtgttctc ccatggaatg ctttccctgg caaggtttgt ggctccaacc 840
ttctgtccat ctgcaaaaca gctgagttcc aaatgacctt ccacctgttt attgctgcat 900
ttgtgggggc tgcagctaca ctggtttccc tgctcacctt catgattgct gccacttaca 960
actttgccgt ccttaaactc atgggccgag gcaccaagtt ctgatccccc gtagaaatcc 1020
ccctttctct aatagcgagg ctctaaccac acagcctaca atgctgcgtc tcccatctta 1080
actctttgcc tttgccacca actggccctc ttcttacttg atgagtgtaa caagaaagga 1140
gagtcttgca gtgattaagg tctctctttg gactctcccc tcttatgtac ctcttttagt 1200
cattttgctt catagctggt tcctgctaga aatgggaaat gcctaagaag atgacttccc 1260
aactgcaagt cacaaaggaa tggaggctct aattgaattt tcaagcatct cctgaggatc 1320
agaaagtaat ttcttctcaa agggtacttc cactgatgga aacaaagtgg aaggaaagat 1380
gctcaggtac agagaaggaa tgtctttggt cctcttgcca tctatagggg ccaaatatat 1440
tctctttggt gtacaaaatg gaattcattc tggtctctct attaccactg aagatagaag 1500
aaaaaagaat gtcagaaaaa caataagagc gtttgcccaa atctgcctat tgcagctggg 1560
agaagggggt caaagcaagg atctttcacc cacagaaaga gagcactgac cccgatggcg 1620
atggactact gaagccctaa ctcagccaac cttacttaca gcataaggga gcgtagaatc 1680
tgtgtagacg aagggggcat ctggccttac acctcgttag ggaagagaaa cagggtgttg 1740
tcagcatctt ctcactccct tctccttgat aacagctacc atgacaaccc tgtggtttcc 1800
aaggagctga gaatagaagg aaactagctt acatgagaac agactggcct gaggagcagc 1860
agttgctggt ggctaatggt gtaacctgag atggccctct ggtagacaca ggatagataa 1920
ctctttggat agcatgtctt tttttctgtt aattagttgt gtactctggc ctctgtcata 1980
tcttcacaat ggtgctcatt tcatgggggt attatccatt cagtcatcgt aggtgatttg 2040
aaggtcttga tttgttttag aatgatgcac atttcatgta ttccagtttg tttattactt 2100
atttggggtt gcatcagaaa tgtctggaga ataattcttt gattatgact gttttttaaa 2160
ctaggaaaat tggacattaa gcatcacaaa tgatattaaa aattggctag ttgaatctat 2220
tgggattttc tacaagtatt ctgcctttgc agaaacagat ttggtgaatt tgaatctcaa 2280
tttgagtaat ctgatcgttc tttctagcta atggaaaatg attttactta gcaatgttat 2340
cttggtgtgt taagagttag gtttaacata aaggttattt tctcctgata tagatcacat 2400
aacagaatgc accagtcatc agctattcag ttggtaagct tccaggaaaa aggacaggca 2460
gaaagagttt gagacctgaa tagctcccag atttcagtct tttcctgttt ttgttaactt 2520
tgggttaaaa aaaaaaaaag tctgattggt tttaattgaa ggaaagattt gtactacagt 2580
tcttttgttg taaagagttg tgttgttctt ttccccccaaa gtggtttcag caatatttaa 2640
ggagatgtaa gagctttaca aaaagacact tgatacttgt tttcaaacca gtatacaaga 2700
taagcttcca ggctgcatag aaggaggaga gggaaaatgt tttgtaagaa accaatcaag 2760
ataaaggaca gtgaagtaat ccgtaccttg tgttttgttt tgatttaata acataacaaa 2820
taaccaaccc ttccctgaaa acctcacatg catacataca catatataca cacacaaaga 2880
gagttaatca actgaaagtg tttccttcat ttctgatata gaattgcaat tttaacacac 2940
ataaaggata aacttttaga aacttatctt acaaagtgta ttttataaaa ttaaagaaaa 3000
taaaattaag aatgttctca atcaaaaaaa aaaaaaaa 3038

<210> SEQ ID NO 88
<211> LENGTH: 3720
<212> TYPE: DNA
<213> ORGANISM: Homo sapiens

<400> SEQUENCE: 88
atgcgcagtg gcgcgagcgc agcggctacg cgggcgcgga gaggtagccg cagagtggac 60
ctgcaggtac ttggatctcc agtgggagct gccctctcga aggcaggaca gcggtggcgg 120
cagatataaa gacctgaaga tagtcttttc tgtccaaaga tggaaaacag tactactacc 180
atttctcggg aggagcttga agaactacaa gaggcattta ataaaataga tattgacaat 240
agtgggtatg tcagtgacta tgaacttcaa gacctgttta aggaagcaag ccttcctctg 300
cctggctaca aggtgcgcga gattgtggag aaaattctat cagttgctga cagcaacaaa 360
gatggcaaaa tcagttttga agagtttgtg tcactaatgc aagaattaaa aagcaaagat 420
atcagcaaaa cattccgaaa aataattaac aagagggaag ggattactgc tattggagga 480
acttcaacta tttccagtga gggcacacag cattcttatt cagaggaaga aaaagtggct 540
tttgttaact ggataaacaa agccctggag aatgaccctg actgtaagca tcttataccc 600
atgaatccca atgatgatag tcttttcaag tcacttgcag atggcatcct tctttgcaaa 660
atgatcaact tatctgaacc agatacaatt gatgaaagag ccatcaataa gaaaaagctc 720

```
acgccattca ctatttctga aaatttaaac ctagctctga attctgcctc agccattggt    780
tgtacagtgg tcaacattgg tgcatcagat ctcaaagaag gaaaacctca cttggtcttg    840
ggacttctct ggcagatcat caaagttggc ctttttgctg atattgagat ttccaggaat    900
gaagctctga ttgcattgtt aaatgaaggt gaggaactag aggagctgat gaagctttct    960
cccgaggaat tactgctgcg atgggtgaac taccatctga ccaatgcagg atggcatacc   1020
atcagcaact tcagccaaga cattaaggac tcgagagcct attttcatct gcttaatcag   1080
attgccccta aaggtgggga agatggacct gccattgcca ttgacctttc aggaattaat   1140
gagacaaatg acctgaagcg tgctggactc atgcttcaag aagcagataa actgggctgc   1200
aaacagtttg ttactcctgc agatgtggtt tcaggcaatc ctaaacttaa tttagctttt   1260
gtagctaatt tgtttaacac atacccgtgc ctgcacaagc cgaataataa tgacatcgat   1320
atgaatttac tggaaggaga gagcaaggaa gagagaacat ttcggaactg gatgaattcc   1380
ttgggagtca acccatacat taatcatttg tacagtgacc ttgcagatgc tttagtgatc   1440
tttcagctct atgagatgat ccgagtgcca gtcaactgga gccatgtcaa caaacctcct   1500
tatcctgccc ttggagggaa catgaagaag attgaaaact gtaactatgc agtggaactt   1560
gggaagaaca aggccaaatt ctccttggtt ggcattgctg ggcaggacct aaatgaaggg   1620
aattcaacac ttaccctggc attggtatgg cagctgatga gaaggtacac attgaatgtg   1680
ttatcggatc ttggagaggg tgaaaaagta aatgatgaaa ttataattaa atgggtcaat   1740
cagactctta aaagtgcaaa caaaaagact tctatttcca gcttcaagga taaatctata   1800
agcacaagtt tacctgtcct agatttaata gatgccattg caccaaatgc agttcgtcaa   1860
gaaatgatca ggagagaaaa cttatctgat gaggacaagc tgaacaatgc taaatacgcc   1920
atttcagttg ctcgaaagat cggtgcccgg atatatgcat tacctgatga cctcgtagaa   1980
gtgaaaccaa agatggttat gacggtgttt gcatgcttaa tgggaaaagg actgaacaga   2040
ataaaaataat catttcatat gattttctgc cacattaaac atattgtatg cctcacagtt   2100
tacaggattc tgaaatgtag tgggtgtaaa accagagatt atttgtatgc tcaaaatagt   2160
tatatattca ttaatgaatt caatatcctg ttcatactag ttagagctgg tcagcctttt   2220
tgggtaacac agttaattta ccaactgata cagataatag aatatattca taatcaagct   2280
gatacttcat gattaaatta tttttgttgc ttaaaagtcg tattagacaa gactaaatca   2340
ttctttttta tggttcaaaa aagatgaata caaacgtttt tgcaggttct gctgtgaaat   2400
gtggtttgat ttttttggtg tgttaatttt gatcataaat gcattcatac tcataatcca   2460
gtttaatcct tttatttgct tcctccaact atttaaagtg gtccaaaaac acttttctgt   2520
aagtttctat actgtctaaa accttatggt gaccagaatt gtttattaat atcaaacttt   2580
tttatatatg agaactaatt cttgaataaa ccccaaagtt cactctcttg tttaagtagc   2640
agcagctttt tacttaaaat ttaattttaa ctacattgat actttacaca tcctagtttg   2700
gtaacacagc tttaactatg tcatgcaaca tatatatgtt ggtaggatgt tattagagag   2760
atatgtgtgc atatatattt ttttgcacct gaatcaccca gcttttcata agtggtatgt   2820
ttaattggtc attcagccaa ccatcagtat tttcccccca caacatgtgt aacacttttc   2880
agtctgtgga tatctgatac attaagattt ctttttataa gtattcattt tgaatgtgca   2940
tatagttatt tgacccccttc caaatacttg tagccaaaca ttggctagaa catcccaaga   3000
tatgctgaca ctgtcctgtt agcttcatat tatacttgct agtttaggtc tctatagaag   3060
```

```
ccctatataa tttagaatat gcccactgaa tatctttaat agaaagtaac ataaagctag   3120
tattcaatgt agagtatttt catatgtttt tcacagcccg ttacaaattg gcaatgtttg   3180
gttaatgttt gtattacttg gaaatcgcta cagcttggac tattttttc taaattttta   3240
gcattagtcc atttctgctg ctaacaattg aatccagaaa tctactttct ccatcttcca   3300
ctgttagtgc cagtgagcaa tactgttgtg caacaaaaat gtcactttat ctcagtgtga   3360
atgagtagtc taaattccct ttctaccatt gatttaaata tatatattgg taagagagac   3420
tgcccatgtg tttagaatag aattttttaa atgaaatgat caacaggtgg aatttgaaat   3480
atattcttct acaaaagaga tttctttccc ttttatattt tgatgattgt tttcttaaga   3540
ttaagatatg ttcttgctct tttataagat tatttaaatt atgtttccct ctgatttttt   3600
ttcaccattg tatttactaa gttattggat ttacatgaaa tctggcactt tagggtgttc   3660
tttttctcac agagtatatt taataaaaat gctgtgtata tagaaaaaaa aaaaaaaaaa   3720
```

```
<210> SEQ ID NO 89
<211> LENGTH: 3390
<212> TYPE: DNA
<213> ORGANISM: Homo sapiens

<400> SEQUENCE: 89
```

```
agactctcag gttgatgcag tgttccctcc cacaactctg acatgtatat aaattctgag     60
ctctccaaag cccactgcca gttctcttcg ggactaact gcaacggaga gactcaagat    120
gattcccttt ttacccatgt tttctctact attgctgctt attgttaacc ctataaacgc    180
caacaatcat tatgacaaga tcttggctca tagtcgtatc aggggtcggg accaaggccc    240
aaatgtctgt gcccttcaac agattttggg caccaaaaag aaatacttca gcacttgtaa    300
gaactggtat aaaaagtcca tctgtggaca gaaaacgact gtgttatatg aatgttgccc    360
tggttatatg agaatggaag gaatgaaagg ctgcccagca gttttgccca ttgaccatgt    420
ttatggcact ctgggcatcg tgggagccac cacaacgcag cgctattctg acgcctcaaa    480
actgagggag gagatcgagg gaaagggatc cttcacttac tttgcaccga gtaatgaggc    540
ttgggacaac ttggattctg atatccgtag aggtttggag agcaacgtga atgttgaatt    600
actgaatgct ttacatagtc acatgattaa taagagaatg ttgaccaagg acttaaaaaa    660
tggcatgatt attccttcaa tgtataacaa tttggggctt ttcattaacc attatcctaa    720
tggggttgtc actgttaatt gtgctcgaat catccatggg aaccagattg caacaaatgg    780
tgttgtccat gtcattgacc gtgtgcttac acaaattggt acctcaattc aagacttcat    840
tgaagcagaa gatgaccttt catcttttag agcagctgcc atcacatcgg acatattgga    900
ggcccttgga agagacggtc acttcacact ctttgctccc accaatgagg cttttgagaa    960
acttccacga ggtgtcctag aaaggatcat gggagacaaa gtggcttccg aagctcttat   1020
gaagtaccac atcttaaata ctctccagtg ttctgagtct attatgggag gagcagtctt   1080
tgagacgctg gaaggaaata caattgagat aggatgtgac ggtgacagta taacagtaaa   1140
tggaatcaaa atggtgaaca aaaaggatat tgtgacaaat aatggtgtga tccatttgat   1200
tgatcaggtc ctaattcctg attctgccaa acaagttatt gagctggctg gaaaacagca   1260
aaccaccttc acggatcttg tggcccaatt aggcttggca tctgctctga ggccagatgg   1320
agaatacact ttgctggcac ctgtgaataa tgcattttct gatgatactc tcagcatgga   1380
tcagcgcctc cttaaattaa ttctgcagaa tcacatattg aaagtaaaag ttggccttaa   1440
tgagctttac aacgggcaaa tactggaaac catcggaggc aaacagctca gagtcttcgt   1500
```

atatcgtaca gctgtctgca ttgaaaattc atgcatggag aaagggagta agcaagggag 1560
aaacggtgcg attcacatat tccgcgagat catcaagcca gcagagaaat ccctccatga 1620
aaagttaaaa caagataagc gctttagcac cttcctcagc ctacttgaag ctgcagactt 1680
gaaagagctc ctgacacaac ctggagactg gacattattt gtgccaacca atgatgcttt 1740
taagggaatg actagtgaag aaaaagaaat tctgatacgg gacaaaaatg ctcttcaaaa 1800
catcattctt tatcacctga caccaggagt tttcattgga aaaggatttg aacctggtgt 1860
tactaacatt ttaaagacca cacaaggaag caaaatcttt ctgaaagaag taaatgatac 1920
acttctggtg aatgaattga aatcaaaaga atctgacatc atgacaacaa atggtgtaat 1980
tcatgttgta gataaactcc tctatccagc agacacacct gttggaaatg atcaactgct 2040
ggaaatactt aataaattaa tcaaatacat ccaaattaag tttgttcgtg gtagcacctt 2100
caaagaaatc cccgtgactg tctatacaac taaaattata accaaagttg tggaaccaaa 2160
aattaaagtg attgaaggca gtcttcagcc tattatcaaa actgaaggac ccacactaac 2220
aaaagtcaaa attgaaggtg aacctgaatt cagactgatt aaagaaggtg aaacaataac 2280
tgaagtgatc catggagagc caattattaa aaaatacacc aaaatcattg atggagtgcc 2340
tgtggaaata actgaaaaag agacacgaga agaacgaatc attacaggtc ctgaaataaa 2400
atacactagg atttctactg gaggtggaga aacagaagaa actctgaaga aattgttaca 2460
agaagaggtc accaaggtca ccaaattcat tgaaggtggt gatggtcatt tatttgaaga 2520
tgaagaaatt aaaagactgc ttcagggaga cacacccgtg aggaagttgc aagccaacaa 2580
aaaagttcaa ggatctagaa gacgattaag ggaaggtcgt tctcagtgaa aatccaaaaa 2640
ccagaaaaaa atgtttatac aaccctaagt caataacctg accttagaaa attgtgagag 2700
ccaagttgac ttcaggaact gaaacatcag cacaaagaag caatcatcaa ataattctga 2760
acacaaattt aatatttttt tttctgaatg agaaacatga gggaaattgt ggagttagcc 2820
tcctgtggta aaggaattga agaaaatata acaccttaca cccttttca tcttgacatt 2880 aaaagttctg gctaactttg gaatccatta gagaaaaatc cttgtcacca gattcattac 2940
aattcaaatc gaagagttgt gaactgttat cccattgaaa agaccgagcc ttgtatgtat 3000
gttatggata cataaaatgc acgcaagcca ttatctctcc atgggaagct aagttataaa 3060
aataggtgct tggtgtacaa aactttttat atcaaaaggc tttgcacatt tctatatgag 3120
tgggtttact ggtaaattat gttatttttt acaactaatt ttgtactctc agaatgtttg 3180
tcatatgctt cttgcaatgc atattttta atctcaaacg tttcaataaa accatttttc 3240
agatataaag agaattactt caaattgagt aattcagaaa aactcaagat ttaagttaaa 3300
aagtggtttg gacttgggaa caggacttta tacctctttt actgtaacaa gtactcatta 3360
aaggaaattg aatgaaatta aaaaaaaaaa 3390

<210> SEQ ID NO 90
<211> LENGTH: 2211
<212> TYPE: DNA
<213> ORGANISM: Homo sapiens

<400> SEQUENCE: 90
cgggcggctg ggcgcgcgcg gcgcagagca ggtgccgggg agcccttcgc atgcggctgc 60
cgggccggag gtggtagcgg cgccgggcgc gctccgcccg cccctcctcc gggccgcact 120
gaggctcggg cgcgcgggga catgtcggtg gcgacgggca gcagcgagac ggccggcggg 180

-continued

```
gccagcggcg gcggcgcacg ggttttcttc caaagccccc ggggtggcgc cggtggcagc    240

cccggctcca gcagcggctc aggctcctcc cgggaggact cggcgcccgt ggccacggcg    300

gccgctgcag ggcaggttca gcagcaacag cagcggcgac accagcaggg aaaagtgaca    360

gtgaaatacg atcgtaagga gcttcggaag cggctggtgc tggaggaatg gatcgtggag    420

cagctgggtc agctctacgg ctgcgaggaa gaagaaatgc cagaggtaga aattgacatt    480

gatgatcttc ttgatgcaga cagtgatgaa gagagagctt caaaattaca ggaagctctt    540

gtagactgct acaaaccaac agaggaattt atcaaagagc tgctttctcg gataagaggc    600

atgaggaaac tgagccctcc gcagaagaag agtgtatgat tctggaacag ggtgaaactc    660

tcccagagac gaagaaagag tcctgggatt tgtacttcat gaagactttt gtgaaagaat    720

aggtgtcctt atgaacaacg tttttgtttt tttttttttc tttttggtg tgaaggtggg    780

ggggtctatt agacatttat tcaagagcgt tcttttttttg gttttaaagg tttttgttaa    840

tgtaatattt taatagcaaa gatatcatga ctctagccac agcctaacca aggattatca    900

aaggaggtgg acactcaagg aagggccacg ccaggctgcg tttcctgcaa ggactcagat    960

gttcagtacc ttatgataca gggaagatag ttttcttaca agtagtttgg taatattttt   1020

tttcttaagt tgtacatttg actcagctgt caaatttctc acacttgtat atatctacac   1080

acaactaagt taaaatgttg atgtgagttt tatttcacat ggatggaata aacttgtggt   1140

tgtcctttaa ctggaggtcc cagcacatgt gttttcaaga ggccactagg cattcttcac   1200

tgagtgctgc tgacttcaac gttcacttta tgcaccaaag tgaaagaatt cagtgtatcc   1260

gttattttaa tgcactacac cacagaaatg ttaagttggt caagggctta atttatggaa   1320

tttctattat ttcattggtt gggatgcttt gccaggtcat gtgcttattg tctcattttg   1380

tagtctttta aagttgtatg aacccttaat ttgaagaact aacttgattt ctagagaaat   1440

atccacacta tctcagtggt attttgcatt ggaaaaagga agcactgtgt agcagtgaat   1500

tgtctgcttt ccaccgagta ctgtgtttat tctctctcca ggaaagcaga tcaaaagaaa   1560

gttagcagat cgagtgtctt cttccttaga aataggttct ggtagcttct gtgcctgggt   1620

agtatcagac cagtgggagt aaaccgagtg ttaagtgtca aggtgagaaa gcctcacatt   1680

ctctcaagac agttgctcta ggagctgagt tgctggtttg gaagtgtgga gattgcattt   1740

ctggcttctc tcaatggctt gtgttgagga ctctgggtgc tcctggccct aattgtgcac   1800

cctgatcccc gtgcttggag ctaggcctgg tggcgtgctc tagccctctc agttaccagc   1860

tctttggaga aggatcaaaa ttcagatgga atgtgggatg ggtaataggt gagagtagaa   1920

acccttccct ccaggaggcc cccgctgact cccacagaaa cccacctacc ataagatgtc   1980

ttcaggtggc cttgtccaag gatgggggtc aggcatttta tatcaagggt gctctgaaca   2040

tattttattt tttaaaaaaa ctatgtttgt gaattttgcg tatactggca agcttttgaa   2100

aatgtattta attttgtatt gtttaccaat gatttattta caagatattt actcaaataa   2160

atggagctgc ttacaagcct gttgacatgt gtggcttgca caacacgtta a            2211
```

<210> SEQ ID NO 91
<211> LENGTH: 1787
<212> TYPE: DNA
<213> ORGANISM: Homo sapiens

<400> SEQUENCE: 91

```
gctgctcctc tgtcgagctg atcacaccca cagttgagct gcgctggcca gagatgcctg     60

cccacagcct ggtgatgagc agcccggccc tcccggcctt cctgctctgc agcacgctgc    120
```

```
tggtcatcaa gatgtacgtg gtggccatca tcacgggcca agtgaggctg cggaagaagg    180
cctttgccaa ccccgaggat gccctgagac acggaggccc ccagtattgc aggagcgacc    240
ccgacgtgga acgctgcctc agggcccacc ggaacgacat ggagaccatc taccccttcc    300
ttttcctggg cttcgtctac tcctttctgg gtcctaaccc ttttgtcgcc tggatgcact    360
tcctggtctt cctcgtgggc cgtgtggcac acaccgtggc ctacctgggg aagctgcggg    420
cacccatccg ctccgtgacc tacaccctgg cccagctccc ctgcgcctcc atggctctgc    480
agatcctctg ggaagcggcc cgccacctgt gaccagcagc tgatgcctcc ttggccacca    540
gaccatgggc caagagccgc cgtggctata cctggggact tgatgttcct tccagattgt    600
ggtgggccct gagtcctggt ttcctggcag cctgctgcgc gtgtgggtct ctgggcacag    660
tgggcctgtg tgtgtgcccg tgtgtgtgta tgtgtgtgtg tatgtttctt agccccttgg    720
attcctgcac gaagtggctg atgggaacca tttcaagaca gattgtgaag attgatagaa    780
aatccttcag ctaaagtaac agagcatcaa aaacatcact ccctctccct ccctaacagt    840
gaaaagagag aagggagact ctatttaaga ttcccaaacc taatgatcat ctgaatcccg    900
ggctaagaat gcagactttt cagactgacc ccagaaattc tggcccagcc aatctagagg    960
caagcctggc catctgtatt tttttttttc caagacagag tcttgctctg ttgcccaagc   1020
tggagtgaag tggtacaatc tggctcactg cagcctccgc ctcccgggtt caagcgattc   1080
tcccgcctca gcctcctgag tagctgggat tacaggcgcg tatcaccata cccagctaat   1140
ttttgtattt ttagtagaga cgggttcacc atgttgccca ggagggtctc gaactcctgg   1200
cctcaagtga tccaccggcc tcggcctccc aaagtgctgg gatgacaggc atgaatcact   1260
gtgctcagcc accatctgga gttttaaaag gctcccatgt gagtccctgt gatggccagg   1320
ccaggggacc cctgccagtt ctctgtggaa gcaaggctgg ggtcttgggt tcctgtatgg   1380
tggaagctgg gtgagccaag gacagggctg gctcctctgc ccccgctgac gcttcccttg   1440
ccgttggctt tggatgtctt tgctgcagtc ttctctctgg ctcaggtgtg ggtgggaggg   1500
gcccacagga agctcagcct tctcctccca aggtttgagt ccctccaaag ggcagtgggt   1560
ggaggaccgg gagctttggg tgaccagcca ctcaaaggaa ctttctggtc ccttcagtat   1620
cttcaaggtt tggaaactgc aaatgtcccc ttgatgggga atccgtgtgt gtgtgtgtgt   1680
gtgtgtgtgt gtgtgtgtgt gtgtgtgtgt gttttctcct agacccgtga cctgagatgt   1740
gtgattttta gtcattaaat ggaagtgtct gccagctggg cccagca                 1787
```

<210> SEQ ID NO 92
<211> LENGTH: 1955
<212> TYPE: DNA
<213> ORGANISM: Homo sapiens

<400> SEQUENCE: 92

```
attcatcccc attcaggctt tcctcagcat ttattaagga ctctctgctc cagcctctca     60
ctctcactct cctccgctca aactcagctc acttgagagt ctcctcccgc cagctgtgga    120
aagaactttg cgtctctcca gcaatgcatc tccttgcgat tctgttttgt gctctctggt    180
ctgcagtgtt ggccgagaac tcggatgatt atgatctcat gtatgtgaat ttggacaacg    240
aaatagacaa tggactccat cccactgagg accccacgcc gtgcgcctgc ggtcaggagc    300
actcggaatg ggacaagctc ttcatcatgc tggagaactc gcagatgaga gagcgcatgc    360
tgctgcaagc cacggacgac gtcctgcggg gcgagctgca gaggctgcgg gaggagctgg    420
```

gccggctcgc ggaaagcctg gcgaggccgt gcgcgccggg ggctcccgca gaggccaggc 480
tgaccagtgc tctggacgag ctgctgcagg cgacccgcga cgcgggccgc aggctggcgc 540
gtatggaggg cgcggaggcg cagcgcccag aggaggcggg gcgcgccctg gccgcggtgc 600
tagaggagct gcggcagacg cgagccgacc tgcacgcggt gcagggctgg gctgcccgga 660
gctggctgcc ggcaggttgt gaaacagcta ttttattccc aatgcgttcc aagaagattt 720
ttggaagcgt gcatccagtg agaccaatga ggcttgagtc ttttagtgcc tgcatttggg 780
tcaaagccac agatgtatta aacaaaacca tcctgttttc ctatggcaca aagaggaatc 840
catatgaaat ccagctgtat ctcagctacc aatccatagt gtttgtggtg ggtggagagg 900
agaacaaact ggttgctgaa gccatggttt ccctgggaag gtggacccac ctgtgcggca 960
cctggaattc agaggaaggg ctcacatcct tgtgggtaaa tggtgaactg gcggctacca 1020
ctgttgagat ggccacaggt cacattgttc ctgagggagg aatcctgcag attggccaag 1080
aaaagaatgg ctgctgtgtg ggtggtggct ttgatgaaac attagccttc tctgggagac 1140
tcacaggctt caatatctgg gatagtgttc ttagcaatga agagataaga gagaccggag 1200
gagcagagtc ttgtcacatc cgggggaata ttgttgggtg gggagtcaca gagatccagc 1260
cacatggagg agctcagtat gtttcataaa tgttgtgaaa ctccacttga agccaaagaa 1320
agaaactcac acttaaaaca catgccagtt gggaaggtct gaaaactcag tgcataatag 1380
gaacacttga gactaatgaa agagagagtt gagaccaatc tttatttgta ctggccaaat 1440
actgaataaa cagttgaagg aaagacattg gaaaaagctt ttgaggataa tgttactaga 1500
ctttatgcca tggtgctttc agtttaatgc tgtgtctctg tcagataaac tctcaaataa 1560
ttaaaaagga ctgtattgtt gaacagaggg acaattgttt tacttttctt tggttaattt 1620
tgttttggcc agagatgaat tttacattgg aagaataaca aaataagatt tgttgtccat 1680
tgttcattgt tattggtatg taccttatta caaaaaaaag atgaaaacat atttatacta 1740
caaggtgact taacaactat aaatgtagtt tatgtgttat aatcgaatgt cacgtttttg 1800
agaagatagt catataagtt atattgcaaa agggatttgt attaatttaa gactattttt 1860
gtaaagctct actgtaaata aaatatttta taaaactagc tcacgtcatt taattataaa 1920
tttaagagat gttttggaaa aaaaaaaaaa aaaaa 1955

<210> SEQ ID NO 93
<211> LENGTH: 2019
<212> TYPE: DNA
<213> ORGANISM: Homo sapiens

<400> SEQUENCE: 93
gaaaaggcgg aggcggcggc ccctccggct cccactgcct cccccgccgc acccccctccc 60 caccttccgc acccgccaaa cttgatgtga ccctggcccg acgcggaggc tgcccctctc 120
actgccccgt gggtcccccg ccacccgctc cgcacccgcg agcgcaccgc tccccgcgcc 180
ccttcccact tcccgcgggg ccggcgccgc gctcgccctc gcgttccttc ccgccgcccc 240 ctccccccgca ccatgagcaa cctgaagccg gacggcgagc acggcggcag caccggcacc 300
ggctccggcg cgggctccgg cggcgccctg gaggaggagg tccggacact gtttgtcagc 360
ggcctccctg tggacattaa acccagagaa ctctacttgc tcttccggcc gttcaagggg 420
tatgaagggt ccctgatcaa gctcactgca agacagcctg ttggttttgt gatctttgac 480
agccgtgcag gagcagaagc ggccaagaat gcgctgaacg gtattcgctt tgatcccgaa 540
aatccacaga ctctgaggct agagtttgcc aaagccaaca ccaagatggc caagagcaag 600
ctaatggcaa ctccaaatcc cagcaacgtg caccccgccc taggagcaca cttcatcgca 660
cgggacccct atgacctgat gggggctgct ctgatccctg catccccaga ggcctgggcc 720
ccctaccctt tgtacaccac agagctgacc ccagccatct cccatgctgc gttcacctac 780
ccaactgcca ctgccgctgc cgccgccctc cacgctcagg tgcgctggta cccttcctct 840
gacaccaccc agcaaggatg gaagtaccgt cagttctgtt agtttttcag tctggtcacc 900
ggggaggtgg ttctggtaat ctgtggtggt gccgggacag gcgccccgag ttcccactgc 960
ccccgggcgg cctgcacaga gctgctgccc tccagagact gtgaatccca agcctgactc 1020
agtggactgc ttcctgttcc cctccctcct cttcctcacc ttgttctgca ccctcaagcc 1080
tttctccaat gcctcccagg aggatttggg gactttctcc ctggggcgcc cagatccagc 1140
tcggaggcct cactgggacc tggcaaggcc tgacctcccg cccaaacttg cttctgtagc 1200
tccccctcga ggaagtgagg tgtttaattt tgcatgtttt ctggcatgaa ttaagacact 1260
tatacttgta tatatgagtg tacagtttgt tctcacactg tcaccatagc gacaggtcct 1320
ggctcccagt ggttcatcct gcctgcccct ctctcctcgc cccgcccctg cacccacccc 1380
gcttcaggga ggcccaagtt ccgtggcccc acacgcttcc aggctcagct cccacctcca 1440
cccaacagat agatggggtt tgctttttca tttcacatgg ggctcctccg ctcctgcctt 1500
ctcggatggg ccaacagtcg taagaaagcc ctctctgccc gttctgttca cctctccaca 1560
gcgcaccccg cccgccgctg ctcctcattc tttccaaacc tcgaaaccaa ccaaaacgtg 1620
agaagtattt ttgtaccctg tgtaacaaaa tatttatgca tcataaagga tttttcatgt 1680
gcgtaccatt aattattaaa gcgacctcgt tcgccctgtc agataagttt aatgtttagt 1740
ttgaggcatg aagaagaaaa gggtttccat tcttcagcag tacgcctttg tgtctggcat 1800
ttgtttaaga aaatgaaatg aaggaaacac tgtgcaatgt tttttgtttt gagcatatca 1860
gtgctttact gtcagccgca gctgtgaccg tctggccatt tcagacttgg gagatgaggc 1920
ggctgttgtc attgctgatc ctgtgagaat gtgaaactgg ataatatatg aaatgcaaaa 1980
taaaacaaaa ccaaaaaaaa aaaaaaaaaa aaaaaaaaa 2019

<210> SEQ ID NO 94
<211> LENGTH: 1517
<212> TYPE: DNA
<213> ORGANISM: Homo sapiens

<400> SEQUENCE: 94
ataagacttt tatggatgga ttgtttttct caaataatat tatcgctttg tgactaaagt 60
aaagattatt aattcctgag gcaagaagat ataaaagctc cagaaacgtt gactgggacc 120
actggagaca ctgaagaagg caggggccct tagagtcttg gttgccaaac agaatgccca 180
tatccgtctt acctgtgagg aagcttgcct tgggcgccct ctgctggccc tcctgaagct 240
aacaggggcg agtgctcggt ggtttacaaa ttgcctccat gcagactatg aaactgttca 300
gcctgctata gttagatctc tggcactggc ccaggaggtc ttgcagattt gcagatcaag 360
gagaacccag gagtttcaaa gaagcgctag taaggtctct gagatccttg cactagctac 420
atcctcaggg taggaggaag atggcttcca gaagcatgcg gctgctccta ttgctgagct 480
gcctggccaa aacaggagtc ctgggtgata tcatcatgag acccagctgt gctcctggat 540
ggttttacca caagtccaat tgctatggtt acttcaggaa gctgaggaac tggtctgatg 600
ccgagctcga gtgtcagtct tacggaaacg gagcccacct ggcatctatc ctgagtttaa 660

-continued

```
aggaagccag caccatagca gagtacataa gtggctatca gagaagccag ccgatatgga    720

ttggcctgca cgacccacag aagaggcagc agtggcagtg gattgatggg gccatgtatc    780

tgtacagatc ctggtctggc aagtccatgg gtgggaacaa gcactgtgct gagatgagct    840

ccaataacaa ctttttaact tggagcagca acgaatgcaa caagcgccaa cacttcctgt    900

gcaagtaccg accatagagc aagaatcaag attctgctaa ctcctgcaca gccccgtcct    960

cttcctttct gctagcctgg ctaaatctgc tcattatttc agaggggaaa cctagcaaac   1020

taagagtgat aagggcccta ctacactggc tttttaggc ttagagacag aaactttagc   1080

attggcccag tagtggcttc tagctctaaa tgtttgcccc gccatccctt tccacagtat   1140

ccttcttccc tcctcccctg tctctggctg tctcgagcag tctagaagag tgcatctcca   1200

gcctatgaaa cagctgggtc tttggccata agaagtaaag atttgaagac agaaggaaga   1260

aactcaggag taagcttcta gacccccttca gcttctacac ccttctgccc tctctccatt   1320

gcctgcaccc caccccagcc actcaactcc tgcttgtttt tcctttggcc atgggaaggt   1380

ttaccagtag aatccttgct aggttgatgt gggccataca ttcctttaat aaaccattgt   1440

gtacataaga ggttgctgtg ttccagttca gtaatggtga atgtggaaaa gtgaaataag   1500

accaagaaat acaccca                                                  1517
```

<210> SEQ ID NO 95
<211> LENGTH: 1162
<212> TYPE: DNA
<213> ORGANISM: Homo sapiens

<400> SEQUENCE: 95

```
acagggcagt gtagttccag aaaataggac tgaccaagaa gcagaaaagc aagatgaatg     60

atgtgaagct tgctgtcttg ggtggtgaag gaacaggcaa atctggtccc tacatcctta    120

aataactgca aatacttggt agtgtctttg tgactattac acatagtacc ttgaagccag    180

actgagtttg acagagaaaa taaacagatg tcaaacttct tgcatctcaa atataatgag    240

aaatctgttt ctgttacaaa agcccttaca gtgaggtttc ttactaagcg attcattgga    300

gaatatgctt ctaattttga atctatctat aagaagcact tgtgtttgga aaggaaacaa    360

ctaaatctag aaatatatga cccttgttct caaacacaga aagcaaaatt ctccctcaca    420

agtgagcttc actgggcaga tgggtttgtt attgtgtatg acatcagtga taggtcttca    480

tttgcttttg caaaagcgct gatctacaga atccgggagc cacaaactag tcattgtaaa    540

agagctgtgg aatcagcagt gtttttggtt ggcaacaaac gagatctttg tcatgtgcga    600

gaggttggct gggaagaagg gcaaaagctg gcactggaaa accgatgcca attctgtgaa    660

ctgtctgcag cagagcagtc tctggaggtg gaaatgatgt ttatcagaat tatcaaggac    720

atcctgataa acttcaaact caaagaaaag agacgtccca gtggatctaa atcaatggcc    780

aaattgatca ataatgtatt tggaaagaga aggaaatctg tttagtagac aggtaatcct    840

gggagatttc ctatatcaga gagtttcaaa cattcacatg ataattaaac taacctttgt    900

atgcaatttt tttttggtaa aaagaattct cttggagata tgaaatgatt gagtatgaac    960

cacagctgtg ttttcaaata tgtagtttgc ctttttggtt gttgtaccct gctcactctc   1020

cttcacacag aacctttcat ttattgtaca acatcacact caccctaacc tactggcgga   1080

cagcgatccc agtttgcctt gccaaataaa ctctgtttat gtgaatttat taaacgacca   1140

tgccataaaa aaaaaaaaaa aa                                            1162
```

<210> SEQ ID NO 96
<211> LENGTH: 4583
<212> TYPE: DNA
<213> ORGANISM: Homo sapiens

<400> SEQUENCE: 96
gcggccgccc cggcggctcc tggaaccccg gttcgcggcg atgccagcca ccccagcgaa 60
gccgccgcag ttcagtgctt ggataatttg aaagtacaat agttggtttc cctgtccacc 120
cgccccactt cgcttgccat cacagcacgc ctatcggatg tgagaggaga agtcccgctg 180
ctcgggcact gtctatatac gcctaacacc tacatatatt ttaaaaacat taaatataat 240
taacaatcaa aagaaagagg agaaaggaag ggaagcatta ctgggttact atgcacttgc 300
gactgatttc ttggcttttt atcattttga actttatgga atacatcggc agccaaaacg 360
cctcccgggg aaggcgccag cgaagaatgc atcctaacgt tagtcaaggc tgccaaggag 420
gctgtgcaac atgctcagat tacaatggat gtttgtcatg taagcccaga ctattttttg 480
ctctggaaag aattggcatg aagcagattg gagtatgtct ctcttcatgt ccaagtggat 540
attatggaac tcgatatcca gatataaata agtgtacaaa atgcaaagct gactgtgata 600
cctgtttcaa caaaaatttc tgcacaaaat gtaaaagtgg attttactta caccttggaa 660
agtgccttga caattgccca gaagggttgg aagccaacaa ccatactatg gagtgtgtca 720
gtattgtgca ctgtgaggtc agtgaatgga atccttggag tccatgcacg aagaagggaa 780
aaacatgtgg cttcaaaaga gggactgaaa cacgggtccg agaaataata cagcatcctt 840
cagcaaaggg taacctgtgt cccccaacaa atgagacaag aaagtgtaca gtgcaaagga 900
agaagtgtca gaagggagaa cgaggaaaaa aaggaaggga gaggaaaaga aaaaaaccta 960
ataaaggaga aagtaaagaa gcaatacctg acagcaaaag tctggaatcc agcaaagaaa 1020
tcccagagca acgagaaaac aaacagcagc agaagaagcg aaaagtccaa gataaacaga 1080
aatcggtatc agtcagcact gtacactaga gggttccatg agattattgt agactcatga 1140
tgctgctatc tcaaccagat gcccaggaca ggtgctctag ccattaggac cacaaatgga 1200
catgtcagtt attgctctgt ctaaacaaca ttcccagtag ttgctatatt cttcatacaa 1260
gcatagttaa caacaaagag ccaaaagatc aaagaaggga tactttcaga tggttgtctt 1320
gtgtgcttct ctgcattttt aaaagacaag acattcttgt acatattatc aataggctat 1380
aagatgtaac aacgaaatga tgacatctgg agaagaaaca tcttttcctt ataaaaatgt 1440
gttttcaagc tgttgtttta agaagcaaaa gatagttctg caaattcaaa gatacagtat 1500
cccttcaaaa caaataggag ttcagggaag agaaacatcc ttcaaaggac agtgttgttt 1560
tgaccgggag atctagagag tgctcagaat tagggcctgg catttggaat cacaggattt 1620
atcatcacag aaacaactgt tttaagatta gttccatcac tctcatcctg tatttttata 1680
agaaacacaa gagtgcatac cagaattgaa tataccatat gggattggag aaagacaaat 1740
gtggaagaaa tcatagagct ggagactact tttgtgcttt acaaaactgt gaaggattgt 1800
ggtcacctgg aacaggtctc caatctatgt tagcactatg tggctcagcc tctgttaccc 1860
cttggattat atatcaacct gtaaacatgt gcctgtaact tacttccaaa aacaaaatca 1920
tacttattag aagaaaattc tgattttata gaaaaaaaat agagcaagga gaatataaca 1980
tgtttgcaaa gtcatgtgtt ttctttctca atgagggaaa aacaatttta ttacctgctt 2040
aatggtccac ctggaactaa aagggatact attttctaac aaggtatatc tagtagggga 2100
gaaagccacc acaataaata tatttgttaa tagtttttca agttttgttc actctgtttt 2160

-continued attgtttgtt ttattgagaa attcttactc ttagagactc atgaattaag aaagagaatt 2220
ctgctaactc agagaacctg gttcctatgt aattcagaat atattacatt tctcagtaat 2280
atttgttttt tgaatccacc tttatctgag ccaatggaga tttacttata gcgtattagg 2340
agatatttat tccattttct tattttaatc aacattctaa ttatagacac atgggcctcc 2400
ctagctgatt tcactgctcc cccttcattg cttagaaatg ggcatcattt cttgtatgtc 2460
agatccccct gcatcttcaa catttagtct tttcttctcc atattttcta tctgtggatc 2520
tctttagggg attgaagtca ccctagctga aggcctcacc agtgtttcac agaggacaca 2580
gcccacccct tgcaggagga ggtatctctg agtgtgcagc acagaatcgc atgacccacc 2640
ttaaccttcc tgttgtcatg gaaggatgca cggctgctct gtccactgtg attcctagcc 2700
ctctcaagat cactgctttc tgaagaattt gcaatgactc tggcttctgg ctgcttatct 2760
ctggacaccc gttctccacc agttgtacag ttcatgtaat ctacttggct taattgattt 2820
tccacttctc tcttcctctt ctaagatata aacattttaa atgatttatt cctgtttctt 2880
attctggtgt ttctttcctt gtccctatga gataagtgtc tcaactcact aaatctattc 2940
ccaatgtata aaataattct aattccattt tcagctaaaa catatattac caagaagaaa 3000
caaactttat cctacagaat gatgttaggt agaaatatgt ccccaggttt gagacctttc 3060
ggatgatttc atataccatc tttcttctga gtgttaccca gtcaagtata agtagccaaa 3120
ttatttttgc acatctttct gtttctcatg tcttcattta ttcaacaagc acttactggg 3180
aaggtctaca cctgcatagg caatgctgga aaaagggtta agtaaaccag gacatgacaa 3240
tggtggcaaa tgactatcag gtcttcccat gtgtttgact caaacttatt accctatggt 3300
ccttctgaca atggcagaag gtctgaatcc ttgatgctaa acttatataa aagtagaatt 3360
attacaaagg aaaaagaaat aaaaactaac attcattttc atatgttgga tgaaatataa 3420
atgaagaaaa agataacatc aattttaact gtaattctcc atccaccagt aacagatcct 3480
taagacaata gaatcataca gtattcaaac cagcagcctt ctcaaatttg agcaaaaact 3540
ctatcaacct ctggtaaagt tcctacacta gtcacagaag gtgttaactt tctactctga 3600
ttctgtctcc ataatggggt aaactgttga tagtttaccc catcaacaga tggtcggtaa 3660
attattgatt cgaagaatcg agagagtgca gcaacataaa tctgttaatg tctgatcaag 3720
ctcctgccct gttctccgaa ttcagcttca taattaaggg aaggcctgtt ttctatcctc 3780
agatttaggt tctagtagca gttgtgtaac cactagtgag tcacttaact cctctgggtc 3840
cccatttctc atgtgcaaca agaaagaggg gaactggaga tgatcactct agttccagac 3900
aagggaacat ttcacacttt gtttacttca gggtgatgtc cctgagtcct cattagtgac 3960
tgcgtccttt ggaagttatc ccaaccctgc ttttctcaaa agtgaaaatg tataggctct 4020
cagaggagac agatttaact ctgcttctct aatgttattg aattaaaagc tgttcacatt 4080
agtggttatt aaatattgaa ataacactgg gaagaaaaag catatataaa tacagctaaa 4140
aacaagaata gatattcatt ctcacaaagg gagacagcaa agaaaatgga aagtgcactg 4200
gtgctagcgt tagacagctt gtgttaatgt ctcaattctg ctactaactg gttgcagctt 4260
gtgtgacctt gggcacattg tatgatctcg cagaatatca tcccaaatct gcaaaatgga 4320
attggcatca tctcttttgc aagattgtta tgagaattaa aaggttcttc attcaatata 4380
ataataaata ttttgtatat aaatgaatat caattaaaag ttatgactaa ttccacaagt 4440
caaacatata aattttattt cttgattcat gatatgtgat agtattcata aaaatgtaca 4500
tgcatgataa tttcaaggaa taagtatata tgtgagaatc atggaaatga aattaataat 4560
attaactagt aattaaattg taa 4583

<210> SEQ ID NO 97
<211> LENGTH: 970
<212> TYPE: DNA
<213> ORGANISM: Homo sapiens

<400> SEQUENCE: 97
ctcccctcac cccggtccag gatgcccagt ccccacgaca cctcccactt cccactgtgg 60
cctgggtggg ctcaggggct gcccttgacc tggcctagag ccctccccca gctggtggtg 120
gagctggcac tctctgggag ggagggggct gggagggaat gagtgggaat ggcaagaggc 180
cagggtttgg tgggatcagg ttgaggcagg tttggtttcc ttaaaatgcc aagttggggg 240
ccagtggggc ccacatataa atcctcaccc tgggagcctg gctgccttgc tctccttcct 300
gggtctgtct ctgccacctg gtctgccaca gatccatgat gtgcagttct ctggagcagg 360
cgctggctgt gctggtcact accttccaca agtactcctg ccaagagggc gacaagttca 420
agctgagtaa gggggaaatg aaggaacttc tgcacaagga gctgcccagc tttgtggggg 480
agaaagtgga tgaggagggg ctgaagaagc tgatgggcag cctggatgag aacagtgacc 540
agcaggtgga cttccaggag tatgctgttt tcctggcact catcactgtc atgtgcaatg 600
acttcttcca gggctgccca gaccgaccct gaagcagaac tcttgacttc ctgccatgga 660
tctcttgggc ccaggactgt tgatgccttt gagttttgta ttcaataaac tttttttgtc 720
tgttgataat attttaattg ctcagtgatg ttccataacc cggctggctc agctggagtg 780
ctgggagatg agggcctcct ggatcctgct cccttctggg ctctgactct cctggaaatc 840
tctccaaggc cagagctatg ctttaggtct caattttgga atttcaaaca ccagcaaaaa 900
attggaaatc gagataggtt gctgactttt attttgtcaa ataaagatat taaaaaaggc 960
aaaaaaaaaa 970

<210> SEQ ID NO 98
<211> LENGTH: 3240
<212> TYPE: DNA
<213> ORGANISM: Homo sapiens

<400> SEQUENCE: 98
aagaaacctc tgaactgttc actaatacag tcaggtagag gttgagactc cactgaataa 60
actctaggtt cccatttctt tcagccagat cctcccaggg aatcactaca ggctggttag 120
ccaaaaagtc ctgattttct gctcaataga ggtccttact ggaaggcagc atgtccaatg 180
ttaccttgag aaaaatgtct cccacaggaa atgagatgaa gagcaccact cagggaacca 240
cacggaagca gcaggatttt cacgaggtga acaaaagaag aactttctta caggataaca 300
gttggataaa gaaacgccct gaagaagaaa aagatgaaaa ttacggtagg gtggtgctca 360
accgacataa ttcccatgat gcattggaca ggaaagtaaa tgagagagat gtgccaaaag 420
ctacaattag tcggtacagt tctgatgaca ctttggacag gatctcagac agaaatgatg 480
ctgctaaaac atataaggcc aataccttgg ataaccaact aaccaatagg agcatgtcca 540
tgtttagatc actggaagta acaaagttgc aacctggcgg ttcattgaat gccaacacct 600
ccaacaccat agcatccact tctgctacta ctcctgtaaa gaagaagagg cagtcctggt 660
ttccaccgcc ccctccaggt tacaatgcct cctcgagcac aggaaccagg agacgggaac 720
caggtgttca ccctccaata cctccaaagc ccagttctcc tgtttcttct cctaaccagc 780

```
tgagacagga taataggcag atacatccac ctaaaccagg tgtatataca gaaaccaaca    840
gatctgctga aagaaatata aggagtcagg atcttgataa catcgtcaaa gtggccactt    900
cacttcagag aagtgacaaa ggtgaagaat tggataatct catcaaaatg aacaaaagct    960
tgaataggaa tcaaggtctt gatagtctct tcagagcaaa tccaaaggta gaagaaagag   1020
agaaaagagc caaaagcctt gaaagtctca tctatatgag tacccggaca gataaagatg   1080
gcaaaggaat ccaaagcctt ggaagtccga ttaaagttaa tcaaaggact gacaaaaatg   1140
agaaaggaag acaaaatctc gaatctgttg ctaaagtgaa tgccaggatg aataaaacga   1200
gcagaagaag tgaagacctt gataatgcta ctgaagtaaa tcccaaagga catgaaaata   1260
ccactggaaa aaaagacctt gatgggctta ttaaagtgga tcctgaaaca aataaaaata   1320
ttacgagggg ccagagcctt gataatctca tcaaagtgac ccctgaagta aagagaagta   1380
accaaggttc caaagacctt aataacttca tcaaagtgta tccaggaaca gaaaaaagta   1440
ctgaaggggg ccaaagtctc gacagcctca ttaaagtgac tcctgaaaga aacagaacta   1500
accaagggaa ccaagacttg gaaaatctta tcaaagtgat cccttcagca aacaaaagca   1560
gtgaacaagg tcttgatgaa catattaatg tcagccccaa agctgtcaaa aacactgatg   1620
gaaaacaaga tcttgataaa ctcatcaagg tgaatcctga aattttcaca aacaaccaaa   1680
gaaaccaaga tcttgctaac ctcatcaaag taaatcctgc agtaatcaga aacaatcaga   1740
gccaagactt ggacaatctt attaaagtga aaccttcagc tcttagaaac actaatcgag   1800
accagaacct ggaaaattta attgaagtaa attctcatgt gtctgaaaac aagaatggaa   1860
gctctaacac tggagccaag caggcaggac cacaggatac tgttgtgtac acaaggacat   1920
atgtggagaa tagtaaatca cccaaggatg gatatcagga gaatatctct ggaaaataca   1980
tacaaactgt ttattcaact tctgataggt ctgtcattga aagagatatg tgcacttact   2040
gccgaaaacc cttgggtgta gaaactaaaa tgattttaga tgaattacaa atttgctgcc   2100
attctacttg ctttaagtgt gaaatatgca agcagccttt ggaaaatcta caagcgggtg   2160
atagtatttg gatttataga cagacaatac actgtgaacc ttgctactct aaaattatgg   2220
caaagtggat tccataactc tggcacaagg aaatcaagat gaaaagcact cattaaggaa   2280
ttaaagttac aagttttatc ttaataatat gtaatctaga aaagctttca cattgaagat   2340
caactcttgt acaaaattaa caattctgtt attgcataag taatctaatt gtcttcaata   2400
aggtcacaca cataaaaaga gccatctggt ctctggctag agttagcaat aaaaagttca   2460
aatggttcca gattccagtg tcaaaggagt gatgcattac actccagcca ggtccatccc   2520
tgctccgtat gttggctgtg agtggtggtt tccatttaaa ccaagtttct catttcttca   2580
cctttttttc tctaagaatt tggattcgta gacattgaca tcccgaagaa ctgtcaagga   2640
agcaagatat gctttcttca tctgcaaaag aaatactaac aacaattttc ttatacagtt   2700
tggcagaaag atgttaacat aaaaagttta tatacctcaa aaatcactaa actttccaga   2760
tctctgtcct attatttgta acacaagggg cattggataa aatgatttct agggttcctt   2820
ttgcttccca aattctctga ttctaaagca gtttttagaa tcattagctc tttggaaaca   2880
tatatgcata catgtttgtt aagcctattg aactaggtag gacatataaa caatttaatt   2940
ttagtgtcat tgtttaatca cagacttagt gtttgaaaac tgtgttttaa aaacagaaac   3000
agattgatgg gtaacaggta aaatatgaca tgtatagctt acatgttatt atttgttaaa   3060
ttttctttgt atacatttca aaatctgggt atacttataa tccattagaa gtaatggtta   3120
tggactaaaa agatatgttc tttagtatgt tatatatact catattacat agcagtatgt   3180
```

ttacaaaagg cttataaaaa taaaatgaac tatcagttac atagaaaaaa aaaaaaaaaa 3240

<210> SEQ ID NO 99
<211> LENGTH: 907
<212> TYPE: DNA
<213> ORGANISM: Homo sapiens

<400> SEQUENCE: 99
cttttcttaa gggaaaaatc actctgtgtt cttttaaaat ccctcaggtt ttatgtttta 60
ttgctaccag agtctgcctc cctgaggttc ttgtatagac tagttatttc cctctgtaaa 120
gaagctgttc tattcgttct cgcctggttt ggaacaaact gaacacttcc aaaggaggca 180
gtccttgcag ccttgtctcc ttccactccc ctcctcccca cagtcctggc tggagcagcg 240
agtctgtcga tcccaggcca gagacaaggc agacaaaggt tcatttgtaa agaagctcct 300
tccagcacct cctctcttct ccttttgccc aaactcaccc agtgagtgtg agcatttaag 360
aagcatcctc tgccaagacc aaaaggaaag aagaaaaagg gccaaaagcc aaaatgaaac 420
tgatggtact tgttttcacc attgggctaa ctttgctgct aggagttcaa gccatgcctg 480
caaatcgcct ctcttgctac agaaagatac taaaagatca caactgtcac aaccttccgg 540
aaggagtagc tgacctgaca cagattgatg tcaatgtcca ggatcatttc tgggatggga 600
agggatgtga gatgatctgt tactgcaact tcagcgaatt gctctgctgc ccaaaagacg 660
ttttctttgg accaaagatc tctttcgtga ttccttgcaa caatcaatga gaatcttcat 720
gtattctgga gaacaccatt cctgatttcc cacaaactgc actacatcag tataactgca 780
tttctagttt ctatatagtg caatagagca tagattctat aaattcttac ttgtctaaga 840
caagtaaatc tgtgttaaac aagtagtaat aaaagttaat tcaatctaat tttctctgt 900 ggaaaaa 907

<210> SEQ ID NO 100
<211> LENGTH: 1793
<212> TYPE: DNA
<213> ORGANISM: Homo sapiens

<400> SEQUENCE: 100
aaatactaac cacagaggga gaggcagcaa gaggagaggc ataaattcag gatctcaccc 60
ttcattccac agacacacat agcctctctg cccacctctg cttcctctag gaacacagga 120
gttccagatc acatcgagtt caccatgaat tcactcagtg aagccaacac caagttcatg 180
ttcgacctgt tccaacagtt cagaaaatca aaagagaaca acatcttcta ttcccctatc 240
agcatcacat cagcattagg gatggtcctc ttaggagcca aagacaacac tgcacaacag 300
attaagaagg ttcttcactt tgatcaagtc acagagaaca ccacaggaaa agctgcaaca 360
tatcatgttg ataggtcagg aaatgttcat caccagtttc aaaagcttct gactgaattc 420
aacaaatcca ctgatgcata tgagctgaag atcgccaaca agctcttcgg agaaaaaacg 480
tatctatttt tacaggaata tttagatgcc atcaagaaat tttaccagac cagtgtggaa 540
tctgttgatt ttgcaaatgc tccagaagaa agtcgaaaga agattaactc ctgggtggaa 600
agtcaaacga atgaaaaaat taaaaaccta attcctgaag gtaatattgg cagcaatacc 660
acattggttc ttgtgaacgc aatctatttc aaagggcagt gggagaagaa atttaataaa 720
gaagatacta aagaggaaaa attttggcca aacaagaata catacaagtc catacagatg 780
atgaggcaat acacatcttt tcattttgcc tcgctggagg atgtacaggc caaggtcctg 840
gaaataccat acaaaggcaa agatctaagc atgattgtgt tgctgccaaa tgaaatcgat 900
ggtctccaga agcttgaaga gaaactcact gctgagaaat tgatggaatg gacaagtttg 960
cagaatatga gagagacacg tgtcgattta cacttacctc ggttcaaagt ggaagagagc 1020
tatgacctca aggacacgtt gagaaccatg ggaatggtgg atatcttcaa tggggatgca 1080
gacctctcag gcatgaccgg gagccgcggt ctcgtgctat ctggagtcct acacaaggcc 1140
tttgtggagg ttacagagga gggagcagaa gctgcagctg ccaccgctgt agtaggattc 1200
ggatcatcac ctacttcaac taatgaagag ttccattgta atcacccttt cctattcttc 1260
ataaggcaaa ataagaccaa cagcatcctc ttctatggca gattctcatc cccgtagatg 1320
caattagtct gtcactccat ttggaaaatg ttcacctgca gatgttctgg taaactgatt 1380
gctggcaaca acagattctc ttggctcata tttcttttct ttctcatctt gatgatgatc 1440
gtcatcatca agaatttaat gattaaaata gcatgccttt ctctctttct cttaataagc 1500
ccacatataa atgtactttt tcttccagaa aaattctcct tgaggaaaaa tgtccaaaat 1560
aagatgaatc acttaatacc gtatcttcta aatttgaaat ataattctgt ttgtgacctg 1620
ttttaaatga accaaaccaa atcatacttt ttctttgaat ttagcaacct agaaacacac 1680
atttctttga atttaggtga tacctaaatc cttcttatgt ttctaaattt tgtgattcta 1740
taaaacacat catcaataaa atagtgacat aaaatcaaaa aaaaaaaaaa aaa 1793

<210> SEQ ID NO 101
<211> LENGTH: 1787
<212> TYPE: DNA
<213> ORGANISM: Homo sapiens

<400> SEQUENCE: 101
aaccacagag ggaaaggcag caagaggaga ggcataaatt taggatctca cccttcattc 60
cacagacaca cacagcctct ctgcccacct ctgcttcctc taggaacaca ggagttccag 120
atcacatcga gttcaccatg aattcactca gtgaagccaa caccaagttc atgttcgatc 180
tgttccaaca gttcagaaaa tcaaaagaga acaacatctt ctattcccct atcagcatca 240
catcagcatt agggatggtc ctcttaggag ccaaagacaa cactgcacaa caaattagca 300
aggttcttca ctttgatcaa gtcacagaga acaccacaga aaaagctgca acatatcatg 360
ttgataggtc aggaaatgtt catcaccagt ttcaaaagct tctgactgaa ttcaacaaat 420
ccactgatgc atatgagctg aagatcgcca acaagctctt cggagaaaag acgtatcaat 480
ttttacagga atatttagat gccatcaaga aattttacca gaccagtgtg gaatctactg 540
attttgcaaa tgctccagaa gaaagtcgaa agaagattaa ctcctgggtg gaaagtcaaa 600
cgaatgaaaa aattaaaaac ctatttcctg atgggactat tggcaatgat acgacactgg 660
ttcttgtgaa cgcaatctat ttcaaagggc agtgggagaa taaatttaaa aaagaaaaca 720
ctaaagagga aaaatttttgg ccaaacaaga atacatacaa atctgtacag atgatgaggc 780
aatacaattc ctttaatttt gccttgctgg aggatgtaca ggccaaggtc ctggaaatac 840
catacaaagg caaagatcta agcatgattg tgctgctgcc aaatgaaatc gatggtctgc 900
agaagcttga agagaaactc actgctgaga aattgatgga atggacaagt ttgcagaata 960
tgagagagac atgtgtcgat ttacacttac ctcggttcaa aatggaagag agctatgacc 1020
tcaaggacac gttgagaacc atgggaatgg tgaatatctt caatggggat gcagacctct 1080
caggcatgac ctggagccac ggtctctcag tatctaaagt cctacacaag gcctttgtgg 1140
aggtcactga ggagggagtg gaagctgcag ctgccaccgc tgtagtagta gtcgaattat 1200

```
catctccttc aactaatgaa gagttctgtt gtaatcaccc tttcctattc ttcataaggc   1260
aaaataagac caacagcatc ctcttctatg gcagattctc atccccatag atgcaattag   1320
tctgtcactc catttagaaa atgttcacct agaggtgttc tggtaaactg attgctggca   1380
acaacagatt ctcttggctc atatttcttt tctatctcat cttgatgatg atagtcatca   1440
tcaagaattt aatgattaaa atagcatgcc tttctctctt tctcttaata agcccacata   1500
taaatgtact tttccttcca gaaaaatttc ccttgaggaa aaatgtccaa gataagatga   1560
atcatttaat accgtgtctt ctaaatttga aatataattc tgtttctgac ctgttttaaa   1620
tgaaccaaac caaatcatac tttctcttca aatttagcaa cctagaaaca cacatttctt   1680
tgaatttagg tgatacctaa atccttctta tgtttctaaa ttttgtgatt ctataaaaca   1740
catcatcaat aaaataatga cataaaatca aaaaaaaaaa aaaaaaa                 1787
```

<210> SEQ ID NO 102
<211> LENGTH: 2633
<212> TYPE: DNA
<213> ORGANISM: Homo sapiens

<400> SEQUENCE: 102

```
agtgggcgtg gcggtgctgc ccaggtgagc caccgctgct tctgcccaga cacggtcgcc     60
tccacatcca ggtctttgtg ctcctcgctt gcctgttcct tttccacgca ttttccagga    120
taactgtgac tccaggcccg caatggatgc cctgcaacta gcaaattcgg cttttgccgt    180
tgatctgttc aaacaactat gtgaaaagga gccactgggc aatgtcctct tctctccaat    240
ctgtctctcc acctctctgt cacttgctca agtgggtgct aaaggtgaca ctgcaaatga    300
aattggacag gttcttcatt ttgaaaatgt caaagatgta ccctttggat ttcaaacagt    360
aacatcggat gtaaacaaac ttagttcctt ttactcactg aaactaatca agcggctcta    420
cgtagacaaa tctctgaatc tttctacaga gttcatcagc tctacgaaga gaccgtatgc    480
aaaggaattg gaaactgttg acttcaaaga taaattggaa gaaacgaaag gtcagatcaa    540
caactcaatt aaggatctca cagatggcca ctttgagaac attttagctg acaacagtgt    600
gaacgaccag accaaaatcc ttgtggttaa tgctgcctac tttgttggca agtggatgaa    660
gaaattttct gaatcagaaa caaaagaatg tcctttcaga gtcaacaaga cagacaccaa    720
accagtgcag atgatgaaca tggaggccac gttctgtatg ggaaacattg acagtatcaa    780
ttgtaagatc atagagcttc cttttcaaaa taagcatctc agcatgttca tcctactacc    840
caaggatgtg gaggatgagt ccacaggctt ggagaagatt gaaaaacaac tcaactcaga    900
gtcactgtca cagtggacta atcccagcac catggccaat gccaaggtca aactctccat    960
tccaaaattt aaggtggaaa agatgattga tcccaaggct tgtctggaaa atctagggct   1020
gaaacatatc ttcagtgaag acacatctga tttctctgga atgtcagaga ccaagggagt   1080
ggccctatca aatgttatcc acaaagtgtg cttagaaata actgaagatg gtggggattc   1140
catagaggtg ccaggagcac ggatcctgca gcacaaggat gaattgaatg ctgaccatcc   1200
ctttatttac atcatcaggc acaacaaaac tcgaaacatc attttctttg gcaaattctg   1260
ttctccttaa gtggcatagc ccatgttaag tcctccctga cttttctgtg gatgccgatt   1320
tctgtaaact ctgcatccag agattcattt tctagataca ataaattgct aatgttgctg   1380
gatcaggaag ccgccagtac ttgtcatatg tagccttcac acagatagac cttttttttt   1440
tttccaattc tatcttttgt ttcctttttt cccataagac aatgacatac gcttttaatg   1500
```

aaaaggaatc acgttagagg aaaaatattt attcattatt tgtcaaattg tccggggtag 1560
ttggcagaaa tacagtcttc cacaaagaaa attcctataa ggaagatttg gaagctcttc 1620
ttcccagcac tatgctttcc ttctttggga tagagaatgt tccagacatt ctcgcttccc 1680
tgaaagactg aagaaagtgt agtgcatggg acccacgaaa ctgccctggc tccagtgaaa 1740
cttgggcaca tgctcaggct actataggtc cagaagtcct tatgttaagc cctggcaggc 1800
aggtgtttat taaaattctg aattttgggg attttcaaaa gataatattt tacatacact 1860
gtatgttata gaacttcatg gatcagatct ggggcagcac cctataaatc aacaccttaa 1920
tatgctgcaa caaaatgtag aatattcaga caaaatggat acataaagac taagtagccc 1980
ataaggggtc aaaatttgct gccaaatgcg tatgccacca acttacaaaa acacttcgtt 2040
cgcagagctt ttcagattgt ggaatgttgg ataaggaatt atagacctct agtagctgaa 2100
atgcaagacc ccaagaggaa gttcagatct taatataaat tcactttcat ttttgatagc 2160
tgtcccatct ggtcatttgg ttggcactag actggtggca ggggcttcta gctgacttgc 2220
acagggattc tcacaatagc cgatatcaga atttgtgttg aaggaacttg tctcttcatc 2280
taatatgata gcgggaaaag gagaggaaac tactgccttt agaaaatata agtaaagtga 2340
ttaaagtgct cacgttacct tgacacatag tttttcagtc tatgggttta gttactttag 2400
atggcaagca tgtaacttat attaatagta atttgtaaag ttggttggat aagctatccg 2460
tgttgcaggt tcatggatta cttctctata aaaaatatgt atttaccaaa aattttgtga 2520
cattccttct cccatctctt ccttgacctg cattgtaaat aggttcttct tgttctgaga 2580
ttcaatattg aatttttcct atgctattga caataaaata ttattgaact aca 2633

<210> SEQ ID NO 103
<211> LENGTH: 2005
<212> TYPE: DNA
<213> ORGANISM: Homo sapiens

<400> SEQUENCE: 103
caacggctca ttctgctccc ccgggtcgga gccccccgga gctgcgcgcg ggcttgcagc 60
gcctcgcccg cgctgtcctc ccggtgtccc gcttctccgc gccccagccg ccggctgcca 120
gcttttcggg gccccgagtc gcacccagcg aagagagcgg gcccgggaca agctcgaact 180
ccggccgcct cgcccttccc cggctccgct ccctctgccc cctcggggtc gcgcgcccac 240
gatgctgcag ggccctggct cgctgctgct gctcttcctc gcctcgcact gctgcctggg 300
ctcggcgcgc gggctcttcc tctttggcca gcccgacttc tcctacaagc gcagcaattg 360
caagcccatc cctgccaacc tgcagctgtg ccacggcatc gaataccaga acatgcggct 420
gcccaacctg ctgggccacg agaccatgaa ggaggtgctg gagcaggccg gcgcttggat 480
cccgctggtc atgaagcagt gccacccgga caccaagaag ttcctgtgct cgctcttcgc 540
ccccgtctgc ctcgatgacc tagacgagac catccagcca tgccactcgc tctgcgtgca 600
ggtgaaggac cgctgcgccc cggtcatgtc cgccttcggc ttcccctggc ccgacatgct 660
tgagtgcgac cgtttccccc aggacaacga cctttgcatc cccctcgcta gcagcgacca 720
cctcctgcca gccaccgagg aagctccaaa ggtatgtgaa gcctgcaaaa ataaaaatga 780
tgatgacaac gacataatgg aaacgctttg taaaaatgat tttgcactga aaataaaagt 840
gaaggagata acctacatca accgagatac caaaatcatc ctggagacca agagcaagac 900
catttacaag ctgaacggtg tgtccgaaag ggacctgaag aaatcggtgc tgtggctcaa 960
agacagcttg cagtgcacct gtgaggagat gaacgacatc aacgcgccct atctggtcat 1020

```
gggacagaaa cagggtgggg agctggtgat cacctcggtg aagcggtggc agaaggggca   1080
gagagagttc aagcgcatct cccgcagcat ccgcaagctg cagtgctagt cccggcatcc   1140
tgatggctcc gacaggcctg ctccagagca cggctgacca tttctgctcc gggatctcag   1200
ctcccgttcc ccaagcacac tcctagctgc tccagtctca gcctgggcag cttccccctg   1260
ccttttgcac gtttgcatcc ccagcatttc ctgagttata aggccacagg agtggatagc   1320
tgttttcacc taaaggaaaa gcccacccga atcttgtaga aatattcaaa ctaataaaat   1380
catgaatatt tttatgaagt ttaaaaatag ctcactttaa agctagtttt gaataggtgc   1440
aactgtgact tgggtctggt tggttgttgt ttgttgtttt gagtcagctg attttcactt   1500
cccactgagg ttgtcataac atgcaaattg cttcaatttt ctctgtggcc caaacttgtg   1560
ggtcacaaac cctgttgaga taaagctggc tgttatctca acatcttcat cagctccaga   1620
ctgagactca gtgtctaagt cttacaacaa ttcatcattt tataccttca atgggaactt   1680
aaactgttac atgtatcaca ttccagctac aatacttcca tttattagaa gcacattaac   1740
catttctata gcatgatttc ttcaagtaaa aggcaaaaga tataaatttt ataattgact   1800
tgagtacttt aagccttgtt taaaacattt cttacttaac ttttgcaaat taaacccatt   1860
gtagcttacc tgtaatatac atagtagttt acctttaaaa gttgtaaaaa tattgcttta   1920
accaacactg taaatatttc agataaacat tatattcttg tatataaact ttacatcctg   1980
ttttacctat aaaaaaaaaa aaaaa                                          2005
```

<210> SEQ ID NO 104
<211> LENGTH: 3687
<212> TYPE: DNA
<213> ORGANISM: Homo sapiens

<400> SEQUENCE: 104

```
tccaccattt tgctagagaa ggccgcggag gctcagagag gtgcgcacac ttgccctgag     60
tcacacagcg aatgccctcc gcggtcccaa cgcagagaga acgagccgat cggcagcctg    120
agcgaggcag tggttagggg gggccccggc cccggccact cccctcaccc cctccccgca    180
gagcgccgcc caggacaggc tgggccccag gccccgcccc gaggtcctgc ccacacaccc    240
ctgacacacc ggcgtcgcca gccaatggcc ggggtcctat aaacgctacg gtccgcgcgc    300
tctctggcaa gaggcaagag gtagcaacag cgagcgtgcc ggtcgctagt cgcgggtccc    360
cgagtgagca cgccagggag caggagacca aacgacgggg gtcggagtca gagtcgcagt    420
gggagtcccc ggaccggagc acgagcctga gcgggagagc gccgctcgca cgcccgtcgc    480
cacccgcgta cccggcgcag ccagagccac cagcgcagcg ctgccatgga gcccagcagc    540
aagaagctga cgggtcgcct catgctggcc gtgggaggag cagtgcttgg ctccctgcag    600
tttggctaca acactggagt catcaatgcc ccccagaagg tgatcgagga gttctacaac    660
cagacatggg tccaccgcta tggggagagc atcctgccca ccacgctcac cacgctctgg    720
tccctctcag tggccatctt ttctgttggg ggcatgattg gctccttctc tgtgggcctt    780
ttcgttaacc gctttggccg gcggaattca atgctgatga tgaacctgct ggccttcgtg    840
tccgccgtgc tcatgggctt ctcgaaactg ggcaagtcct ttgagatgct gatcctgggc    900
cgcttcatca tcggtgtgta ctgcggcctg accacaggct tcgtgcccat gtatgtgggt    960
gaagtgtcac ccacagccct tcgtggggcc ctgggcaccc tgcaccagct gggcatcgtc   1020
gtcggcatcc tcatcgccca ggtgttcggc ctggactcca tcatgggcaa caaggacctg   1080
```

tggcccctgc tgctgagcat catcttcatc ccggccctgc tgcagtgcat cgtgctgccc 1140
ttctgccccg agagtccccg cttcctgctc atcaaccgca acgaggagaa ccgggccaag 1200
agtgtgctaa agaagctgcg cgggacagct gacgtgaccc atgacctgca ggagatgaag 1260
gaagagagtc ggcagatgat gcgggagaag aaggtcacca tcctggagct gttccgctcc 1320
cccgcctacc gccagcccat cctcatcgct gtggtgctgc agctgtccca gcagctgtct 1380
ggcatcaacg ctgtcttcta ttactccacg agcatcttcg agaaggcggg ggtgcagcag 1440
cctgtgtatg ccaccattgg ctccggtatc gtcaacacgg ccttcactgt cgtgtcgctg 1500
tttgtggtgg agcgagcagg ccggcggacc ctgcacctca taggcctcgc tggcatggcg 1560
ggttgtgcca tactcatgac catcgcgcta gcactgctgg agcagctacc ctggatgtcc 1620
tatctgagca tcgtggccat ctttggcttt gtggccttct ttgaagtggg tcctggcccc 1680
atcccatggt tcatcgtggc tgaactcttc agccagggtc cacgtccagc tgccattgcc 1740
gttgcaggct tctccaactg gacctcaaat ttcattgtgg gcatgtgctt ccagtatgtg 1800
gagcaactgt gtggtcccta cgtcttcatc atcttcactg tgctcctggt tctgttcttc 1860
atcttcacct acttcaaagt tcctgagact aaaggccgga ccttcgatga gatcgcttcc 1920
ggcttccggc aggggggagc cagccaaagt gacaagacac ccgaggagct gttccatccc 1980
ctgggggctg attcccaagt gtgagtcgcc ccagatcacc agcccggcct gctcccagca 2040
gccctaagga tctctcagga gcacaggcag ctggatgaga cttccaaacc tgacagatgt 2100
cagccgagcc gggcctgggg ctcctttctc cagccagcaa tgatgtccag aagaatattc 2160
aggacttaac ggctccagga ttttaacaaa agcaagactg ttgctcaaat ctattcagac 2220
aagcaacagg ttttataatt tttttattac tgattttgtt atttttatat cagcctgagt 2280
ctcctgtgcc cacatcccag gcttcaccct gaatggttcc atgcctgagg gtggagacta 2340
agccctgtcg agacacttgc cttcttcacc cagctaatct gtagggctgg acctatgtcc 2400
taaggacaca ctaatcgaac tatgaactac aaagcttcta tcccaggagg tggctatggc 2460
cacccgttct gctggcctgg atctccccac tctaggggtc aggctccatt aggatttgcc 2520
ccttcccatc tcttcctacc caaccactca aattaatctt tctttacctg agaccagttg 2580
ggagcactgg agtgcaggga ggagagggga agggccagtc tgggctgccg ggttctagtc 2640
tcctttgcac tgagggccac actattacca tgagaagagg gcctgtggga gcctgcaaac 2700
tcactgctca agaagacatg gagactcctg ccctgttgtg tatagatgca agatatttat 2760
atatattttt ggttgtcaat attaaataca gacactaagt tatagtatat ctggacaagc 2820
caacttgtaa atacaccacc tcactcctgt tacttaccta aacagatata aatggctggt 2880
ttttagaaac atggttttga aatgcttgtg gattgagggt aggaggtttg gatgggagtg 2940
agacagaagt aagtggggtt gcaaccactg caacggctta gacttcgact caggatccag 3000
tcccttacac gtacctctca tcagtgtcct cttgctcaaa aatctgtttg atccctgtta 3060
cccagagaat atatacattc tttatcttga cattcaaggc atttctatca catatttgat 3120
agttggtgtt caaaaaaaca ctagttttgt gccagccgtg atgctcaggc ttgaaatgca 3180
ttattttgaa tgtgaagtaa atactgtacc tttattggac aggctcaaag aggttatgtg 3240
cctgaagtcg cacagtgaat aagctaaaac acctgctttt aacaatggta ccatacaacc 3300
actactccat taactccacc cacctcctgc acccctcccc acacacacaa aatgaaccac 3360
gttctttgta tgggcccaat gagctgtcaa gctgccctgt gttcatttca tttggaattg 3420
ccccctctgg ttcctctgta tactactgct tcatctctaa agacagctca tcctcctcct 3480

```
tcacccctga atttccagag cacttcatct gctccttcat cacaagtcca gttttctgcc   3540

actagtctga atttcatgag aagatgccga tttggttcct gtgggtcctc agcactattc   3600

agtacagtgc ttgatgcaca gcaggcactc agaaaatact ggaggaaata aaacaccaaa   3660

gatatttgtc aaaaaaaaaa aaaaaaa                                        3687
```

<210> SEQ ID NO 105
<211> LENGTH: 2643
<212> TYPE: DNA
<213> ORGANISM: Homo sapiens

<400> SEQUENCE: 105

```
agggcggggc gggcagcagg tgagacgcca ggtctccagg gctccaatca ctccggagac     60

tgagccatgg ggggaaagca gcgggacgag gatgacgagg cctacgggaa gccagtcaaa    120

tacgacccct cctttcgagg ccccatcaag aacagaagct gcacagatgt catctgctgc    180

gtcctcttcc tgctcttcat tctaggttac atcgtggtgg ggattgtggc ctggttgtat    240

ggagaccccc ggcaagtcct ctaccccagg aactctactg ggcctactg tggcatgggg     300

gagaacaaag ataagccgta tctcctgtac ttcaacatct tcagctgcat cctgtccagc    360

aacatcatct cagttgctga gaacggccta cagtgcccca caccccaggt gtgtgtgtcc    420

tcctgcccgg aggacccatg gactgtggga aaaaacgagt tctcacagac tgttggggaa    480

gtcttctata caaaaaacag gaacttttgt ctgccagggg taccctggaa tatgacggtg    540

atcacaagcc tgcaacagga actctgcccc agtttcctcc tcccctctgc tccagctctg    600

gggcgctgct ttccatggac caacgttact ccaccggcgc tcccagggat caccaatgac    660

accaccatac agcaggggat cagcggtctt attgacagcc tcaatgcccg agacatcagt    720

gttaagatct ttgaagattt tgcccagtcc tggtattgga ttcttgttgc cctgggggtg    780

gctctggtct tgagcctact gtttatcttg cttctgcgcc tggtggctgg gccccctggtg   840

ctggtgctga tcctgggagt gctgggcgtg ctggcatacg gcatctacta ctgctgggag    900

gagtaccgag tgctgcggga caagggcgcc tccatctccc agctgggttt caccaccaac    960

ctcagtgcct accagagcgt gcaggagacc tggctggccg ccctgatcgt gttggcggtg   1020

cttgaagcca tcctgctgct gatgctcatc ttcctgcggc agcggattcg tattgccatc   1080

gccctcctga aggaggccag caaggctgtg ggacagatga tgtctaccat gttctaccca   1140

ctggtcacct ttgtcctcct cctcatctgc attgcctact gggccatgac tgctctgtac   1200

ctggctacat cggggcaacc ccagtatgtg ctctgggcat ccaacatcag ctcccccggc   1260

tgtgagaaag tgccaataaa tacatcatgc aaccccacgg cccaccttgt gaactcctcg   1320

tgcccagggc tgatgtgcgt cttccagggc tactcatcca aaggcctaat ccaacgttct   1380

gtcttcaatc tgcaaatcta tggggtcctg ggctcttct ggacccttaa ctgggtactg    1440

gccctgggcc aatgcgtcct cgctggagcc tttgcctcct tctactgggc cttccacaag   1500

ccccaggaca tccctacctt cccccttaatc tctgccttca tccgcacact ccgttaccac  1560

actgggtcat tggcatttgg agccctcatc ctgacccttg tgcagatagc ccgggtcatc   1620

ttggagtata ttgaccacaa gctcagagga gtgcagaacc ctgtagcccg ctgcatcatg   1680

tgctgtttca agtgctgcct ctggtgtctg gaaaaattta tcaagttcct aaaccgcaat   1740

gcatacatca tgatcgccat ctacgggaag aatttctgtg tctcagccaa aaatgcgttc   1800

atgctactca tgcgaaacat tgtcagggtg gtcgtcctgg acaaagtcac agacctgctg   1860
```

ctgttctttg ggaagctgct ggtggtcgga ggcgtggggg tcctgtcctt cttttttttc 1920
tccggtcgca tcccggggct gggtaaagac tttaagagcc cccacctcaa ctattactgg 1980
ctgcccatca tgacctccat cctgggggcc tatgtcatcg ccagcggctt cttcagcgtt 2040
ttcggcatgt gtgtggacac gctcttcctc tgcttcctgg aagacctgga gcggaacaac 2100
ggctccctgg accggcccta ctacatgtcc aagagccttc taaagattct gggcaagaag 2160
aacgaggcgc ccccggacaa caagaagagg aagaagtgac agctccggcc ctgatccagg 2220
actgcacccc acccccaccg tccagccatc caacctcact tcgccttaca ggtctccatt 2280
ttgtggtaaa aaaaggtttt aggccaggcg ccgtggctca cgcctgtaat ccaacacttt 2340
gagaggctga ggcgggcgga tcacctgagt caggagttcg agaccagcct ggccaacatg 2400
gtgaaacctc cgtctctatt aaaaatacaa aaattagccg agagtggtgg catgcacctg 2460
tcatcccagc tactcgggag gctgaggcag gagaatcgct tgaacccggg aggcagaggt 2520
tgcagtgagc cgagatcgcg ccactgcact ccaacctggg tgacagactc tgtctccaaa 2580
acaaaacaaa caaacaaaaa gattttatta aagatatttt gttaactcag taaaaaaaaa 2640
aaa 2643

<210> SEQ ID NO 106
<211> LENGTH: 3604
<212> TYPE: DNA
<213> ORGANISM: Homo sapiens

<400> SEQUENCE: 106
gggagaagga ggaggccggg ggaaggagga gacaggagga ggagggacca cggggtggag 60
gggagataga cccagcccag agctctgagt ggtttcctgt tgcctgtctc taaacccctc 120
cacattcccg cggtccttca gactgcccgg agagcgcgct ctgcctgccg cctgcctgcc 180
tgccactgag ggttcccagc accatgaggg cctggatctt ctttctcctt tgcctggccg 240
ggagggcctt ggcagcccct cagcaagaag ccctgcctga tgagacagag gtggtggaag 300
aaactgtggc agaggtgact gaggtatctg tgggagctaa tcctgtccag gtggaagtag 360
gagaatttga tgatggtgca gaggaaaccg aagaggaggt ggtggcggaa aatccctgcc 420
agaaccacca ctgcaaacac ggcaaggtgt gcgagctgga tgagaacaac acccccatgt 480
gcgtgtgcca ggaccccacc agctgcccag cccccattgg cgagtttgag aaggtgtgca 540
gcaatgacaa caagaccttc gactcttcct gccacttctt tgccacaaag tgcaccctgg 600
agggcaccaa gaagggccac aagctccacc tggactacat cgggccttgc aaatacatcc 660
ccccttgcct ggactctgag ctgaccgaat tcccccctgcg catgcgggac tggctcaaga 720
acgtcctggt caccctgtat gagagggatg aggacaacaa ccttctgact gagaagcaga 780
agctgcgggt gaagaagatc catgagaatg agaagcgcct ggaggcagga gaccaccccg 840
tggagctgct ggcccgggac ttcgagaaga actataacat gtacatcttc cctgtacact 900
ggcagttcgg ccagctggac cagcacccca ttgacgggta cctctcccac accgagctgg 960
ctccactgcg tgctcccctc atccccatgg agcattgcac cacccgcttt ttcgagacct 1020
gtgacctgga caatgacaag tacatcgccc tggatgagtg ggccggctgc ttcggcatca 1080
agcagaagga tatcgacaag gatcttgtga tctaaatcca ctccttccac agtaccggat 1140
tctctcttta accctcccct tcgtgtttcc cccaatgttt aaaatgtttg gatggtttgt 1200
tgttctgcct ggagacaagg tgctaacata gatttaagtg aatacattaa cggtgctaaa 1260
aatgaaaatt ctaacccaag acatgacatt cttagctgta acttaactat taaggccttt 1320

```
tccacacgca ttaatagtcc catttttctc ttgccatttg tagctttgcc cattgtctta   1380
ttggcacatg ggtggacacg gatctgctgg gctctgcctt aaacacacat tgcagcttca   1440
acttttctct ttagtgttct gtttgaaact aatacttacc gagtcagact ttgtgttcat   1500
ttcatttcag ggtcttggct gcctgtgggc ttccccaggt ggcctggagg tgggcaaagg   1560
gaagtaacag acacacgatg ttgtcaagga tggttttggg actagaggct cagtggtggg   1620
agagatccct gcagaaccca ccaaccagaa cgtggtttgc ctgaggctgt aactgagaga   1680
aagattctgg ggctgtgtta tgaaaatata gacattctca cataagccca gttcatcacc   1740
atttcctcct ttacctttca gtgcagtttc ttttcacatt aggctgttgg ttcaaacttt   1800
tgggagcacg gactgtcagt tctctgggaa gtggtcagcg catcctgcag ggcttctcct   1860
cctctgtctt ttggagaacc agggctcttc tcaggggctc tagggactgc caggctgttt   1920
cagccaggaa ggccaaaatc aagagtgaga tgtagaaagt tgtaaaatag aaaaagtgga   1980
gttggtgaat cggttgttct ttcctcacat ttggatgatt gtcataaggt ttttagcatg   2040
ttcctccttt tcttcaccct ccccttttt cttctattaa tcaagagaaa cttcaaagtt   2100
aatgggatgg tcggatctca caggctgaga actcgttcac ctccaagcat ttcatgaaaa   2160
agctgcttct tattaatcat acaaactctc accatgatgt gaagagtttc acaaatcctt   2220
caaaataaaa agtaatgact tagaaactgc cttcctgggt gatttgcatg tgtcttagtc   2280
ttagtcacct tattatcctg acacaaaaac acatgagcat acatgtctac acatgactac   2340
acaaatgcaa acctttgcaa acacattatg cttttgcaca cacacacctg tacacacaca   2400
ccggcatgtt tatacacagg gagtgtatgg ttcctgtaag cactaagtta gctgttttca   2460
tttaatgacc tgtggtttaa cccttttgat cactaccacc attatcagca ccagactgag   2520
cagctatatc cttttattaa tcatggtcat tcattcattc attcattcac aaaatattta   2580
tgatgtattt actctgcacc aggtcccatg ccaagcactg gggacacagt tatggcaaag   2640
tagacaaagc atttgttcat ttggagctta gagtccagga ggaatacatt agataatgac   2700
acaatcaaat ataaattgca agatgtcaca ggtgtgatga agggagagta ggagagacca   2760
tgagtatgtg taacaggagg acacagcatt attctagtgc tgtactgttc cgtacggcag   2820
ccactaccca catgtaactt tttaagattt aaatttaaat tagttaacat tcaaaacgca   2880
gctccccaat cacactagca acatttcaag tgcttgagag ccatgcatga ttagtggtta   2940
ccctattgaa taggtcagaa gtagaatctt ttcatcatca cagaaagttc tattggacag   3000
tgctcttcta gatcatcata agactacaga gcacttttca aagctcatgc atgttcatca   3060
tgttagtgtc gtattttgag ctggggtttt gagactcccc ttagagatag agaaacagac   3120
ccaagaaatg tgctcaattg caatgggcca catacctaga tctccagatg tcatttcccc   3180
tctcttattt taagttatgt taagattact aaaacaataa aagctcctaa aaaatcaaac   3240
tgtattctgg tgttctcttc tacacagtgg gagggcgagc agtaggagag attggcccat   3300
ttggtgctgg ccatttgagg aatgcaagcc cagcactagt ctcataatct ctaggaatct   3360
gtagagagag gaattgaagt aaatttcagc attggctcat tcagtcattc ggcgacattc   3420
atcaggtacc tgcaatgtgt taggggatct tatgagtagg cagcgtgcgt gatccttgct   3480
cccctggagc tttctaacat tctagcaggc agaccacaca taaatttgca atactgtttc   3540
tgataaaaac gtgctgtaaa ggaaataaag cagagaacta tcatggaaaa aaaaaaaaaa   3600
aaaa                                                                3604
```

<210> SEQ ID NO 107
<211> LENGTH: 386
<212> TYPE: DNA
<213> ORGANISM: Homo sapiens

<400> SEQUENCE: 107
ccaggatcag catggccgtc cgccagtggg taatcgccct ggccttggct gccctccttg 60
ttgtggacag ggaagtgcca gtggcagcag gaaagctccc tttctcaaga atgcccatct 120
gtgaacacat ggtagagtct ccaacctgtt cccagatgtc caacctggtc tgcggcactg 180
atgggctcac atatacgaat gaatgccagc tctgcttggc ccggataaaa accaaacagg 240
acatccagat catgaaagat ggcaaatgct gatcccacag gagcacctca agccatgaag 300
tgtcagctgg agaacagtgg tgggcatgga gaggatatga catgaaataa aagatccagc 360
ccaactgaaa aaaaaaaaaa aaaaaa 386

<210> SEQ ID NO 108
<211> LENGTH: 641
<212> TYPE: DNA
<213> ORGANISM: Homo sapiens

<400> SEQUENCE: 108
accagttcta agggaccata cagagtattc ctctcttcac accaggacca gtcactgttg 60
cagcatgagt tcccagcagc agaagcagcc ttgcacccca ccccctcagc ttcagcagca 120
gcaggtgaaa cagccttgcc agcctccacc tcaggaacca tgcatcccca aaaccaagga 180
gccctgccac cccaaggtgc ctgagccctg ccaccccaaa gtgcccgagc cctgccagcc 240
caaggttcca gagccatgcc accccaaggt gcctgagccc tgcccttcaa tagtcactcc 300
agcaccagcc cagcagaaga ccaagcagaa gtaatgtggt ccacagccat gcccttgagg 360
agccggccac cagatgctga atcccctatc ccattctgcg tatgagtccc atttgccttg 420
caattagcat tctgtctccc ccaaaaaaga atgtgctatg aagctttctt tcctacacac 480
tctgagtctc tgaatgaagc tgaaggtctt agtaccagag ctagttttca gctgctcaga 540
attcatctga agagagactt aagatgaaag caaatgattc agctccctta tacccccatt 600
aaattcactt tcaattccaa aaaaaaaaaa aaaaaaaaaa a 641

<210> SEQ ID NO 109
<211> LENGTH: 1002
<212> TYPE: DNA
<213> ORGANISM: Homo sapiens

<400> SEQUENCE: 109
tcaccagatc ccagaggctg aacacctcga ccttctctgc acagcagatg atccctgagc 60
agctgaagac cagaaaagcc actaagactt tctgcttaat tcaggagctt agaggattct 120
tcaaagagtg tgtccagcat cctttgaagc atgagttctt accagcagaa gcagaccttt 180
accccaccac ctcagcttca acagcagcag gtgaaacaac ccagccagcc tccacctcag 240
gaaatatttg ttcccacaac caaggagcca tgccactcaa aggttccaca acctggaaac 300
acaaagattc cagagccagg ctgtaccaag gtccctgagc caggctgtac caaggtccct 360
gagccaggct gtaccaaggt ccctgagcca ggttgtacca aggtccctga gccaggctgt 420
accaaggtcc ctgagccagg ttgtaccaag gtccctgagc caggctacac caaggtccct 480
gaaccaggca gcatcaaggt ccctgaccaa ggcttcatca agtttcctga gccaggtgcc 540
atcaaagttc ctgagcaagg atacaccaaa gttcctgtgc caggctacac aaagctacca 600
gagccatgtc cttcaacggt cactccaggc ccagctcagc agaagaccaa gcagaagtaa 660
tttggtgcac agacaagccc ttgagaagcc aaccaccaga tgctggacac cctcttccca 720
tctgtttctg tgtcttaatt gtctgtagac cttgtaatca gcacattgtc accccaagcc 780
atagtctctc tcttatttgt atcctaaaaa tacgtactat aaagcttttg ttcacacaca 840
ctctgaagaa tcctgtaagc ccctgaatta agcagaaagt cttcatggct tttctggtct 900
tcggctgctc agggttcatc tgaagattcg aatgaaaaga aatgcatgtt tcctgctctt 960
ccctcattaa attgctttta attccaaaaa aaaaaaaaaa aa 1002

<210> SEQ ID NO 110
<211> LENGTH: 2593
<212> TYPE: DNA
<213> ORGANISM: Homo sapiens

<400> SEQUENCE: 110
ataagccttc atacagcagt gaaggcggtt cctcccttcc caggcagaga ctgataaact 60
cagcacttgc cggagtggct cattgttaag acaaagggtg tgcacttcct ggccaggaaa 120
cctgagcggt gagactccca gctgcctaca tcaaggcccc aggacatgca gaaccttcct 180
ctagaacccg acccaccacc atgaggtcct gcctgtggag atgcaggcac ctgagccaag 240
gcgtccagtg gtccttgctt ctggctgtcc tggtcttctt tctcttcgcc ttgccctctt 300
ttattaagga gcctcaaaca aagccttcca ggcatcaacg cacagagaac attaaagaaa 360
ggtctctaca gtccctggca aagcctaagt cccaggcacc cacaagggca aggaggacaa 420
ccatctatgc agagccagtg ccagagaaca atgccctcaa cacacaaacc cagcccaagg 480
cccacaccac cggagacaga ggaaaggagg ccaaccaggc accgccggag gagcaggaca 540
aggtgcccca cacagcacag agggcagcat ggaagagccc agaaaaagag aaaaccatgg 600
tgaacacact gtcacccaga gggcaagatg cagggatggc ctctggcagg acagaggcac 660
aatcatggaa gagccaggac acaaagacga cccaaggaaa tgggggccag accaggaagc 720
tgacggcctc caggacggtg tcagagaagc accagggcaa agcggcaacc acagccaaga 780
cgctcattcc caaaagtcag cacagaatgc tggctcccac aggagcagtg tcaacaagga 840
cgagacagaa aggagtgacc acagcagtca tcccacctaa ggagaagaaa cctcaggcca 900
ccccaccccc tgcccctttc cagagcccca cgacgcagag aaaccaaaga ctgaaggccg 960
ccaacttcaa atctgagcct cggtgggatt ttgaggaaaa atacagcttc gaaataggag 1020
gccttcagac gacttgccct gactctgtga agatcaaagc ctccaagtcg ctgtggctcc 1080
agaaactctt tctgcccaac ctcactctct tcctggactc cagacacttc aaccagagtg 1140
agtgggaccg cctggaacac tttgcaccac cctttggctt catggagctc aactactcct 1200
tggtgcagaa ggtcgtgaca cgcttccctc cagtgcccca gcagcagctg ctcctggcca 1260
gcctccccgc tgggagcctc cggtgcatca cctgtgccgt ggtgggcaac gggggcatcc 1320
tgaacaactc ccacatgggc caggagatag acagtcacga ctacgtgttc cgattgagcg 1380
gagctctcat taaaggctac gaacaggatg tggggactcg gacatccttc tacggcttta 1440
ccgccttctc cctgacccag tcactcctta tattgggcaa tcggggtttc aagaacgtgc 1500
ctcttgggaa ggacgtccgc tacttgcact tcctggaagg cacccgggac tatgagtggc 1560
tggaagcact gcttatgaat cagacggtga tgtcaaaaaa ccttttctgg ttcaggcaca 1620
gaccccagga agcttttcgg gaagccctgc acatggacag gtacctgttg ctgcacccag 1680
actttctccg atacatgaag aacaggtttc tgaggtctaa gaccctggat ggtgcccact 1740
ggaggatata ccgccccacc actggggccc tcctgctgct cactgccctt cagctctgtg 1800
accaggtgag tgcttatggc ttcatcactg agggccatga gcgcttttct gatcactact 1860
atgatacatc atggaagcgg ctgatctttt acataaacca tgacttcaag ctggagagag 1920
aagtctggaa gcggctacac gatgaaggga taatccggct gtaccagcgt cctggtcccg 1980
gaactgccaa agccaagaac tgaccggggc cagggctgcc atggtctcct tgcctgctcc 2040
aaggcacagg atacagtggg aatcttgaga ctctttggcc atttcccatg gctcagacta 2100
agctccaagc ccttcaggag ttccaaggga acacttgaac catggacaag actctctcaa 2160
gatggcaaat ggctaattga ggttctgaag ttcttcagta cattgctgta ggtcctgagg 2220
ccagggattt ttaattaaat ggggtgatgg gtggccaata ccacaattcc tgctgaaaaa 2280
cactcttcca gtccaaaagc ttcttgatac agaaaaaaga gcctggattt acagaaacat 2340
atagatctgg tttgaattcc agatcgagtt tacagttgtg aaatcttgaa ggtattactt 2400
aacttcacta cagattgtct agaagacctt tctaggagtt atctgattct agaagggtct 2460
atacttgtcc ttgtctttaa gctatttgac aactctacgt gttgtagaaa actgataata 2520
atacaaatga ttgttgtcca tggaaaggca aataaatttt ctacagtgaa gatgcaaaaa 2580
aaaaaaaaaa aaa 2593

<210> SEQ ID NO 111
<211> LENGTH: 5716
<212> TYPE: DNA
<213> ORGANISM: Homo sapiens

<400> SEQUENCE: 111
gtgatgataa taatacgcgg gcttatataa ccgtcttcat cttgcgagca cttcgcagac 60
cgtcgctaat gaatcttggg gccggtgtcg ggccggggcg gcttgatcgg caactaggaa 120
accccaggcg cagaggccag gagcgagggc agcgaggatc agaggccagg ccttcccggc 180
tgccggcgct cctcggaggt cagggcagat gaggaacatg actctccccc ttcggaggag 240
gaaggaagtc ccgctgccac cttatctctg ctcctctgcc tcctccctgt tcccagagct 300
ttttctctag agaagatttt gaaggcggct tttggattct tcacttctct tgaacaagga 360
actcactcag agactaacac aaaggaagta atttcttacc tggtcattat ttagtctaca 420
ataagttcat ccttcttcag tgtgaccagt aaattcttcc catactcttg aagagagcat 480
aattggaatg gagaggtgct gacggccacc caccatcatc taaagaagat aaacttggca 540
aatgacatgc aggttcttca aggcagaata attgcagaaa atcttcaaag gaccctatct 600
gcagatgttc tgaatacctc tgagaataga gattgattat tcaaccagga tacctaattc 660
aagaactcca gaaatcagga gacggagaca ttttgtcagt tttgcaacat tggaccaaat 720
acaatgaagt attcttgctg tgctctggtt ttggctgtcc tgggcacaga attgctggga 780
agcctctgtt cgactgtcag atccccgagg ttcagaggac ggatacagca ggaacgaaaa 840
aacatccgac ccaacattat tcttgtgctt accgatgatc aagatgtgga gctggggtcc 900
ctgcaagtca tgaacaaaac gagaaagatt atggaacatg gggggccac cttcatcaat 960
gcctttgtga ctacacccat gtgctgcccg tcacggtcct ccatgctcac cgggaagtat 1020
gtgcacaatc acaatgtcta caccaacaac gagaactgct cttccccctc gtggcaggcc 1080
atgcatgagc ctcggacttt tgctgtatat cttaacaaca ctggctacag aacagccttt 1140
tttggaaaat acctcaatga atataatggc agctacatcc cccctgggtg gcgagaatgg 1200
cttggattaa tcaagaattc tcgcttctat aattacactg tttgtcgcaa tggcatcaaa 1260
gaaaagcatg gatttgatta tgcaaaggac tacttcacag acttaatcac taacgagagc 1320
attaattact tcaaaatgtc taagagaatg tatccccata ggcccgttat gatggtgatc 1380
agccacgctg cgccccacgg ccccgaggac tcagccccac agttttctaa actgtacccc 1440
aatgcttccc aacacataac tcctagttat aactatgcac caaatatgga taaacactgg 1500
attatgcagt acacaggacc aatgctgccc atccacatgg aatttacaaa cattctacag 1560
cgcaaaaggc tccagacttt gatgtcagtg gatgattctg tggagaggct gtataacatg 1620
ctcgtggaga cgggggagct ggagaatact tacatcattt acaccgccga ccatggttac 1680
catattgggc agtttggact ggtcaagggg aaatccatgc catatgactt tgatattcgt 1740
gtgccttttt ttattcgtgg tccaagtgta gaaccaggat caatagtccc acagatcgtt 1800
ctcaacattg acttggcccc cacgatcctg gatattgctg ggctcgacac acctcctgat 1860
gtggacggca agtctgtcct caaacttctg gacccagaaa agccaggtaa caggtttcga 1920
acaaacaaga aggccaaaat ttggcgtgat acattcctag tggaaagagg caaatttcta 1980
cgtaagaagg aagaatccag caagaatatc caacagtcaa atcacttgcc caaatatgaa 2040
cgggtcaaag aactatgcca gcaggccagg taccagacag cctgtgaaca accggggcag 2100
aagtggcaat gcattgagga tacatctggc aagcttcgaa ttcacaagtg taaaggaccc 2160
agtgacctgc tcacagtccg gcagagcacg cggaacctct acgctcgcgg cttccatgac 2220
aaagacaaag agtgcagttg tagggagtct ggttaccgtg ccagcagaag ccaaagaaag 2280
agtcaacggc aattcttgag aaaccagggg actccaaagt acaagcccag atttgtccat 2340
actcggcaga cacgttcctt gtccgtcgaa tttgaaggtg aaatatatga cataaatctg 2400
gaagaagaag aagaattgca agtgttgcaa ccaagaaaca ttgctaagcg tcatgatgaa 2460
ggccacaagg ggccaagaga tctccaggct tccagtggtg gcaacagggg caggatgctg 2520
gcagatagca gcaacgccgt gggcccacct accactgtcc gagtgacaca caagtgtttt 2580
attcttccca atgactctat ccattgtgag agagaactgt accaatcggc cagagcgtgg 2640
aaggaccata aggcatacat tgacaaagag attgaagctc tgcaagataa aattaagaat 2700
ttaagagaag tgagaggaca tctgaagaga aggaagcctg aggaatgtag ctgcagtaaa 2760
caaagctatt acaataaaga gaaaggtgta aaaaagcaag agaaattaaa gagccatctt 2820
cacccattca aggaggctgc tcaggaagta gatagcaaac tgcaactttt caaggagaac 2880
aaccgtagga ggaagaagga gaggaaggag aagagacggc agaggaaggg ggaagagtgc 2940
agcctgcctg gcctcacttg cttcacgcat gacaacaacc actggcagac agccccgttc 3000
tggaacctgg gatctttctg tgcttgcacg agttctaaca ataacaccta ctggtgtttg 3060
cgtacagtta atgagacgca taattttctt ttctgtgagt ttgctactgg ctttttggag 3120
tattttgata tgaatacaga tccttatcag ctcacaaata cagtgcacac ggtagaacga 3180
ggcattttga atcagctaca cgtacaacta atggagctca gaagctgtca aggatataag 3240
cagtgcaacc caagacctaa gaatcttgat gttggaaata aagatggagg aagctatgac 3300
ctacacagag gacagttatg ggatggatgg gaaggttaat cagccccgtc tcactgcaga 3360
catcaactgg caaggcctag aggagctaca cagtgtgaat gaaaacatct atgagtacag 3420
acaaaactac agacttagtc tggtggactg gactaattac ttgaaggatt tagatagagt 3480
atttgcactg ctgaagagtc actatgagca aaataaaaca aataagactc aaactgctca 3540
aagtgacggg ttcttggttg tctctgctga gcacgctgtg tcaatggaga tggcctctgc 3600
tgactcagat gaagacccaa ggcataaggt tgggaaaaca cctcatttga ccttgccagc 3660
tgaccttcaa accctgcatt tgaaccgacc aacattaagt ccagagagta aacttgaatg 3720
gaataacgac attccagaag ttaatcattt gaattctgaa cactggagaa aaaccgaaaa 3780
atggacgggg catgaagaga ctaatcatct ggaaaccgat ttcagtggcg atggcatgac 3840
agagctagag ctcgggccca gccccaggct gcagcccatt cgcaggcacc cgaaagaact 3900
tccccagtat ggtggtcctg gaaaggacat tttgaagat caactatatc ttcctgtgca 3960
ttccgatgga atttcagttc atcagatgtt caccatggcc accgcagaac accgaagtaa 4020
ttccagcata gcggggaaga tgttgaccaa ggtggagaag aatcacgaaa aggagaagtc 4080
acagcaccta gaaggcagcg cctcctcttc actctcctct gattagatga aactgttacc 4140
ttaccctaaa cacagtattt ctttttaact tttttatttg taaactaata aaggtaatca 4200
cagccaccaa cattccaagc taccctgggt acctttgtgc agtagaagct agtgagcatg 4260
tgagcaagcg gtgtgcacac ggagactcat cgttataatt tactatctgc caagagtaga 4320
aagaaaggct ggggatattt gggttggctt ggttttgatt ttttgcttgt ttgtttgttt 4380
tgtactaaaa cagtattatc ttttgaatat cgtagggaca taagtatata catgttatcc 4440
aatcaagatg gctagaatgg tgcctttctg agtgtctaaa acttgacacc cctggtaaat 4500
ctttcaacac acttccactg cctgcgtaat gaagttttga ttcattttta accactggaa 4560
tttttcaatg ccgtcatttt cagttagatg attttgcact ttgagattaa aatgccatgt 4620
ctatttgatt agtcttattt ttttattttt acaggcttat cagtctcact gttggctgtc 4680
attgtgacaa agtcaaataa acccccaagg acgacacaca gtatggatca catattgttt 4740
gacattaagc ttttgccaga aaatgttgca tgtgttttac ctcgacttgc taaaatcgat 4800
tagcagaaag gcatggctaa taatgttggt ggtgaaaata aataaataag taaacaaaat 4860
gaagattgcc tgctctctct gtgcctagcc tcaaagcgtt catcatacat catacettta 4920 agattgctat attttgggtt attttcttga caggagaaaa agatctaaag atcttttatt 4980
ttcatctttt ttggttttct tggcatgact aagaagctta aatgttgata aaatatgact 5040
agttttgaat ttacaccaag aacttctcaa taaaagaaaa tcatgaatgc tccacaattt 5100
caacatacca caagagaagt taatttctta acattgtgtt ctatgattat ttgtaagacc 5160
ttcaccaagt tctgatatct tttaaagaca tagttcaaaa ttgcttttga aaatctgtat 5220
tcttgaaaat atccttgttg tgtattaggt ttttaaatac cagctaaagg attacctcac 5280
tgagtcatca gtaccctcct attcagctcc ccaagatgat gtgtttttgc ttaccctaag 5340
agaggttttc ttcttatttt tagataattc aagtgcttag ataaattatg ttttctttaa 5400
gtgtttatgg taaactcttt taaagaaaat ttaatatgtt atagctgaat ctttttggta 5460
actttaaatc tttatcatag actctgtaca tatgttcaaa ttagctgctt gcctgatgtg 5520
tgtatcatcg gtgggatgac agaacaaaca tatttatgat catgaataat gtgctttgta 5580
aaaagatttc aagttattag gaagcatact ctgtttttta atcatgtata atattccatg 5640
atacttttat agaacaattc tggcttcagg aaagtctaga agcaatattt cttcaaataa 5700
aaggtgttta aacttt 5716

<210> SEQ ID NO 112
<211> LENGTH: 7355
<212> TYPE: DNA
<213> ORGANISM: Homo sapiens

<400> SEQUENCE: 112
agtctgcggg cctccggggc agcggcgagg ccggagcgtc gcggcggaga ggacgagacc 60
gggacaagac cagggcagga gggagccggc cagccgcgag aaccccgcac gcccggcaag 120
atgctgtcct ggcggctgca gacgggcccc gagaaggccg agctccagga gctcaacgcc 180
cggctctatg actacgtgtg tcgggtgcgg gagctggagc gcgaaaacct actcctggag 240
gaggagctgc gcggccggcg cgggcgagag ggcctgtggg ccgaggggca ggcccgctgc 300
gccgaggagg cgcgcagctt gcggcagcag ctggacgagc tgagctgggc cactgcgctg 360
gcggagggcg agcgggacgc tctgcggcgc gagctgcggg agctgcagcg cctggatgcg 420
gaggagcgcg ccgcccgcgg ccgcctggac gccgagctgg gtgcgcagca gcgcgagctg 480
caggaggcgc tgggcgcgcg cgccgccctc gaggcgctgc tgggccggct gcaggccgag 540
cgccgaggcc tcgacgcggc ccacgaacgc gacgtgaggg agctgcgcgc gcgcgccgcc 600
agccttacca tgcatttccg cgcccgcgcc accggccccg ccgcgccgcc gccacgcctg 660
cgggaggtgc acgacagcta cgcactgctg gtggccgagt cgtggcggga gacggtgcag 720
ctgtacgagg acgaggtgcg cgagctggag gaggcgctgc ggcgcggcca ggagagcaga 780
ctccaggcgg aggaagagac gcggctgtgc gcgcaggagg cagaggcgct gcggcgcgag 840
gcgctcgggt tggagcagct gcgcgcgcgg ctggaggacg cgctgctgcg gatgcgcgag 900
gagtacggga tacaggccga ggagcggcag agagtgattg actgcctgga ggatgagaag 960
gcaaccctca ccttggccat ggctgactgg ctgcgggact atcaggacct cctgcaggtg 1020
aagaccggcc tcagtctgga ggtggcgacc taccgggcct tattggaagg agaaagtaat 1080
ccagagatag tgatctgggc tgagcacgtt gaaaacatgc cgtcagaatt cagaaacaaa 1140
tcctatcact ataccgactc actactacag agggaaaatg aaaggaatct attttcaagg 1200
cagaaagcac ctttggcaag tttcaatcac agctcggcac tgtattctaa cctgtcaggg 1260
caccgtggat ctcagacggg cacatctatt ggaggtgatg ccagaagagg cttcttgggc 1320
tcgggatatt cttcctcggc cactacccag caggaaaact catacggaaa agccgtcagc 1380
agtcaaacca acgtcagaac tttctctcca acctatggcc ttttaagaaa tactgaggct 1440
caagtgaaaa cattccctga cagaccaaaa gccggagata caagggaggt ccccgtttac 1500
ataggtgaag attccacaat tgcccgcgag tcgtaccggg atcgccgaga caaggtggca 1560
gcaggtgctt cggaaagcac acggtcaaat gagaggaccg tcattctggg aaagaaaaca 1620
gaagtgaaag ccacgaggga gcaagaaaga aacagaccag aaaccatccg aacaaagcca 1680
gaagagaaaa tgttcgattc taaagagaag gcttccgagg agagaaacct aagatgggaa 1740
gaattgacaa agttagataa ggaagcgaga cagagagaaa gccagcagat gaaggagaag 1800
gctaaggaga aggactcacc gaaggagaag agcgtgcgag agagagaggt gccgattagt 1860
ctagaagtat cccaggacag aagagcagag gtgtccccga aaggtttgca gacgcctgtg 1920
aaggatgctg gtggtgggac cggtagagag gcagaagcaa gagagctacg gttcaggttg 1980
ggcaccagtg atgccactgg ttctctgcaa ggcgattcca tgacagaaac cgtagcagaa 2040
aacatcgtta ccagtatcct gaagcagttc actcagtctc cagagacaga agcatctgct 2100
gattcttttc cagacacaaa agtcacttac gtggacagga aagagcttcc tggggaaagg 2160
aaaacaaaga ctgaaatagt tgtggagtct aaactgactg aggatgttga tgtttccgat 2220
gaagctggcc tggactacct tttaagcaag gatattaagg aagtggggct gaaaggcaag 2280

-continued

```
tcagccgagc agatgatagg agacatcatc aacctcggcc tgaaagggag ggaggggaga   2340
gcaaaggtcg tcaacgtgga gatcgtggag gagcccgtga gttatgtcag cggggagaag   2400
ccggaggagt tttccgtccc attcaaagtg gaggaggtcg aagatgtgtc gccaggcccc   2460
tgggggttgg ttaaggagga ggaaggttat ggagaaagcg atgtcacatt ctcagttaat   2520
cagcatcgaa ggaccaagca gcctcaggag aacacgactc acgtggaaga agtgacagag   2580
gcaggtgatt cagagggcga gcagagttat tttgtgtcca ctccagatga acaccccggg   2640
gggcacgaca gagatgacgg ctcggtgtac gggcagatcc acatcgagga ggaatccacc   2700
atcaggtact cttggcagga tgaaatcgtg caggggactc gaaggaggac acagaaggac   2760
ggtgcagtgg gcgagaaggt tgtgaagccc ttggatgtcc cagcgccctc tctggagggg   2820
gacctgggtt ccactcactg gaaagaacaa gctagaagcg gtgaatttca tgccgaaccc   2880
acagtcattg aaaaagaaat taaaataccc cacgaattcc acacctccat gaagggcatc   2940
tcctccaagg agccccggca gcagctggtg gaggtcatcg ggcagctgga ggaaaccctt   3000
cccgagcgca tgagggagga gctgtccgcc ctcaccagag aggggcaggg tgggccgggg   3060
agcgtttccg tggatgtcaa gaaggtccag ggtgctggtg gcagttccgt gaccctggtt   3120
gctgaagtca acgtctcaca aactgtggat gccgatcggt tagacctgga ggagctgagc   3180
aaagatgagg ccagtgagat ggagaaggct gtggagtcgg tggttcggga gagcctgagc   3240
aggcaacgca gcccagcgcc tggcagccca gatgaggaag gtggagcgga ggccccggct   3300
gctggcattc gctttaggcg ttgggccacc cgggagctgt acatcccttc aggcgagagc   3360
gaggttgctg gtggggcctc tcacagctcg ggacagcgca ctccccaggg cccagtgtcg   3420
gccactgtgg aggtcagcag ccccacaggc tttgcccagt cacaggtgct ggaggatgtg   3480
agccaggctg caaggcacat aaaactcggc ccctctgaag tctggaggac tgagcgaatg   3540
tcatatgaag gacccactgc agaagtggtg gaggtaagtg cgggaggtga cctaagtcag   3600
gcagcgagcc cgaccggagc cagccggtct gtgaggcatg tcacgctggg tcccggtcaa   3660
agtccactgt ccagagaagt catcttccta ggccctgccc ctgcctgtcc agaggcatgg   3720
ggctcgccag aacctggccc agcagagtct tctgcagata tggacggatc agggaggcac   3780
agcacatttg gctgcagaca atttcatgct gaaaaggaga ttatttttca gggccccatt   3840
tctgctgcag ggaaggttgg tgattatttt gcaacagaag agtcagtggg tacccagact   3900
tctgtcaggc aactccagtt aggccctaaa gaagggttca gtgggcaaat ccagttcaca   3960
gctccacttt cagacaaggt ggagttgggt gtcataggag attctgtaca catggaaggg   4020
ttgccaggga gcagcacatc catcaggcac atcagcattg ggcctcagag gcatcagacc   4080
acccagcaga tagtttacca tgggctggtt ccccaactgg gggaatctgg tgactcagag   4140
agcactgtgc acggagaggg ctcagcagat gtgcaccagg ccactcacag tcatacctcg   4200
ggtagacaaa ccgttatgac tgaaaagagc accttccaaa gtgtcgtttc tgaatctccc   4260
caggaggata gtgcagagga cacatcaggg gcagaaatga catcgggtgt tagcagatcc   4320
tttaggcaca ttcgactagg tcctacagaa acggaaacct ctgaacacat tgccatccgt   4380
ggacccgtgt ccagaacatt tgtgcttgct ggttcagcgg actcccctga gctaggcaag   4440
ttagcagaca gcagcagaac gctaaggcac attgcaccag ggcccaaaga aacttcgttt   4500
acctttcaga tggatgtgag taacgtagag gcgatccgca gccggacaca ggaagcggga   4560
gctctcggtg tgtctgaccg tggttcctgg agagacgcgg acagtaggaa tgaccaggca   4620
gttggtgtga gctttaaggc ctctgctggg gaaggagacc aggcccacag agaacagggc   4680
```

aaggagcagg ccatgtttga taagaaggtg cagctccaga gaatggtaga ccaaaggtcg 4740
gtgatttcag atgaaaagaa agttgccctc ctctatctag acaatgagga ggaggagaat 4800
gatgggcatt ggttttaata agcagaaaca ttttgtttta atggcagcct gttggcgacg 4860
tgccaacatc caaaggcctt aacttatttt aagaggccga gggagtctat gaaaatctcc 4920
cctttttttac ttttttaaag agtactcccg gcatggtcaa tttcctttat agttaatccg 4980
taaaggtttc cagttaattc atgccttaaa aggcactgca attttatttt tgagttggga 5040
cttttacaaa acactttttt ccctggagtc ttctctccac ttctggagat gaatttctat 5100
gttttgcacc tggtcacaga catggcttgc atctgtttga aactacaatt aattatagat 5160
gtcaaaacat taaccagatt aaagtaatat atttaagagt aaattttgct tgcatgtgct 5220
aatatgaaat aacagactaa cattttaggg gaaaaataaa tacaatttag actctaaaaa 5280
gtcttttcaa aaagaaatgg gaaataggca gactgtttat gttaaaaaaa ttcttgctaa 5340
atgatttcat ctttaggaaa aaattacttg ccatatagag ctaaattcat cttaagactt 5400
gaatgaattg ctttctatgt acagaacttt aaacaatata gtatttatgg cgaggacagc 5460
tgtagtctgt tgtgatattt cacattctat ttgcacaggt tccctggcac tggtagggta 5520
gatgattatt gggaatcgct tacagtacca tttcattttt tggcactagg tcattaagta 5580
gcacacagtc tgaatgccct tttctggagt ggccagttcc tatcagactg tgcagacttg 5640
cgcttctctg caccttatcc cttagcaccc aaacatttaa tttcactggt gggaggtaga 5700
ccttgaagac aatgaagaga atgccgatac tcagactgca gctggaccgg caagctggct 5760
gtgtacagga aaattggaag cacacagtgg actgtgcctc ttaaagatgc ctttcccaac 5820
cctccattca tgggatgcag gtctttctga gctcaagggt gaaagatgaa tacaataaca 5880
accatgaacc cacctcacgg aagctttttt tgcactttga acagaagtca ttgcagttgg 5940
ggtgttttgt ccagggaaac agtttattaa atagaaggat gttttgggga aggaactgga 6000
tatctctcct gcagcccagc accgagatac ccaggacggg cctggggggc gagaaaggcc 6060
cccatgctca tgggccgcgg agtgtggacc tgtagatagg caccaccgag tttaagatac 6120
tgggatgagc atgcttcatt ggattcattt tattttacac gtcagtattg ttttaaagtt 6180
tctgtctgta aagtgtagca tcatatataa aaagagtttc gctagcagcg cattttttttt 6240
agttcaggct agcttctttc acataatgct gtctcagctg tatttccagt aacacagcat 6300
catcgcactg actgtggcgc actggggaat aacagtctga gctagcacca ccctcagcca 6360
ggctacaacg acagcactgg agggtcttcc ctctcagatt cacctggagg ccctcagacc 6420
cccagggtgc acgtctcccc aggtcctggg agtggctacc gcaggtagtt tctggagagc 6480
acgttttctt cattgataag tggaggagaa atgcagcaca gctttcaaga tactatttta 6540
aaaacaccat gaatcagata gggaaagaaa gttgattgga atagcaagtt taaacctttg 6600
ttgtccatct gccaaatgaa ctagtgattg tcagactggt atggaggtga ctgctttgta 6660
aggttttgtc gtttctaata cagacagaga tgtgctgatt ttgttttagc tgtaacaggt 6720
aatggttttt ggatagatga ttgactggtg agaatttggt caaggtgaca gcctcctgtc 6780
tgatgacagg acagactggt ggtgaggagt ctaagtgggc tcagtttgat gtcagtgtct 6840
gggctcatga cttgtaaatg gaagctgatg tgaacaggta attaatatta tgacccactt 6900
ctatttactt tgggaaatat cttggatctt aattatcatc tgcaagtttc aagaagtatt 6960
ctgccaaaag tatttacaag tatggactca tgagctattg ttggttgcta aatgtgaatc 7020

-continued

```
acgcgggagt gagtgtgccc ttcacactgt gacattgtga cattgtgaca agctccatgt   7080
cctttaaaat cagtcactct gcacacaaga gaaatcaact tcgtggttgg atggggccgg   7140
aacacaacca gtctttttgt atttattgtt actgagacaa aacagtactc actgagtgtt   7200
tttcagtttc ctactggtgg ttttgatatt gtttgtttaa gatgtatatt tagaatgaca   7260
tcatctaaga agctgatttt gctaaactcc tgttccctac aatgggaaat gtcacaagaa   7320
tgtgcaaaaa taaaaatctg aggaaaaaac ccaca                              7355
```

<210> SEQ ID NO 113
<211> LENGTH: 2356
<212> TYPE: DNA
<213> ORGANISM: Homo sapiens

<400> SEQUENCE: 113

```
atcataccct ttacagaaga atagagaggc tgttgcagcc ccgtgctttc tcctgctgct     60
ggccgattgc ttgctctgaa ctaaccctct aacccttggg agtctgtgtg cagcagtgat    120
gtgagctgca tccgggctga aatgggagct cccgctatgg cactggctca aggagctaat    180
ctaaagagaa aatcaagcaa aagtagataa tcagccagaa gaattagtgc gtagtgctga    240
agatgatgag aaaccagatc agaagccagt tacaaatgaa tgcgtaccaa gaatttccac    300
agtgcctaca caacctgata atccattttc tcaccctgac aaactcaaaa ggatgagcaa    360
gtctgttcca gcatttctcc aagatgaggt gagtggcagt gtgatgagtg tttatagtgg    420
agactttggc aatctggaag ttaaaggaaa tattcagttt gcaattgaat atgtggagtc    480
actgaaggag ttgcatgttt ttgtggccca gtgtaaggac ttagcagcag cggatgtaaa    540
aaaacagcgt tcagacccat atgtaaaggc ctatttgcta ccagacaaag gcaaaatggg    600
caagaagaaa acactcgtag tgaagaaaac cttgaatcct gtgtataacg aaatactgcg    660
gtataaaatt gaaaaacaaa tcttaaagac acagaaattg aacctgtcca tttggcatcg    720
ggatacattt aagcgcaata gtttcctagg ggaggtggaa cttgatttgg aaacatggga    780
ctgggataac aaacagaata aacaattgag atggtaccct ctgaagcgga agacagcacc    840
agttgccctt gaagcagaaa acagaggtga aatgaaacta gctctccagt atgtcccaga    900
gccagtccct ggtaaaaagc ttcctacaac tggagaagtg cacatctggg tgaaggaatg    960
ccttgatcta ccactgctaa ggggaagtca tctaaattct tttgttaaat gtaccatcct   1020
tccagataca agtaggaaaa gtcgccagaa gacaagagct gtagggaaaa ccaccaaccc   1080
tatcttcaac cacactatgg tgtatgatgg gttcaggcct gaagatctga tggaagcctg   1140
tgtagagctt actgtctggg accattacaa attaaccaac caatttttgg gaggtcttcg   1200
tattggcttt ggaacaggta aaagttatgg gactgaagtg gactggatgg actctacttc   1260
agaggaagtt gctctctggg agaagatggt aaactccccc aatacttgga ttgaagcaac   1320
actgcctctc agaatgcttt tgattgccaa gatttccaaa tgagcccaaa ttccactggc   1380
tcctccactg aaaactacta aaccggtgga atctgatctt gaaaatctga gtaggtggac   1440
aaatatcctc actttctatc tattgcacct aaggaatact acacagcatg taaaagtcaa   1500
tctgcatgtg cttctttgat tacaaggccc aagggattta aatataacaa aatgtgtaat   1560
ttgtgactct aatattaaat aagatatttg aacaagctag gaaaattgaa tttctgctgc   1620
tgcttcaaag aaaaagctgc cccagagcat taaacatggg gtattgttaa gaagcaaaat   1680
gttcttgttt gccatcatgt gtttcacacc acaattctgt gccacagtta agagggtctg   1740
gtacccttgc aggacctttg taggttgtgg gaaaaagtcg cagaaagata ctcaaagtgg   1800
```

agcagggaat ggagacagac atcagtgatg ataaaaaaaa aaatggacct taagaaacta 1860
tttactctgt aatctctaat aaaatatgga attccatatt agggcaatga gactgaaact 1920
actggtgttt ttctgccttg agaaaacaaa cagttaaaac aagcctcaaa tgtattttag 1980
tgccacccac tggccatagg tacaattcag ttgttggctt gttttgactt aattctaaaa 2040
taggtctcaa gcctgtattt ttatgagttt attttttaa aaccctgcat atatatgatt 2100
gtttttctta taactttact atatgaaagc agcataagag tagtcacaaa catgttttgc 2160
aacaaagttt taattagaat gtaagttgct cagttatact gttcttctta tgtatgtaaa 2220
attttcgtat tttgtaaaaa cccttagaat aaattatcat ttgatttaaa ttgtattaga 2280
aaattagcgt gacttctcat tttaaataaa atattttagg aattctaaac atctaaaaaa 2340
aaaaaaaaaa aaaaaa 2356

<210> SEQ ID NO 114
<211> LENGTH: 508
<212> TYPE: DNA
<213> ORGANISM: Homo sapiens

<400> SEQUENCE: 114
atccctgact cggggtcgcc tttggagcag agaggaggca atggccacca tggagaacaa 60
ggtgatctgc gccctggtcc tggtgtccat gctggccctc ggcaccctgg ccgaggccca 120
gacagagacg tgtacagtgg ccccccgtga aagacagaat tgtggttttc ctggtgtcac 180
gccctcccag tgtgcaaata agggctgctg tttcgacgac accgttcgtg gggtcccctg 240
gtgcttctat cctaatacca tcgacgtccc tccagaagag gagtgtgaat tttagacact 300
tctgcaggga tctgcctgca tcctgacgcg gtgccgtccc cagcacggtg attagtccca 360
gagctcggct gccacctcca ccggacacct cagacacgct tctgcagctg tgcctcggct 420
cacaacacag attgactgct ctgactttga ctactcaaaa ttggcctaaa aattaaaaga 480
gatcgatatt aaaaaaaaaa aaaaaaaa 508

<210> SEQ ID NO 115
<211> LENGTH: 717
<212> TYPE: DNA
<213> ORGANISM: Homo sapiens

<400> SEQUENCE: 115
cacggtggaa gggctggggc cacggggcag agaagaaagg ttatctctgc ttgttggaca 60
aacagagggg agattataaa acatacccgg cagtggacac catgcattct gcaagccacc 120
ctggggtgca gctgagctag acatgggacg gcgagacgcc cagctcctgg cagcgctcct 180
cgtcctgggg ctatgtgccc tggcggggag tgagaaaccc tccccctgcc agtgctccag 240
gctgagcccc cataacagga cgaactgcgg cttccctgga atcaccagtg accagtgttt 300
tgacaatgga tgctgtttcg actccagtgt cactggggtc ccctggtgtt tccacccccct 360 cccaaagcaa gagtcggatc agtgcgtcat ggaggtctca gaccgaagaa actgtggcta 420
cccgggcatc agccccgagg aatgcgcctc tcggaagtgc tgcttctcca acttcatctt 480
tgaagtgccc tggtgcttct tcccgaagtc tgtggaagac tgccattact aagagaggct 540
ggttccagag gatgcatctg gctcaccggg tgttccgaaa ccaaagaaga aacttcgcct 600
tatcagcttc atacttcatg aaatcctggg ttttcttaac catcttttcc tcattttcaa 660
tggtttaaca tataatttct ttaaataaaa cccttaaaat ctgctaaaaa aaaaaaa 717

<210> SEQ ID NO 116
<211> LENGTH: 1054
<212> TYPE: DNA
<213> ORGANISM: Homo sapiens

<400> SEQUENCE: 116
gccaaaacag tgggggctga actgacctct cccctttggg agagaaaaac tgtctgggag 60
cttgacaaag gcatgcagga gagaacagga gcagccacag ccaggaggga gagccttccc 120
caagcaaaca atccagagca gctgtgcaaa caacggtgca taaatgaggc ctcctggacc 180
atgaagcgag tcctgagctg cgtcccggag cccacggtgg tcatggctgc cagagcgctc 240
tgcatgctgg ggctggtcct ggccttgctg tcctccagct ctgctgagga gtacgtgggc 300
ctgtctgcaa accagtgtgc cgtgccagcc aaggacaggg tggactgcgg ctacccccat 360
gtcaccccca aggagtgcaa caaccggggc tgctgctttg actccaggat ccctggagtg 420
ccttggtgtt tcaagcccct gcaggaagca gaatgcacct tctgaggcac ctccagctgc 480
ccccggccgg gggatgcgag gctcggagca cccttgcccg gctgtgattg ctgccaggca 540
ctgttcatct cagcttttct gtccctttgc tcccggcaag cgcttctgct gaaagttcat 600
atctggagcc tgatgtctta acgaataaag gtcccatgct ccacccgagg acagttcttc 660
gtgcctgaga ctttctgagg ttgtgcttta tttctgctgc gtcgtgggag agggcgggag 720
ggtgtcaggg gagagtctgc ccaggcctca agggcaggaa aagactccct aaggagctgc 780
agtgcatgca aggatatttt gaatccagac tggcacccac gtcacaggaa agcctaggaa 840
cactgtaagt gccgcttcct cgggaaagca gaaaaaatac atttcaggta gaagttttca 900
aaaatcacaa gtctttcttg gtgaagacag caagccaata aaactgtctt ccaaagtggt 960
cctttatttc acaaccactc tcgctactgt tcaatacttg tactattcct gggttttgtt 1020
tctttgtaca gtaaacatta tgaacaaaca ggca 1054

<210> SEQ ID NO 117
<211> LENGTH: 5898
<212> TYPE: DNA
<213> ORGANISM: Homo sapiens

<400> SEQUENCE: 117
aaaagtgagt ccctgccttc cctctctccg tctggctcct cccaggcctg tctggcaggg 60
gccggggtgc aggaggagga gacggcatcc agtacagagg ggctggactt ggacccctgc 120
agcagccctg cacaggagaa gcggcatata aagccgcgct gcccgggagc cgctcggcca 180
cgtccaccgg agcatcctgc actgcagggc cggtctctcg ctccagcaga gcctgcgcct 240
ttctgactcg gtccggaaca ctgaaaccag tcatcactgc atctttttgg caaaccagga 300
gctcagctgc aggaggcagg atggtctgga ggctggtcct gctggctctg tgggtgtggc 360
ccagcacgca agctggtcac caggacaaag acacgacctt cgaccttttc agtatcagca 420
acatcaaccg caagaccatt ggcgccaagc agttccgcgg gcccgacccc ggcgtgccgg 480
cttaccgctt cgtgcgcttt gactacatcc caccggtgaa cgcagatgac ctcagcaaga 540
tcaccaagat catgcggcag aaggagggct tcttcctcac ggcccagctc aagcaggacg 600
gcaagtccag gggcacgctg ttggctctgg agggccccgg tctctcccag aggcagttcg 660
agatcgtctc caacggcccc gcggacacgc tggatctcac ctactggatt gacggcaccc 720
ggcatgtggt ctccctggag gacgtcggcc tggctgactc gcagtggaag aacgtcaccg 780
tgcaggtggc tggcgagacc tacagcttgc acgtgggctg cgacctcata gacagcttcg 840
ctctggacga gcccttctac gagcacctgc aggcggaaaa gagccggatg tacgtggcca 900
aaggctctgc cagagagagt cacttcaggg gtttgcttca gaacgtccac ctagtgtttg 960
aaaactctgt ggaagatatt ctaagcaaga agggttgcca gcaaggccag ggagctgaga 1020
tcaacgccat cagtgagaac acagagacgc tgcgcctggg tccgcatgtc accaccgagt 1080
acgtgggccc cagctcggag aggaggcccg aggtgtgcga acgctcgtgc gaggagctgg 1140
gaaacatggt ccaggagctc tcggggctcc acgtcctcgt gaaccagctc agcgagaacc 1200
tcaagagagt gtcgaatgat aaccagtttc tctgggagct cattggtggc cctcctaaga 1260
caaggaacat gtcagcttgc tggcaggatg gccggttctt tgcggaaaat gaaacgtggg 1320
tggtggacag ctgcaccacg tgtacctgca agaaatttaa aaccatttgc caccaaatca 1380
cctgcccgcc tgcaacctgc gccagtccat cctttgtgga aggcgaatgc tgcccttcct 1440
gcctccactc ggtggacggt gaggagggct ggtctccgtg ggcagagtgg acccagtgct 1500
ccgtgacgtg tggctctggg acccagcaga gaggccggtc ctgtgacgtc accagcaaca 1560
cctgcttggg gccctccatc cagacacggg cttgcagtct gagcaagtgt gacacccgca 1620
tccggcagga cggcggctgg agccactggt caccttggtc ttcatgctct gtgacctgtg 1680
gagttggcaa tatcacacgc atccgtctct gcaactcccc agtgccccag atggggggca 1740
agaattgcaa agggagtggc cgggagacca aagcctgcca gggcgcccca tgcccaatcg 1800
atggccgctg gagcccctgg tccccgtggt cggcctgcac tgtcacctgt gccggtggga 1860
tccgggagcg cacccgggtc tgcaacagcc ctgagcctca gtacggaggg aaggcctgcg 1920
tgggggatgt gcaggagcgt cagatgtgca acaagaggag ctgccccgtg gatggctgtt 1980
tatccaaccc ctgcttcccg ggagcccagt gcagcagctt ccccgatggg tcctggtcat 2040
gcggctcctg ccctgtgggc ttcttgggca atggcaccca ctgtgaggac ctggacgagt 2100
gtgccctggt ccccgacatc tgcttctcca ccagcaaggt gcctcgctgt gtcaacactc 2160
agcctggctt ccactgcctg ccctgcccgc cccgatacag agggaaccag cccgtcgggg 2220
tcggcctgga agcagccaag acggaaaagc aagtgtgtga gcccgaaaac ccatgcaagg 2280
acaagacaca caactgccac aagcacgcgg agtgcatcta cctgggccac ttcagcgacc 2340
ccatgtacaa gtgcgagtgc cagacaggct acgcgggcga cgggctcatc tgcggggagg 2400
actcggacct ggacggctgg cccaacctca atctggtctg cgccaccaac gccacctacc 2460
actgcatcaa ggataactgc cccatctgc caaattctgg gcaggaagac tttgacaagg 2520
acgggattgg cgatgcctgt gatgatgacg atgacaatga cggtgtgacc gatgagaagg 2580
acaactgcca gctcctcttc aatccccgcc aggctgacta tgacaaggat gaggttgggg 2640
accgctgtga caactgccct tacgtgcaca accctgccca gatcgacaca gacaacaatg 2700
gagagggtga cgcctgctcc gtggacattg atggggacga tgtcttcaat gaacgagaca 2760
attgtcccta cgtctacaac actgaccaga gggacacgga tggtgacggt gtgggggatc 2820
actgtgacaa ctgcccccctg gtgcacaacc ctgaccagac cgacgtggac aatgaccttg 2880
ttggggacca gtgtgacaac aacgaggaca tagatgacga cggccaccag aacaaccagg 2940
acaactgccc ctacatctcc aacgccaacc aggctgacca tgacagagac ggccagggcg 3000
acgcctgtga ccctgatgat gacaacgatg gcgtccccga tgacagggac aactgccggc 3060
ttgtgttcaa cccagaccag gaggacttgg acggtgatgg acggggtgat atttgtaaag 3120
atgattttga caatgacaac atcccagata ttgatgatgt gtgtcctgaa aacaatgcca 3180

```
tcagtgagac agacttcagg aacttccaga tggtcccctt ggatcccaaa gggaccaccc   3240
aaattgatcc caactgggtc attcgccatc aaggcaagga gctggttcag acagccaact   3300
cggaccccgg catcgctgta ggttttgacg agtttgggtc tgtggacttc agtggcacat   3360
tctacgtaaa cactgaccgg gacgacgact atgccggctt cgtctttggt taccagtcaa   3420
gcagccgctt ctatgtggtg atgtggaagc aggtgacgca gacctactgg gaggaccagc   3480
ccacgcgggc ctatggctac tccggcgtgt ccctcaaggt ggtgaactcc accacgggga   3540
cgggcgagca cctgaggaac gcgctgtggc acacggggaa cacgccgggg caggtgcgaa   3600
ccttatggca cgaccccagg aacattggct ggaaggacta cacggcctat aggtggcacc   3660
tgactcacag gcccaagact ggctacatca gagtcttagt gcatgaagga aaacaggtca   3720
tggcagactc aggacctatc tatgaccaaa cctacgctgg cgggcggctg ggtctatttg   3780
tcttctctca agaaatggtc tatttctcag acctcaagta cgaatgcaga gatatttaaa   3840
caagatttgc tgcatttccg gcaatgccct gtgcatgcca tggtccctag acacctcagt   3900
tcattgtggt ccttgtggct tctctctcta gcagcacctc ctgtcccttg accttaactc   3960
tgatggttct tcacctcctg ccagcaaccc caaacccaag tgccttcaga ggataaatat   4020
caatggaact cagagatgaa catctaaccc actagaggaa accagtttgg tgatatatga   4080
gactttatgt ggagtgaaaa ttgggcatgc cattacattg ctttttcttg tttgtttaaa   4140
aagaatgacg tttacatata aaatgtaatt acttattgta tttatgtgta tatggagttg   4200
aagggaatac tgtgcataag ccattatgat aaattaagca tgaaaaatat tgctgaacta   4260
cttttggtgc ttaaagttgt cactattctt gaattagagt tgctctacaa tgacacacaa   4320
atcccattaa ataaattata aacaagggtc aattcaaatt tgaagtaatg ttttagtaag   4380
gagagattag aagacaacag gcatagcaaa tgacataagc taccgattaa ctaatcggaa   4440
catgtaaaac agttacaaaa ataaacgaac tctcctcttg tcctacaatg aaagccctca   4500
tgtgcagtag agatgcagtt tcatcaaaga acaaacatcc ttgcaaatgg gtgtgacgcg   4560
gttccagatg tggatttggc aaaacctcat ttaagtaaaa ggttagcaga gcaaagtgcg   4620
gtgctttagc tgctgcttgt gccgctgtgg cgtcggggag gctcctgcct gagcttcctt   4680
ccccagcttt gctgcctgag aggaaccaga gcagacgcac aggccggaaa aggcgcatct   4740
aacgcgtatc taggctttgg taactgcgga caagttgctt ttacctgatt tgatgataca   4800
tttcattaag gttccagtta taaatatttt gttaatattt attaagtgac tatagaatgc   4860
aactccattt accagtaact tattttaaat atgcctagta acacatatgt agtataattt   4920
ctagaaacaa acatctaata agtatataat cctgtgaaaa tatgaggctt gataatatta   4980
ggttgtcacg atgaagcatg ctagaagctg taacagaata catagagaat aatgaggagt   5040
ttatgatgga accttaaata tataatgttg ccagcgattt tagttcaata tttgttactg   5100
ttatctatct gctgtatatg gaattctttt aattcaaacg ctgaaaagaa tcagcattta   5160
gtcttgccag gcacacccaa taatcagtca tgtgtaatat gcacaagttt gtttttgttt   5220
ttgttttttt tgttggttgg tttgtttttt tgctttaagt tgcatgatct ttctgcagga   5280
aatagtcact catcccactc cacataaggg gtttagtaag agaagtctgt ctgtctgatg   5340
atggataggg ggcaaatctt tttccccttt ctgttaatag tcatcacatt tctatgccaa   5400
acaggaacaa tccataactt tagtcttaat gtacacattg cattttgata aaattaattt   5460
tgttgtttcc tttgaggttg atcgttgtgt tgttgttttg ctgcactttt tacttttttg   5520
cgtgtggagc tgtattcccg agaccaacga agcgttggga tacttcatta aatgtagcga   5580
```

-continued

```
ctgtcaacag cgtgcaggtt ttctgtttct gtgttgtggg gtcaaccgta caatggtgtg   5640

ggagtgacga tgatgtgaat atttagaatg taccatattt tttgtaaatt atttatgttt   5700

ttctaaacaa atttatcgta taggttgatg aaacgtcatg tgttttgcca aagactgtaa   5760

atatttattt atgtgttcac atggtcaaaa tttcaccact gaaaccctgc acttagctag   5820

aacctcattt ttaaagatta acaacaggaa ataaattgta aaaaaggttt tctatacatg   5880

aaaaaaaaaa aaaaaaaa                                                 5898


<210> SEQ ID NO 118
<211> LENGTH: 2207
<212> TYPE: DNA
<213> ORGANISM: Homo sapiens

<400> SEQUENCE: 118

acgcacttgg cgcgcggcgc gggctgcaga cggctgcgag gcgctgggca caggtgtcct     60

gatggcaaat ttcaagggcc acgcgcttcc agggagtttc ttcctgatca ttgggctgtg    120

ttggtcagtg aagtacccgc tgaagtactt tagccacacg cggaagaaca gcccactaca    180

ttactatcag cgtctcgaga tcgtcgaagc cgcaattagg actttgtttt ccgtcactgg    240

gatcctggca gagcagtttg ttccggatgg gccccacctg cacctctacc atgagaacca    300

ctggataaag ttaatgaatt ggcagcacag caccatgtac ctattctttg cagtctcagg    360

aattgttgac atgctcacct atctggtcag ccacgttccc ttgggggtgg acagactggt    420

tatggctgtg gcagtattca tggaaggttt cctcttctac taccacgtcc acaaccggcc    480

tccgctggac cagcacatcc actcactcct gctgtatgct ctgttcggag ggtgtgttag    540

tatctcccta gaggtgatct tccgggacca cattgtgctg gaacttttcc gaaccagtct    600

catcattctt cagggaacct ggttctggca gattgggttt gtgctgttcc caccttttgg    660

aacacccgaa tgggaccaga aggatgatgc caacctcatg ttcatcacca tgtgcttctg    720

ctggcactac ctggctgccc tcagcattgt ggccgtcaac tattctcttg tttactgcct    780

tttgactcgg atgaagagac acggaagggg agaaatcatt ggaattcaga agctgaattc    840

agatgacact taccagaccg ccctcttgag tggctcagat gaggaatgag ccgagatgcg    900

gagggcgcag atgtcccact gcacagctgg aatgaatgga gttcatcccc tccacctgaa    960

tgcctgctgt ggtctgatct taagggtcta tatatttgca cctcctcatt caacacaggg   1020

ctggaggttc tacaacagga aatcaggcct acagcatcct gtgtatcttg cagttgggat   1080

ttttaaacat actataaagt ctgtgttggt atagtaccct tcataaggaa aaatgaagta   1140

atgcctataa gtagcaggcc tttgtgcctc agtgtcaaga gaaatcaaga gatgctaaaa   1200

gctttacaat ggaagtggcc tcatggatga atccggggta tgagcccagg agaacgtgct   1260

gcttttggta acttatccct ttttctctta agaaagcagg tactttctta ttagaaatat   1320

gttagaatgt gtaagcaaac gacagtgcct ttagaattac aattctaact tacatatttt   1380

ttgaaagtaa aataattcac aagctttggt attttaaaat tattgttaaa catatcataa   1440

ctaatcatac cagggtactg caataccact gtttataagt gacaaaatta ggccaaaggt   1500

gatttttttt taaatcagga agctggttac tggctctact gagagttgga gccctgatgt   1560

tctgattctt caaagtcacc ctaaaagaag atctgacagg aaagctgtat aatgagatag   1620

aaaaacgtca ggtatggaag gctttcagtt ttaatatggc tgaaagcaaa ggataacgaa   1680

ttcagaatta gtaatgtaaa atcttgatac cctaatcttg cttctggatc tgttcttttt   1740
```

ttaaaaaaac ttccttcacc gcgcctataa tcctagcact ttgggaggcc gaggcaggca 1800
gatcacgggg tcaggagatc aagaccatcc tggctaacat ggtgaaaccc cgtctctact 1860
gaaaatacaa aaaattagcc gggtgtggtg gcgggcgcct gtagttccag ctactcggga 1920
ggctgaggca agagaatggc atgaacccgg taggggagct tgcagtgagc ccagatcatg 1980
ccactgtact ccagcctagg tgacagagca agactctgtc tcaaaaacaa gcaaacagac 2040
ttccttcaac aaatatttat taaatatcca ctttgcaaca gcactgaaat ggctgtaagg 2100
actcctgaga tatgtgtcca gcaaggagtt tacagtcaaa caggagagac atgcctgtag 2160
ttacatccag tgtgatgggt gctgagaggc aagtacaaac cacgatg 2207

<210> SEQ ID NO 119
<211> LENGTH: 4090
<212> TYPE: DNA
<213> ORGANISM: Homo sapiens

<400> SEQUENCE: 119
ggactctgag tcgtcttggt cccaggagcc agtagtgaag gcaacagtct gcccacctgt 60
ggacaccaga tcctgggagc tcctggttag caagtgagat ctctgggatg tcagtgaggc 120
tggttgaaga ccagaggtaa actgcagagg tcaccacccc caccatgtcc caggtgatgt 180
ccagcccact gctggcagga ggccatgctg tcagcttggc gccttgtgat gagcccagga 240
ggaccctgca cccagcaccc agccccagcc tgccacccca gtgttcttac tacaccacgg 300
aaggctgggg agcccaggcc ctgatggccc ccgtgccctg catggggccc cctggccgac 360
tccagcaagc cccacaggtg gaggccaaag ccacctgctt cctgccgtcc cctggtgaga 420
aggccttggg gaccccagag gaccttgact cctacattga cttctcactg gagagcctca 480
atcagatgat cctggaactg gaccccacct tccagctgct tcccccaggg actgggggct 540
cccaggctga gctggcccag agcaccatgt caatgagaaa gaaggaggaa tctgaagcct 600
tggacataaa gtacatcgag gtgacctccg ccagatcaag gtgccacgat ggcccccagc 660
actgctccag cccctctgtc accccgccct tcggctccct tcgcagtggt ggcctcctcc 720
tttccagaga cgtcccccga gagacacgaa gcagcagtga gagcctcatc ttctctggga 780
accagggcag ggggcaccag cgccctctgc ccccctcaga gggtctctcc cctcgacccc 840
caaattcccc cagcatctca atcccttgca tggggagcaa ggcctcgagc cccccatggtt 900 tgggctcccc gctggtggct tctccaagac tggagaagcg gctgggaggc ctggccccac 960
agcggggcag caggatctct gtgctgtcag ccagcccagt gtctgatgtc agctatatgt 1020
ttggaagcag ccagtccctc ctgcactcca gcaactccag ccatcagtca tcttccagat 1080
ccttggaaag tccagccaac tcttcctcca gcctccacag ccttggctca gtgtccctgt 1140
gtacaagacc cagtgacttc caggctccca gaaaccccac cctaaccatg ggccaaccca 1200
gaacacccca ctctccacca ctggccaaag aacatgccag cagctgcccc ccatccatca 1260
ccaactccat ggtggacata cccattgtgc tgatcaacgg ctgcccagaa ccagggtctt 1320
ctccacccca gcggacccca ggacaccaga actccgttca acctggagct gcttctccca 1380
gcaacccctg tccagccacc aggagcaaca gccagaccct gtcagatgcc ccctttacca 1440
catgcccaga gggtcccgcc agggacatgc agcccaccat gaagttcgtg atggacacat 1500
ctaaatactg gtttaagcca aacatcaccc gagagcaagc aatcgagctg ctgaggaagg 1560
aggagccagg ggcttttgtc ataagggaca gctcttcata ccgaggctcc ttcggcctgg 1620
ccctgaaggt gcaggaggtt cccgcgtctg ctcagagtcg accaggtgag gacagcaatg 1680

```
acctcatccg acacttcctc atcgagtcgt ctgccaaagg agtgcatctc aaaggagcag   1740
atgaggagcc ctactttggg agcctctctg ccttcgtgtg ccagcattcc atcatggccc   1800
tggccctgcc ctgcaaactc accatcccac agagagaact gggaggtgca gatggggcct   1860
cggactctac agacagccca gcctcctgcc agaagaaatc tgcgggctgc cacaccctgt   1920
acctgagctc agtgagcgtg gagaccctga ctggagccct ggccgtgcag aaagccatct   1980
ccaccacctt tgagagggac atcctcccca cgcccaccgt ggtccacttc aaagtcacag   2040
agcagggcat cactctgact gatgtccaga ggaaggtgtt tttccggcgc cattacccac   2100
tcaccaccct ccgcttctgt ggtatggacc ctgagcaacg gaagtggcag aagtactgca   2160
aaccctcctg gatctttggg tttgtggcca agagccagac agagcctcag gagaacgtat   2220
gccacctctt tgcggagtat gacatggtcc agccagcctc gcaggtcatc ggcctggtga   2280
ctgctctgct gcaggacgca gaaaggatgt aggggagaga ctgcctgtgc acctaaccaa   2340
cacctccagg ggctcgctaa ggagcccccc tccacccccct gaatgggtgt ggcttgtggc   2400
catattgaca gaccaatcta tgggactagg gggattggca tcaagttgac acccttgaac   2460
ctgctatggc cttcagcagt caccatcatc cagaccccc gggcctcagt ttcctcaatc   2520
atagaagaag accaatagac aagatcagct gttcttagat gctggtgggc atttgaacat   2580
gctcctccat gattctgaag catgcacacc tctgaagacc cctgcatgaa aataacctcc   2640
aaggaccctc tgaccccatc gacctgggcc ctgcccacac aacagtctga gcaagagacc   2700
tgcagcccct gtttcgtggc agacagcagg tgcctggcgg tgacccacgg ggctcctggc   2760
ttgcagctgg tgatggtcaa gaactgacta caaaacagga atggatagac tctatttcct   2820
tccatatctg ttcctctgtt ccttttccca ctttctgggt ggctttttgg gtccacccag   2880
ccaggatgct gcaggccaag ctgggtgtgg tatttagggc agctcagcag ggggaacttg   2940
tccccatggt cagaggagac ccagctgtcc tgcacccccct tgcagatgag tatcacccca   3000
tcttttcttt ccacttggtt tttattttta tttttttttg agacagagtc tcactgtcac   3060
ccaggctgaa ctgcagtggt gtgatctagg ctcactgcaa cctccacctc ccaggttcaa   3120
gcaattatcc tgcctcaggc tcccaagtag ctgggattac aggcatgtgc aactcaccca   3180
gctaattttg tatttttagt agagacaggg tttcaccatg ttggccaggc tggtcttgaa   3240
ctcctgaccg caggtaatcc acctgcttcg gcctcccaaa gtgctgggat tacaggcgca   3300
agccacccag cccagcttct ttccattcct tgataggcga gtattccaaa gctggtatcg   3360
tagctgccct aatgttgcat attaggcggc gggggcagag ataagggcca tctctctgtg   3420
attctgcctc agctcctgtc ttgctgagcc ctcccccaac ccacgctcca acacacacac   3480
acacacacac acacacacac acacacacac acacacacac acacacacac gcccctctac   3540
tgctatgtgg cttcaaccag cctcacagcc acacggggga agcagagagt caagaatgca   3600
aagaggccgc ttccctaaga ggcttggagg agctgggctc tatcccacac ccacccccac   3660
cccaccccca cccagcctcc agaagctgga accatttctc ccgcaggcct gagttcctaa   3720
ggaaaccacc ctaccggggt ggaagggagg gtcagggaag aaacccactc ttgctctacg   3780
aggagcaagt gcctgccccc tcccagcagc cagccctgcc aaagttgcat tatctttggc   3840
caaggctggg cctgacggtt atgatttcag ccctgggcct gcaggagagg ctgagaccag   3900
cccacccagc cagtggtcga gcactgcccc gccgccaaag tctgcagaat gtgagatgag   3960
gttctcaagg tcacaggccc cagtcccagc ctgggggctg gcagaggccc ccatatactc   4020
```

tgctacagct cctatcatga aaaataaaat gtttgtcttt gcaaaacagt aaaaaaaaaa 4080
aaaaaaaaaa 4090

<210> SEQ ID NO 120
<211> LENGTH: 3679
<212> TYPE: DNA
<213> ORGANISM: Homo sapiens

<400> SEQUENCE: 120
ctgcagcctc cgcagaggcg attggctgaa gctaccggcc gcgtggggcg ggactcggtt 60
gccagggagc ggcgcgggag ccctgagggg actgcggcgg ctgcgcggag gagcgaggca 120
cttgctgggg tcggggctgc gcgacggcgc aggggctgcg gggagcgccg cgcaggccgt 180
gcagttccta gcgaggaggc gccgccgcca ttgccgctct ctcggtgagc gcagccccgc 240
tctccgggcc gggccttcgc gggccaccgg cgccatgggc cagtgcggca tcacctcctc 300
caagaccgtg ctggtctttc tcaacctcat cttctggttt gtcatcatcc tgctcttggt 360
ttttgtcaca gaagttgttg tagtggtttt gggatatgtt tacagagcaa aggtggaaaa 420
tgaggttgat cgcagcattc agaaagtgta taagacctac aatggaacca accctgatgc 480
tgctagccgg gctattgatt atgtacagag acagctgcat tgttgtggaa ttcacaacta 540
ctcagactgg gaaaatacag attggttcaa agaaaccaaa aaccagagtg tccctcttag 600
ctgctgcaga gagactgcca gcaattgtaa tggcagcctg gcccaccctt ccgacctcta 660
tgctgagggg tgtgaggctc tagtagtgaa gaagctacaa gaaatcatga tgcatgtgat 720
ctgggccgca ctggcatttg cagctattca gctgctgggc atgctgtgtg cttgcatcgt 780
gttgtgcaga aggagtagag atcctgctta cgagctcctc atcactggcg gaacctatgc 840
atagttgaca actcaagcct gagctttttg gtcttgttct gatttggaag gtgaattgag 900
caggtctgct gctgttggcc tctggagttc atttagttaa agcacatgta cactggtgtt 960
ggacagagca gcttggcttt tcatgtgccc acctacttac ctactacctg cgactttctt 1020
tttccttgtt ctagctgact cttcatgccc ctaagatttt aagtacgatg gtgaacgttc 1080
taatttcaga accaattgcg agtcatgtag tgtggtagaa ttaaaggagg acacgagcct 1140
gcttctgtta cctccaagtg gtaacaggac tgatgccgaa atgtcaccag gtcctttcag 1200
tcttcacagt ggagaactct tggccaaagg tttttgcggg gaggaggagg aaaccagctt 1260
tctggttaag gttaacacca gatggtgccc ctcattggtg tccttttaaa aaatatttac 1320
tgtagtccaa taagatagca gctgtacaaa atgactaaaa tagattgtag gatcatatgg 1380
cgtatatctt ggttcatctt caaaatcaga gactgagctt tgaaactagt ggtttttaat 1440
caaagttggc tttataggag gagtataatg tatgcactac tgttttaaaa gaattagtgt 1500
gagtgtgttt ttgtatgaat gagcccattc atggtaagtc ttaagcttgt tggaaataat 1560
gtacccatgt agactagcaa aatagtatgt agatgtgatc tcagttgtaa atagaaaaat 1620
ctaattcaat aaactctgta tcagccccca acatattatt tttcattatt tgggggatat 1680
ttcagttcca gagcagcagt atcatgtttt ctttgttggt gctgtctata gttcatcatg 1740
gtttacgtgt gttttcgtta tagctgttgc cagattctaa agggcttgat attcaaaaaa 1800
ccacagatgc tttcagtcca gtatatccta gaaatataga gctctacttt gtgcaatgca 1860
ctggggatac agtggcgata ctgtccttgt cttcaaggag ttcggagtcc tagtatagga 1920
gacatacata ggagaagata attttcacac tgcagtggtt gtagtaatag aatgggagtc 1980
caaaggggag ttccggagag gtcaggggtg acttcctgga ggagatgccc aagcttggag 2040
gctggatagg ctttgttgaa agatggtaca caagagtgtg aaacaaaatt gtgtgtgcag 2100
ggagcttaaa atacaaggct ggggaaagaa gttggagaag caggaaagcc caggccctct 2160
agtgtcttac ggaacatcct gtggaggtga gagctgactt gtaggtggaa gcagctcttt 2220
ggaggtttga tttggaaggt gaactgagaa gaaggtggtg atgcaagccg gccgtgctga 2280
agccaggatg aattggtgtg actgggcttc agttaggctg gcatagcagt tgagagagct 2340
tagcagtggg cagcagggca ctgttggggg cggtggtgag cggtggattc tggctgtttg 2400
gaggcaggac agtggtggaa ttcgatcatt gattggacgt gggacagaga agggagaaga 2460
gaagactcat ctaggatgag tcccaggttt ctggctcagt caactgggga aacaaagtca 2520
cagagctagg gagtagttag agaacacatc tgggggtgtg actcatggtc agttttgggc 2580
tcgtcagttt tgagatgccc aaatatcatg cagatctgtc ccacctgaaa atggagaaga 2640
cacgggaaag gagaggagta aaaactaact ccttttcaca aagtggaagt taccagaatg 2700
tgatttcaga ggccccgggg gatttatcat gtgactactg acccatccca cctcttgccc 2760
ctgcctgttg cacagtgggc aagaatgttt gtgacctttc actaccacca cctcccccga 2820
gcatggtccc cccagttttc aatatgaacc atcctgtggg taccctgtca caggctggcc 2880
ctgaggtgag caatatttgg actgtgatgt tggttgttct ccactctttc tacaggacag 2940
aacagggcct ctagagtggg aaatggcttt gggaaatatg ccaagcagta gccttgttct 3000
tcaacttgcc caagaggata attctccaca cccttcctgt actcagtcct cagtttgcct 3060
ggtgagagag cagcctcctc ccgtgtgctc tgccagctgg acccagactg gccatattac 3120
cagtgagacc aaaaagatgg aggtggggag gtagctctga ggtctgggaa accattccag 3180
ctcctgccag ttttaacttg tgtttaattc ctggcacagt tgtcctggaa atgccttttt 3240
ctcttgcctg ggaaccacta gaaggggatg ttgtctgtgt tggccagggc catgcaaatt 3300
caacatcttg tttctgccct tcccccgtgt agctgaggct aggtgttggc attacccagt 3360
gcttgttctt cagagagcaa aagcactgct cgtcatgtct gaaatttagt gagtgagctc 3420
acccactagg ctggtgtttc ctgcccgtgg ctgcacattg gaagcaccgg ggcactttga 3480
gaactacaga tgcctgggtc ccagagcatc taaggtgctc tagggtgtgt ccaggacaca 3540
gccctggttg aggaccactg ctatattgta tggcctcttt taaaaaagtt aattttactt 3600
ggaaatgatt tcaaagctac agaaaagttg caagaataaa aactgtacaa atgaggctca 3660
aaaaaaaaaa aaaaaaaaa 3679

<210> SEQ ID NO 121
<211> LENGTH: 1442
<212> TYPE: DNA
<213> ORGANISM: Homo sapiens

<400> SEQUENCE: 121
ttgacattct tctggacaat gagtcccatc atctctccac catgcacctt gtgactccct 60
cctctgctga caacagataa ccacctttaa ctgtaacttt ccacagccta ccccagccct 120
ataaagctgc ctctctccta tctcccttcg ctgactctct tttcagactc agcccacttg 180
cacccaagtg aattaacagc cttgttgctc acacaaagcc tgtttaggtg gtcttctata 240
tggacatgcg tgacacttgg tgccaaaatc tgggccaggg ggactccttt gtgagaccgg 300
ccccctgtcc tggccctcac tccgtgaaga gatccacctg cgacctcggg tcctcagacc 360
agcccaagga acatctcacc aatttcaaat cggatctcct cggcttagtg gctgaagact 420

```
gatgctgccc gatcgcctca gaagcccccct ggaccatcac agatgccgag cttcgggtaa    480

ctcttacggt ggaggattcc cagccatatg aagacaccct agctggacga tcagtccttg    540

tcaaaagtct gacccctcaa actctacagc ctcaatggac cagaccctac ccggtcattt    600

atagcacacc aactgccgtc catctgcagg accctctcca ttgggttcac cattccagaa    660

taaagccatg cccatcagac agccagcttg atctctcctc ttcctcctgg aagccacaag    720

attaggccga gagccgatca gacaaacaac ctacaaccct taagctcctg gcagcgccca    780

gccaaggcca tgcttccatg caacactcct tccaaatggc catcccagca tgcttccaag    840

caggcttcat ccgttcctct ggaccctcat ctcttaagac ctgccgccta taaaaaggat    900

tatatcttga gaccctatcc tctaaaattt tttccacacc caaaacaaaa aatctctggg    960

tcaaaagtct aaaacgctta ggctggcaac catcagatcc ttgcccatgg tgtcctcaag   1020

cctactctca tgaaatggac aacagtacac gcatatgggg ccagttccac atatttggca   1080

accagaccag catccaggac aacacaaagt atgttgtttg ttgttagagg gcttgggaca   1140

tttcactctt tgccagcctc agcttaatcc aggagacaaa gattattttc cttattatct   1200

cttctgcata ggatctgcaa tcagaactat tgaacttctc cattcagacc gccactcaca   1260

cctatgggaa aagggtaatg tatcatcggc ttagcaacag ggaatactat tcgtatgatg   1320

gaaaatgggg acaaaaggct ttggtacata aaacattatt ccttccttgg cctaaaaact   1380

catcgccacc tacattaaag ctaatatgcc tgataaaaaa aaaaaaaaaa aaaaaaaaaa   1440

aa                                                                  1442
```

<210> SEQ ID NO 122
<211> LENGTH: 12416
<212> TYPE: DNA
<213> ORGANISM: Homo sapiens

<400> SEQUENCE: 122

```
cttcttctcg ctgagtctcc tcctcggctc tgacggtaca gtgatataat gatgatgggt     60

gtcacaaccc gcatttgaac ttgcaggcga gctgccccga gcctttctgg ggaagaactc    120

caggcgtgcg gacgcaacag ccgagaacat taggtgttgt ggacaggagc tgggaccaag    180

atcttcggcc agccccgcat cctcccgcat cttccagcac cgtcccgcac cctccgcatc    240

cttccccggg ccaccacgct tcctatgtga cccgcctggg caacgccgaa cccagtcgcg    300

cagcgctgca gtgaattttc cccccaaact gcaataagcc gccttccaag gccaagatgt    360

tcataaatat aaagagcatc ttatggatgt gttcaacctt aatagtaacc catgcgctac    420

ataaagtcaa agtgggaaaa agcccaccgg tgaggggctc cctctctgga aaagtcagcc    480

taccttgtca tttttcaacg atgcctactt tgccacccag ttacaacacc agtgaatttc    540

tccgcatcaa atggtctaag attgaagtgg acaaaaatgg aaaagatttg aaagagacta    600

ctgtccttgt ggcccaaaat ggaaatatca agattggtca ggactacaaa gggagagtgt    660

ctgtgcccac acatcccgag gctgtgggcg atgcctccct cactgtggtc aagctgctgg    720

caagtgatgc gggtctttac cgctgtgacg tcatgtacgg gattgaagac acacaagaca    780

cggtgtcact gactgtggat ggggttgtgt ttcactacag ggcggcaacc agcaggtaca    840

cactgaattt tgaggctgct cagaaggctt gtttggacgt tggggcagtc atagcaactc    900

cagagcagct ctttgctgcc tatgaagatg gatttgagca gtgtgacgca ggctggctgg    960

ctgatcagac tgtcagatat cccatccggg ctcccagagt aggctgttat ggagataaga   1020

tgggaaaggc aggagtcagg acttatggat tccgttctcc ccaggaaact tacgatgtgt   1080
```

```
attgttatgt ggatcatctg gatggtgatg tgttccacct cactgtcccc agtaaattca   1140
ccttcgagga ggctgcaaaa gagtgtgaaa accaggatgc caggctggca acagtggggg   1200
aactccaggc ggcatggagg aacggctttg accagtgcga ttacgggtgg ctgtcggatg   1260
ccagcgtgcg ccaccctgtg actgtggcca gggcccagtg tggaggtggt ctacttgggg   1320
tgagaaccct gtatcgtttt gagaaccaga caggcttccc tccccctgat agcagatttg   1380
atgcctactg ctttaaacct aaagaggcta caaccatcga tttgagtatc ctcgcagaaa   1440
ctgcatcacc cagtttatcc aaagaaccac aaatggtttc tgatagaact acaccaatca   1500
tccctttagt tgatgaatta cctgtcattc caacagagtt ccctcccgtg ggaaatattg   1560
tcagttttga acagaaagcc acagtccaac ctcaggctat cacagatagt ttagccacca   1620
aattacccac acctactggc agtaccaaga agccctggga tatggatgac tactcacctt   1680
ctgcttcagg acctcttgga aagctagaca tatcagaaat taaggaagaa gtgctccaga   1740
gtacaactgg cgtctctcat tatgctacgg attcatggga tggtgtcgtg gaagataaac   1800
aaacacaaga atcggttaca cagattgaac aaatagaagt gggtcctttg gtaacatcta   1860
tggaaatctt aaagcacatt ccttccaagg aattccctgt aactgaaaca ccattggtaa   1920
ctgcaagaat gatcctggaa tccaaaactg aaaagaaaat ggtaagcact gtttctgaat   1980
tggtaaccac aggtcactat ggattcacct tgggagaaga ggatgatgaa gacagaacac   2040
ttacagttgg atctgatgag agcaccttga tctttgacca aattcctgaa gtcattacgg   2100
tgtcaaagac ttcagaagac accatccaca ctcatttaga agacttggag tcagtctcag   2160
catccacaac tgtttcccct ttaattatgc ctgataataa tggatcatcc atggatgact   2220
gggaagagag acaaactagt ggtaggataa cggaagagtt tcttggcaaa tatctgtcta   2280
ctacaccttt tccatcacag catcgtacag aaatagaatt gtttccttat tctggtgata   2340
aaatattagt agagggaatt tccacagtta tttatccttc tctacaaaca gaaatgacac   2400
atagaagaga aagaacagaa acactaatac cagagatgag aacagatact tatacagatg   2460
aaatacaaga agagatcact aaaagtccat ttatgggaaa aacagaagaa gaagtcttct   2520
ctgggatgaa actctctaca tctctctcag agccaattca tgttacagag tcttctgtgg   2580
aaatgaccaa gtcttttgat ttcccaacat tgataacaaa gttaagtgca gagccaacag   2640
aagtaagaga tatggaggaa gactttacag caactccagg tactacaaaa tatgatgaaa   2700
atattacaac agtgcttttg gcccatggta ctttaagtgt tgaagcagcc actgtatcaa   2760
aatggtcatg ggatgaagat aatacaacat ccaagccttt agagtctaca gaaccttcag   2820
cctcttcaaa attgccccct gccttactca caactgtggg gatgaatgga aaggataaag   2880
acatcccaag tttcactgaa gatggagcag atgaatttac tcttattcca gatagtactc   2940
aaaagcagtt agaggaggtt actgatgaag acatagcagc ccatggaaaa ttcacaatta   3000
gatttcagcc aactacatca actggtattg cagaaaagtc aactttgaga gattctacaa   3060
ctgaagaaaa agttccacct atcacaagca ctgaaggcca agtttatgca accatggaag   3120
gaagtgcttt gggtgaagta gaagatgtgg acctctctaa gccagtatct actgttcccc   3180
aatttgcaca cacttcagag gtggaaggat tagcatttgt tagttatagt agcacccaag   3240
agcctactac ttatgtagac tcttcccata ccattcctct ttctgtaatt cccaagacag   3300
actggggagt gttagtacct tctgttccat cagaagatga agttctaggt gaaccctctc   3360
aagacatact tgtcattgat cagactcgcc ttgaagcgac tatttctcca gaaactatga   3420
```

gaacaacaaa aatcacagag ggaacaactc aggaagaatt cccttggaaa gaacagactg 3480
cagagaaacc agttcctgct ctcagttcta cagcttggac tcccaaggag gcagtaacac 3540
cactggatga acaagagggc gatggatcag catatacagt ctctgaagat gaattgttga 3600
caggttctga gagggtccca gttttagaaa caactccagt tggaaaaatt gatcacagtg 3660
tgtcttatcc accaggtgct gtaactgagc acaaagtgaa aacagatgaa gtggtaacac 3720
taacaccacg cattgggcca aaagtatctt taagtccagg gcctgaacaa aaatatgaaa 3780
cagaaggtag tagtacaaca ggatttacat catctttgag tccttttagt acccacatta 3840
cccagcttat ggaagaaacc actactgaga aaacatccct agaggatatt gatttaggct 3900
caggattatt tgaaaagccc aaagccacag aactcataga attttcaaca atcaaagtca 3960
cagttccaag tgatattacc actgccttca gttcagtaga cagacttcac acaacttcag 4020
cattcaagcc atcttccgcg atcactaaga aaccacctct catcgacagg gaacctggtg 4080
aagaaacaac cagtgacatg gtaatcattg gagaatcaac atctcatgtt cctcccacta 4140
cccttgaaga tattgtagcc aaggaaacag aaaccgatat tgatagagag tatttcacga 4200
cttcaagtcc tcctgctaca cagccaacaa gaccacccac tgtggaagac aaagaggcct 4260
ttggacctca ggcgctttct acgccacagc cccagcaaag cacaaaattt caccctgaca 4320
ttaatgttta tattattgag gtcagagaaa ataagacagg tcgaatgagt gatttgagtg 4380
taattggtca tccaatagat tcagaatcta aagaagatga accttgtagt gaagaaacag 4440
atccagtgca tgatctaatg gctgaaattt tacctgaatt ccctgacata attgaaatag 4500
acctatacca cagtgaagaa aatgaagaag aagaagaaga gtgtgcaaat gctactgatg 4560
tgacaaccac cccatctgtg cagtacataa atgggaagca tctcgttacc actgtgccca 4620
aggacccaga agctgcagaa gctaggcgtg gccagtttga aagtgttgca ccttctcaga 4680
atttctcgga cagctctgaa agtgatactc atccatttgt aatagccaaa acggaattgt 4740
ctactgctgt gcaacctaat gaatctacag aaacaactga gtctcttgaa gttacatgga 4800
agcctgagac ttaccctgaa acatcagaac atttttcagg tggtgagcct gatgttttcc 4860
ccacagtccc attccatgag gaatttgaaa gtggaacagc caaaaaaggg gcagaatcag 4920
tcacagagag agatactgaa gttggtcatc aggcacatga acatactgaa cctgtatctc 4980
tgtttcctga agagtcttca ggagagattg ccattgacca agaatctcag aaaatagcct 5040
ttgcaagggc tacagaagta acatttggtg aagaggtaga aaaaagtact tctgtcacat 5100
acactcccac tatagttcca agttctgcat cagcatatgt ttcagaggaa gaagcagtta 5160
ccctaatagg aaatccttgg ccagatgacc tgttgtctac caaagaaagc tgggtagaag 5220
caactcctag acaagttgta gagctctcag ggagttcttc gattccaatt acagaaggct 5280
ctggagaagc agaagaagat gaagatacaa tgttcaccat ggtaactgat ttatcacaga 5340
gaaatactac tgatacactc attactttag acactagcag gataatcaca gaaagctttt 5400
ttgaggttcc tgcaaccacc atttatccag tttctgaaca accttctgca aaagtggtgc 5460
ctaccaagtt tgtaagtgaa acagacactt ctgagtggat ttccagtacc actgttgagg 5520
aaaagaaaag gaaggaggag gagggaacta caggtacggc ttctacattt gaggtatatt 5580
catctacaca gagatcggat caattaattt taccctttga attagaaagt ccaaatgtag 5640
ctacatctag tgattcaggt accaggaaaa gttttatgtc cttgacaaca ccaacacagt 5700
ctgaaaggga aatgacagat tctactcctg tctttacaga aacaaataca ttagaaaatt 5760
tgggggcaca gaccactgag cacagcagta tccatcaacc tggggttcag gaagggctga 5820

```
ccactctccc acgtagtcct gcctctgtct ttatggagca gggctctgga gaagctgctg   5880
ccgacccaga aaccaccact gtttcttcat tttcattaaa cgtagagtat gcaattcaag   5940
ccgaaaagga agtagctggc actttgtctc cgcatgtgga aactacattc tccactgagc   6000
caacaggact ggttttgagt acagtaatgg acagagtagt tgctgaaaat ataacccaaa   6060
catccaggga aatagtgatt tcagagcgat taggagaacc aaattatggg gcagaaataa   6120
ggggcttttc cacaggtttt cctttggagg aagatttcag tggtgacttt agagaatact   6180
caacagtgtc tcatcccata gcaaaagaag aaacggtaat gatggaaggc tctggagatg   6240
cagcatttag ggacacccag acttcaccat ctacagtacc tacttcagtt cacatcagtc   6300
acatatctga ctcagaagga cccagtagca ccatggtcag cacttcagcc ttcccctggg   6360
aagagtttac atcctcagct gagggctcag gtgagcaact ggtcacagtc agcagctctg   6420
ttgttccagt gcttcccagt gctgtgcaaa agttttctgg tacagcttcc tccattatcg   6480
acgaaggatt gggagaagtg ggtactgtca atgaaattga tagaagatcc accattttac   6540
caacagcaga agtggaaggt acgaaagctc cagtagagaa ggaggaagta aaggtcagtg   6600
gcacagtttc aacaaacttt ccccaaacta tagagccagc caaattatgg tctaggcaag   6660
aagtcaaccc tgtaagacaa gaaattgaaa gtgaaacaac atcagaggaa caaattcaag   6720
aagaaaagtc atttgaatcc cctcaaaact ctcctgcaac agaacaaaca atctttgatt   6780
cacagacatt tactgaaact gaactcaaaa ccacagatta ttctgtacta acaacaaaga   6840
aaacttacag tgatgataaa gaaatgaagg aggaagacac ttctttagtt aacatgtcta   6900
ctccagatcc agatgcaaat ggcttggaat cttacacaac tctccctgaa gctactgaaa   6960
agtcacattt tttcttagct actgcattag taactgaatc tataccagct gaacatgtag   7020
tcacagattc accaatcaaa aaggaagaaa gtacaaaaca ttttccgaaa ggcatgagac   7080
caacaattca agagtcagat actgagctct tattctctgg actgggatca ggagaagaag   7140
ttttacctac tctaccaaca gagtcagtga attttactga agtggaacaa atcaataaca   7200
cattatatcc ccacacttct caagtggaaa gtacctcaag tgacaaaatt gaagacttta   7260
acagaatgga aaatgtggca aaagaagttg gaccactcgt atctcaaaca gacatctttg   7320
aaggtagtgg gtcagtaacc agcacaacat taatagaaat tttaagtgac actggagcag   7380
aaggacccac ggtggcacct ctccctttct ccacggacat cggacatcct caaaatcaga   7440
ctgtcaggtg ggcagaagaa atccagacta gtagaccaca aaccataact gaacaagact   7500
ctaacaagaa ttcttcaaca gcagaaatta acgaaacaac aacctcatct actgattttc   7560
tggctagagc ttatggtttt gaaatggcca aagaatttgt tacatcagca ccaaaaccat   7620
ctgacttgta ttatgaacct tctggagaag gatctggaga agtggatatt gttgattcat   7680
ttcacacttc tgcaactact caggcaacca gacaagaaag cagcaccaca tttgtttctg   7740
atgggtccct ggaaaaacat cctgaggtgc caagcgctaa agctgttact gctgatggat   7800
tcccaacagt ttcagtgatg ctgcctcttc attcagagca gaacaaaagc tcccctgatc   7860
caactagcac actgtcaaat acagtgtcat atgagaggtc cacagacggt agtttccaag   7920
accgtttcag ggaattcgag gattccacct taaaacctaa cagaaaaaaa cccactgaaa   7980
atattatcat agacctggac aaagaggaca aggatttaat attgacaatt acagagagta   8040
ccatccttga aattctacct gagctgacat cggataaaaa tactatcata gatattgatc   8100
atactaaacc tgtgtatgaa gacattcttg gaatgcaaac agatatagat acagaggtac   8160
```

catcagaacc acatgacagt aatgatgaaa gtaatgatga cagcactcaa gttcaagaga 8220
tctatgaggc agctgtcaac ctttctttaa ctgaggaaac atttgagggc tctgctgatg 8280
ttctggctag ctacactcag gcaacacatg atgaatcaat gacttatgaa gatagaagcc 8340
aactagatca catgggcttt cacttcacaa ctgggatccc tgctcctagc acagaaacag 8400
aattagacgt tttacttccc acggcaacat ccctgccaat tcctcgtaag tctgccacag 8460
ttattccaga gattgaagga ataaaagctg aagcaaaagc cctggatgac atgtttgaat 8520
caagcacttt gtctgatggt caagctattg cagaccaaag tgaaataata ccaacattgg 8580
gccaatttga aaggactcag gaggagtatg aagacaaaaa acatgctggt ccttcttttc 8640
agccagaatt ctcttcagga gctgaggagg cattagtaga ccatactccc tatctaagta 8700
ttgctactac ccaccttatg gatcagagtg taacagaggt gcctgatgtg atggaaggat 8760
ccaatccccc atattacact gatacaacat tagcagtttc aacatttgcg aagttgtctt 8820
ctcagacacc atcatctccc ctcactatct actcaggcag tgaagcctct ggacacacag 8880
agatccccca gcccagtgct ctgccaggaa tagacgtcgg ctcatctgta atgtccccac 8940
aggattcttt taaggaaatt catgtaaata ttgaagcgac tttcaaacca tcaagtgagg 9000
aataccttca cataactgag cctccctctt tatctcctga cacaaaatta gaaccttcag 9060
aagatgatgg taaacctgag ttattagaag aaatggaagc ttctcccaca gaacttattg 9120
ctgtggaagg aactgagatt ctccaagatt tccaaaacaa aaccgatggt caagtttctg 9180
gagaagcaat caagatgttt cccaccatta aaacacctga ggctggaact gttattacaa 9240
ctgccgatga aattgaatta gaaggtgcta cacagtggcc acactctact tctgcttctg 9300
ccacctatgg ggtcgaggca ggtgtggtgc cttggctaag tccacagact tctgagaggc 9360
ccacgctttc ttcttctcca gaaataaacc ctgaaactca agcagcttta atcagagggc 9420
aggattccac gatagcagca tcagaacagc aagtggcagc gagaattctt gattccaatg 9480
atcaggcaac agtaaaccct gtggaattta atactgaggt tgcaacacca ccattttccc 9540
ttctggagac ttctaatgaa acagatttcc tgattggcat taatgaagag tcagtggaag 9600
gcacggcaat ctatttacca ggacctgatc gctgcaaaat gaacccgtgc cttaacggag 9660
gcacctgtta tcctactgaa acttcctacg tatgcacctg tgtgccagga tacagcggag 9720
accagtgtga acttgatttt gatgaatgtc actctaatcc ctgtcgtaat ggagccactt 9780
gtgttgatgg ttttaacaca ttcaggtgcc tctgccttcc aagttatgtt ggtgcacttt 9840
gtgagcaaga taccgagaca tgtgactatg gctggcacaa attccaaggg cagtgctaca 9900
aatactttgc ccatcgacgc acatgggatg cagctgaacg ggaatgccgt ctgcagggtg 9960
cccatctcac aagcatcctg tctcacgaag aacaaatgtt tgttaatcgt gtgggccatg 10020
attatcagtg gataggcctc aatgacaaga tgtttgagca tgacttccgt tggactgatg 10080
gcagcacact gcaatacgag aattggagac ccaaccagcc agacagcttc ttttctgctg 10140
gagaagactg tgttgtaatc atttggcatg agaatggcca gtggaatgat gttccctgca 10200
attaccatct cacctatacg tgcaagaaag gaacagtcgc ttgcggccag ccccctgttg 10260
tagaaaatgc caagaccttt ggaaagatga aacctcgtta tgaaatcaac tccctgatta 10320
gataccactg caaagatggt ttcattcaac gtcaccttcc aactatccgg tgcttaggaa 10380
atggaagatg ggctatacct aaaattacct gcatgaaccc atctgcatac caaaggactt 10440
attctatgaa atactttaaa aattcctcat cagcaaagga caattcaata aatacatcca 10500
aacatgatca tcgttggagc cggaggtggc aggagtcgag gcgctgatcc ctaaaatggc 10560

```
gaacatgtgt tttcatcatt tcagccaaag tcctaacttc ctgtgccttt cctatcacct  10620
cgagaagtaa ttatcagttg gtttggattt ttggaccacc gttcagtcat tttgggttgc  10680
cgtgctccca aaacatttta aatgaaagta ttggcattca aaaagacagc agacaaaatg  10740
aaagaaaatg agagcagaaa gtaagcattt ccagcctatc taatttcttt agttttctat  10800
ttgcctccag tgcagtccat ttcctaatgt ataccagcct actgtactat ttaaaatgct  10860
caatttcagc accgatggcc atgtaaataa gatgatttaa tgttgatttt aatcctgtat  10920
ataaaataaa aagtcacaat gagtttgggc atatttaatg atgattatgg agccttagag  10980
gtctttaatc attggttcgg ctgcttttat gtagtttagg ctggaaatgg tttcacttgc  11040
tctttgactg tcagcaagac tgaagatggc ttttcctgga cagctagaaa acacaaaatc  11100
ttgtaggtca ttgcacctat ctcagccata ggtgcagttt gcttctacat gatgctaaag  11160
gctgcgaatg ggatcctgat ggaactaagg actccaatgt cgaactcttc tttgctgcat  11220
tcctttttct tcacttacaa gaaaggcctg aatggaggac ttttctgtaa ccaggaacat  11280
tttttagggg tcaaagtgct aataattaac tcaaccaggt ctacttttta atggctttca  11340
taacactaac tcataaggtt accgatcaat gcatttcata cggatataga cctagggctc  11400
tggagggtgg gggattgtta aaacacatgc aaaaaaaaaa aaaaaaaaaa aaaaagaaat  11460
tttgtatata taaccatttt aatcttttat aaagttttga atgttcatgt atgaatgctg  11520
cagctgtgaa gcatacataa ataaatgaag taagccatac tgatttaatt tattggatgt  11580
tattttccct aagacctgaa aatgaacata gtatgctagt tatttttcag tgttagcctt  11640
ttactttcct cacacaattt ggaatcatat aatataggta ctttgtccct gattaaataa  11700
tgtgacggat agaatgcatc aagtgtttat tatgaaaaga gtggaaaagt atatagcttt  11760
tagcaaaagg tgtttgccca ttctaagaaa tgagcgaata tatagaaata gtgtgggcat  11820
ttcttcctgt taggtggagt gtatgtgttg acatttctcc ccatctcttc ccactctgtt  11880
ttctccccat tatttgaata aagtgactgc tgaagatgac tttgaatcct tatccactta  11940
atttaatgtt taaagaaaaa cctgtaatgg aaagtaagac tccttcccta atttcagttt  12000
agagcaactt gaagaagagt agacaaaaaa taaaatgcac atagaaaaag agaaaaaggg  12060
cacaaaggga ttggcccaat attgattctt tttttataaa acctcctttg gcttagaagg  12120
aatgactcta gctacaataa tacacagtat gtttaagcag gttcccttgg ttgttgcatt  12180
aaatgtaatc cacctttagg tattttagag cacagaacaa cactgtgttg atctagtagg  12240
tttctatttt tcctttctct ttacaatgca cataatactt tcctgtattt atatcataac  12300
gtgtatagtg taaaatgtga atgacttttt ttgtgaatga aaatctaaaa tctttgtaac  12360
tttttatatc tgcttttgtt tcaccaaaga aacctaaaat ccttctttta ctacac      12416
```

<210> SEQ ID NO 123
<211> LENGTH: 1242
<212> TYPE: DNA
<213> ORGANISM: Homo sapiens

<400> SEQUENCE: 123

```
ctagaggggc ggaaagtaac aaggaggtgg gggtacaaat cctcagctcc tgcttccgca     60
agcactaacc tgctctgaag tgagccaggc agctctggcc atcttttccc agccacagaa    120
tcaggtgatg gtccagaatt aagagctgtc acctgtgtca ttcactcaca atggaagaaa    180
tgaagaagac tgccatccgg ctgcccaaag gcaaacagaa gcctataaag acggaatgga    240
```

```
attcccggtg tgtccttttc acctacttcc aaggggacat cagcagcgta gtggatgaac    300
acttctccag agctctgagc aatatcaaga gcccccagga attgaccccc tcgagtcaga    360
gtgaaggtgt gatgctgaaa aacgatgata gcatgtctcc aaatcagtgg cgttactcgt    420
ctccatggac aaagccacaa ccagaagtac ctgtcacaaa ccgtgccgcc aactgcaact    480
tgcatgtgcc tggtcccatg gctgtgaatc agttctcacc gtccctggct aggagggcct    540
ctgttcggcc tggggagctg tggcatttct cctccctggc gggcaccagc tccttagagc    600
ctggctactc tcatcccttc cccgctcggc acctggttcc agagccccag cctgatggga    660
aacgtgagcc tctcctaagt ctcctccagc aagacagatg cctagcccgt cctcaggaat    720
ctgccgccag ggagaatggc aaccctggcc agatagctgg aagcacaggg ttgctcttca    780
acctgcctcc cggctcagtt cactataaga aactatatgt atctcgtgga tctgccagta    840
ccagccttcc aaatgaaact ctttcagagt tagagacacc tgggaaatac tcacttacac    900
caccaaacca ctggggccac ccacatcgat acctgcagca tctttagtca agttggagga    960
gaaagacaac acttggtcta agacacggca gcaagacatc cctgcatatt gttccagata   1020
aaaatgaaag ctgctcacac ccacttgcct ccccaatctg ttaaacagct tcgtgtctag   1080
tatgagctca gtacttgccc tgtgaaaatc ccagaagccc ccgctgtcaa tgttccccat   1140
ccacaccctg cttgctcctg tgtaacagct cagatgatga ataataataa aactgtactt   1200
ttttggatgg tgctaaaaaa aaaaaaaaaa aaaaaaaaaa aa                      1242
```

<210> SEQ ID NO 124
<211> LENGTH: 2832
<212> TYPE: DNA
<213> ORGANISM: Homo sapiens

<400> SEQUENCE: 124

```
aattcagcac taaaaccagt gtgagaagca gtatgtgtga gcatgtgtgt gtgtgtatgt     60
gtgtgggggg gggtgtaaaa tgtgtttttc aaagtactga gaggttgatg ggactgttcg    120
attagctcct ctgagaagaa gagaaaaggt tcttggacct ctccctgttt cttccttaga    180
ataatttgga tgggatttgt gatgcaggaa agcctaaggg aaaaagaata ttcattctgt    240
gtggtgaaaa ttttttgaaa aaaaaattgc cttcttcaaa caagggtgtc attctgatat    300
ttatgaggac tgttgttctc actatgaagg catctgttat tgaaatgttc cttgttttgc    360
tggtgactgg agtacattca aacaaagaaa cggcaaagaa gattaaaagg cccaagttca    420
ctgtgcctca gatcaactgc gatgtcaaag ccggaaagat catcgatcct gagttcattg    480
tgaaatgtcc agcaggatgc caagacccca aataccatgt ttatggcact gacgtgtatg    540
catcctactc cagtgtgtgt ggcgctgccg tacacagtgg tgtgcttgat aattcaggag    600
ggaaaatact tgttcggaag gttgctggac agtctggtta caaagggagt tattccaacg    660
gtgtccaatc gttatcccta ccacgatgga gagaatcctt tatcgtctta gaaagtaaac    720
ccaaaaaggg tgtaacctac ccatcagctc ttacatactc atcatcgaaa agtccagctg    780
cccaagcagg tgagaccaca aaagcctatc agaggccacc tattccaggg acaactgcac    840
agccggtcac tctgatgcag cttctggctg tcactgtagc tgtggccacc cccaccacct    900
tgccaaggcc atccccttct gctgcttcta ccaccagcat ccccagacca caatcagtgg    960
gccacaggag ccaggagatg gatctctggt ccactgccac ctacacaagc agccaaaaca   1020
ggcccagagc tgatccaggt atccaaaggc aagatccttc aggagctgcc ttccagaaac   1080
ctgttggagc ggatgtcagc ctgggagaga tggactcatg gaaacctgga tcggtccttt   1140
```

```
tagatgaagg acttgttcca aaagaagaat tgagcacaca gtctttggag ccagtatccc   1200

tgggagatcc aaactgcaaa attgacttgt cgtttttaat tgatgggagc accagcattg   1260

gcaaacggcg attccgaatc cagaagcagc tcctggctga tgttgcccaa gctcttgaca   1320

ttggccctgc cggtccactg atgggtgttg tccagtatgg agacaaccct gctactcact   1380

ttaacctcaa gacacacacg aattctcgag atctgaagac agccatagag aaaattactc   1440

agagaggagg actttctaat gtaggtcggg ccatctcctt tgtgaccaag aacttctttt   1500

ccaaagccaa tggaaacaga agcggggctc ccaatgtggt ggtggtgatg gtggatggct   1560

ggcccacgga caaagtggag gaggcttcaa gacttgcgag agagtcagga atcaacattt   1620

tcttcatcac cattgaaggt gctgctgaaa atgagaagca gtatgtggtg gagcccaact   1680

ttgcaaacaa ggccgtgtgc agaacaaacg gcttctactc gctccacgtg cagagctggt   1740

ttggcctcca caagaccctg cagcctctgg tgaagcgggt ctgcgacact gaccgcctgg   1800

cctgcagcaa gacctgcttg aactcggctg acattggctt cgtcatcgac ggctccagca   1860

gtgtggggac gggcaacttc cgcaccgtcc tccagtttgt gaccaacctc accaaagagt   1920

ttgagatttc cgacacggac acgcgcatcg gggccgtgca gtacacctac gaacagcggc   1980

tggagtttgg gttcgacaag tacagcagca agcctgacat cctcaacgcc atcaagaggg   2040

tgggctactg gagtggtggc accagcacgg gggctgccat caacttcgcc ctggagcagc   2100

tcttcaagaa gtccaagccc aacaagagga agttaatgat cctcatcacc gacgggaggt   2160

cctacgacga cgtccggatc ccagccatgg ctgcccatct gaagggagtg atcacctatg   2220

cgataggcgt tgcctgggct gcccaagagg agctagaagt cattgccact caccccgcca   2280

gagaccactc cttctttgtg gacgagtttg acaacctcca tcagtatgtc cccaggatca   2340

tccagaacat ttgtacagag ttcaactcac agcctcggaa ctgaattcag agcaggcaga   2400

gcaccagcaa gtgctgcttt actaactgac gtgttggacc accccaccgc ttaatggggc   2460

acgcacggtg catcaagtct tgggcagggc atggagaaac aaatgtcttg ttattattct   2520

ttgccatcat gctttttcat attccaaaac ttggagttac aaagatgatc acaaacgtat   2580

agaatgagcc aaaaggctac atcatgttga gggtgctgga gattttacat tttgacaatt   2640

gttttcaaaa taaatgttcg gaatacagtg cagcccttac gacaggctta cgtagagctt   2700

ttgtgagatt tttaagttgt tatttctgat tagaactctg taaccctcag caagtttcat   2760

ttttgtcatg acaatgtagg aattgctgaa ttaaatgttt agaaggatga catgcaaaaa   2820

aaaaaaaaaa aa                                                       2832
```

<210> SEQ ID NO 125
<211> LENGTH: 1138
<212> TYPE: DNA
<213> ORGANISM: Homo sapiens

<400> SEQUENCE: 125

```
cccttccctg cccgacaccc agaccgacct tgaccgccca cctggcagga gcaggacagg     60

acggccggac gcggccatgg ccgagctccc ggggcccttt ctctgcgggg ccctgctagg    120

cttcctgtgc ctgagtgggc tggccgtgga ggtgaaggta cccacagagc cgctgagcac    180

gcccctgggg aagacagccg agctgacctg cacctacagc acgtcggtgg gagacagctt    240

cgccctggag tggagctttg tgcagcctgg gaaacccatc tctgagtccc atccaatcct    300

gtacttcacc aatggccatc tgtatccaac tggttctaag tcaaagcggg tcagcctgct    360
```

```
tcagaacccc cccacagtgg gggtggccac actgaaactg actgacgtcc acccctcaga    420

tactggaacc tacctctgcc aagtcaacaa cccaccagat ttctacacca atgggttggg    480

gctaatcaac cttactgtgc tggttccccc cagtaatccc ttatgcagtc agagtggaca    540

aacctctgtg ggaggctcta ctgcactgag atgcagctct tccgaggggg ctcctaagcc    600

agtgtacaac tgggtgcgtc ttggaacttt tcctacacct tctcctggca gcatggttca    660

agatgaggtg tctggccagc tcattctcac caacctctcc ctgacctcct cgggcaccta    720

ccgctgtgtg gccaccaacc agatgggcag tgcatcctgt gagctgaccc tctctgtgac    780

cgaaccctcc caaggccgag tggccggagc tctgattggg gtgctcctgg gcgtgctgtt    840

gctgtcagtt gctgcgttct gcctggtcag gttccagaaa gagaggggga agaagcccaa    900

ggagacatat gggggtagtg accttcggga ggatgccatc gctcctggga tctctgagca    960

cacttgtatg agggctgatt ctagcaaggg gttcctggaa agaccctcgt ctgccagcac   1020

cgtgacgacc accaagtcca agctccctat ggtcgtgtga cttctcccga tccctgaggg   1080

cggtgagggg gaatatcaat aattaaagtc tgtgggtacc aaaaaaaaaa aaaaaaaa     1138


<210> SEQ ID NO 126
<211> LENGTH: 13203
<212> TYPE: DNA
<213> ORGANISM: Homo sapiens

<400> SEQUENCE: 126

atgcctgggg agcgccccg aggagcgccg ccccccacca tgactggaga cctgcagccc     60

cgccaagttg ccagcagccc ggggcacccc tcccagccgc cactggagga caacacccca    120

gctaccagga ccaccaaggg tgccagggag gctggcggcc aggcccaggc catggagctc    180

cccgaggccc agccaaggca ggccagggac ggggagctca agcccccatc cctgagaggc    240

caggccccga gcagcaccc tgggaagagg ggcagccccc agaccccacc ggggagaagc    300

cccttgcagg ctccctcaag gctggcgggc agggcagagg gcagcccccc acagcgctac    360

attctgggca tcgccagctc gaggaccaag cccaccctgg acgagacacc agagaaccca    420

cagctggagg ctgcccagct ccctgaggtg gacacccccc agggccctgg gactggagct    480

ccactcaggc cgggcctccc aaggactgag gcccaacccg ccgccgaaga gcttggcttc    540

cacaggtgct tccaggagcc accctccagc tttacctcca ccaactatac ctcaccaagc    600

gccaccccca ggcccccagc cccggggccc ccccagagca ggggcaccag ccccctccag    660

cccggttcct atcccgaata ccaggccagt ggggccgact cctggcctcc cgctgctgag    720

aatagcttcc caggtgctaa tttcggggtt ccccccgccg agccggaacc tattcccaaa    780

ggcagcaggc ccggcggcag ccccagggga gtttccttcc agttcccctt cccggcactg    840

catggggcca gcacaaaacc cttccctgcg gatgtggctg ggcacgcatt caccaatggg    900

ccactggtgt ttgccttcca tcagccccag ggagcgtggc cggaggaggc cgtgggcacg    960

ggccctgcct acccgctgcc cacccagcct gcgccctcac ccctgccctg ctaccagggc   1020

cagccaggtg gcctgaaccg ccacagcgac ctcagtggtg ccctctcttc ccctggagct   1080

gctcactcgg ccccgagacc cttctctgac agtttacaca agagcctgac caaaatcctt   1140

cccgaaagac caccttcagc ccaggatggg ctggggagca cgagagggcc ccctagctcc   1200

ctaccccaga ggcactttcc agggcaggcg tacagagcca gtggggtgga caccagcccg   1260

gggcctccgg acaccgagct ggccgcccca gggcccccac ccgccaggct gccccagctg   1320

tgggacccca cagcagcccc ttaccccaca cctcctgggg gcccccctggc tgccaccagg   1380
```

```
agtatgttct ttaacggcca gcccagccca ggccagcggc tctgcctccc ccagagtgcc   1440
cccctgcctt ggccccaagt gctcccgacc gcccggccaa gtccccacgg aatggagatg   1500
ctgagccggc tgcctttccc cgcggggggc cccgagtggc aggggggcag ccaaggagcc   1560
ctgggcactg ctggcaagac accgggaccc agagagaagc tgccagccgt gagaagcagc   1620
cagggcggct ccccagcact gttcacctac aacggaatga cagaccctgg ggctcagccc   1680
ctgttcttcg gggtggccca gccccaggtt tcaccccacg ggacacccag cctgccccca   1740
ccgagggtag tgggagcctc cccagcgag tccccactgc cgtcaccggc caccaacacg   1800
gccggcagca cctgctcttc cctgtcgccg atgtccagca gcccagccaa ccccagctca   1860
gaggaaagcc agctccccgg ccccctcggg ccctcggcct tcttccaccc acccactcac   1920
ccccaggaga cgggcagccc cttcccgtcc ccggagcccc cccactccct ccccacccac   1980
taccagccag agccagccaa ggccttccct tttcccgcag atgggctggg agccgagggt   2040
gccttccagt gcctggagga gaccccattc cccccacgagg gccccgaggt gggtcgggga   2100
gggctgcagg gcttcccccg tgcgccgcct ccgtacccca cacaccactt ctccctcagc   2160
agcgccagcc tggaccagct ggacgtgctg ctgacctgca ggcagtgtga ccgcaactac   2220
agcagcctgg cggccttcct ggcccaccgg cagttctgtg gcctgctcct ggccagggcc   2280
aaggatggcc accagcggtc tccaggcccc cctgggctcc cctcgccccc cgctgccccc   2340
agagtccctg ccgacgcaca cgcgggcttg ctcagccacg cgaagacctt cctgttagct   2400
ggggacgccc aggccgaggg caaagacgac cccctgagga caggcttcct gcccagcctg   2460
gccgccaccc ccttcccgct ccctgcctcg gacctggaca tggaggatga cgccaagctg   2520
gacagcctca tcacagaggc gctcaacggc atggagtacc agtcggacaa cccggagatc   2580
gacagcagct tcatcgacgt cttcgcggac gaggagcctt ccggccccag aggtcccagc   2640
tccggacacc cccttaagag caaggcgggg gtgactccag agagcaaagc tccgcccccg   2700
ctcccagcag ccacgccgga cccccaaacc ccccgccctg gggacagggg ctgcccagcc   2760
cgaggcaggc ccaaaacgcg ttccctgggt ctggccccca ccgaggcgga tgcgcccagc   2820
cagggcaggc agcagaggag ggggaagcag ttgaagctgt tccggaagga tctggactcg   2880
ggcggcgcag cagaggggtc ggggtcgggc ggcggcggca gagcctccgg cctgaggccc   2940
cggaggaacg acggtctcgg ggagcggccc ccaccccgtc cccggcgccc tagaacgcag   3000
gcccccggga gccgcgcaga ccccgcgccc cgggtcccga gagccgccgc cctccccgag   3060
gagacccgca gctcccggcg ccgccggctg ccccccagga aggaccccag gaagaggaag   3120
gctcggggcg gcgcctgggg caaggagctc attctgaaga tcgtgcagca gaagaacagg   3180
ctccgcgagt acgacttcgc ctcggagtcc gaggaggacg agcagcctcc gccgcggggc   3240
cccggcttca gaggccggcg gggccgaggc gagaagagga aggaagtgga gctgacccag   3300
ggtcccagag aggatgagcc acagaaaccc cggaaggcgg cgaggcagga agccggcggg   3360
gacggagccc ccgcgaaccc cgaggagccg ggcgggtctc gcccgggccc cggcaggagc   3420
cctcaggccc gtggcccgtc tcgaagcctg gagacgggag cggccgccag ggagggaggc   3480
cccaagtgtg ctgatcgccc ctcagtggcc cccaaggatc ccctgcaggt ccccaccaac   3540
accgagacct cagaggaaac ccgcccgtcg ctggactttc cccaggaggc caaggagcct   3600
gaaactgccg aagagtcagc cccggacagc acagaattca cagaggcttt gcgttctcct   3660
ccagccgcct gtgcgggaga aatgggagca agccccggtc tcctgatacc agagcagccg   3720
```

```
ccgcccagca gacatgacac cggcaccccc aagccgtcgg gaagcctcgc caacacggcg   3780
ccccacggaa gctcgccaac gccaggtgtg ggcagcctgc tgggtggtcc tgggggcaca   3840
caggccccag tctcccacaa cagcaaggac ccccctgccc gccagcctgg agaatttctg   3900
gcacccgtgg ctaacccctc aagtaccgcc tgccccaaac ccagtgttct gtcttcaaag   3960
atctccagtt ttggctgtga ccctgctggt tttaacagag accccttggg ggttccagtt   4020
gccaaaaagg ggcctcagcc ctacagcagc ccccacagtg agttgttcct cggacccaaa   4080
gacctggctg gctgtttcct ggaagaactg caccccaagc cctcagccag ggatgccccg   4140
ccggccagca gctcctgcct ttgccaggac ggcgaggatg ccggttccct cgagccacag   4200
ctgccaagga gcccacctgg caccgctgag acggagccag gcagggctgc atcgccaccg   4260
accttggagt cctcatccct cttcccagac ctgccggtgg acagattcga cccacccctc   4320
tatggcagcc tgtctgcgaa cagggactcc ggtctgccgt tcgcatgtgc cgaccctccc   4380
cagaagacgg tgccgtcaga tccaccgtac ccctcttttt tgctgcttga ggaagtatcc   4440
ccgatgctgc ctagccattt tcctgatctc tcgggggggaa aggtgctcag taagacgtgt   4500
ccccctgaac ggacagtggt tcccggcgcc gccccatctt tgcctgggaa ggggagtgga   4560
tgtagcgttg ctcttatgag tcacctgtcc gaggatgaac tggagatcca gaaattggtc   4620
accgaattag aaagtcagct gcaaaggagc aaagacacac gtggggcccc gagagagctt   4680
gcagaagctg agtcggtggg cagggtggag ctcggcacag gcacagagcc accctcccaa   4740
cggcgcacct gccaggccac cgtgccccac gaggacacgt tctcggcagc tgacctcacg   4800
cgcgttggag aatccactgc acatcgggag ggtgcggaat cggctgtggc caccgtggaa   4860
gcggttcagg ggaggcctgg ggggacgtgg ccctgcccag cctccttcca tccgggacat   4920
gcagcccttc tcccctgtgc ccaggaagac ctggtttctg ggctcctttt cagccccagg   4980
ggagccaact tccattttca gccagtgcag aaagccggag cctccaagac tggactttgc   5040
caggcagaag gagacagcag gcccccccaa gatgtctgcc tgcctgagcc cagcaagcag   5100
cctggcccac agctggatgc cgggagttta gcaaagtgca gccccgacca ggaactttca   5160
tttcctaaga ataaggaggc cgccagctca caagaaagtg aagactccct gcggctgctt   5220
ccctgtgaac agagaggagg gttcctccca gagcccggca cagcagacca gccccaccga   5280
ggggccccctg ctccagaagc ttttggcagc cctgctgtcc atctggcccc tgacttggca   5340
tttcagggtg acggggctcc acctctggat gccacctggc cttttggtgc cagtcccagc   5400
catgctgccc agggacattc tgcaggcaga gcaggtgggc acctccaccc cacggcaggg   5460
aggcctggct ttgagggtaa tgagtttgca ccggcggggg cctcctcact gactgccccc   5520
cggggcaggg aggcttggtt ggtccctgtg ccaagtcccg cctgtgtatc caacacccac   5580
cctagcagga ggtcccagga cccagctttg agccccccca tacgtcagct ccagctccca   5640
gggcctggag tggctaagag taaagatggc atcctgggct tgcaggagct gacacctgct   5700
gcccagagcc ctccacgagt gaacccctca ggtctggaag ggggcactgt ggaaggaggg   5760
aaggtggcct gtggccccgc ccagggctcc ccagggggtg tgcaggtgac aactctccct   5820
gcagtggccg gacatcagct ggggctggag gcagatggac attggggctt gcttggccaa   5880
gccgagaaaa cccagggcca aggcacagcc aaccagcttc agccagagaa cggggtgagc   5940
ccaggggggca cggacaacca cgcctcagtc aatgccagtc ccaaaaacagc gctgaccggc   6000
cccaccgagg gtgcagtcct gctagagaaa tgcaagggaa gcagggcagc catgagcctt   6060
caggaggagg ccgagcccac cccaagcccc ccgtccccta atagggagtc cctggcgctg   6120
```

```
gccttgacag cagcccacag ccgaagtgga tctgagggcc ggactccaga gagggcgtcc   6180
agccccggcc tgaacaagcc actgctggcc acaggggata gcccagcacc ctctgtcggg   6240
gacctggccg cctgcgcccc ctcacccact tcagccgccc acatgccctg cagccttggg   6300
cccctgcccc gtgaagaccc acttacctcg ccttccaggg cccaaggtgg gctggggggg   6360
cagctgccag catctccgtc ctgcagggac cctcccggcc cccagcagct gctggcctgt   6420
tctcctgcct gggcacctct ggaagaggca gatggcgtcc aagccacgac agatactggg   6480
gctgaggatt ccccggtggc tcccccgtct ttgacaacaa gcccctgcga tcccaaggaa   6540
gccctggctg gttgccttct ccagggggag ggcagccccc tggaagaccc ttcctcctgg   6600
cctcctggct ccgtcagtgc tgtaacctgc actcacagtg ggacaccccc caaagacagc   6660
actttaagaa ttccagagga ttccagaaaa gagaagctgt gggagtctcc tggccgagcc   6720
acctctcctc ctctggcagg ggccgtctcc cccagcgtgg ccgtcagggc tactggcctg   6780
tccagcactc ccaccggaga tgaggcacag gcaggcaggg gactcccagg gccagacccc   6840
cagagcaggg gagccccgcc ccacaccaac cctgacagga tgcccagggg ccactcctcg   6900
tattctccaa gcaatactgc ccgcctcggc cacagggagg gccaggctgt cacagctgtg   6960
cccactgagc ctcccacgct acagggtgca gggccggact cccccgcctg cctggaaggt   7020
gagatgggga ccagcagcaa ggagccggag gacccaggga cccctgagac cgggcgctct   7080
ggtgctacca agatgcccag ggtcacctgc ccttccacag gactgggctt gggaagaacc   7140
acagccccaa gcagcacagc cagtgacttc cagtctgact ccccccaaag ccacagaaat   7200
gcctcccacc agactcccca gggggacccc ctcggccccc aagacctcaa acagaggtcc   7260
cgtggctata aaaagaagcc tgcatctaca gagaacggcc agtggaaggg ccaagctcca   7320
catgggcctg tgacctgtga ggtctgcgca gcctccttcc gctccgggcc gggcctgagc   7380
cggcacaagg ccaggaagca ccggccacac ccgggagccc ccgcggagcc gagcccagcg   7440
gccttgcctg ctcagcagcc tctagagccc ctagcccaaa agtgccagcc gcccaggaag   7500
aaaagccaca gggtgtctgg gaaggagaga ccaaatcact cacggggaga ccccagccac   7560
gtcacccagc caccgcctgc ccagggctca aaggaggttc tcagagcacc ggggtcccca   7620
cacagccagc agctgcaccc tccaagccct actgagcatg aggtagatgt gaagactccg   7680
gcctccaagc ccagaccaga ccaggccagg gaagatgagc tgcatcccaa acaggcagaa   7740
aaaagagaag gccggaggtg gcgccgagag cccaccgtgg actctcctag ccactcagag   7800
gggaagtcaa ataagaaaag gggaaagctg agagggagaa ggctccggga ggagagcatt   7860
cttccagtct ctgctgatgt gatttcagat gggcgcggct ccagaccatc ccctgcaatg   7920
gccagttacg cagcctctcc gagccactgc ctctctgtgg aaggagggcc tgaggctgac   7980
ggggagcagc cgcctcgctt ggccactctg ggacctgggg tgatggaggg tgcagcggag   8040
actgaccagg aggctctgtg tgcaggggag actggggccc agaagccacc tggagatcgg   8100
atgctgtgtc cagggaggat ggatggtgca gctctggggg aacagccaac tgggcagaag   8160
ggagcctcgg caaggggggtt ctggggacca agagagacca aggcgttggg tgtgtgcaaa   8220
gagtctggga gcgagcctgc ggaggacagc agcagggccc acagccgatc agaggaaggt   8280
gtctgggagg agaacacgcc cccccttgggc cccctgggtt ttcccgagac ttccagctct   8340
ccggcggaca gcaccaccag cagctgcctc cagggcctcc cggacaaccc agacacccag   8400
ggtggagtcc aggggcctga aggccccact cctgatgcct ctggctccag tgccaaggat   8460
```

```
cctccaagct tgtttgatga tgaggtctct ttctcccagc tcttccctcc aggcggtcgc   8520
ttgactagaa agaggaaccc gcatgtctac gggaagcgct gtgagaagcc ggtgctcccg   8580
ctgccaaccc agcccagctt tgaggagggc ggtgacccca cgctgggccc agcccgcctg   8640
cccacggacc tcagcgactc cagctccctc tgcctctgcc atgaggaccc gtgggaggac   8700
gaggatcccg caggtctgcc cgagtccttc ctcctggatg ggttcctcaa tagcagggtg   8760
cctggcattg accccctgggc ccccggcctc agcctgtggg ccctggagcc cagcagggaa   8820
gctggtgcag agaagctgcc ctcccactgc cccgaggacg atcggccgga ggccattcct   8880
gagctgcaca tggtcccagc ggcttggcga ggcctggaga tgccggcccc tgccgatgac   8940
tcctcctctt ctctcggaga tgtgagcccc gagcccccca gcctggagag agaacgctgt   9000
gacggtgggc ttcccgggaa cacccacctg ctgccgctcc gtgccacgga ctttgaggtg   9060
ctcagcacca agtttgagat gcaagacctg tgctttctgg gaccctttga agaccccgtg   9120
ggtctccccg gccccagctt cttagacttc gagggcacgg cgagctcaca ggggccacag   9180
agccgaagga cagaggaggc tgcaggggca gggagggccc aaggcagagg ccggccggcc   9240
aagggcaggc gggcctccta caagtgcaaa gtgtgcttcc agcgcttccg cagcctgggc   9300
gagctggacc tgcacaagct ggcccacacg cccgcgccgc cgcccacctg ctacatgtgc   9360
gtggagcgca ggtttggctc gcgggagctg ctgcgggggc acctgcagga gaggcacgcg   9420
cagagcaagg ccgggccctg ggcgtgcggc atgtgcctga aggaggtggc cgacgtctgg   9480
atgtacaacg agcacctgcg tgagcacgcg gtccgcttcg cccgcagggg gcaggcgcgg   9540
aggtccttgg gggacctgcc cggaggcctg gagggcagca gcgctgtcgc ccaccttctg   9600
aacagcatca cggaacccgc gcccaaacac cacaggggca agcgctccgc cggcaaggcc   9660
gccgggagcc cgggagaccc gtgggggcaa gagggagaag ccaagaaaga cagcccgggc   9720
gagagggcga aaccccgggc acgcagcacc cccagcaacc cagacggggc cgcgacccca   9780
gacagcgcct ctgccaccgc cctggctgac gccggcagcc cgggcccccc caggacgacc   9840
cccagcccgt cccccgaccc ctgggccggc ggggagcccc tcctgcaagc caccccggtg   9900
cacgaggcct gcaaggaccc ctcccgcgac tgccaccact gcgggaagcg cttccccaag   9960
cccttcaagc tgcagcgcca cctggcggtg cacagcccgc agcgcgtcta cctgtgcccc  10020
cggtgccccc gggtctaccc cgagcacggg gagctgctgg cacacctggg cggggcgcac  10080
gggctgctgg agcggccgga gctgcagcac acgccgctgt atgcctgcga gctctgcgcc  10140
acggttatgc gcatcatcaa gaagtccttc gcctgcagct cctgcaacta caccttcgcc  10200
aagaaggagc agttcgaccg ccacatgaac aagcacctca gggggggcgcg gcagcccttc  10260
gcgttccgcg gcgtgcggag gccgggagcg ccgggacaga aggcccgggc cctcgagggc  10320
acactgccca gcaaacggcg cagggtggcc atgcccggca gtgcccctgg gcccggcgag  10380
gacaggcctc ctccccgggg aagcagcccc atcctgagtg agggctctct cccggccctg  10440
ctccacctgt gttcggaggt ggctcccagc accaccaagg gatggcccga gaccctagag  10500
aggcctgtag accccgtgac ccacccgatc agaggttgtg agctgccatc caaccaccag  10560
gagtgtcccc cgccgtctct gtctcccttc ccagctgcct tggctgatgg cagaggagac  10620
tgcgcgctgg acggagccct ggagaggcca gagaacgagg cttccccagg cagccccggg  10680
cctcttctcc agcaagctct ccctctgggg gcatctctgc cgcggccggg agccagaggc  10740
caagatgcgg agggaaagag ggctcctctc gtgttctcag ggaaacgcag ggccccgggt  10800
gcccgtggca ggtgtgcccc tgaccatttc caggaagacc acctacttca gaaagagaag  10860
```

```
gaggtgtcct caagccacat ggtgtctgag ggggggcccc gaggcacctt ccacaagggc  10920
agcgccacca agcctgcggg ctgccagagc tcatcaaagg acaggtcggc agcatccacc  10980
cccagcaaag cactcaagtt cccagtgcac ccaaggaagg cggtggggag cctggcaccc  11040
ggggagctgg cccgtggcac agagaatggg atgaagcccg ccaccccaa agccaaaccc  11100
ggccccagct cccagggcag tggaagccct cgcccggca ccaagacagg aggtggcagc  11160
cagccccagc cagccagcgg gcagctccag agcgagacag ccaccacccc agccaagccc  11220
agcttcccca gccggagccc tgcaccagag aggctccccg ctcgagccca agccaagagc  11280
tgcaccaagg ggccaaggga agctggtgag caggggcccc acgggagcct aggtcccaag  11340
gagaagggag agagcagtac gaagaggaaa aagggccagg tcccagggcc agccaggagt  11400
gaaagtgtgg ggagcttcgg gagagccccc tcagcccctg acaagccccc ccggacccct  11460
cggaagcagg caactcccag ccgcgtgctc ccgaccaagc ccaagcccaa cagccagaac  11520
aaacccaggc cgccaccatc agagcagcgg aaggcagagc cgggccacac acagaggaag  11580
gacagactgg gcaaggcctt cccccagggg agacccctgc tcaggccccc caagaggggc  11640
acagctgtcc acggtgctga acctgccgag ccacacaccc accggacggc cgaggcccag  11700
agtgacctcc tcagccagct cttcgggcag agactaactg gcttcaaaat ccctttaaag  11760
aaagatgctt ccgagtaatt tctaggagca agagcctggg accggagctg ggcgttcctg  11820
tctcggcctg cctccttggc cagctccggc tccctgagat ggtccactct gtggccactt  11880
gacttcttgt gcaactgctc aggccttgat gtcagagctg aggtggtgat gctttgaaca  11940
gggcccaggt gggcagcatt ccctttcttg ctggaaggct gggggtgaaa gacggggcca  12000
ctgcagccct tttgagacca cacagctgtt ttcttggtac caagtacttg aagagacagc  12060
agcccatccc ctcagcccac accctgcgc cctgtgggca ccgacaccac agaagccaat  12120
gtttggagat ttgcacaacc tcccgttccc ccacatggag aagggaagta agttgaggca  12180
gccgtgggat ggtggtaggt tccctcttag tcttgctgct gttgctggaa ttccaaagtg  12240
accttagaaa ccacgtgggg gaaggcagtg ctcactactt agaagggttg cttctgagcc  12300
gcctggtccc ccaagagcac aacaggcctc ctccctctga ccacagggtc atgcctcctc  12360
cctctgacca cagggtcatg ccagcctcca tttgctctgc gggagaaaag cccatctcta  12420
gcacaccttg accccaggaa ccgggttccc gtatggaact gggaagaaac cgcccctgtg  12480
ccagctcccg cgggccctcc tcgttccctc ccagcctcca tggccgccct ctagagcctc  12540
cctgctgtac ggagctctgg gctccgccta tttgcaatgt tactctgaag tttctggtgc  12600
tatttttgtg ttgtaatgtg aatacaggct tccttgattt tttttttaa tgggggtatt  12660
gggtgggaca gacggggtca gggaggcccc accatggctt gtcgagggca cgggcacctg  12720
catggcggcg ctctccctgc ctcccctgcc gggctgcaag cctgaggtct gtgctgccag  12780
acggggatgc tcagggctgg ggctgcagag ccgctgccct ggccagggca ccctcatgca  12840
ccgacccaac ccaggcctgg gacgcacgtg tcctctcaca gcgtcgtgcc tgtgaaggtg  12900
ggtcaaaggg tgagagggct tccttctcac ccttctctcc ataagtatct tgaagatcca  12960
tggtttgttt tgctctattg tttagttttt acttgggtgc aatgtgtacg tcaaaagttt  13020
ttattttgat atttgaaaga gaccaaatca ggcccagacc gcctctctgg aaggtgttgt  13080
```

-continued

```
aggccattca aaacgcctcc ggagtgtcgc aaaccaagtg cggaggggcc ctgaggttgt  13140

actgtaaaca tcatagtgac ttgtcttttc aaatatattc ccactatttt cgcagaaaac  13200

ctc                                                                13203
```

GENE-EXPRESSION BASED SUBTYPING OF PANCREATIC DUCTAL ADENOCARCINOMA

CROSS REFERENCE TO RELATED APPLICATIONS

This application is a United States National Stage Application filed under 35 U.S.C. § 371 of PCT International Patent Application Serial No. PCT/2015/055565, filed Oct. 14, 2015, which itself is based on and claims priority to U.S. Provisional Patent Application Ser. No. 62/063,719, filed Oct. 14, 2015, and United States of America Provisional Patent Application Ser. No. 62/201,793, filed Aug. 6, 2015. The disclosure of each of these applications is incorporated by reference herein in its entirety.

GOVERNMENT INTEREST

This invention was made with United States government support under Grant Nos. CA009156 and CA014024 awarded by National Institutes of Health of the United States. The United States government has certain rights in the invention.

REFERENCE TO SEQUENCE LISTING

The Sequence Listing associated with the instant disclosure has been electronically submitted to the United States Patent and Trademark Office as the Receiving Office as a 525 kilobyte ASCII text file created on Oct. 14, 2015 and entitled “421_357_PCT_US_ST25.txt”. The Sequence Listing submitted via EFS-Web is hereby incorporated by reference in its entirety.

TECHNICAL FIELD

The presently disclosed subject matter relates to compositions and methods for producing gene expression profiles for subjects that have or are suspected of having pancreatic cancer and employing the same to identify appropriate treatment approaches.

BACKGROUND

Pancreatic ductal adenocarcinoma (PDAC), comprising over 90% of all pancreatic cancers, remains a lethal disease with an estimated 232,000 new cases and an estimated 227,000 deaths per year worldwide in 2008 (Parkin et al., 2002; Boyle & Levin, 2008). Incremental improvements in the treatment of this cancer have been made in the last two decades, but the estimated five-year survival worldwide remains at less than 5% (Boyle & Levin, 2008).

Currently, the standard of care for the 20% of patients who are diagnosed with localized disease is surgery followed by chemotherapy with gemcitabine. Unfortunately, despite the use of adjuvant therapy, median survival remains at less than two years (Neuhaus et al., 2008), with only 12% of patients undergoing curative surgery surviving more than five years (Conlon et al., 1996; Ahmad et al., 2001; Cleary et al., 2004; Han et al., 2006; Winter et al., 2006; Ferrone et al., 2008; Schnelldorfer et al., 2008).

PDAC is thus characterized by a lack of effective targeted therapies, clinically useful biomarkers, and consensus subtypes. Therefore, understanding molecular mechanisms of disease underlying PDAC has the potential to facilitate the development of rationally designed therapies, and could assist in tailoring the use of the same to individual patients.

Interestingly, in large retrospective studies examining actual long-term (five- and ten-year) survivors (Conlon et al., 1996; Ahmad et al., 2001; Cleary et al., 2004; Han et al., 2006; Winter et al., 2006; Ferrone et al., 2008; Schnelldorfer et al., 2008), only two studies (Ahmad et al., 2001; Winter et al., 2006) have found that adjuvant therapy was associated with improved survival, suggesting that the benefits of adjuvant therapy are still controversial. In addition, gene sequencing of rare long-term survivors suggests that gene mutations in those tumors are no different than PDAC patients with more aggressive disease. One possible conclusion from these studies is that tumor biology in PDAC is more complex than gene mutations. Unfortunately, previous work using gene expression has been hampered by the low cellularity of malignant epithelium in PDAC patient samples. The low cellularity of PDAC poses a diagnostic dilemma as well in that biopsies of the tumor many times is non-diagnostic.

Despite these difficulties, defining subtypes of PDAC that would dictate the type whether it be tumor extirpation, chemotherapy or molecular and immunotherapy and timing of those therapies for patients would be beneficial. For PDAC in particular, better diagnostic tests independent of tumor cellularity would be beneficial. Achieving these goals is the ultimate goal of precision medicine.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides methods for generating a prognostic and/or subtype signature for a subject with pancreatic ductal adenocarcinoma (PDAC). In some embodiments, the methods comprise determining expression levels for one or more genes selected from the group consisting of those genes listed in Tables 2-5 in PDAC cells obtained from the subject, wherein the determining provides a prognostic and/or subtype signature for the subject. In some embodiments, the methods comprise determining expression levels for one or more genes listed in Table 1 as corresponding to the DE-S or DE-T subset in PDAC cells obtained from the subject, wherein the determining provides a prognostic and/or subtype signature and/or subtype identification that can be a diagnostic, prognostic, and/or treatment-determinative call for the subject. In some embodiments, the methods comprise determining expression levels for all of the genes listed in Tables 2-5 and/or for all of the genes listed in Table 1 as corresponding to the DE-S or DE-T subset in PDAC cells obtained from the subject.

In some embodiments, the methods further comprise comparing a first prognostic and/or subtype signature determined for the genes in Table 2 to a second prognostic and/or subtype signature for the genes in Table 3, wherein the comparing classifies the subject as having a PDAC subtype that is associated with either normal or activated stroma.

In some embodiments, the methods further comprise comparing a first prognostic and/or subtype signature determined for the genes in Table 4 to a second prognostic and/or subtype signature for the genes in Table 5, wherein the comparing classifies the subject as having a PDAC subtype that is a classical subtype or a basal subtype.

The presently disclosed subject matter also provides methods for classifying a subject diagnosed with pancreatic ductal adenocarcinoma (PDAC) as having an activated stroma subtype or a normal stroma subtype of PDAC. In some embodiments, the methods comprise (a) determining expression levels of the genes listed in Table 2 or an informative subset thereof and in Table 3 or an informative subset thereof in a biological sample comprising PDAC cells obtained from the PDAC of the subject; (b) creating an expression profile, wherein the expression profile encompasses expression levels of the genes listed in Table 23 or the informative subset thereof and the genes listed in Table 3 or the informative subset thereof; and (c) using the expression profiles created in the form of analysis of top scoring pairs of genes, wherein the analysis employs a trained logistic model in which binary input from discriminatory gene pairs are input and classification odds results are produced, whereby the subject is classified as having an activated stroma subtype or a normal stroma subtype of PDAC. In some embodiments, the method comprises comparing the expression profiles created to a standard, wherein the comparing employs a Bayesian classification reflecting a distance from (1) an activated stroma centroid that is high magnitude for all activated stroma genes and low magnitude for all normal stroma discriminatory genes; and (2) a normal stroma centroid that is high magnitude for all normal stroma genes and low magnitude for all activated stroma discriminatory genes. In some embodiments, the comparing determines whether the expression profile is closer to the activated stroma centroid or the normal stroma centroid, whereby the subject is classified as having an activated stroma subtype or a normal stroma subtype of PDAC. In some embodiments, the expression profiles comprise expression levels for each of the genes listed in Table 10, and the using comprises calculating a value d using EQUATION 2,

EQUATION 2

$$P_i = \begin{cases} 1 & \text{if } A_i > B_i \\ 0 & \text{if } B_i \geq A_i \end{cases}$$

$$d = I + \sum_i P_i C_i$$

$$\text{decision} = \begin{cases} \text{Activated Stroma} & \text{if } d > 0 \\ \text{Normal Stroma} & \text{if } d \leq 0 \end{cases}$$

wherein $A_i$ and $B_i$ are measured expression levels of each Gene A and each Gene B of Table 10 in the $i^{th}$ row, respectively, $C_i$ is the $i^{th}$ coefficient, and I is the intercept, and further wherein if d is greater than 0, the subject is classified as having an activated stroma subtype, and if d is less than or equal to 0, the subject is classified as having a normal stroma subtype of PDAC.

The presently disclosed subject matter also provides methods for classifying a subject diagnosed with pancreatic ductal adenocarcinoma (PDAC) as having a basal subtype or a classical subtype of PDAC. In some embodiments, the methods comprise (a) determining expression levels of the genes listed in Table 4 or an informative subset thereof and in Table 5 or an informative subset thereof in a biological sample comprising PDAC cells obtained from the PDAC of the subject; (b) creating an expression profile, wherein the expression profile encompasses expression levels of the genes listed in Table 4 or the informative subset thereof and the genes listed in Table 5 or the informative subset thereof; and (c) using the expression profiles created in the form of analysis of top scoring pairs of genes, wherein the analysis is composed of a trained logistic model in which binary input from discriminatory gene pairs are input and classification odds results are produced, whereby the subject is classified as having a basal subtype or a classical subtype of PDAC. In some embodiments, the method comprises (c) comparing the expression profiles created to a standard, wherein the comparing employs a Bayesian classification reflecting a distance from (1) a basal centroid that is high magnitude for all basal genes and low magnitude for all classical discriminatory genes; and (2) a classical centroid that is high magnitude for all classical genes and low magnitude for all basal discriminatory genes. In some embodiments, the comparing determines whether the expression profile is closer to the basal centroid or the classical centroid, whereby the subject is classified as having a basal subtype or a classical subtype of PDAC. In some embodiments, the expression profiles comprise expression levels for each of the genes listed in Table 11, and the using comprises calculating a value d using EQUATION 3,

EQUATION 3

$$P_i = \begin{cases} 1 & \text{if } A_i > B_i \\ 0 & \text{if } B_i \geq A_i \end{cases}$$

$$d = I + \sum_i P_i C_i$$

$$\text{decision} = \begin{cases} \text{Basal-like} & \text{if } d > 0 \\ \text{Classical} & \text{if } d \leq 0 \end{cases}$$

wherein $A_i$ and $B_i$ are measured expression levels of each Gene A and each Gene B of Table 11 in the $i^{th}$ row, respectively, $C_i$ is the $i^{th}$ coefficient, and I is the intercept, and further wherein if d is greater than 0, the subject is classified as having a basal-like subtype, and if d is less than or equal to 0, the subject is classified as having a classical subtype of PDAC.

In some embodiments, the presently disclosed subject matter also provides methods for identifying a differential treatment strategy for a subject diagnosed with pancreatic ductal adenocarcinoma (PDAC) and/or for diagnosing PDAC on low cellularity biopsies. In some embodiments, the methods comprise (a) determining the expression levels of the genes listed in Tables 2-5 in a biological sample comprising PDAC cells obtained from the PDAC of the subject; (b) creating an expression profile for the subject based on the expression levels of the genes listed in Tables 2-5; (c) classifying the subject as having an activated stroma subtype or a normal stroma subtype of PDAC, a basal subtype or a classical subtype of PDAC, or both; and (d) selecting a treatment strategy for the subject based on the classification of the subject as having an activated stroma subtype or a normal stroma subtype of PDAC, a basal subtype or a classical subtype of PDAC, an activated stroma/basal subtype of PDAC, a normal stroma/basal subtype of PDAC, an activated stroma/classical subtype of PDAC, or a normal stroma/classical subtype of PDAC, wherein a differential treatment strategy for the subject is identified. In some embodiments, the method further comprises (e) diagnosing PDAC on a patient with inadequate tumor cells by classifying the subject as having an activated stroma subtype or a normal stroma subtype of PDAC.

In some embodiments of the instantly disclosed methods where the genes to be assayed are those set forth in Tables 2-5, the genes referred to herein as DE-S and/or DE-T can be employed rather than those in Tables 2-5.

In some embodiments of the presently disclosed methods, the subject is a human.

It is thus an object of the presently disclosed subject matter to provide methods for predicting outcomes of subjects with pancreatic cancer.

An object of the presently disclosed subject matter having been stated hereinabove, and which is achieved in whole or in part by the presently disclosed subject matter, other objects will become evident as the description proceeds when taken in connection with the accompanying Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1A depicts liver metastases showing regions of tumor and normal tissue. FIG. 1B depicts a primary pancreatic tumor sample showing normal pancreatic tissue and tumor cells in the same field. FIG. 1C depicts a primary pancreatic tumor with high tumor cellularity. FIG. 1D depicts a primary pancreatic tumor with abundant tumor stroma. Black arrowheads show areas of tumor stroma. Black arrows show areas of tumor. White arrowheads show normal tissue. Scale bars, 200 μm.

FIG. 3A is a cartoon depicting the major cell types in primary tumor and liver metastasis samples. FIG. 3B (above) is an overlap of sample types (solid colors) with factor weights (grayscale heat maps), and (below) heat maps of five exemplar genes for all tumors and adjacent normal tissues. Gene expression shown in the heat map has been Z-normalized. FIG. 3C is a series of Box and Whiskers plots comparing NMF factor weights across tissue types and corresponding t-test result. FIG. 3D is a series of plots showing percent tumor cellularity versus NMF liver factor weight, and NMF basal tumor factor weight for metastases to the liver and adjacent liver samples. Linear regression lines are shown in red along with corresponding statistics.

FIG. 4A is a consensus clustered heat map of UNC primary tumor samples, metastases, and cell lines using genes from stromal factors. Samples clustered into 3 groups, describing samples with activated stroma, normal stroma, and samples with low or absent stromal gene expression. FIG. 4B is a Kaplan-Meier survival analysis of resected PDAC patients from the activated and normal stromal clusters shows that samples in the activated stroma group have worse prognosis, with a hazard ratio of 1.94 (CI=[1.11, 3.37], p=0.019). FIG. 4C shows gene expressions of various stromal signatures were overexpressed in cancer associated fibroblasts (CAFs) as compared to tumor cell lines. FIG. 4D is a series of plots showing that genes from both stromal signatures were specifically overexpressed by the mouse stroma in PDX tumors, and not expressed by the human tumor cells.

FIG. 7A is a consensus clustered heat map of primary tumors, metastatic tumors, and cell line models of PDAC using correlation as the underlying distance function shows two subtypes of PDAC FIG. 7B is a Kaplan-Meier survival analysis of resected primary patients from each tumor subtype (36 basal-like, 89 classical) in FIG. 7A shows differential prognosis among subtypes with a hazard ratio of 1.89, and a 95% CI of [1.19, 3.02]. FIG. 7C is a consensus clustered heat map of tumors in the ICGC PDAC cohort split by basal and classical factor gene expression into basal-like (n=56) and classical (n=47) tumors. FIG. 7D is a plot showing that basal-like tumors in the ICGC data set had a hazard ratio of 2.11, with a 95% CI of [1.14, 3.89]. Median follow up was 20 months. FIG. 7E is a consensus clustered heat map of The Cancer Genome Atlas (TCGA) Bladder cancer (BLCA) samples split by basal and classical factor gene expression into basal-like (n=128) and classical-like (n=95) tumors strongly agrees with BASE47 basal calls shown above the heat map. FIG. 7F shows subtyping in the TCGA BLCA data set had a hazard ratio of 1.43, with a 95% CI of [0.84, 2.42] FIG. 7G is a consensus clustered heat map of the Perou breast cancer data set as split by basal factor genes (n=72 basal-like, n=223 not basal) strongly agrees with the division of samples into previously published basal and non-basal subtypes. FIG. 7H shows that basal-like breast cancer, as defined by the presently disclosed subject matter, had a hazard ratio of 3.52, with a 95% CI of [1.94, 6.38].

FIG. 8D shows staining of T3M4 cells as a positive control for EpCAM. FIG. 8E shows staining of T3M4 cells as a negative control for vimentin, and FIG. 8F shows staining of T3M4 cells as a negative control for SMAα. Scale bars are 50 μm.

FIG. 10A is a consensus clustered heat map of normalized data from UNC and Collisson et al. using Collisson et al.'s gene sets. Primary tumors, normal pancreas, and cell lines are shown. Collisson samples were previously classified as exocrine-like (magenta or black), classical (cyan or dark grey), and quasimesenchymal (yellow or light gray). FIG. 10B is a Kaplan-Meier plots of UNC samples classified by PAM into Collisson et al.'s subtypes. FIG. 10C is a series of plots of mouse and human specific gene expression of the Collisson et al. gene lists in PDX shown in $log_2(1+RPKM)$. Classical genes are expressed by tumor cells, quasimesenchymal genes are expressed by a mix of human and mouse, while exocrine-like genes are lowly expressed throughout.

FIG. 11A is a heat map of tumor samples using 25 genes from each of the tumor and stromal factors, with samples sorted horizontally by classification. Signature scores for selected gene sets appear above for each sample. FIG. 11B is a combined Kaplan-Meier survival analysis of resected primary patients from basal-like or classical tumor types and normal or activated stroma subtypes with differential survival (p<0.001 log-rank test). Differential prognosis among subtypes shows complementarity. Classical tumors with normal stroma subtypes (n=24) had the lowest hazard ratio of 0.39, and a 95% CI of [0.21, 0.73], while basal-like tumors with activated stroma subtypes (n=26) had the highest hazard ratio of 2.28 with a 95% CI of [1.34, 3.87]. FIG. 11C is a Kaplan-Meir survival analysis showing that patients with classical subtype tumors show less response to adjuvant therapy (HR=0.76, 95% CI [0.40, 1.43]) compared to FIG. 11D is a plot showing basal-like tumors (HR of 0.38, and a 95% CI of [0.14, 1.09]). FIG. 11E is a Kaplan-Meir survival analysis showing that African-Americans have worse overall survival in both basal-like and classical subtypes, with a Hazard ratio of 2.28 and a 95% CI of [1.16,4.5].

FIG. 12A shows anti-mouse Collagen I staining of stroma in a representative PDX tumor. FIG. 12B is a corresponding H&E stain of the section adjacent to that shown in FIG. 12A. Anti-mouse Collagen I staining of mouse skin (FIG. 12C) and human skin (FIG. 12D) are also depicted. Black arrowheads show areas of tumor stroma. Black arrows show areas of tumor. Scale bars, 200 μm.

FIG. 13A is a series of plots of mouse and human specific gene expression of basal-like and classical subtype gene lists in 37 PDX tumors shown in $log_2(1+RPKM)$. Both gene sets were robustly expressed by the human (tumor) but not the mouse (stroma) cells in PDX samples. FIG. 13B is a consensus clustering of these PDX tumors using basal-like and classical gene lists divides samples into 2 groups.

FIG. 14A is a series of pie charts showing that tumor subtype was not associated with PDX graft success rate (p=0.417). FIG. 14B is a series of pie charts showing that activated stromal subtype samples engrafted with higher success rates than low or normal stromal subtype samples (p=0.019) FIG. 14C is a plot showing that basal-like tumor subtype PDX reached 200 $mm^3$ faster than classical subtype PDX (p=0.032). FIG. 14D is a plot showing that PDX from samples with activated stroma subtype or normal stroma subtype did not have significantly different times to reach 200 $mm^3$ (p=0.170). FIG. 14E is a plot showing that PDX tumors with faster growth rates were associated with earlier recurrences in patients (HR=0.31, 95% CI [0.10, 0.92]. FIG. 14F is a series of pie charts showing that KRAS mutation type was not uniformly distributed among race or subtype. KRAS G12D mutations were more prevalent in basal-like subtype tumors than classical tumors (p=0.030). FIG. 14G is a series of pie charts showing that African Americans had more G12V mutations, while Caucasians had more G12D mutations (p<0.001). FIG. 14H is a plot showing that SMAD4 staining in to primary tumors was predictive of successful PDX engraftment (p=0.044). FIG. 14I is a plot showing that basal-like subtype PDX exhibited weaker SMAD4 staining than classical subtype PDX (p=0.015).

FIG. 17A shows that the basal-like subtype showed downregulation of GATA6. FIG. 17B shows that the classical subtype tumors were enriched in genes associated with mucinous ovarian cancer. FIG. 17C shows that basal-like subtype tumors were enriched in genes related to KRAS activation and STK11 loss.

FIG. 18A is a series of pie charts showing that number of samples with low (<10%) compared to high (≥10%) extracelluar mucin content. Representative H&E stains of a sample with low degree (FIG. 18B) and high degree (FIG. 18C) of extracellular mucin content are also depicted. Scale bars are 200 μm.

FIG. 19A shows that sample-sample correlations of matched primary and metastatic tumors using the 50 most differentially expressed genes across all samples ("DE50") caused samples to group by organ location. FIG. 19B shows that sample-sample correlations using 25 genes each from classical and basal-like tumor lists ("T50") caused samples to cluster instead by tumor subtype and patient of origin. FIG. 19C is a plot showing that the correlation of samples within the same patient was higher when using T50 genes than when using DE50 genes. FIG. 19D is a plot showing that correlation of samples originating in the same organ was higher when using DE50 than when using T50. FIG. 19E shows clustering of multiple samples from two patients using the DE50 divides samples by organ. Genes expressed highly in lung and liver tissue are noted with brackets. FIG. 19F shows clustering of the same samples from (e) using T50 genes separates samples by patient. Brackets note genes which differentiate the two patients. FIG. 19G is an diagram of sampled locations for these patients indicated by concentric circles and illustrating how samples simultaneously exhibit both patient (inner color) and organ (outer color) specific gene expression.

BRIEF DESCRIPTION OF THE SEQUENCES

Figure 1A:
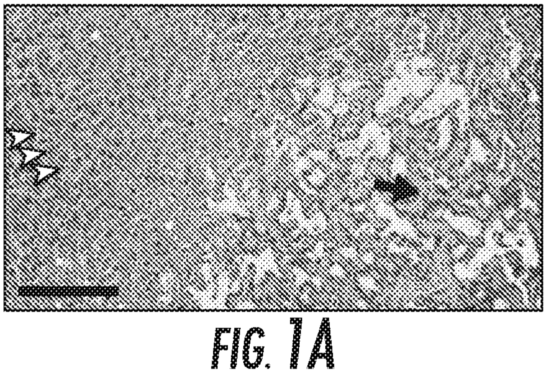
FIGS. 1A-1D are representative hematoxylin and eosin (H&E) staining of patient tumor samples.
Figure 1B:
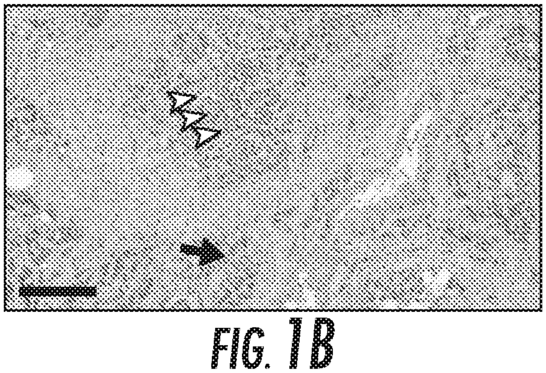
Figure 1C:
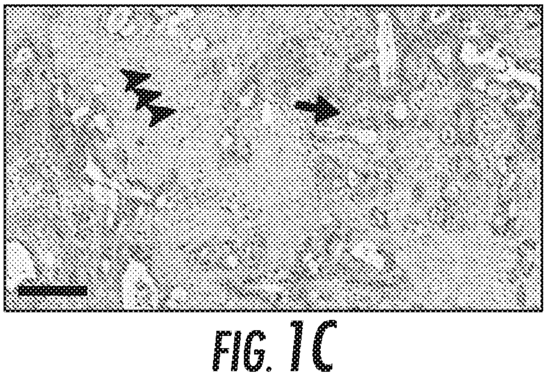
Figure 1D:
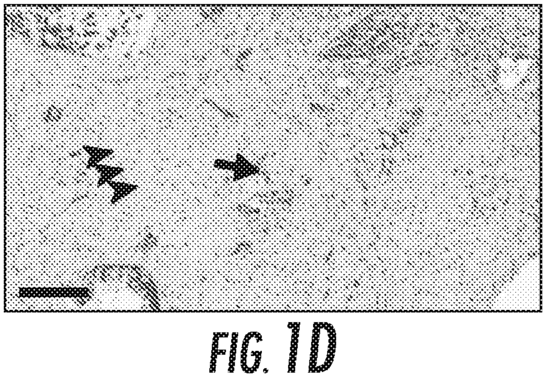
Figure 2:
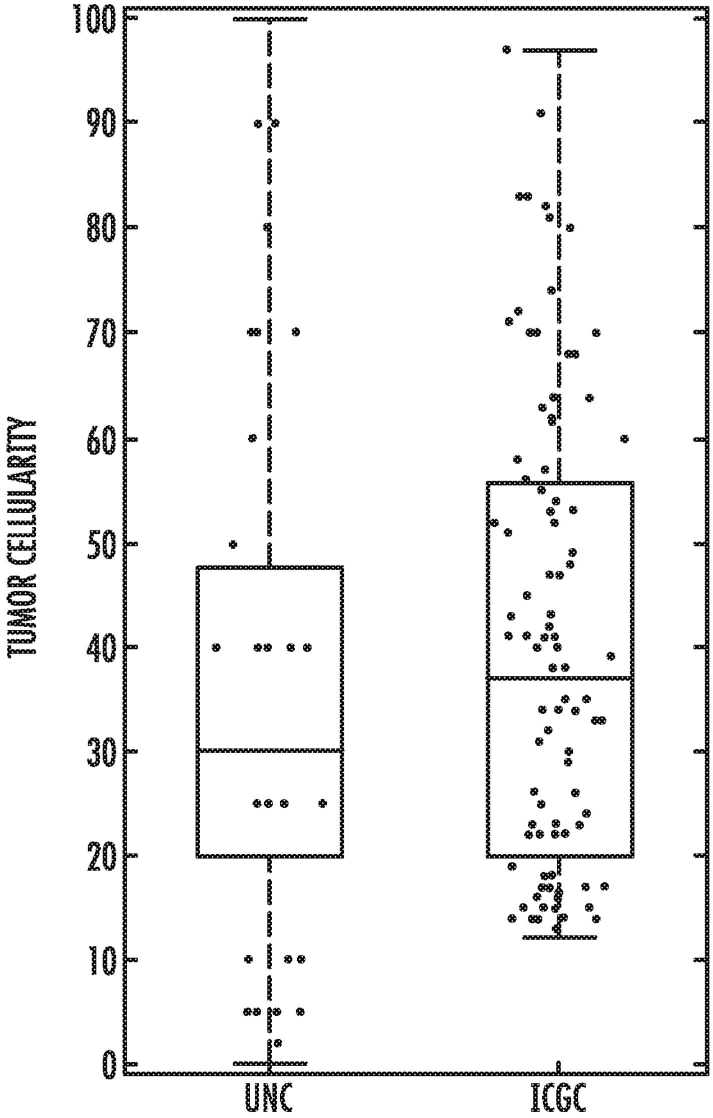
FIG. 2 depicts the percentage of tumor in primary pancreatic tumors in the UNC and International Cancer Genome Consortium (ICGC) cohorts.

The biosequences summarized in Table 1 are Accession Numbers for exemplary human nucleic acid sequences that are present in the GENBANK® biosequence database, the expression of which can be assayed in the practice of the presently disclosed methods. It is noted that the GENBANK® biosequence database Accession Numbers presented in Table 1 are exemplary only and that other nucleic acids including but not limited to other transcript variants that are also listed in the GENBANK® biosequence database under the corresponding Gene Names and/or that are derived from the listed loci can be employed for the analysis of subjects. Similarly, in the event that any of the sequences set forth in Table 1 are updated in the GENBANK® biosequence database, the updated sequences are also understood to be encompassed by the presently disclosed subject matter.

TABLE 1

Listing of GENBANK ® Accession Numbers for Nucleic Acid Sequences of Exemplary Human Gene Products

| Gene Symbol | GENBANK ® Accession No. | SEQ ID No. |
|---|---|---|
| ABCA8$^N$ | NM_001288985.1 | 1 |
| ACTG2$^N$ | NM_001615.3 | 2 |
| ADAMTS1$^N$ | NM_006988.3 | 3 |
| AGR2$^C$ | NM_006408.3 | 4 |
| AGR3$^C$ | NM_176813.3 | 5 |
| ANGPTL7$^N$ | NM_021146.3 | 6 |
| ANXA8L2$^B$ | NM_001098845.2 | 7 |
| ANXA10$^C$ | NM_007193.4 | 8 |
| AREG$^B$ | NM_001657.3 | 9 |
| ATAD4$^C$ | NM_024320.3 | 10 |
| ATP10B | NM_025153.2 | 11 |
| B3GNT5 | NM_032047.4 | 12 |
| BCAS1 | NM_003657.2 | 13 |
| BTNL8$^C$ | NM_024850.2 | 14 |
| C2ORF40$^N$ | NM_032411.2 | 15 |
| C10ORF116$^N$ | NM_006829.2 | 16 |
| C16orf74 | NM_206967.2 | 17 |
| CAPN9 | NM_006615.2 | 18 |
| CD109 | NM_133493.4 | 19 |
| CDH11$^A$ | NM_001797.2 | 20 |
| CDH17$^C$ | NM_004063.3 | 21 |
| CDH19$^N$ | NM_021153.3 | 22 |
| CEACAM6$^C$ | NM_002483.6 | 23 |
| CHST6 | NM_021615.4 | 24 |
| CLRN3$^C$ | NM_152311.3 | 25 |
| COL1A1$^A$ | NM_000088.3 | 26 |
| COL1A2$^A$ | NM_000089.3 | 27 |
| COL3A1$^A$ | NM_000090.3 | 28 |
| COL5A1$^A$ | NM_000093.4 | 29 |
| COL5A2$^A$ | NM_000393.3 | 30 |
| COL10A1$^A$ | NM_000493.3 | 31 |
| COL11A1$^A$ | NM_001854.3 | 32 |
| COMP$^A$ | NM_000095.2 | 33 |
| CST6$^B$ | NM_001323.3 | 34 |
| CTHRC1$^A$ | NM_138455.3 | 35 |
| CTSE$^C$ | NM_001910.3 | 36 |
| CTSL2$^B$ | NM_001333.3 | 37 |

TABLE 1-continued

Listing of GENBANK ® Accession Numbers for Nucleic Acid Sequences of Exemplary Human Gene Products

| Gene Symbol | GENBANK ® Accession No. | SEQ ID No. |
|---|---|---|
| CYP3A7$^C$ | NM_000765.4 | 38 |
| DCBLD2 | NM_080927.3 | 39 |
| DDC | NM_001082971.1 | 40 |
| DES$^N$ | NM_001927.3 | 41 |
| DHRS9$^B$ | NM_199204.1 | 42 |
| FABP4$^N$ | NM_001442.2 | 43 |
| FAM3D$^C$ | NM_138805.2 | 44 |
| FAM83A$^B$ | NM_032899.5 | 45 |
| FAP$^A$ | NM_004460.3 | 46 |
| FGFBP1$^B$ | NM_005130.4 | 47 |
| FN1$^A$ | NM_212482.1 | 48 |
| FNDC1$^A$ | NM_032532.2 | 49 |
| GPM6B$^N$ | NM_001001995.1 | 50 |
| GPR87$^B$ | NM_023915.3 | 51 |
| GPR160 | NM_014373.2 | 52 |
| GREM1$^A$ | NM_013372.6 | 53 |
| HPGD | NM_000860.5 | 54 |
| ID4$^N$ | NM_001546.3 | 55 |
| IGF1$^N$ | NM_001111283.1 | 56 |
| IL20RB | NM_144717.3 | 57 |
| INHBA$^A$ | NM_002192.2 | 58 |
| ITGA11$^A$ | NM_001004439.1 | 59 |
| KCNE3 | NM_005472.4 | 60 |
| KRT6A$^B$ | NM_005554.3 | 61 |
| KRT6C$^B$ | NM_173086.4 | 62 |
| KRT7$^B$ | NM_005556.3 | 63 |
| KRT15$^B$ | NM_002275.3 | 64 |
| KRT16 | NM_005557.3 | 65 |
| KRT17$^B$ | NM_000422.2 | 66 |
| KRT20$^C$ | NM_019010.2 | 67 |
| LEMD1$^B$ | NM_001199050.1 | 68 |
| LGALS4$^C$ | NM_006149.3 | 69 |
| LMOD1$^N$ | NM_012134.2 | 70 |
| LOC400573$^C$ | BC063383 | 71 |
| LPHN3$^N$ | NM_015236.4 | 72 |
| LUM$^A$ | NM_002345.3 | 73 |
| LY6D$^B$ | NM_003695.2 | 74 |
| LYZ$^C$ | NM_000239.2 | 75 |
| MEOX2$^N$ | NM_005924.4 | 76 |
| MET | NM_001127500.1 | 77 |
| MMP11$^A$ | NM_005940.3 | 78 |
| MS4A8B | NM_031457.1 | 79 |
| MSLN | NM_005823.5 | 80 |
| MYH11$^N$ | NM_002474.2 | 81 |
| MYO1A$^C$ | NM_001256041.1 | 82 |
| NAB1 | NM_005966.3 | 83 |
| OGN$^N$ | NM_033014.2 | 84 |
| PLA2G10$^C$ | NM_003561.1 | 85 |
| PLEKHA6 | NM_014935.4 | 86 |
| PLP1$^N$ | NM_000533.3 | 87 |
| PLS1 | NM_001145319.1 | 88 |
| POSTN$^A$ | NM_006475.2 | 89 |
| PPP1R14C | NM_030949.2 | 90 |
| PTGES | NM_004878.4 | 91 |
| PTX3$^N$ | NM_002852.3 | 92 |
| RBPMS2$^N$ | NM_194272.1 | 93 |
| REG4$^C$ | NM_001159352.1 | 94 |
| RERGL$^N$ | NM_024730.3 | 95 |
| RSPO3$^N$ | NM_032784.4 | 96 |
| S100A2$^B$ | NM_005978.3 | 97 |
| SCEL$^B$ | NM_144777.2 | 98 |
| SCRG1$^N$ | NM_007281.2 | 99 |
| SERPINB3$^B$ | NM_006919.2 | 100 |
| SERPINB4$^B$ | NM_002974.3 | 101 |
| SERPINB5 | NM_002639.4 | 102 |
| SFRP2$^A$ | NM_003013.2 | 103 |
| SLC2A1$^B$ | NM_006516.2 | 104 |
| SLC44A4 | NM_025257.2 | 105 |
| SPARC$^A$ | NM_003118.3 | 106 |
| SPINK4$^C$ | NM_014471.1 | 107 |
| SPRR1B$^B$ | NM_003125.2 | 108 |
| SPRR3$^B$ | NM_005416.2 | 109 |
| ST6GALNAC1$^C$ | NM_018414.4 | 110 |

TABLE 1-continued

Listing of GENBANK ® Accession Numbers for Nucleic Acid Sequences of Exemplary Human Gene Products

| Gene Symbol | GENBANK ® Accession No. | SEQ ID No. |
|---|---|---|
| SULF1[A] | NM_001128205.1 | 111 |
| SYNM[N] | NM_145728.2 | 112 |
| SYTL2 | NM_001289610.1 | 113 |
| TFF1[C] | NM_003225.2 | 114 |
| TFF2[C] | NM_005423.4 | 115 |
| TFF3[C] | NM_003226.3 | 116 |
| THBS2[A] | NM_003247.3 | 117 |
| TMEM45B | NM_138788.3 | 118 |
| TNS4[B] | NM_032865.5 | 119 |
| TSPAN8[C] | NM_001168412.1 | 120 |
| UCA1[B] | EU334869.1 | 121 |
| VCAN[A] | NM_004385.4 | 122 |
| VGLL1[B] | NM_016267.3 | 123 |
| VIT[N] | NM_053276.3 | 124 |
| VSIG2[C] | NM_014312.3 | 125 |
| ZNF469[A] | NM_001127464.1 | 126 |

[A]Member of the DE-S stromal subtype differentiation gene subset that is associated with the Activated stroma subtype
[B]Member of the DE-T tumor subtype differentiation gene subset that is associated with the Basal tumor subtype
[C]Member of the DE-T tumor subtype differentiation gene subset that is associated with the Classical tumor subtype
[N]Member of the DE-S stromal subtype differentiation gene subset that is associated with the Normal stroma subtype All of the nucleic acid sequences that correspond to the gene names listed in Table 1 and throughout the instant disclosure, including the corresponding GENBANK® biosequence database Accession Numbers, all annotations and references cited in the corresponding GENBANK® biosequence database entries, and all other nucleic acid sequences that correspond to the listed genetic loci that are present in the GENBANK® biosequence database and related annotations and references, are incorporated herein by reference in their entireties.

DETAILED DESCRIPTION

The present subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

I. General Considerations

Pancreatic ductal adenocarcinoma (PDAC) remains a lethal disease with a 5-year survival of 4%. Roughly half of PDAC patients present with metastases at the time of diagnosis, and metastatic disease remains the primary cause of mortality in patients. In this study, we set out to identify subtypes among PDAC patients, with a focus on understanding factors which contribute to patient outcome. A key hallmark of PDAC is the presence of extensive stromal and immune involvement, as well as the presence of endocrine, exocrine, and normal ductal pancreas cells. Additionally, metastatic samples often include cell types from the host organ. Thus, PDAC tumors are in fact complex mixtures in which malignant epithelial cells often represent only a minority of the bulk tumor. For this reason, normal and PDAC tissues often cluster separately from cell lines which are assumed to be purely neoplastic (Iacobuzio-Donahue et al., 2003).

Separating molecular signatures of tissue compartments from measurement of bulk tumor belongs to the general class of problems called blind source separation. Previous studies have used samples of chronic pancreatitis to control for the presence of desmoplastic stroma in tumor samples (Logsdon et al., 2003). In prostate cancer, Stuart et al. have used pathologist assessments of cell types to train models of gene expression signatures of tumor, stroma, and normal tissue (Stuart et al., 2004). In a follow up study, they used their learned gene lists for in silico estimation of tissue components in a larger set of data (Wang et al., 2010). A similar approach has also been used to quantify stromal content across multiple TCGA data sets (Yoshihara et al., 2013). Among source separation techniques, nonnegative matrix factorization (NMF) is especially well suited for biological data, because it constrains all sources to be positive in nature, reflecting the goal of identifying positive gene expression exemplars, rather than pairwise differences between tissue types. Alexandrov et al. have recently demonstrated that NMF is useful for a similar problem of identifying mutational signatures from the aggregate list of somatic mutations in human cancer samples (Alexandrov et al., 2013a,b).

As disclosed herein, NMF was applied to a large microarray data set of primary and metastatic samples of PDAC to evaluate tumor and stroma specific gene expression signatures. Briefly, NMF was defined as modeling the matrix X of expression for g genes and s samples, as the product of a matrix G of g gene weights for k factors and a matrix S of s sample weights for k factors. By looking at samples with mixed tumor and stroma cellularity, two tumor subtypes have been identified that were validated in multiple data sets, as well as important contributions from normal, immune, and stromal compartments.

II. Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a," "an," and "the" mean "one or more" when used in this application, including the claims. Thus, the phrase "a cell" refers to one or more cells, unless the context clearly indicates otherwise.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising," which is synonymous with "including," "containing," and "characterized by," is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, the presently disclosed subject matter in some embodiments can "consist essentially of" determining expression levels for one or more genes listed in Table 1 in PDAC cells present in a sample (e.g., a biopsy) obtained from a subject, which means that the recited gene(s) is/are the only genes for which an expression level or expression levels are determined. It is noted, however, that expression levels for various positive and/or negative control genes can also be determined, for example, to standardize and/or normalize the expression levels in PDAC cells of the genes employed, if desired, and still be within the scope of the phrase consist essentially of determining expression levels for one or more genes listed in Table 1.

With respect to the terms "comprising," "consisting essentially of," and "consisting of," where one of these three terms is used herein, the presently disclosed and claimed subject matter can include the use of either of the other two terms. For example, it is understood that the methods of the presently disclosed subject matter in some embodiments comprise the steps that are disclosed herein and/or that are recited in the claims, in some embodiments consist essentially of the steps that are disclosed herein and/or that are recited in the claims, and in some embodiments consist of the steps that are disclosed herein and/or that are recited in the claim.

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), Amphibia (amphibians), Reptilia (reptiles), Ayes (birds), and Mammalia (mammals)), and all Orders and Families encompassed therein. In some embodiments, the presently disclosed subject matter relates to human subjects.

Similarly, all genes, gene names, and gene products disclosed herein are intended to correspond to orthologs from any species for which the compositions and methods disclosed herein are applicable. Thus, the terms include, but are not limited to genes and gene products from humans. It is understood that when a gene or gene product from a particular species is disclosed, this disclosure is intended to be exemplary only, and is not to be interpreted as a limitation unless the context in which it appears clearly indicates. Thus, for example, the genes and/or gene products disclosed herein are also intended to encompass homologous genes and gene products from other animals including, but not limited to other mammals, fish, amphibians, reptiles, and birds.

The methods and compositions of the presently disclosed subject matter are particularly useful for warm-blooded vertebrates. Thus, the presently disclosed subject matter concerns mammals and birds. More particularly provided is the use of the methods and compositions of the presently disclosed subject matter on mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the application of the methods and compositions of the presently disclosed subject matter to livestock, including but not limited to domesticated swine (pigs and hogs), ruminants, horses, poultry, and the like.

The term "about," as used herein when referring to a measurable value such as an amount of weight, time, dose, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods and/or to employ the presently disclosed arrays.

As used herein the term "gene" refers to a hereditary unit including a sequence of DNA that occupies a specific location on a chromosome and that contains the genetic instruction for a particular characteristic or trait in an organism. Similarly, the phrase "gene product" refers to biological molecules that are the transcription and/or translation products of genes. Exemplary gene products include, but are not limited to mRNAs and polypeptides that result from translation of mRNAs. Any of these naturally occurring gene products can also be manipulated in vivo or in vitro using well known techniques, and the manipulated derivatives can also be gene products. For example, a cDNA is an enzymatically produced derivative of an RNA molecule (e.g., an mRNA), and a cDNA is considered a gene product. Additionally, polypeptide translation products of mRNAs can be enzymatically fragmented using techniques well known to those of skill in the art, and these peptide fragments are also considered gene products.

It is understood that while exemplary nucleotide sequences for the human orthologs of the genes listed in Table 1 are disclosed herein, orthologs of these genes from other species are also included within the presently disclosed subject matter.

The term "isolated," as used in the context of a nucleic acid or polypeptide (including, for example, a nucleotide sequence, a polypeptide, and/or a peptide), indicates that the nucleic acid or polypeptide exists apart from its native environment. An isolated nucleic acid or polypeptide can exist in a purified form or can exist in a non-native environment.

Further, as used for example in the context of a cell, nucleic acid, polypeptide, or peptide, the term "isolated" indicates that the cell, nucleic acid, polypeptide, or peptide exists apart from its native environment. In some embodiments, "isolated" refers to a physical isolation, meaning that the cell, nucleic acid, polypeptide, or peptide has been removed from its native environment (e.g., from a subject).

The terms "nucleic acid molecule" and "nucleic acid" refer to deoxyribonucleotides, ribonucleotides, and polymers thereof, in single-stranded or double-stranded form.

Unless specifically limited, the term encompasses nucleic acids containing known analogues of natural nucleotides that have similar properties as the reference natural nucleic acid. The terms “nucleic acid molecule” and “nucleic acid” can also be used in place of “gene,” “cDNA,” and “mRNA.” Nucleic acids can be synthesized, or can be derived from any biological source, including any organism.

As used herein, the terms “peptide” and “polypeptide” refer to polymers of at least two amino acids linked by peptide bonds. Typically, “peptides” are shorter than “polypeptides,” but unless the context specifically requires, these terms are used interchangeably herein.

As used herein, a cell, nucleic acid, or peptide exists in a “purified form” when it has been isolated away from some, most, or all components that are present in its native environment, but also when the proportion of that cell, nucleic acid, or peptide in a preparation is greater than would be found in its native environment. As such, “purified” can refer to cells, nucleic acids, and peptides that are free of all components with which they are naturally found in a subject, or are free from just a proportion thereof.

III. Methods for Generating Prognostic and/or Subtype Signatures

In some embodiments, the presently disclosed subject matter provides methods for generating prognostic and/or subtype signatures for a subject with cancer (e.g., pancreatic ductal adenocarcinoma (PDAC)). As used herein, the phrase “prognostic and/or subtype signature” refers to a gene expression profile comprising gene expression levels for one or more of the genes disclosed in Table 1 in PDAC cells obtained from the subject, wherein the determining provides a prognostic and/or subtype signature for the subject. In some embodiments, a gene expression profile of the presently disclosed subject matter can comprise gene expression levels for one, five, ten, 25, 50, or 100 of more of the genes listed in Tables 2-5. In some embodiments, a gene expression profile of the presently disclosed subject matter can comprise gene expression levels for all of the genes listed in Tables 2-5.

As disclosed herein, such gene expression profiles can be predictive of various clinical outcomes, for example, by comparing to appropriate standards.

In some embodiments, methods for generating prognostic and/or subtype signatures further comprise comparing the derived prognostic and/or subtype signatures to one or more standards. As used herein, the term “standard” refers to an entity to which another entity (e.g., a prognostic and/or subtype signature) can be compared such that the comparison provides information of interest. An exemplary standard that is described herein is a test set. Additional discussion of standards can be found herein below. Such a comparison can be carried out on an apparatus, such as a system comprising a suitably programmed computer.

Thus, a profile can be created once an expression level is determined for a gene. As used herein, the term “profile” (e.g., a “gene expression profile”) refers to a repository of the expression level data that can be used to compare the expression levels of one or more genes, such as but not limited to one or more different genes among various subjects. For example, for a given subject, the term “profile” can encompass the expression levels of one or more of the genes disclosed herein detected in whatever units are chosen.

The term “profile” is also intended to encompass manipulations of the expression level data derived from a subject. For example, once relative expression levels are determined for a given set of genes in a subject, the relative expression levels for that subject can be compared to a standard to determine if the expression levels in that subject are higher or lower than for the same genes in the standard. Standards can include any data deemed to be relevant for comparison. Such a comparison can be carried out on an apparatus, such as a system comprising a suitably programmed computer. In some embodiments, an expression profile with respect to a plurality of the genes listed in Table 1 is presented such that a subject can be assigned into one particular treatment category (i.e., normal vs. activated stroma or classical vs. basal subtypes) based on the expression profile.

IV. Methods for Selecting a Treatment

The presently disclosed subject matter also provides methods for selecting a treatment for a subject diagnosed with pancreatic ductal adenocarcinoma (PDAC). In some embodiments, the methods comprise assigning the subject into a classification based on an analysis of a gene expression profile with respect to one or more of the genes listed in Table 1, wherein the analysis classifies the subject as having a tumor that corresponds to either a normal vs. an activated stroma subtype, or alternatively a classical vs. basal subtype.

In some embodiments a method for selecting a treatment comprises classifying a patient as being in a normal vs. an activated stroma subtype or a classical vs. basal subtype using one or more of Algorithms A-C described herein below.

IV.A. Overview of Exemplary Diagnostic Algorithms

The presently disclosed subject matter provides in some embodiments algorithms that can be employed for classifying PDAC subtypes in patient samples. In some embodiments, a to particular algorithm is selected based on whether or not cytopathological assessment of the sample provides a reasonable basis for an initial diagnosis, and if so, whether the presence of metastatic disease is suggested thereby.

IV.A.1. Algorithm A: Diagnosing Pancreatic Cancer from a Non-Diagnostic Specimen on Traditional Cytopathology Low tumor cellularity and high stroma content has long hampered the ability to diagnose pancreatic cancer on biopsies. According to pathology assessments, stroma comprises on average 39% of the primary tumor samples examined. At least 8% of endoscopic ultrasound biopsies are non-diagnostic (Gress et al., 2001). Biopsy results can alter the decision to proceed with surgery, which involves an operation that has an attendant postoperative complication and hospital readmission rates of 59% and mortality of 6% (DeOliveira et al., 2006; Eppsteiner et al., 2009; Yermilov et al., 2009). Therefore, clarity of biopsy results can be a key factor for correctly diagnosing patients and for assisting their physicians in determining appropriate treatment strategies.

The stroma subtypes disclosed herein have the potential to overcome the cellularity problem and provides a much needed diagnostic tool that leverages the most abundant component of tumor biopsies of pancreatic cancer. An example of the decision making process based on the genomic subtypes disclosed herein is described herein.

IV.A.2. Algorithm B: Diagnostic Specimen on Traditional Cytopathology or Diagnosis after Application of Algorithm A—Determining Tumor Subtype in the Non-Metastatic Setting Despite curative operations, pancreatic cancer patients who have had their tumors fully resected only have a median survival of 23 months (Neuhaus et al., 2008). The majority of patients relapse with metastatic disease.

Thus, there has been much interest in using systemic therapies preoperatively in an attempt to treat micrometastatic disease that might be present at the time of surgery (i.e., neoadjuvant approaches). The tumor and stroma subtypes disclosed herein are independently prognostic and diagnostic, and can add value to prognosticating the outcome of patients. Algorithm B provides an exemplary treatment approach based on findings of specific subtype mixtures with classical/normal being the best and basal/activated the worst.

IV.A.3. Algorithm C: Determining Tumor Subtype in the Metastatic Setting

Recent studies have shown two promising chemotherapeutic regimens for patients with metastatic pancreatic cancer (Louvet et al., 2005; Conroy et al., 2011). However, promising targeted therapies have been lacking. Algorithm C provides an exemplary treatment approach dependent on subtype identified using the methods and compositions disclosed herein.

IV.B. Determination of Subtypes

Patient samples can be profiled for mRNA expression by any method that provides for an analysis of quantitative gene expression. Non-limiting examples of such techniques include whole transcriptome RNAseq, targeted RNAseq, SAGE, RT-PCR (particularly QRT-PCR), and cDNA microarray analyses. With respect to the presently disclosed methods, gene expression from the following lists are measured: (1) the four "core" expression lists for each of the four subtypes, which describe genes which are overexpressed in each subtype; and (2) the four "differential" expression lists, which define genes which are uniquely expressed in each subtype. Genes from the core lists are not mutually exclusive, as there are genes which are expressed by both tumor subtypes, and could be relevant targets for treatment in both groups. Genes from the core lists are used to select from among appropriate therapeutic targets for a particular subtype. Genes from differential lists are, by design, mutually exclusive and represent the most discriminatory biomarkers for subtype diagnosis. For classification purposes, the union of tumor subtype differential genes are referred to herein as "DE-T" (see Table 1), and the union of stromal subtype differentiation genes are referred to herein as "DE-S" (see Table 1).

Two classifiers, (one using DE-T, and one using DE-S), are used to classify new samples using a Bayesian framework that allows for incorporation of a priori evidence such as population prevalence, and allows for the assessment of confidence in each decision (Duda et al., 2012). For example, DE-S gene expression from an unknown sample is compared to the DE-S gene expression of each of two template centroids representing the two stromal subtypes. Or, for example, DE-T gene expression is assessed with a top-scoring-pairs logistic regression model to estimate probability of class membership. Samples are classified as the subtype with which they exhibit the highest degree of likelihood as formalized by maximum a posteriori probability and associated confidence level. Thus, each sample has both a stroma and a tumor classification type with associated confidences for clinical use.

Alternatively or in addition, the gene pairs disclosed in Tables 9-11 below can be employed for determining tumor and stromal subtypes in cancers including, but not limited to the breast, bladder, or pancreas. For example, cancers in these tissues can be identified as being basal-like or not basal-like using the gene pairs disclosed in Table 9 below. To classify each sample, gene expression from pairs of genes in Table 9 below can be compared such that for each gene pair, if Gene A expression is greater than Gene B expression, the coefficient for that gene pair was added to a running sum. If the sum of all such coefficients and the intercept from Table 9 below is greater than zero, the sample is classified as basal (see EQUATION 1).

Using the gene pairs in Table 9 below for breast, bladder, or pancreas, if $A_i$ and $B_i$ are the measured expression of Genes A and B of Table 9 in the $i^{th}$ row, $C_i$ is the $i^{th}$ coefficient, and I is the intercept, then a decision can be calculated as follows:

EQUATION 1

$$P_i = \begin{cases} 1 & \text{if } A_i > B_i \\ 0 & \text{if } B_i \geq A_i \end{cases}$$

$$d = I + \sum_i P_i C_i$$

$$\text{decision} = \begin{cases} \text{Basal} & \text{if } d > 0 \\ \text{Not Basal} & \text{if } d \leq 0 \end{cases}$$

More particularly in the case of cancer of the pancreas, the gene pairs listed in Table 10 below can be employed for classifying a pancreas tumor as being of the activated stroma subtype or the normal stroma subtype. Using Table 10 below, if $A_i$ and $B_i$ are the measured expression of Genes A and B of Table 10 in the $i^{th}$ row, $C_i$ is the $i^{th}$ coefficient, and I is the intercept, then a decision can be calculated as in EQUATION 2:

EQUATION 2

$$P_i = \begin{cases} 1 & \text{if } A_i > B_i \\ 0 & \text{if } B_i \geq A_i \end{cases}$$

$$d = I + \sum_i P_i C_i$$

$$\text{decision} = \begin{cases} \text{Activated Stroma} & \text{if } d > 0 \\ \text{Normal Stroma} & \text{if } d \leq 0 \end{cases}$$

Also more particularly in the case of cancer of the pancreas, the gene pairs listed in Table 11 below can be employed for classifying a pancreas tumor as being of the basal subtype or the classical subtype. Using Table 11 below, if $A_i$ and $B_i$ are the measured expression of Genes A and B of Table 11 in the $i^{th}$ row, $C_i$ is the $i^{th}$ coefficient, and I is the intercept, then a decision can be calculated as in EQUATION 3:

EQUATION 3

$$P_i = \begin{cases} 1 & \text{if } A_i > B_i \\ 0 & \text{if } B_i \geq A_i \end{cases}$$

$$d = I + \sum_i P_i C_i$$

$$\text{decision} = \begin{cases} \text{Basal-like} & \text{if } d > 0 \\ \text{Classical} & \text{if } d \leq 0 \end{cases}$$

IV.C. Determination of Subtype-Specific Treatment Strategies

Many of the genes that are descriptive for each subtype have yet to have an available drug. However, the majority are targetable and as drugs become available, and thus are expected to guide therapeutic decisions in the future.

At the current time, treatment of pancreatic cancer is limited to three regimens: gemcitabine, gemcitabine in combination with nab-paclitaxel (Von Hoff et al., 2013), and treatment with FOLFIRINOX (composed of folinic acid (leucovorin), fluorouracil, irinotecan, and oxaliplatin; Conroy et al., 2011). In those patients with non-metastatic disease, the subset of patients classified as classical/normal are offered surgery as the first stage of therapy. In those patients classified as classical/activated, the basal/activated subset and the basal/normal subset are offered chemotherapy (FOLFIRINOX or gemcitabine+nab-paclitaxel, dependent on oncologist and patient preference and patient tolerance) prior to surgery as outcome in patients with basal subtypes after surgery is poor, with 50% of patients relapsing and dying about 1 year after the surgery that had been intended to cure the disease. As therapies in trial become available, all patients with activated subtypes will be offered stroma modulating therapies (see examples described herein below) prior to surgery. In some embodiments, patients with basal subtypes derive greater benefit from chemotherapy after surgery as described herein.

For those patients with metastatic disease, the classical/normal subset of patients can proceed with currently available chemotherapies. For the subset of patients with other subtypes, therapies are tailored as described in more detail herein below. In some embodiments, different subtypes respond to different therapies, so as newer therapies develop the selected strategies can be altered.

Drug regimens can be further tailored by tumor and/or stroma subtype as drugs currently in early phase clinical trials become available. For instance, patients with activated stroma subtypes could benefit from extracellular matrix-associated therapies such as hyaluronidase treatment (currently in clinical trials) and/or collagenase treatment in combination with other therapies.

Patients with normal subtype tumors might not benefit from similar stroma-modulating agents, which conversely could be harmful. Rather, such patients' disease could be sensitive to anti-PDGFRB—or anti-TEK-directed therapy.

Patients with the basal subtype might benefit from AGS-14CD4, crizotinib, or erlotinib, or other kinase inhibitors that have anti-MET activity. Patients with classical subtypes might benefit from varespladib, cobicistat, traztuzumab, or other kinase inhibitors with anti-ERBB2 or anti-EGFR activity.

Finally, Table 6 shows a list of kinases that can be considered as therapeutic targets for patients with classical and basal subtype tumors.

Tables 2-5 list the genes that define each subtype and the currently known drugs and/or combination(s) of drugs that can be used based on the overall subtype. The gene lists in Tables 2-5 are descriptive for each subtype and are relevant to designing treatment regimens for each subtype, but are not necessarily mutually exclusive as multiple treatment possibilities can be considered for each subtype. For diagnostic purposes, subsets of these genes, which are unique to each subtype, were used (see DE-S and DE-T above).

Regardless of whether specific drugs have been effective in pancreatic cancer, the results disclosed herein suggested that pancreatic cancer is not one singular disease, and unless specific therapies are appropriately tailored, individual patients are unlikely to benefit from the current one size fits all approach to treatment. The findings disclosed herein can thus be used to personalize therapies to individual patients by reference to their tumor and/or stroma subtype.

V. Methods of Gene Expression/Transcriptome Analysis

V.A. Assay Formats

The genes identified as being differentially expressed in, for example, normal subtype vs. activated stroma subtype PDAC, or alternatively classical subtype vs. basal subtype PDAC, can be used in a variety of nucleic acid detection assays to detect and/or quantitate the expression level of a gene or multiple genes in a given sample. For example, Northern blotting, nuclease protection, RT-PCR (e.g., quantitative RT-PCR; QRT-PCR), and/or differential display methods can be used for detecting gene expression levels. In some embodiments, methods and assays of the presently disclosed subject matter are employed with array or chip hybridization-based methods and systems for detecting the expression of a plurality of genes. However, it is noted that any nucleotide analysis method can be employed with the presently disclosed subject matter, including in some embodiments RNA sequencing and transcriptome analysis.

Any hybridization assay format can be used, including solution-based and solid support-based assay formats. Representative solid supports containing oligonucleotide probes for differentially expressed genes of the presently disclosed subject matter can be filters, polyvinyl chloride dishes, silicon, glass based chips, etc. Such wafers and hybridization methods are widely available and include, for example, those disclosed in PCT International Patent Application Publication WO 1995/011755). Any solid surface to which oligonucleotides can be bound, either directly or indirectly, either covalently or non-covalently, can be used. An exemplary solid support is a high-density array or DNA chip. These contain a particular oligonucleotide probe in a predetermined location on the array. Each predetermined location can contain more than one molecule of the probe, but in some embodiments each molecule within the predetermined location has an identical sequence. Such predetermined locations are termed features. There can be any number of features on a single solid support including, for example, about 2, 10, 100, 1000, 10,000, 100,000, or 400,000 of such features on a single solid support. The solid support, or the area within which the probes are attached, can be of any convenient size (for example, on the order of a square centimeter).

Oligonucleotide probe arrays for differential gene expression monitoring can be made and employed according to any techniques known in the art (see e.g., Lockhart et al., 1996; McGall et al., 1996). Such probe arrays can contain at least two or more oligonucleotides that are complementary to or hybridize to two or more of the genes described herein. Such arrays can also contain oligonucleotides that are complementary or hybridize to at least about 2, 3, 4, 5, 6, 7, 8, 9, 10, 15, 20, 25, 30, 50, 70, 100, or more of the nucleic acid sequences disclosed herein.

The genes that are assayed according to the presently disclosed subject matter are typically in the form of RNA (e.g., total RNA or mRNA) and/or reverse transcribed RNA (i.e., cDNA), including subsequences thereof. The genes can be cloned or not, and the genes can be amplified or not. In some embodiments, poly g RNA is employed as a source.

Probes based on the sequences of the genes described herein can be prepared by any commonly available method. Oligonucleotide probes for assaying the tissue or cell sample are in some embodiments of sufficient length to specifically hybridize only to appropriate complementary genes or transcripts. Typically, the oligonucleotide probes are at least 10, 12, 14, 16, 18, 20, or 25 nucleotides in length. In some embodiments, longer probes of at least 30, 40, 50, or 60 nucleotides are employed.

As used herein, oligonucleotide sequences that are complementary to one or more of the genes described herein are oligonucleotides that are capable of hybridizing under stringent conditions to at least part of the nucleotide sequence of said genes. Such hybridizable oligonucleotides will typically exhibit in some embodiments at least about 75% sequence identity, in some embodiments about 80% sequence identity, in some embodiments about 85% sequence identity, in some embodiments about 90% sequence identity, in some embodiments about 91% sequence identity, in some embodiments about 92% sequence identity, in some embodiments about 93% sequence identity, in some embodiments about 94% sequence identity, in some embodiments about 95% sequence identity, and in some embodiments greater than 95% sequence identity (e.g., 96%, 97%, 98%, 99%, or 100% sequence identity) at the nucleotide level to the nucleic acid sequences disclosed herein.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals can also be produced by intrinsic fluorescence of the array components themselves. A single background signal can be calculated for the entire array, or a different background signal can be calculated for each target nucleic acid. In some embodiments, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background can be calculated as the average hybridization signal intensity produced by hybridization to probes that are not complementary to any sequence found in the sample (e.g., probes directed to nucleic acids of the opposite sense or to genes not found in the sample such as bacterial genes where the sample is mammalian nucleic acids). Background can also be calculated as the average signal intensity produced by regions of the array that lack probes.

Assays, methods, and systems of the presently disclosed subject matter can utilize available formats to simultaneously screen in some embodiments at least about 10, in some embodiments at least about 50, in some embodiments at least about 100, in some embodiments at least about 1000, in some embodiments at least about 10,000, and in some embodiments at least about 40,000 or more different nucleic acid hybridizations.

As used herein, a "probe" is defined as a nucleic acid that is capable of binding to a target nucleic acid of complementary sequence through one or more types of chemical bonds, usually through complementary base pairing, usually through hydrogen bond formation. As used herein, a probe can include natural (i.e., A, G, U, C, or T) or modified bases (7-deazaguanosine, inosine, etc.). In addition, the bases in probes can be joined by a linkage other than a phosphodiester bond, so long as it does not interfere with hybridization. Thus, probes can be peptide nucleic acids in which the constituent bases are joined by peptide bonds rather than phosphodiester linkages.

The terms "mismatch control" and "mismatch probe" refer to a probe comprising a sequence that is deliberately selected not to be perfectly complementary to a particular target sequence. For each mismatch (MM) control in a high-density array there typically exists a corresponding perfect match (PM) probe that is perfectly complementary to the same particular target sequence. The mismatch can comprise one or more bases.

While the mismatch(s) can be located anywhere in the mismatch probe, terminal mismatches are less desirable as a terminal mismatch is less likely to prevent hybridization of the target sequence. In some embodiments, the mismatch is located at or near the center of the probe such that the mismatch is most likely to destabilize the duplex with the target sequence under the test hybridization conditions.

The phrase "perfect match probe" refers to a probe that has a sequence that is perfectly complementary to a particular target sequence. The test probe is typically perfectly complementary to a portion (subsequence) of the target sequence. The perfect match (PM) probe can be a "test probe," a "normalization control" probe, an expression level control probe, or the like. A perfect match control or perfect match probe is, however, distinguished from a "mismatch control" or "mismatch probe."

V.B. Probe Design

Upon review of the present disclosure, one of skill in the art will appreciate that an enormous number of array designs are suitable for the practice of the presently disclosed subject matter. The high-density array typically includes a number of probes that specifically hybridize to the sequences of interest. See PCT International Patent Application Publication WO 1999/032660, incorporated herein by reference in its entirety, for methods of producing probes for a given gene or genes. In addition, in some embodiments, the array includes one or more control probes.

High-density array chips of the presently disclosed subject matter include in some embodiments "test probes." Test probes can be oligonucleotides that in some embodiments range from about 5 to about 500 or about 5 to about 50 nucleotides, in some embodiments from about 10 to about 40 nucleotides, and in some embodiments from about 15 to about 40 nucleotides in length. In some embodiments, the probes are about 20 to 25 nucleotides in length. In some embodiments, test probes are double or single strand DNA sequences. DNA sequences are isolated or cloned from natural sources and/or amplified from natural sources using natural nucleic acid as templates. These probes have sequences complementary to particular subsequences of the genes the expression of which they are designed to detect. Thus, the test probes are capable of specifically hybridizing to the target nucleic acid they are to detect.

In addition to test probes that bind the target nucleic acid(s) of interest, the high-density array can contain a number of control probes. The control probes fall into three categories referred to herein as (1) normalization controls; (2) expression level controls; and (3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that can cause the signal of a perfect hybridization to vary between arrays. In some embodiments, signals (e.g., fluorescence intensity) read from some or all other probes in the array are divided by the signal (e.g., fluorescence intensity) from the control probes, thereby normalizing the measurements.

Virtually any probe can serve as a normalization control. However, it is recognized that hybridization efficiency varies with base composition and probe length. Exemplary normalization probes can be selected to reflect the average length of the other probes present in the array; however, they can be selected to cover a range of lengths. The normalization control(s) can also be selected to reflect the (average) base composition of the other probes in the array; however, in some embodiments, only one or a few probes are used and they are selected such that they hybridize well (i.e., no secondary structure) and do not match any target-specific probes.

Expression level controls are probes that hybridize specifically with constitutively expressed genes in the biological sample. Virtually any constitutively expressed gene provides a suitable target for expression level controls. Typical expression level control probes have sequences complementary to subsequences of constitutively expressed "housekeeping genes" including, but not limited to, the (3-actin gene, the transferrin receptor gene, the GAPDH gene, and the like. Exemplary human housekeeping genes are disclosed in Eisenberg & Levanon, 2003. It is noted that certain of the genes listed in Eisenberg & Levanon, 2003 are also listed in one or more of Tables 2-5. In some embodiments, a gene that appears in Eisenberg & Levanon, 2003 and also in one or more of Tables 2-5 is not selected for use as an expression level control.

Mismatch controls can also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent). In some embodiments, mismatch probes contain one or more central mismatches. Thus, for example, where a probe is a 20-mer, a corresponding mismatch probe will have the identical sequence except for a single base mismatch (e.g., substituting a G, a C, or a T for an A) at any of positions 6 through 14 (the central mismatch).

Mismatch probes thus provide a control for non-specific binding or cross hybridization to a nucleic acid in the sample other than the target to which the probe is directed. Mismatch probes also indicate whether a given hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (IBM)-I(MM)) provides a good measure of the concentration of the hybridized material.

V.C. Nucleic Acid Samples

A biological sample that can be analyzed in accordance with the presently disclosed subject matter comprises in some embodiments a nucleic acid. The terms "nucleic acid," "nucleic acids," and "nucleic acid molecules" each refer in some embodiments to deoxyribonucleotides, ribonucleotides, and polymers and folded structures thereof in either single- or double-stranded form. Nucleic acids can be derived from any source, including any organism. Deoxyribonucleic acids can comprise genomic DNA, cDNA derived from ribonucleic acid, DNA from an organelle (e.g., mitochondrial DNA or chloroplast DNA), or combinations thereof. Ribonucleic acids can comprise genomic RNA (e.g., viral genomic RNA), messenger RNA (mRNA), ribosomal RNA (rRNA), transfer RNA (tRNA), or combinations thereof.

V.C.1. Isolation of Nucleic Acid Samples

Nucleic acid samples used in the methods and assays of the presently disclosed subject matter can be prepared by any available method or process. Methods of isolating total mRNA are also known to those of skill in the art. For example, methods of isolation and purification of nucleic acids are described in detail in Chapter 3 of Tijssen, 1993. Such samples include RNA samples, but also include cDNA synthesized from an mRNA sample isolated from a cell or tissue of interest. Such samples also include DNA amplified from the cDNA, an RNA transcribed from the amplified DNA, and combinations thereof. One of skill in the art would appreciate that it can be desirable to inhibit or destroy RNase present in homogenates before homogenates are used as a source of RNA.

The presently disclosed subject matter encompasses use of a sufficiently large biological sample to enable a comprehensive survey of low abundance nucleic acids in the sample. Thus, the sample can optionally be concentrated prior to isolation of nucleic acids. Several protocols for concentration have been developed that alternatively use slide supports (Kohsaka & Carson, 1994; Millar et al., 1995), filtration columns (Bej et al., 1991), or immunomagnetic beads (Albert et al., 1992; Cousins et al., 1992). Such approaches can significantly increase the sensitivity of subsequent detection methods.

As one example, SEPHADEX® matrix (Sigma of St. Louis, Mo., United States of America) is a matrix of diatomaceous earth and glass suspended in a solution of chaotropic agents and has been used to bind nucleic acid material (Boom et al., 1990; Buffone et al., 1991). After the nucleic acid is bound to the solid support material, impurities and inhibitors are removed by washing and centrifugation, and the nucleic acid is then eluted into a standard buffer. Target capture also allows the target sample to be concentrated into a minimal volume, facilitating the automation and reproducibility of subsequent analyses (Lanciotti et al., 1992).

Methods for nucleic acid isolation can comprise simultaneous isolation of total nucleic acid, or separate and/or sequential isolation of individual nucleic acid types (e.g., genomic DNA, cDNA, organelle DNA, genomic RNA, mRNA, poly $A^+$ RNA, rRNA, tRNA) followed by optional combination of multiple nucleic acid types into a single sample.

When RNA (e.g., mRNA) is selected for analysis, the disclosed methods allow for an assessment of gene expression in the tissue or cell type from which the RNA was isolated. RNA isolation methods are known to one of skill in the art. See Albert et al., 1992; Busch et al., 1992; Hamel et al., 1995; Herrewegh et al., 1995; Izraeli et al., 1991; McCaustland et al., 1991; Natarajan et al., 1994; Rupp et al., 1988; Tanaka et al., 1994; and Van Kerckhoven et al., 1994.

Simple and semi-automated extraction methods can also be used for nucleic acid isolation, including for example, the SPLIT SECOND™ system (Boehringer Mannheim of Indianapolis, Ind., United States of America), the TRIZOL™ Reagent system (Life Technologies of Gaithersburg, Md., United States of America), and the FASTPREP™ system (Bio 101 of La Jolla, Calif., United States of America). See also Smith 1998a; and Paladichuk 1999.

In some embodiments, nucleic acids that are used for subsequent amplification and labeling are analytically pure as determined by spectrophotometric measurements or by visual inspection following electrophoretic resolution. In some embodiments, the nucleic acid sample is free of contaminants such as polysaccharides, proteins, and inhibitors of enzyme reactions. When a biological sample comprises an RNA molecule that is intended for use in producing a probe, it is preferably free of DNase and RNase. Contaminants and inhibitors can be removed or substantially reduced using resins for DNA extraction (e.g., CHELEX™ 100 from Bio-Rad Laboratories of Hercules, Calif., United States of America) or by standard phenol extraction and ethanol precipitation.

V.C.2. Amplification of Nucleic Acid Samples

In some embodiments, a nucleic acid isolated from a biological sample is amplified prior to being used in the methods disclosed herein. In some embodiments, the nucleic acid is an RNA molecule, which is converted to a complementary DNA (cDNA) prior to amplification. Techniques for the isolation of RNA molecules and the production of cDNA molecules from the RNA molecules are known (see generally, Silhavy et al., 1984; Sambrook & Russell, 2001; Ausubel et al., 2002; and Ausubel et al., 2003). In some embodiments, the amplification of RNA molecules isolated from a biological sample is a quantitative amplification (e.g., by quantitative RT-PCR).

The terms "template nucleic acid" and "target nucleic acid" as used herein each refer to nucleic acids isolated from a biological sample as described herein above. The terms "template nucleic acid pool," "template pool," "target nucleic acid pool," and "target pool" each refer to an amplified sample of "template nucleic acid." Thus, a target pool comprises amplicons generated by performing an amplification reaction using the template nucleic acid. In some embodiments, a target pool is amplified using a random amplification procedure as described herein.

The term "target-specific primer" refers to a primer that hybridizes selectively and predictably to a target sequence, for example a subsequence of one of the six genes disclosed herein, in a target nucleic acid sample. A target-specific primer can be selected or synthesized to be complementary to known nucleotide sequences of target nucleic acids.

The term "random primer" refers to a primer having an arbitrary sequence. The nucleotide sequence of a random primer can be known, although such sequence is considered arbitrary in that it is not specifically designed for complementarity to a nucleotide sequence of the presently disclosed subject matter. The term "random primer" encompasses selection of an arbitrary sequence having increased probability to be efficiently utilized in an amplification reaction. For example, the Random Oligonucleotide Construction Kit (ROCK) is a macro-based program that facilitates the generation and analysis of random oligonucleotide primers (Strain & Chmielewski, 2001). Representative primers include but are not limited to random hexamers and rapid amplification of polymorphic DNA (RAPD)-type primers as described by Williams et al., 1990.

A random primer can also be degenerate or partially degenerate as described by Telenius et al., 1992. Briefly, degeneracy can be introduced by selection of alternate oligonucleotide sequences that can encode a same amino acid sequence.

In some embodiments, random primers can be prepared by shearing or digesting a portion of the template nucleic acid sample. Random primers so-constructed comprise a sample-specific set of random primers.

The term "heterologous primer" refers to a primer complementary to a sequence that has been introduced into the template nucleic acid pool. For example, a primer that is complementary to a linker or adaptor, as described below, is a heterologous primer. Representative heterologous primers can optionally include a poly(dT) primer, a poly(T) primer, or as appropriate, a poly(dA) or poly(A) primer.

The term "primer" as used herein refers to a contiguous sequence comprising in some embodiments about 6 or more nucleotides, in some embodiments about 10-20 nucleotides (e.g., 15-mer), and in some embodiments about 20-30 nucleotides (e.g., a 22-mer). Primers used to perform the methods of the presently disclosed subject matter encompass oligonucleotides of sufficient length and appropriate sequence so as to provide initiation of polymerization on a nucleic acid molecule.

U.S. Pat. No. 6,066,457 to Hampson et al. describes a method for substantially uniform amplification of a collection of single stranded nucleic acid molecules such as RNA. Briefly, the nucleic acid starting material is anchored and processed to produce a mixture of directional shorter random size DNA molecules suitable for amplification of the sample.

In accordance with the methods and systems of the presently disclosed subject matter, any PCR technique or related technique can be employed to perform the step of amplifying the nucleic acid sample. In addition, such methods can be optimized for amplification of a particular subset of nucleic acid (e.g., genomic DNA versus RNA), and representative optimization criteria and related guidance can be found in the art. See Cha & Thilly, 1993; Linz et al., 1990; Robertson & Walsh-Weller, 1998; Roux 1995; Williams 1989; and McPherson et al., 1995.

V.C.3. Labeling of Nucleic Acid Samples

Optionally, a nucleic acid sample (e.g., a quantitatively amplified RNA sample) further comprises a detectable label. In some embodiments of the presently disclosed subject matter, the amplified nucleic acids can be labeled prior to hybridization to an array. Alternatively, randomly amplified nucleic acids are hybridized with a set of probes, without prior labeling of the amplified nucleic acids. For example, an unlabeled nucleic acid in the biological sample can be detected by hybridization to a labeled probe. In some embodiments, both the randomly amplified nucleic acids and the one or more probes include a label, wherein the proximity of the labels following hybridization enables detection. An exemplary procedure using nucleic acids labeled with chromophores and fluorophores to generate detectable photonic structures is described in U.S. Pat. No. 6,162,603 to Heller.

In accordance with the methods and systems of the presently disclosed subject matter, the amplified nucleic acids and/or probes/probe sets can be labeled using any detectable label. It will be understood to one of skill in the art that any suitable method for labeling can be used, and no particular detectable label or technique for labeling should be construed as a limitation of the disclosed methods.

Direct labeling techniques include incorporation of radioisotopic or fluorescent to nucleotide analogues into nucleic acids by enzymatic synthesis in the presence of labeled nucleotides or labeled PCR primers. A radio-isotopic label can be detected using autoradiography or phosphorimaging. A fluorescent label can be detected directly using emission and absorbance spectra that are appropriate for the particular label used. Any detectable fluorescent dye can be used, including but not limited to FITC (fluorescein isothiocyanate), FLUOR X™, ALEXA FLUOR® 488, OREGON GREEN® 488, 6-JOE (6-carboxy-4',5'-dichloro-2',7'-dimethoxyfluorescein, succinimidyl ester), ALEXA FLUOR® 532, Cy3, ALEXA FLUOR® 546, TMR (tetramethylrhodamine), ALEXA FLUOR® 568, ROX (X-rhodamine), ALEXA FLUOR® 594, TEXAS RED®, BODIPY® 630/650, and Cy5 (available from Amersham Pharmacia Biotech of Piscataway, N.J., United States of America or from Molecular Probes Inc. of Eugene, Oreg., United States of America). Fluorescent tags also include sulfonated cyanine dyes (available from Li-Cor, Inc. of Lincoln, Nebr., United States of America) that can be detected using infrared imaging. Methods for direct labeling of a heterogeneous nucleic acid sample are known in the art and representative protocols can be found in, for example, DeRisi et al., 1996; Sapolsky & Lipshutz, 1996; Schena et al., 1995; Schena et al., 1996; Shalon et al., 1996; Shoemaker et al., 1996; and Wang et al., 1989.

In some embodiments, nucleic acid molecules isolated from different cell types (e.g., primary versus metastatic PDAC) are labeled with different detectable markers, allowing the nucleic acids to be analyzed simultaneously on an array. For example, a first RNA sample can be reverse transcribed into cDNAs labeled with cyanine 3 (a green dye fluorophore; Cy3) while a second RNA sample to which the first RNA sample is to be compared can be labeled with cyanine 5 (a red dye fluorophore; Cy5).

The quality of probe or nucleic acid sample labeling can be approximated by determining the specific activity of label incorporation. For example, in the case of a fluorescent label, the specific activity of incorporation can be determined by the absorbance at 260 nm and 550 nm (for Cy3) or 650 nm (for Cy5) using published extinction coefficients (Randolph & Waggoner, 1995). Very high label incorporation (specific activities of >1 fluorescent molecule/20 nucleotides) can result in a decreased hybridization signal compared with probe with lower label incorporation. Very low specific activity (<1 fluorescent molecule/100 nucleotides) can give unacceptably low hybridization signals. See Worley et al., 2000. Thus, it will be understood to one of skill in the art that labeling methods can be optimized for performance in microarray hybridization assay, and that optimal labeling can be unique to each label type.

V.D. Forming High-Density Arrays

In some embodiments of the presently disclosed subject matter, probes or probe sets are immobilized on a solid support such that a position on the support identifies a particular probe or probe set. In the case of a probe set, constituent probes of the probe set can be combined prior to placement on the solid support or by serial placement of constituent probes at a same position on the solid support.

A microarray can be assembled using any suitable method known to one of skill in the art, and any one microarray configuration or method of construction is not considered to be a limitation of the presently disclosed subject matter. Representative microarray formats that can be used in accordance with the methods of the presently disclosed subject matter are described herein below and include, but are not limited to light-directed chemical coupling, and mechanically directed coupling (see U.S. Pat. No. 5,143,854 to Pirrung et al.; U.S. Pat. No. 5,800,992 to Fodor et al.; and U.S. Pat. No. 5,837,832 to Chee et al.).

V.D.1. Array Substrate and Configuration

The substrate for printing the array should be substantially rigid and amenable to DNA immobilization and detection methods (e.g., in the case of fluorescent detection, the substrate must have low background fluorescence in the region of the fluorescent dye excitation wavelengths). The substrate can be nonporous or porous as determined most suitable for a particular application. Representative substrates include but are not limited to a glass microscope slide, a glass coverslip, silicon, plastic, a polymer matrix, an agar gel, a polyacrylamide gel, and a membrane, such as a nylon, nitrocellulose or ANAPORE™ (Whatman of Maidstone, United Kingdom) membrane.

Porous substrates (membranes and polymer matrices) are preferred in that they permit immobilization of relatively large amount of probe molecules and provide a three-dimensional hydrophilic environment for biomolecular interactions to occur (Dubiley et al., 1997; Yershov et al., 1996). A BIOCHIP ARRAYER™ dispenser (Packard Instrument Company of Meriden, Conn., United States of America) can effectively dispense probes onto membranes such that the spot size is consistent among spots whether one, two, or four droplets were dispensed per spot (Englert, 2000).

A microarray substrate for use in accordance with the methods of the presently disclosed subject matter can have either a two-dimensional (planar) or a three-dimensional (non-planar) configuration. An exemplary three-dimensional microarray is the FLOW-THRU™ chip (Gene Logic, Inc. of Gaithersburg, Md., United States of America), which has implemented a gel pad to create a third dimension. Such a three-dimensional microarray can be constructed of any suitable substrate, including glass capillary, silicon, metal oxide filters, or porous polymers. See Yang et al., 1998.

Briefly, a FLOW-THRU™ chip (Gene Logic, Inc.) comprises a uniformly porous substrate having pores or microchannels connecting upper and lower faces of the chip. Probes are immobilized on the walls of the microchannels and a hybridization solution comprising sample nucleic acids can flow through the microchannels. This configuration increases the capacity for probe and target binding by providing additional surface relative to two-dimensional arrays. See U.S. Pat. No. 5,843,767 to Beattie.

V.D.2. Surface Chemistry

The particular surface chemistry employed is inherent in the microarray substrate and substrate preparation. Probe immobilization of nucleic acids probes post-synthesis can be accomplished by various approaches, including adsorption, entrapment, and covalent attachment. Typically, the binding technique is designed to not disrupt the activity of the probe.

For substantially permanent immobilization, covalent attachment is generally performed. Since few organic functional groups react with an activated silica surface, an intermediate layer is advisable for substantially permanent probe immobilization. Functionalized organosilanes can be used as such an intermediate layer on glass and silicon substrates (Liu & Hlady, 1996; Shriver-Lake 1998). A hetero-bifunctional cross-linker requires that the probe have a different chemistry than the surface, and is preferred to avoid linking reactive groups of the same type. A representative hetero-bifunctional cross-linker comprises gamma-maleimidobutyryloxy-succimide (GMBS) that can bind maleimide to a primary amine of a probe. Procedures for using such linkers are known to one of skill in the art and are summarized in Hermanson, 1990. A representative protocol for covalent attachment of DNA to silicon wafers is described by O'Donnell et al., 1997.

When using a glass substrate, the glass should be substantially free of debris and other deposits and have a substantially uniform coating. Pretreatment of slides to remove organic compounds that can be deposited during their manufacture can be accomplished, for example, by washing in hot nitric acid. Cleaned slides can then be coated with 3-aminopropyltrimethoxysilane using vapor-phase techniques. After silane deposition, slides are washed with deionized water to remove any silane that is not attached to the glass and to catalyze unreacted methoxy groups to cross-link to neighboring silane moieties on the slide. The uniformity of the coating can be assessed by known methods, for example electron spectroscopy for chemical analysis (ESCA) or ellipsometry (Ratner & Castner, 1997; Schena et al., 1995). See also Worley et al., 2000.

For attachment of probes greater than about 300 base pairs, noncovalent binding is suitable. A representative technique for noncovalent linkage involves use of sodium isothiocyanate (NaSCN) in the spotting solution. When using this method, amino-silanized slides are typically employed because this coating improves nucleic acid binding when compared to bare glass. This method works well for spotting applications that use about 100 ng/μl (Worley et al., 2000).

In the case of nitrocellulose or nylon membranes, the chemistry of nucleic acid binding chemistry to these membranes has been well characterized (Southern, 1975; Sambrook & Russell, 2001).

V.D.3. Arraying Techniques

A microarray for the analysis of gene expression in a biological sample can be constructed using any one of several methods available in the art, including but not limited to photolithographic and microfluidic methods, further described herein below. In some embodiments, the method of construction is flexible, such that a microarray can be tailored for a particular purpose.

Exemplary arraying techniques include, but are not limited to light-directed synthesis (Fodor et al., 1991; Fodor et al., 1993), commercialized by Affymetrix of Santa Clara, Calif., United States of America; Digital Optical Chemistry (PCT International Patent Application Publication No. WO 1999/063385; Warrington et al., 2000); Contact Printing (Maier et al., 1994; Mace et al., 2000; Rose, 2000); Non-contact Ink-Jet Printing U.S. Pat. No. 5,965,352 to Stoughton & Friend; see also Theriault et al., 1999); Syringe-Solenoid Printing (U.S. Pat. Nos. 5,743,960 and 5,916,524, both to Tisone); Electronic Addressing (U.S. Pat. No. 6,225,059 to Ackley et al. and PCT International Patent Application Publication No. WO 2001/023082); and Nanoelectrode Synthesis (U.S. Pat. No. 6,123,819 to Peeters).;

In addition to the foregoing, other methods that can be used to generate an array of oligonucleotides on a single substrate are described in PCT International Patent Application Publication WO 1993/009668. High-density nucleic acid arrays can also be fabricated by depositing pre-made and/or natural nucleic acids in predetermined positions. Synthesized or natural nucleic acids are deposited on specific locations of a substrate by light directed targeting and oligonucleotide directed targeting. A dispenser that moves from region to region to deposit nucleic acids in specific spots can also be employed.

V.E. Hybridization

V.E.1. General Considerations

The terms "specifically hybridizes" and "selectively hybridizes" each refer to binding, duplexing, or hybridizing of a molecule only to a particular nucleotide sequence under stringent conditions when that sequence is present in a complex nucleic acid mixture (e.g., total cellular DNA or RNA).

The phrase "substantially hybridizes" refers to complementary hybridization between a probe nucleic acid molecule and a substantially identical target nucleic acid molecule as defined herein. Substantial hybridization is generally permitted by reducing the stringency of the hybridization conditions using art-recognized techniques.

"Stringent hybridization conditions" and "stringent hybridization wash conditions" in the context of nucleic acid hybridization experiments are both sequence- and environment-dependent. Longer sequences hybridize specifically at higher temperatures. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. Typically, under "stringent conditions" a probe hybridizes specifically to its target sequence, but to no other sequences.

An extensive guide to the hybridization of nucleic acids is found in Tijssen, 1993. In general, a signal to noise ratio of 2-fold (or higher) than that observed for a negative control probe in a same hybridization assay indicates detection of specific or substantial hybridization.

V.E.2. Hybridization on a Solid Support

In some embodiments of the presently disclosed subject matter, an amplified and/or labeled nucleic acid sample is hybridized to specific probes or probe sets that are immobilized on a continuous solid support comprising a plurality of identifying positions. Representative formats of such solid supports are described herein.

Examples of hybridization and wash conditions that can be employed are known to those of skill in the art (see Sambrook & Russell, 2001; Ausubel et al., 2002; and Ausubel et al., 2003; each of which is incorporated herein in its entirety).

For some high-density glass-based microarray experiments, hybridization at 65° C. is too stringent for typical use, at least in part because the presence of fluorescent labels destabilizes the nucleic acid duplexes (Randolph & Waggoner, 1995). Alternatively, hybridization can be performed in a formamide-based hybridization buffer as described in Piétu et al., 1996.

A microarray format can be selected for use based on its suitability for electrochemical-enhanced hybridization. Provision of an electric current to the microarray, or to one or more discrete positions on the microarray facilitates localization of a target nucleic acid sample near probes immobilized on the microarray surface. Concentration of target nucleic acid near arrayed probe accelerates hybridization of a nucleic acid of the sample to a probe. Further, electronic stringency control allows the removal of unbound and nonspecifically bound DNA after hybridization. See U.S. Pat. No. 6,017,696 to Heller and U.S. Pat. No. 6,245,508 to Heller & Sosnowski.

V.E.3. Hybridization in Solution

In some embodiments of the presently disclosed subject matter, an amplified and/or labeled nucleic acid sample is hybridized to one or more probes in solution. Exemplary hybridization conditions are also disclosed in Sambrook & Russell, 2001; Ausubel et al., 2002; and Ausubel et al., 2003.

Alternate capture techniques can be used as will be understood to one of skill in the art, for example, purification by a metal affinity column when using probes comprising a histidine tag. As another example, the hybridized sample can be hydrolyzed by alkaline treatment wherein the double-stranded hybrids are protected while non-hybridizing single-stranded template and excess probe are hydrolyzed. The hybrids are then collected using any nucleic acid purification technique for further analysis.

To assess the expression of multiple genes and/or samples from multiple different sources simultaneously, probes or probe sets can be distinguished by differential labeling of probes or probe sets. Alternatively, probes or probe sets can be spatially separated in different hybridization vessels.

In some embodiments, a probe or probe set having a unique label is prepared for each gene or source to be detected. For example, a first probe or probe set can be labeled with a first fluorescent label, and a second probe or probe set can be labeled with a second fluorescent label. Multi-labeling experiments should consider label characteristics and detection techniques to optimize detection of each label. Representative first and second fluorescent labels are Cy3 and Cy5 (Amersham Pharmacia Biotech of Piscataway, N.J. United States of America), which can be analyzed with good contrast and minimal signal leakage.

A unique label for each probe or probe set can further comprise a labeled microsphere to which a probe or probe set is attached. A representative system is LabMAP (Luminex Corporation of Austin, Tex., United States of America). Briefly, LabMAP (Laboratory Multiple Analyte Profiling) technology involves performing molecular reactions, including hybridization reactions, on the surface of color-coded microscopic beads called microspheres. When used in accordance with the methods of the presently disclosed subject matter, an individual probe or probe set is attached to beads having a single color-code such that they can be identified throughout the assay. Successful hybridization is measured using a detectable label of the amplified nucleic acid sample, wherein the detectable label can be distinguished from each color-code used to identify individual microspheres. Following hybridization of the randomly amplified, labeled nucleic acid sample with a set of microspheres comprising probe sets, the hybridization mixture is analyzed to detect the signal of the color-code as well as the label of a sample nucleic acid bound to the microsphere. See Vignali 2000; Smith et al., 1998b; and PCT International Patent Application Publication Nos. WO 2001/013120; WO 2001/014589; WO 1999/019515; WO 1999/032660; and WO 1997/014028.

V.F. Detection

Methods and systems for detecting hybridization are typically selected according to the label employed.

In the case of a radioactive label (e.g., $^{32}$P-dNTP) detection can be accomplished by autoradiography or by using a phosphorimager as is known to one of skill in the art. In some embodiments, a detection method can be automated and is adapted for simultaneous detection of numerous samples.

Common research equipment has been developed to perform high-throughput fluorescence detecting, including instruments from GSI Lumonics (Watertown, to Massachusetts, United States of America), Amersham Pharmacia Biotech/Molecular Dynamics (Sunnyvale, Calif., United States of America), Applied Precision Inc. (Issauah, Wash., United States of America), Genomic Solutions Inc. (Ann Arbor, Mich., United States of America), Genetic MicroSystems Inc. (Woburn, Mass., United States of America), Axon (Foster City, Calif., United States of America), Hewlett Packard (Palo Alto, Calif., United States of America), and Virtek (Woburn, Mass., United States of America). Most of the commercial systems use some form of scanning technology with photomultiplier tube detection. Criteria for consideration when analyzing fluorescent samples are summarized by Alexay et al., 1996.

In some embodiments, a nucleic acid sample or probe is labeled with far infrared, near infrared, or infrared fluorescent dyes. Following hybridization, the mixture of nucleic acids and probes is scanned photoelectrically with a laser diode and a sensor, wherein the laser scans with scanning light at a wavelength within the absorbance spectrum of the fluorescent label, and light is sensed at the emission wavelength of the label. See U.S. Pat. No. 6,086,737 to Patonay et al.; U.S. Pat. No. 5,571,388 to Patonay et al.; U.S. Pat. No. 5,346,603 to Middendorf & Brumbaugh; U.S. Pat. No. 5,534,125 to Middendorf et al.; U.S. Pat. No. 5,360,523 to Middendorf et al.; U.S. Pat. No. 5,230,781 to Middendorf & Patonay; U.S. Pat. No. 5,207,880 to Middendorf & Brumbaugh; and U.S. Pat. No. 4,729,947 to Middendorf & Brumbaugh. An ODYSSEY™ infrared imaging system (Li-Cor, Inc. of Lincoln, Nebr., United States of America) can be used for data collection and analysis.

If an epitope label has been used, a protein or compound that binds the epitope can be used to detect the epitope. For example, an enzyme-linked protein can be subsequently detected by development of a colorimetric or luminescent reaction product that is measurable using a spectrophotometer or luminometer, respectively.

In some embodiments, INVADER technology (Third Wave Technologies of Madison, Wis., United States of America) is used to detect target nucleic acid/probe complexes. Briefly, a nucleic acid cleavage site (such as that recognized by a variety of enzymes having 5' nuclease activity) is created on a target sequence, and the target sequence is cleaved in a site-specific manner, thereby indicating the presence of specific nucleic acid sequences or specific variations thereof. See U.S. Pat. No. 5,846,717 to Brow et al.; U.S. Pat. No. 5,985,557 to Prudent et al.; U.S. Pat. No. 5,994,069 to Hall et al.; U.S. Pat. No. 6,001,567 to Brow et al.; and U.S. Pat. No. 6,090,543 to Prudent et al.

In some embodiments, target nucleic acid/probe complexes are detected using an amplifying molecule, for example a poly-dA oligonucleotide as described by Lisle et al., 2001. Briefly, a tethered probe is employed against a target nucleic acid having a complementary nucleotide sequence. A target nucleic acid having a poly-dT sequence, which can be added to any nucleic acid sequence using methods known to one of skill in the art, hybridizes with an amplifying molecule comprising a poly-dA oligonucleotide. Short oligo-d$T_{40}$ signaling moieties are labeled with any suitable label (e.g., fluorescent, chemiluminescent, radioisotopic labels). The short oligo-d$T_{40}$ signaling moieties are subsequently hybridized along the molecule, and the label is detected.

The presently disclosed subject matter also envisions use of electrochemical technology for detecting a nucleic acid hybrid according to the disclosed method. In this case, the detection method relies on the inherent properties of DNA, and thus a detectable label on the target sample or the probe/probe set is not required. In some embodiments, probe-coupled electrodes are multiplexed to simultaneously detect multiple genes using any suitable microarray or multiplexed liquid hybridization format. To enable detection, gene-specific and control probes are synthesized with substitution of the non-physiological nucleic acid base inosine for guanine, and subsequently coupled to an electrode. Following hybridization of a nucleic acid sample with probe-coupled electrodes, a soluble redox-active mediator (e.g., ruthenium 2,2'-bipyridine) is added, and a potential is applied to the sample. In the absence of guanine, each mediator is oxidized only once. However, when a guanine-containing nucleic acid is present, by virtue of hybridization of a sample nucleic acid molecule to the probe, a catalytic cycle is created that results in the oxidation of guanine and a measurable current enhancement. See U.S. Pat. No. 6,127,127 to Eckhardt et al.; U.S. Pat. No. 5,968,745 to Thorp et al.; and U.S. Pat. No. 5,871,918 to Thorp et al.

Surface plasmon resonance spectroscopy can also be used to detect hybridization. See e.g., Heaton et al., 2001; Nelson et al., 2001; and Guedon et al., 2000.

V.G. Data Analysis

Databases and software designed for use with microarrays is discussed in U.S. Pat. No. 6,229,911 to Balaban & Aggarwal, a computer-implemented method for managing information, stored as indexed tables, collected from small or large numbers of microarrays, and U.S. Pat. No. 6,185,561 to Balaban & Khurgin, a computer-based method with data mining capability for collecting gene expression level data, adding additional attributes and reformatting the data to produce answers to various queries. U.S. Pat. No. 5,974,164 to Chee, disclose a software-based method for identifying mutations in a nucleic acid sequence based on differences in probe fluorescence intensities between wild type and mutant sequences that hybridize to reference sequences.

Analysis of microarray data can also be performed using the method disclosed in Tusher et al., 2001, which describes the Significance Analysis of Microarrays (SAM) method for determining significant differences in gene expression among two or more samples.

VI. Devices, Systems, and Compositions for Use in the Presently Disclosed Methods The presently disclosed subject matter also provides devices, systems, and compositions that can be employed in the practice of the methods disclosed herein.

The methods and systems disclosed herein relate in some embodiments to generating gene expression profiles from biological samples that comprise PDAC cells obtained from a subject. The gene expression profiles are then in some embodiments compared to standards such as, but not limited to gene expression profiles of metastatic PDAC cells and/or primary (i.e., non-metastatic) PDAC cells.

As such, the presently disclosed methods can employ various techniques to generate the gene expression profiles required for the comparisons. See e.g., PCT International Patent Application Publication Nos. WO 2004/046098; WO 2004/110244; WO 2006/089268; WO 2007/001324; WO 2007/056332; WO 2007/070252, each of which is incorporated herein by reference in its entirety.

Generally, a gene expression profile can be generated using the following basic steps:

(1) a biological sample such as, but not limited to a PDAC biopsy or resected PDAC cells are obtained; and (2) the expression levels of one or more (e.g., 1, 2, 3, 4, 5, 6, 7, 8, 9, 10, 20, 25, 50, 100, or all) of the genes listed in Tables 2-5 are determined.

As is known to one of ordinary skill in the art, gene expression levels can be assayed either at the level of RNA or at the level of protein. As such, in some embodiments RNA is extracted from the biological sample and analyzed by techniques that include, but are not limited to PCR analysis (in some embodiments, quantitative reverse transcription PCR) and/or array analysis. In each case, one of ordinary skill in the art would be aware of techniques that can be employed to determine the expression level of a gene product in the biological sample.

With respect to PCR analyses, the sequences of nucleic acids that correspond to one or more of the genes listed in Tables 2-5 are present within the GENBANK® biosequence to database, and oligonucleotide primers can be designed for the purpose of determining expression levels.

Alternatively, arrays can be produced that include single-stranded nucleic acids that can hybridize to nucleic acids derived from one or more of the genes listed in Tables 2-5. Exemplary, non-limiting methods that can be used to produce and screen arrays are described herein above.

Therefore, in some embodiments the presently disclosed subject matter provides arrays comprising polynucleotides that are capable of hybridizing to one or more up to all of the genes listed in Tables 2-5 and/or comprising specific peptide or polypeptide gene products of one or more up to all of the genes listed in Tables 2-5.

Alternatively or in addition, gene expression can be assayed by determining the levels at which polypeptides are present in PDAC tissue. This can also be done using arrays, and exemplary methods for producing peptide and/or polypeptide arrays attached to nitrocellulose-coated glass slides (Espejo et al., 2002), alkanethiol-coated gold surfaces (Houseman et al., 2002), poly-L-lysine-treated glass slides (Haab et al., 2001), aldehyde-treated glass slides (MacBeath & Schreiber, 2000; Salisbury et al., 2002), silane-modified glass slides (Fang et al., 2002; Seong, 2002), and nickel-treated glass slides (Zhu et al., 2001), among others, have been reported.

In some embodiments, the presently disclosed subject matter provides arrays that comprise peptides or polypeptides that are correspond to one or more up to all of the genes listed in Tables 2-5. In these embodiments, arrays are produced from proteins isolated from PDAC tissue, and these arrays are then probed with molecules that specifically bind to the various gene products of interest, if present. Exemplary molecules that specifically bind to one or more up to all of the genes listed in Tables 2-5 include antibodies (as well as fragments and derivatives thereof that include at least one Fab fragment). Antibodies to many of the polypeptides that correspond to the genes listed in Tables 2-5 are commercially available, and antibodies that specifically bind to gene products that are not commercially available can be produced using routine techniques.

Peptide and/or polypeptide arrays can be designed quantitatively such that the amount of each individual peptide or polypeptide is reflective of the amount of that individual peptide or polypeptide in the PDAC tissue.

Further, the arrays can be designed such that specific peptide or polypeptide gene products that correspond to one or more of the genes listed in Tables 2-5 can be localized (sometimes referred to as "spotted") on the array such that the array can be interrogated with at least one antibody that specifically binds to one of the specific peptide or polypeptide gene products.

In some embodiments, gene expression at the level of protein is assayed without isolating the relevant peptides and/or polypeptides from the PDAC cells. For example, immunohistochemistry and/or immunocytochemistry can be employed, in which the expression levels of gene products that correspond to one or more of the genes listed in Tables 2-5 can be determined by incubating appropriate binding molecules to PDAC cells and/or tissue. In some embodiments, the PDAC cells and/or tissue is mounted in paraffin blocks before the immunohistochemistry and/or immunocytochemistry is performed.

As would be understood by one of ordinary skill in the art upon consideration of the present disclosure, many of the manipulations disclosed herein can be automated, and it is intended that such automation is encompassed by the presently disclosed subject matter.

EXAMPLES

The following Examples provide further illustrative embodiments. In light of the present disclosure and the general level of skill in the art, those of skill will appreciate that the following Example is intended to be exemplary only and that numerous changes, modifications, and alterations can be employed without departing from the scope of the presently disclosed subject matter.

TABLE 2

Exemplary Genes Associated with Activated Stroma Subtype and Exemplary Chemotherapeutics Applicable Thereto

| Gene symbol | Possible drug(s) |
|---|---|
| ANXA1 | Hydrocortisone, hydrocortisone/prednisone, hydrocortisone/mitoxantrone |
| AOC3 | Hydralazine, hydralazine/hydrochlorothiazide/reserpine, hydralazine/hydrochlorothiazide, hydralazine/isosorbide dinitrate |
| APP | Bapineuzumab, florbetapir F18, florbetaben F |
| ATP1A1 | Digoxin, trichloromethiazide, ciclopirox olamine, ethacrynic acid, reserpine/trichloromethiazide, bretylium, perphenazine, ouabain, digitoxin |
| AXL | Cabozantinib, cabozantinib/erlotinib |
| BDKRB2 | Anatibant, icatibant |
| C1S | SERPING1 |
| CCR5 | Maraviroc, vicriviroc, ancriviroc |
| CD52 | Alemtuzumab, alemtuzumab/cyclosporin A, alemtuzumab/cyclophosphamide/fludarabine phosphate/rituximab, alemtuzumab/fludarabine phosphate, alemtuzumab/rituximab, alemtuzumab/cyclophosphamide/fludarabine phosphate/mitoxantrone, alemtuzumab/pentostatin, alemtuzumab/bendamustine |
| CFTR | Crofelemer, ivacaftor |
| COL10A1 | Collagenase *clostridium histolyticum* |
| COL11A1 | Collagenase *clostridium histolyticum* |
| COL12A1 | Collagenase *clostridium histolyticum* |
| COL16A1 | Collagenase *clostridium histolyticum* |
| COL1A1 | Collagenase *clostridium histolyticum* |
| COL1A2 | Collagenase *clostridium histolyticum* |
| COL3A1 | Collagenase *clostridium histolyticum* |
| COL4A2 | Collagenase *clostridium histolyticum* |
| COL5A1 | Collagenase *clostridium histolyticum* |
| COL5A2 | Collagenase *clostridium histolyticum* |
| COL8A1 | Collagenase *clostridium histolyticum* |
| COL8A2 | Collagenase *clostridium histolyticum* |
| CSF1R | Nilotinib, sunitinib, pazopanib |
| CXCR4 | Cladribine/cytarabine/filgrastim/idarubicin/plerixafor, plerixafor |
| EDNRA | Bosentan, avosentan, clazosentan, ambrisentan, sitaxsentan, zibotentan, SB 234551, TBC 3214, BSF 302146, macitentan, fandosentan, atrasentan |
| EPCAM | Tucotuzumab celmoleukin, catumaxomab, adecatumumab |
| ERBB2 | Trastuzumab, BMS-599626, varlitinib, XL647, CP-724,714, afatinib, pertuzumab, sapitinib, trastuzumab emtansine, lapatinib/pazopanib, lapatinib/letrozole, paclitaxel/trastuzumab, capecitabine/lapatinib, cyclophosphamide/docetaxel/epirubicin/5-fluorouracil/trastuzumab, docetaxel/trastuzumab, paclitaxel/pertuzumab/trastuzumab, trastuzumab/vinorelbine, capecitabine/trastuzumab, lapatinib/paclitaxel, pertuzumab/trastuzumab, lapatinib/trastuzumab, neratinib, lapatinib, erlotinib |
| F2R | Chrysalin, argatroban, bivalirudin |
| FCGR1B | IgG |
| FCGR2A | IgG |
| FN1 | Ocriplasmin |
| FYN | Dasatinib |
| GABRP | Alphadolone, nitrazepam, adinazolam, sevoflurane, isoflurane, isoniazid, felbamate, etomidate, halothane, fluoxetine/olanzapine, estazolam, eszopiclone, quazepam, diazepam, temazepam, zolpidem, lorazepam, olanzapine, triazolam, flurazepam, midazolam, oxazepam, zaleplon, secobarbital, phenobarbital, pentobarbital, desflurane, methoxyflurane, enflurane |
| HLA-DRB1 | Apolizumab |
| IL1R1 | Anakinra |
| ITGAV | Abciximab, CNTO 95, cilengitide |
| ITGB5 | Cilengitide |
| KCNJ8 | Gliquidone, thiamylal |
| KCNN4 | Betamethasone/clotrimazole, clotrimazole, senicapoc |
| KCNQ1 | Dextromethorphan/quinidine indapamide, quinidine |

TABLE 2-continued

Exemplary Genes Associated with Activated Stroma Subtype and Exemplary Chemotherapeutics Applicable Thereto

| Gene symbol | Possible drug(s) |
|---|---|
| KIT | Dasatinib, sunitinib, pazopanib, tivozanib, motesanib, OSI-930, telatinib, tandutinib, cabozantinib, regorafenib, ponatinib, bortezomib/sorafenib, lapatinib/pazopanib, dexamethasone/lenalidomide/sorafenib, bevacizumab/sorafenib, imatinib/sirolimus, cabozantinib/erlotinib, imatinib, sorafenib |
| MET | Crizotinib, tivantinib, cabozantinib, INC280, cabozantinib/erlotinib |
| MMP11 | Marimastat |
| MMP7 | Marimastat |
| MUC1 | HuHMFG1 |
| NNMT | Atorvastatin/niacin, nicotinic acid/pioglitazone, nicotinic acid, lovastatin/niacin |
| PDGFRA | Sunitinib, pazopanib, axitinib, telatinib, regorafenib, lapatinib/pazopanib, imatinib/sirolimus, imatinib, becaplermin |
| PDGFRB | Nilotinib, dasatinib, sunitinib, pazopanib, axitinib, tivozanib, tandutinib, regorafenib, bortezomib/sorafenib, lapatinib/pazopanib, dexamethasone/lenalidomide/sorafenib, bevacizumab/sorafenib, imatinib/sirolimus, imatinib, sorafenib, becaplermin |
| PLA2G7 | Darapladib |
| PLAT | 6-aminocaproic acid |
| PTGER2 | Misoprostol, prostaglandin E2, prostaglandin E1, CP 533536, diclofenac/misoprostol |
| RAMP1 | Pramlintide |
| SLC12A2 | Bumetanide, quinethazone |
| TEK | Cabozantinib, regorafenib, ponatinib, cabozantinib/erlotinib, vandetanib |
| TLR4 | Resatorvid |
| TLR7 | UC-1V150, 5-fluorouracil/imiquimod, resiquimod, hydroxychloroquine, imiquimod |

TABLE 3

Exemplary Genes Associated with Normal Stroma Subtype and Exemplary Chemotherapeutics Applicable Thereto

| Gene symbol | Possible Drug(s) |
|---|---|
| ACE2 | Hydrochlorothiazide/lisinopril, hydrochlorothiazide/moexipril, moexipril, lisinopril |
| ADH1A | Caffeine/ethanol, 4-methylpyrazole (Fomepizole), ethanol |
| ADH1C | Caffeine/ethanol, 4-methylpyrazole (Fomepizole), ethanol |
| ADRB2 | Articaine/epinephrine, bupivacaine/epinephrine, carteolol, dipivefrin, meluadrine, epinephrine/prilocaine, epinephrine/lidocaine, bedoradrine, KUL 7211, arformoterol, indacaterol, myogane, budesonide/formoterol, nebivolol, vilanterol, olodaterol, formoterol/mometasone furoate, glycopyrrolate/indacaterol, fluticasone furoate/vilanterol, latanoprost/timolol, umeclidinium/vilanterol, fluticasone/salmeterol, albuterol/ipratropium, isoprenaline, carvedilol, ephedrine, guanethidine, levalbuterol, propranolol, pindolol, esmolol, metoprolol, alprenolol, salmeterol, dorzolamide/timolol, fluoxetine/olanzapine, guanadrel, bendroflumethiazide/nadolol, isoxsuprine, hydrochlorothiazide/propranolol, hydrochlorothiazide/timolol, isoproterenol, sotalol, bambuterol, nadolol, timolol, isoetharine, ritodrine, olanzapine, venlafaxine, labetalol, formoterol, bitolterol, albuterol, terbutaline, procaterol, pirbuterol, clenbuterol, fenoterol, norepinephrine, metaproterenol sulfate, epinephrine, dobutamine, droxidopa, arbutamine |
| AGTR1 | Amlodipine/olmesartan medoxomil, olmesartan, amlodipine/hydrochlorothiazide/valsartan, amlodipine/telmisartan, aliskiren/valsartan, azilsartan kamedoxomil, amlodipine/hydrochlorothiazide/olmesartan medoxomil, aspirin/dipyridamole/telmisartan, clopidogrel/telmisartan, amlodipine/valsartan, hydrochlorothiazide/losartan, hydrochlorothiazide/valsartan, candesartan, candesartan cilexetil, olmesartan medoxomil, irbesartan, losartan potassium, telmisartan, eprosartan, candesartan cilexetil/hydrochlorothiazide, hydrochlorothiazide/irbesartan, eprosartan/hydrochlorothiazide, hydrochlorothiazide/telmisartan, hydrochlorothiazide/olmesartan medoxomil, valsartan |
| ANXA1 | Hydrocortisone, hydrocortisone/prednisone, hydrocortisone/mitoxantrone |
| AOC3 | Hydralazine, hydralazine/hydrochloro-thiazide/reserpine; hydralazine/hydrochlorothiazide; hydralazine/isosorbide dinitrate |

TABLE 3-continued

Exemplary Genes Associated with Normal Stroma Subtype and Exemplary Chemotherapeutics Applicable Thereto

| Gene symbol | Possible Drug(s) |
|---|---|
| APP | Bapineuzumab, florbetapir F18, florbetaben F |
| ATP1A1 | Digoxin, trichloromethiazide, ciclopirox olamine, ethacrynic acid, reserpine/trichloromethiazide, bretylium, perphenazine, ouabain, digitoxin |
| ATP1A2 | Digoxin, ethacrynic acid, perphenazine |
| AXL | Cabozantinib, cabozantinib/erlotinib |
| BDKRB2 | Anatibant, icatibant |
| C1S | Serpin peptidase inhibitor (SERPING1) |
| CNR1 | Trans-(A±)-nabilone, SLV 319, rimonabant, BAY 38-7271, delta-8-tetrahydrocannabinol, delta-9-tetrahydrocannabinol |
| CSF1R | Nilotinib, sunitinib, pazopanib |
| CXCR4 | Cladribine/cytarabine/filgrastim/idarubicin/plerixafor, plerixafor |
| ERBB2 | Trastuzumab, BMS-599626, varlitinib, XL647, CP-724,714, afatinib, pertuzumab, sapitinib, trastuzumab emtansine, lapatinib/pazopanib, lapatinib/letrozole, paclitaxel/trastuzumab, capecitabine/lapatinib, cyclophosphamide/docetaxel/epirubicin/5-fluorouracil/trastuzumab, docetaxel/trastuzumab, paclitaxel/pertuzumab/trastuzumab, trastuzumab/vinorelbine, capecitabine/trastuzumab, lapatinib/paclitaxel, pertuzumab/trastuzumab, lapatinib/trastuzumab, neratinib, lapatinib, erlotinib |
| FYN | Dasatinib |
| GHR | GH1, pegvisomant, somatrem |
| HBB | Iron dextran |
| HLA-DRB1 | Apolizumab |
| IL1R1 | Anakinra |
| ITGAV | Abciximab, CNTO 95, cilengitide |
| ITGB5 | Cilengitide |
| KCNJ8 | Gliquidone, thiamylal |
| KCNK1 | |
| KCNMB4 | Tedisamil |
| KIT | Dasatinib, sunitinib, pazopanib, tivozanib, motesanib, OSI-930, telatinib, tandutinib, cabozantinib, regorafenib, ponatinib, bortezomib/sorafenib, lapatinib/pazopanib, dexamethasone/lenalidomide/sorafenib, bevacizumab/sorafenib, imatinib/sirolimus, cabozantinib/erlotinib, imatinib, sorafenib |
| LEPR | Recombinant-methionyl human leptin |
| LPL | Atorvastatin/niacin, nicotinic acid/pioglitazone, nicotinic acid, tyloxapol, lovastatin/niacin |
| PDGFRA | Sunitinib, pazopanib, axitinib, telatinib, regorafenib, lapatinib/pazopanib, imatinib/sirolimus, imatinib, becaplermin |
| PDGFRB | Nilotinib, dasatinib, sunitinib, pazopanib, axitinib, tivozanib, tandutinib, regorafenib, bortezomib/sorafenib, lapatinib/pazopanib, dexamethasone/lenalidomide/sorafenib, bevacizumab/sorafenib, imatinib/sirolimus, imatinib, sorafenib, becaplermin |
| PLA2G2A | Varespladib methyl, varespladib, indomethacin |
| RAMP1 | Pramlintide |
| RAMP3 | Pramlintide |
| S1PR1 | Fingolimod |
| SCN7A | Riluzole |
| TEK | Cabozantinib, regorafenib, ponatinib, cabozantinib/erlotinib, vandetanib |

TABLE 4

Exemplary Genes Associated with Basal Subtype and Exemplary Chemotherapeutics Applicable Thereto

| Gene symbol | Possible drug(s) |
|---|---|
| ADORA2B | Adenosine, enprofylline, dyphylline, aspirin/butalbital/caffeine, acetaminophen/caffeine/dihydrocodeine, acetaminophen/aspirin/caffeine, caffeine/ergotamine, aspirin/caffeine/propoxyphene, aspirin/butalbital/caffeine/codeine, aspirin/caffeine/dihydrocodeine, acetaminophen/butalbital/caffeine, aminophylline, aspirin/caffeine/orphenadrine, acetaminophen/butalbital/caffeine/codeine, theophylline, caffeine, acetaminophen/caffeine/chlorpheniramine/hydrocodone/phenylephrine |
| ANXA1 | Hydrocortisone, hydrocortisone/prednisone, hydrocortisone/mitoxantrone |
| ATP1A1 | Digoxin, trichloromethiazide, ciclopirox olamine, ethacrynic acid, reserpine/trichloromethiazide, bretylium, perphenazine, ouabain, digitoxin |
| AXL | Cabozantinib, cabozantinib/erlotinib |
| BDKRB2 | Anatibant, icatibant |
| COL17A1 | Collagenase *clostridium histolyticum* |

TABLE 4-continued

Exemplary Genes Associated with Basal Subtype and Exemplary Chemotherapeutics Applicable Thereto

| Gene symbol | Possible drug(s) |
|---|---|
| DDR1 | Nilotinib |
| EGFR | Cetuximab, AEE 788, panitumumab, BMS-599626, varlitinib, XL647, bevacizumab/erlotinib, afatinib, sapitinib, cetuximab/irinotecan, lapatinib/pazopanib, irinotecan/panitumumab, erlotinib/vismodegib, erlotinib/gemcitabine, lapatinib/letrozole, capecitabine/lapatinib, bevacizumab/panitumumab, bevacizumab/cetuximab, capecitabine/erlotinib, lapatinib/paclitaxel, cabozantinib/erlotinib, lapatinib/trastuzumab, canertinib, gefitinib, neratinib, PD 153035, lapatinib, vandetanib, erlotinib |
| EPCAM | Tucotuzumab celmoleukin, catumaxomab, adecatumumab |
| ERBB2 | Trastuzumab, BMS-599626, varlitinib, XL647, CP-724,714, afatinib, pertuzumab, sapitinib, trastuzumab emtansine, lapatinib/pazopanib, lapatinib/letrozole, paclitaxel/trastuzumab, capecitabine/lapatinib, cyclophosphamide/docetaxel/epirubicin/5-fluorouracil/trastuzumab, docetaxel/trastuzumab, paclitaxel/pertuzumab/trastuzumab, trastuzumab/vinorelbine, capecitabine/trastuzumab, lapatinib/paclitaxel, pertuzumab/trastuzumab, lapatinib/trastuzumab, neratinib, lapatinib, erlotinib |
| GABRP | Alphadolone, nitrazepam, adinazolam, sevoflurane, isoflurane, isoniazid, felbamate, etomidate, halothane, fluoxetine/olanzapine, estazolam, eszopiclone, quazepam, diazepam, temazepam, zolpidem, lorazepam, olanzapine, triazolam, flurazepam, midazolam, oxazepam, zaleplon, secobarbital, phenobarbital, pentobarbital, desflurane, methoxyflurane, enflurane |
| IFNAR1 | Interferon alfacon-1, PEG-interferon alfa-2a, interferon beta-1a, recombinant interferon, PEG-interferon alfa-2a/telaprevir, pegintron/ribavirin, interferon alfa-n1, PEG-interferon alfa-2a/ribavirin, IFNA2, hydroxyurea/recombinant interferon, interferon alfa-2b/ribavirin, pegintron, interferon beta-1b |
| ITGAV | Abciximab, CNTO 95, cilengitide |
| ITGB5 | Cilengitide |
| KCNMB4 | Tedisamil |
| KCNN4 | Betamethasone/clotrimazole, clotrimazole, senicapoc |
| MET | Crizotinib, tivantinib, cabozantinib, INC280, cabozantinib/erlotinib |
| MMP7 | Marimastat |
| MST1R | Crizotinib |
| MUC1 | HuHMFG1 |
| NOXO1 | Ecabet |
| P2RY2 | Suramin |
| PLAT | 6-aminocaproic acid |
| PSCA | AGS-1C4D4 |
| PTK6 | Vandetanib |
| RAMP1 | Pramlintide |
| SCNN1A | Hydrochlorothiazide/triamterene, amiloride, amiloride/hydrochloro-thiazide, triamterene |

TABLE 5

Exemplary Genes Associated with Classical Subtype and Exemplary Chemotherapeutics Applicable Thereto

| Gene symbol | Possible drug(s) |
|---|---|
| ACE2 | Hydrochlorothiazide/lisinopril, hydrochlorothiazide/moexipril, moexipril, lisinopril |
| ATP1A1 | Digoxin, trichloromethiazide, ciclopirox olamine, ethacrynic acid, reserpine/trichloromethiazide, bretylium, perphenazine, ouabain, digitoxin |
| BDKRB2 | Anatibant, icatibant |
| CFTR | Crofelemer, ivacaftor |
| CYP3A4 | Cobicistat, cobicistat/elvitegravir/emtricitabine/tenofovir disoproxil, ketoconazole |
| CYP3A7 | Cobicistat, cobicistat/elvitegravir/emtricitabine/tenofovir disoproxil |
| DDR1 | Nilotinib |
| EPCAM | Tucotuzumab celmoleukin, catumaxomab, adecatumumab |
| ERBB2 | Trastuzumab, BMS-599626, varlitinib, XL647, CP-724,714, afatinib, pertuzumab, sapitinib, trastuzumab emtansine, lapatinib/pazopanib, lapatinib/letrozole, paclitaxel/trastuzumab, capecitabine/lapatinib, cyclophosphamide/docetaxel/epirubicin/5-fluorouracil/trastuzumab, docetaxel/trastuzumab, paclitaxel/pertuzumab/trastuzumab, trastuzumab/vinorelbine, capecitabine/trastuzumab, lapatinib/paclitaxel, |

TABLE 5-continued

Exemplary Genes Associated with Classical Subtype and Exemplary Chemotherapeutics Applicable Thereto

| Gene symbol | Possible drug(s) |
|---|---|
| | pertuzumab/trastuzumab, lapatinib/trastuzumab, neratinib, lapatinib, erlotinib |
| F5 | Drotrecogin alfa, antithrombin alfa |
| GABRP | Alphadolone, nitrazepam, adinazolam, sevoflurane, isoflurane, isoniazid, felbamate, etomidate, halothane, fluoxetine/olanzapine, estazolam, eszopiclone, quazepam, diazepam, temazepam, zolpidem, lorazepam, olanzapine, triazolam, flurazepam, midazolam, oxazepam, zaleplon, secobarbital, phenobarbital, pentobarbital, desflurane, methoxyflurane, enflurane |
| HLA-DRB1 | Apolizumab |
| ITGB5 | Cilengitide |
| KCNN4 | Betamethasone/clotrimazole, clotrimazole, senicapoc |
| KCNQ1 | Dextromethorphan/quinidine, indapamide, quinidine |
| MET | Crizotinib, tivantinib, cabozantinib, INC280, cabozantinib/erlotinib |
| MMP7 | Marimastat |
| MST1R | Crizotinib |
| MUC1 | HuHMFG1 |
| NOXO1 | Ecabet |
| P2RY2 | Suramin |
| PLA2G10 | Varespladib methyl, varespladib |
| PSCA | AGS-1C4D4 |
| RAMP1 | Pramlintide |
| SCNN1A | Hydrochlorothiazide/triamterene, amiloride, amiloride/hydrochlorothiazide, triamterene |
| SLC12A2 | Bumetanide, quinethazone |

TABLE 6

Exemplary Kinases as Therapeutic Targets for Classical and Basal Subtype tumors

| Gene Name | Description | Subtype |
|---|---|---|
| CDK1 | Cyclin-dependent kinase 1 | Basal |
| CDK6 | Cyclin-dependent kinase 6 | Basal |
| EPHA1 | Ephrin type-A receptor 1 | Basal |
| EPHB2 | Ephrin type-B receptor 2 | Basal |
| KAPCA | cAMP-dependent protein kinase catalytic subunit alpha | Classical |
| KAPCB | cAMP-dependent protein kinase catalytic subunit beta | Classical |
| KCC2D | Calcium/calmodulin-dependent protein kinase type II subunit delta | Classical |
| KGP1 | cGMP-dependent protein kinase 1 | Classical |
| LIMK1 | LIM domain kinase 1 | Basal |
| PGFRB | Platelet-derived growth factor receptor beta | Classical |
| RIPK2 | Receptor-interacting serine/threonine-protein kinase 2 | Basal |

By applying a computational approach to a large cohort of data, the presently disclosed subject matter overcame the low cellularity problem and generated new insights into the complex molecular composition of PDAC. The results disclosed herein and their prognostic values can thus provide decision support in a clinical setting for the choice and timing of treatment regimens.

Co-expression of stromal gene signatures was largely conserved across other large primary tumor datasets (The Cancer Genome Atlas Research Network, 2014a,b; Nones et al., 2014). Co-expression was particularly high in lung adenocarcinoma (The Cancer Genome Atlas Research Network, 2012b), which was previously shown to be low in purity (Carter et al., 2012) and high in stromal content (Yoshihara et al., 2013). Both expression and co-expression was low in primary acute myeloid leukemia (The Cancer Genome Atlas Research Network, 2013c), which lacks stroma.

Materials and Methods for Examples 1-8

Decomposition by Factors and Gene Ranking.

For all analyses in this manuscript, we used k=14 as the number of factors. Unsupervised NMF was performed on a gene-by-sample matrix X first with 20 randomly initialized instances of NMF using the MATLAB (MathWorks R2013a) multiplicative update NMF solver for 10 steps. The lowest-residual solution pair from these 20 instances was then used to seed NMF of X to convergence with the alternating least-squares solver. The result was a matrix of gene loadings, G, and a matrix of sample loadings, S. G and S were then scaled such that the mean of each column of G was 1 to facilitate cross-factor comparisons.

For each of the k factors, a set of distinct exemplar genes for the $i^{th}$ factor was established by ranking genes in descending order of the difference between the loading value in the $i^{th}$ column of matrix G and the largest loading value not in the $i^{th}$ column of matrix G.

200 iterations of 5-fold resampling, i.e. training on a partition of approximately 80% of the samples, were performed to achieve stable NMF results. For each of these 200 data partitions, unsupervised NMF was performed, and the genes which appeared ranked in the top 50 of any factor together were recorded in a gene by gene consensus matrix. This gene factor-co-occurrence-consensus matrix was then used as the basis of a hierarchical clustering operation using correlation as a distance metric and an appropriate cutoff as to yield k gene clusters. These k gene-clusters were used to create a seed matrix, $G_0$ such that the $i^{th}$ column of $G_0$ contained 0.01 for all genes except those in gene cluster i, which were set to 1. $G_0$ was then used to seed a final NMF using the multiplicative update solver to completion.

Gene set analysis was performed on the ranked list of genes for each factor with all sets available from MSigDB v3.1 (Subramanian et al., 2005). Sets were assessed for significance via Kolmogorov-Smirnov statistic with Benjamini-Hochberg correction. Due to the positive nature of the ranked gene list, only gene sets with positive enrichment were considered.

Patients and Samples.

Multiple samples were obtained from 15 patients with metastatic PDAC from the University of Nebraska Medical Center Rapid Autopsy Pancreatic Program, and 17 patients from Johns Hopkins Medical Institutions and the Johns Hopkins Gastrointestinal Cancer Rapid Medical Donation Program. Informed consent was obtained from all subjects. To ensure minimal degradation of tissue, organs were harvested within 3 hours post mortem and the specimens flash frozen in liquid nitrogen. The cohort further included patients with resected PDAC and/or normal tissue from Johns Hopkins Medical Institutions, Northwestern Memorial Hospital, NorthShore Hospital, and the University of North Carolina (UNC) hospitals. All samples were collected between 1999 and 2009, flash frozen in liquid nitrogen at the time of operation after approval by each individual IRB. The UNC IRB approved use of all de-identified samples for this study. Some of these samples were previously published using a different normalization procedure as part of GSE21501 (Garrido-Laguna et al., 2011). All available samples were reviewed by a single pathologist (KEV).

The microarray cohort employed herein consisted of 145 primary (125 with survival data) and 61 metastatic PDAC tumors, 17 cell lines, 47 pancreas and 89 distant site adjacent to normal samples, providing a rare diversity of tissue types with which to train our model. This data set represents an expansion from the 106 primary tumors in the previously published cohort GSE21501 (Garrido-Laguna et al., 2011) which was a bulk analysis of gene expression confined to primary tumors. The BxPC-3, MIA PaCa-2, HPAC, Panc 02.03, SW1990, HPAF-II, CFPAC-1, PANC-1, Capan-1, Capan-2, Panc 10.05, Hs 766T, Panc 03.27, and T3M4 PDAC cell lines were obtained from ATCC (Manassas, Va., United States of America). HuPT3 cells (obtained from Dan Billadeau, Mayo Clinic, Rochester, Minn., United States of America) and the immortalized human pancreatic duct-derived (HPNE) cells were described previously (Neel et al., 2014). All cell lines were authenticated via short tandem repeat profiling (Genetica), and all cell lines were *Mycoplasma* negative by indirect staining. For survival analysis, only data from patients with localized resected tumors were used. RNA sequencing was performed on an additional 15 primary tumors, 37 pancreatic cancer patient-derived xenografts (PDX), 3 cell lines (HuPT3 plus 2 PDX-derived), and 6 cancer associated fibroblast (CAF) lines derived from deidentified patients with pancreatic cancer. Expression data have been uploaded to GEO.

PDX and Derived Cells.

Fresh tumor samples from deidentified pancreatic ductal adenocarcinoma patients were obtained under protocols approved by the UNC IRB. All patient tissues were stained with hematoxylin and eosin (H&E) to confirm histology. The tumors were implanted subcutaneously into the flanks of 6-8 week old female NSG or NOD/SCID mice and subsequently passaged into other mice under protocols approved by the Institutional Animal Care and Use Committee.

Cell lines were derived from PDX as follows. At the time of passage, a section of the tumor was cut into approximately 3 mm pieces and rinsed with PBS containing penicillin and streptomycin (P/S). The tissue was minced with the GENTLEMACS™ Dissociator (Miltenyi Biotec) and incubated for 30 minutes in a Collagenase/Dispase (Roche 11097113001) solution. After incubation, mincing was repeated, the dissociation media was removed and the tissue was resuspended in DMEM/F12 media with 5 ng/ml EGF, 10 μg/ml insulin (Life Technologies, 11330-032, PHG0311 and 12585-014 respectively), 10% FBS and 1×P/S and seeded onto tissue culture treated plates. Once culture was established, differential trypsinization was used to remove the fibroblasts and the cells were seeded on gelatin coated glass coverslips for immunofluorescence confirmation. Epithelial tumor cells were confirmed based on their expression of cytokeratin 18 or 19 and EpCAM (using Abcam ab133302, ab76539 and BioLegend 324209 antibodies).

Primary CAF cell lines from tumors of patients with PDAC were isolated using the outgrowth method as follows (Bachem et al., 2005). Fresh tumor was minced into pieces no larger than 1 $mm^3$ and cultured with DMEM/Ham's F12 (1:1) media supplemented with 10% FBS. Immunofluorescence was used to confirm the presence of CAFs as defined by the presence of smooth muscle actin alpha (SMAα Santa Cruz Biotechnology 32251) and a mesenchymal marker, vimentin, (Cell Signaling 5741) as well as the absence of an epithelial marker, EpCAM (BioLegend 324209).

Statistical Analysis.

For all analyses, sample size was limited to all appropriate cases with full data (i.e., no imputation was performed to estimate missing clinical information). Disease-specific survival or recurrence free survival was analyzed using the Kaplan-Meier product-limit method and the significance of clinicopathologic or subtype variables were measured by Cox proportional hazards regression. Multi-variable associations with survival were also performed using the Cox proportional hazards regression method. When more than 2 survival cohorts were compared, the log-rank test was used to assess global differences in survival. Fisher's exact test was used to analyze associations between 2 categorical variables. For continuous variables, e.g. stain intensity, factor weights, unpaired two-tailed two-sample t-tests were performed under the equal variance assumption. Box and whiskers plots show median, quartiles and range of continuous data to demonstrate variability of data and demonstrate degree of normality. Unless otherwise mentioned, sample to sample or gene to gene similarities were measured by correlation based on $\log_2$ transformed gene expression after normalizing each gene's expression to have a mean of zero and variance of one. Unless otherwise noted, clustering was done via consensus clustering of row-normalized gene expression. Consensus clustering consisted of 1000 iterations of k-means clustering, with 50% feature hold-out at each iteration, followed by hierarchical clustering of the consensus matrix with average linkage.

Microarray Data.

All RNA isolation and hybridization was performed at UNC on Agilent human whole genome 4x44K microarrays (Agilent Technologies). RNA was extracted from macrodissected snap-frozen tumor samples using Allprep Kits (Qiagen) and quantified using nanodrop spectrophotometry (ThermoScientific). RNA quality was assessed with the use of the Bioanalyzer 2100 (Agilent Technologies). RNA was selected for hybridization using RNA integrity number and by inspection of the 18S and 28S ribosomal RNA. Similar RNA quality was selected across samples. One microgram of RNA was used as a template for cDNA preparations. cDNA was labeled with Cy5-dUTP and a reference control (Stratagene) was labeled with Cy3-dUTP using the Agilent low RNA input linear amplification kit (Agilent Technologies) and hybridized overnight at 65 uC to Agilent 4x44 K whole human genome arrays (Agilent Technologies). Arrays were washed and scanned using an Agilent scanner (Agilent Technologies).

Arrays were annotated using GEO platform GPL4133, and analyzed using $\log_2$ background corrected Cy5 signal to maintain positivity. Multiple probes mapping to the same gene symbol were collapsed by mean probe expression. Samples were normalized to each other via quantile normalization.

RNAseq.

200-1000 ng of total RNA was used to prepare libraries with the TruSeq Stranded mRNA Sample Prep Kit (Illumina). 75*b* paired-end reads were sequenced on a NextSeq 500 Desktop Sequencer using a high output flow cell kit (Illumina). Reads were separated by species of origin using Xenome (Conway et al., 2012). Human or mouse specific reads were then aligned and quantified using Tophat2 (Kim et al., 2013), Cufflinks (Trapnell et al., 2012), hg 19, mm10, and the UCSC knownGene transcript and gene definitions see the UCSC Genome Browser Gateway available on the website of the University of California at Santa Cruz). mRNA gene expression was analyzed as $\log_2(1+\text{FPKM})$, and KRAS mutation status was determined by manual curation of aligned human reads.

Validation Data Sets.

Gene expression array data from resected primary tumor samples from the Australian Pancreatic Cancer Genome Initiative and International Cancer Genome Consortium (ICGC) data were obtained from GSE50827 (Biton et al., 2014). Associated open access clinical data were obtained from the ICGC data portal, ÷ release 16 at the ICGC website. Patients with death events before 30 days were assumed to have postoperative complications and were censored. Patients with metastases were excluded from survival analyses. Genomic subtypes, mutations, and amplifications were obtained from supplemental materials available from Waddell et al., 2015.

Normalized gene expression, survival data, and PAM50 (Stolze et al., 2015) classification from primary breast cancer (Perou) samples (n=295) as part of the UNC337 set were obtained from GSE18229 (Dal Molin et al., 2015).

Normalized RNAseq expression data of 845 primary tumor data were obtained as described by Hoadley et al., 2014 from the website of The Cancer Genome Atlas (TCGA) Program of the National Cancer Institute (Zhong et al., 2015), Normalized RNAseq gene expression and partial survival data from 223 urothelial bladder carcinoma (BLCA) samples were obtained from the website of The Cancer Genome Atlas (TCGA) Program of the National Cancer Institute Alexandrov et al., 2013b). Samples were classified as basal or luminal with BASE47 classifications provided by Damrauer et al. (Isella et al., 2015).

Example 1

Virtual Microdissection of PDAC

Gene expression in a cohort of microarray data from 145 primary and 61 metastatic PDAC tumors, 17 cell lines, 47 pancreas and 89 distant site adjacent normal samples were analyzed using Agilent (Agilent Technologies) human whole genome 4x44K DNA microarrays (106 primary tumors were previously used in a separate analysis of gene expression (GSE2150115; Stratford et al., 2010). To validate the findings, further RNA sequencing was performed on 15 primary tumors, 37 pancreatic cancer patient-derived xenografts (PDX), 3 cells lines, and 6 cancer associated fibroblast (CAF) lines derived from deidentified patients with pancreatic cancer. Histology of all available samples was reviewed by a single blinded pathologist (KEV). Table 7 summarizes the demographic and clinical characteristics of patients in our cohorts.

TABLE 7

Demographics and Univariate Cox Analysis

| | | All | Resected with Survival | Univariate Cox p-value | Microarray Primary | RNAseq Primary | RNAseq PDX |
|---|---|---|---|---|---|---|---|
| Race | Caucasian | 128 | 121 | 0.507 | 99 | 9 | 25 |
| | African-American | 23 | 18 | 0.333 | 10 | 3 | 8 |
| | Other | 8 | 7 | 0.821 | 5 | 0 | 3 |
| Gender | F | 90 | 83 | 0.348 | 67 | 5 | 23 |
| | M | 80 | 68 | 0.348 | 55 | 8 | 14 |
| T | T1 | 4 | 4 | 0.420 | 2 | 1 | 2 |
| Stage | T2 | 22 | 20 | 0.530 | 20 | 2 | 5 |
| | T3 | 131 | 122 | 0.743 | 91 | 9 | 28 |
| | T4 | 1 | 1 | 0.115 | 1 | 0 | 0 |
| N Stage | N0 | 49 | 43 | 0.068 | 36 | 7 | 10 |
| | N1 | 112 | 106 | 0.068 | 80 | 5 | 25 |
| M | M0 | 160 | 149 | — | 129 | 12 | 35 |
| Stage | M1 | 15 | 0 | — | 14 | 0 | 1 |
| Adjuvant | Yes | 74 | 70 | 0.055 | 44 | 5 | 21 |
| Therapy | No | 30 | 28 | 0.055 | 27 | 3 | 7 |
| Differentiation | Well | 16 | 13 | 0.940 | 16 | 0 | 1 |
| | Moderate | 49 | 47 | 0.398 | 49 | 1 | 3 |
| | Poor | 34 | 31 | 0.407 | 34 | 1 | 2 |
| PDX | Graft Success | 44 | 37 | 0.164 | 11 | 8 | 37 |
| | Graft Failure | 18 | 12 | 0.164 | 9 | 3 | 0 |
| Margin | Positive | 58 | 52 | 0.026 | 34 | 5 | 17 |
| | Negative | 93 | 88 | 0.026 | 75 | 7 | 17 |
| TOTAL | | 193 | 163 | | 143 | 15 | 37 |

Example 2

NMF Distinguishes Normal and Tumor Compartments

Figure 3A:
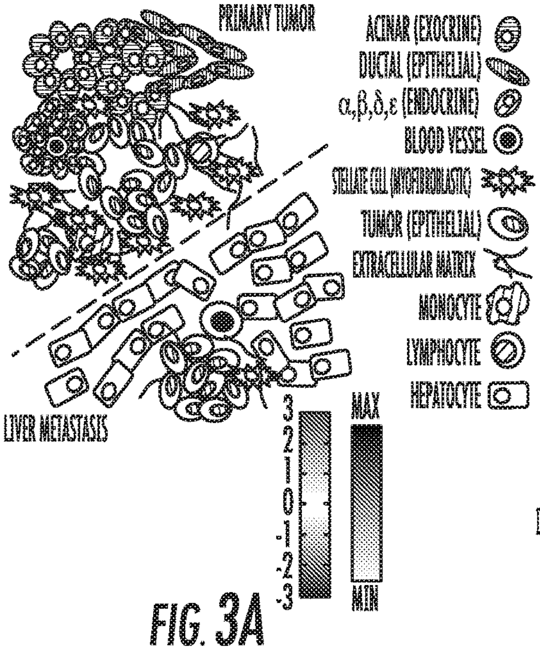
FIGS. 3A-3D depict the results of Successful Deconvolution of Normal Tissue with NMF.
Figure 3B:
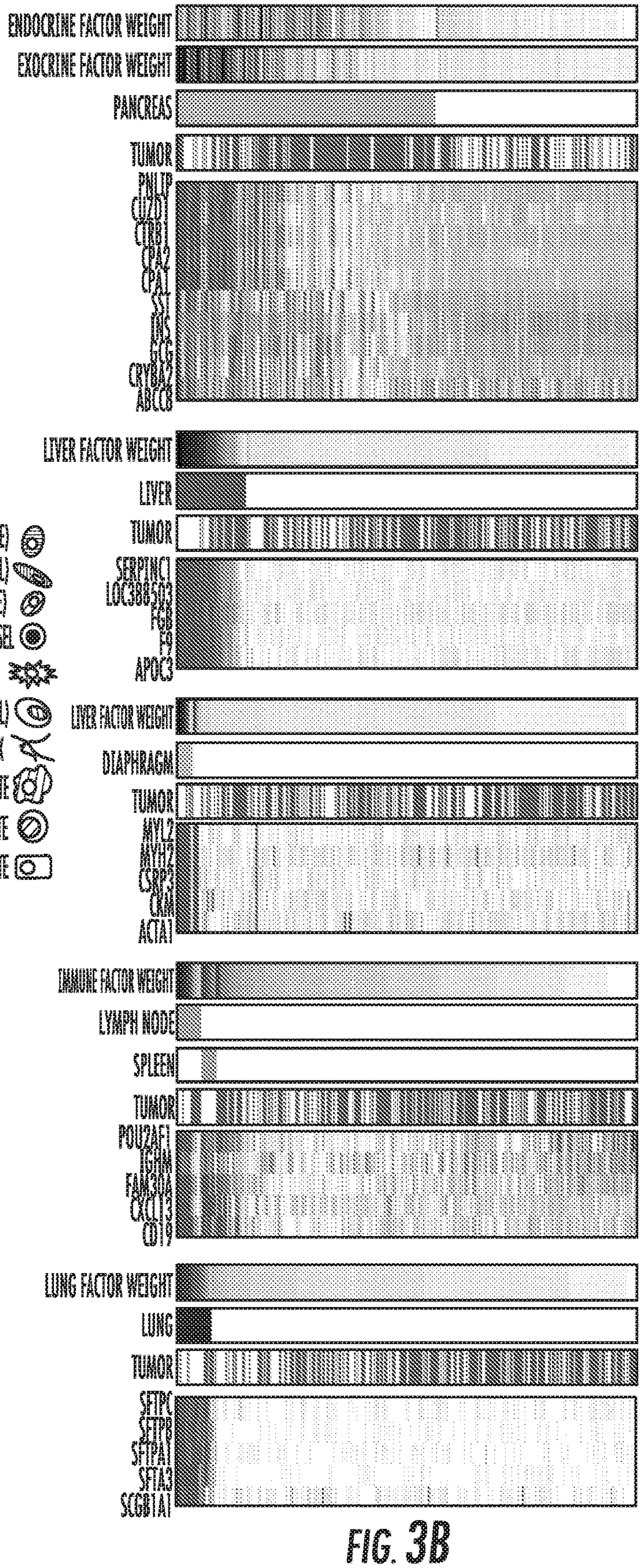
Figure 3C:
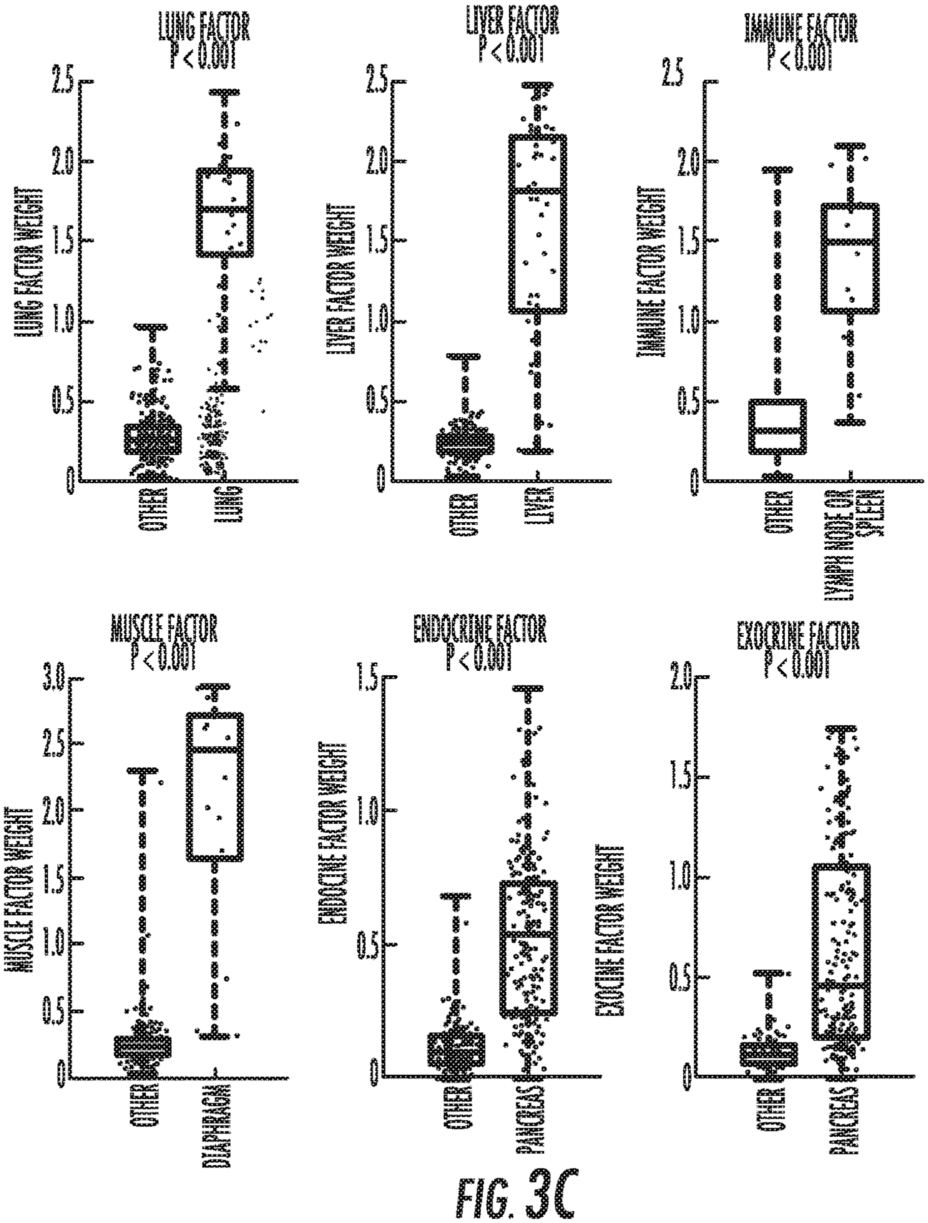
Figure 5:
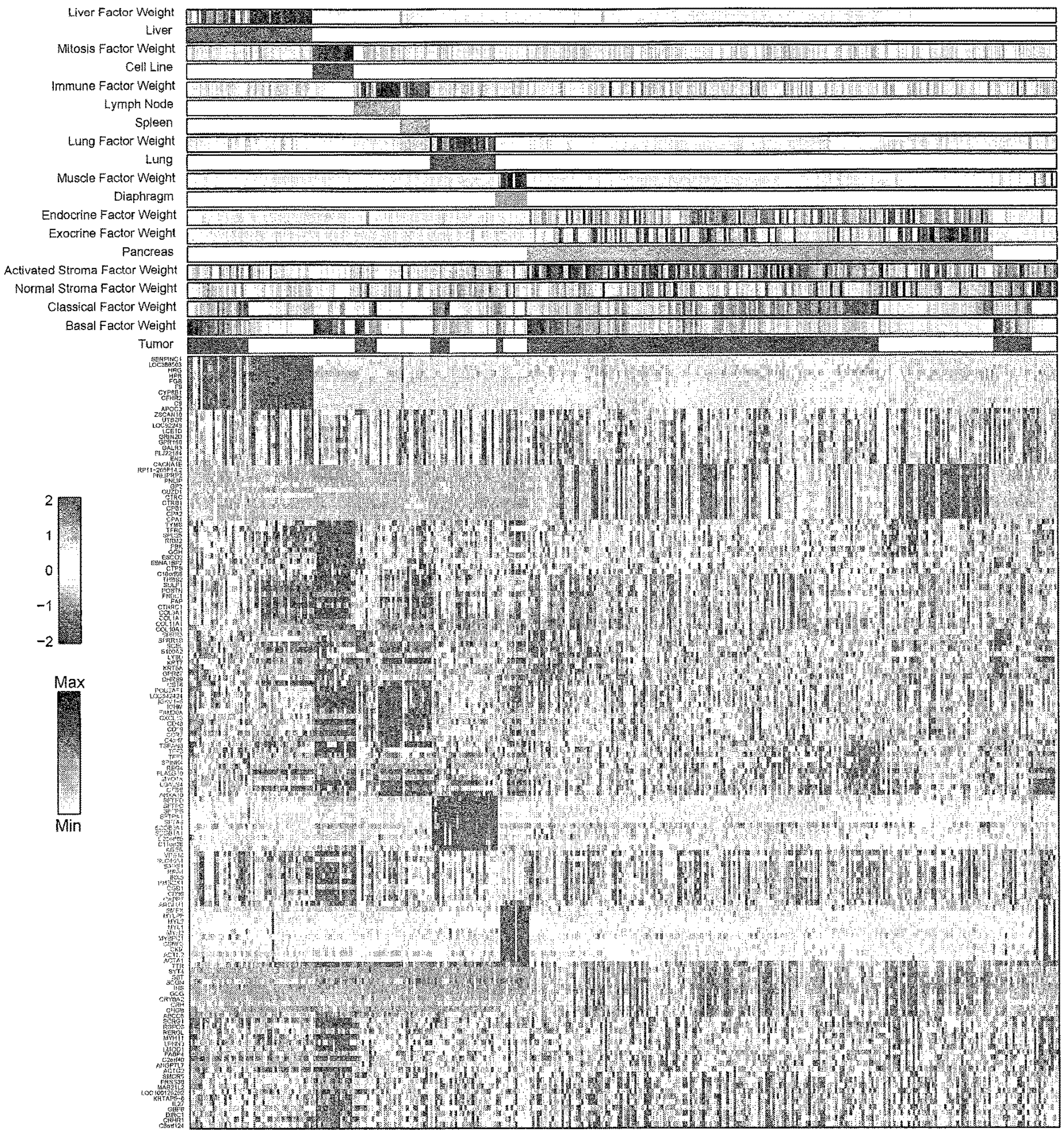
FIG. 5 depicts deconvolution of a large cohort of PDAC revealed distinct gene expression patterns from multiple tissue types. Solid color bars above the heat map show the tissue of origin and tumor status of the samples, which were used to order the samples horizontally. Factor weights derived by NMF for selected factors are shown as grayscale bars. Heat maps show Z-normalized gene expression of five exemplar genes from each factor. All tumors, cell lines, and adjacent normal tissues from the present cohort are shown.

A key obstacle in the analysis of gene expression data, particularly in PDAC, is the removal of confounding normal or stroma gene expression from local and distant organ sites. FIGS. 1A-1D shows example histology of samples with both tumor, normal, and stromal tissue. NMF was employed to identify gene expression which we attribute to normal pancreas, liver, lung, muscle, and immune tissues. Expression of exemplar genes from these factors, i.e., genes with distinctly large weights in a single column of G, as well as factor weights for the samples, i.e., rows of S, showed excellent agreement with known tissue labels (see FIG. 3B, FIG. 3C, and FIG. 5). Investigation of the exemplar genes from these factors further confirmed their role as confounding normal tissue. For example, using the Kolmogorov-Smirnov test, the top-weighted genes from the liver factor showed significant ($p<10^{-10}$) enrichment in the MSigDB term SU_LIVER, and the highest weighted gene, fibrinogen beta (FGB), was specifically expressed in normal human liver tissue.

In addition to normal tissue from distant organs, two factors were identified that were exclusive to pancreas tissue, but were differentiated from each other by their respective gene lists. One factor described endocrine function including expression of glucagon and insulin (GCG and INS), while the other factor described exocrine function including expression of digestive enzyme genes such as pancreatic lipase, PNLIP. This unsupervised discovery of two molecularly distinct yet highly co-localized factors related to normal pancreatic function represented an important proof of concept in the use of NMF to identify novel features without pre-defined expression knowledge.

Figure 3D:
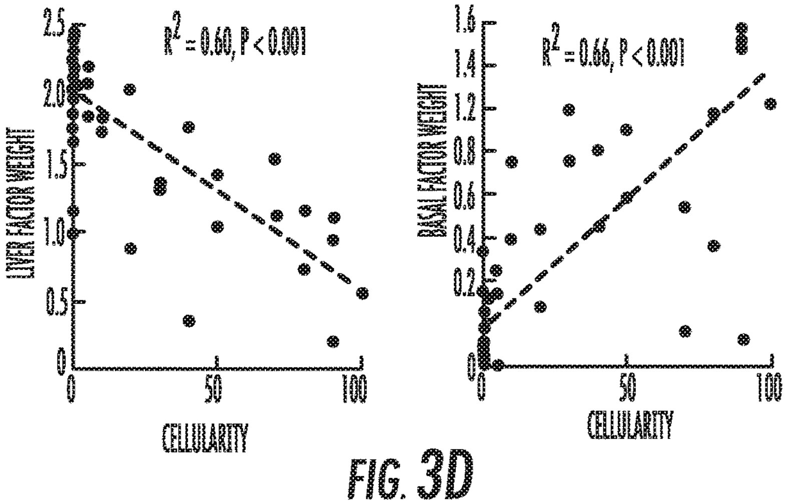
Figure 6:
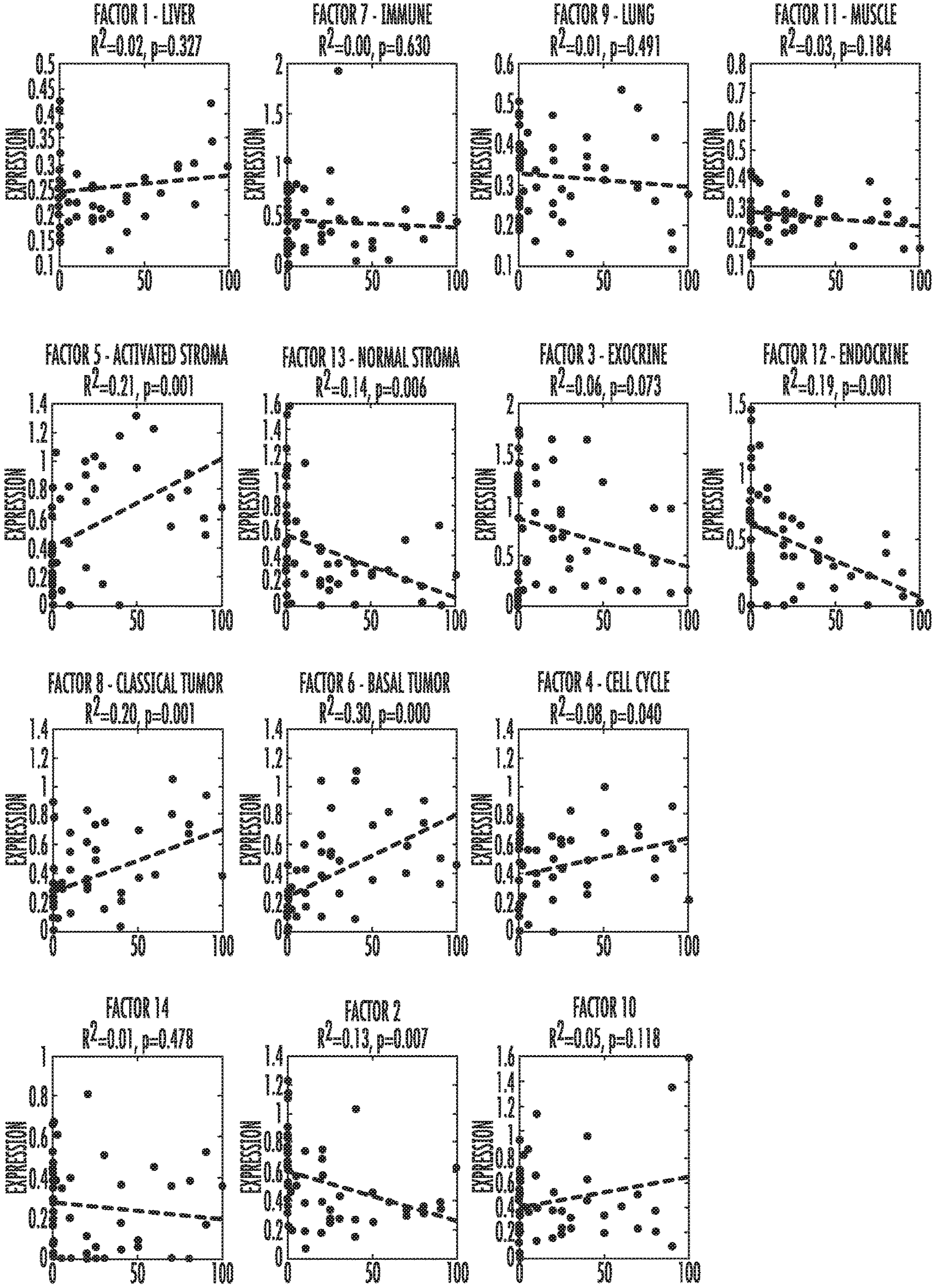
FIG. 6 depicts a correlation of pathology assessments of tumor with factor weights in normal pancreas and primary tumors. Horizontal axes all show tumor cellularity, while vertical axes show factor weight. Red dashed lines show best linear fits. p values are given for each $R^2$.
Figure 7:
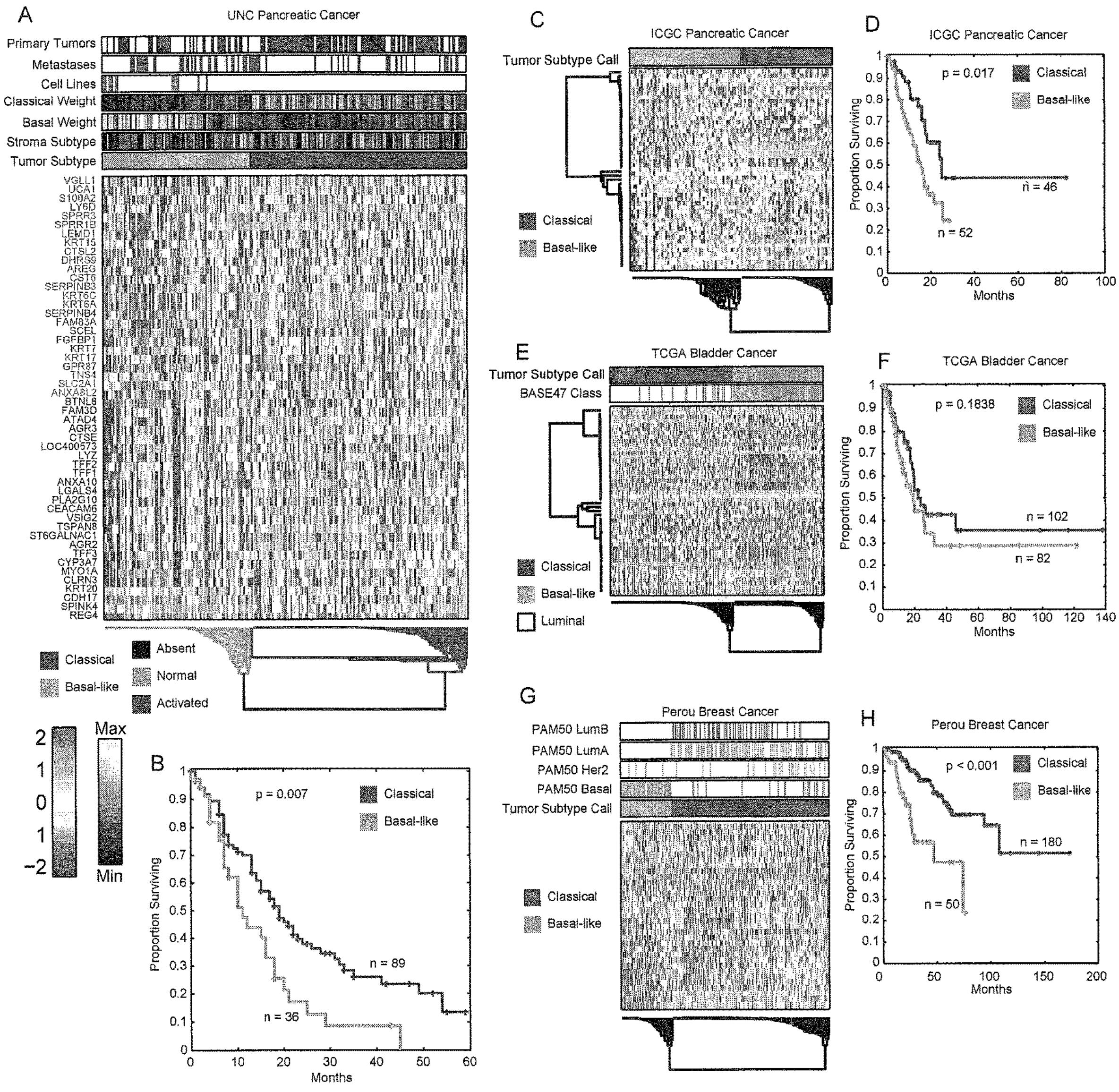
FIGS. 7A-7H depict the results of a series of experiments that showed that tumor specific gene expression suggested two subtypes of PDAC with similarities to other tumor types.
Figure 8:
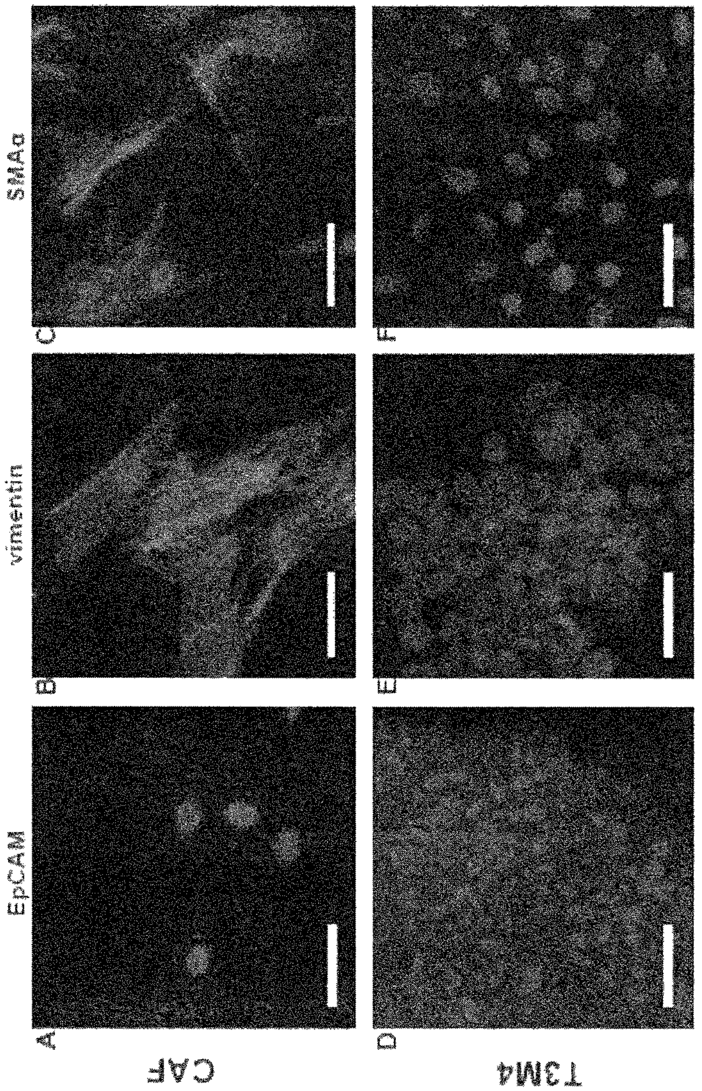
FIGS. 8A-8F are a series of immunofluorescence images of Cancer Associated Fibroblasts (CAFs). Staining using antibodies against EpCAM (FIG. 8A), vimentin (FIG. 8B), and SMAα (FIG. 8C).

To validate the normal expression signatures disclosed herein, all available samples were reviewed by a single pathologist to independently assess the amount of tumor, normal, and stroma cellularity. It was determined that many factor weights were correlated or anti-correlated to tumor cellularity (FIG. 6). Among normal and metastatic liver samples, for example, tumor-specific basal-like factor weights were correlated with cellularity, whereas the normal-specific liver factor weight was inversely related to the tumor content of a sample (FIG. 3D). These findings support the hypothesis that factor weights obtained from NMF were quantitatively indicative of underlying sample composition.

Example 3

Identification of Stroma-Specific Subtypes

Figure 4:
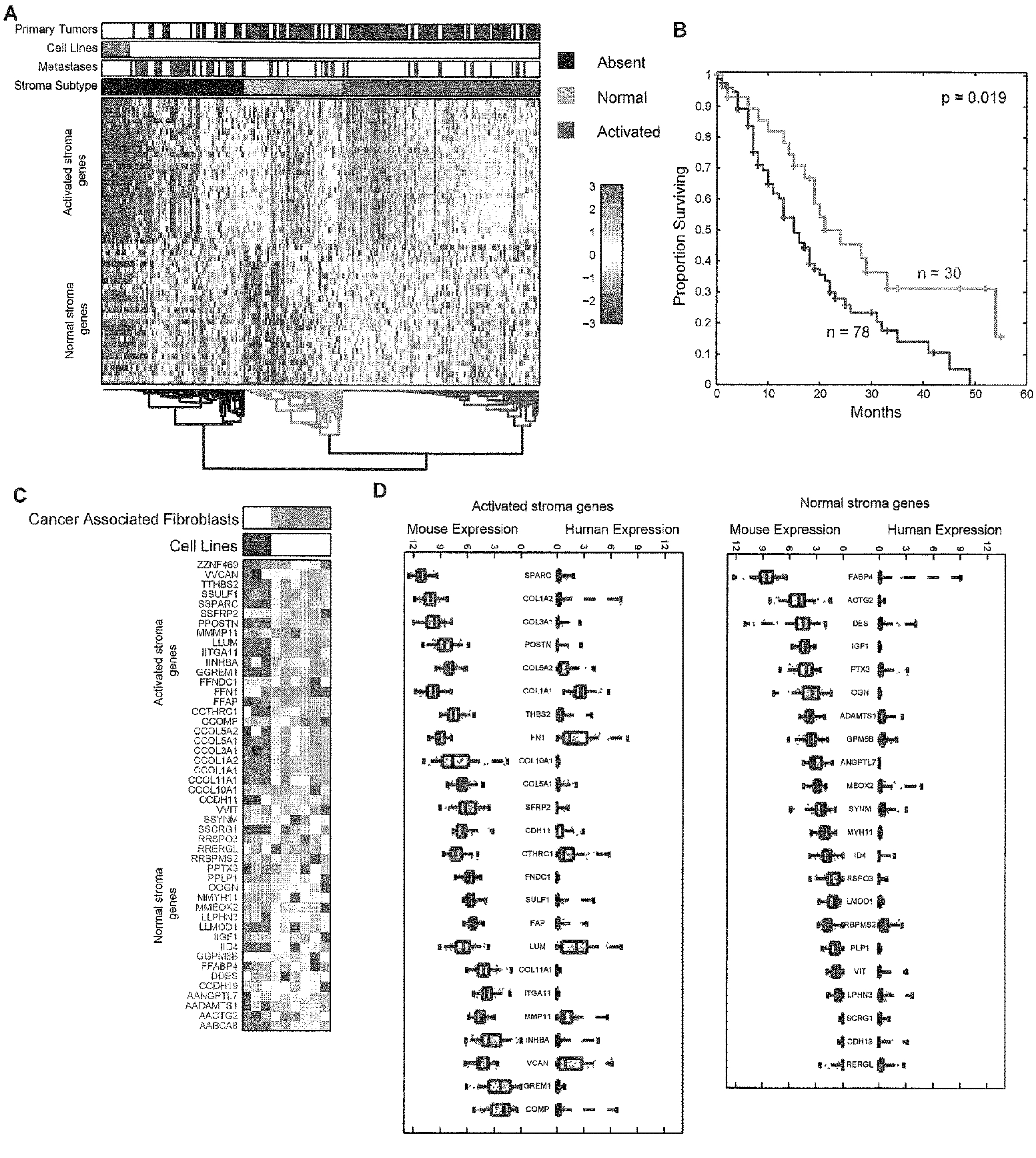
FIGS. 4A-4D depict the results of a series of experiments that demonstrated that a dual action of stroma is described by distinct gene expression patterns which are not expressed in cell lines.

Stroma is particularly important in PDAC. According to pathology assessments, stroma varies, and comprises on average 48% of the primary tumor samples employed herein, with a standard deviation of 30%. The instant analysis identified two factors which described gene expression from the stroma, which were distinctly different from the normal factors shown in FIGS. 3A-3D. Consensus clustering on exemplar genes from these two stroma factors divided tumor samples into two stromal subtypes, which were classified as “normal” and “activated” (FIG. 4A). Patients with samples with an activated stroma subtype had worse median survival (15 months) and 60% 1-year survival, when compared to patients with a normal stroma subtype (median 24 months, 1-year survival 82%; FIG. 4B). Both were notably absent in PDAC cell lines (FIG. 4C), which exhibited a distinct mitotic expression signature associated with mitotic checkpoints and DNA replication (Table 8). Whitfield et al., 2002. The fact that cell lines do not express these stromal factors and many metastatic samples do express them at low levels suggested that these genes were not expressed by the tumor epithelium. To further validate the stromal origin of these gene expression signatures, 6 CAF lines were isolated from primary tumors (FIGS. 8A-8F), and it was determined that they robustly overexpressed the stromal signatures disclosed herein as compared to PDAC tumor cell lines which had no expression of the stromal signatures (FIG. 4C).

The vast majority of collagen gene expression was attributable to stromal compartments, with the lone exception being COL17A1, which was high in tumors. “Normal” stroma was characterized by relatively high expression of known markers for pancreatic stellate cells, smooth muscle actin, vimentin, and desmin, (ACTA2, VIM, and DES). Stellate cells have been shown to promote cancer cell survival in vitro (Froeling et al., 2011), but at the same time may restrain PDAC in mouse models (Özdemir et al., 2014; Rhim et al., 2014), or inhibit delivery of chemotherapy (Olive et al., 2009). In patients, the ratio of smooth muscle actin stained area to the collagen-stained area has been shown to be predictive of poor outcomes (Erkan et al., 2008). “Activated” stroma was characterized by a more diverse set of genes associated with macrophages, such as the integrin ITGAM, and the chemokine ligands CCL13 and CCL18. “Activated” stroma also expressed other genes which point to its role in tumor promotion, including the secreted protein SPARC, WNT family members WNT2, and WNT5A, gelatinase B (MMP9), and stromelysin 3 (MMP11). The presence of fibroblast activation protein (FAP) in the activated stroma, which has previously been related to worse prognosis, suggested that an activated fibroblast state may be partially responsible for the poor outcomes for these patients (Cohen et al., 2008). This observation led to the hypothesis that the “normal” stroma factor may describe a “good” version of stroma and that “activated” stroma factor may describe the activated inflammatory stromal response that has been seen in previous studies to be responsible for disease progression (Hwang et al., 2008; Vonlaufen et al., 2008; Herrera et al., 2013). The multifactor analysis disclosed herein supported a complex, multi-gene model of stroma in PDAC, which may explain why single gene analysis has yielded mixed results.

Example 4

Identification of Tumor-Specific Subtypes

Figure 9:
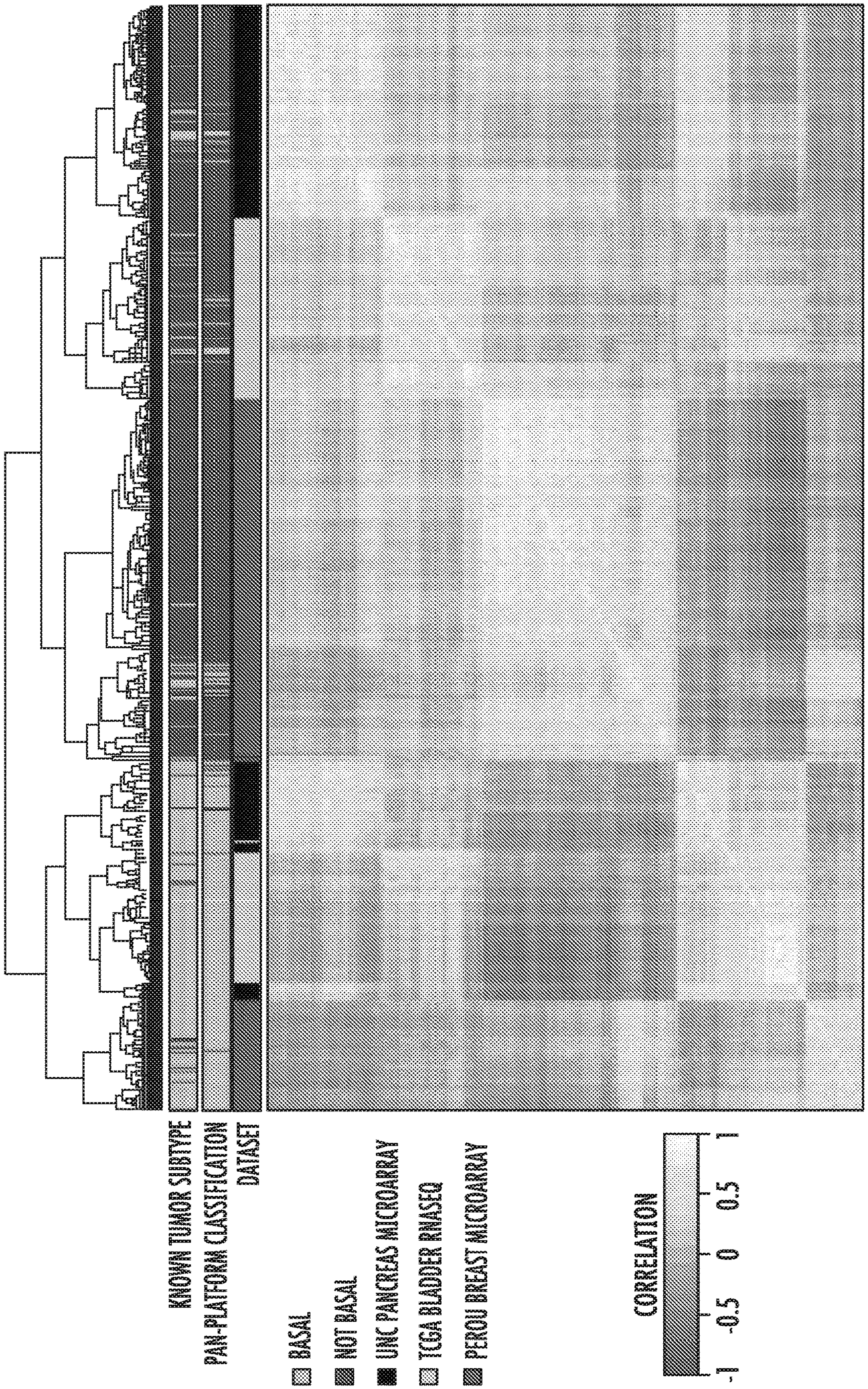
FIG. 9 is a hierarchical clustering of Spearman correlation of samples from UNC, TCGA Bladder, and Perou data sets showing similarities among basal-like subtype samples. Color bars above the heat map show subtype, either from original publication (Known Tumor Subtype), or from the cross-platform classifier (Pan-platform classification).

Independent of normal and stromal factors, it was determined that two tumor-specific factors define “classical” and “basal-like” subtypes of PDAC. When the presently disclosed samples were split into the two tumor subtypes (FIG. 7A), patients with basal-like subtype tumors had an overall worse median survival of 11 months and 44% 1-year survival compared to 19 months and 70% 1-year survival for those with classical subtype tumors (p=0.006, FIG. 7B). All cell lines assayed in this study (p<0.001), as well as a majority of metastatic samples (p=0.002), were classified as “basal-like”, suggesting that cell line models represent only one subset of PDAC. These subtypes as well as their prognostic and/or diagnostic value were independently validated within the recently published International Cancer Genome Consortium (ICGC) PDAC microarray data set (FIGS. 7C and 7D; Nones et al., 2014). Genes from the "basal-like" factor, including laminins and keratins, were also consistent with basal subtypes previously defined in bladder (Rubio-Viqueira et al., 2006; Alexandrov et al., 2013b; Isella et al., 2015) and breast (Stolze et al., 2015) cancers (FIGS. 7E-7H). Interestingly, genes from the "basal-like" subtype reproduced subtype calls ($p<0.001$) in breast cancer, had prognostic value in breast cancer samples ($p<0.001$) and reproduced previous subtype calls in bladder cancer ($p<0.001$). Given these promising results, a single-sample cross-platform classifier of basal-like subtype which was trained on the presently disclosed microarray was developed, TCGA bladder, and Perou breast cancer data, with a 93% cross validation accuracy, which was able to classify TCGA breast cancer data with 92% accuracy during external validation (FIG. 9).

Figure 10:
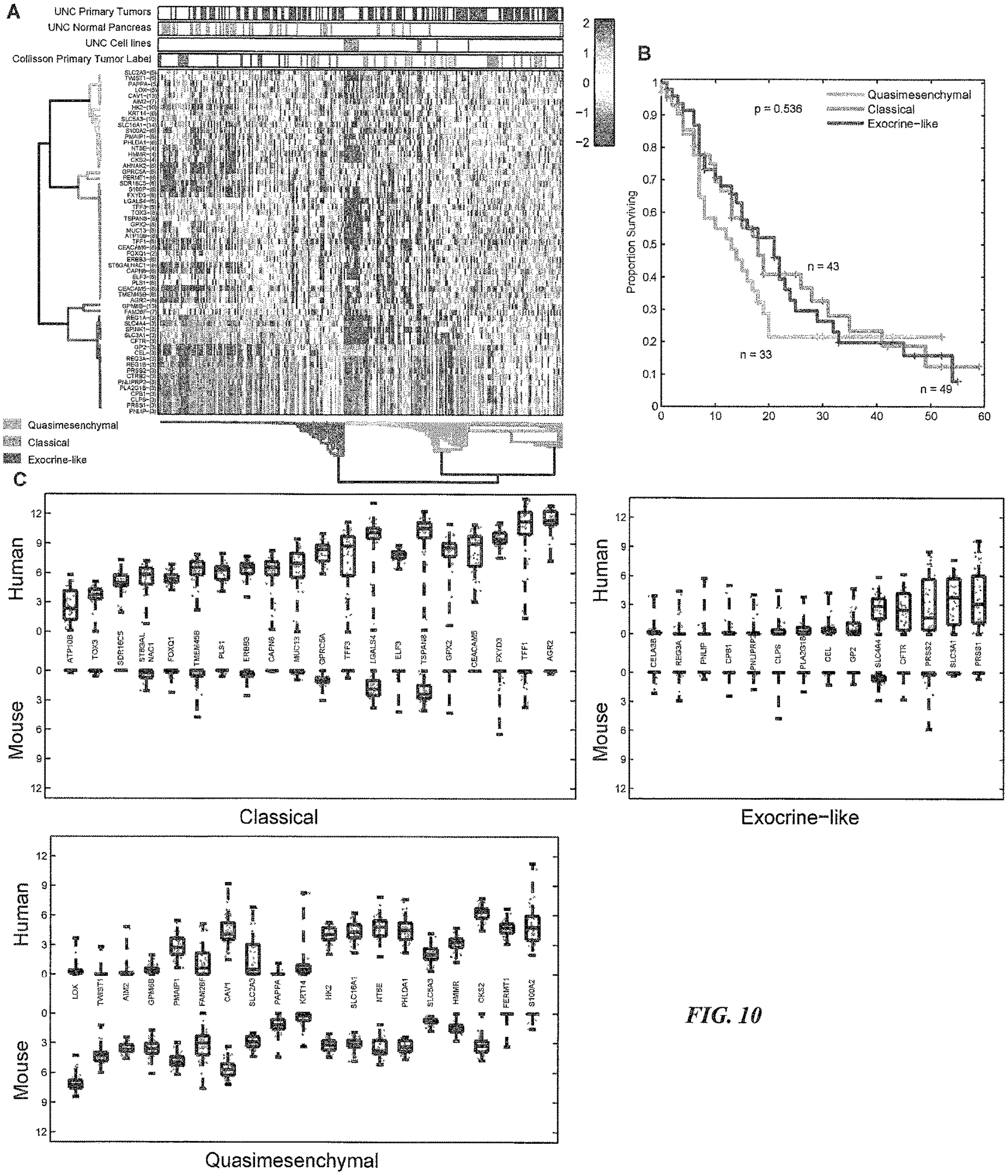
FIGS. 10A-10C depict comparisons to the subtypes disclosed in Collisson et al., 2011.

Potential subtypes of PDAC have previously been described by Collisson et al., 2011. The published exemplar genes were employed for "exocrine-like", "classical", and "quasimesenchymal" subtypes to cluster normal pancreas, cell lines, and primary PDAC tumors from the presently disclosed cohort (FIG. 10A). The three previous classifications were also observed in the data presented herein, but none held prognostic power either by cluster label or by supervised classification with PAM (FIG. 10B; Ihle et al., 2012). Furthermore, inclusion of the Collisson et al. subtypes into a multivariate Cox regression with the proposed tumor subtypes described herein did not remove the predictive power of the presently disclosed subtyping ($p=0.014$). By cross-referencing the genes from Collisson et al.'s model with the NMF model disclosed herein, three key findings were observed. First, "exocrine-like" genes overlapped with genes from the exocrine pancreas factor (17/17). Tumors in this cluster had expression indistinguishable from adjacent normal samples from the presently disclosed data set. Second, Collisson et al.'s "classical" genes overlapped with the "classical" subtype genes disclosed herein (20/22), for which the naming convention "classical" was retained herein. Third, the gene set associated with "quasimesenchymal" subtype appeared to be a mixed collection of genes from the presently disclosed "basal-like" tumor (6/20) and stromal subtypes (6/20). Thus, the appearance of stromal factors in the Collisson et al. list of "quasimesenchymal" class genes may explain the apparent mesenchymal-like gene expression that was observed.

Figure 11:
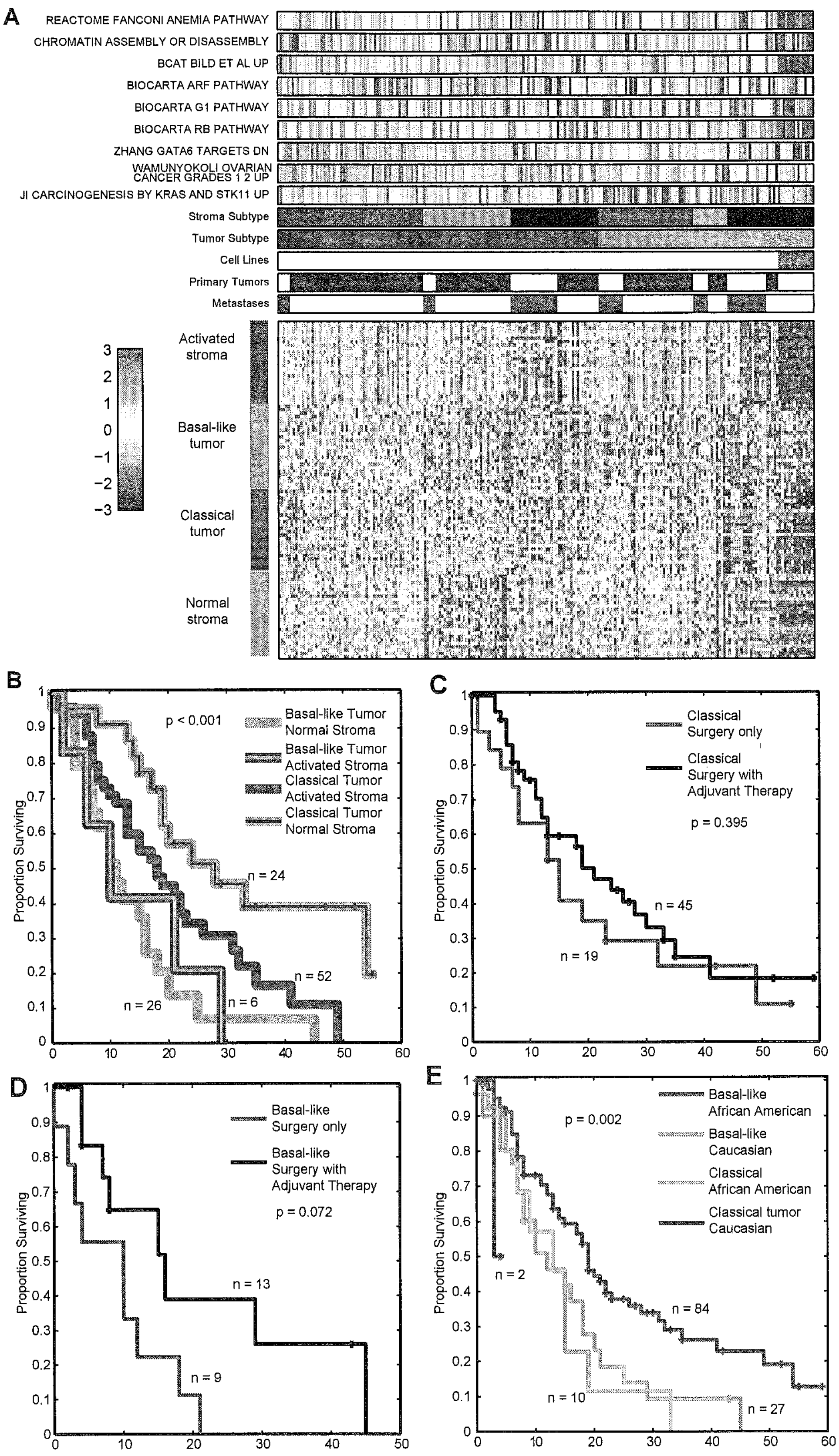
FIGS. 11A-11E depict the results of multivariate survival analysis of tumor and stromal subtypes.
Figure 12A:
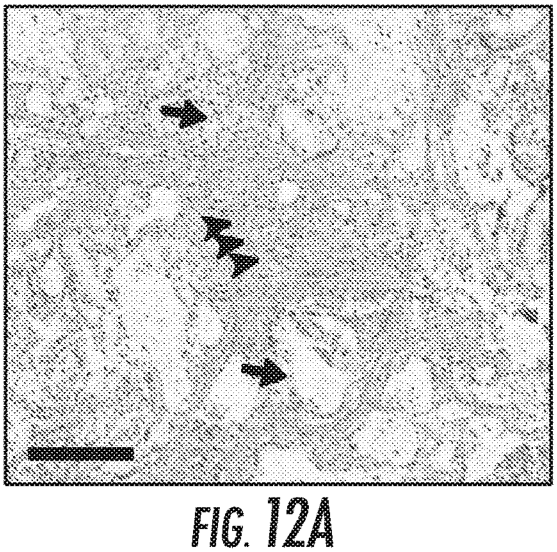
FIGS. 12A-12D are a series of immunohistochemical panels of Collagen I staining to define mouse stroma in PDX.
Figure 12B:
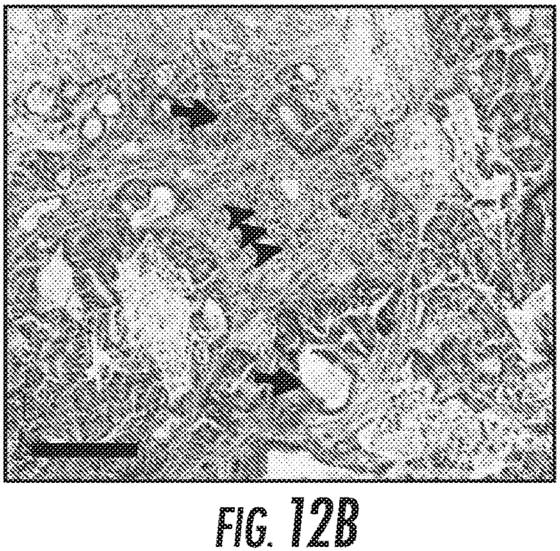
Figure 12C:
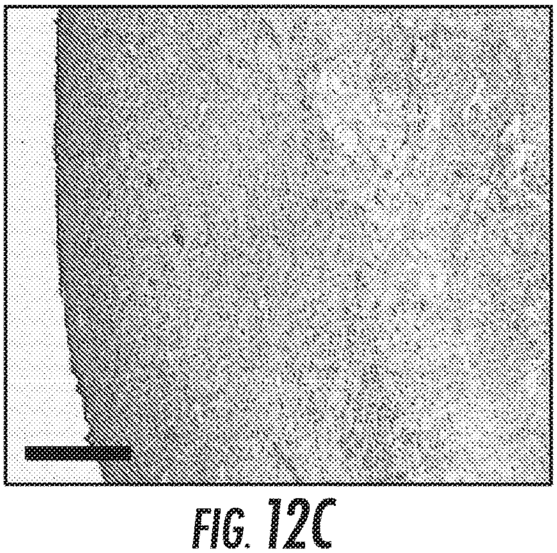
Figure 12D:
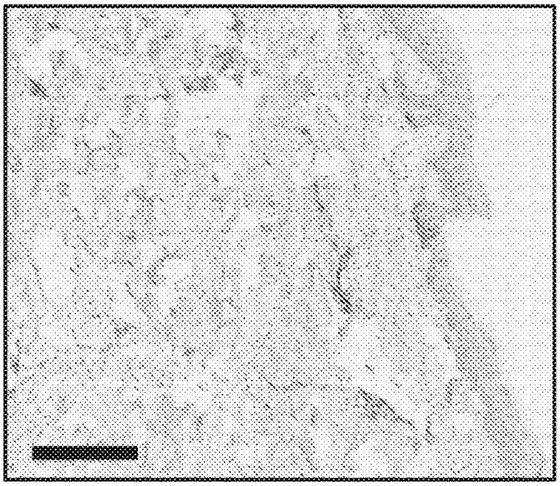

"Basal-like" and "classical" tumors were found within both "normal" and "activated" stroma subtypes (FIG. 11A). Differential prognosis among tumor and stroma subtypes was cumulative, as "classical" subtype tumors with "normal" stroma subtypes ($n=24$) had the lowest hazard ratio of 0.39 with and a 95% CI of [0.21, 0.73], while the "basal-like" subtype tumors with "activated" stroma subtypes ($n=26$) had the highest hazard ratio of 2.28 with a 95% CI of [1.34, 3.87] (FIG. 11B). In a multivariate Cox regression model, which included tumor subtypes, stromal subtypes, and clinical variables (gender, race, T stage, N stage, margin status, adjuvant therapy, histological grade, and age), both classifications were independently associated with survival (stroma subtypes: $p=0.037$, tumor subtypes: $p=0.003$).

Although basal-like subtype tumors have a worse prognosis, patients with basal-like subtype tumors showed a strong trend towards better response to adjuvant therapy ($p=0.072$; FIG. 11C). Among basal-like subtype patients, adjuvant therapy provided a hazard ratio of 0.38, (95% CI of [0.14, 1.09]), while in patients with classical subtype tumors, adjuvant therapy is associated with a hazard ratio of only 0.76 (95% CI [0.40, 1.43]). In the presently disclosed cohort, there was no association of most clinical variables (race, gender, T stage, N stage, differentiation, or tumor cellularity) with survival, although positive nodal status trended towards significance, and positive margin status was significantly associated with worse survival (Table 7). Table 8 shows two-way associations of all subtype calls with clinical and pathological information from the presently disclosed cohort of PDAC patients. No association of tumor or stroma subtype with standard clinical or pathological variables was found, with the notable exception of mucinous features.

TABLE 8

Summary of Associations with Clinical Covariates and Subtypes

| | | Tumor Subtype | | Fischer's | Stroma Subtype | | Fischer's |
|---|---|---|---|---|---|---|---|
| | Covariate | Classical | Basal-like | Exact p-value | Normal | Activated | Exact p-value |
| Race | Caucasian | 90 | 27 | 0.521 | 26 | 65 | 1 |
| | African-American | 13 | 2 | | 3 | 7 | |
| Gender | F | 64 | 19 | 0.849 | 17 | 43 | 1 |
| | M | 50 | 16 | | 15 | 36 | |
| T | T2 | 16 | 6 | 0.590 | 5 | 14 | 1 |
| Stage | T3 | 87 | 25 | | 25 | 59 | |
| N | N0 | 35 | 9 | 0.532 | 11 | 22 | 0.649 |
| Stage | N1 | 72 | 25 | | 21 | 54 | |
| Margin | Positive | 38 | 8 | 0.385 | 7 | 22 | 0.629 |
| | Negative | 65 | 22 | | 22 | 49 | |
| Adjuvant | Yes | 48 | 13 | 0.437 | 10 | 30 | 0.769 |
| Theraphy | No | 21 | 9 | | 5 | 19 | |
| Differentiation | Poor | 23 | 11 | 0.479 | 11 | 18 | 0.203 |
| | Well | 49 | 16 | | 13 | 44 | |
| Extracellular | Low Mucin | 49 | 24 | 0.042 | 18 | 43 | 0.792 |
| Mucin | High Mucin | 23 | 3 | | 6 | 19 | |
| Stroma | Normal | 31 | 8 | 0.144 | | | |
| | Activated | 57 | 31 | | | | |

Example 5

Tumor-Specific Subtypes Found in Patient-Derived Xenografts

Figure 13:
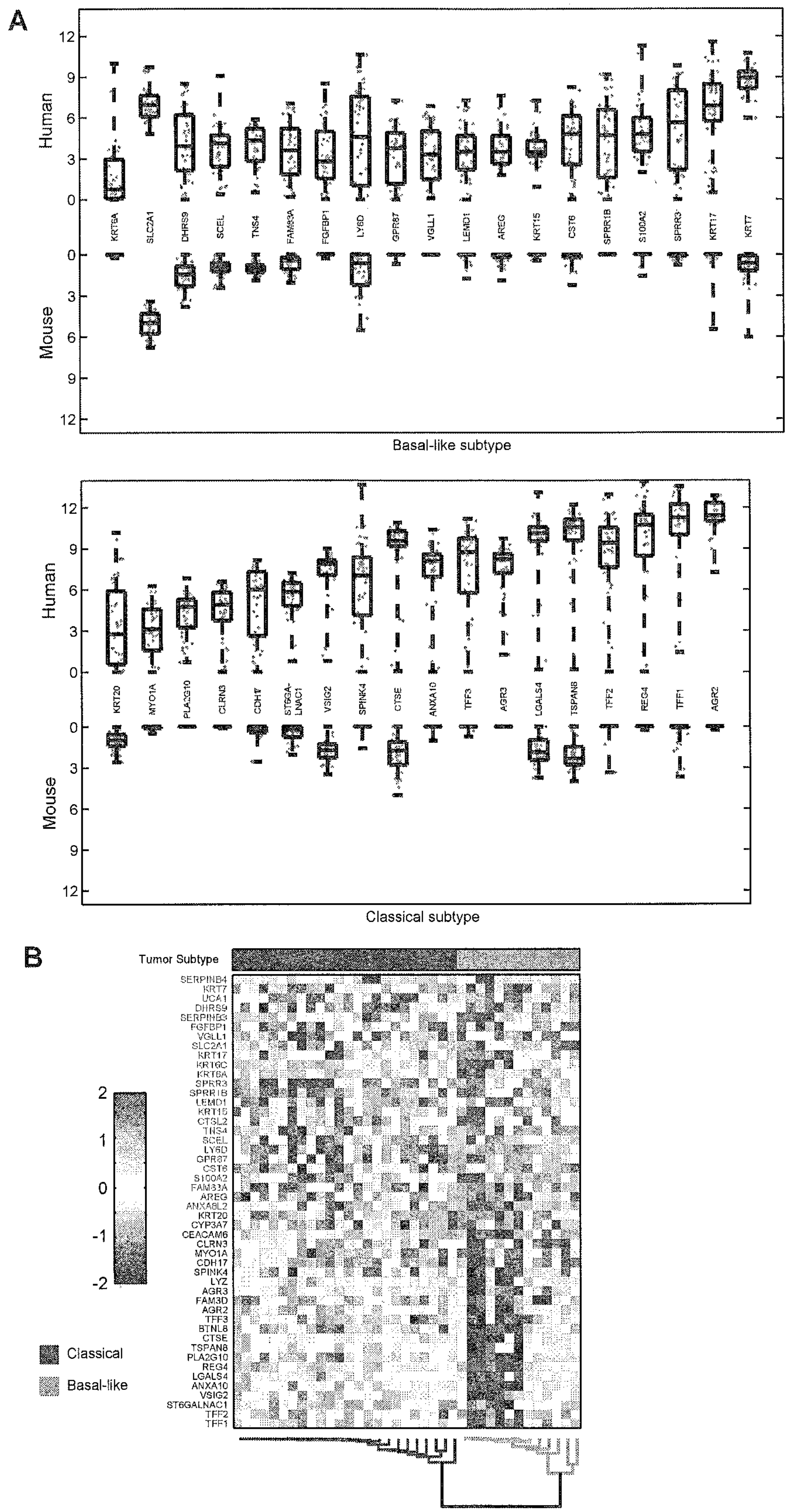
FIGS. 13A and 13B depict the results of tumor gene expression in PDX models.
Figure 14:
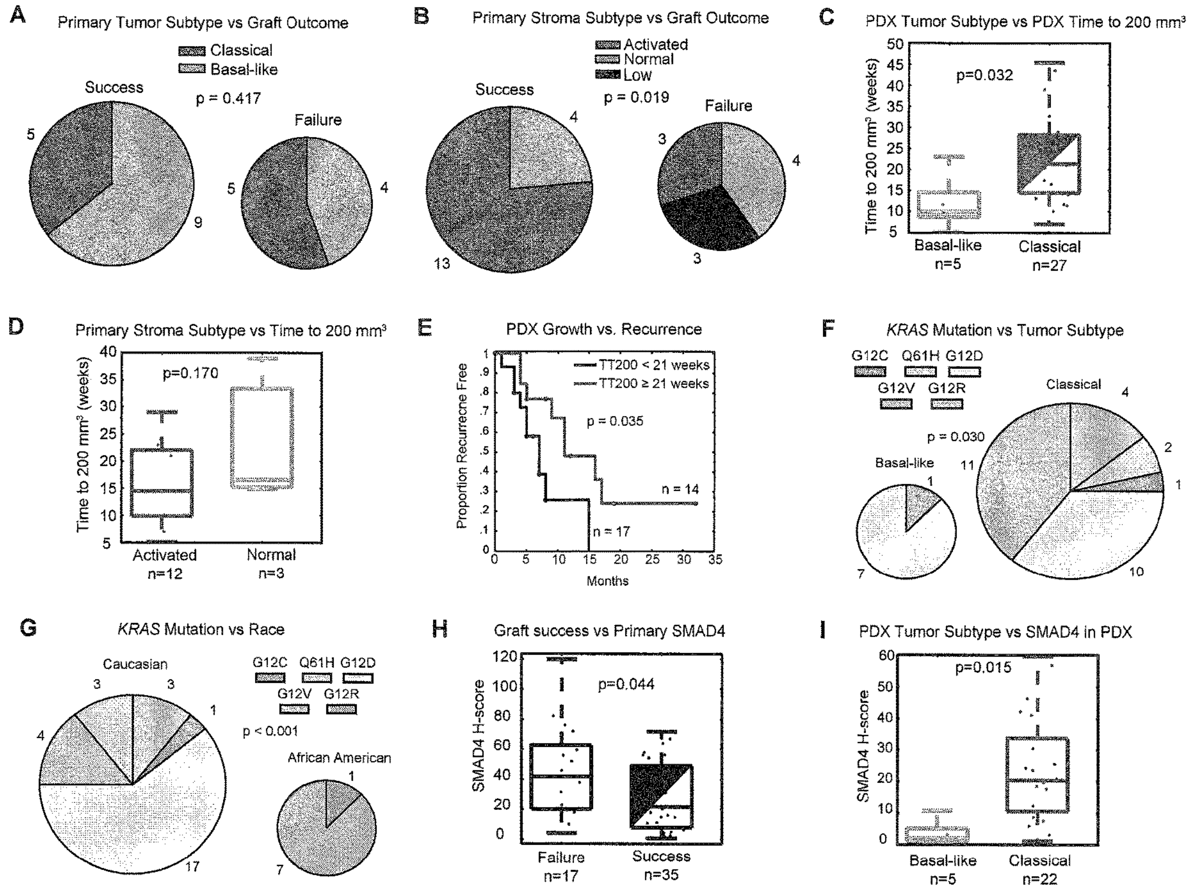
FIGS. 14A-14I depict associations between tumor and stroma subtypes, PDX tumors, KRAS mutations, and SMAD4 expression.
Figure 15A:
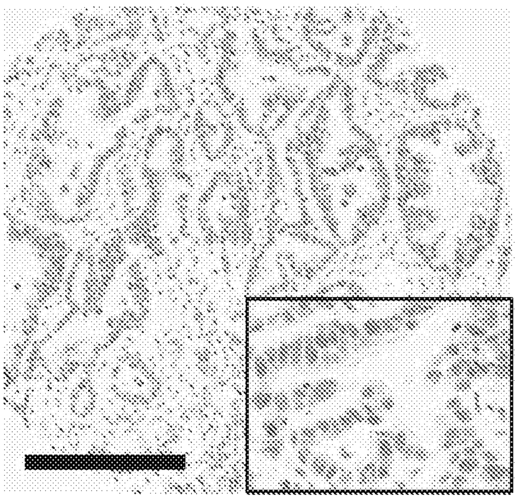
FIGS. 15A-15G are a series of immunohistochemical panels showing SMAD4 staining of representative patient and matched PDX tumors. Positive SMAD4 staining of a patient adenocarcinoma is shown in FIG. 15A, and the corresponding PDX at passage 4 is shown in FIG. 15B. SMAD4 loss in a patient adenocarcinoma is shown in FIG. 15C and corresponding PDX at passage 2 is shown in FIG. 15D. SMAD4 staining of control human skin is shown in FIG. 15E, and is shown in mouse skin in FIG. 15F and in human normal pancreas in FIG. 15G. Scale bars are 200 μm.
Figure 15B:
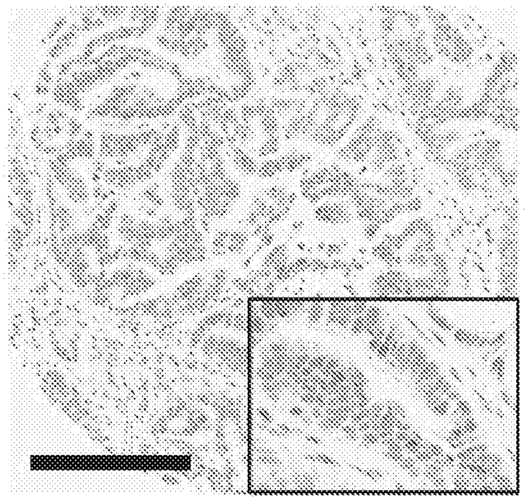
Figure 15C:
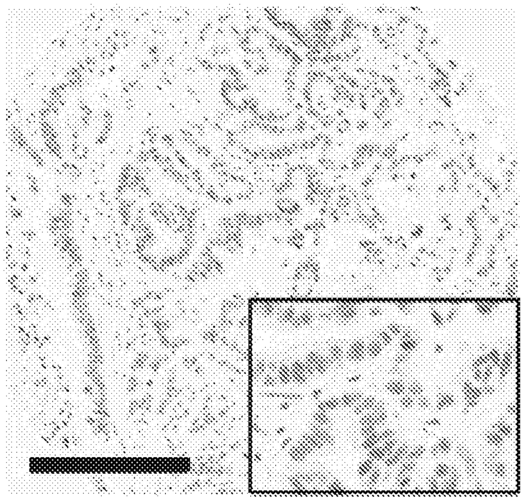
Figure 15D:
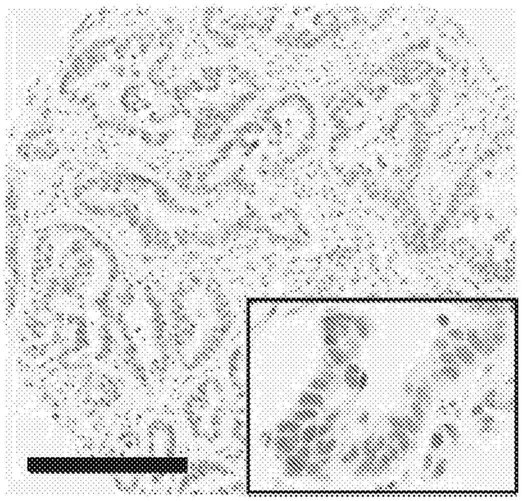
Figure 15E:
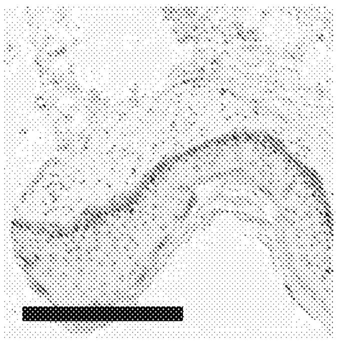
Figure 15F:
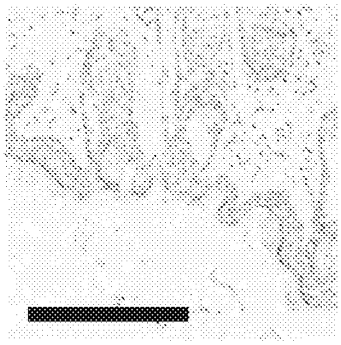
Figure 15G:
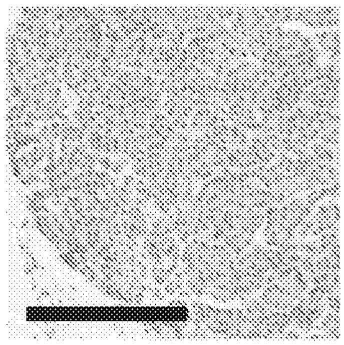

To assess the tumor or stromal specificity of the presently disclosed signatures, RNAseq was performed on a group of 37 PDX tumors. PDX tumors were composed of human tumor cells surrounded by mouse stroma (FIGS. 12A-12D; Isella et al., 2015). Genes from both of the presently disclosed tumor signatures were expressed as human transcripts, whereas genes from both of the presently disclosed stromal signatures were expressed as mouse transcripts (FIG. 4D, FIG. 13A). PDX RNAseq expression was found to divide PDX into both classical and basal-like groupings (FIG. 13B) while predominantly expressing an activated stromal signature (FIG. 4D). Additionally, while tumor-specific subtype was not predictive of graft success (FIG. 14A), patient tumors with an activated stroma subtype had significantly higher graft success rates than those with normal stroma subtype or low amounts of stroma (FIG. 14B; p=0.019). Basal-like subtype tumors also exhibited faster growth rates than classical tumors (p=0.032) as measured by the length of time that tumors took to grow to 200 $mm^3$ (TT200; FIGS. 14C and 14D), a previously used metric for PDX growth (Rubio-Viqueira et al., 2006). Retrospective analysis of patients who had matched PDX tumors found that a shorter TT200 was associated with an unfavorable recurrence-free survival (p=0.035; FIG. 14E), suggesting that PDX tumor growth rate may reflect patient biology.

Both mouse and human-specific expression of the Collisson et al. genes were measured in the presently disclosed PDX models. It was determined that while genes from the "classical" subtype were expressed by human cells in PDX, "quasimesenchymal" transcripts were expressed by a mixture of human and mouse cells, and "exocrine-like" transcripts were infrequently expressed (FIG. 10C). This supported the hypothesis that while the "classical" subtype was a bona fide group, the "quasimesenchymal" subtype was partially driven by non-tumor contributions of stroma and the "exocrine-like" subtype by normal pancreas.

Example 6

KRAS Codon Mutations, Tumor-Specific Subtypes, and Race

Studies of KRAS codon mutations have demonstrated that different codon mutations may have differential functions (Ihle et al., 2012; Stolze et al., 2015) and in some clinical studies, have been shown to be associated with differential outcome. Because PDX tumors are enriched for human-specific tumor cells, KRAS codon mutations were evaluated in the presently disclosed PDX cohort using manually curated RNAseq data. While the overall frequency of KRAS codon mutations was similar to a recent study of PDAC (Witkiewicz et al., 2015), it was noted that the KRAS G12D mutation was significantly overrepresented in the presently disclosed basal-like subtype while G12V was isolated to the classical subtype (FIG. 14F; p=0.030). Furthermore, an overrepresentation of KRAS G12V mutations was found in African-Americans (FIG. 14G; p<0.001). In contrast to basal-like breast cancers, which occur most frequently in African-American women and have a worse prognosis (Carey et al., 2010), African-American patients in the presently disclosed cohort tended to have mainly classical subtype tumors (13 vs 2). Similar to other cancers, African-Americans had a worse prognosis after adjusting for tumor subtype (FIG. 11E; p=0.017). African-American patients with classical subtype tumors had a mean survival of 13 months compared to to Caucasian patients with classical subtype tumors, who had a median survival of 19 months.

Example 7

Other Commonly Mutated Genes and Altered Pathways in PDAC

Previously, loss of SMAD4 has been shown to promote tumor growth (Bardeesy et al., 2006; Haeger et al., 2015). Similar to previous PDX studies of PDAC, loss of SMAD4 was also found to be associated with graft success in PDX models (Garrido-Laguna et al., 2011; see FIG. 14H, FIG. 15A-15G; p=0.044). Furthermore, in the presently disclosed PDX cohort, SMAD4 expression was significantly higher in classical compared to basal-like subtype PDX tumors (FIG. 14I; p=0.015), consistent with the observation that SMAD4 loss confers a more aggressive phenotype.

Figure 16:
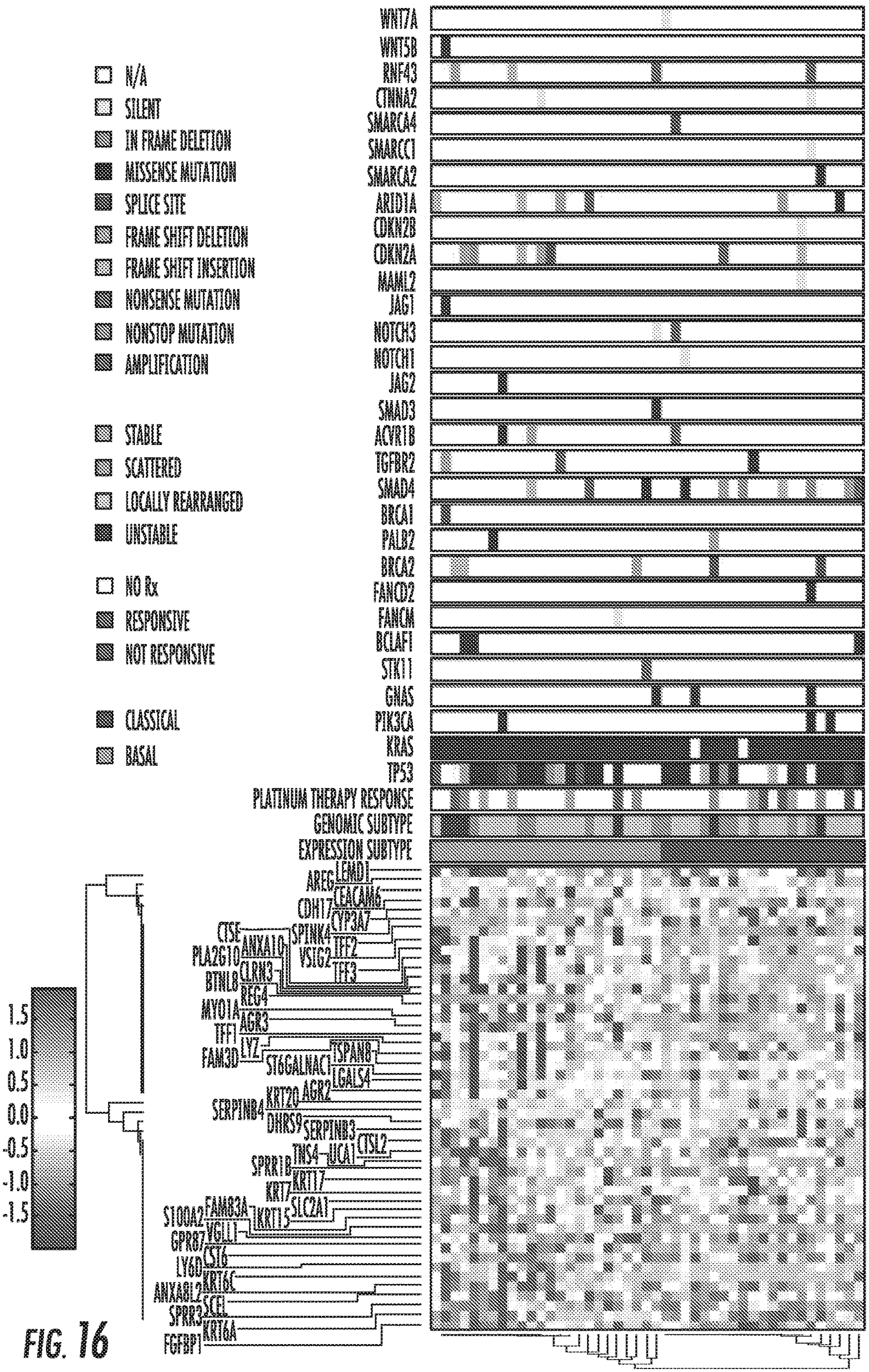
FIG. 16 depicts a consensus clustered heat map of ICGC data for which genetic information was available. Color bars above the heat map show subtypes and genetic alterations for key genes in PDAC. Heat maps show Z-normalized gene expression of basal-like and classical tumor genes.

Using mutation, genomic subtype (Waddell et al., 2015), and gene expression (Nones et al., 2014) data from publically available ICGC data in which recapitulation of the presently disclosed subtypes and prognosis were shown, significantly mutated genes and pathways in PDAC were also evaluated, including ones recently identified through whole-exome sequencing of microdissected primary PDAC tumors (Jones et al., 2008; Biankin et al., 2012; Waddell et al., 2015; Witkiewicz et al., 2015). No significant associations between the presently disclosed expression subtypes and these mutationally altered pathways, i.e., TGFβ, RB, NOTCH, CTNNB1, SWI/SNF, and DNA repair, were found (FIG. 16). Furthermore, no overlap was found between the presently disclosed subtypes and recently identified genomic subtypes, or response to platinum therapy (Waddell et al., 2015). Consistent with this, a recent comprehensive study of somatic mutations in PDAC long-term survivors suggested that somatic mutations alone will not be sufficient to explain clinical outcome (Dal Molin et al., 2015).

Figure 17A:
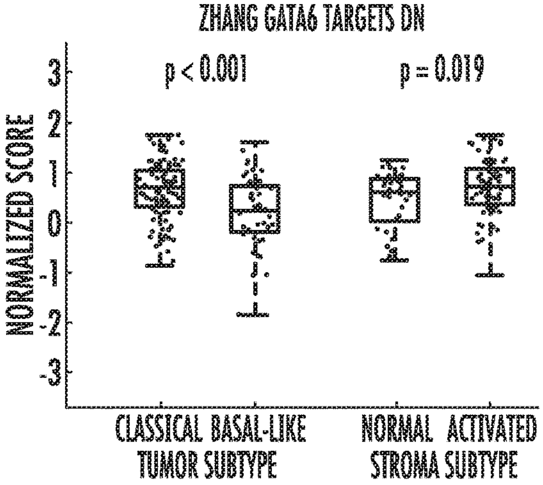
FIGS. 17A-17C are a series of plots showing Gene signature scores by subtype normalized across the cohort, and calculated as the mean expression across a panel of genes obtained from MsigDB.
Figure 17B:
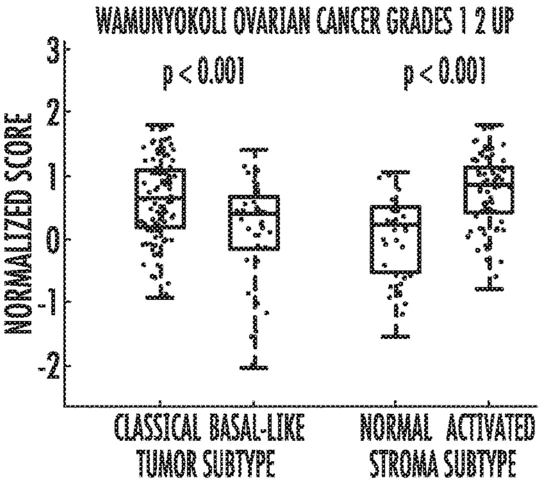
Figure 17C:
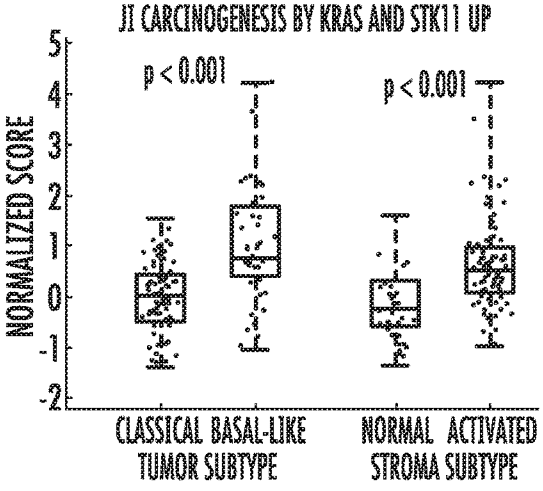
Figure 18A:
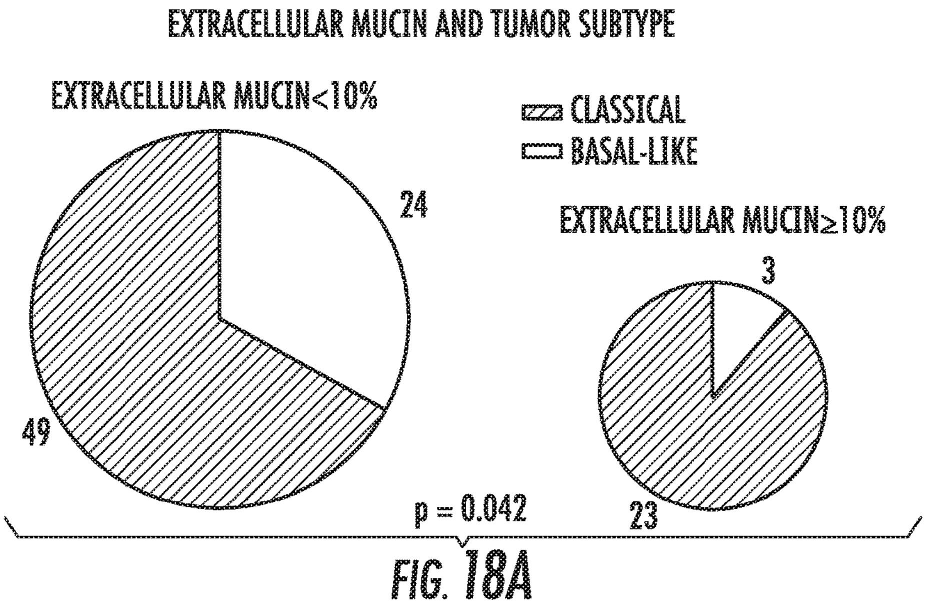
FIGS. 18A-18C depict differences in extracellular mucin in classical and basal-like subtype tumors.
Figure 18B:
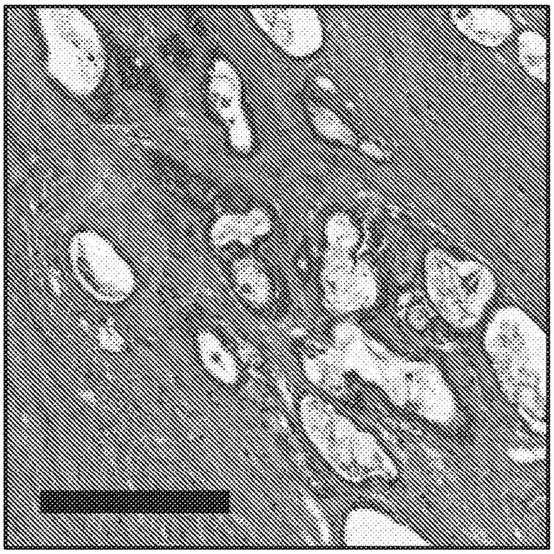
Figure 18C:
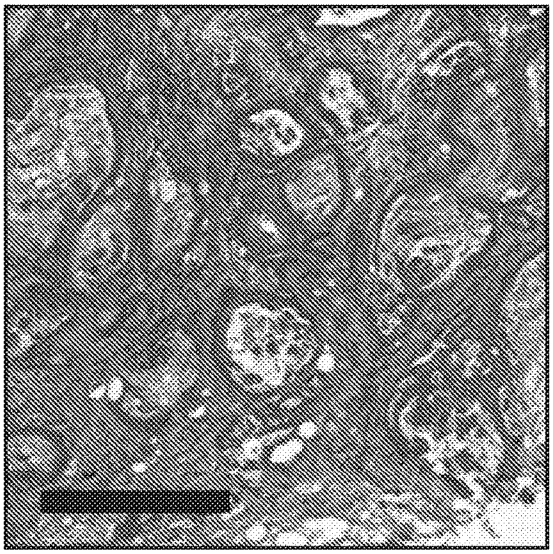

Given the overlap of the presently disclosed classical subtype with that of Collisson et al. 2011, it was not surprising to find that the presently disclosed classical subtype was also enriched for genes associated with GATA6 overexpression (Zhang et al., 2008; FIG. 17A, FIG. 11A). GATA6 has been found to promote epithelial cell differentiation (Zhang et al., 2008; Zhong et al., 2015). More detailed histological markers of differentiation were evaluated in the presently disclosed samples, and it was found that samples with greater than 10% extracellular mucin, a marker of differentiation, comprised mostly of classical subtype tumors (88.5%, n=23) compared to only 11.5% (n=3) of basal-like subtype tumors (FIGS. 18A-18C, p=0.042; Table 9). Consistent with the increased presence of extracellular mucin, the presently disclosed classical subtype was enriched for genes upregulated in mucinous ovarian cancer (WAMAUNYOKOLI_OVARIAN CANCER_GRADES_1_2_UP; Wamunyokoli et al., 2006). Interestingly, the presently disclosed basal-like subtype was enriched for genes related to KRAS activation and STK11 loss in a lung cancer mouse model where STK11-deficient tumors demonstrated shorter latency and more frequent metastasis (Ji et al., 2007). One sample with STK11 inactivation was found in the ICGC data; this sample was a basal-like subtype (FIG. 16). Notably, the presently disclosed subtypes were not associated with other known signaling pathways in PDAC, including Fanconi anemia, DNA repair, chromatin remodeling, beta-catenin, RB, ARF, G1 (FIG. 11A). However, all of these pathways except for beta-catenin were considerably differentially expressed in cell lines compared to patient tumors, suggesting that gene expression in cell lines might be a deceptive representation of most tumors.

Example 8

Figure 19:
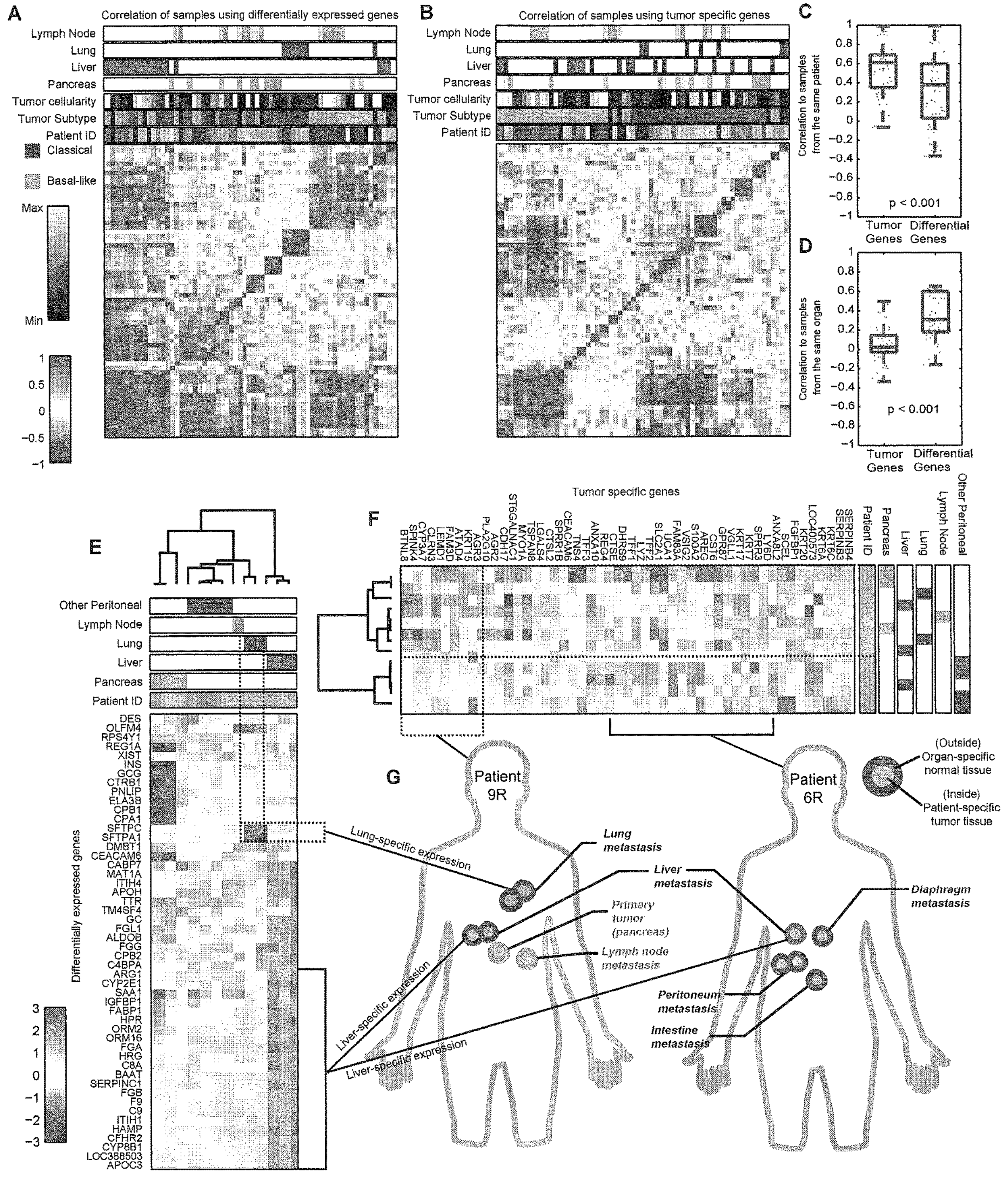
FIGS. 19A-19G depict the results of experiments showing that overcoming tumor cellularity revealed true heterogeneity among matched primary and metastatic sites.

Tumor-Specific Subtypes Suggested Low Intrapatient Heterogeneity Between Primary and Metastatic Lesions It is likely that only a subset of genes are relevant to the question of intra- and inter-patient heterogeneity in PDAC. Many methods exist to pre-select genes for supervised analysis (Carey et al., 2010), but selection of the most differentially expressed genes is a common preprocessing step during unsupervised analysis (Bardeesy et al., 2006). When clustering matched samples of metastatic and primary lesions using the 50 most differentially expressed genes among all matched samples, samples separated primarily by organ site instead of by patient (FIGS. 19A and 19C). In contrast, when considering 25 top ranked exemplar genes each from the "basal-like" and "classical" factors, samples from the same patient clustered closer together, and were less dependent of organ site (FIGS. 19B and 19D).

This was further illustrated in a focused analysis of two patients (FIGS. 19A-19G), whose tumor samples appeared patient-specific when considering the presently disclosed tumor subtype gene list, but clustered by site when considering differentially expressed genes. Overall, it was found that the presently disclosed tumor subtype gene list showed higher similarity (mean Pearson's $\rho=0.53$) between all other samples from the same patient than did the differentially expressed gene list ($\rho=0.32$, t-test $p\leq0.001$). Furthermore, the presently disclosed tumor subtype gene list produced much lower similarity among all other samples from the same organ site across different patients ($\rho=0.04$) than the differentially expressed gene list ($\rho=0.34$, $p\leq0.001$). This observed similarity of tumor gene expression among tumors within the same patient suggested overall high inter-patient tumor heterogeneity and low heterogeneity between primary and metastatic sites. However, examples of intra-patient heterogeneity were not observed between metastatic sites. For example, lung metastases, even those from patients with "basal-like" tumors in other locations, clustered exclusively with the "classical" tumors, suggesting that some intra-patient heterogeneity may exist among metastatic sites, and supporting the previously reported divergent patterns of failure in PDAC (Haeger et al., 2015).

Discussion of Examples 1-8

The studies disclosed herein represent the largest investigation of primary and metastatic PDAC gene expression to date. NMF was used to identify novel prognostic and/or diagnostic subtypes of PDAC which may have been previously obscured by confounding normal and stromal tissue. The identification of normal-, tumor-, and stroma-specific gene expression signatures was supported by both their overlap with previously identified gene lists and their expression in appropriate tissue types. The presently disclosed tumor subtypes were further supported by their relationship to previously identified basal tumor subtypes in breast and bladder cancers and their prognostic and/or diagnostic relevance in external cohorts. The present findings of two different stroma subtypes may help explain the differential effects of stroma previously seen in preclinical models.

Tumor and stroma specific gene expression classified PDAC into four distinct subtypes with prognostic and/or diagnostic relevance. The orthogonal nature of tumor- and stroma-specific subtypes suggested an important interplay in patient tumors that will need to be taken into account as stroma and immune modulating therapies are studied. In the presently disclosed cohort, patients with basal-like tumors appeared to derive more benefit from adjuvant therapy. Whether basal-like and classical subtypes may be associated with response to specific therapies can be studied further as more effective therapies become available. One challenge will be defining preclinical model systems that recapitulate these subtypes as the presently disclosed results suggested that traditional cell lines are lacking in the classical subtype. Although it has been demonstrated that PDX models recapitulate tumor-specific subtypes, these models alone may not be sufficient due to either the lack of human stroma or overrepresentation of the activated stroma subtype in the tumors that are successfully grafted. Thus, more detailed characterization of genetically engineered mouse models of PDAC models can be employed to determine which models best reflect both our tumor- and stroma-specific subtypes.

Recent exome sequencing studies have confirmed commonly mutated genes in PDAC but have not uncovered mutations that clearly confer survival differences (Jones et al., 2008; Waddell et al., 2015; Witkiewicz et al., 2015). In fact, exome sequencing of a cohort of very long-term survivors of PDAC (Dal Molin et al., 2015) found no differences in somatic mutations to explain the improved biology of tumors from these rare patients compared to the majority of patients with PDAC, suggesting that examining somatic mutations alone may not be sufficient to understand the biological and clinical differences in PDAC tumors. Furthermore, exome sequencing studies and studies of microdissected samples are limited to the tumor compartment and overlook the stroma compartment which has been shown to be biologically critical in PDAC, with both tumor-promoting and tumor-inhibiting effects. The results provided herein suggested that RNA subtypes may better capture the molecular landscape of PDAC and its reflection on patient outcome. As such, the RNA subtypes disclosed herein may reflect the broad effect of somatic mutations while also capturing the importance of the neoplastic stroma.

These results provide new insight into the molecular composition of PDAC which may be used for precision medicine. Furthermore, knowledge of these subtypes and their prognostic and/or diagnostic value can provide decision support in a clinical setting where the choice and timing of therapies can be critical.

Example 9

Construction of a Cross-Platform Basal-Like Classifier

Having established a method for classifying cohorts of PDAC expression data into basal-like and classical samples, a more clinically applicable classification scheme that works on single samples was constructed. Such a single-sample classifier can be valuable in a clinical setting, where access to a large cohort of comparative cases is prohibitive. Furthermore, the ability of such a classifier to work across gene expression platforms and across relevant cancer types was assessed.

As such, a platform-independent classifier was developed and tested to discriminate between "basal-like" samples versus others across various cancers, given a sample's individual gene expression profile. Rank-based classifiers such as the Top Scoring Pair (TSP; Leek, 2009) and kTSP (Afsari et al., 2014) depend only on the relative ranks of the expression of genes within a sample, allowing such classifiers to be robust against platform-specific effects and study-to-study variations due to data normalization and preprocessing (Patil et al., 2015)

Briefly, the kTSP approach selects k pairs of genes A and B such that gene A expression >gene B expression implies sample membership to class 1, otherwise implying membership to class 2. The default decision rule in Afsari et al., 2015 following feature selection weights each TSP equally in their class prediction ("voting"), despite the fact that some TSPs may better discriminate between classes than others. The kTSP approach of Afsari et al., 2015 was extended as set forth herein by implementing a custom decision rule that inputs the selected k gene pairs into a penalized logistic regression classifier to estimate the relative contribution each of the k selected TSPs in predicting class membership (defined here as basal-like versus otherwise), similar to (Shi et al., 2011). In fitting the model, class membership was the binary outcome variable, and each covariate corresponded to a TSP, consisting of a binary integer vector which took on the value of 1 for a sample if gene A >gene B in expression for that TSP, and 0 otherwise for each sample.

A penalized logistic regression model was fit using the ncvreg package (Breheny & Huang, 2011) to account for potential correlation between TSPs (ridge penalty) and to remove TSPs unhelpful in prediction given the presence of other features in the model (MCP penalty). Given the fitted model and a new sample's expression profile, a predicted probability of basal-like class membership could be obtained.

To build the presently disclosed classifier to predict the basal-like class across various cancers, the presently disclosed classifier was trained on a "metadataset" consisting of the TCGA Bladder (RNA-seq, 20533 genes), UNC Pancreas (Microarray, 19749 genes), and Perou Breast Cancer (Microarray, 17631 genes) data sets, totaling 788 samples. Each data set was reduced to a common set of genes found across each study to the described 50 gene signature described herein. The Perou Breast Cancer data set was further filtered to remove genes that had missing values for more than 10 samples, leaving 11526 genes. The remaining missing data was imputed using the impute package (Hastie et al. impute: impute: Imputation for microarray data. R package version 1.42.0.) in R using default parameters. Only 29 of the 50 genes from the original gene signature remained for feature selection after filtering. Because of this small number, a larger 500 gene set encompassing the original 50 gene set, to which was derived in a similar fashion, was utilized. From this larger gene set, 302 genes were found across all three training datasets.

Basal-like samples were identified in the TCGA bladder and Perou Breast Cancer data sets from their associated clinical annotation files, and in the UNC Pancreas data, the basal-like clustering calls from the present disclosure were utilized. Given the known classes (basal-like versus otherwise) and gene expression profiles in each data set, the presently disclosed feature selection was performed using the switchBox package (Afsari et al., 2015) to select the k TSPs from the 302 candidate genes, resulting in 16 TSPs being selected. The ncvreg function from (Breheny & Huang, 2011) was applied using the MCP penalty and an alpha parameter of 0.5, allowing for equal contribution of the ridge penalty to account for correlation between TSPs and the MCP penalty for feature selection. The appropriate penalty was chosen via leave-one-out cross validation using the cv.ncreg function (788 folds).

The final model described herein was found to contain 14 TSPs when derived from the larger 500 gene signature. The fitted estimates can be found in Table 9. Calculating the pair-wise spearman correlation between samples across the classifier's genes, it was determined that samples from the basal-like state (orange) tended to cluster together in terms of similarity (see FIG. 16). It was also determined that the predictions described herein tended to match the known classes for each sample regardless of platform or tumor type.

TABLE 9

Fitted Estimates for the Final Model

| Gene A | Gene B | Coefficient | Estimated Increase in Odds of Basal Class Membership when A > B |
|---|---|---|---|
| CD109 | GPR160 | 0.87 | 2.38 |
| SLC2A1 | AGR2 | 1.22 | 3.39 |
| KRT16 | SLC44A4 | 0.52 | 1.68 |
| CTSL2 | TMEM45B | 1.43 | 4.17 |
| KRT6A | BCAS1 | 0.70 | 2.01 |
| B3GNT5 | VSIG2 | 0.41 | 1.51 |
| MET | TFF3 | 0.72 | 2.06 |
| CHST6 | PLA2G10 | 0.80 | 2.24 |
| SERPINB5 | HPGD | 0.76 | 2.13 |
| DCBLD2 | PLS1 | 1.40 | 4.07 |
| IL20RB | FAM3D | 1.33 | 3.79 |
| PPP1R14C | SYTL2 | 1.58 | 4.85 |
| NAB1 | PLEKHA6 | 0.41 | 1.50 |
| MSLN | CAPN9 | 1.58 | 4.83 |
| | (Intercept) | −7.16 | |

To classify each sample, gene expression from pairs of genes in Table 9 were compared such that for each gene pair, if Gene A expression is greater than Gene B expression, the coefficient for that gene pair was added to a running sum. If the sum of all such coefficients and the intercept from Table 9 was greater than zero, the sample was classified as basal (see EQUATION 1).

To validate the 14 TSP classifier, the presently disclosed model was applied to two independent data sets: the TCGA Breast Cancer (RNAseq) data set and the ICGC pancreas cancer data sat (Microarray). It was determined that the predictions matched well in the independent TCGA data set, demonstrating a 92.3% classification accuracy. The only validation data set that did not have existing subtype calls is the ICGC pancreas data set. It was further determined that the presently disclosed TSP predictions did not match as well with the presently disclosed clustering results, with a match rate between clustering-based calls and classifier prediction of 85.5%. Finally, it was also determined that spearman correlation of gene expression as a whole was much worse between the ICGC platform and any of the various RNAseq or Agilent Microarray data described herein.

Accordingly, the present disclosure demonstrated excellent within-training set performance of the described classifier across multiple platforms, in addition to accurate prediction of the classifier in an independent RNAseq data set.

Extending the methodology described above, a stroma-specific (activated versus normal stroma; see EQUATION 2) and a tumor-specific (basal versus classical; see EQUATION 3) classifier was trained within only the pancreatic cancer data. Table 10 and Table 11 show the coefficients of the fitted model sufficient for classifying between activated and normal stroma subtypes, or between basal-like and classical subtypes, respectively.

TABLE 10

Fitted Estimates for the Pancreas-specific Stromal Model

| Gene A | Gene B | Coefficient | Estimated Increase in odds of activated stroma class membership when A > B |
|---|---|---|---|
| ITGA11 | SCRG1 | 0.67 | 1.95 |
| COL5A1 | IGF1 | 1.25 | 3.48 |
| COL11A1 | ANGPTL7 | 3.23 | 25.37 |
| MMP11 | ACTG2 | 1.67 | 5.30 |
| FNDC1 | SYNM | 1.43 | 4.18 |
| ZNF469 | MYH11 | 1.51 | 4.54 |
| RBPMS2 | RERGL | 1.25 | 3.49 |
| COL1A1 | COL1A2 | 0.18 | 1.20 |
| | Intercept | −6.17 | |

TABLE 11

Fitted Estimates for the Pancreas-specific Tumor Subtype Model

| Gene A | Gene B | Coefficient | Estimated Increase in odds of basal class membership when A > B |
|---|---|---|---|
| GPR87 | MS4A8B | 1.084442 | 2.96 |
| KRT6C | BTNL8 | 2.622242 | 13.77 |
| ANXA8L2 | PLA2G10 | 2.73881 | 15.47 |
| KRT6A | KCNE3 | 1.891903 | 6.63 |
| C16orf74 | DDC | 1.898285 | 6.67 |
| SCEL | MYO1A | 2.161549 | 8.68 |
| DCBLD2 | PLS1 | 2.189532 | 8.93 |
| FAM83A | REG4 | 2.855056 | 17.38 |
| PTGES | ATP10B | 1.674513 | 5.34 |
| | Intercept | −9.255835 | |

Example 10

Exemplary Clinical Approaches to Care

Figure 20:
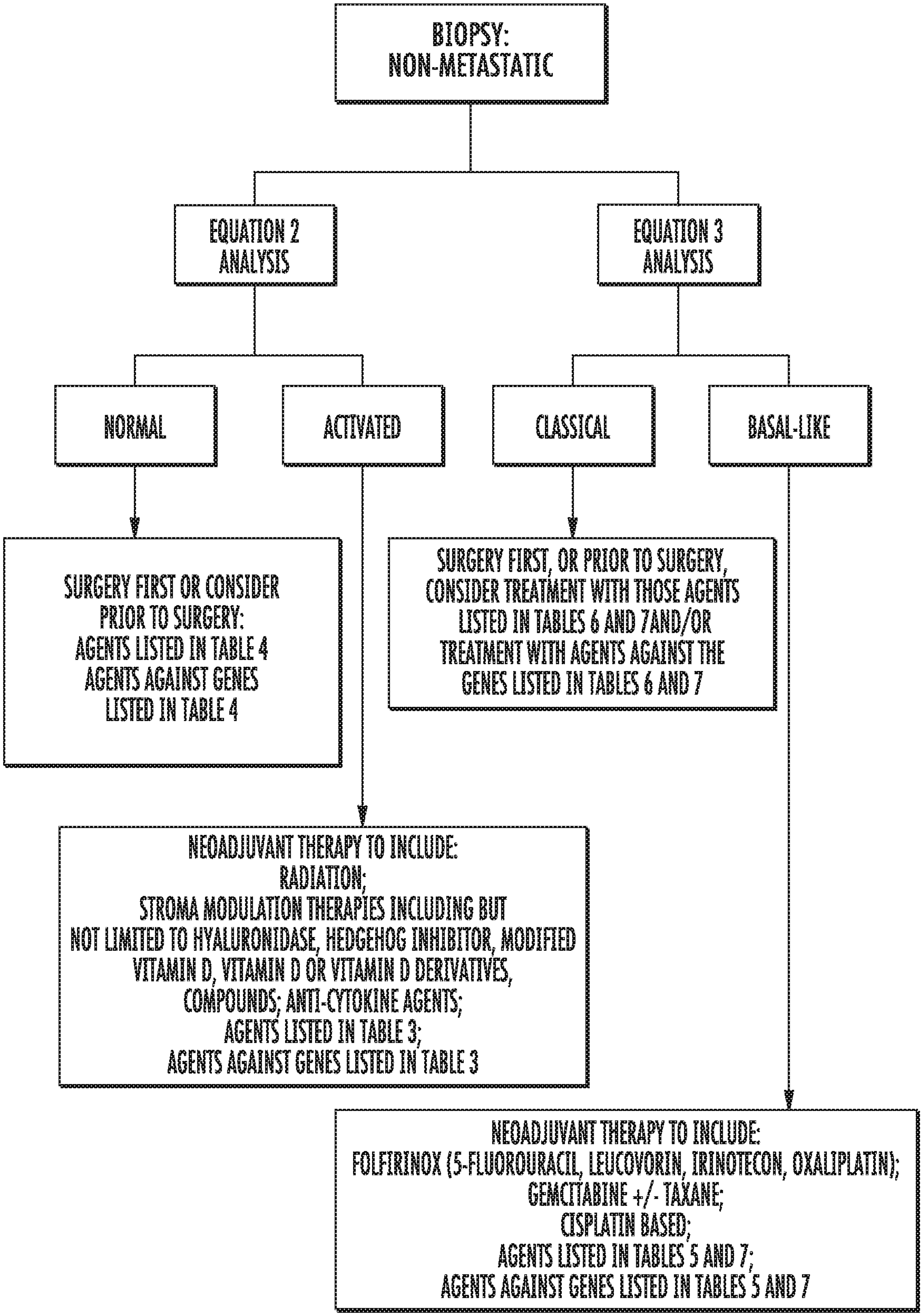
FIG. 20 is a summary of exemplary, non-limiting treatment strategy considerations for patients with non-metastatic disease based on stromal subtype as identified using EQUATION 2 or tumor subtype as identified using EQUATION 3 below.
Figure 21:
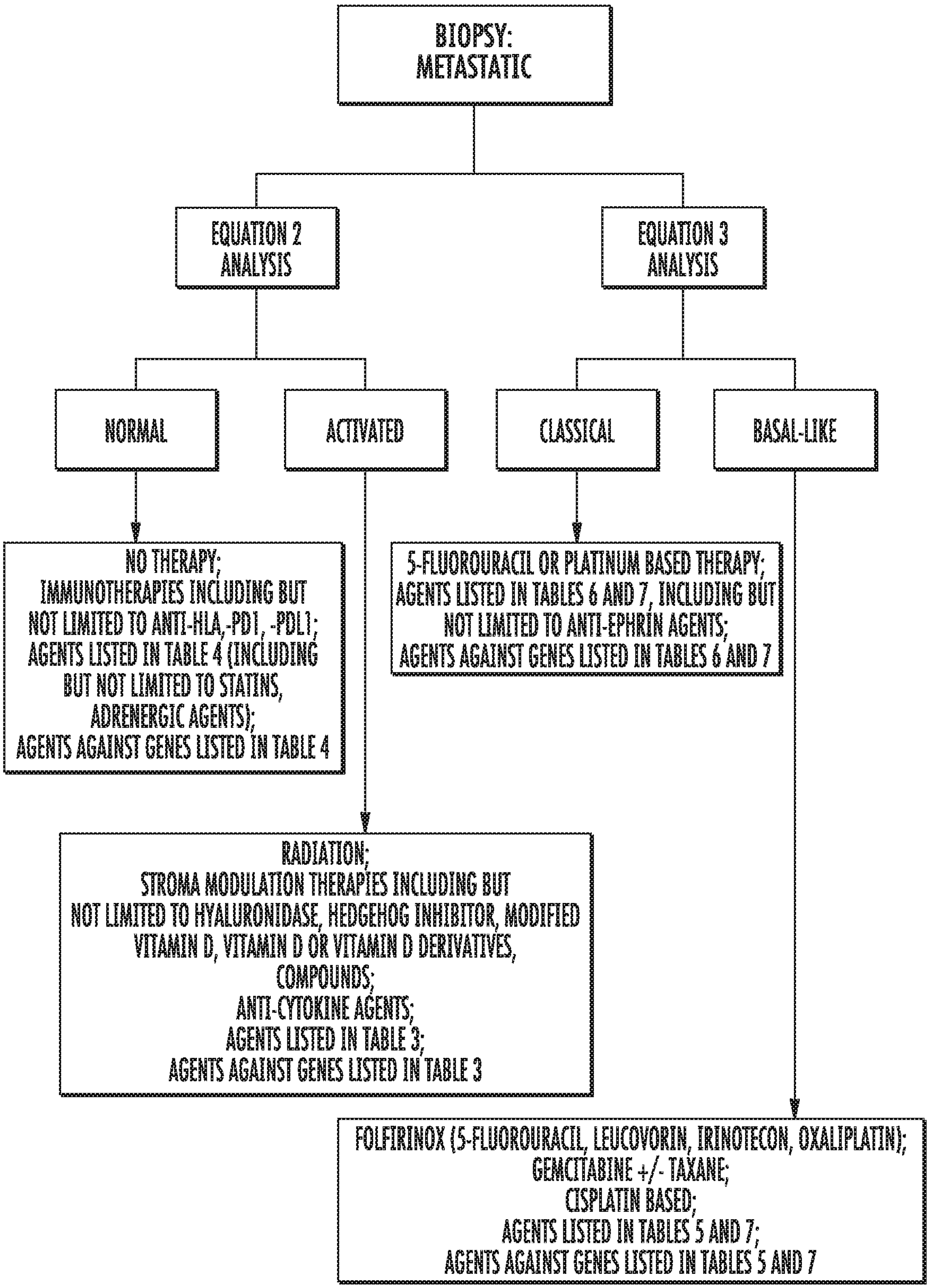
FIG. 21 is a summary of exemplary, non-limiting treatment strategy considerations for patients with metastatic disease based on stromal subtype as identified using EQUATION 2 or tumor subtype as identified using EQUATION 3 below.

FIGS. 20 and 21 show exemplary, non-limiting clinical approaches to care based on tumor and stroma subtype determinations employing EQUATIONS 2 and 3 above.

In FIG. 20, exemplary treatment considerations for patients with a pancreatic mass that has no evidence of distant (metastatic) spread to other organs (i.e., tumor is confined to the pancreas) is presented. In this case, a patient undergoes a biopsy. If the stroma subtype is determined to be normal using EQUATION 2, the patient proceeds to surgery. However, as agents such as those listed in Table 3 become available or are developed against the genes in Table 3, a patient with normal stroma subtypes also considers neoadjuvant therapy using the Table 3 agents prior to surgery. If this patient is determined to have an activated stroma subtype, the patient considers radiation and other stroma modulation therapies noted in FIG. 20, including but not limited to hyaluronidase, hedgehog inhibition, modified vitamin D, vitamin D derivatives or compounds, anti-cytokine agents, or agents listed in or directed against the genes listed in Table 2. Additionally, the patient considers the therapies recommended based on tumor subtype (classical or basal-like) as described herein below.

If the biopsy shows classical subtype as determined using EQUATION 3, the patient is moved directly to surgery or prior to surgery, treatment with one or more agents listed in Table 5 or Table 6 or directed against the genes listed in Tables 5 and 6 is commenced. If the patient has a basal-like tumor, surgery alone would not be adequate. Therefore, this patient is recommended to undergo chemotherapy with the agents listed in FIG. 20 and/or with agents listed in Tables 4 and 6 and/or against the genes listed in Tables 4 and 6.

FIG. 21 shows exemplary treatment considerations for patients with a pancreatic mass that has evidence of distant (metastatic) spread to other organs. In this case, the patient would also undergo a biopsy. If the biopsy shows classical subtype as per EQUATION 3, the patient considers 5-fluorouracil or platinum based therapy. In some instances, other chemotherapies are also considered. However, as other agents such as those listed in Tables 5 and 6 become available or are developed against the genes listed in Tables 5 and 6, these therapies are considered in conjunction with the chemotherapy. If the patient has a basal-like tumor, cisplatin- or oxaliplatin-based therapies or gemcitabine as listed in FIG. 21 are considered. In some instances other chemotherapies are appropriate. In addition, the agents listed in Tables 4 and 6 or agents against the genes listed in Tables 4 and 6 are added to the chemotherapy.

If the patient has a normal stroma subtype as per EQUATION 2, no additional therapy besides those based on the tumor subtype is considered. However, immunotherapies to augment immune response can be considered. As additional agents such as those listed in Table 3 become available or are developed against the genes in Table 3, a patient with normal stroma subtypes considers using Table 3 agents in conjunction with the tumor subtype specific therapy regimen such as chemotherapy. For patients with activated stroma, radiation and other stroma modulation therapies listed in FIG. 21 are considered in conjunction with the tumor subtype specific therapy, including but not limited to hyaluronidase, hedgehog inhibition, modified vitamin D, vitamin D derivatives or compounds, and anti-cytokine agents. In addition, the agents listed in Table 2 and/or agents against the genes listed in Table 2 are also considered.

REFERENCES

The references listed below as well as all references cited in the specification including, but not limited to patents, patent application publications, journal articles, and database entries (e.g., GENBANK® biosequence database entries including all annotations and references cited therein) are incorporated herein by reference to the extent that they supplement, explain, provide a background for, or teach methodology, techniques, and/or compositions employed herein. With respect to GENBANK® biosequence database entries, if a sequence listed herein is or has been updated with a new sequence, it is understood that the instant disclosure also incorporates by reference to the sequence listed herein any such new sequences.

Afsari et al. (2014) *Ann Appl Stat* 8:1469-1491.
Afsari et al. (2015) *Bioinformatics* 31:273-274
Ahmad et al. (2001) *Am J Gastroenterol* 96:2609-2615.
Albert et al. (1992) *J Virol* 66:5627-5630.
Alexandrov eta. (2013a) *Cell Rep* 3:246-259.
Alexandrov et al. (2013b) *Nature* 500:415-421.
Alexay et al. (1996) *Proc SPIE* 2705, Fluorescence Detection IV, 6363.

Ausubel et al. (2002) *Short Protocols in Molecular Biology*, Fifth ed. Wiley, New York, N.Y., United States of America.
Ausubel et al. (2003) *Current Protocols in Molecular Biology*, John Wylie & Sons, Inc., New York, N.Y., United States of America.
Bachem et al. (2005) *Gastroenterol* 128:907-921.
Bardeesy et al. (2006) *Genes Dev* 20:3130-3146.
Bej et al. (1991) *Appl Environ Microbiol* 57:3529-3534.
Biankin et al. (2012) *Nature* 491:399-405.
Biton et al. (2014) *Cell Rep* 9:1235-1245.
Boom et al. (1990) *J Clin Microbiol* 28:495-503.
Boyle & Levin (2008) *World Cancer Report* 2008. Lyon, International Agency for Research on Cancer.
Breheny & Huang (2011) *Ann Appl Stat* 5:232-253.
Buffone et al. (1991) *Clin Chem* 37:1945-1949.
Busch et al. (1992) *Transfusion* 32:420-425.
Cancer Genome Atlas Research Network, The (2011) *Nature* 474:609-615.
Cancer Genome Atlas Research Network, The (2012a) *Nature* 487:330-337.
Cancer Genome Atlas Research Network, The (2012b) *Nature* 489:519-525.
Cancer Genome Atlas Research Network, The (2012c) *Nature* 490:61-70.
Cancer Genome Atlas Research Network, The (2013a) *Nature* 497:67-73.
Cancer Genome Atlas Research Network, The (2013b) *Nature* 499:43-49.
Cancer Genome Atlas Research Network, The (2013c) *New Eng J Med* 368:2059.
Cancer Genome Atlas Research Network, The (2014a) *Nature* 507:315-322.
Cancer Genome Atlas Research Network, The (2014b) *Nature* 511:543-550.
Carey et al. (2010) *Nat Rev Clin Oncol* 7:683-692.
Carter et al. (2012) *Nat Biotechnol* 30:413-421.
Cha & Thilly (1993) *PCR Methods Appl* 3:S18-S29.
Cleary et al. (2004) *J Am Coll Surg* 198:722-731.
Cohen et al. (2008) *Pancreas* 37:154-158.
Cohen et al. (2008) *Pancreas* 37:154-158.
Collisson et al. (2011) *Nat Med* 17:500-503.
Conlon et al. (1996) *Ann Surg* 223:273-279.
Conroy et al. (2011) *New Eng J Med* 364:1817-1825.
Conway et al. (2012) *Bioinformatics* 28:i172-i178.
Cousins et al. (1992) *J Clin Microbiol* 30:255-258.
Crnogorac-Jurcevic et al. (2002) *Oncogene* 21:4587-4594.
Dal Molin et al. (2015) *Clin Cancer Res* 21:1944-1950.
Damrauer et al. (2014) *Proc Nat Acad Sci USA* 111:3110-3115.
DeOliveira et al. (2006) *Annals Surg* 244:931-937.
DeRisi et al. (1996) *Nat Genet* 14:457-460.
Dubiley et al. (1997) *Nucl Acids Res* 25:2259-2265.
Duda et al. (2012) *Pattern Classification*. John Wiley & Sons, New York, N.Y., United States of America.
Eisenberg & Levanon (2003) *Trends Genet* 19:362-365.
Englert (2000) in Schena, ed., *Microarray Biochip Technology*, pp. 231-246, Eaton Publishing, Natick, Mass., United States of America.
Eppsteiner et al. (2009) *Annals Surg* 249:635-640.
Erkan et al. (2008) *Clin Gastroenterol Hepatol* 6:1155-1161.
Espejo et al. (2002) *Biochem J* 367:697-702.
Fang et al. (2002) *Chembiochem* 3:987-991.
Ferrone et al. (2008) *J Gastrointest Surg* 12:701-706.
Fodor et al. (1991) *Science* 251:767-773.
Fodor et al. (1993) *Nature* 364:555-556.
Froeling et al. (2011) *Gastroenterol* 141:1486-1497.
Garrido-Laguna et al. (2011) *Clin Cancer Res* 17:5793-5800.
Gress et al. (2001) *Annals Internal Med* 134:459-464.
Guedon et al. (2000) *Anal Chem* 72(24):6003-6009.
Haab et al. (2001) *Genome Biol* 2:RESEARCH0004.
Haeger et al. (2015) *Oncogene* April 20. doi: 10.1038/onc.2015.112. [Epub ahead of print].
Hamel et al. (1995) *J Clin Microbiol* 33:287-291.
Han et al. (2006) *Pancreas* 32:271-275.
Heaton et al. (2001) *Proc Natl Acad Sci USA* 98(7):3701-3704.
Hermanson (1990) *Bioconjugate Techniques*, Academic Press, San Diego, Calif., United States of America.
Herrera et al. (2013) *Clin Cancer Res* 19:5914-5926.
Herrewegh et al. (1995) *J Clin Microbiol* 33:684-689.
Hoadley et al. (2014) *Cell* 158:929-944.
Houseman et al. (2002) *Nat Biotechnol* 20:270-274.
Hwang et al. (2008) *Cancer Res* 68:918-926.
Iacobuzio-Donahue et al. (2003) *Am J Pathol* 162:1151-1162.
Iacobuzio-Donahue et al. (2009) *J Clin Oncol* 27:1806-1813.
Ihle et al. (2012) *J Natl Cancer Inst* 104:228-239.
Isella et al. (2015) *Nat Genet* 47:312-319.
Izraeli et al. (1991) *Nucl Acids Res* 19:6051.
Ji et al. (2007) *Nature* 448:807-810.
Jones et al. (2008) *Science* 321:1801-1806.
Kim et al. (2013) *Genome Biol* 14:R36.
Kohsaka & Carson (1994) *J Clin Lab Anal* 8:452-455.
Krapp et al. (1998) *Genes Dev* 12:3752-3763.
Lanciotti et al. (1992) *J Clin Microbiol* 30:545-551.
Leek (2009) *Bioinformatics* 25:1203-1204.
Linz et al. (1990) *J Clin Chem Clin Biochem* 28:5-13.
Lisle et al. (2001) *BioTechniques* 30:1268-1272.
Liu & Hlady (1996) *Colloids Surfaces B Biointerfaces* 8:25-37.
Lockhart et al. (1996) *Nat Biotechnol* 14:1675-1680.
Logsdon et al. (2003) *Cancer Res* 63:2649-2657.
Louvet et al. (2005) *J Clin Oncol* 23:3509-3516.
MacBeath & Schreiber (2000) *Science* 289:1760-1763.
Mace et al. (2000) in Schena, ed., *Microarray Biochip Technology*, pp. 39-64, Eaton Publishing, Natick, Mass., United States of America.
Maier et al. (1994) *J Biotechnol* 35:191-203.
McCaustland et al. (1991) *J Virol Methods* 35:331-342.
McConkey et al. (2014) *Eur Urol* 66:609-910.
McGall et al. (1996) *Proc Nat Acad Sci USA* 93:13555-13460.
McLendon et al. (2008) *Nature* 455:1061-1068.
McPherson et al. (1995) *PCR 2: A Practical Approach*, IRL Press, New York, N.Y., United States of America.
Millar et al. (1995) *Anal Biochem* 226:325-330.
Natarajan et al. (1994) *PCR Methods Appl* 3:346-350.
Neel et al. (2014) *Mol Cancer Ther* 13:122-133.
Nelson et al. (2001) *Anal Chem* 73(1):1-7.
Neuhaus et al. (2008) *J Clin Oncol* May 20 Suppl; Abstr LBA4504.
Nones et al. (2014) *Int J Cancer* 135:1110-1118.
O'Donnell et al. (1997) *Anal Chem* 69:2438-2443.
Olive et al. (2009) *Science* 324:1457-1461.
Özdemir et al. (2014) *Cancer Cell* 25:719-734.
Paladichuk (1999) *The Scientist* 13:20-23.
Parker et al. (2009) *J Clin Oncol* 27:1160-1167.
Parkin et al. (2005) *CA Cancer J Clin* 55:74-108.
Patil et al. (2015) *Bioinformatics* btv157 [Epub ahead of print].

PCT International Patent Application Publication Nos. WO 1993/009668; WO 1995/011755; WO 1997/014028; WO 1999/019515; WO 1999/032660; WO 1999/032660; WO 1999/063385; WO 2001/013120; WO 2001/014589; WO 2001/023082; WO 2004/046098; WO 2004/110244; WO 2006/089268; WO 2007/001324; WO 2007/056332; WO 2007/07025.

Piétu et al. (1996) *Genome Res* 6:492-503.

Prat et al. (2010) *Breast Cancer Res* 12:R68.

Randolph & Waggoner (1995) *Nucl Acids Res* 25:2923-2929.

Ratner & Castner (1997) in Vickerman, ed., *Surface Analysis: The Principal Techniques*, John Wiley & Sons, New York, N.Y., United States of America.

Rhim et al. (2014) *Cancer Cell* 16:735-747.

Robertson & Walsh-Weller (1998) *Methods Mol Biol* 98:121-154.

Rose (2000) in Schena, ed., *Microarray Biochip Technology*, pp. 19-38, Eaton Publishing, Natick, Mass., United States of America.

Roux (1995) *PCR Methods Appl* 4:S185-S194.

Rubio-Viqueira et al. (2006) *Clin Cancer Res* 12:4652-4661.

Rupp et al. (1988) *BioTechniques* 6:56-60.

Salisbury et al. (2002) *J Am Chem Soc* 124:14868-14870.

Sambrook & Russell (2001) *Molecular Cloning: A Laboratory Manual*, 3rd. Edition, Cold Spring Harbor Press, Cold Spring Harbor, N.Y., United States of America.

Sapolsky & Lipshutz (1996) *Genomics* 33:445-456.

Schena et al. (1995) *Science* 270:467-470.

Schena et al. (1996) *Proc Natl Acad Sci USA* 93:10614-10619.

Schnelldorfer et al. (2008) *Ann Surg* 247:456-462.

Seong (2002) *Clin Diagn Lab Immunol* 9:927-930.

Shalon et al. (1996) *Genome Res* 6:639-645.

Shi et al. (2010) *Nat Biotechnol* 28:827-838.

Shi et al. (2011) *Bmc Bioinformatics* 12:375.

Shoemaker et al. (1996) *Nat Genet* 14:450-456.

Shriver-Lake (1998) in Cass & Ligler, eds., *Immobilized Biomolecules in Analysis*, pp. 1-14, Oxford Press, Oxford, United Kingdom.

Silhavy et al. (1984) *Experiments with Gene Fusions*, Cold Spring Harbor Laboratory, Cold Spring Harbor, N.Y., United States of America.

Smith (1998a) *The Scientist* 12(14):21-24.

Smith et al. (1998b) *Clin Chem* 44(9):2054-2056.

Southern (1975) *J Mol Biol* 98:503-517.

Stolze et al. (2015) *Sci Rep* 5:8535.

Strain & Chmielewski (2001) *BioTechniques* 30(6):1286-1291.

Stratford et al. (2010) *PLoS Med* 7:e1000307.

Stuart et al. (2004) *Proc Nat Acad Sci USA* 101:615-620.

Subramanian et al. (2005) *Proc Nat Acad Sci USA* 102:15545-15550.

Tanaka et al. (1994) *J Gen Virol* 75:2691-2698.

Theriault et al. (1999) in Schena, ed., *DNA Microarrays: A Practical Approach*, pp. 101-120, Oxford University Press Inc., New York, N.Y., United States of America.

Tibshirani et al. (2002) *Proc Nat Acad Sci USA* 99:6567-6572.

Tijssen (ed.) (1993) *Laboratory Techniques in Biochemistry and Molecular Biology: Hybridization With Nucleic Acid Probes, Part I: Part I. Theory and Nucleic Acid Preparation*, Elsevier Press, New York, N.Y., United States of America.

Trapnell et al. (2012) *Nature Protoc* 7:562-578.

Tusher et al. (2001) *Proc Natl Acad Sci USA* 98:5116-5121.

U.S. Pat. Nos. 4,729,947; 5,143,854; 5,207,880; 5,230,781; 5,346,603; 5,360,523; 5,534,125; 5,571,388; 5,743,960; 5,800,992; 5,837,832; 5,843,767; 5,846,717; 5,871,918; 5,916,524; 5,965,352; 5,968,745; 5,974,164; 5,985,557; 5,994,069; 6,001,567; 6,017,696; 6,066,457; 6,086,737; 6,090,543; 6,123,819; 6,127,127; 6,162,603; 6,185,561; 6,225,059; 6,229,911; 6,245,508.

Van Kerckhoven et al. (1994) *J Clin Microbiol* 32:1669-1673.

Vignali (2000) *J Immunol Methods* 243(1-2):243-255.

Von Hoff et al. (2013)*N Engl J Med* 369:1691-703.

Vonlaufen et al. (2008) *Cancer Res* 68:2085-2093.

Waddell et al. (2015) *Nature* 518:495-501.

Wamunyokoli et al. (2006) *Clin Cancer Res* 12:690-700.

Wang et al. (1989) *Proc Natl Acad Sci USA* 86:9717-9721.

Wang et al. (2010) *Cancer Res* 70:6448-6455.

Whitfield et al. (2002) *Mol Biol Cell* 13:1977-2000.

Williams (1989) *BioTechniques* 7:762-769.

Williams et al. (1990) *Nucl Acids Res* 18(22):6531-6535.

Winter et al. (2006) *J Gastrointest Surg* 10:1199-1210; discussion 1210-1211.

Witkiewicz et al. (2015) *Nature Commun* 6:6744.

Worley et al. (2000) in Schena, ed., *Microarray Biochip Technology*, pp. 65-86, Eaton Publishing, Natick, Mass., United States of America.

Yachida et al. (2010) *Nature* 467:1114-1117.

Yang et al. (1998) *Science* 282:2244-2246.

Yermilov et al. (2009) *Annals Surg Oncol* 16:554-561.

Yershov et al. (1996) *Proc Natl Acad Sci USA* 93:4913-4918.

Yoshihara et al. (2013) *Nat Commun* 4:2612.

Zhang et al. (2008) *Nat Genet* 40:862-870.

Zhong et al. (2015) *PLoS One* 6:e22129.

Zhu et al. (2001) *Science* 293:2101-2105.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of assaying pancreatic ductal adenocarcinoma (PDAC) cells obtained from a subject with PDAC, the method comprising measuring a nucleic acid expression level for each gene of at least 10 genes selected from the group consisting of only the genes listed in Tables 2-5, genes listed in Table 1 that correspond to the DE-S subset of genes and genes listed in Table 1 that correspond to the DE-T subset of genes in the PDAC cells obtained from the subject.

2. The method of claim 1, wherein the at least 10 genes comprises all of the genes selected from the group consisting of only the genes listed in Tables 2-5, the genes listed in Table 1 that correspond to the DE-S subset of genes and genes listed in Table 1 that correspond to the DE-T subset of genes in PDAC cells obtained from the subject.

3. The method of claim 1, wherein the measuring comprises measuring each gene of at least 10 genes from only Table 2 in the PDAC cells of the subject and measuring each gene of at least 10 genes from only Table 3 in the PDAC cells of the subject.

4. The method of claim 1, comprising measuring each gene of at least 10 genes from only Table 4 in the PDAC cells of the subject and measuring each gene of at least 10 genes from only Table 5 in the PDAC cells of the subject.

5. The method of claim 1, wherein the subject is a human.

6. The method of claim 1, wherein the at least 10 genes comprises at least 25 of the genes selected from the group consisting of only the genes listed in Tables 2-5, the genes listed in Table 1 that correspond to the DE-S subset of genes and genes listed in Table 1 that correspond to the DE-T subset of genes in PDAC cells obtained from the subject.

7. A method for treating a subject diagnosed with pancreatic ductal adenocarcinoma (PDAC), the method comprising:

(a) measuring a nucleic acid expression level of each gene of at least 10 genes selected from the group consisting of only genes listed in Tables 2-5, genes listed in Table 1 that correspond to the DE-S subset of genes and genes listed in Table 1 that correspond to the DE-T subset of genes in a biological sample comprising PDAC cells obtained from the PDAC of the subject;

(b) creating an expression profile for the subject based on the nucleic acid expression levels of each gene of at least 10 genes selected from the group consisting of only the genes listed in Tables 2-5, the genes listed in Table 1 that correspond to the DE-S subset of genes and the genes listed in Table 1 that correspond to the DE-T subset of genes;

(c) classifying the subject as having an activated stroma subtype or a normal stroma subtype of PDAC, a basal subtype or a classical subtype of PDAC, or an activated stroma/basal subtype of PDAC, a normal stroma/basal subtype of PDAC, an activated stroma/classical subtype of PDAC or a normal stroma/classical subtype of PDAC; and (d) administering a treatment for the subject based on the subject being classified as having an activated stroma subtype or a normal stroma subtype of PDAC, a basal subtype or a classical subtype of PDAC, an activated stroma/basal subtype of PDAC, a normal stroma/basal subtype of PDAC, an activated stroma/classical subtype of PDAC, or a normal stroma/classical subtype of PDAC based on steps (a)-(c), wherein the treatment is selected from:

(i) agents listed in Table 5, 5-flourouracil and platinum based therapy if the subject is classified as having the classical subtype of PDAC, (ii) agents listed in Table 4, cisplatin- or oxaliplatin-based therapies and gemcitabine if the subject is classified as having the basal subtype of PDAC, (iii) agents listed in Table 3 if the subject is classified as having the normal stroma subtype of PDAC, (iv) agents listed in Table 2, radiation, hyaluronidase, hedgehog inhibition, modified vitamin D and anti-cytokine agents if the subject is classified as having the activated stroma subtype of PDAC, (v) agents listed in Table 5, 5-flourouracil and platinum based therapy in conjunction with agents selected from the agents listed in Table 3 if the subject is classified as having the normal stroma/classical subtype of PDAC, (vi) agents listed in Table 5, 5-flourouracil and platinum based therapy in conjunction with agents selected from the agents listed in Table 2, radiation, hyaluronidase, hedgehog inhibition, modified vitamin D and anti-cytokine agents if the subject is classified as having the activated stroma/classical subtype of PDAC, (vii) agents listed in Table 4, cisplatin- or oxaliplatin-based therapies and gemcitabine in conjunction with agents selected from the agents listed in Table 3 if the subject is classified as having the normal stroma/basal subtype of PDAC, or (viii) agents listed in Table 4, cisplatin- or oxaliplatin-based therapies and gemcitabine in conjunction with agents selected from the agents listed in Table 2, radiation, hyaluronidase, hedgehog inhibition, modified vitamin D and anti-cytokine agents if the subject is classified as having the activated stroma/basal subtype of PDAC.

8. The method of claim 7, wherein determining the activated stroma subtype or the normal stroma subtype of PDAC comprises:

(a) measuring the nucleic acid expression level of each gene of the at least 10 genes listed in only Table 2 and in only Table 3 or the nucleic acid expression level of each gene of at least 10 genes listed in only Table 1 that correspond to the DE-S subset of genes in the biological sample comprising PDAC cells obtained from the PDAC of the subject;

(b) creating the expression profile, wherein the expression profile encompasses the nucleic acid expression levels of each of the at least 10 genes listed only in Table 2 and the genes listed only in Table 3 or the nucleic acid expression levels of each of the at least 10 genes listed only in Table 1 that correspond to the DE-S subset of genes; and (c) classifying the subject as having the activated stroma subtype or the normal stroma using the expression profiles created in the form of analysis of top scoring pairs of genes, wherein the analysis employs a trained logistic model in which binary input from discriminatory gene pairs are input and classification odds results are produced, whereby the subject is classified as having the activated stroma subtype or the normal stroma subtype of PDAC.

9. The method of claim 8, wherein the using comprises comparing the expression profiles created to a standard, wherein the comparing employs a Bayesian classification reflecting a distance from (1) an activated stroma centroid that is high magnitude for all activated stroma genes and low magnitude for all normal stroma discriminatory genes; and (2) a normal stroma centroid that is high magnitude for all normal stroma genes and low magnitude for all activated stroma discriminatory genes.

10. The method of claim 9, wherein the comparing determines whether the expression profile is closer to the activated stroma centroid or the normal stroma centroid, whereby the subject is classified as having an activated stroma subtype or a normal stroma subtype of PDAC.

11. The method of claim 7, wherein determining the basal subtype or the classical subtype of PDAC comprises:

(a) measuring the nucleic acid expression level of each gene of the at least 10 genes listed in only Table 4 and in only Table 5 or the nucleic acid expression level of each gene of the at least 10 genes listed in only Table 1 that correspond to the DE-T subset of genes in the biological sample comprising PDAC cells obtained from the PDAC of the subject;

(b) creating the expression profile, wherein the expression profile encompasses the nucleic acid expression levels of each of the at least 10 genes listed in only Table 4 and the genes listed in only Table 5 or the nucleic acid expression levels of each of the at least 10 genes listed in only Table 1 that correspond to the DE-T subset of genes; and (c) classifying the subject as having the basal subtype or the classical stroma using the expression profiles created in the form of analysis of top scoring pairs of genes, wherein the analysis employs a trained logistic model in which binary input from discriminatory gene pairs are input and classification odds results are produced, whereby the subject is classified as having the basal subtype or the classical subtype of PDAC.

12. The method of claim 11, wherein the using comprises comparing the expression profiles created to a standard, wherein the comparing employs a Bayesian classification reflecting a distance from (1) a basal subtype centroid that is high magnitude for all basal subtype genes and low magnitude for all classical subtype discriminatory genes; and (2) a classical subtype centroid that is high magnitude for all classical subtype genes and low magnitude for all basal subtype discriminatory genes.

13. The method of claim 12, wherein the comparing determines whether the expression profile is closer to the basal subtype centroid or the classical subtype centroid, whereby the subject is classified as having the basal subtype or the classical subtype of PDAC.

* * * * *